(12) United States Patent
Baloglu et al.

(10) Patent No.: US 9,938,258 B2
(45) Date of Patent: Apr. 10, 2018

(54) SUBSTITUTED 2,3-DIHYDROBENZOFURANYL COMPOUNDS AND USES THEREOF

(71) Applicant: Karyopharm Therapeutics Inc., Newton, MA (US)

(72) Inventors: Erkan Baloglu, Stoneham, MA (US); Sharon Shechter, Andover, MA (US); Sharon Shacham, Newton, MA (US); Dilara McCauley, Arlington, MA (US); William Senapedis, Millis, MA (US); Gali Golan, Mesilat Zion (IL); Ori Kalid, Pardes Hanna (IL)

(73) Assignee: Karyopharm Therapeutics Inc., Newton, MA (US)

( * ) Notice: Subject to any disclaimer, the term of this patent is extended or adjusted under 35 U.S.C. 154(b) by 0 days.

(21) Appl. No.: 14/647,662

(22) PCT Filed: Nov. 27, 2013

(86) PCT No.: PCT/US2013/072264
§ 371 (c)(1),
(2) Date: May 27, 2015

(87) PCT Pub. No.: WO2014/085607
PCT Pub. Date: Jun. 5, 2014

(65) Prior Publication Data
US 2016/0221994 A1    Aug. 4, 2016

Related U.S. Application Data

(60) Provisional application No. 61/731,377, filed on Nov. 29, 2012, provisional application No. 61/799,429, filed on Mar. 15, 2013, provisional application No. 61/809,785, filed on Apr. 8, 2013, provisional application No. 61/842,746, filed on Jul. 3, 2013, provisional application No. 61/879,003, filed on Sep. 17, 2013, provisional application No. 61/904,897, filed on Nov. 15, 2013.

(51) Int. Cl.

| C07D 405/12 | (2006.01) |
|---|---|
| C07D 413/14 | (2006.01) |
| C07D 495/04 | (2006.01) |
| C07D 409/12 | (2006.01) |
| C07D 417/14 | (2006.01) |
| C07D 409/14 | (2006.01) |
| C07D 409/04 | (2006.01) |
| C07D 405/14 | (2006.01) |

(52) U.S. Cl.
CPC ......... *C07D 405/12* (2013.01); *C07D 405/14* (2013.01); *C07D 409/04* (2013.01); *C07D 409/12* (2013.01); *C07D 409/14* (2013.01); *C07D 413/14* (2013.01); *C07D 417/14* (2013.01); *C07D 495/04* (2013.01)

(58) Field of Classification Search
CPC .. C07D 405/12; C07D 413/14; C07D 495/04; C07D 409/12; C07D 417/14; C07D 409/14; C07D 409/04
USPC .......... 514/233.5, 236.5, 237.2, 249, 252.01, 514/252.05, 253.11, 255.05, 256, 275, 514/303, 318, 333, 337, 338, 339, 340, 514/343; 544/114, 122, 131, 238, 331, 544/333, 353, 364, 405; 546/13, 119, 546/193, 194, 196, 256, 272.1, 273.7, 546/277.1, 279.1, 280.4, 282.7, 284.1
See application file for complete search history.

(56) References Cited

U.S. PATENT DOCUMENTS

| 8,173,677 B2 | 5/2012 | Roulston et al. |
|---|---|---|
| 8,912,184 B1 | 12/2014 | Fleischer et al. |
| 2004/0186114 A1 | 9/2004 | Cirillo et al. |
| 2008/0020413 A1 | 1/2008 | Tong et al. |
| 2012/0053170 A1 | 3/2012 | Arigon et al. |

(Continued)

FOREIGN PATENT DOCUMENTS

| EP | 1627873 A1 | 2/2006 |
|---|---|---|
| EP | 1798224 A1 | 6/2007 |

(Continued)

OTHER PUBLICATIONS

Database Registry Chemical Abstracts, Database Accession No. 1070271-09-8; CAS Registry No. 1070271-09-08 (Nov. 3, 2008).

(Continued)

*Primary Examiner* — Brenda L Coleman
(74) *Attorney, Agent, or Firm* — Foley Hoag LLP

(57) ABSTRACT

The invention generally relates to substituted 2,3-dihydrobenzofuranyl compounds, and more particularly to a compound represented by Structural Formula I:

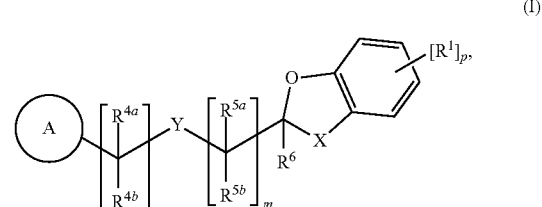

or a pharmaceutically acceptable salt thereof, wherein the variables are as defined and described herein. The invention also includes the synthesis and use of a compound of Structural Formula I, or a pharmaceutically acceptable salt or composition thereof, e.g., in the treatment of cancer (e.g., mantle cell lymphoma), and other diseases and disorders.

12 Claims, 13 Drawing Sheets

(56) References Cited

U.S. PATENT DOCUMENTS

| | | |
|---|---|---|
| 2012/0329786 A1 | 12/2012 | Willardsen et al. |
| 2013/0317027 A1 | 11/2013 | Willardsen et al. |
| 2016/0221994 A1 | 8/2016 | Baloglu et al. |
| 2017/0096417 A1 | 4/2017 | Baloglu et al. |

FOREIGN PATENT DOCUMENTS

| | | |
|---|---|---|
| EP | 2 003 118 A1 | 12/2008 |
| EP | 2098231 A1 | 9/2009 |
| WO | WO-97/48397 A1 | 12/1997 |
| WO | WO 97/48696 | 12/1997 |
| WO | WO-99/53920 A1 | 10/1999 |
| WO | WO-03/008365 A2 | 1/2003 |
| WO | WO-03/080054 A1 | 10/2003 |
| WO | WO-2006/106326 A1 | 10/2006 |
| WO | WO 2006/116136 A1 | 11/2006 |
| WO | WO-2008/025857 A2 | 3/2008 |
| WO | WO-2008/026018 A1 | 3/2008 |
| WO | WO-2009/072004 A2 | 6/2009 |
| WO | WO-2009/109610 A1 | 9/2009 |
| WO | WO-2011/109441 A1 | 9/2011 |
| WO | WO 2012/150952 A1 | 11/2012 |
| WO | WO-2012/177782 A1 | 12/2012 |
| WO | WO-2013/082150 A1 | 6/2013 |
| WO | WO-2014/074715 A1 | 5/2014 |
| WO | WO-2014/085607 A1 | 6/2014 |
| WO | WO-2014/111871 A1 | 7/2014 |
| WO | WO-2015/003166 A1 | 1/2015 |
| WO | WO-2015/042414 A1 | 3/2015 |
| WO | WO-2015/054060 A1 | 4/2015 |
| WO | WO-2016/100515 A1 | 6/2016 |

OTHER PUBLICATIONS

Database Registry Chemical Abstracts, Database Accession No. 1069903-74-7; CAS Registry No. 1069646-70-3 (Nov. 2, 2008).
Database Registry Chemical Abstracts, Database Accession No. 1067055-04-2; CAS Registry No. 1067055-04-2 (Oct. 28, 2008).
Database Registry Chemical Abstracts, Database Accession No. 1067037-85-7; CAS Registry No. 1067037-85-7 (Oct. 27, 2008).
Database Registry Chemical Abstracts, Database Accession No. 1065636-94-3; CAS Registry No. 106563694-3 (Oct. 24, 2008).
Database Registry Chemical Abstracts, Database Accession No. 1060535-75-2; CAS Registry No. 1060535-75-2; 1060530-87-1; 1060527-21-0; 1060421-07-9; 1060400-89-6 (Oct. 13, 2008).
International Search Report for International Application No. PCT/US2013/072264, "Substituted 2,3-Dihydrobenzofuranyl Compounds and Uses Thereof"; dated May 16, 2014.
Written Opinion of International Application No. PCT/US2013/072264, "Substituted 2,3-Dihydrobenzofuranyl Compounds and Uses Thereof"; dated May 16, 2014.
Bhatia et al., "Autoimmunity and autoimmune disease in 6," Principles of Medical Biology, 239-263, 244 (1996).
Database Registry Chemical Abstracts, Database Accession No. 1025224-12-7, CAS Registry No. 1025224-12-7 (Jun. 4, 2008).
Database Registry Chemical Abstracts, Database Accession No. 1025516-17-9, CAS Registry No. 1025516-17-9 (Jun. 5, 2008).
Database Registry Chemical Abstracts, Database Accession No. 1110694-76-2, CAS Registry No. 1110694-76-2 (Feb. 23, 2009).
Database Registry Chemical Abstracts, Database Accession No. 1110698-05-9, CAS Registry No. 1110698-05-9 (Feb. 23, 2009).
Database Registry Chemical Abstracts, Database Accession No. 1110699-54-1, CAS Registry No. 1110699-54-1 (Feb. 23, 2009).
Database Registry Chemical Abstracts, Database Accession No. 1110699-68-7, CAS Registry No. 1110699-68-7 (Feb. 23, 2009).
Database Registry Chemical Abstracts, Database Accession No. 1110701-07-9, CAS Registry No. 1110701-07-9 (Feb. 23, 2009).
Database Registry Chemical Abstracts, Database Accession No. 1110701-73-9, CAS Registry No. 1110701-73-9 (Feb. 23, 2009).
Database Registry Chemical Abstracts, Database Accession No. 1110705-13-9, CAS Registry No. 1110705-13-9 (Feb. 23, 2009).
Database Registry Chemical Abstracts, Database Accession No. 1110707-61-3, CAS Registry No. 1110707-61-3 (Feb. 23, 2009).
Database Registry Chemical Abstracts, Database Accession No. 1110708-07-0, CAS Registry No. 1110708-07-0 (Feb. 23, 2009).
Database Registry Chemical Abstracts, Database Accession No. 1110708-69-4, CAS Registry No. 1110708-69-4 (Feb. 23, 2009).
Eswaran et al., "UnPAKing the class differences among p21-activated kinases," Trends Biochem Sci, 33(8): 394-403 (2008).
Galli et al., "Medicinal chemistry of nicotinamide phosphoribosyltransferase (NAMPT) inhibitors," J Med Chem, 56:6279-96 (2013).
Giannetti et al., "Fragment-Based Identification of Amides Derived from trans-2-(Pyridin-2-yl) cyclopropanecarboxylic Acid as Potent Inhibitors of Human Nicotinamide Phosphoribosyltransferase (NAMPT)," J Med Chem, 57(3): 770-792 (2014).
Girouard et al., "Neurovascular coupling in the normal brain and in hypertension, stroke, and Alzheimer disease," J Appl Physiol, 100(1): 328-335, 332 (2006).
Guo et al., "Discovery of pyrroloaminopyrazoles as novel PAK inhibitors," J Med Chem, 55(10): 4728-4739 (2012).
Hayter et al., "Updated assessment of the prevalence, spectrum and case definition of autoimmune disease," Autoimmun Rev, 11(10): 754-765, 756 (2012).
Houtkooper et al., "Exploring the therapeutic space around NAD+," J Cell Biol, 199(2):205-9 (2012).
International Search Report and Written Opinion for International Application No. PCT/US2016/047566, "Substituted Benzofuranyl Compounds and Uses Thereof," dated Oct. 4, 2016.
International Search Report and Written Opinion for International Application No. PCT/US2016/069241, "Substituted Benzofuranyl Compounds and Uses Thereof," dated Mar. 16, 2017.
International Search Report and Written Opinion for International Application No. PCT/US2015/066098, "Cyclic Compounds and Uses Thereof," dated Mar. 16, 2016.
International Search Report and Written Opinion for International Application No. PCT/US2016/047337, "Cyclic Compounds and Uses Thereof," dated Oct. 6, 2016.
International Search Report and Written Opinion for International Application No. PCT/US2016/047358, "Cyclic Compounds and Uses Thereof," dated Oct. 26, 2016.
International Search Report for International Application No. PCT/US2014/045479, "Substituted Benzofuranyl and Benzoxazolyl Compounds and Uses Thereof"; dated Oct. 27, 2014.
International Search Report for International Application No. PCT/US2014/056580, "Multicyclic Compounds and Methods of Using Same"; dated Nov. 27, 2014.
Kreis et al., "PAK signalling in neuronal physiology," Cell Signal, 21: 384-393 (2009).
Ma et al., "PAK in Alzheimer disease, Huntington disease and X-linked mental retardation," Cell Logist, 2(2): 2159-2799 (2012).
Marelli et al., "Tumor targeting via integrin ligands," Front Oncol, 3: 1-12 (2013).
O'Brien et al., "Vascular cognitive impairment," Lancet Neurol, 2(2): 89-98, 96 (2003).
Sampath et al., "Inhibition of nicotinamide phosphoribosyltransferase (NAMPT) as a therapeutic strategy in cancer," Pharmacol Therapeut (2014).
Shah et al., "Current approaches in the treatment of Alzheimer's disease," Biomed & Pharmacother, 62: 199-207 (2008).
Wang et al., "Mathematical modeling in cancer drug discovery," Drug Discov Today, 19(2): 145-150 (2014).
Yin et al., "Intrinsic directionality of migrating vascular smooth muscle cells is regulated by NAD+ biosynthesis," J Cell Sci, 125:5770-80 (2012).

SUBSTITUTED 2,3-DIHYDROBENZOFURANYL COMPOUNDS AND USES THEREOF

RELATED APPLICATIONS

This application is the U.S. National Stage of International Application No.: PCT/US2013/072264, filed on Nov. 27, 2013, which designates the U.S., published in English, and claims the benefit of U.S. Provisional Application No. 61/731,377, filed on Nov. 29, 2012, U.S. Provisional Application No. 61/799,429, filed on Mar. 15, 2013, U.S. Provisional Application No. 61/809,785, filed on Apr. 8, 2013, U.S. Provisional Application No. 61/842,746, filed on Jul. 3, 2013, U.S. Provisional Application No. 61/879,003, filed on Sep. 17, 2013 and U.S. Provisional Application No. 61/904,897, filed on Nov. 15, 2013. The entire teachings of the above applications are incorporated herein by reference.

BACKGROUND OF THE INVENTION

Cancer remains a disease for which existing treatments are insufficient. For example, of the approximately 66,360 new cases of non-Hodgkin lymphoma in the United States each year, about 6% of the cases involve mantle cell lymphoma (MCL). Treatments for MCL include combination therapies, chemotherapy and stem cell transplantation. Like many cancers, although treatments for MCL have improved, relapses remain common, and treatment resistance is observed.

There is a clear need for additional drug-like compounds that are effective for the treatment of cancer, such as non-Hodgkin lymphoma.

SUMMARY OF THE INVENTION

The present invention relates to substituted 2,3-dihydrobenzofuranyl compounds, or pharmaceutically acceptable salts or compositions thereof, useful as anti-cancer agents. In one embodiment of the invention, the substituted 2,3-dihydrobenzofuranyl compounds are represented by Structural Formula II:

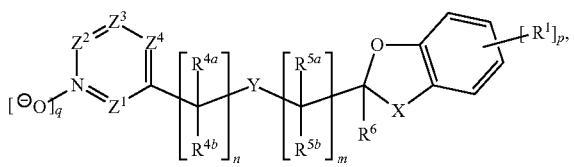

(II)

or a pharmaceutically acceptable salt thereof, wherein each variable is as defined and described herein.

Another embodiment of the invention is a composition comprising a compound of the invention, or a pharmaceutically acceptable salt thereof, and a pharmaceutically acceptable carrier.

Yet another embodiment of the invention is a method for treating cancer in a subject in need thereof, the method comprising administering to a subject in need thereof a therapeutically effective amount of a compound of the invention, or a pharmaceutically acceptable salt thereof, or a composition comprising a compound of the invention, or a pharmaceutically acceptable salt thereof.

Without being bound by a particular theory, it is believed that the compounds described herein can modulate (e.g., inhibit) one or more p21-activated kinases (PAK), for example, one or more of PAKs 1-6. More specifically, and without being bound by a particular theory, it is believed that the compounds described herein can bind to one or more PAKs and function as allosteric modulators of one or more PAKs. For example, the compounds described herein may exert their modulatory effect(s) on one or more PAKs by binding to and destabilizing one or more PAKs or contributing to the degradation of one or more PAKs, thereby modulating (e.g., inhibiting) the effect of one or more PAKs on one or more proteins downstream of the one or more PAKs, for example, growth signaling proteins such as Akt, ERK1/2, p90RSK, β-catenin, cofilin, p21 and cyclin D1.

In a particular embodiment, one or more of the Group I PAKs (e.g., PAK1, PAK2, PAK3) is modulated. For example, PAK1 is modulated, PAK2 is modulated, PAK3 is modulated or a combination of PAK1, PAK2 and PAK3, such as PAK1 and PAK2, PAK1 and PAK3, PAK2 and PAK3, or PAK1, PAK2 and PAK3 is modulated. In a particular embodiment, one or more of the group II PAKs (e.g., PAK4, PAK5, PAK6) is modulated. For example, PAK4 is modulated, PAK5 is modulated, PAK6 is modulated or a combination of PAK4, PAK5 and PAK6, such as PAK4 and PAK5, PAK4 and PAK6, PAK5 and PAK6 or PAK4, PAK5 and PAK6 is modulated. Therefore, the compounds described herein can be useful for treating PAK-mediated disorders.

In another particular embodiment, one or more of the Group I PAKs (e.g., PAK1, PAK2, PAK3) is inhibited. For example, PAK1 is inhibited, PAK2 is inhibited, PAK3 is inhibited or a combination of PAK1, PAK2 and PAK3, such as PAK1 and PAK2, PAK1 and PAK3, PAK2 and PAK3, or PAK1, PAK2 and PAK3 is inhibited. In a particular embodiment, one or more of the group II PAKs (e.g., PAK4, PAK5, PAK6) is inhibited. For example, PAK4 is inhibited, PAK5 is inhibited, PAK6 is inhibited or a combination of PAK4, PAK5 and PAK6, such as PAK4 and PAK5, PAK4 and PAK6, PAK5 and PAK6 or PAK4, PAK5 and PAK6 is inhibited. Therefore, the compounds described herein can be useful for treating PAK-mediated disorders.

As such, in another embodiment, the invention is a method of treating a PAK-mediated disorder in a subject in need thereof, comprising administering to the subject in need thereof a therapeutically effective amount of a compound of the invention, or a pharmaceutically acceptable salt thereof, or a pharmaceutical composition comprising a compound of the invention, or a pharmaceutically acceptable salt thereof.

Another embodiment of the invention is use of a compound of the invention for treating cancer in a subject.

Another embodiment of the invention is use of a compound of the invention for the manufacture of a medicament for treating cancer in a subject.

Compounds of the present invention, and pharmaceutically acceptable salts and/or compositions thereof, are useful for treating a variety of cancers, such as lymphoma and, more specifically, mantle cell lymphoma.

BRIEF DESCRIPTION OF THE DRAWINGS

The foregoing will be apparent from the following more particular description of example embodiments of the invention.

DETAILED DESCRIPTION OF THE INVENTION

Figure 1A:
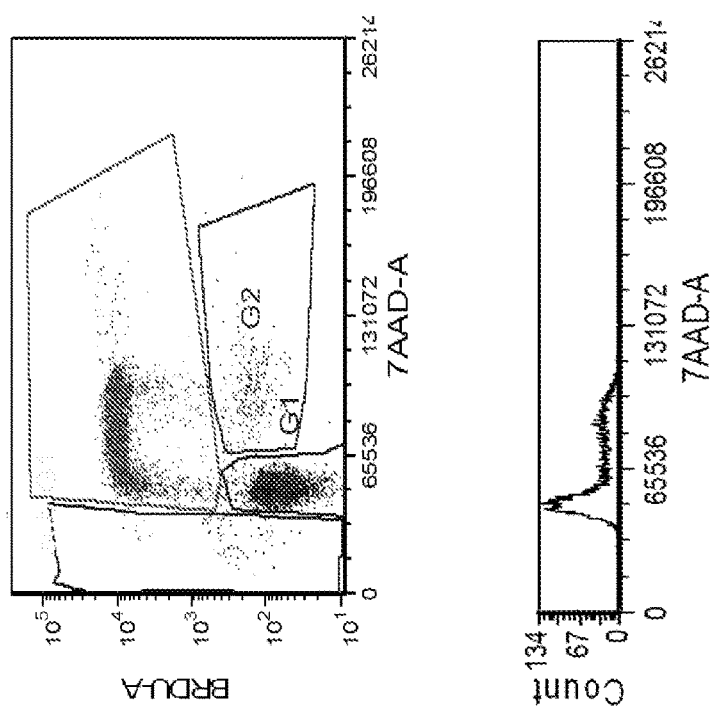
FIG. 1A is a single-cell scatter plot and shows BrdU versus 7-AAD for Z138 cells treated with no drug. A graph showing cell count versus 7-AAD intensity is depicted below its corresponding scatter plot.
Figure 1B:
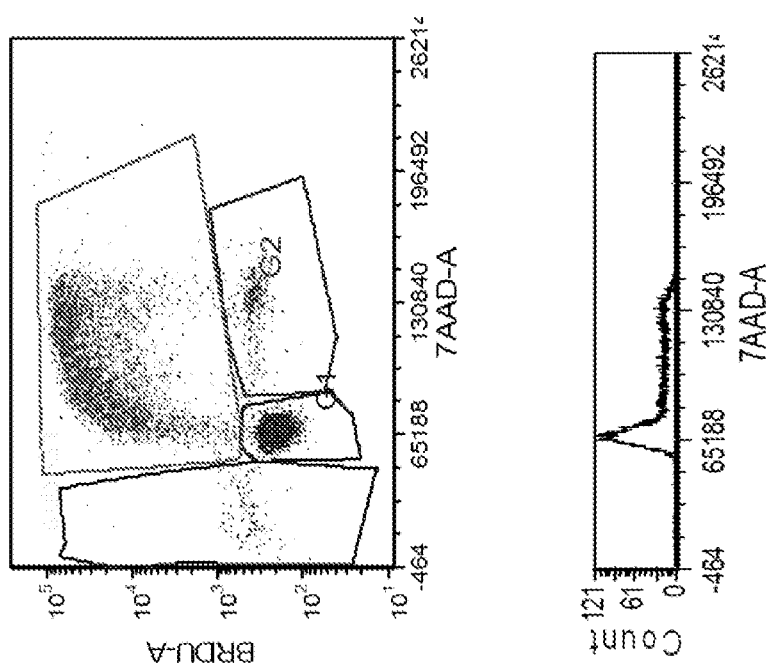
FIG. 1B is a single-cell scatter plot and shows BrdU versus 7-AAD for Z138 cells treated with 1 μM Compound 123 for 1 day. A graph showing cell count versus 7-AAD intensity is depicted below its corresponding scatter plot.
Figure 1C:
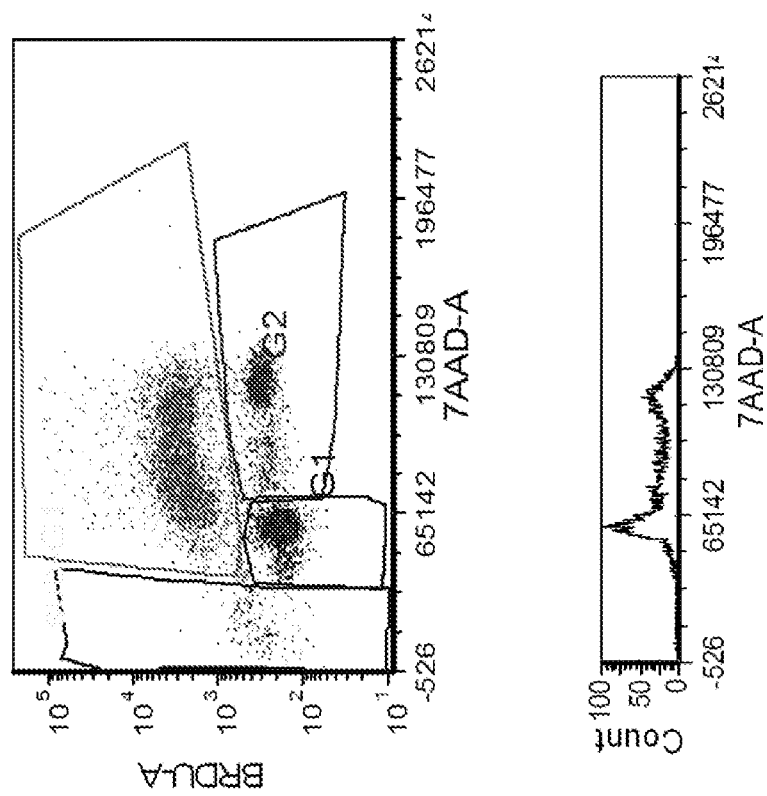
FIG. 1C is a single-cell scatter plot and shows BrdU versus 7-AAD for Z138 cells treated with 1 μM Compound 123 for 2 days. A graph showing cell count versus 7-AAD intensity is depicted below its corresponding scatter plot.

A description of example embodiments of the invention follows.

Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

Compounds of the present invention may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers or enantiomers, with all possible isomers and mixtures thereof, including optical isomers, being included in the present invention.

"Alkyl" means an optionally substituted saturated aliphatic branched or straight-chain monovalent hydrocarbon radical having the specified number of carbon atoms. Thus, "$(C_1-C_6)$ alkyl" means a radical having from 1-6 carbon atoms in a linear or branched arrangement. "$(C_1-C_6)$alkyl" includes methyl, ethyl, propyl, butyl, pentyl and hexyl.

"Alkenyl" means an optionally substituted aliphatic branched or straight-chain monovalent hydrocarbon radical having at least one carbon-carbon double bond and the specified number of carbon atoms. Thus, "$(C_1-C_6)$ alkenyl" means a radical having at least one carbon-carbon double bond and from 1-6 carbon atoms in a linear or branched arrangement. "$(C_1-C_6)$alkenyl" includes allyl and vinyl.

"Alkylene" means an optionally substituted saturated aliphatic branched or straight-chain divalent hydrocarbon radical having the specified number of carbon atoms. Thus, "$(C_1-C_6)$alkylene" means a divalent saturated aliphatic radical having from 1-6 carbon atoms in a linear arrangement, e.g., —$[(CH_2)_n]$—, where n is an integer from 1 to 6, "$(C_1-C_6)$alkylene" includes methylene, ethylene, propylene, butylene, pentylene and hexylene. Alternatively, "$(C_1-C_6)$ alkylene" means a divalent saturated radical having from 1-6 carbon atoms in a branched arrangement, for example: —$[(CH_2CH_2CH_2CH_2CH(CH_3))]$—, —$[(CH_2CH_2CH_2CH_2C(CH_3)_2)]$—, —$[(CH_2C(CH_3)_2CH(CH_3))]$—, and the like. A specific branched $C_3$-alkylene is

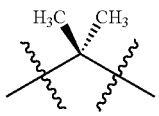

and a specific $C_4$-alkylene is

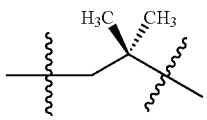

"Acyl" means —C(O)-alkyl, wherein alkyl is as defined herein.

"Alkanoate" means —C(O)O-alkyl, wherein alkyl is as defined herein.

"Amino" means —$NH_2$.

As used herein, the term "dialkylamino" means (alkyl)$_2$—N—, wherein the alkyl groups, which may be the same or different, are as herein defined. Particular dialkylamino groups are ((C$_1$-C$_4$)alkyl)$_2$—N—, wherein the alkyl groups may be the same or different. Exemplary dialkylamino groups include dimethylamino, diethylamino and methylethylamino.

As used herein, the term "monoalkylamino" means a radical of the formula alkyl-NH, wherein the alkyl group is as herein defined. In one aspect, a monoalkylamino is a (C$_1$-C$_6$) alkyl-amino-. Exemplary monoalkylamino groups include methylamino and ethylamino.

"Aryl" or "aromatic" means an aromatic monocyclic or polycyclic (e.g., bicyclic or tricyclic) carbocyclic ring system. In one embodiment, "aryl" is a 6-12 membered monocylic or bicyclic system. Aryl systems include, but are not limited to, phenyl, naphthalenyl, fluorenyl, indenyl, azulenyl, and anthracenyl.

"Carboxyl" means —COOH.

As used herein, the term "carboxamide" means a radical of the formula R'R"N—C(═O)—, where R' and R" are independently hydrogen or alkyl, as defined herein.

"Carbocyclyl" means a cyclic group with only ring carbon atoms. "Carbocyclyl" includes 3-12 membered saturated, partially saturated or unsaturated aliphatic cyclic hydrocarbon rings or 6-12 membered aryl rings. A carbocyclyl moiety can be monocyclic, fused bicyclic, bridged bicyclic, spiro bicyclic, or polycyclic.

Monocyclic carbocyclyls are saturated or unsaturated aliphatic cyclic hydrocarbon rings or aromatic hydrocarbon rings having the specified number of carbon atoms. Monocyclic carbocyclyls include cycloalkyl, cycloalkenyl, cycloalkynyl and phenyl.

A fused bicyclic carbocyclyl has two rings which have two adjacent ring atoms in common. The first ring is a monocyclic carbocyclyl and the second ring is a monocyclic carbocyclyl or a monocyclic heterocyclyl.

A bridged bicyclic carbocyclyl has two rings which have three or more adjacent ring atoms in common. The first ring is a monocyclic carbocyclyl and the second ring is a monocyclic carbocyclyl or a monocyclic heterocyclyl.

A spiro bicyclic carbocyclyl has two rings which have only one ring atom in common. The first ring is a monocyclic carbocyclyl and the second ring is a monocyclic carbocyclyl or a monocyclic heterocyclyl.

Polycyclic carbocyclyls have more than two rings (e.g., three rings resulting in a tricyclic ring system) and adjacent rings have at least one ring atom in common. The first ring is a monocyclic carbocyclyl and the remainder of the ring structures are monocyclic carbocyclyls or monocyclic heterocyclyls. Polycyclic ring systems include fused, bridged and spiro ring systems. A fused polycyclic ring system has at least two rings that have two adjacent ring atoms in common. A spiro polycyclic ring system has at least two rings that have only one ring atom in common. A bridged polycyclic ring system has at least two rings that have three or more adjacent ring atoms in common.

"Cycloalkyl" means a saturated aliphatic cyclic hydrocarbon ring. Thus, "C$_3$-C$_7$ cycloalkyl" means a hydrocarbon radical of a (3-7 membered) saturated aliphatic cyclic hydrocarbon ring. A C$_3$-C$_7$ cycloalkyl includes, but is not limited to cyclopropyl, cyclobutyl, cyclopentyl, cyclohexyl and cycloheptyl.

"Hetero" refers to the replacement of at least one carbon atom member in a ring system with at least one heteroatom selected from N, S, and O. "Hetero" also refers to the replacement of at least one carbon atom member in an acyclic system. A hetero ring system or a hetero acyclic system may have 1, 2, 3 or 4 carbon atom members replaced by a heteroatom.

"Heterocyclyl" means a cyclic 4-13 membered saturated or unsaturated aliphatic or aromatic ring containing 1, 2, 3, 4 or 5 heteroatoms independently selected from N, O or S. When one heteroatom is S, it can be optionally mono- or di-oxygenated (i.e., —S(O)— or —S(O)$_2$—). The heterocyclyl can be monocyclic, fused bicyclic, bridged bicyclic, spiro bicyclic or polycyclic.

"Saturated heterocyclyl" means an aliphatic heterocyclyl group without any degree of unsaturation (i.e., no double bond or triple bond). It can be monocyclic, fused bicyclic, bridged bicyclic, spiro bicyclic or polycyclic.

Examples of monocyclic saturated heterocyclyls include, but are not limited to, azetidine, pyrrolidine, piperidine, piperazine, azepane, hexahydropyrimidine, tetrahydrofuran, tetrahydropyran, morpholine, thiomorpholine, thiomorpholine 1,1-dioxide, tetrahydro-2H-1,2-thiazine, tetrahydro-2H-1,2-thiazine 1,1-dioxide, isothiazolidine, isothiazolidine 1,1-dioxide.

A fused bicyclic heterocyclyl has two rings which have two adjacent ring atoms in common. The first ring is a monocyclic heterocyclyl and the second ring is a monocyclic carbocycle (such as a cycloalkyl or phenyl) or a monocyclic heterocyclyl. For example, the second ring is a (C$_3$-C$_6$)cycloalkyl, such as cyclopropyl, cyclobutyl, cyclopentyl and cyclohexyl. Alternatively, the second ring is phenyl. Examples of fused bicyclic heterocyclyls include, but are not limited to, octahydrocyclopenta[c]pyrrolyl, indoline, isoindoline, 2,3-dihydro-1H-benzo[d]imidazole, 2,3-dihydrobenzo[d]oxazole, 2,3-dihydrobenzo[d]thiazole, octahydrobenzo[d]oxazole, octahydro-1H-benzo[d]imidazole, octahydrobenzo[d]thiazole, octahydrocyclopenta[c]pyrrole, 3-azabicyclo[3.1.0]hexane, and 3-azabicyclo[3.2.0]heptane.

A spiro bicyclic heterocyclyl has two rings which have only one ring atom in common. The first ring is a monocyclic heterocyclyl and the second ring is a monocyclic carbocycle (such as a cycloalkyl or phenyl) or a monocyclic heterocyclyl. For example, the second ring is a (C$_3$-C$_6$) cycloalkyl. Alternatively, the second ring is phenyl. Example of spiro bicyclic heterocyclyl includes, but are not limited to, azaspiro[4.4]nonane, 7-azaspiro[4.4]nonane, azasprio[4.5]decane, 8-azaspiro[4.5]decane, azaspiro[5.5]undecane, 3-azaspiro[5.5]undecane and 3,9-diazaspiro[5.5]undecane.

A bridged bicyclic heterocyclyl has two rings which have three or more adjacent ring atoms in common. The first ring is a monocyclic heterocyclyl and the other ring is a monocyclic carbocycle (such as a cycloalkyl or phenyl) or a monocyclic heterocyclyl. Examples of bridged bicyclic heterocyclyls include, but are not limited to, azabicyclo[3.3.1]nonane, 3-azabicyclo[3.3.1]nonane, azabicyclo[3.2.1]octane, 3-azabicyclo[3.2.1]octane, 6-azabicyclo[3.2.1]octane and azabicyclo[2.2.2]octane, 2-azabicyclo[2.2.2]octane.

Polycyclic heterocyclyls have more than two rings, one of which is a heterocyclyl (e.g., three rings resulting in a tricyclic ring system) and adjacent rings having at least one ring atom in common. Polycyclic ring systems include fused, bridged and spiro ring systems. A fused polycyclic ring system has at least two rings that have two adjacent ring atoms in common. A spiro polycyclic ring system has at least two rings that have only one ring atom in common. A bridged polycyclic ring system has at least two rings that have three or more adjacent ring atoms in common.

"Heteroaryl" or "heteroaromatic ring" means a 5-12 membered monovalent heteroaromatic monocyclic or bicylic ring radical. A herteroaryl contains 1, 2, 3 or 4 heteroatoms independently selected from N, O, and S. Heteroaryls include, but are not limited to, furan, oxazole, thiophene, 1,2,3-triazole, 1,2,4-triazine, 1,2,4-triazole, 1,2, 5-thiadiazole 1,1-dioxide, 1,2,5-thiadiazole 1-oxide, 1,2,5-thiadiazole, 1,3,4-oxadiazole, 1,3,4-thiadiazole, 1,3,5-triazine, imidazole, isothiazole, isoxazole, pyrazole, pyridazine, pyridine, pyridine-N-oxide, pyrazine, pyrimidine, pyrrole, tetrazole, and thiazole. Bicyclic heteroaryl rings include, but are not limited to, bicyclo[4.4.0] and bicyclo[4.3.0] fused ring systems such as indolizine, indole, isoindole, indazole, benzimidazole, benzthiazole, purine, quinoline, isoquinoline, cinnoline, phthalazine, quinazoline, quinoxaline, 1,8-naphthyridine, and pteridine.

"Halogen" and "halo" are used interchangeably herein and each refers to fluorine, chlorine, bromine, or iodine.

"Chloro" means —Cl.

"Fluoro" means —F.

"Cyano" means —CN.

"Alkoxy" means an alkyl radical attached through an oxygen linking atom. "($C_1$-$C_6$)alkoxy" includes methoxy, ethoxy, propoxy, butoxy, pentoxy and hexoxy.

"Thioalkoxy" means an alkyl radical attached through a sulfur linking atom.

"Haloalkyl" include mono, poly, and perhaloalkyl groups, where each halogen is independently selected from fluorine, chlorine, and bromine.

"Hydroxyalkyl" means an HO-alkylene- group and includes mono and polyhydroxyalkyl groups.

"Sulfonate" means —$SO_2H$.

It is understood that substituents and substitution patterns on the compounds of the invention can be selected by one of ordinary skill in the art to provide compounds that are chemically stable and that can be readily synthesized by techniques known in the art, as well as those methods set forth below. In general, the term "substituted," whether preceded by the term "optionally" or not, means that one or more hydrogens of the designated moiety are replaced with a suitable substituent. Unless otherwise indicated, an "optionally substituted group" can have a suitable substituent at each substitutable position of the group and, when more than one position in any given structure may be substituted with more than one substituent selected from a specified group, the substituent can be either the same or different at every position. Alternatively, an "optionally substituted group" can be unsubstitued.

Combinations of substituents envisioned by this invention are preferably those that result in the formation of stable or chemically feasible compounds. If a substituent is itself substituted with more than one group, it is understood that these multiple groups can be on the same carbon atom or on different carbon atoms, as long as a stable structure results. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted group" are independently halogen; halo($C_1$-$C_4$)alkyl; hydroxy($C_1$-$C_4$)alkyl; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}$-carbocyclyl, which may be substituted with R°; —$(CH_2)_{0-4}$-heterocyclyl, which may be substituted with R°; —$(CH_2)_{0-4}Ph$, which may be substituted with R°; —$(CH_2)_{0-4}O(CH_2)_{0-1}Ph$ which may be substituted with R°; —CH═CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$(CH_2)_{0-4}C(O)NR°NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —($C_{1-4}$ straight or branched alkylene)O—$N(R°)_2$; or —($C_{1-4}$ straight or branched alkylene)C(O)O—$N(R°)_2$, wherein each R° may be substituted as defined below and is independently hydrogen, $C_{1-6}$ aliphatic, —$O(CH_2)_{0-1}Ph$, —$CH_2$-(5-6 membered carbocyclyl), —$CH_2$-(5-6 membered heterocyclyl) or a 5-6-membered saturated, partially unsaturated, or aryl ring having 0-4 heteroatoms independently selected from nitrogen, oxygen, and sulfur, or, notwithstanding the definition above, two independent occurrences of R°, taken together with their intervening atom(s), form a 3-12-membered saturated, partially unsaturated, or aryl monocyclic or bicyclic ring having 0-4 heteroatoms independently selected from nitrogen, oxygen, and sulfur, which may be substituted as defined below.

In some embodiments, suitable monovalent substituents on a substitutable carbon atom of an "optionally substituted group" are independently halogen; halo($C_1$-$C_4$)alkyl; hydroxy($C_1$-$C_4$)alkyl; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}$-carbocyclyl, which may be substituted with R°; —$(CH_2)_{0-4}$-heterocyclyl, which may be substituted with R°; —$(CH_2)_{0-4}Ph$, which may be substituted with R°; —$(CH_2)_{0-4}O(CH_2)_{0-1}Ph$ which may be substituted with R°; —CH═CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —($C_{1-4}$ straight or branched alkylene)O—$N(R°)_2$; or —($C_{1-4}$ straight or branched) alkylene)C(O)O—$N(R°)_2$, wherein each R° may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, and sulfur, or, notwithstanding the definition above, two independent occurrences of R°, taken together with their intervening atom(s), form a 3-12-membered saturated, partially unsaturated, or aryl monocyclic or bicyclic ring having 0-4 heteroatoms independently selected from nitrogen, oxygen, and sulfur, which may be substituted as defined below.

In some embodiments, suitable monovalent substituents on a substitutable carbon atom of an "optionally substituted group" are independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR$—$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$(CH_2)_{0-4}O(CH_2)_{0-1}$-pyridyl which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR$—, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°_2$; —$OP(O)R°_2$; —$OP(O)(OR°)_2$; $SiR°_3$; —$(C_{1-4}$ straight or branched alkylene)O—$N(R°)_2$; or —$(C_{1-4}$ straight or branched alkylene)C(O)O—$N(R°)_2$, wherein each R° may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, and sulfur, or, notwithstanding the definition above, two independent occurrences of R°, taken together with their intervening atom(s), form a 3-12-membered saturated, partially unsaturated, or aryl monocyclic or bicyclic ring having 0-4 heteroatoms independently selected from nitrogen, oxygen, and sulfur, which may be substituted as defined below.

Suitable monovalent substituents on R° (or the ring formed by taking two independent occurrences of R° together with their intervening atoms), are independently halogen, —$(CH_2)_{0-2}R^•$, -(haloR$^•$), —$(CH_2)_{0-2}OH$, —$(CH_2)_{0-2}OR^•$, —$(CH_2)_{0-2}CH(OR^•)_2$; —O(haloR$^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)C(O)OR$^•$, or —SSR$^•$ wherein each R$^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur. Suitable divalent substituents on a saturated carbon atom of R° include =O and =S.

"Heteroaryl substituent," as used herein, refers to a substituent on a heteroaryl group. Such substituents include the suitable monovalent substituents for a substitutable carbon atom, as described above. Preferred heteroaryl substituents include halogen; —$(CH_2)_{0-4}R°$; —$(CH_2)_{0-4}OR°$; —$O(CH_2)_{0-4}R°$, —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —$NO_2$; —CN; —$N_3$; or —$(CH_2)_{0-4}N(R°)_2$, wherein each R° is defined above and may be substituted as defined above. Particularly preferred heteroaryl substituents include halogen; $(C_1-C_4)$alkyl; $(C_1-C_4)$alkoxy; $(C_1-C_4)$thioalkoxy; —$NO_2$; —CN; —$N_3$; —$N(R°)_2$; carbocyclyl; or heterocyclyl, wherein each R° is defined above and may be substituted as defined above.

Suitable divalent substituents on a saturated carbon atom of an "optionally substituted group" include the following: =O, =S, =NNR*$_2$, =NNHC(O)R*, =NNHC(O)OR*, =NNHS(O)$_2$R*, =NR*, =NOR*, —$O(C(R^*_2))_{2-3}O$—, and —$S(C(R^*_2))_{2-3}S$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —$O(CR^*_2)_{2-3}O$—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —$NH_2$, —NHR$^•$, —NR$^•_2$, and —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted group" include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, and —N(R$^†$)S(O)$_2$R$^†$; wherein each R$^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^†$, taken together with their intervening atom(s) form an unsubstituted 3-12-membered saturated, partially unsaturated, or aryl monocyclic or bicyclic ring having 0-4 heteroatoms independently selected from nitrogen, oxygen, and sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —$NH_2$, —NHR$^•$, —NR$^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, the relevant teachings of which are incorporated herein by reference in their entirety. Pharmaceutically acceptable salts of the compounds of this invention include salts derived from suitable inorganic and organic acids and bases that are compatible with the treatment of patients.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable acid addition salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

In some embodiments, exemplary inorganic acids which form suitable salts include, but are not limited thereto, hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms.

In some embodiments, acid addition salts of the compounds of formula I are most suitably formed from pharmaceutically acceptable acids, and include, for example, those formed with inorganic acids, e.g., hydrochloric, sulfuric or phosphoric acids and organic acids e.g. succinic, maleic, acetic or fumaric acid.

Other non-pharmaceutically acceptable salts, e.g., oxalates can be used, for example, in the isolation of compounds of formula I for laboratory use, or for subsequent conversion to a pharmaceutically acceptable acid addition salt. Also included within the scope of the invention are base addition salts (such as sodium, potassium and ammonium salts), solvates and hydrates of compounds of the invention. The conversion of a given compound salt to a desired compound salt is achieved by applying standard techniques, well known to one skilled in the art.

A "pharmaceutically acceptable basic addition salt" is any non-toxic organic or inorganic base addition salt of the acid compounds represented by formula I, or any of its intermediates. Illustrative inorganic bases which form suitable salts include, but are not limited to, lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality, if any, elsewhere in the molecule is not hydrolyzed. The selection criteria for the appropriate salt will be known to one skilled in the art.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxyl, sulfate, phosphate, nitrate, lower alkyl sulfonate and aryl sulfonate.

Pharmaceutically acceptable salts include $(C_1-C_6)$alkylhalide salts. A $(C_1-C_6)$alkylhalide salt of a compound described herein can be formed, for example, by treating a compound of Formula II (e.g., wherein q is 0) with a $(C_1-C_6)$alkylhalide salt, thereby alkylating a nitrogen atom (e.g., the nitrogen atom beta to the group $—[C(R^{4a})(R^{4b})]_n—$ in Formula II) and forming a $(C_1-C_6)$alkylhalide salt of a compound of Formula II. Examples of $(C_1-C_6)$ alkylhalide salts include methyl iodide and ethyl iodide.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds produced by the replacement of a hydrogen with deuterium or tritium, or of a carbon with a $^{13}C-$ or $^{14}C$-enriched carbon are within the scope of this invention. Such compounds are useful, for example, as analytical tools, as probes in biological assays, or as therapeutic agents in accordance with the present invention.

The term "stereoisomers" is a general term for all isomers of an individual molecule that differ only in the orientation of their atoms in space. It includes mirror image isomers (enantiomers), geometric (cis/trans) isomers and isomers of compounds with more than one chiral center that are not mirror images of one another (diastereomers). The carbon atom at the 2-position of the dihydrobenzofuranyl moiety of the compounds described herein is a stereocenter. Accordingly, this carbon atom can have an R configuration or an S configuration. The carbon atom at the 2-position of the dihydrobenofuranyl moiety of the compound of Structural Formula II is indicated with an asterisk in the following structure:

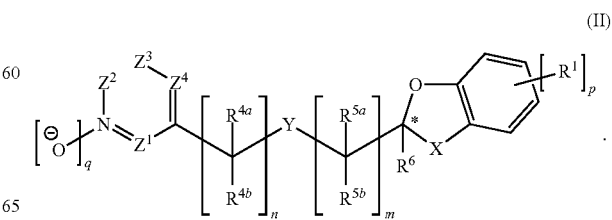

(II)

In some embodiments of the invention, the carbon atom at the 2-position of the dihydrobenzofuranyl moiety of the compounds described herein has an S configuration. In some embodiments of the invention, the carbon atom at the 2-position of the dihydrobenzofuranyl moiety of the compounds described herein has an R configuration.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of being administered to a patient. One example of such a carrier is pharmaceutically acceptable oil typically used for parenteral administration. Pharmaceutically acceptable carriers are well known in the art.

When introducing elements disclosed herein, the articles "a," "an," "the," and "said" are intended to mean that there are one or more of the elements. The terms "comprising," "having" and "including" are intended to be open-ended and mean that there may be additional elements other than the listed elements.

Compounds of the Invention

A first embodiment is a compound represented by Structural Formula I:

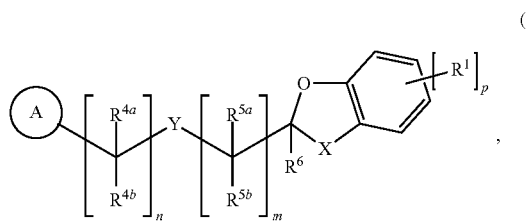

(I)

or a pharmaceutically acceptable salt thereof, wherein:
Ring A is selected from ($C_6$-$C_{12}$)aryl and ($C_5$-$C_{12}$)heteroaryl;
X is C=O, $CH_2$, $CD_2$ or CHD;
Y is selected from —N($R^9$)—$R^7$—C($R^{8a}$)($R^{8b}$)—C($R^{8c}$)($R^{8d}$)—*, —C($R^{8d}$)($R^{8c}$)—C($R^{8b}$)($R^{8a}$)—$R^7$—N($R^9$)—*, —N($R^9$)—$R^7$—C(=C$R^{8a}R^{8b}$)—*, —C(=C$R^{8a}R^{8b}$)—$R^7$—N($R^9$)—*, —N($R^9$)—$R^7$—C≡C—*, —C≡C—$R^7$—N($R^9$)—*, —N($R^9$)—$R^7$—C($R^8$)=C($R^{10}$)—* and —C($R^{10}$)=C($R^8$)—$R^7$—N($R^9$)—*, wherein "*" represents a portion of Y bound to —[C($R^{5a}$)($R^{5b}$)]$_m$—;
$R^7$ is selected from —C(O)— and —S(O)$_2$—;
each $R^8$, $R^{8a}$, $R^{8b}$, $R^{8c}$ and $R^{8c}$ is independently selected from hydrogen, CN, and ($C_1$-$C_4$)alkyl;
$R^9$ and $R^{10}$ are each independently selected from hydrogen and ($C_1$-$C_4$)alkyl;
each $R^1$ is independently selected from halo, hydroxyl, halo($C_1$-$C_4$)alkyl, ($C_1$-$C_4$)alkyl, ($C_1$-$C_4$)alkoxy, carbocyclyl, heterocyclyl, —O-carbocyclyl, —O-heterocyclyl, cyano, sulfonate, and —S(O)$_{0-2}$($C_1$-$C_4$)alkyl;
each of $R^{4a}$ and $R^{4b}$, if present, is independently selected from hydrogen, ($C_1$-$C_4$)alkyl, and ($C_3$-$C_6$)cycloalkyl;
each of $R^{5a}$ and $R^{5b}$, if present, is independently selected from hydrogen and ($C_1$-$C_4$)alkyl;
$R^6$ is hydrogen or ($C_1$-$C_3$)alkyl;
m is 0, 1 or 2;
n is 0 or 1; and
p is 0, 1, 2, 3 or 4;
wherein each aryl, heteroaryl, carbocyclyl, heterocyclyl, cycloalkyl or alkyl is optionally and independently substituted.

In a first aspect of the first embodiment, the compound of Structural Formula I is not a compound in Table 1A. The values for the remaining variables are as described for the first embodiment.

TABLE 1A

| Compound Structure | Compound Name |
|---|---|
| 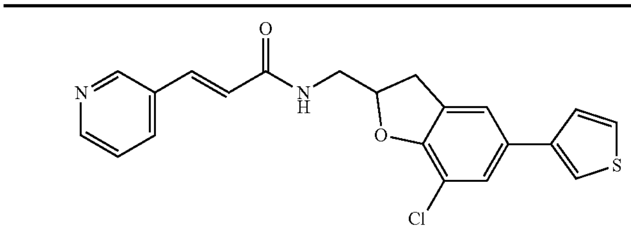 | (E)-N-((7-chloro-5-(thiophen-3-yl)-2,3-dihydrobenzofuran-2-yl)methyl)-3-(pyridin-3-yl)acrylamide |
| 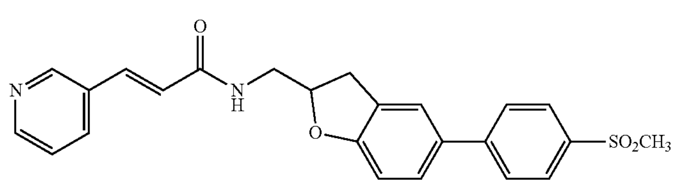 [SMILES: CS(=O)(=O)c1ccc(-c2ccc3c(c2)CC(CNC(=O)/C=C/c2cccnc2)O3)cc1] | (E)-N-((5-(4-(methylsulfonyl)phenyl)-2,3-dihydrobenzofuran-2-yl)methyl)-3-(pyridin-3-yl)acrylamide |
| 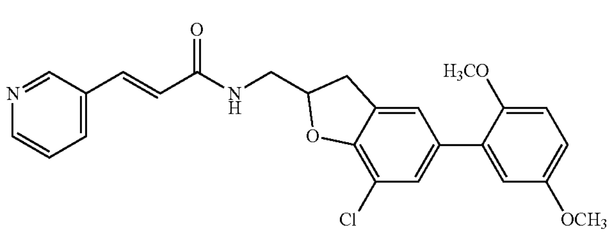 | (E)-N-((7-chloro-5-(2,5-dimethoxyphenyl)-2,3-dihydrobenzofuran-2-yl)methyl)-3-(pyridin-3-yl)acrylamide |

TABLE 1A-continued

| Compound Structure | Compound Name |
|---|---|
| 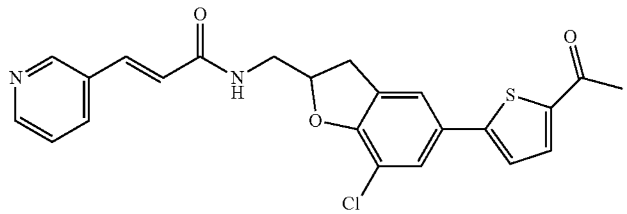 [SMILES: CC(=O)c1ccc(-c2cc(Cl)c3c(c2)CC(CNC(=O)/C=C/c2cccnc2)O3)s1] | (E)-N-((5-(5-acetylthiophen-2-yl)-7-chloro-2,3-dihydrobenzofuran-2-yl)methyl)-3-(pyridin-3-yl)acrylamide |
| 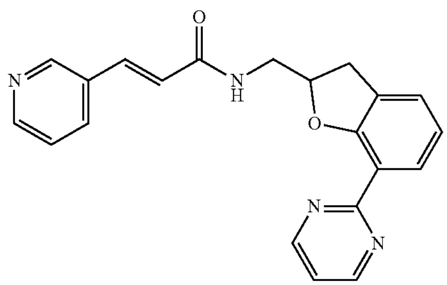 [SMILES: O=C(/C=C/c1cccnc1)NCC1Cc2cccc(-c3ncccn3)c2O1] | (E)-3-(pyridin-3-yl)-N-((7-(pyrimidin-2-yl)-2,3-dihydrobenzofuran-2-yl)methyl)acrylamide |
| 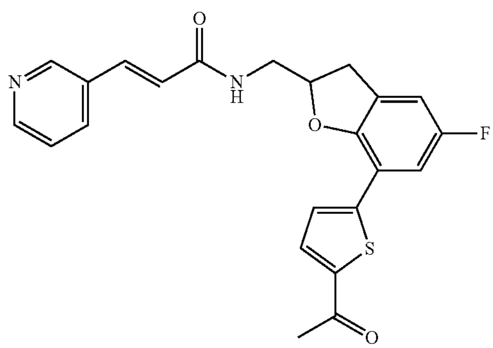 [SMILES: CC(=O)c1ccc(-c2cc(F)cc3c2OC(CNC(=O)/C=C/c2cccnc2)C3)s1] | (E)-N-((7-(5-acetylthiophen-2-yl)-5-fluoro-2,3-dihydrobenzofuran-2-yl)methyl)-3-(pyridin-3-yl)acrylamide |
| 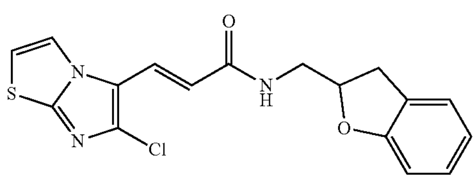 [SMILES: O=C(/C=C/c1c(Cl)nc2sccn12)NCC1Cc2ccccc2O1] | (E)-3-(6-chloroimidazo[2,1-b]thiazol-5-yl)-N-((2,3-dihydrobenzofuran-2-yl)methyl)acrylamide |
| 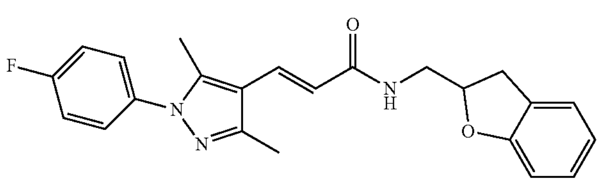 [SMILES: Cc1nn(-c2ccc(F)cc2)c(C)c1/C=C/C(=O)NCC1Cc2ccccc2O1] | (E)-N-((2,3-dihydrobenzofuran-2-yl)methyl)-3-(1-(4-fluorophenyl)-3,5-dimethyl-1H-pyrazol-4-yl)acrylamide |
| 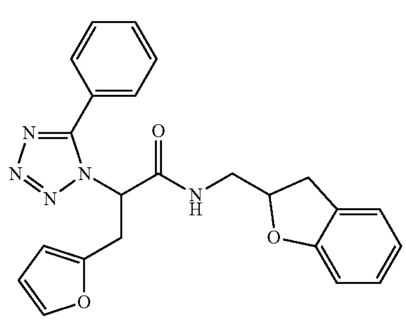 [SMILES: O=C(NCC1Cc2ccccc2O1)C(Cc1ccco1)n1nnnc1-c1ccccc1] | (Z)-N-((2,3-dihydrobenzofuran-2-yl)methyl)-3-(furan-2-yl)-2-(5-phenyl-1H-tetrazol-1-yl)acrylamide |

TABLE 1A-continued

| Compound Structure | Compound Name |
|---|---|
| 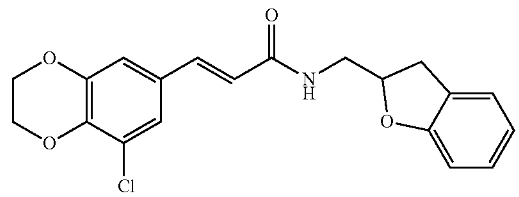 [SMILES: O=C(/C=C/c1cc(Cl)c2c(c1)OCCO2)NCC1Cc2ccccc2O1] | (E)-3-(8-chloro-2,3-dihydrobenzo[b][1,4]dioxin-6-yl)-N-((2,3-dihydrobenzofuran-2-yl)methyl)acrylamide |
| 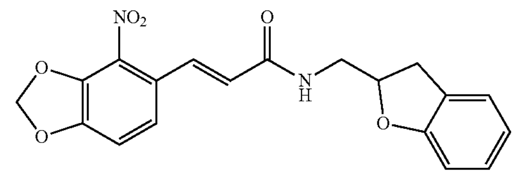 [SMILES: O=C(/C=C/c1ccc2c(c1[N+](=O)[O-])OCO2)NCC1Cc2ccccc2O1] | (E)-N-((2,3-dihydrobenzofuran-2-yl)methyl)-3-(4-nitrobenzo[d][1,3]dioxol-5-yl)acrylamide |
| 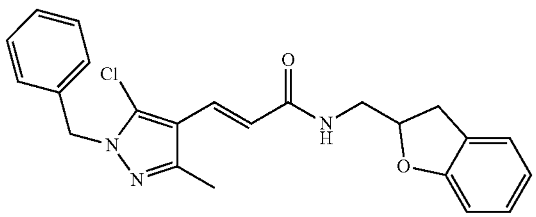 [SMILES: Cc1nn(Cc2ccccc2)c(Cl)c1/C=C/C(=O)NCC1Cc2ccccc2O1] | (E)-3-(1-benzyl-5-chloro-3-methyl-1H-pyrazol-4-yl)-N-((2,3-dihydrobenzofuran-2-yl)methyl)acrylamide |
| 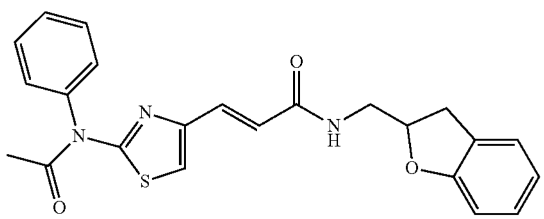 [SMILES: CC(=O)N(c1ccccc1)c1nc(/C=C/C(=O)NCC2Cc3ccccc3O2)cs1] | (E)-N-((2,3-dihydrobenzofuran-2-yl)methyl)-3-(2-(N-phenylacetamido)thiazol-4-yl)acrylamide |
| 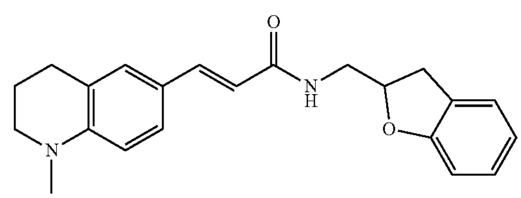 [SMILES: CN1CCCc2cc(/C=C/C(=O)NCC3Cc4ccccc4O3)ccc21] | (E)-N-((2,3-dihydrobenzofuran-2-yl)methyl)-3-(1-methyl-1,2,3,4-tetrahydroquinolin-6-yl)acrylamide |
| 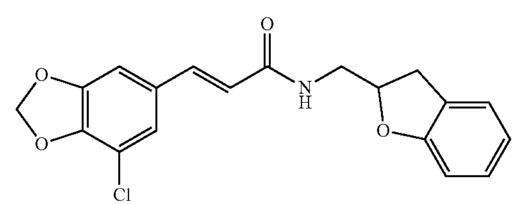 [SMILES: O=C(/C=C/c1cc(Cl)c2c(c1)OCO2)NCC1Cc2ccccc2O1] | (E)-3-(7-chlorobenzo[d][1,3]dioxol-5-yl)-N-((2,3-dihydrobenzofuran-2-yl)methyl)acrylamide |
| 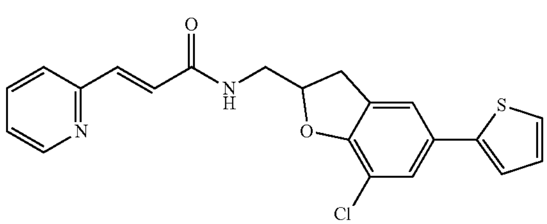 [SMILES: O=C(/C=C/c1ccccn1)NCC1Cc2cc(-c3cccs3)cc(Cl)c2O1] | (E)-N-((7-chloro-5-(thiophen-2-yl)-2,3-dihydrobenzofuran-2-yl)methyl)-3-(pyridin-2-yl)acrylamide |

TABLE 1A-continued

| Compound Structure | Compound Name |
|---|---|
| 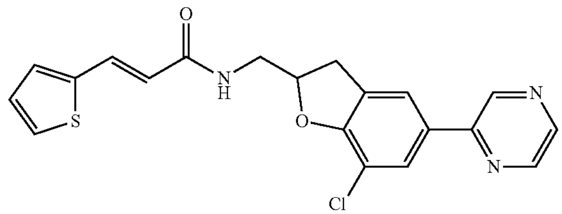 | (E)-N-((7-chloro-5-(pyrazin-2-yl)-2,3-dihydrobenzofuran-2-yl)methyl)-3-(thiophen-2-yl)acrylamide |
| 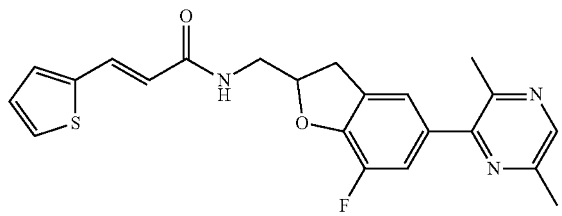 [SMILES: Cc1cnc(C)c(-c2cc(F)c3c(c2)CC(CNC(=O)/C=C/c2cccs2)O3)n1] | (E)-N-((5-(3,6-dimethylpyrazin-2-yl)-7-fluoro-2,3-dihydrobenzofuran-2-yl)methyl)-3-(thiophen-2-yl)acrylamide |
| 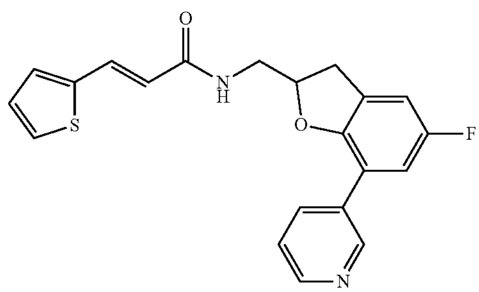 [SMILES: O=C(/C=C/c1cccs1)NCC1Cc2cc(F)cc(-c3cccnc3)c2O1] | (E)-N-((5-fluoro-7-(pyridin-3-yl)-2,3-dihydrobenzofuran-2-yl)methyl)-3-(thiophen-2-yl)acrylamide |
| 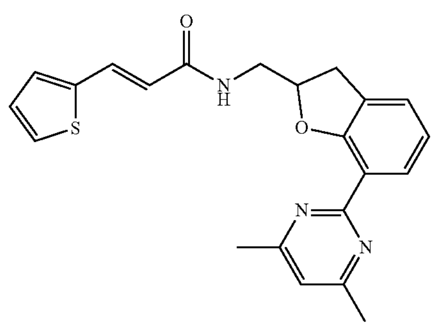 [SMILES: Cc1cc(C)nc(-c2cccc3c2OC(CNC(=O)/C=C/c2cccs2)C3)n1] | (E)-N-((7-(4,6-dimethylpyrimidin-2-yl)-2,3-dihydrobenzofuran-2-yl)methyl)-3-(thiophen-2-yl)acrylamide |
| 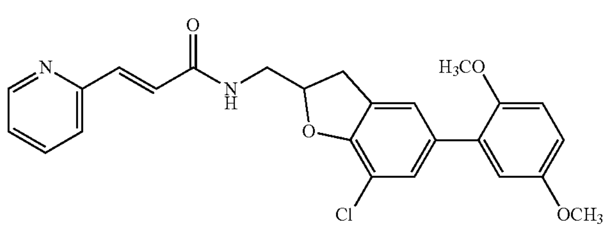 [SMILES: COc1ccc(OC)c(-c2cc(Cl)c3c(c2)CC(CNC(=O)/C=C/c2ccccn2)O3)c1] | (E)-N-((7-chloro-5-(2,5-dimethoxyphenyl)-2,3-dihydrobenzofuran-2-yl)methyl)-3-(pyridin-2-yl)acrylamide |
| 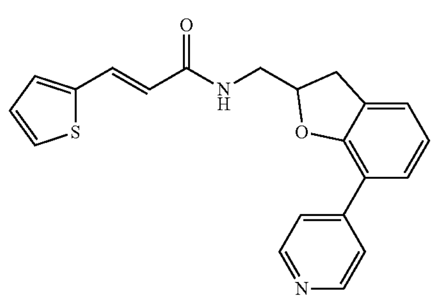 [SMILES: O=C(/C=C/c1cccs1)NCC1Cc2cccc(-c3ccncc3)c2O1] | (E)-N-((7-(pyridin-4-yl)-2,3-dihydrobenzofuran-2-yl)methyl)-3-(thiophen-2-yl)acrylamide |

TABLE 1A-continued

| Compound Structure | Compound Name |
| --- | --- |
| 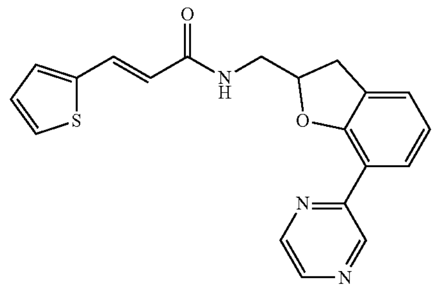 [SMILES: O=C(/C=C/c1cccs1)NCC1Cc2cccc(-c3cnccn3)c2O1] | (E)-N-((7-(pyrazin-2-yl)-2,3-dihydrobenzofuran-2-yl)methyl)-3-(thiophen-2-yl)acrylamide |
| 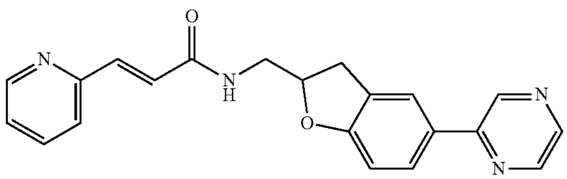 [SMILES: O=C(/C=C/c1ccccn1)NCC1Cc2cc(-c3cnccn3)ccc2O1] | (E)-N-((5-(pyrazin-2-yl)-2,3-dihydrobenzofuran-2-yl)methyl)-3-(pyridin-2-yl)acrylamide |
| 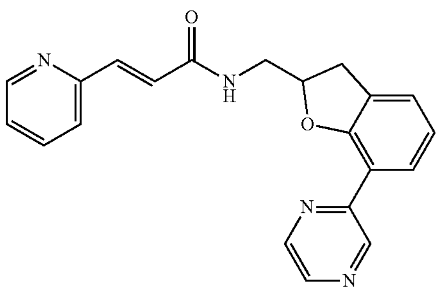 [SMILES: O=C(/C=C/c1ccccn1)NCC1Cc2cccc(-c3cnccn3)c2O1] | (E)-3-(pyridin-2-yl)-N-((7-(pyrimidin-2-yl)-2,3-dihydrobenzofuran-2-yl)methyl)acrylamide |
| 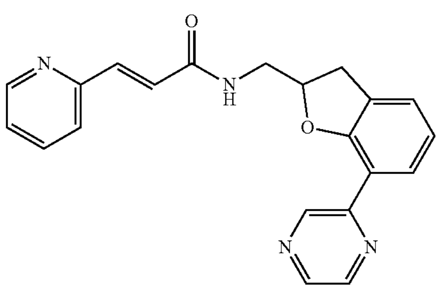 [SMILES: O=C(/C=C/c1ccccn1)NCC1Cc2cccc(-c3cnccn3)c2O1] | (E)-N-((7-(pyrazin-2-yl)-2,3-dihydrobenzofuran-2-yl)methyl)-3-(pyridin-2-yl)acrylamide |
| 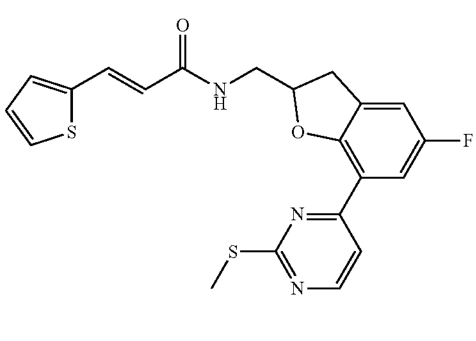 [SMILES: CSc1nccc(-c2cc(F)cc3c2OC(CNC(=O)/C=C/c2cccs2)C3)n1] | (E)-N-((5-fluoro-7-(2-(methylthio)pyrimidin-4-yl)-2,3-dihydrobenzofuran-2-yl)methyl)-3-(thiophen-2-yl)acrylamide |

TABLE 1A-continued

| Compound Structure | Compound Name |
|---|---|
| 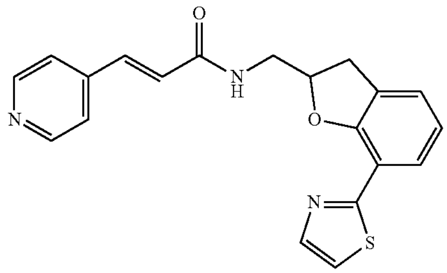 [SMILES: O=C(/C=C/c1ccncc1)NCC1Cc2cccc(-c3nccs3)c2O1] | (E)-3-(pyridin-4-yl)-N-((7-(thiazol-2-yl)-2,3-dihydrobenzofuran-2-yl)methyl)acrylamide |
| 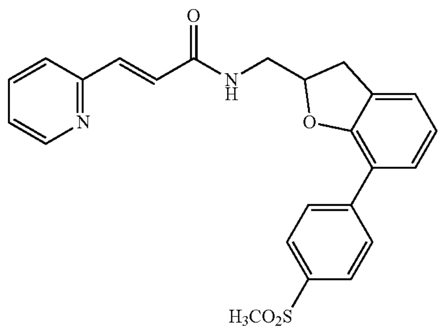 | (E)-N-((7-(4-(methylsulfonyl)phenyl)-2,3-dihydrobenzofuran-2-yl)methyl)-3-(pyridin-2-yl)acrylamide |
| 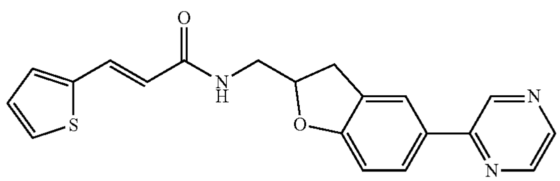 [SMILES: O=C(/C=C/c1cccs1)NCC1Cc2cc(-c3cnccn3)ccc2O1] | (E)-N-((5-(pyrazin-2-yl)-2,3-dihydrobenzofuran-2-yl)methyl)-3-(thiophen-2-yl)acrylamide |
| 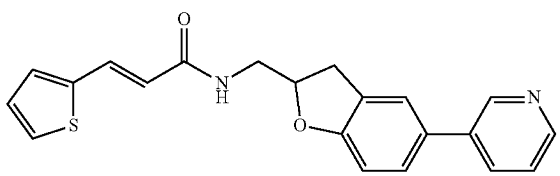 [SMILES: O=C(/C=C/c1cccs1)NCC1Cc2cc(-c3cccnc3)ccc2O1] | (E)-N-((5-(pyridin-3-yl)-2,3-dihydrobenzofuran-2-yl)methyl)-3-(thiophen-2-yl)acrylamide |
| 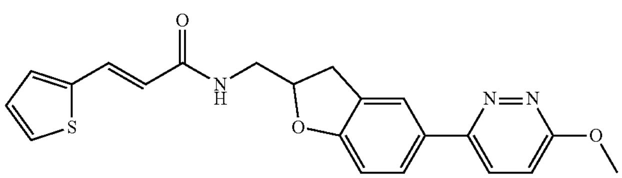 [SMILES: COc1ccc(-c2ccc3c(c2)CC(CNC(=O)/C=C/c2cccs2)O3)nn1] | (E)-N-((5-(6-methoxypyridazin-3-yl)-2,3-dihydrobenzofuran-2-yl)methyl)-3-(thiophen-2-yl)acrylamide |
| 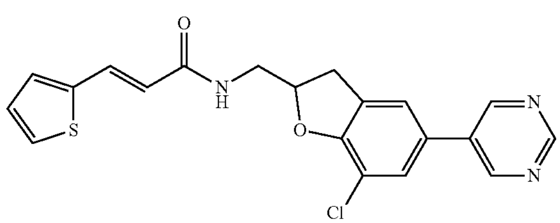 [SMILES: O=C(/C=C/c1cccs1)NCC1Cc2cc(-c3cncnc3)cc(Cl)c2O1] | (E)-N-((7-chloro-5-(pyrimidin-5-yl)-2,3-dihydrobenzofuran-2-yl)methyl)-3-(thiophen-2-yl)acrylamide |
| 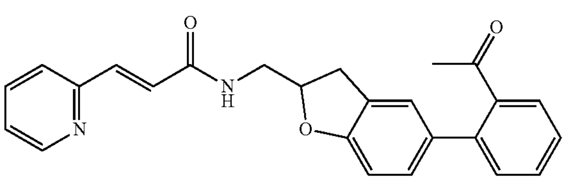 [SMILES: CC(=O)c1ccccc1-c1ccc2c(c1)CC(CNC(=O)/C=C/c1ccccn1)O2] | (E)-N-((5-(2-acetylphenyl)-2,3-dihydrobenzofuran-2-yl)methyl)-3-(pyridin-2-yl)acrylamide |

TABLE 1A-continued

| Compound Structure | Compound Name |
| --- | --- |
| 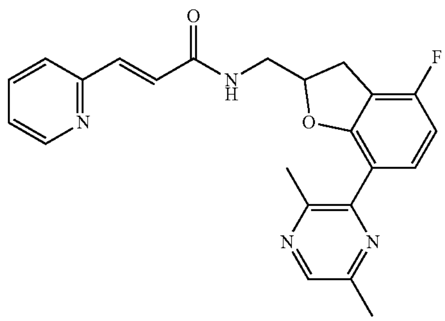 [SMILES: Cc1cnc(C)c(-c2ccc(F)c3c2OC(CNC(=O)/C=C/c2ccccn2)C3)n1] | (E)-N-((7-(3,6-dimethylpyrazin-2-yl)-4-fluoro-2,3-dihydrobenzofuran-2-yl)methyl)-3-(pyridin-2-yl)acrylamide |
| 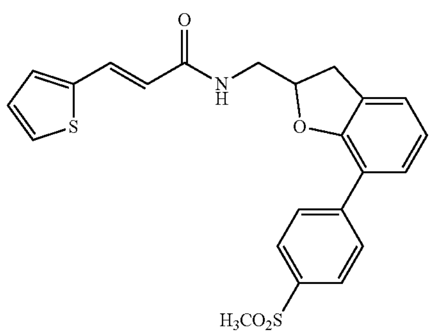 | (E)-N-((7-(4-(methylsulfonyl)phenyl)-2,3-dihydrobenzofuran-2-yl)methyl)-3-(thiophen-2-yl)acrylamide |
| 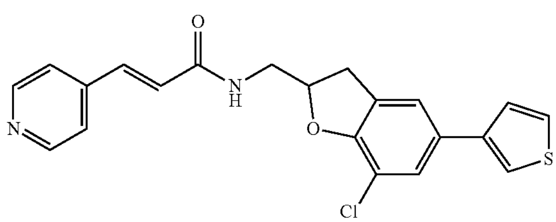 [SMILES: O=C(/C=C/c1ccncc1)NCC1Cc2cc(-c3ccsc3)cc(Cl)c2O1] | (E)-N-((7-chloro-5-(thiophen-3-yl)-2,3-dihydrobenzofuran-2-yl)methyl)-3-(pyridin-4-yl)acrylamide |
| 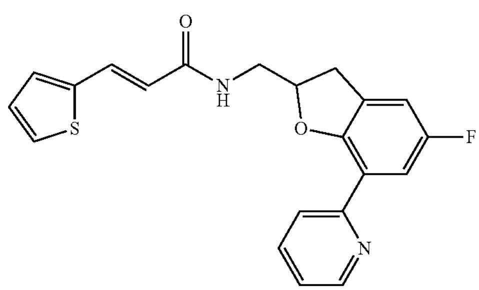 [SMILES: O=C(/C=C/c1cccs1)NCC1Cc2cc(F)cc(-c3ccccn3)c2O1] | (E)-N-((5-fluoro-7-(pyridin-2-yl)-2,3-dihydrobenzofuran-2-yl)methyl)-3-(thiophen-2-yl)acrylamide |
| 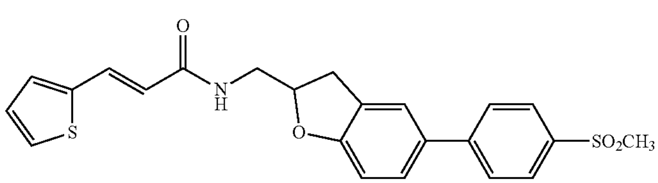 [SMILES: CS(=O)(=O)c1ccc(-c2ccc3c(c2)CC(CNC(=O)/C=C/c2cccs2)O3)cc1] | (E)-N-((5-(4-(methylsulfonyl)phenyl)-2,3-dihydrobenzofuran-2-yl)methyl)-3-(thiophen-2-yl)acrylamide |

TABLE 1A-continued

| Compound Structure | Compound Name |
| --- | --- |
| 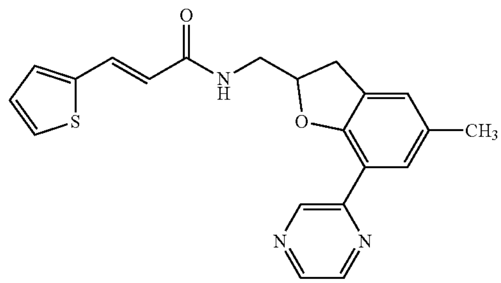 [SMILES: Cc1cc2c(c(-c3cnccn3)c1)OC(CNC(=O)/C=C/c1cccs1)C2] | (E)-N-((5-methyl-7-(pyrazin-2-yl)-2,3-dihydrobenzofuran-2-yl)methyl)-3-(thiophen-2-yl)acrylamide |
| 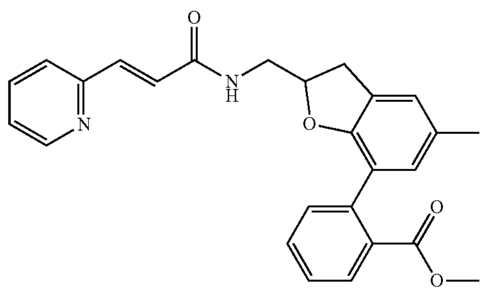 [SMILES: COC(=O)c1ccccc1-c1cc(C)cc2c1OC(CNC(=O)/C=C/c1ccccn1)C2] | (E)-methyl 2-(5-methyl-2-((3-(pyridin-2-yl)acrylamido)methyl)-2,3-dihydrobenzofuran-7-yl)benzoate |
| 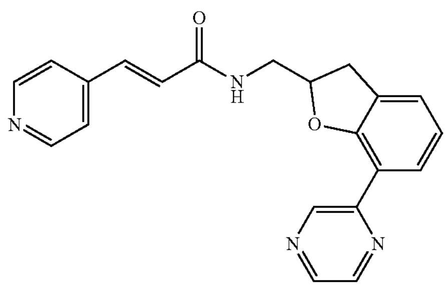 [SMILES: O=C(/C=C/c1ccncc1)NCC1Cc2cccc(-c3cnccn3)c2O1] | (E)-N-((7-(pyrazin-2-yl)-2,3-dihydrobenzofuran-2-yl)methyl)-3-(pyridin-4-yl)acrylamide |
| 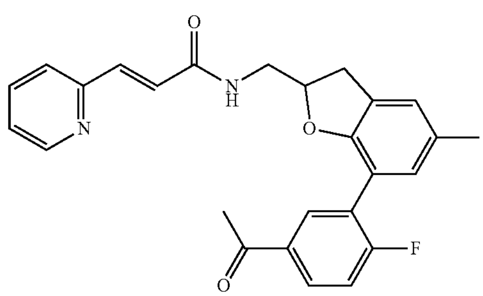 [SMILES: CC(=O)c1ccc(F)c(-c2cc(C)cc3c2OC(CNC(=O)/C=C/c2ccccn2)C3)c1] | (E)-N-((7-(5-acetyl-2-fluorophenyl)-5-methyl-2,3-dihydrobenzofuran-2-yl)methyl)-3-(pyridin-2-yl)acrylamide |
| 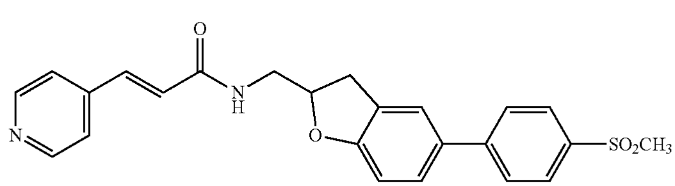 | (E)-N-((5-(4-(methylsulfonyl)phenyl)-2,3-dihydrobenzofuran-2-yl)methyl)-3-(pyridin-4-yl)acrylamide |

TABLE 1A-continued

| Compound Structure | Compound Name |
|---|---|
| 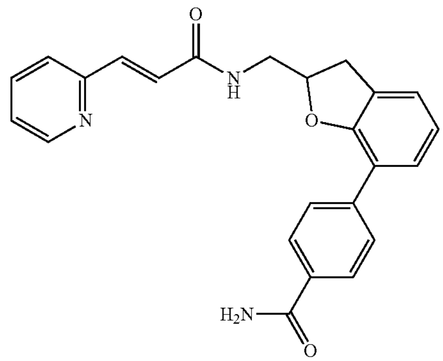 [SMILES: NC(=O)c1ccc(-c2cccc3c2OC(CNC(=O)/C=C/c2ccccn2)C3)cc1] | (E)-4-(2-((3-(pyridin-2-yl)acrylamido)methyl)-2,3-dihydrobenzofuran-7-yl)benzamide |
| 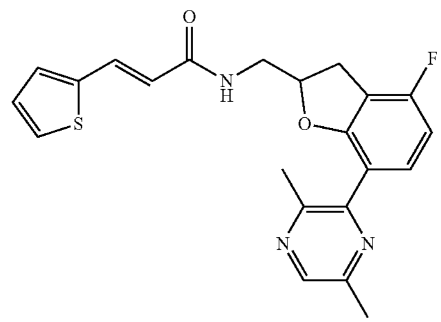 [SMILES: Cc1cnc(C)c(-c2ccc(F)c3c2OC(CNC(=O)/C=C/c2cccs2)C3)n1] | (E)-N-((7-(3,6-dimethylpyrazin-2-yl)-4-fluoro-2,3-dihydrobenzofuran-2-yl)methyl)-3-(thiophen-2-yl)acrylamide |
| 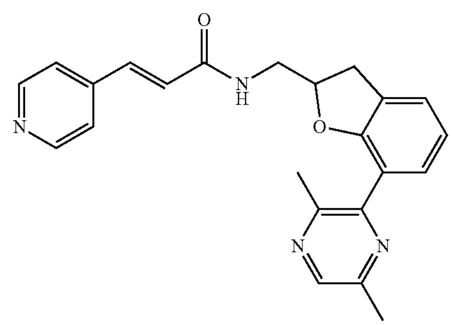 [SMILES: Cc1cnc(C)c(-c2cccc3c2OC(CNC(=O)/C=C/c2ccncc2)C3)n1] | (E)-N-((7-(3,6-dimethylpyrazin-2-yl)-2,3-dihydrobenzofuran-2-yl)methyl)-3-(pyridin-4-yl)acrylamide |
| 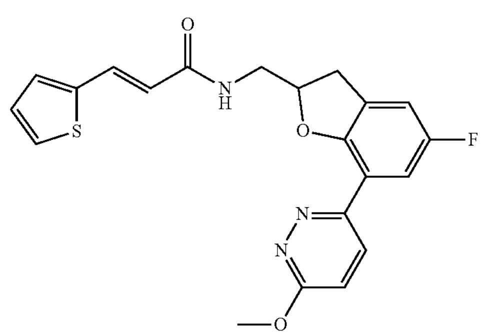 [SMILES: COc1ccc(-c2cc(F)cc3c2OC(CNC(=O)/C=C/c2cccs2)C3)nn1] | (E)-N-((5-fluoro-7-(6-methoxypyridazin-3-yl)-2,3-dihydrobenzofuran-2-yl)methyl)-3-(thiophen-2-yl)acrylamide |

TABLE 1A-continued

| Compound Structure | Compound Name |
| --- | --- |
| 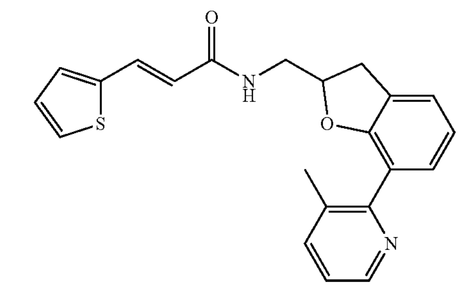 [SMILES: Cc1cccnc1-c1cccc2c1OC(CNC(=O)/C=C/c1cccs1)C2] | (E)-N-((7-(3-methylpyridin-2-yl)-2,3-dihydrobenzofuran-2-yl)methyl)-3-(thiophen-2-yl)acrylamide |
| 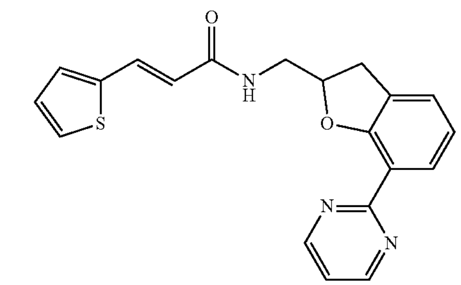 [SMILES: O=C(/C=C/c1cccs1)NCC1Cc2cccc(-c3ncccn3)c2O1] | (E)-N-((7-(pyrimidin-2-yl)-2,3-dihydrobenzofuran-2-yl)methyl)-3-(thiophen-2-yl)acrylamide |
| 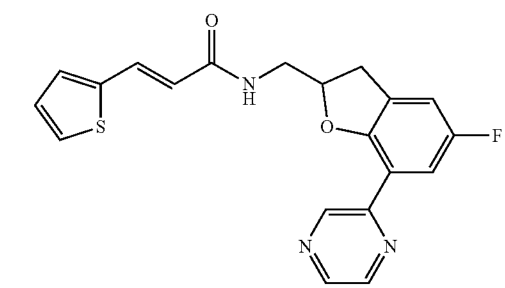 | (E)-N-((5-fluoro-7-(pyrazin-2-yl)-2,3-dihydrobenzofuran-2-yl)methyl)-3-(thiophen-2-yl)acrylamide |
| 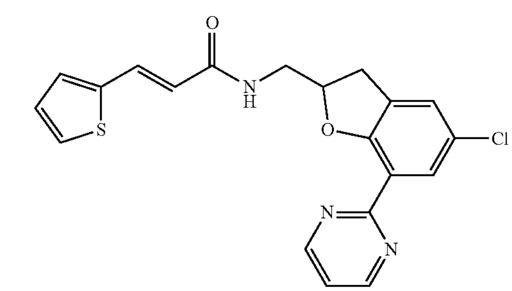 [SMILES: O=C(/C=C/c1cccs1)NCC1Cc2cc(Cl)cc(-c3ncccn3)c2O1] | (E)-N-((5-chloro-7-(pyrimidin-2-yl)-2,3-dihydrobenzofuran-2-yl)methyl)-3-(thiophen-2-yl)acrylamide |
| 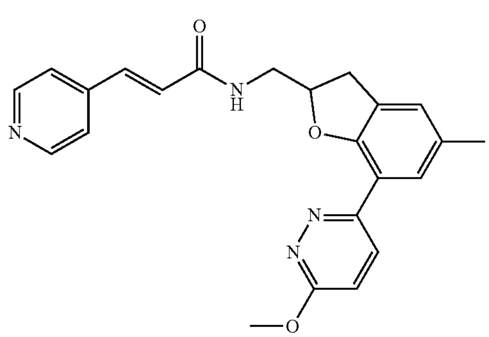 [SMILES: COc1ccc(-c2cc(C)cc3c2OC(CNC(=O)/C=C/c2ccncc2)C3)nn1] | (E)-N-((7-(6-methoxypyridazin-3-yl)-5-methyl-2,3-dihydrobenzofuran-2-yl)methyl)-3-(pyridin-4-yl)acrylamide |

TABLE 1A-continued

| Compound Structure | Compound Name |
|---|---|
| 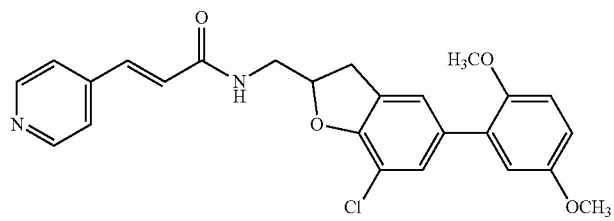 [SMILES: COc1ccc(OC)c(-c2cc(Cl)c3c(c2)CC(CNC(=O)/C=C/c2ccncc2)O3)c1] | (E)-N-((7-chloro-5-(2,5-dimethoxyphenyl)-2,3-dihydrobenzofuran-2-yl)methyl)-3-(pyridin-4-yl)acrylamide |

In a second aspect of the first embodiment, Ring A is ($C_6$-$C_{12}$)aryl. The values for the remaining variables are as described for the first embodiment, or first aspect thereof.

In a third aspect of the first embodiment, Ring A is phenyl. The values for the remaining variables are as described for the first embodiment, or first aspect thereof.

In a fourth aspect of the first embodiment, Ring A is ($C_5$-$C_{12}$)heteroaryl. The values for the remaining variables are as described for the first embodiment, or first aspect thereof.

In a fifth aspect of the first embodiment, Ring A is a fused bicyclic ($C_8$-$C_{10}$)heteroaryl. The values for the remaining variables are as described for the first embodiment, or first aspect thereof.

In a sixth aspect of the first embodiment, Ring A is selected from quinoxalinyl, 3,5-dihydroimidazo[1,2-a]pyridine-3-yl and imidazo[2,1-b]thiazol-5-yl. The values for the remaining variables are as described for the first embodiment, or first aspect thereof.

In a seventh aspect of the first embodiment, Ring A is ($C_5$-$C_6$)heteroaryl. The values for the remaining variables are as described for the first embodiment, or first aspect thereof In an eighth aspect of the first embodiment, Ring A is selected from pyridine, pyrimidine, pyrazine, pyridizine, isoxazole, thiazole, pyrazole, furan, thiophene, pyrrole, and imidazole. The values for the remaining variables are as described for the first embodiment, or first aspect thereof.

In a ninth aspect of the first embodiment, Ring A is selected from pyridine, pyrimidine, isoxazole, thiazole, pyrazole, furan, pyrrole, and imidazole. The values for the remaining variables are as described for the first embodiment, or first aspect thereof.

In a further aspect of the first embodiment, or the fifth through ninth aspects of the first embodiment, Ring A is ($C_5$-$C_{10}$)heteroaryl, contains at least one nitrogen atom, and is bound to —[C($R^{4a}$)($R^{4b}$)]$_n$— via a ring carbon atom.

In a tenth aspect of the first embodiment, $R^6$ is hydrogen. The values for the remaining variables are as described for the first embodiment, or the first through ninth aspects thereof.

In an eleventh aspect of the first embodiment, Y is —C($R^{10}$)=C($R^8$)—$R^7$—N($R^9$)—*. The values for the remaining variables are as described for the first embodiment, or the first through tenth aspects thereof.

In a twelfth aspect of the first embodiment, $R^7$ is —C(O)—. The values for the remaining variables are as described for the first embodiment, or the first through eleventh aspects thereof.

In a thirteenth aspect of the first embodiment, n is 0. The values for the remaining variables are as described for the first embodiment, or the first through twelfth aspects thereof.

In a fourteenth aspect of the first embodiment, m is 1. The values for the remaining variables are as described for the first embodiment, or the first through thirteenth aspects thereof.

In a fifteenth aspect of the first embodiment, n is 0 and m is 1. The values for the remaining variables are as described for the first embodiment, or the first through fourteenth aspects thereof.

In a sixteenth aspect of the first embodiment, $R^9$ is selected from hydrogen and methyl. The values for the remaining variables are as described for the first embodiment, or the first through fifteenth aspects thereof.

In a seventeenth aspect of the first embodiment, $R^9$ is hydrogen. The values for the remaining variables are as described for the first embodiment, or the first through sixteenth aspects thereof.

In an eighteenth aspect of the first embodiment, $R^8$ and $R^{10}$ are each hydrogen. The values for the remaining variables are as described for the first embodiment, or the first through seventeenth aspects thereof.

In a nineteenth aspect of the first embodiment, p is 0, 1 or 2. The values for the remaining variables are as described for the first embodiment, or the first through eighteenth aspects thereof.

In a twentieth aspect of the first embodiment, each $R^1$ is independently selected from halo, halo($C_1$-$C_4$)alkyl, ($C_1$-$C_4$)alkyl, carbocyclyl and heterocyclyl. The values for the remaining variables are as described for the first embodiment, or the first through nineteenth aspects thereof.

In a twenty-first aspect of the first embodiment, the carbocyclyl and heterocyclyl of $R^1$ are each optionally and independently substituted with a group selected from amino, cyano, nitro, halo, halo($C_1$-$C_4$)alkyl, ($C_1$-$C_4$)alkyl, ($C_1$-$C_4$) acyl, ($C_1$-$C_4$)alkoxy, carbocyclyl-C(O)—, heterocyclyl-C(O)—, carboxyl, ($C_1$-$C_4$)alkanoate, hydroxy($C_1$-$C_4$)alkyl, ($C_1$-$C_4$)dialkylamino, ($C_1$-$C_4$)monoalkylamino, carboxamide, and —S(O)$_{0-2}$($C_1$-$C_4$)alkyl. The values for the remaining variables are as described for the first embodiment, or the first through twentieth aspects thereof.

In a twenty-second aspect of the first embodiment, Y is selected from —N($R^9$)—$R^7$—C($R^8$)=C($R^{10}$)—* and —C($R^{10}$)=C($R^8$)—$R^7$—N($R^9$)—*; and $R^1$ is selected from halo, halo($C_1$-$C_4$)alkyl, ($C_1$-$C_4$)alkyl, carbocyclyl, heterocyclyl, cyano, sulfonate, and —S(O)$_{0-2}$($C_1$-$C_4$)alkyl. The values for the remaining variables are as described for the first embodiment, or the first through twenty-first aspects thereof.

In a twenty-third aspect of the first embodiment, the compound is represented by Structural Formula Ia:

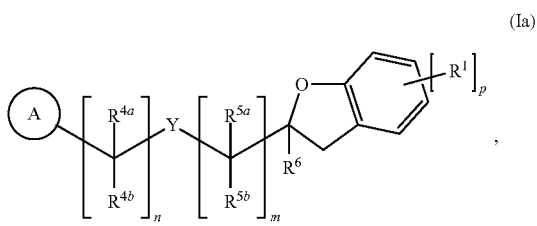

(Ia)

or a pharmaceutically acceptable salt thereof, wherein:
  Y is selected from —N($R^9$)—$R^7$—C≡C—*, —C≡C—$R^7$—N($R^9$)—*, —N($R^9$)—$R^7$—C($R^8$)=C($R^{10}$)—* and —C($R^{10}$)=C($R^8$)—$R^7$—N($R^9$)—*; and
  each $R^1$ is independently selected from halo, halo($C_1$-$C_4$)alkyl, ($C_1$-$C_4$)alkyl, carbocyclyl, heterocyclyl, —O-carbocyclyl, —O-heterocyclyl, cyano, sulfonate, and —S(O)$_{0-2}$($C_1$-$C_4$)alkyl,
  wherein each aryl, heteroaryl, carbocyclyl, heterocyclyl, or alkyl is optionally and independently substituted. The values for the remaining variables are as described for the first embodiment, of the first through twenty-second aspects thereof.

In a twenty-fourth aspect of the first embodiment, Ring A is optionally substituted with one or more substituents independently selected from the group consisting of hydrogen, amino, ($C_1$-$C_4$)alkylamino, ($C_1$-$C_4$)dialkylamino, halogen, ($C_1$-$C_4$)alkyl, ($C_1$-$C_4$)alkoxy and ($C_1$-$C_4$)haloalkyl. The values for the remaining variables are as described for the first embodiment, of the first through twenty-third aspects thereof.

In a twenty-fifth aspect of the first embodiment, Y is selected from —N($R^9$)—$R^7$—C($R^8$)=C($R^{10}$)—* and —C($R^{10}$)=C($R^8$)—$R^7$—N($R^9$)—*. The values for the remaining variables are as described for the first embodiment, of the first through twenty-fourth aspects thereof.

In a twenty-sixth aspect of the first embodiment, Y is selected from —NH—C(O)—CH=CH—* and —CH=CH—C(O)—NH—*. The values for the remaining variables are as described for the first embodiment, of the first through twenty-fifth aspects thereof.

In a twenty-seventh aspect of the first embodiment, Y is —CH=CH—C(O)—NH—*. The values for the remaining variables are as described for the first embodiment, of the first through twenty-sixth aspects thereof.

In a twenty-eighth aspect of the first embodiment, n is 1. The values for the remaining variables are as described for the first embodiment, of the first through twenty-seventh aspects thereof.

In a twenty-ninth aspect of the first embodiment, m is 0. The values for the remaining variables are as described for the first embodiment, of the first through twenty-eighth aspects thereof.

In a thirtieth aspect of the first embodiment, each of $R^{4a}$ and $R^{4b}$, if present, is hydrogen. The values for the remaining variables are as described for the first embodiment, of the first through twenty-ninth aspects thereof.

In a thirty-first aspect of the first embodiment, each of $R^{5a}$ and $R^{5b}$, if present, is hydrogen. The values for the remaining variables are as described for the first embodiment, of the first through thirtieth aspects thereof.

In a thirty-second aspect of the first embodiment, each $R^{8a}$, $R^{8b}$, $R^{8c}$ and $R^{8d}$ is hydrogen. The values for the remaining variables are as described for the first embodiment, or the first through thirty-first aspects thereof.

In a thirty-third aspect of the first embodiment, X is $CH_2$. The values for the remaining variables are as described for the first embodiment, or the first through thirty-second aspects thereof.

A second embodiment is a compound represented by Structural Formula II:

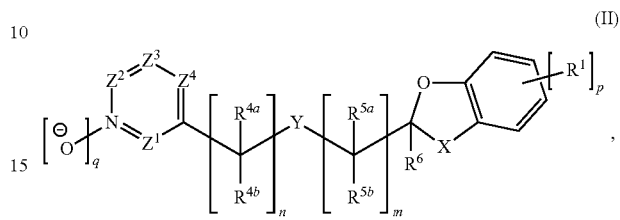

(II)

or a pharmaceutically acceptable salt thereof, wherein:
  X is C=O, $CH_2$, $CD_2$ or CHD;
  Y is selected from —N($R^9$)—$R^7$—C($R^{8a}$)($R^{8b}$)—C($R^{8c}$)($R^{8d}$)—*, —C($R^{8d}$)($R^{8c}$)—C($R^{8b}$)($R^{8a}$)—$R^7$—N($R^9$)—*, —N($R^9$)—$R^7$—C(=C$R^{8a}R^{8b}$)—*, —C(=C$R^{8a}R^{8b}$)—$R^7$—N($R^9$)—*, —N($R^9$)—$R^7$—C≡C—*, —C≡C—$R^7$—N($R^9$)—*, —N($R^9$)—$R^7$—C($R^8$)=C($R^{10}$)—* and —C($R^{10}$)=C($R^8$)—$R^7$—N($R^9$)—*, wherein "*" represents a portion of Y bound to —[C($R^{5a}$)($R^{5b}$)]$_m$—;
  $R^7$ is selected from —C(O)— and —S(O)$_2$—;
  each $R^8$, $R^{8a}$, $R^{8b}$, $R^{8c}$ and $R^{8d}$ is independently selected from hydrogen, CN, and ($C_1$-$C_4$)alkyl;
  $R^9$ and $R^{10}$ are each independently selected from hydrogen and ($C_1$-$C_4$)alkyl;
  each of $Z^1$, $Z^2$, $Z^3$ and $Z^4$ is independently selected from N and C($R^3$), wherein no more than one of $Z^1$, $Z^2$, $Z^3$ and $Z^4$ is nitrogen, and each $R^3$ is independently selected from hydrogen and a heteroaryl substituent or two $R^3$, taken together with the carbon atoms to which they are attached, form a six-membered carbocyclyl or a 5-6-membered heterocyclyl;
  each $R^1$ is independently selected from halo, hydroxyl, halo($C_1$-$C_4$)alkyl, ($C_1$-$C_4$)alkyl, ($C_1$-$C_4$)alkoxy, carbocyclyl, heterocyclyl, —O-carbocyclyl, —O-heterocyclyl, cyano, sulfonate, and —S(O)$_{0-2}$($C_1$-$C_4$)alkyl;
  each of $R^{4a}$ and $R^{4b}$, if present, is independently selected from hydrogen, ($C_1$-$C_4$)alkyl, and ($C_3$-$C_6$)cycloalkyl;
  each of $R^{5a}$ and $R^{5b}$, if present, is independently selected from hydrogen and ($C_1$-$C_4$)alkyl;
  $R^6$ is hydrogen or ($C_1$-$C_3$)alkyl;
  m is 0, 1 or 2;
  n is 0 or 1;
  p is 0, 1, 2, 3 or 4; and
  q is 0 or 1;
  wherein each carbocyclyl, heterocyclyl, cycloalkyl or alkyl is optionally and independently substituted.

In a first aspect of the second embodiment, the compound of Structural Formula (II) is not a compound in Table 1B. The values for the remaining variables are as described for the first embodiment, or any aspect thereof, or the second embodiment.

TABLE 1B

| Compound Structure | Compound Name |
|---|---|
| 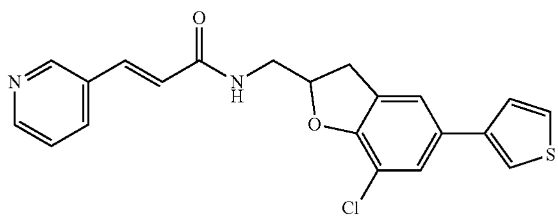 [SMILES: O=C(/C=C/c1cccnc1)NCC1Cc2cc(-c3ccsc3)cc(Cl)c2O1] | (E)-N-((7-chloro-5-(thiophen-3-yl)-2,3-dihydrobenzofuran-2-yl)methyl)-3-(pyridin-3-yl)acrylamide |
| 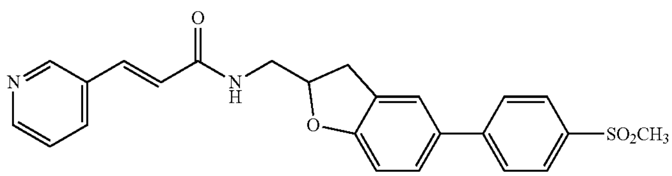 [SMILES: CS(=O)(=O)c1ccc(-c2ccc3c(c2)CC(CNC(=O)/C=C/c2cccnc2)O3)cc1] | (E)-N-((5-(4-(methylsulfonyl)phenyl)-2,3-dihydrobenzofuran-2-yl)methyl)-3-(pyridin-3-yl)acrylamide |
| 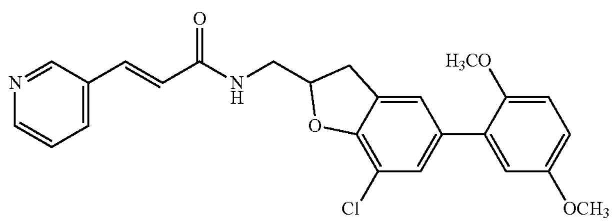 [SMILES: COc1ccc(OC)c(-c2cc(Cl)c3c(c2)CC(CNC(=O)/C=C/c2cccnc2)O3)c1] | (E)-N-((7-chloro-5-(2,5-dimethoxyphenyl)-2,3-dihydrobenzofuran-2-yl)methyl)-3-(pyridin-3-yl)acrylamide |
| 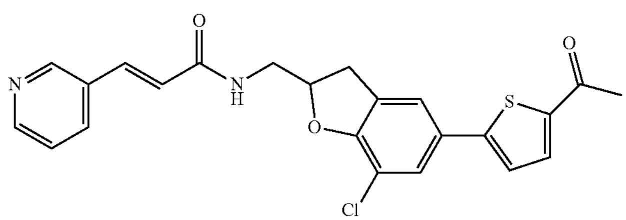 [SMILES: CC(=O)c1ccc(-c2cc(Cl)c3c(c2)CC(CNC(=O)/C=C/c2cccnc2)O3)s1] | (E)-N-((5-(5-acetylthiophen-2-yl)-7-chloro-2,3-dihydrobenzofuran-2-yl)methyl)-3-(pyridin-3-yl)acrylamide |
| 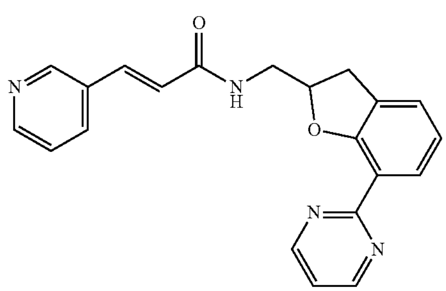 [SMILES: O=C(/C=C/c1cccnc1)NCC1Cc2cccc(-c3ncccn3)c2O1] | (E)-3-(pyridin-3-yl)-N-((7-(pyrimidin-2-yl)-2,3-dihydrobenzofuran-2-yl)methyl)acrylamide |
| 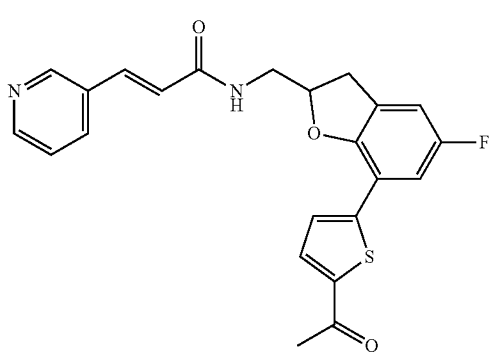 [SMILES: CC(=O)c1ccc(-c2cc(F)cc3c2OC(CNC(=O)/C=C/c2cccnc2)C3)s1] | (E)-N-((7-(5-acetylthiophen-2-yl)-5-fluoro-2,3-dihydrobenzofuran-2-yl)methyl)-3-(pyridin-3-yl)acrylamide |

In a second aspect of the second embodiment, $R^6$ is hydrogen. The values for the remaining variables are as described for the first embodiment, or any aspect thereof, or the second embodiment, or first aspect thereof.

In a third aspect of the second embodiment, the portion of the compound represented by

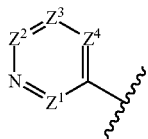

is selected from:

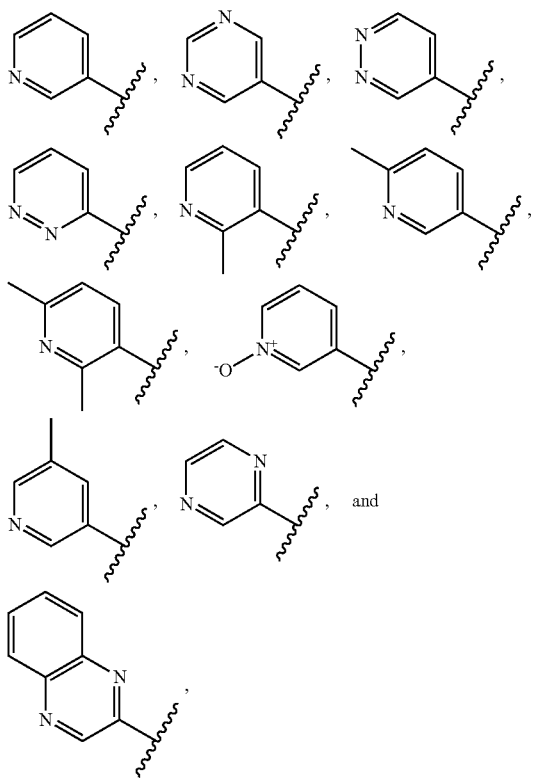

and is optionally further substituted. The values for the remaining variables are as described for the first embodiment, or any aspect thereof, or the second embodiment, or first or second aspect thereof.

In a fourth aspect of the second embodiment, each of $Z^1$, $Z^2$, $Z^3$ and $Z^4$ is CH. The values for the remaining variables are as described for the first embodiment, or any aspect thereof, or the second embodiment, or first, second, or third aspect thereof.

In a fifth aspect of the second embodiment, Y is —C($R^{10}$)=C($R^8$)—$R^7$—N($R^9$)—*. The values for the remaining variables are as described for the first embodiment, or any aspect thereof, or the second embodiment, or first, second, third, or fourth aspect thereof.

In a sixth aspect of the second embodiment, $R^7$ is —C(O)—. The values for the remaining variables are as described for the first embodiment, or any aspect thereof, or the second embodiment, or first, second, third, or fourth aspect thereof.

In a seventh aspect of the second embodiment, n is 0. The values for the remaining variables are as described for the first embodiment, or any aspect thereof, or the second embodiment, or first, second, third, fourth, or fifth aspect thereof.

In an eighth aspect of the second embodiment, m is 1. The values for the remaining variables are as described for the first embodiment, or any aspect thereof, or the second embodiment, or first, second, third, fourth, fifth, sixth, or seventh aspect thereof.

In a ninth aspect of the second embodiment, n is 0 and m is 1. The values for the remaining variables are as described for the first embodiment, or any aspect thereof, or the second embodiment, or first, second, third, fourth, fifth, sixth, seventh, or eighth aspect thereof.

In a tenth aspect of the second embodiment, $R^9$ is selected from hydrogen and methyl. The values for the remaining variables are as described for the first embodiment, or any aspect thereof, or the second embodiment, or first, second, third, fourth, fifth sixth, seventh, eighth, or ninth aspect thereof.

In an eleventh aspect of the second embodiment, $R^9$ is hydrogen. The values for the remaining variables are as described for the first embodiment, or any aspect thereof, or the second embodiment, or first, second, third, fourth, fifth sixth, seventh, eighth, ninth, or tenth aspect thereof.

In a twelfth aspect of the second embodiment, $R^8$ and $R^{10}$ are each hydrogen. The values for the remaining variables are as described for the first embodiment, or any aspect thereof, or the second embodiment, or first, second, third, fourth, fifth, sixth, seventh, eighth, ninth, tenth, or eleventh aspect thereof.

In a thirteenth aspect of the second embodiment, p is 0, 1 or 2. The values for the remaining variables are as described for the first embodiment, or any aspect thereof, or the second embodiment, or first, second, third, fourth, fifth, sixth, seventh, eighth, ninth, tenth, eleventh, or twelfth aspect thereof.

In a fourteenth aspect of the second embodiment, each $R^1$ is independently selected from halo, halo($C_1$-$C_4$)alkyl, ($C_1$-$C_4$)alkyl, carbocyclyl and heterocyclyl. The values for the remaining variables are as described for the first embodiment, or any aspect thereof, or the second embodiment, or first, second, third, fourth, fifth, sixth, seventh, eighth, ninth, tenth, eleventh, twelfth, or thirteenth aspect thereof.

In a fifteenth aspect of the second embodiment, the carbocyclyl and heterocyclyl of $R^1$ are each optionally and independently substituted with a group selected from amino, cyano, nitro, halo, halo($C_1$-$C_4$)alkyl, ($C_1$-$C_4$)alkyl, ($C_1$-$C_4$) acyl, ($C_1$-$C_4$)alkoxy, carbocyclyl-C(O)—, heterocyclyl-C(O)—, carboxyl, ($C_1$-$C_4$)alkanoate, hydroxy($C_1$-$C_4$)alkyl, ($C_1$-$C_4$)dialkylamino, ($C_1$-$C_4$)monoalkylamino, carboxamide, and —S(O)$_{0-2}$($C_1$-$C_4$)alkyl. The values for the remaining variables are as described for the first embodiment, or any aspect thereof, or the second embodiment, or first, second, third, fourth, fifth, sixth, seventh, eighth, ninth, tenth, eleventh, twelfth, thirteenth, or fourteenth aspect thereof.

In a sixteenth aspect of the second embodiment, Y is selected from —N($R^9$)—$R^7$—C($R^8$)=C($R^{10}$)—* and —C($R^{10}$)=C($R^8$)—$R^7$—N($R^9$)—*; and each $R^1$ is independently selected from halo, halo($C_1$-$C_4$)alkyl, ($C_1$-$C_4$)alkyl, carbocyclyl, heterocyclyl, cyano, sulfonate, and —S(O)$_{0-2}$($C_1$-$C_4$)alkyl. The values for the remaining variables are as described for the first embodiment, or any aspect thereof, or the second embodiment, or first through fifteenth aspects thereof.

In a seventeenth aspect of the second embodiment, the compound is represented by Formula IIa:

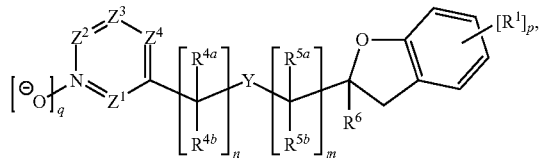
(IIa)

or a pharmaceutically acceptable salt thereof, wherein:
Y is selected from —N($R^9$)—$R^7$—C≡C—*, —C≡C—$R^7$—N($R^9$)—*, —N($R^9$)—$R^7$—C($R^8$)=C($R^{10}$)—* and —C($R^{10}$)=C($R^8$)—$R^7$—N($R^9$)—*;

each of $Z^1$, $Z^2$, $Z^3$ and $Z^4$ is independently selected from N and C($R^3$), wherein no more than one of $Z^1$, $Z^2$, $Z^3$ and $Z^4$ is nitrogen, and each $R^3$ is independently selected from hydrogen and a heteroaryl substituent; and each $R^1$ is independently selected from halo, halo($C_1$-$C_4$)alkyl, ($C_1$-$C_4$)alkyl, carbocyclyl, heterocyclyl, —O-carbocyclyl, —O-heterocyclyl, cyano, sulfonate, and —S(O)$_{0-2}$($C_1$-$C_4$)alkyl, wherein each carbocyclyl, heterocyclyl, cycloalkyl or alkyl is optionally and independently substituted. The values for the remaining variables are as described for the first embodiment, or any aspect thereof, or the second embodiment, or first through sixteenth aspects thereof.

In an eighteenth aspect of the second embodiment, each $R^3$ is independently selected from the group consisting of hydrogen, amino, ($C_1$-$C_4$)alkylamino, ($C_1$-$C_4$)dialkylamino, halogen, ($C_1$-$C_4$)alkyl, ($C_1$-$C_4$)alkoxy and ($C_1$-$C_4$)haloalkyl. The values for the remaining variables are as described for the first embodiment, or any aspect thereof, or the second embodiment, or first through seventeenth aspects thereof.

In a nineteenth aspect of the second embodiment, the portion of the compound represented by

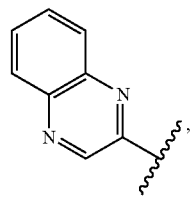

is selected from:

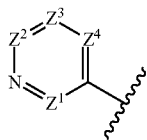

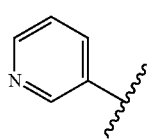

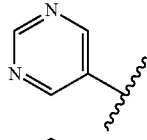

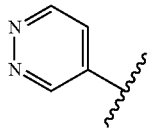

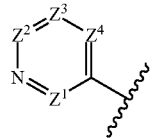

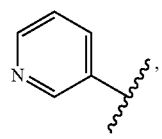 and

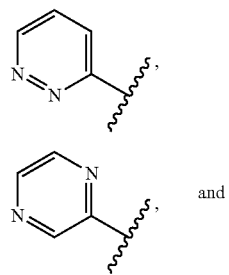

and is optionally further substituted. The values for the remaining variables are as described for the first embodiment, or any aspect thereof, or the second embodiment, or first through eighteenth aspects thereof.

In a twentieth aspect of the second embodiment, the portion of the compound represented by is selected from:

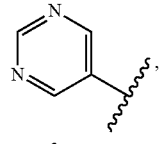

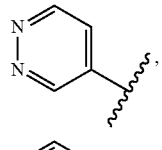

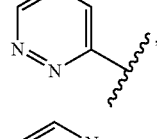

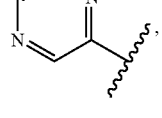 and

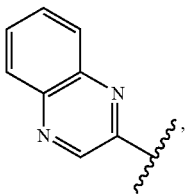

and is optionally further substituted with one or two substituents independently selected from the group consisting of hydrogen, amino, $(C_1-C_4)$alkylamino, $(C_1-C_4)$dialkylamino, halogen, $(C_1-C_4)$alkyl, $(C_1-C_4)$alkoxy and $(C_1-C_4)$haloalkyl. The values for the remaining variables are as described for the first embodiment, or any aspect thereof, or the second embodiment, or first through nineteenth aspects thereof.

In a twenty-first aspect of the second embodiment, the portion of the compound represented by

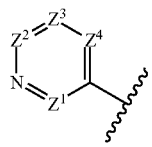

is optionally substituted pyridin-3-yl. The values for the remaining variables are as described for the first embodiment, or any aspect thereof, or the second embodiment, or first through twentieth aspects thereof.

In a twenty-second aspect of the second embodiment, the portion of the compound represented by

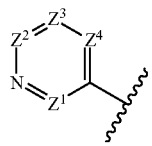

is selected from pyridin-3-yl and 4-aminopyridin-3-yl. The values for the remaining variables are as described for the first embodiment, or any aspect thereof, or the second embodiment, or first through twenty-first aspects thereof.

In a twenty-third aspect of the second embodiment, Y is selected from —N($R^9$)—$R^7$—C($R^8$)═C($R^{10}$)—* and —C($R^{10}$)═C($R^8$)—$R^7$—N($R^9$)—*. The values for the remaining variables are as described for the first embodiment, or any aspect thereof, or the second embodiment, or first through twenty-second aspects thereof.

In a twenty-fourth aspect of the second embodiment, Y is selected from —NH—C(O)—CH═CH—* and —CH═CH—C(O)—NH—*. The values for the remaining variables are as described for the first embodiment, or any aspect thereof, or the second embodiment, or first through twenty-third aspects thereof.

In a twenty-fifth aspect of the second embodiment, Y is —CH═CH—C(O)—NH—*. The values for the remaining variables are as described for the first embodiment, or any aspect thereof, or the second embodiment, or first through twenty-fourth aspects thereof.

In a twenty-sixth aspect of the second embodiment, n is 1. The values for the remaining variables are as described for the first embodiment, or any aspect thereof, or the second embodiment, or first through twenty-fifth aspects thereof.

In a twenty-seventh aspect of the second embodiment, m is 0. The values for the remaining variables are as described for the first embodiment, or any aspect thereof, or the second embodiment, or first through twenty-sixth aspects thereof.

In a twenty-eighth aspect of the second embodiment, each of $R^{4a}$ and $R^{4b}$, if present, is hydrogen. The values for the remaining variables are as described for the first embodiment, or any aspect thereof, or the second embodiment, or first through twenty-seventh aspects thereof.

In a twenty-ninth aspect of the second embodiment, each of $R^{5a}$ and $R^{5b}$, if present, is hydrogen. The values for the remaining variables are as described for the first embodiment, or any aspect thereof, or the second embodiment, or first through twenty-eighth aspects thereof.

In a thirtieth aspect of the second embodiment, q is 0. The values for the remaining variables are as described for the first embodiment, or any aspect thereof, or the second embodiment, or first through twenty-ninth aspects thereof.

In a thirty-first aspect of the second embodiment, each $R^{8a}$, $R^{8b}$, $R^{8c}$ and $R^{8d}$ is hydrogen. The values for the remaining variables are as described for the first embodiment, or any aspect thereof, or the second embodiment, or first through thirtieth aspects thereof.

In a thirty-second aspect of the second embodiment, Y is —NH—C(O)—CH═CH—*. The values for the remaining variables are as described for the first embodiment, or any aspect thereof, or the second embodiment, or first through thirty-first aspects thereof.

A third embodiment is a compound represented by Structural Formula III:

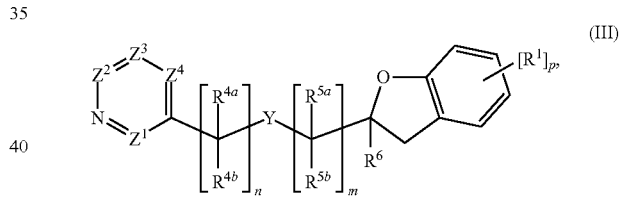

(III)

or a pharmaceutically acceptable salt thereof, wherein the values for the variables are as described in the first or second embodiment, or any aspect thereof.

In a first aspect of the third embodiment, the compound is represented by Structural Formula IIIa:

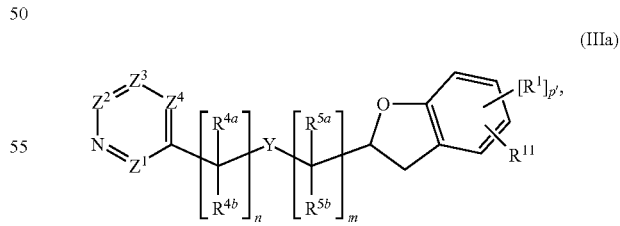

(IIIa)

or a pharmaceutically acceptable salt thereof, wherein:
each $R^1$ is independently selected from halo, hydroxyl, halo$(C_1-C_4)$alkyl, $(C_1-C_4)$alkyl and $(C_1-C_4)$alkoxy;
$R^{11}$ is optionally substituted carbocyclyl or optionally substituted heterocyclyl; and
p' is 0, 1, 2 or 3. The values for the remaining variables are as described for the first or second embodiment, or any aspect of the foregoing, or the third embodiment.

In a second aspect of the third embodiment, each $R^1$, if present, is independently selected from halo and halo($C_1$-$C_4$)alkyl. The values for the remaining variables are as described for the first or second embodiment, or any aspect of the foregoing, or the third embodiment, or first aspect thereof.

In a third aspect of the third embodiment, each $R^1$, if present, is independently selected from fluoro, chloro, —$CF_3$ and —$CHF_2$. The values for the remaining variables are as described for the first or second embodiment, or any aspect of the foregoing, or the third embodiment, or first or second aspect thereof.

In a fourth aspect of the third embodiment, p' is 0 or 1. The values for the remaining variables are as described for the first or second embodiment, or any aspect of the foregoing, or the third embodiment, or first through third aspects thereof.

In a fifth aspect of the third embodiment, p' is 1. The values for the remaining variables are as described for the first or second embodiment, or any aspect of the foregoing, or the third embodiment, or first through fourth aspects thereof.

In a sixth aspect of the third embodiment, $R^{11}$ is optionally substituted aryl or optionally substituted heteroaryl. The values for the remaining variables are as described for the first or second embodiment, or any aspect of the foregoing, or the third embodiment, or first through fifth aspects thereof.

In a seventh aspect of the third embodiment, $R^{11}$ is optionally and independently substituted with 1, 2 or 3 optional substituents and is phenyl or a 5-6-membered heteroaryl having 1, 2 or 3 heteroatoms selected from nitrogen, oxygen and sulfur. The values for the remaining variables are as described for the first or second embodiment, or any aspect of the foregoing, or the third embodiment, or first through sixth aspects thereof.

In an eighth aspect of the third embodiment, $R^{11}$ is substituted with one, two or three substituents independently selected from halogen, ($C_1$-$C_4$)alkyl optionally substituted with hydroxyl, ($C_2$-$C_4$)alkenyl, ($C_1$-$C_4$)alkoxy, ($C_1$-$C_4$)haloalkyl, —C(O)($C_1$-$C_4$)alkyl, —C(O)O($C_1$-$C_4$)alkyl, —$CO_2$H, amino, ($C_1$-$C_4$)alkylamino, ($C_1$-$C_4$)dialkylamino, —$SO_2$($C_1$-$C_4$)alkyl, —C(O)($C_3$-$C_7$)carbocyclyl, phenyl, —C(O)$NR^{12}R^{13}$ and —S(O)$_2NR^{12}R^{13}$, wherein:

$R^{12}$ and $R^{13}$ are each independently hydrogen, $C_1$-$C_4$ alkyl, optionally substituted carbocyclyl, or optionally substituted heterocyclyl; or $R^{12}$ and $R^{13}$ are taken together with the nitrogen atom to which they are commonly attached to form an optionally substituted saturated heterocyclyl.

The values for the remaining variables are as described for the first or second embodiment, or any aspect of the foregoing, or the third embodiment, or first through seventh aspects thereof.

In a ninth aspect of the third embodiment, $R^{11}$ is substituted with one substituent selected from halogen; ($C_1$-$C_4$) alkyl optionally substituted with hydroxyl; ($C_2$-$C_4$)alkenyl; ($C_1$-$C_4$)haloalkyl; —C(O)($C_1$-$C_4$)alkyl; —C(O)O($C_1$-$C_4$) alkyl; —C(O)($C_3$-$C_7$)carbocyclyl; phenyl; —C(O)$NR^{12}R^{13}$, wherein $R^{12}$ and $R^{13}$ are each methyl, or $R^{12}$ and $R^{13}$ are taken together with the nitrogen atom to which they are commonly attached to form an optionally substituted saturated ($C_3$-$C_7$)heterocyclyl; and —S(O)$_2NR^{12}R^{13}$, wherein $R^{12}$ and $R^{13}$ are taken together with the nitrogen atom to which they are commonly attached to form an optionally substituted saturated ($C_3$-$C_7$)heterocyclyl, and is further optionally substituted with one substituent selected from halogen, ($C_1$-$C_4$)alkyl and ($C_1$-$C_4$)haloalkyl. The values for the remaining variables are as described for the first or second embodiment, or any aspect of the foregoing, or the third embodiment, or first through eighth aspects thereof.

In a tenth aspect of the third embodiment, $R^{11}$ is selected from phenyl, thiophenyl, pyridinyl, pyrimidinyl, isoxazolyl, furanyl, pyridazinyl and oxadiazolyl, and is substituted with 1, 2 or 3 independently selected substituents. The values for the remaining variables are as described for the first or second embodiment, or any aspect of the foregoing, or the third embodiment, or first through ninth aspects thereof.

In an eleventh aspect of the third embodiment, the saturated heterocyclyl formed by $R^{12}$ and $R^{13}$ together with the nitrogen atom to which they are attached is optionally substituted with 1 or 2 substituents independently selected from halogen, ($C_1$-$C_4$)alkyl and ($C_1$-$C_4$)haloalkyl. The values for the remaining variables are as described for the first or second embodiment, or any aspect of the foregoing, or the third embodiment, or first through tenth aspects thereof.

In a twelfth aspect of the third embodiment, $R^{11}$ is substituted with one, two or three substituents independently selected from halogen, ($C_1$-$C_4$)alkyl optionally substituted with hydroxyl, ($C_2$-$C_4$)alkenyl, ($C_1$-$C_4$)alkoxy, ($C_1$-$C_4$)haloalkyl, —C(O)($C_1$-$C_4$)alkyl, —C(O)O($C_1$-$C_4$)alkyl, —$CO_2$H, amino, ($C_1$-$C_4$)alkylamino, ($C_1$-$C_4$)dialkylamino, —$SO_2$($C_1$-$C_4$)alkyl, —C(O)($CH_2$)$_{0-1}$($C_3$-$C_7$)carbocyclyl, phenyl, —C(O)($CH_2$)$_{0-1}NR^{12}R^{13}$ and —S(O)$_2NR^{12}R^{13}$, wherein:

$R^{12}$ and $R^{13}$ are each independently hydrogen, $C_1$-$C_4$ alkyl, optionally substituted carbocyclyl, or optionally substituted heterocyclyl; or $R^{12}$ and $R^{13}$ are taken together with the nitrogen atom to which they are commonly attached to form an optionally substituted saturated heterocyclyl.

The values for the remaining variables are as described for the first or second embodiment, or any aspect of the foregoing, or the third embodiment, or first through eleventh aspects thereof.

In a thirteenth aspect of the third embodiment, $R^{11}$ is substituted with a first substituent selected from halogen; ($C_1$-$C_4$)alkyl optionally substituted with hydroxyl; ($C_2$-$C_4$) alkenyl; ($C_1$-$C_4$)haloalkyl; —C(O)($C_1$-$C_4$)alkyl; —C(O)O ($C_1$-$C_4$)alkyl; —C(O)($CH_2$)$_{0-1}$($C_3$-$C_7$)carbocyclyl; phenyl; —C(O)($CH_2$)$_{0-1}NR^{12}R^{13}$, wherein $R^{12}$ and $R^{13}$ are each methyl, or $R^{12}$ and $R^{13}$ are taken together with the nitrogen atom to which they are commonly attached to form an optionally substituted saturated ($C_3$-$C_7$)heterocyclyl; and —S(O)$_2NR^{12}R^{13}$, wherein $R^{12}$ and $R^{13}$ are taken together with the nitrogen atom to which they are commonly attached to form an optionally substituted saturated ($C_3$-$C_7$)heterocyclyl, and a second substituent selected from halogen, ($C_1$-$C_4$)alkyl and ($C_1$-$C_4$)haloalkyl. The values for the remaining variables are as described for the first or second embodiment, or any aspect of the foregoing, or the third embodiment, or first through twelfth aspects thereof.

In a fourteenth aspect of the third embodiment, $R^{11}$ is substituted with one substituent selected from halogen; ($C_1$-$C_4$)alkyl optionally substituted with hydroxyl; ($C_2$-$C_4$) alkenyl; ($C_1$-$C_4$)haloalkyl; —C(O)($C_1$-$C_4$)alkyl; —C(O)O ($C_1$-$C_4$)alkyl; —C(O)($CH_2$)$_{0-1}$($C_3$-$C_7$)carbocyclyl; phenyl; —C(O)($CH_2$)$_{0-1}NR^{12}R^{13}$, wherein $R^{12}$ and $R^{13}$ are each methyl, or $R^{12}$ and $R^{13}$ are taken together with the nitrogen atom to which they are commonly attached to form an optionally substituted saturated ($C_3$-$C_7$)heterocyclyl; and —S(O)$_2NR^{12}R^{13}$, wherein $R^{12}$ and $R^{13}$ are taken together with the nitrogen atom to which they are commonly attached to form an optionally substituted saturated ($C_3$-$C_7$)heterocyclyl. The values for the remaining variables are as described for the first or second embodiment, or any aspect of the foregoing, or the third embodiment, or first through thirteenth aspects thereof.

A fourth embodiment is a compound of Structural Formula IV:

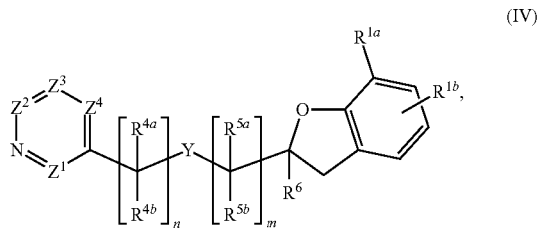

(IV)

or a pharmaceutically acceptable salt thereof, wherein $R^{1a}$ and $R^{1b}$ are each independently selected from hydrogen, halo, halo($C_1$-$C_4$)alkyl, ($C_1$-$C_4$)alkyl, carbocyclyl, heterocyclyl, cyano, sulfonate, and —S(O)$_{0-2}$($C_1$-$C_4$)alkyl; and the values for the remaining variables are as described for the first through third embodiments, or any aspect thereof.

In a first aspect of the fourth embodiment, $R^{1a}$ is selected from hydrogen, chloro, fluoro, and methyl. The values for the remaining variables are as described for the first through third embodiments, or any aspect thereof, or the fourth embodiment.

In a second aspect of the fourth embodiment, $R^{1a}$ is chloro. The values for the remaining variables are as described for the first through third embodiments, or any aspect thereof, or the fourth embodiment, or first aspect thereof.

In a third aspect of the fourth embodiment, $R^{1b}$ is selected from hydrogen, ($C_1$-$C_3$)alkyl, optionally substituted phenyl, optionally substituted pyridinyl, optionally substituted isoxazolyl, optionally substituted furanyl, optionally substituted oxazolyl, and optionally substituted thiophenyl. The values for the remaining variables are as described for the first through third embodiments, or any aspect thereof, or the fourth embodiment, or first or second aspect thereof.

In a fourth aspect of the fourth embodiment, $R^{1b}$ is selected from 5-acetylthiophen-2-yl, 4-methylphenyl, pyridin-3-yl, 2,3-difluorophenyl, 2-fluoro-4-chlorophenyl, 2-fluorophenyl, 3,5-dichlorophenyl, 3,5-bis(trifluoromethyl)phenyl, phenyl, 3,4,5-trifluorophenyl, 4-(morpholine-4-carbonyl)phenyl, 5-(1-hydroxyethyl)thiophen-2-yl, 3,5-dimethylisoxazol-4-yl, 3-ethoxycarbonylphenyl, furan-2-yl, 5-acetylfuran-2-yl, 2-aminophenyl, 2-methoxy-5-fluorophenyl, 3-hydroxycarbonylphenyl, methyl, 2-fluoro-3-methoxyphenyl, 3-methylsulfonylphenyl, 4-dimethylaminophenyl, 3-hydroxymethylphenyl, 5-methylsulfonylpyridin-3-yl, 1,3,4-oxazol-2-yl, 1,2,4-oxazol-5-yl, and thiophen-2-yl. The values for the remaining variables are as described for the first through third embodiments, or any aspect thereof, or the fourth embodiment, or first, second, or third aspect thereof.

In a fifth aspect of the fourth embodiment, $R^{1b}$ is selected from 5-acetylthiophen-2-yl, 4-methylphenyl, pyridin-3-yl, 2,3-difluorophenyl, 2-fluoro-4-chlorophenyl, 2-fluorophenyl, 3,5-dichlorophenyl, 3,5-bis(trifluoromethyl)phenyl, phenyl, 3,4,5-trifluorophenyl, 4-(morpholine-4-carbonyl)phenyl, 5-(1-hydroxyethyl)thiophen-2-yl, 3,5-dimethylisoxazol-4-yl, and 3-ethoxycarbonylphenyl. The values for the remaining variables are as described for the first through third embodiments, or any aspect thereof, or the fourth embodiment, or first, second, third, or fourth aspect thereof.

In a sixth aspect of the fourth embodiment, $R^{1b}$ is optionally substituted carbocyclyl or optionally substituted heterocyclyl. The values for the remaining variables are as described for the first through third embodiments, or any aspect thereof, or the fourth embodiment, or first or second aspect thereof.

In a seventh aspect of the fourth embodiment, the carbocyclyl and heterocyclyl of $R^{1b}$ are each optionally substituted with a substituent selected from amino, cyano, nitro, halo, halo($C_1$-$C_4$)alkyl, ($C_1$-$C_4$)alkyl, ($C_1$-$C_4$)acyl, ($C_1$-$C_4$)alkoxy, ($C_1$-$C_4$)thioalkoxy, carbocyclyl-C(O)—, heterocyclyl-C(O)—, carboxyl, ($C_1$-$C_4$)alkanoate, hydroxy($C_1$-$C_4$)alkyl, ($C_1$-$C_4$)dialkylamino, ($C_1$-$C_4$)monoalkylamino, carboxamide, and —S(O)$_{0-2}$($C_1$-$C_4$)alkyl. The values for the remaining variables are as described for the first through third embodiments, or any aspect thereof, or the fourth embodiment, or first, second, third, fourth, fifth, or sixth aspect thereof.

In an eighth aspect of the fourth embodiment, $R^{1a}$ and $R^{1b}$ are each independently selected from hydrogen, halo, halo ($C_1$-$C_4$)alkyl, ($C_1$-$C_4$)alkyl, carbocyclyl, heterocyclyl, cyano, sulfonate, and —S(O)$_{0-2}$($C_1$-$C_4$)alkyl. The values for the remaining variables are as described for the first through third embodiments, or any aspect thereof, or the fourth embodiment, or first, second, third, fourth, fifth, sixth or seventh aspect thereof.

A fifth embodiment is a compound of Structural Formula V:

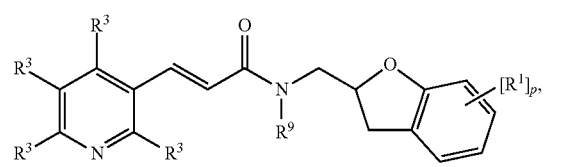

(V)

or a pharmaceutically acceptable salt thereof, wherein $R^1$, $R^3$, $R^9$, and p are as defined in the first, second, third, or fourth embodiment, or any aspect thereof.

In a first aspect of the fifth embodiment the compound is represented by Structural Formula VI:

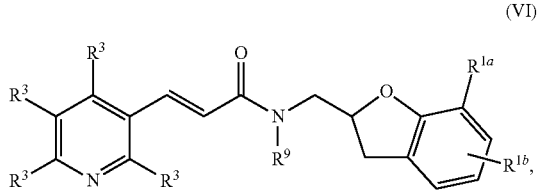

(VI)

or a pharmaceutically acceptable salt thereof, wherein the values for $R^{1a}$, $R^{1b}$, $R^3$, $R^9$, and p are as defined in the first through fourth embodiments, or any aspect thereof.

A sixth embodiment is a compound represented by Structural Formula VII:

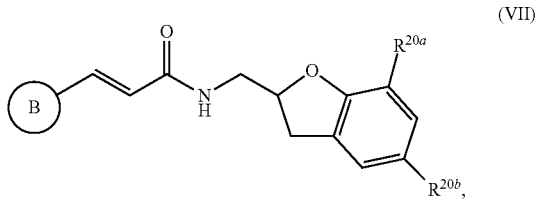

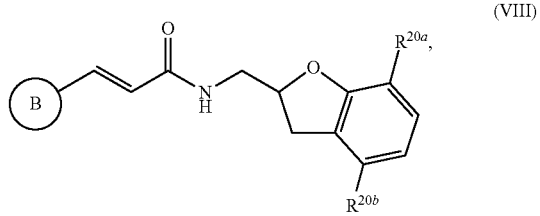

or a pharmaceutically acceptable salt thereof, wherein:

Ring B is selected from 6-aminopyridin-3-yl; and pyridin-3-yl;

$R^{20a}$ is selected from methyl or chloro;

$R^{20b}$ is selected from phenyl, thiophen-2-yl, furan-2-yl, isoxazol-4-yl, pyridin-3-yl, pyridin-2-yl, and pyrimidin-2-yl, wherein $R^{20b}$ is optionally substituted with 1-3 substituents independently selected from fluoro, —C(O)N($R^{21}$)($R^{21}$), —C(O)—$C_1$-$C_4$ alkyl, —C(O)—O—$C_1$-$C_4$ alkyl. —$C_1$-$C_4$ alkyl optionally substituted with —OH, and -phenyl, wherein each $R^{21}$ is independently $C_1$-$C_3$ alkyl, or two $R^{21}$ are taken together with the nitrogen atom to which they are bound to form an saturated heterocyclyl, optionally comprising an additional heteroatom selected from N and O, and optionally substituted with 1-2 substituents independently selected from fluoro and methyl.

In a first aspect of the sixth embodiment, $R^{20a}$ is chloro. The values for the remaining variables are as described for the sixth embodiment.

In a second aspect of the sixth embodiment, $R^{20b}$ is optionally substituted with 1-3 substituents independently selected from fluoro, methyl, phenyl, morpholin-4-carbonyl, 4-methylpiperazin-1-carbonyl, piperazin-1-carbonyl, piperidin-1-carbonyl, 2-hydroxypropan-2-yl, 3,3-difluoroazetidin-1-carbonyl, acetyl, 1-hydroxyethyl, ethoxycarbonyl, and dimethylaminocarbonyl. The values for the remaining variables are as described for the sixth embodiment, or first aspect thereof.

In a third aspect of the sixth embodiment, $R^{20b}$ is selected from 4-(3,3-difluoroazetidine-1-carbonyl)-3-fluorophenyl; 2,5-difluoro-4-(morpholine-4-carbonyl)phenyl; 3,5-difluoro-4-(morpholine-4-carbonyl)phenyl; 5-(morpholine-4-carbonyl)pyrimidin-2-yl; 5-(morpholine-4-carbonyl)pyridin-2-yl; 4-(4-methylpiperazine-1-carbonyl)phenyl; 2-hydroxypropan-2-yl)thiophen-2-yl; 3-(morpholine-4-carbonyl)phenyl; 4-(3,3-difluoroazetidine-1-carbonyl)-3,5-difluorophenyl; 3-methyl-4-(morpholine-4-carbonyl)phenyl; 4-(morpholine-4-carbonyl)phenyl; 4-(piperazine-1-carbonyl)phenyl; 4-(3,3-difluoroazetidine-1-carbonyl)phenyl; 5-acetyl-3,4-dimethylthiophen-2-yl; 5-(dimethyaminocarbonyl)furan-2-yl; 4-(piperidine-1-carbonyl)phenyl; 5-methyl-3-phenylisoxazol-4-yl; 5-(2-hydroxypropan-2-yl)thiophen-2-yl; 5-acetylfuran-2-yl; 4-(dimethylaminocarbonyl)phenyl; 6-(morpholine-4-carbonyl)pyridin-3-yl; 5-acetylthiophen-2-yl; 3,5-dimethylisoxazol-4-yl; 5-(1-hydroxyethyl)thiophen-2-yl; and 4-(ethoxycarbonyl)phenyl. The values for the remaining variables are as described for the sixth embodiment, or first or second aspect thereof.

A seventh embodiment is a compound represented by Structural Formula VIII:

or a pharmaceutically acceptable salt thereof, wherein:

Ring B is selected from 6-aminopyridin-3-yl; and pyridin-3-yl;

$R^{20a}$ is selected from methyl or chloro;

$R^{20b}$ is selected from phenyl, thiophen-2-yl, furan-2-yl, isoxazol-4-yl, pyridin-3-yl, pyridin-2-yl, and pyrimidin-2-yl, wherein $R^{20b}$ is optionally substituted with 1-3 substituents independently selected from fluoro, —C(O)N($R^{21}$)($R^{21}$), —C(O)—$C_1$-$C_4$ alkyl, —C(O)—O—$C_1$-$C_4$ alkyl. —$C_1$-$C_4$ alkyl optionally substituted with —OH, and -phenyl, wherein each $R^{21}$ is independently $C_1$-$C_3$ alkyl, or two $R^{21}$ are taken together with the nitrogen atom to which they are bound to form an saturated heterocyclyl, optionally comprising an additional heteroatom selected from N and O, and optionally substituted with 1-2 substituents independently selected from fluoro and methyl.

In a first aspect of the seventh embodiment, $R^{20a}$ is chloro. The values for the remaining variables are as described for the sixth embodiment, or any aspect thereof, or the seventh embodiment.

In a second aspect of the seventh embodiment, ring B is 6-aminopyridin-3-yl. The values for the remaining variables are as described for the sixth embodiment, or any aspect thereof, or the seventh embodiment, or first aspect thereof.

In a third aspect of the seventh embodiment, $R^{20b}$ is optionally substituted with morpholin-4-carbonyl, or acetyl. The values for the remaining variables are as described for the sixth embodiment, or any aspect thereof, or the seventh embodiment, or first or second aspect thereof.

In a fourth aspect of the seventh embodiment, $R^{20b}$ is selected from 4-(morpholin-4-carbonyl)phenyl and 5-acetylthiophen-2-yl. The values for the remaining variables are as described for the sixth embodiment, or any aspect thereof, or the seventh embodiment, or first through third aspects thereof.

An eighth embodiment of the invention is a compound represented by Structural Formula IIIb or IIIc:

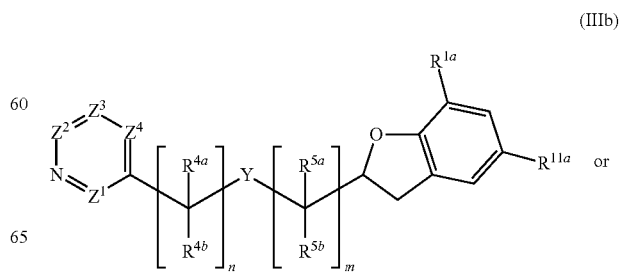

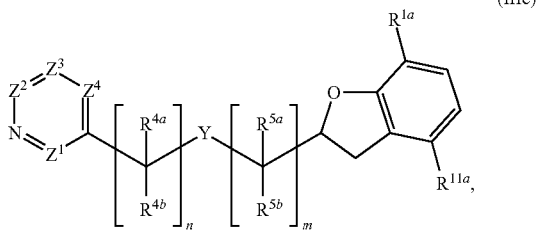

(IIIc)

or a pharmaceutically acceptable salt thereof, wherein:

$R^{1a}$ is selected from halo, hydroxyl, halo($C_1$-$C_4$)alkyl, ($C_1$-$C_4$)alkyl and ($C_1$-$C_4$)alkoxy; and $R^{11a}$ is optionally substituted aryl or optionally substituted heteroaryl.

The values for the remaining variables are as described in the first through seventh embodiments, or any aspect of the foregoing.

In a first aspect of the eighth embodiment, $R^{1a}$ is selected from hydrogen, halogen and halo($C_1$-$C_4$)alkyl. The values for the remaining variables are as described in the first through seventh embodiments, or any aspect of the foregoing, or the eighth embodiment.

In a second aspect of the eighth embodiment, $R^{1a}$ is selected from fluoro, chloro, —$CF_3$ and —$CHF_2$. The values for the remaining variables are as described in the first through seventh embodiments, or any aspect of the foregoing, or the eighth embodiment, or first aspect thereof.

In a third aspect of the eighth embodiment, $R^{11a}$ is optionally and independently substituted with 1, 2 or 3 optional substituents and is phenyl or a 5-6-membered heteroaryl having 1, 2 or 3 heteroatoms selected from nitrogen, oxygen and sulfur. The values for the remaining variables are as described in the first through seventh embodiments, or any aspect of the foregoing, or the eighth embodiment, or first or second aspect thereof.

In a fourth aspect of the eighth embodiment, $R^{11a}$ is substituted with one, two or three substituents independently selected from halogen, ($C_1$-$C_4$)alkyl optionally substituted with hydroxyl, ($C_2$-$C_4$)alkenyl, ($C_1$-$C_4$)alkoxy, ($C_1$-$C_4$)haloalkyl, —C(O)($C_1$-$C_4$)alkyl, —C(O)O($C_1$-$C_4$)alkyl, —$CO_2H$, amino, ($C_1$-$C_4$)alkylamino, ($C_1$-$C_4$)dialkylamino, —$SO_2$($C_1$-$C_4$)alkyl, —C(O)($C_3$-$C_7$)carbocyclyl, phenyl, —C(O)$NR^{12}R^{13}$ and —$S(O)_2NR^{12}R^{13}$, wherein:

$R^{12}$ and $R^{13}$ are each independently hydrogen, $C_1$-$C_4$ alkyl, optionally substituted carbocyclyl, or optionally substituted heterocyclyl; or $R^{12}$ and $R^{13}$ are taken together with the nitrogen atom to which they are commonly attached to form an optionally substituted saturated heterocyclyl.

The values for the remaining variables are as described in the first through seventh embodiments, or any aspect of the foregoing, or the eighth embodiment, or first through third aspects thereof.

In a fifth aspect of the eighth embodiment, $R^{11a}$ is substituted with a first substituent selected from halogen; ($C_1$-$C_4$)alkyl optionally substituted with hydroxyl; ($C_2$-$C_4$)alkenyl; ($C_1$-$C_4$)haloalkyl; —C(O)($C_1$-$C_4$)alkyl; —C(O)O($C_1$-$C_4$)alkyl; —C(O)($C_3$-$C_7$)carbocyclyl; phenyl; —C(O)$NR^{12}R^{13}$, wherein $R^{12}$ and $R^{13}$ are each methyl, or $R^{12}$ and $R^{13}$ are taken together with the nitrogen atom to which they are commonly attached to form an optionally substituted saturated ($C_3$-$C_7$)heterocyclyl; and —$S(O)_2NR^{12}R^{13}$, wherein $R^{12}$ and $R^{13}$ are taken together with the nitrogen atom to which they are commonly attached to form an optionally substituted saturated ($C_3$-$C_7$)heterocyclyl, and a second substituent selected from halogen, ($C_1$-$C_4$)alkyl and ($C_1$-$C_4$)haloalkyl. The values for the remaining variables are as described in the first through seventh embodiments, or any aspect of the foregoing, or the eighth embodiment, or first through fourth aspects thereof.

In a sixth aspect of the eighth embodiment, $R^{11a}$ is selected from phenyl, thiophenyl, pyridinyl, pyrimidinyl, isoxazolyl, furanyl, pyridazinyl and oxadiazolyl, and is substituted with 1, 2 or 3 independently selected substituents. The values for the remaining variables are as described in the first through seventh embodiments, or any aspect of the foregoing, or the eighth embodiment, or first through fifth aspects thereof.

In a seventh aspect of the eighth embodiment, the saturated heterocyclyl formed by $R^{12}$ and $R^{13}$ together with the nitrogen atom to which they are attached is optionally substituted with 1 or 2 substituents independently selected from halogen, ($C_1$-$C_4$)alkyl and ($C_1$-$C_4$)haloalkyl. The values for the remaining variables are as described in the first through seventh embodiments, or any aspect of the foregoing, or the eighth embodiment, or first through sixth aspects thereof.

In an eighth aspect of the eighth embodiment, $R^{11a}$ is substituted with one, two or three substituents independently selected from halogen, ($C_1$-$C_4$)alkyl optionally substituted with hydroxyl, ($C_2$-$C_4$)alkenyl, ($C_1$-$C_4$)alkoxy, ($C_1$-$C_4$)haloalkyl, —C(O)($C_1$-$C_4$)alkyl, —C(O)O($C_1$-$C_4$)alkyl, —$CO_2H$, amino, ($C_1$-$C_4$)alkylamino, ($C_1$-$C_4$)dialkylamino, —$SO_2$($C_1$-$C_4$)alkyl, —C(O)($CH_2$)$_{0-1}$($C_3$-$C_7$)carbocyclyl, phenyl, —C(O)($CH_2$)$_{0-1}NR^{12}R^{13}$ and —$S(O)_2NR^{12}R^{13}$, wherein:

$R^{12}$ and $R^{13}$ are each independently hydrogen, $C_1$-$C_4$ alkyl, optionally substituted carbocyclyl, or optionally substituted heterocyclyl; or $R^{12}$ and $R^{13}$ are taken together with the nitrogen atom to which they are commonly attached to form an optionally substituted saturated heterocyclyl.

The values for the remaining variables are as described in the first through seventh embodiments, or any aspect of the foregoing, or the eighth embodiment, or first through seventh aspects thereof.

In a ninth aspect of the eighth embodiment, $R^{11a}$ is substituted with a first substituent selected from halogen; ($C_1$-$C_4$)alkyl optionally substituted with hydroxyl; ($C_2$-$C_4$)alkenyl; ($C_1$-$C_4$)haloalkyl; —C(O)($C_1$-$C_4$)alkyl; —C(O)O($C_1$-$C_4$)alkyl; —C(O)($CH_2$)$_{0-1}$($C_3$-$C_7$)carbocyclyl; phenyl; —C(O)($CH_2$)$_{0-1}NR^{12}R^{13}$, wherein $R^{12}$ and $R^{13}$ are each methyl, or $R^{12}$ and $R^{13}$ are taken together with the nitrogen atom to which they are commonly attached to form an optionally substituted saturated ($C_3$-$C_7$)heterocyclyl; and —$S(O)_2NR^{12}R^{13}$, wherein $R^{12}$ and $R^{13}$ are taken together with the nitrogen atom to which they are commonly attached to form an optionally substituted saturated ($C_3$-$C_7$)heterocyclyl, and a second substituent selected from halogen, ($C_1$-$C_4$)alkyl and ($C_1$-$C_4$)haloalkyl. The values for the remaining variables are as described in the first through seventh embodiments, or any aspect of the foregoing, or the eighth embodiment, or first through eighth aspects thereof.

In a tenth aspect of the eighth embodiment, $R^{11a}$ is substituted with one substituent selected from halogen; ($C_1$-$C_4$)alkyl optionally substituted with hydroxyl; ($C_2$-$C_4$)alkenyl; ($C_1$-$C_4$)haloalkyl; —C(O)($C_1$-$C_4$)alkyl; —C(O)O($C_1$-$C_4$)alkyl; —C(O)($CH_2$)$_{0-1}$($C_3$-$C_7$)carbocyclyl; phenyl; —C(O)($CH_2$)$_{0-1}NR^{12}R^{13}$, wherein $R^{12}$ and $R^{13}$ are each methyl, or $R^{12}$ and $R^{13}$ are taken together with the nitrogen atom to which they are commonly attached to form an optionally substituted saturated ($C_3$-$C_7$)heterocyclyl; and —S(O)$_2$NR$^{12}$R$^{13}$, wherein R$^{12}$ and R$^{13}$ are taken together with the nitrogen atom to which they are commonly attached to form an optionally substituted saturated ($C_3$-$C_7$)heterocyclyl. The values for the remaining variables are as described in the first through seventh embodiments, or any aspect of the foregoing, or the eighth embodiment, or first through ninth aspects thereof.

A ninth embodiment of the invention is a compound represented by Structural Formula IX or X:

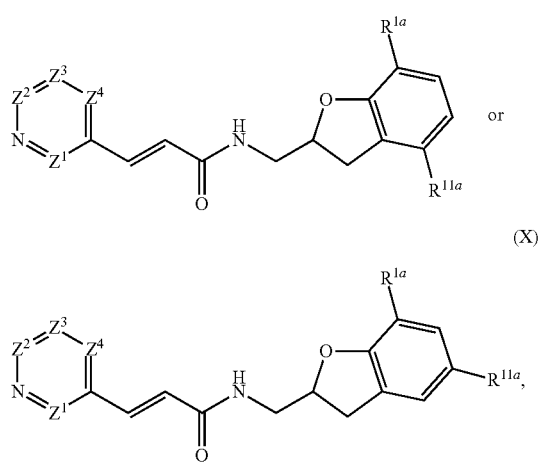

or a pharmaceutically acceptable salt thereof, wherein values and alternative values for the variables are as described in the first through eighth embodiments, or any aspect of the foregoing.

A tenth embodiment of the invention is a compound represented by Structural Formula IIId or IIIe:

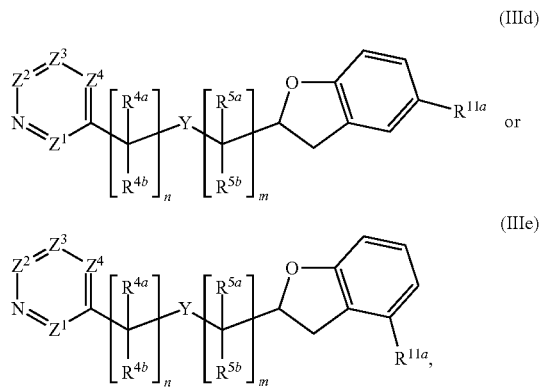

or a pharmaceutically acceptable salt thereof, wherein R$^{11a}$ is optionally substituted aryl or optionally substituted heteroaryl. Values and alternative values for the variables are as described in the first through ninth embodiments, or any aspect of the foregoing.

An eleventh embodiment of the invention is a compound represented by Structural Formula IXb or Xb:

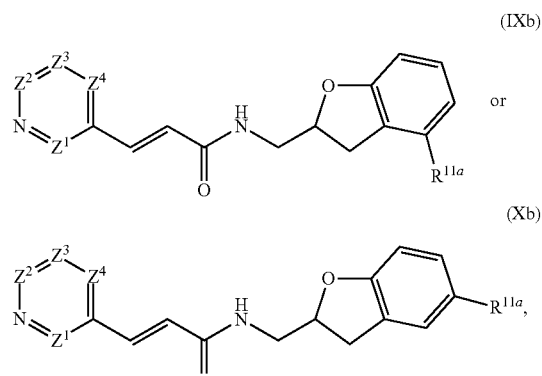

or a pharmaceutically acceptable salt thereof, wherein values and alternative values for the variables are as described in the first through tenth embodiments, or any aspect of the foregoing.

Exemplary compounds are set forth in Table 2.

Formulation and Administration

Another embodiment of the invention is a composition comprising a compound of the invention, or a pharmaceutically acceptable salt thereof, and a pharmaceutically acceptable carrier, adjuvant, or vehicle. In certain embodiments, a composition of the invention is formulated for administration to a patient in need of the composition. In some embodiments, a composition of the invention is formulated for oral, intravenous, subcutaneous, intraperitoneal or dermatological administration to a patient in need thereof.

The term "patient," as used herein, means an animal. In some embodiments, the animal is a mammal. In certain embodiments, the patient is a veterinary patient (i.e., a non-human mammal patient). In some embodiments, the patient is a dog. In other embodiments, the patient is a human.

"Pharmaceutically or pharmacologically acceptable" includes molecular entities and compositions that do not produce an adverse, allergic or other untoward reaction when administered to an animal, or a human, as appropriate. For human administration, preparations should meet sterility, pyrogenicity, and general safety and purity standards, as required by FDA Office of Biologics standards.

The phrase "pharmaceutically acceptable carrier, adjuvant, or vehicle" refers to a non-toxic carrier, adjuvant, or vehicle that does not destroy the pharmacological activity of the compound with which it is formulated and is nontoxic when administered in doses sufficient to deliver a therapeutic amount of the compound. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally (including subcutaneous, intramuscular, intravenous and intradermal), by inhalation spray, topically, rectally, nasally, buccally, vaginally or via an implanted reservoir. In some embodiments, provided compounds or compositions are administrable intravenously and/or intraperitoneally.

The term "parenteral," as used herein, includes subcutaneous, intracutaneous, intravenous, intramuscular, intraocular, intravitreal, intra-articular, intra-arterial, intra-synovial, intrasternal, intrathecal, intralesional, intrahepatic, intraperitoneal intralesional and intracranial injection or infusion techniques. Preferably, the compositions are administered orally, subcutaneously, intraperitoneally or intravenously.

Pharmaceutically acceptable compositions of this invention can be orally administered in any orally acceptable dosage form including, but not limited to, capsules, tablets, aqueous suspensions, dispersions and solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions and/or emulsions are required for oral use, the active ingredient can be suspended or dissolved in an oily phase and combined with emulsifying and/or suspending agents. If desired, certain sweetening, flavoring or coloring agents may also be added.

In some embodiments, an oral formulation is formulated for immediate release or sustained/delayed release.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders, such as carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium salts, g) wetting agents, such as acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using excipients such as lactose or milk sugar, as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

A compound of the invention can also be in microencapsulated form with one or more excipients, as noted above. In such solid dosage forms, the compound of the invention can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose.

Compositions for oral administration may be designed to protect the active ingredient against degradation as it passes through the alimentary tract, for example, by an outer coating of the formulation on a tablet or capsule.

In another embodiment, a compound of the invention can be provided in an extended (or "delayed" or "sustained") release composition. This delayed-release composition comprises a compound of the invention in combination with a delayed-release component. Such a composition allows targeted release of a provided compound into the lower gastrointestinal tract, for example, into the small intestine, the large intestine, the colon and/or the rectum. In certain embodiments, the delayed-release composition comprising a compound of the invention further comprises an enteric or pH-dependent coating, such as cellulose acetate phthalates and other phthalates (e.g., polyvinyl acetate phthalate, methacrylates (Eudragits)). Alternatively, the delayed-release composition provides controlled release to the small intestine and/or colon by the provision of pH sensitive methacrylate coatings, pH sensitive polymeric microspheres, or polymers which undergo degradation by hydrolysis. The delayed-release composition can be formulated with hydrophobic or gelling excipients or coatings. Colonic delivery can further be provided by coatings which are digested by bacterial enzymes such as amylose or pectin, by pH dependent polymers, by hydrogel plugs swelling with time (Pulsincap), by time-dependent hydrogel coatings and/or by acrylic acid linked to azoaromatic bonds coatings.

In certain embodiments, the delayed-release composition of the present invention comprises hypromellose, microcrystalline cellulose, and a lubricant. The mixture of a compound of the invention, hypromellose and microcrystalline cellulose can be formulated into a tablet or capsule for oral administration. In certain embodiments, the mixture is granulated and pressed into tablets.

Alternatively, pharmaceutically acceptable compositions of this invention can be administered in the form of suppositories for rectal administration. These can be prepared by mixing the compound of the invention with a suitable non-irritating excipient that is solid at room temperature but liquid at rectal temperature and, therefore, will melt in the rectum to release the drug. Such materials include cocoa butter, beeswax and polyethylene glycols.

Pharmaceutically acceptable compositions of this invention can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches can also be used.

For other topical applications, the pharmaceutically acceptable compositions of the invention can be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water and penetration enhancers. Alternatively, pharmaceutically acceptable compositions of the invention can be formulated in a suitable lotion or cream containing the active component suspended or dissolved in one or more pharmaceutically acceptable carriers. Alternatively, the pharmaceutical composition can be formulated with a suitable lotion or cream containing the active compound suspended or dissolved in a carrier with suitable emulsifying agents. In some embodiments, suitable carriers include, but are not limited to, mineral oil, sorbitan monostearate, polysorbate 60, cetyl esters wax, cetearyl alcohol, 2-octyldodecanol, benzyl alcohol and water. In other embodiments, suitable carriers include, but are not limited to, mineral oil, sorbitan monostearate, polysorbate 60, cetyl esters wax, cetearyl alcohol, 2-octyldodecanol, benzyl alcohol and water and penetration enhancers.

For ophthalmic use, pharmaceutically acceptable compositions of the invention can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions can be formulated in an ointment such as petrolatum.

Pharmaceutically acceptable compositions of this invention can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions of this invention are formulated for oral administration.

In some embodiments, pharmaceutically acceptable compositions of this invention are formulated for intra-peritoneal administration.

In some embodiments, pharmaceutically acceptable compositions of this invention are formulated for topical administration.

The amount of compounds of the present invention that can be combined with the carrier materials to produce a composition in a single dosage form will vary depending upon the host treated, the particular mode of administration and the activity of the compound employed. Preferably, compositions should be formulated so that a dosage of between 0.01-100 mg/kg body weight/day of the inhibitor can be administered to a patient receiving the composition.

It should also be understood that a specific dosage and treatment regimen for any particular patient will depend upon a variety of factors, including the activity of the specific compound employed, the age, body weight, general health, sex, diet, time of administration, rate of excretion, drug combination, the judgment of the treating physician and the severity of the particular disease being treated. The amount of a compound of the present invention in the composition will also depend upon the particular compound in the composition.

Other pharmaceutically acceptable carriers, adjuvants and vehicles that can be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be advantageously used to enhance delivery of compounds described herein.

The pharmaceutical compositions of this invention are preferably administered by oral administration or by injection. The pharmaceutical compositions of this invention can contain any conventional non-toxic pharmaceutically-acceptable carriers, adjuvants or vehicles. In some cases, the pH of the formulation can be adjusted with pharmaceutically acceptable acids, bases or buffers to enhance the stability of the formulated compound or its delivery form.

The pharmaceutical compositions can be in the form of a sterile injectable preparation, for example, as a sterile injectable aqueous or oleaginous suspension. This suspension can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms can also be used for the purposes of formulation.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agent(s) can be administered separately, as part of a multiple dose regimen, from the compounds of this invention. Alternatively, the additional agent(s) can be part of a single dosage form, mixed together with the compound of this invention in a single composition.

The compounds described herein can, in certain embodiments, be administered by injection, intravenously, intraarterially, intraocularly, intravitreally, subdermally, orally, buccally, nasally, transmucosally, topically, in an ophthalmic preparation, or by inhalation, with a dosage ranging from about 0.1 mg/kg to about 1000 mg/kg of body weight, particularly, from about 1 mg/kg to about 250 mg/kg body weight, more particularly, from about 1 mg/kg to about 100 mg/kg body weight, yet more particularly, from about 1 mg/kg to about 10 mg/kg body weight, for example, from about 1 mg/kg to about 5 mg/kg body weight, from about 5 mg/kg to about 10 mg/kg body weight, about 5 mg/kg body weight, about 10 mg/kg body weight, about 30 mg/kg body weight, about 50 mg/kg body weight or about 100 mg/kg body weight, every 4 to 120 hours, or according to the requirements of the particular drug. The compounds described herein can, for example, be administered by injection, intravenously, intraarterially, intraocularly, intravitreally, subdermallym, orally, buccally, nasally, transmucosally, topically, in an ophthalmic preparation, or by inhalation, with a dosage ranging from about 0.5 to about 100 mg/kg of body weight or, alternatively, in a dosage ranging from about 1 mg to about 1000 mg/dose, every 4 to 120 hours, or according to the requirements of the particular drug. The methods herein contemplate administration of an effective amount of a compound of the invention, or a composition thereof, to achieve the desired or stated effect. Typically, the pharmaceutical compositions of this invention will be administered from about 1 to about 6 times per day or, alternatively, as a continuous infusion. Such administration can be used as a chronic or acute therapy. The amount of active ingredient that can be combined with a carrier material to produce a single dosage form will vary depending upon the host treated and the particular mode of administration. A typical preparation will contain from about 5% to about 95% active compound (w/w). Alternatively, a preparation can contain from about 20% to about 80% active compound.

Doses lower or higher than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention can be administered, if necessary. Subsequently, the dosage or frequency of administration, or both, can be reduced, as a function of the symptoms, to a level at which the improved condition is retained when the symptoms have been alleviated to the desired level. Patients may, however, require intermittent treatment on a long-term basis upon recurrence of disease symptoms.

Uses of Compounds and Pharmaceutically Acceptable Compositions

As used herein, "PAK-mediated" disorder or condition means any disease or other deleterious condition in which one or more p21-activated kinases (PAK) plays a role. Accordingly, another embodiment of the present invention relates to treating, for example, lessening the severity of, a PAK-mediated disorder or condition. PAK-mediated disorders include cancer, neurodegenerative diseases and immune system diseases. Specific examples of PAK-mediated disorders are set forth in detail below.

P21-activated kinases (PAKs) can be classified into two groups: group I and group II. Group I comprises PAK1, PAK2 and PAK3, and group II comprises PAK4, PAK5 and PAK6. Some embodiments of the invention relate to treating a group I PAK-mediated disorder or condition, for example, a PAK1-mediated disorder or condition, a PAK2-mediated disorder or condition, a PAK3-mediated disorder or condition or a disorder or condition mediated by a combination of PAK1, PAK2, and PAK3, for example, a disorder or condition mediated by PAK1 and PAK2, PAK1 and PAK3, PAK2 and PAK3 or PAK1, PAK2 and PAK3. Other embodiments of the invention relate to treating a group II PAK-mediated disorder or condition, for example, a PAK4-mediated disorder or condition, a PAK5-mediated disorder or condition, a PAK6-mediated disorder or condition or a disorder or condition mediated by a combination of PAK4, PAK5 and PAK6, for example, a disorder or condition mediated by PAK4 and PAK5, PAK4 and PAK6, PAK5 and PAK6 or PAK4, PAK5 and PAK6.

When "PAK" is followed by a numeral, as in "PAK4", the particular PAK isoform corresponding to that numeral is being designated. Thus, as used herein, "PAK4-mediated" disorder or condition means any disease or other deleterious condition in which PAK4 is known to play a role. Accordingly, another embodiment of the present invention relates to treating, for example, lessening the severity of, a PAK4-mediated disorder or condition. PAK4-mediated disorders include cancer, neurodegenerative diseases and immune system diseases. Specific examples of PAK4-mediated disorders are set forth in detail below.

Compounds provided by this invention are also useful as tools, for example, to study PAK modulation in biological and pathological phenomena, to study cancer or for the identification and/or comparative evaluation of PAK modulators. Accordingly, in particular embodiments, the present invention provides a method for studying an effect of a compound described herein, or a salt or composition thereof, on a sample, the method comprising contacting a sample comprising cells in culture or one or more PAKs with the compound, or the salt or composition thereof; and measuring the effect of the compound, or salt or composition thereof, on the cells or the one or more PAKs. For example, the compounds described herein can be used as a standard or control substance in binding assays (e.g., competitive binding assays) to identify or evaluate potential PAK modulators or as a discovery tool to probe the role of PAK modulation in certain disorders or conditions, such as those described herein, including cancer and PAK-mediated disorders or conditions.

Modulation, for example, modulation of one or more PAKs, can be accomplished by ligands, particularly PAK ligands, that act as, for example, agonists, partial agonists, inverse agonists, antagonists or allosteric modulators (e.g., allosteric agonists, positive allosteric modulators, negative allosteric modulators). Agonists act directly to activate a receptor, whereas antagonists act indirectly to block receptor signaling by preventing agonist activity through their association with the receptor. Allosteric modulation occurs when a ligand binds at an allosteric site of a receptor, rather than at an orthosteric binding site. Allosteric modulators can include both positive and negative modulators of orthosteric ligand-mediated activity. Without being bound by a particular theory, it is believed that the compounds described herein can bind to one or more PAKs and function as allosteric modulators.

Compounds and compositions described herein are also useful for treating cancer in a subject in need thereof. Thus, in certain embodiments, the present invention provides a method for treating cancer, comprising the step of administering to a patient in need thereof a therapeutically effective amount of a compound of the present invention, or pharmaceutically acceptable salt or composition thereof The compounds and compositions described herein can also be administered to cells in culture, e.g., in vitro or ex vivo, or to a subject, e.g., in vivo, to treat, prevent, and/or diagnose a variety of disorders, including those described herein below.

The activity of a compound utilized in this invention as an anti-cancer agent may be assayed in vitro, in vivo or in a cell line. Detailed conditions for assaying a compound utilized in this invention as an anti-cancer agent are set forth in the Exemplification.

As used herein, the term "treat" or "treatment" is defined as the application or administration of a compound, alone or in combination with a second compound, to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, in order to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

As used herein, an amount of a compound effective to treat a disorder, or a "therapeutically effective amount" refers to an amount of the compound which is effective, upon single or multiple dose administration to a subject or a cell, in curing, alleviating, relieving or improving one or more symptoms of a disorder.

As used herein, an amount of a compound effective to prevent a disorder, or a "prophylactically effective amount" of the compound refers to an amount effective, upon single- or multiple-dose administration to the subject, in preventing or delaying the onset or recurrence of a disorder or one or more symptoms of the disorder.

As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, cow, pig, etc., and companion animals (dog, cat, horse, etc.).

For example, provided herein are methods of treating various cancers in mammals (including humans and non-humans), comprising administering to a patient in need thereof a therapeutically effective amount of a compound of the invention, or a pharmaceutically acceptable salt thereof. Such cancers include hematologic malignancies (leukemias, lymphomas, myelomas, myelodysplastic and myeloproliferative syndromes) and solid tumors (carcinomas such as oral, gall bladder, prostate, breast, lung, colon, pancreatic, renal, ovarian as well as soft tissue and osteosarcomas, and stromal tumors). Breast cancer (BC) can include basal-like breast cancer (BLBC), triple negative breast cancer (TNBC) and breast cancer that is both BLBC and TNBC. In addition, breast cancer can include invasive or non-invasive ductal or lobular carcinoma, tubular, medullary, mucinous, papillary, cribriform carcinoma of the breast, male breast cancer, recurrent or metastatic breast cancer, phyllodes tumor of the breast and Paget's disease of the nipple. In some embodiments, the present invention provides a method of treating lymphoma, specifically, mantle cell lymphoma.

In some embodiments, the present invention provides a method of treating inflammatory disorders in a patient, comprising administering to the patient a therapeutically effective amount of a compound of the invention, or a pharmaceutically acceptable salt thereof. Inflammatory disorders treatable by the compounds of this invention include, but are not limited to, multiple sclerosis, rheumatoid arthritis, degenerative joint disease, systemic lupus, systemic sclerosis, vasculitis syndromes (small, medium and large vessel), atherosclerosis, inflammatory bowel disease, irritable bowel syndrome, Crohn's disease, mucous colitis, ulcerative colitis, gastritis, sepsis, psoriasis and other dermatological inflammatory disorders (such as eczema, atopic dermatitis, contact dermatitis, urticaria, scleroderma, and dermatosis with acute inflammatory components, pemphigus, pemphigoid, allergic dermatitis), and urticarial syndromes.

Viral diseases treatable by the compounds of this invention include, but are not limited to, acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, and herpes zoster. Viral diseases treatable by the compounds of this invention also include chronic viral infections, including hepatitis B and hepatitis C.

Exemplary ophthalmology disorders include, but are not limited to, macular edema (diabetic and nondiabetic macular edema), aged related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epitheliitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency or cataract.

Neurodegenerative diseases treatable by a compound of Formula I include, but are not limited to, Parkinson's, Alzheimer's, and Huntington's, and Amyotrophic lateral sclerosis (ALS/Lou Gehrig's Disease).

Compounds and compositions described herein may also be used to treat disorders of abnormal tissue growth and fibrosis including dilative cardiomyopathy, hypertrophic cardiomyopathy, restrictive cardiomyopathy, pulmonary fibrosis, hepatic fibrosis, glomerulonephritis, polycystic kidney disorder (PKD) and other renal disorders.

Compounds and compositions described herein may also be used to treat disorders related to food intake such as obesity and hyperphagia.

In another embodiment, a compound or composition described herein may be used to treat or prevent allergies and respiratory disorders, including asthma, bronchitis, pulmonary fibrosis, allergic rhinitis, oxygen toxicity, emphysema, chronic bronchitis, acute respiratory distress syndrome, and any chronic obstructive pulmonary disease (COPD).

Other disorders treatable by the compounds and compositions described herein include muscular dystrophy, arthritis, for example, osteoarthritis and rheumatoid arthritis, ankylosing spondilitis, traumatic brain injury, spinal cord injury, sepsis, rheumatic disease, cancer atherosclerosis, type 1 diabetes, type 2 diabetes, leptospiriosis renal disease, glaucoma, retinal disease, ageing, headache, pain, complex regional pain syndrome, cardiac hypertrophy, musclewasting, catabolic disorders, obesity, fetal growth retardation, hypercholesterolemia, heart disease, chronic heart failure, ischemia/reperfusion, stroke, cerebral aneurysm, angina pectoris, pulmonary disease, cystic fibrosis, acid-induced lung injury, pulmonary hypertension, asthma, chronic obstructive pulmonary disease, Sjogren's syndrome, hyaline membrane disease, kidney disease, glomerular disease, alcoholic liver disease, gut diseases, peritoneal endometriosis, skin diseases, nasal sinusitis, mesothelioma, anhidrotic ecodermal dysplasia-ID, behcet's disease, incontinentia pigmenti, tuberculosis, asthma, crohn's disease, colitis, ocular allergy, appendicitis, paget's disease, pancreatitis, periodontitis, endometriosis, inflammatory bowel disease, inflammatory lung disease, silica-induced diseases, sleep apnea, AIDS, HIV-1, autoimmune diseases, antiphospholipid syndrome, lupus, lupus nephritis, familial mediterranean fever, hereditary periodic fever syndrome, psychosocial stress diseases, neuropathological diseases, familial amyloidotic polyneuropathy, inflammatory neuropathy, parkinson's disease, multiple sclerosis, alzheimer's disease, amyotropic lateral sclerosis, huntington's disease, cataracts, or hearing loss.

Yet other disorders treatable by the compounds and compositions described herein include head injury, uveitis, inflammatory pain, allergen induced asthma, non-allergen induced asthma, glomerular nephritis, ulcerative colitis, necrotizing enterocolitis, hyperimmunoglobulinemia D with recurrent fever (HIDS), TNF receptor associated periodic syndrome (TRAPS), cryopyrin-associated periodic syndromes, Muckle-Wells syndrome (urticaria deafness amyloidosis), familial cold urticaria, neonatal onset multisystem inflammatory disease (NOMID), periodic fever, aphthous stomatitis, pharyngitis and adenitis (PFAPA syndrome), Blau syndrome, pyogenic sterile arthritis, pyoderma gangrenosum,acne (PAPA), deficiency of the interleukin-1-receptor antagonist (DIRA), subarachnoid hemorrhage, polycystic kidney disease, transplant, organ transplant, tissue transplant, myelodysplastic syndrome, irritant-induced inflammation, plant irritant-induced inflammation, poison ivy/urushiol oil-induced inflammation, chemical irritant-induced inflammation, bee sting- induced inflammation, insect bite-induced inflammation, sunburn, burns, dermatitis, endotoxemia, lung injury, acute respiratory distress syndrome, alcoholic hepatitis, or kidney injury caused by parasitic infections.

In further aspects, the present invention provides a use of a compound of the invention, of a pharmaceutically acceptable salt thereof, for the manufacture of a medicament for the treatment of cancer. In some embodiments, the present invention provides a use of a compound of the invention in the manufacture of a medicament for the treatment of any of cancer and/or neoplastic disorders, angiogenesis, autoimmune disorders, inflammatory disorders and/or diseases, epigenetics, hormonal disorders and/or diseases, viral diseases, neurodegenerative disorders and/or diseases, wounds, and ophthamalogic disorders.

Neoplastic Disorders

A compound or composition described herein can be used to treat a neoplastic disorder. A "neoplastic disorder" is a disease or disorder characterized by cells that have the capacity for autonomous growth or replication, e.g., an abnormal state or condition characterized by proliferative cell growth. Exemplary neoplastic disorders include: carcinoma, sarcoma, metastatic disorders, e.g., tumors arising from prostate, brain, bone, colon, lung, breast, ovarian, and liver origin, hematopoietic neoplastic disorders, e.g., leukemias, lymphomas, myeloma and other malignant plasma cell disorders, and metastatic tumors. Prevalent cancers include: breast, prostate, colon, lung, liver, and pancreatic cancers. Treatment with the compound can be in an amount effective to ameliorate at least one symptom of the neoplastic disorder, e.g., reduced cell proliferation, reduced tumor mass, etc.

The disclosed methods are useful in the prevention and treatment of cancer, including for example, solid tumors, soft tissue tumors, and metastases thereof, as well as in familial cancer syndromes such as Li Fraumeni Syndrome, Familial Breast-Ovarian Cancer (BRCA1 or BRAC2 mutations) Syndromes, and others. The disclosed methods are also useful in treating non-solid cancers. Exemplary solid tumors include malignancies (e.g., sarcomas, adenocarcinomas, and carcinomas) of the various organ systems, such as those of lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine.

Exemplary cancers described by the National Cancer Institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non- Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Mantle Cell Lymphoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non- Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T- Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Further exemplary cancers include diffuse large B-cell lymphoma (DLBCL), mantle cell lymphoma (MCL) and serous and endometrioid cancer.

In particular embodiments, the present invention provides a method for treating pancreatic cancer, comprising the step of administering to a patient in need thereof a therapeutically effective amount of a compound of the present invention, or pharmaceutically acceptable salt or composition thereof.

Metastases of the aforementioned cancers can also be treated or prevented in accordance with the methods described herein.

Combination Therapies

In some embodiments, a compound described herein is administered together with an additional "second" therapeutic agent or treatment. The choice of second therapeutic agent may be made from any agent that is typically used in a monotherapy to treat the indicated disease or condition. As used herein, the term "administered together" and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of any of the formulas described herein, an additional therapeutic agent, and a pharmaceutically acceptable carrier, adjuvant, or vehicle.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art. The additional agents may be administered separately, as part of a multiple dose regimen, from the compounds of this invention. Alternatively, those agents may be part of a single dosage form, mixed together with the compounds of this invention in a single composition.

Cancer Combination Therapies

In some embodiments, a compound described herein is administered together with an additional cancer treatment. Exemplary cancer treatments include, for example, chemotherapy, targeted therapies such as antibody therapies, kinase inhibitors, immunotherapy, and hormonal therapy, and anti-angiogenic therapies. Examples of each of these treatments are provided below.

As used herein, the term "combination," "combined," and related terms refer to the simultaneous or sequential administration of therapeutic agents in accordance with this invention. For example, a compound of the present invention can be administered with another therapeutic agent simultaneously or sequentially in separate unit dosage forms or together in a single unit dosage form. Accordingly, the present invention provides a single unit dosage form comprising a compound of the invention, an additional therapeutic agent, and a pharmaceutically acceptable carrier, adjuvant, or vehicle.

The amount of both a compound of the invention and additional therapeutic agent (in those compositions which comprise an additional therapeutic agent as described above) that can be combined with the carrier materials to produce a single dosage form will vary depending upon the host treated and the particular mode of administration. Preferably, compositions of this invention should be formulated so that a dosage of between 0.01-100 mg/kg body weight/day of a compound of the invention can be administered.

Chemotherapy

In some embodiments, a compound described herein is administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, topoisomerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, Bendamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein.

Targeted therapy

Targeted therapy constitutes the use of agents specific for the deregulated proteins of cancer cells. Small molecule targeted therapy drugs are generally inhibitors of enzymatic domains on mutated, overexpressed, or otherwise critical proteins within a cancer cell. Prominent examples are the tyrosine kinase inhibitors such as axitinib, bosutinib, cediranib, desatinib, erolotinib, imatinib, gefitinib, lapatinib, lestaurtinib, nilotinib, semaxanib, sorafenib, sunitinib, and vandetanib, and also cyclin-dependent kinase inhibitors such as alvocidib and seliciclib. Monoclonal antibody therapy is another strategy in which the therapeutic agent is an antibody which specifically binds to a protein on the surface of the cancer cells. Examples include the anti-HER2/neu antibody trastuzumab (Herceptin®) typically used in breast cancer, and the anti-CD20 antibody rituximab and tositumomab typically used in a variety of B-cell malignancies. Other exemplary antibodies include cetuximab, panitumumab, trastuzumab, alemtuzumab, bevacizumab, edrecolomab, and gemtuzumab. Exemplary fusion proteins include aflibercept and denileukin diftitox. In some embodiments, targeted therapy can be used in combination with a compound described herein, e.g., Gleevec (Vignari and Wang 2001).

Targeted therapy can also involve small peptides as "homing devices" which can bind to cell surface receptors or affected extracellular matrix surrounding a tumor. Radionuclides which are attached to these peptides (e.g., RGDs) eventually kill the cancer cell if the nuclide decays in the vicinity of the cell. An example of such therapy includes BEXXAR®.

Angiogenesis

Compounds and methods described herein may be used to treat or prevent a disease or disorder associated with angiogenesis. Diseases associated with angiogenesis include cancer, cardiovascular disease and macular degeneration.

Angiogenesis is the physiological process involving the growth of new blood vessels from pre-existing vessels. Angiogenesis is a normal and vital process in growth and development, as well as in wound healing and in granulation tissue. However, it is also a fundamental step in the transition of tumors from a dormant state to a malignant one. Angiogenesis may be a target for combating diseases characterized by either poor vascularisation or abnormal vasculature.

Application of specific compounds that may inhibit or induce the creation of new blood vessels in the body may help combat such diseases. The presence of blood vessels where there should be none may affect the mechanical properties of a tissue, increasing the likelihood of failure. The absence of blood vessels in a repairing or otherwise metabolically active tissue may inhibit repair or other essential functions. Several diseases, such as ischemic chronic wounds, are the result of failure or insufficient blood vessel formation and may be treated by a local expansion of blood vessels, thus bringing new nutrients to the site, facilitating repair. Other diseases, such as age-related macular degeneration, may be created by a local expansion of blood vessels, interfering with normal physiological processes.

Vascular endothelial growth factor (VEGF) has been demonstrated to be a major contributor to angiogenesis, increasing the number of capillaries in a given network. Upregulation of VEGF is a major component of the physiological response to exercise and its role in angiogenesis is suspected to be a possible treatment in vascular injuries. In vitro studies clearly demonstrate that VEGF is a potent stimulator of angiogenesis because, in the presence of this growth factor, plated endothelial cells will proliferate and migrate, eventually forming tube structures resembling capillaries.

Tumors induce blood vessel growth (angiogenesis) by secreting various growth factors (e.g., VEGF). Growth factors such as bFGF and VEGF can induce capillary growth into the tumor, which some researchers suspect supply required nutrients, allowing for tumor expansion.

Angiogenesis represents an excellent therapeutic target for the treatment of cardiovascular disease. It is a potent, physiological process that underlies the natural manner in which our bodies respond to a diminution of blood supply to vital organs, namely the production of new collateral vessels to overcome the ischemic insult.

Overexpression of VEGF causes increased permeability in blood vessels in addition to stimulating angiogenesis. In wet macular degeneration, VEGF causes proliferation of capillaries into the retina. Since the increase in angiogenesis also causes edema, blood and other retinal fluids leak into the retina, causing loss of vision.

Anti-angiogenic therapy can include kinase inhibitors targeting vascular endothelial growth factor (VEGF) such as sunitinib, sorafenib, or monoclonal antibodies or receptor "decoys" to VEGF or VEGF receptor including bevacizumab or VEGF-Trap, or thalidomide or its analogs (lenalidomide, pomalidomide), or agents targeting non-VEGF angiogenic targets such as fibroblast growth factor (FGF), angiopoietins, or angiostatin or endostatin.

Epigenetics

Compounds and methods described herein may be used to treat or prevent a disease or disorder associated with epigenetics. Epigenetics is the study of heritable changes in phenotype or gene expression caused by mechanisms other than changes in the underlying DNA sequence. One example of epigenetic changes in eukaryotic biology is the process of cellular differentiation. During morphogenesis, stem cells become the various cell lines of the embryo which in turn become fully differentiated cells. In other words, a single fertilized egg cell changes into the many cell types including neurons, muscle cells, epithelium, blood vessels etc. as it continues to divide. It does so by activating some genes while inhibiting others.

Epigenetic changes are preserved when cells divide. Most epigenetic changes only occur within the course of one individual organism's lifetime, but, if a mutation in the DNA has been caused in sperm or egg cell that results in fertilization, then some epigenetic changes are inherited from one generation to the next. Specific epigenetic processes include paramutation, bookmarking, imprinting, gene silencing, X chromosome inactivation, position effect, reprogramming, transvection, maternal effects, the progress of carcinogenesis, many effects of teratogens, regulation of histone modifications and heterochromatin, and technical limitations affecting parthenogenesis and cloning.

Exemplary diseases associated with epigenetics include ATR-syndrome, fragile X-syndrome, ICF syndrome, Angelman's syndrome, Prader-Wills syndrome, BWS, Rett syndrome, α-thalassaemia, cancer, leukemia, Rubinstein-Taybi syndrome and Coffin-Lowry syndrome.

The first human disease to be linked to epigenetics was cancer. Researchers found that diseased tissue from patients with colorectal cancer had less DNA methylation than normal tissue from the same patients. Because methylated genes are typically turned off, loss of DNA methylation can cause abnormally high gene activation by altering the arrangement of chromatin. On the other hand, too much methylation can undo the work of protective tumor suppressor genes.

DNA methylation occurs at CpG sites, and a majority of CpG cytosines are methylated in mammals. However, there are stretches of DNA near promoter regions that have higher concentrations of CpG sites (known as CpG islands) that are free of methylation in normal cells. These CpG islands become excessively methylated in cancer cells, thereby causing genes that should not be silenced to turn off This abnormality is the trademark epigenetic change that occurs in tumors and happens early in the development of cancer. Hypermethylation of CpG islands can cause tumors by shutting off tumor-suppressor genes. In fact, these types of changes may be more common in human cancer than DNA sequence mutations.

Furthermore, although epigenetic changes do not alter the sequence of DNA, they can cause mutations. About half of the genes that cause familial or inherited forms of cancer are turned off by methylation. Most of these genes normally suppress tumor formation and help repair DNA, including O6-methylguanine-DNA methyltransferase (MGMT), MLH1 cyclin-dependent kinase inhibitor 2B (CDKN2B), and RASSF1A. For example, hypermethylation of the promoter of MGMT causes the number of G-to-A mutations to increase.

Hypermethylation can also lead to instability of microsatellites, which are repeated sequences of DNA. Microsatellites are common in normal individuals, and they usually consist of repeats of the dinucleotide CA. Too much methylation of the promoter of the DNA repair gene MLH1 can make a microsatellite unstable and lengthen or shorten it. Microsatellite instability has been linked to many cancers, including colorectal, endometrial, ovarian, and gastric cancers.

Fragile X syndrome is the most frequently inherited mental disability, particularly in males. Both sexes can be affected by this condition, but because males only have one X chromosome, one fragile X will impact them more severely. Indeed, fragile X syndrome occurs in approximately 1 in 4,000 males and 1 in 8,000 females. People with this syndrome have severe intellectual disabilities, delayed verbal development, and "autistic-like" behavior.

Fragile X syndrome gets its name from the way the part of the X chromosome that contains the gene abnormality looks under a microscope; it usually appears as if it is hanging by a thread and easily breakable. The syndrome is caused by an abnormality in the FMR1 (fragile X mental retardation 1) gene. People who do not have fragile X syndrome have 6 to 50 repeats of the trinucleotide CGG in their FMR1 gene. However, individuals with over 200 repeats have a full mutation, and they usually show symptoms of the syndrome. Too many CGGs cause the CpG islands at the promoter region of the FMR1 gene to become methylated; normally, they are not. This methylation turns the gene off, stopping the FMR1 gene from producing an important protein called fragile X mental retardation protein. Loss of this specific protein causes fragile X syndrome. Although a lot of attention has been given to the CGG expansion mutation as the cause of fragile X, the epigenetic change associated with FMR1 methylation is the real syndrome culprit.

Fragile X syndrome is not the only disorder associated with mental retardation that involves epigenetic changes. Other such conditions include Rubenstein-Taybi, Coffin-Lowry, Prader-Willi, Angelman, Beckwith-Wiedemann, ATR-X, and Rett syndromes.

Epigenetic therapies include inhibitors of enzymes controlling epigenetic modifications, specifically DNA methyltransferases and histone deacetylases, which have shown promising anti-tumorigenic effects for some malignancies, as well as antisense oligonucloetides and siRNA.

Immunotherapy

In some embodiments, a compound described herein is administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, prostate cancer vaccine Provenge, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound described herein.

Hormonal Therapy

In some embodiments, a compound described herein is administered with a hormonal therapy. The growth of some cancers can be inhibited by providing or blocking certain hormones. Common examples of hormone-sensitive tumors include certain types of breast and prostate cancers, as well as certain types of leukemia which respond to certain retinoids/retinoic acids. Removing or blocking estrogen or testosterone is often an important additional treatment. In certain cancers, administration of hormone agonists, such as progestogens may be therapeutically beneficial. In some embodiments, the hormonal therapy agents can be used in combination with a compound described herein.

Hormonal therapy agents include the administration of hormone agonists or hormone antagonists and include retinoids/retinoic acid, compounds that inhibit estrogen or testosterone, as well as administration of progestogens.

Inflammation and Autoimmune Disease

The compounds and methods described herein may be used to treat or prevent a disease or disorder associated with inflammation, particularly in humans and other mammals. A therapeutically effective amount of a compound described herein may be administered prior to the onset of, at, or after the initiation of inflammation. When used prophylactically, the compounds are preferably provided in advance of any inflammatory response or symptom. Administration of the compounds can prevent or attenuate inflammatory responses or symptoms. Exemplary inflammatory conditions include, for example, multiple sclerosis, rheumatoid arthritis, psoriatic arthritis, degenerative joint disease, spondouloarthropathies, other seronegative inflammatory arthridities, polymyalgia rheumatica, various vasculidities (e.g., giant cell arteritis, ANCA+ vasculitis), gouty arthritis, systemic lupus erythematosus, juvenile arthritis, juvenile rheumatoid arthritis, osteoarthritis, osteoporosis, diabetes (e.g., insulin dependent diabetes mellitus or juvenile onset diabetes), menstrual cramps, cystic fibrosis, inflammatory bowel disease, irritable bowel syndrome, Crohn's disease, mucous colitis, ulcerative colitis, gastritis, esophagitis, pancreatitis, peritonitis, Alzheimer's disease, shock, ankylosing spondylitis, gastritis, conjunctivitis, pancreatis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, thermal injury (i.e., sunburn), necrotizing enterocolitis, granulocyte transfusion associated syndrome, and/or Sjogren's syndrome. Exemplary inflammatory conditions of the skin include, for example, eczema, atopic dermatitis, contact dermatitis, urticaria, schleroderma, psoriasis, and dermatosis with acute inflammatory components.

In another embodiment, a compound or method described herein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, a compound or method described herein may be used to treat autoimmune diseases and/or inflammation associated with autoimmune diseases, such as organ-tissue autoimmune diseases (e.g., Raynaud's syndrome), scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and Grave's disease.

In a particular embodiment, the compounds described herein can be used to treat multiple sclerosis.

Combination Therapy

In certain embodiments, a compound described herein may be administered alone or in combination with other compounds useful for treating or preventing inflammation. Exemplary anti-inflammatory agents include, for example, steroids (e.g., Cortisol, cortisone, fludrocortisone, prednisone, 6[alpha]-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine). In one embodiment, the other compound is drotrecogin alfa.

Further examples of anti-inflammatory agents include, for example, aceclofenac, acemetacin, e-acetamidocaproic acid, acetaminophen, acetaminosalol, acetanilide, acetylsalicylic acid, S-adenosylmethionine, alclofenac, alclometasone, alfentanil, algestone, allylprodine, alminoprofen, aloxiprin, alphaprodine, aluminum bis(acetylsalicylate), amcinonide, amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antrafenine, apazone, beclomethasone, bendazac, benorylate, benoxaprofen, benzpiperylon, benzydamine, benzylmorphine, bermoprofen, betamethasone, betamethasone-17-valerate, bezitramide, [alpha]-bisabolol, bromfenac, p-bromoacetanilide, 5-bromosalicylic acid acetate, bromosaligenin, bucetin, bucloxic acid, bucolome, budesonide, bufexamac, bumadizon, buprenorphine, butacetin, butibufen, butorphanol, carbamazepine, carbiphene, caiprofen, carsalam, chlorobutanol, chloroprednisone, chlorthenoxazin, choline salicylate, cinchophen, cinmetacin, ciramadol, clidanac, clobetasol, clocortolone, clometacin, clonitazene, clonixin, clopirac, cloprednol, clove, codeine, codeine methyl bromide, codeine phosphate, codeine sulfate, cortisone, cortivazol, cropropamide, crotethamide, cyclazocine, deflazacort, dehydrotestosterone, desomorphine, desonide, desoximetasone, dexamethasone, dexamethasone-21-isonicotinate, dexoxadrol, dextromoramide, dextropropoxyphene, deoxycorticosterone, dezocine, diampromide, diamorphone, diclofenac, difenamizole, difenpiramide, diflorasone, diflucortolone, diflunisal, difluprednate, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, enoxolone, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, fluazacort, flucloronide, flufenamic acid, flumethasone, flunisolide, flunixin, flunoxaprofen, fluocinolone acetonide, fluocinonide, fluocinolone acetonide, fluocortin butyl, fluocoitolone, fluoresone, fluorometholone, fluperolone, flupirtine, fluprednidene, fluprednisolone, fluproquazone, flurandrenolide, flurbiprofen, fluticasone, formocortal, fosfosal, gentisic acid, glafenine, glucametacin, glycol salicylate, guaiazulene, halcinonide, halobetasol, halometasone, haloprednone, heroin, hydrocodone, hydro cortamate, hydrocortisone, hydrocortisone acetate, hydrocortisone succinate, hydrocortisone hemisuccinate, hydrocortisone 21-lysinate, hydrocortisone cypionate, hydromorphone, hydroxypethidine, ibufenac, ibuprofen, ibuproxam, imidazole salicylate, indomethacin, indoprofen, isofezolac, isoflupredone, isoflupredone acetate, isoladol, isomethadone, isonixin, isoxepac, isoxicam, ketobemidone, ketoprofen, ketorolac, p-lactophenetide, lefetamine, levallorphan, levorphanol, levophenacylmorphan, lofentanil, lofentanil, lonazolac, lornoxicam, loxoprofen, lysine acetylsalicylate, mazipredone, meclofenamic acid, medrysone, mefenamic acid, meloxicam, meperidine, meprednisone, meptazinol, mesalamine, metazocine, methadone, methotrimeprazine, methylprednisolone, methylprednisolone acetate, methylprednisolone sodium succinate, methylprednisolone suleptnate, metiazinic acid, metofoline, metopon, mofebutazone, mofezolac, mometasone, morazone, morphine, morphine hydrochloride, morphine sulfate, morpholine salicylate, myrophine, nabumetone, nalbuphine, nalorphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paramethasone, paranyline, parsalmide, pentazocine, perisoxal, phenacetin, phenadoxone, phenazocine, phenazopyridine hydrochloride, phenocoll, phenoperidine, phenopyrazone, phenomorphan, phenyl acetylsalicylate, phenylbutazone, phenyl salicylate, phenyramidol, piketoprofen, piminodine, pipebuzone, piperylone, pirazolac, piritramide, piroxicam, pirprofen, pranoprofen, prednicarbate, prednisolone, prednisone, prednival, prednylidene, proglumetacin, proheptazine, promedol, propacetamol, properidine, propiram, propoxyphene, propyphenazone, proquazone, protizinic acid, proxazole, ramifenazone, remifentanil, rimazolium metilsulfate, salacetamide, salicin, salicylamide, salicylamide o-acetic acid, salicylic acid, salicylsulfuric acid, salsalate, salverine, simetride, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tixocortol, tolfenamic acid, tolmetin, tramadol, triamcinolone, triamcinolone acetonide, tropesin, viminol, xenbucin, ximoprofen, zaltoprofen and zomepirac.

In one embodiment, a compound described herein may be administered with a selective COX-2 inhibitor for treating or preventing inflammation. Exemplary selective COX-2 inhibitors include, for example, deracoxib, parecoxib, celecoxib, valdecoxib, rofecoxib, etoricoxib, and lumiracoxib.

In some embodiments, a provided compound is administered in combination with an anthracycline or a Topo II inhibitor. In certain embodiments, a provided compound is administered in combination with Doxorubicin (Dox). In certain embodiments, a provided compound is administered in combination with bortezomib (and more broadly including carfilzomib).

Viral Infections

Compounds and methods described herein may be used to treat or prevent a disease or disorder associated with a viral infection, particularly in humans and other mammals. A therapeutically effective amount of a compound described herein may be administered prior to the onset of, at, or after the initiation of viral infection. When used prophylactically, the compounds are preferably provided in advance of any viral infection or symptom thereof.

Exemplary viral diseases include acute febrile pharyngitis, pharyngoconjunctival fever, epidemic keratoconjunctivitis, infantile gastroenteritis, Coxsackie infections, infectious mononucleosis, Burkitt lymphoma, acute hepatitis, chronic hepatitis, hepatic cirrhosis, hepatocellular carcinoma, primary HSV-1 infection (e.g., gingivostomatitis in children, tonsillitis and pharyngitis in adults, keratoconjunctivitis), latent HSV-1 infection (e.g., herpes labialis and cold sores), primary HSV-2 infection, latent HSV-2 infection, aseptic meningitis, infectious mononucleosis, Cytomegalic inclusion disease, Kaposi's sarcoma, multicentric Castleman disease, primary effusion lymphoma, AIDS, influenza, Reye syndrome, measles, postinfectious encephalomyelitis, Mumps, hyperplastic epithelial lesions (e.g., common, flat, plantar and anogenital warts, laryngeal papillomas, epidermodysplasia verruciformis), cervical carcinoma, squamous cell carcinomas, croup, pneumonia, bronchiolitis, common cold, Poliomyelitis, Rabies, influenza-like syndrome, severe bronchiolitis with pneumonia, German measles, congenital rubella, Varicella, and herpes zoster.

Exemplary viral pathogens include Adenovirus, Coxsackievirus, Dengue virus, Encephalitis Virus, Epstein-Barr virus, Hepatitis A virus, Hepatitis B virus, Hepatitis C virus, Herpes simplex virus type 1, Herpes simplex virus type 2, cytomegalovirus, Human herpesvirus type 8, Human immunodeficiency virus, Influenza virus, measles virus, Mumps virus, Human papillomavirus, Parainfluenza virus, Poliovirus, Rabies virus, Respiratory syncytial virus, Rubella virus, Varicella-zoster virus, West Nile virus, Dungee, and Yellow fever virus. Viral pathogens may also include viruses that cause resistant viral infections.

Antiviral drugs are a class of medications used specifically for treating viral infections. Antiviral action generally falls into one of three mechanisms: interference with the ability of a virus to infiltrate a target cell (e.g., amantadine, rimantadine and pleconaril), inhibition of the synthesis of virus (e.g., nucleoside analogues, e.g., acyclovir and zidovudine (AZT), and inhibition of the release of virus (e.g., zanamivir and oseltamivir).

In some embodiments, the viral pathogen is selected from the group consisting of herpesviridae, flaviviridae, bunyaviridae, arenaviridae, picornaviridae, togaviridae, papovaviridae, poxviridae, respiratory viruses, hepatic viruses, and other viruses.

Exemplary herpesviridae include herpes simplex virus-1; herpes simplex virus-2; cytomegalovirus, for example, human cytomegalovirus; Varicella-Zoster virus; Epstein-Barr virus; herpes virus-6, for example, human herpes virus-6; and herpes virus-8, for example, human herpes virus-8.

Exemplary flaviviridae include Dengue virus, West Nile virus, yellow fever virus, Japanese encephalitis virus, and Powassen virus.

Exemplary bunyaviridae include Rift Valley fever virus, Punta Toro virus, LaCrosse virus, and Marporal virus.

Exemplary arenaviridae include Tacaribe virus, Pinchinde virus, Junin virus, and Lassa fever virus.

Exemplary picornaviridae include polio virus; enterovirus, for example, enterovirus-71; and Coxsackie virus, for example, Coxsackie virus B3.

Exemplary togaviridae include encephalitis virus, for example, Venezuelan equine encephalitis virus, Eastern equine encephalitis virus, and Western equine encephalitis virus; and Chikungunya virus.

Exemplary papoviridae include BK virus, JC virus, and papillomavirus.

Exemplary poxviridae include vaccinia virus, cowpox virus, and monkeypox virus.

Exemplary respiratory viruses include SARS coronavirus; influenza A virus, for example, H1N1 virus; and respiratory syncytial virus.

Exemplary hepatic viruses include hepatitis B and hepatitis C viruses.

Exemplary other viruses include adenovirus, for example, adenovirus-5; rabies virus; measles virus; ebola virus; nipah virus; and norovirus.

Ophthamology

Compounds and methods described herein may be used to treat or prevent an ophthamology disorder. Exemplary ophthamology disorders include macular edema (diabetic and nondiabetic macular edema), age related macular degeneration wet and dry forms, aged disciform macular degeneration, cystoid macular edema, palpebral edema, retina edema, diabetic retinopathy, chorioretinopathy, neovascular maculopathy, neovascular glaucoma, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, ophthalmic disease associated with hypoxia or ischemia, retinopathy of prematurity, proliferative diabetic retinopathy, polypoidal choroidal vasculopathy, retinal angiomatous proliferation, retinal artery occlusion, retinal vein occlusion, Coats' disease, familial exudative vitreoretinopathy, pulseless disease (Takayasu's disease), Eales disease, antiphospholipid antibody syndrome, leukemic retinopathy, blood hyperviscosity syndrome, macroglobulinemia, interferon-associated retinopathy, hypertensive retinopathy, radiation retinopathy, corneal epithelial stem cell deficiency and cataract.

Other ophthalmology disorders treatable using the compounds and methods described herein include proliferative vitreoretinopathy and chronic retinal detachment.

Inflammatory eye diseases are also treatable using the compounds and methods described herein.

Neurodegenerative Disease

Neurodegeneration is the umbrella term for the progressive loss of structure or function of neurons, including death of neurons. Many neurodegenerative diseases including Parkinson's, Alzheimer's, and Huntington's occur as a result of neurodegenerative processes. As research progresses, many similarities appear which relate these diseases to one another on a sub-cellular level. Discovering these similarities offers hope for therapeutic advances that could ameliorate many diseases simultaneously. There are many parallels between different neurodegenerative disorders including atypical protein assemblies as well as induced cell death.

Alzheimer's disease is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus.

Huntington's disease causes astrogliosis and loss of medium spiny neurons. Areas of the brain are affected according to their structure and the types of neurons they contain, reducing in size as they cumulatively lose cells. The areas affected are mainly in the striatum, but also the frontal and temporal cortices. The striatum's subthalamic nuclei send control signals to the globus pallidus, which initiates and modulates motion. The weaker signals from subthalamic nuclei thus cause reduced initiation and modulation of movement, resulting in the characteristic movements of the disorder. Exemplary treatments for Huntington's disease include tetrabenazine, neuroleptics, benzodiazepines, amantadine, remacemide, valproic acid, selective serotonin reuptake inhibitors (SSRIs), mirtazapine and antipsychotics.

The mechanism by which the brain cells in Parkinson's are lost may consist of an abnormal accumulation of the protein alpha-synuclein bound to ubiquitin in the damaged cells. The alpha-synuclein-ubiquitin complex cannot be directed to the proteosome. This protein accumulation forms proteinaceous cytoplasmic inclusions called Lewy bodies. The latest research on pathogenesis of disease has shown that the death of dopaminergic neurons by alpha-synuclein is due to a defect in the machinery that transports proteins between two major cellular organelles—the endoplasmic reticulum (ER) and the Golgi apparatus. Certain proteins like Rab1 may reverse this defect caused by alpha-synuclein in animal models. Exemplary Parkinson's disease therapies include levodopa, dopamine agonists such as include bromocriptine, pergolide, pramipexole, ropinirole, piribedil, cabergoline, apomorphine and lisuride, dopa decarboxylate inhibitors, MAO-B inhibitors such as selegilene and rasagilene, anticholinergics and amantadine.

Amyotrophic lateral sclerosis (ALS/Lou Gehrig's Disease) is a disease in which motor neurons are selectively targeted for degeneration. Exemplary ALS therapies include riluzole, baclofen, diazepam, trihexyphenidyl and amitriptyline.

Other exemplary neurodegenerative therapeutics include antisense oligonucleotides and stem cells.

Wound Healing

Wounds are a type of condition characterized by cell or tissue damage. Wound healing is a dynamic pathway that optimally leads to restoration of tissue integrity and function. The wound healing process consists of three overlapping phases. The first phase is an inflammatory phase, which is characterized by homeostasis, platelet aggregation and degranulation. Platelets as the first response, release multiple growth factors to recruit immune cells, epithelial cells, and endothelial cells. The inflammatory phase typically occurs over days 0-5. The second stage of wound healing is the proliferative phase during which macrophages and granulocytes invade the wound. Infiltrating fibroblasts begin to produce collagen. The principle characteristics of this phase are epithelialization, angiogenesis, granulation tissue formation and collagen production. The proliferative phase typically occurs over days 3-14. The third phase is the remodeling phase where matrix formation occurs. The fibroblasts, epithelial cells, and endothelial cells continue to produce collagen and collagenase as well as matrix metalloproteases (MMPs) for remodeling. Collagen crosslinking takes place and the wound undergoes contraction. The remodeling phase typically occurs from day 7 to one year.

Compounds and compositions described herein can be used for promoting wound healing (e.g., promoting or accelerating wound closure and/or wound healing, mitigating scar fibrosis of the tissue of and/or around the wound, inhibiting apoptosis of cells surrounding or proximate to the wound). Thus, in certain embodiments, the present invention provides a method for promoting wound healing in a subject, comprising administering to the subject a therapeutically effective amount of a compound, or pharmaceutically acceptable salt or composition thereof The method need not achieve complete healing or closure of the wound; it is sufficient for the method to promote any degree of wound closure. In this respect, the method can be employed alone or as an adjunct to other methods for healing wounded tissue.

The compounds and compositions described herein can be used to treat wounds during the inflammatory (or early) phase, during the proliferative (or middle) wound healing phase, and/or during the remodeling (or late) wound healing phase.

In some embodiments, the subject in need of wound healing is a human or an animal, for example, a horse, a pig, or a rodent, such as a mouse.

In some embodiments, the compounds and compositions described herein useful for wound healing are administered topically, for example, proximate to the wound site, or systemically.

More specifically, the compound or composition described herein can be administered (optionally in combination with other agents) to the wound site by coating the wound or applying a bandage, packing material, stitches, etc., that are coated or treated with the compound or composition described herein. As such, the compounds and compositions described herein can be formulated for topical administration to treat surface wounds. Topical formulations include those for delivery via the mouth (buccal) and to the skin such that a layer of skin (i.e., the epidermis, dermis, and/or subcutaneous layer) is contacted with the compound or composition described herein. Topical delivery systems may be used to administer topical formulations of the compounds and compositions described herein.

Alternatively, the compounds and compositions described herein can be administered at or near the wound site by, for example, injection of a solution, injection of an extended release formulation, or introduction of a biodegradable implant comprising the compound or composition described herein.

The compounds and compositions described herein can be used to treat acute wounds or chronic wounds. A chronic wound results when the normal reparative process is interrupted. Chronic wounds can develop from acute injuries as a result of unrecognized persistent infections or inadequate primary treatment. In most cases however, chronic lesions are the end stage of progressive tissue breakdown owing to venous, arterial, or metabolic vascular disease, pressure sores, radiation damage, or tumors.

In chronic wounds, healing does not occur for a variety of reasons, including improper circulation in diabetic ulcers, significant necrosis, such as in burns, and infections. In these chronic wounds, viability or the recovery phase is often the rate-limiting step. The cells are no longer viable and thus initial recovery phase is prolonged by unfavorable wound bed environment.

Chronic wounds include, but are not limited to the following: chronic ischemic skin lesions; scleroderma ulcers; arterial ulcers; diabetic foot ulcers; pressure ulcers; venous ulcers; non-healing lower extremity wounds; ulcers due to inflammatory conditions; and/or long-standing wounds.

In a particular embodiment, the compounds and compositions described herein can be used for diabetic wound healing or accelerating healing of leg and foot ulcers secondary to diabetes or ischemia in a subject.

In one embodiment, the wound is a surface wound. In another embodiment, the wound is a surgical wound (e.g., abdominal or gastrointestinal surgical wound). In a further embodiment, the wound is a burn. In yet another embodiment, the wound is the result of radiation exposure.

The compounds and compositions described herein can also be used for diabetic wound healing, gastrointestinal wound healing, or healing of an adhesion due, for example, to an operation.

The compounds and compositions described herein can also be used to heal wounds that are secondary to another disease. For example, in inflammatory skin diseases, such as psoriasis and dermatitis, there are numerous incidents of skin lesions that are secondary to the disease, and are caused by deep cracking of the skin, or scratching of the skin. The compounds and compositions described herein can be used to heal wounds that are secondary to these diseases, for example, inflammatory skin diseases, such as psoriasis and dermatitis.

In a further embodiment, the wound is an internal wound. In a specific aspect, the internal wound is a chronic wound. In another specific aspect, the wound is a vascular wound. In yet another specific aspect, the internal wound is an ulcer.

Examples of wounds include, but are not limited to, abrasions, avulsions, blowing wounds (i.e., open pneumothorax), burn wounds, contusions, gunshot wounds, incised wounds, open wounds, penetrating wounds, perforating wounds, puncture wounds, séton wounds, stab wounds, surgical wounds, subcutaneous wounds, diabetic lesions, or tangential wounds. Additional examples of wounds that can be treated by the compounds and compositions described herein include acute conditions or wounds, such as thermal burns, chemical burns, radiation burns, burns caused by excess exposure to ultraviolet radiation (e.g., sunburn); damage to bodily tissues, such as the perineum as a result of labor and childbirth; injuries sustained during medical procedures, such as episiotomies; trauma-induced injuries including cuts, incisions, excoriations; injuries sustained from accidents; post-surgical injuries, as well as chronic conditions, such as pressure sores, bedsores, conditions related to diabetes and poor circulation, and all types of acne. In addition, the wound can include dermatitis, such as impetigo, intertrigo, folliculitis and eczema, wounds following dental surgery; periodontal disease; wounds following trauma; and tumor-associated wounds. Yet other examples of wounds include animal bites, arterial disease, insect stings and bites, bone infections, compromised skin/muscle grafts, gangrene, skin tears or lacerations, skin aging, surgical incisions, including slow or non-healing surgical wounds, intracerebral hemorrhage, aneurysm, dermal asthenia, and post-operation infections.

In preferred embodiments, the wound is selected from the group consisting of a burn wound, an incised wound, an open wound, a surgical or post surgical wound, a diabetic lesion, a thermal burn, a chemical burn, a radiation burn, a pressure sore, a bedsore, and a condition related to diabetes or poor circulation.

The present disclosure also relates to methods and compositions of reducing scar formation during wound healing in a subject. The compounds and compositions described herein can be administered directly to the wound or to cells proximate the wound at an amount effective to reduce scar formation in and/or around the wound.

The wound can include any injury to any portion of the body of a subject. According to embodiments, methods are provided to ameliorate, reduce, or decrease the formation of scars in a subject that has suffered a burn injury. According to preferred embodiments, methods are provided to treat, reduce the occurrence of, or reduce the probability of developing hypertrophic scars in a subject that has suffered an acute or chronic wound or injury.

Other Disorders

Compounds and compositions described herein may also be used to treat disorders of abnormal tissue growth and fibrosis including dilative cardiomyopathy, hypertrophic cardiomyopathy, restrictive cardiomyopathy, pulmonary fibrosis, hepatic fibrosis, glomerulonephritis, and other renal disorders.

Combination Radiation Therapy

Compounds and compositions described herein are useful as radiosensitizers. Therefore, compounds and compositions described herein can be administered in combination with radiation therapy. Radiation therapy is the medical use of high-energy radiation (e.g., x-rays, gamma rays, charged particles) to shrink tumors and kill malignant cells, and is generally used as part of cancer treatment. Radiation therapy kills malignant cells by damaging their DNA.

Radiation therapy can be delivered to a patient in several ways. For example, radiation can be delivered from an external source, such as a machine outside the patient's body, as in external beam radiation therapy. External beam radiation therapy for the treatment of cancer uses a radiation source that is external to the patient, typically either a radioisotope, such as $^{60}$Co, $^{137}$Cs, or a high energy x-ray source, such as a linear accelerator. The external source produces a collimated beam directed into the patient to the tumor site. External-source radiation therapy avoids some of the problems of internal-source radiation therapy, but it undesirably and necessarily irradiates a significant volume of non-tumorous or healthy tissue in the path of the radiation beam along with the tumorous tissue.

The adverse effect of irradiating of healthy tissue can be reduced, while maintaining a given dose of radiation in the tumorous tissue, by projecting the external radiation beam into the patient at a variety of "gantry" angles with the beams converging on the tumor site. The particular volume elements of healthy tissue, along the path of the radiation beam, change, reducing the total dose to each such element of healthy tissue during the entire treatment.

The irradiation of healthy tissue also can be reduced by tightly collimating the radiation beam to the general cross section of the tumor taken perpendicular to the axis of the radiation beam. Numerous systems exist for producing such a circumferential collimation, some of which use multiple sliding shutters which, piecewise, can generate a radio-opaque mask of arbitrary outline.

For administration of external beam radiation, the amount can be at least about 1 Gray (Gy) fractions at least once every other day to a treatment volume. In a particular embodiment, the radiation is administered in at least about 2 Gray (Gy) fractions at least once per day to a treatment volume. In another particular embodiment, the radiation is administered in at least about 2 Gray (Gy) fractions at least once per day to a treatment volume for five consecutive days per week. In another particular embodiment, radiation is administered in 10 Gy fractions every other day, three times per week to a treatment volume. In another particular embodiment, a total of at least about 20 Gy is administered to a patient in need thereof. In another particular embodiment, at least about 30 Gy is administered to a patient in need thereof. In another particular embodiment, at least about 40 Gy is administered to a patient in need thereof.

Typically, the patient receives external beam therapy four or five times a week. An entire course of treatment usually lasts from one to seven weeks depending on the type of cancer and the goal of treatment. For example, a patient can receive a dose of 2 Gy/day over 30 days.

Internal radiation therapy is localized radiation therapy, meaning the radiation source is placed at the site of the tumor or affected area. Internal radiation therapy can be delivered by placing a radiation source inside or next to the area requiring treatment. Internal radiation therapy is also called brachytherapy. Brachytherapy includes intracavitary treatment and interstitial treatment. In intracavitary treatment, containers that hold radioactive sources are put in or near the tumor. The sources are put into the body cavities. In interstitial treatment, the radioactive sources alone are put into the tumor. These radioactive sources can stay in the patient permanently. Typically, the radioactive sources are removed from the patient after several days. The radioactive sources are in containers.

There are a number of methods for administration of a radiopharmaceutical agent. For example, the radiopharmaceutical agent can be administered by targeted delivery or by systemic delivery of targeted radioactive conjugates, such as a radiolabeled antibody, a radiolabeled peptide and a liposome delivery system. In one particular embodiment of targeted delivery, the radiolabelled pharmaceutical agent can be a radiolabelled antibody. See, for example, Ballangrud A. M., et al. Cancer Res., 2001; 61:2008-2014 and Goldenber, D. M. J. Nucl. Med., 2002; 43(5):693-713, the contents of which are incorporated by reference herein.

In another particular embodiment of targeted delivery, the radiopharmaceutical agent can be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. See, for example, Emfietzoglou D, Kostarelos K, Sgouros G. An analytical dosimetry study for the use of radionuclide-liposome conjugates in internal radiotherapy. J Nucl Med 2001; 42:499-504, the contents of which are incorporated by reference herein.

In yet another particular embodiment of targeted delivery, the radiolabeled pharmaceutical agent can be a radiolabeled peptide. See, for example, Weiner R E, Thakur M L. Radiolabeled peptides in the diagnosis and therapy of oncological diseases. Appl Radiat Isot 2002 November; 57(5): 749-63, the contents of which are incorporated by reference herein.

In addition to targeted delivery, brachytherapy can be used to deliver the radiopharmaceutical agent to the target site. Brachytherapy is a technique that puts the radiation sources as close as possible to the tumor site. Often the source is inserted directly into the tumor. The radioactive sources can be in the form of wires, seeds or rods. Generally, cesium, iridium or iodine are used.

Systemic radiation therapy is another type of radiation therapy and involves the use of radioactive substances in the blood. Systemic radiation therapy is a form of targeted therapy. In systemic radiation therapy, a patient typically ingests or receives an injection of a radioactive substance, such as radioactive iodine or a radioactive substance bound to a monoclonal antibody.

A "radiopharmaceutical agent," as defined herein, refers to a pharmaceutical agent which contains at least one radiation-emitting radioisotope. Radiopharmaceutical agents are routinely used in nuclear medicine for the diagnosis and/or therapy of various diseases. The radiolabelled pharmaceutical agent, for example, a radiolabelled antibody, contains a radioisotope (RI) which serves as the radiation source. As contemplated herein, the term "radioisotope" includes metallic and non-metallic radioisotopes. The radioisotope is chosen based on the medical application of the radiolabeled pharmaceutical agents. When the radioisotope is a metallic radioisotope, a chelator is typically employed to bind the metallic radioisotope to the rest of the molecule. When the radioisotope is a non-metallic radioisotope, the non-metallic radioisotope is typically linked directly, or via a linker, to the rest of the molecule.

As used herein, a "metallic radioisotope" is any suitable metallic radioisotope useful in a therapeutic or diagnostic procedure in vivo or in vitro. Suitable metallic radioisotopes include, but are not limited to: Actinium-225, Antimony-124, Antimony-125, Arsenic-74, Barium-103, Barium-140, Beryllium-7, Bismuth-206, Bismuth-207, Bismuth212, Bismuth213, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-60, Copper-62, Copper-64, Copper-67, Erbium-169, Europium-152, Gallium-64, Gallium-67, Gallium-68, Gadolinium153, Gadolinium-157 Gold-195, Gold-199, Hafnium-175, Hafnium-175-181, Holmium-166, Indium-110, Indium-111, Iridium-192, Iron 55, Iron-59, Krypton85, Lead-203, Lead-210, Lutetium-177, Manganese-54, Mercury-197, Mercury203, Molybdenum-99, Neodymium-147, Neptunium-237, Nickel-63, Niobium95, Osmium-185+191, Palladium-103, Palladium-109, Platinum-195m, Praseodymium-143, Promethium-147, Promethium-149, Protactinium-233, Radium-226, Rhenium-186, Rhenium-188, Rubidium-86, Ruthenium-97, Ruthenium-103, Ruthenium-105, Ruthenium-106, Samarium-153, Scandium-44, Scandium-46, Scandium-47, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, Zirconium-89, and Zirconium-95.

As used herein, a "non-metallic radioisotope" is any suitable nonmetallic radioisotope (non-metallic radioisotope) useful in a therapeutic or diagnostic procedure in vivo or in vitro. Suitable non-metallic radioisotopes include, but are not limited to: Iodine-131, Iodine-125, Iodine-123, Phosphorus-32, Astatine-211, Fluorine-18, Carbon-11, Oxygen-15, Bromine-76, and Nitrogen-13.

Identifying the most appropriate isotope for radiotherapy requires weighing a variety of factors. These include tumor uptake and retention, blood clearance, rate of radiation delivery, half-life and specific activity of the radioisotope, and the feasibility of large-scale production of the radioisotope in an economical fashion. The key point for a therapeutic radiopharmaceutical is to deliver the requisite amount of radiation dose to the tumor cells and to achieve a cytotoxic or tumoricidal effect while not causing unmanageable side-effects.

It is preferred that the physical half-life of the therapeutic radioisotope be similar to the biological half-life of the radiopharmaceutical at the tumor site. For example, if the half-life of the radioisotope is too short, much of the decay will have occurred before the radiopharmaceutical has reached maximum target/background ratio. On the other hand, too long a half-life could cause unnecessary radiation dose to normal tissues. Ideally, the radioisotope should have a long enough half-life to attain a minimum dose rate and to irradiate all the cells during the most radiation sensitive phases of the cell cycle. In addition, the half-life of a radioisotope has to be long enough to allow adequate time for manufacturing, release, and transportation.

Other practical considerations in selecting a radioisotope for a given application in tumor therapy are availability and quality. The purity has to be sufficient and reproducible, as trace amounts of impurities can affect the radiolabeling and radiochemical purity of the radiopharmaceutical.

The target receptor sites in tumors are typically limited in number. As such, it is preferred that the radioisotope have high specific activity. The specific activity depends primarily on the production method. Trace metal contaminants must be minimized as they often compete with the radioisotope for the chelator and their metal complexes compete for receptor binding with the radiolabeled chelated agent.

The type of radiation that is suitable for use in the methods of the present invention can vary. For example, radiation can be electromagnetic or particulate in nature. Electromagnetic radiation useful in the practice of this invention includes, but is not limited to, x-rays and gamma rays. Particulate radiation useful in the practice of this invention includes, but is not limited to, electron beams (beta particles), protons beams, neutron beams, alpha particles, and negative pi mesons. The radiation can be delivered using conventional radiological treatment apparatus and methods, and by intraoperative and stereotactic methods. Additional discussion regarding radiation treatments suitable for use in the practice of this invention can be found throughout Steven A. Leibel et al., Textbook of Radiation Oncology (1998) (publ. W. B. Saunders Company), and particularly in Chapters 13 and 14. Radiation can also be delivered by other methods such as targeted delivery, for example by radioactive "seeds," or by systemic delivery of targeted radioactive conjugates. J. Padawer et al., Combined Treatment with Radioestradiol lucanthone in Mouse C3HBA Mammary Adenocarcinoma and with Estradiol lucanthone in an Estrogen Bioassay, Int. J. Radiat. Oncol. Biol. Phys. 7:347-357 (1981). Other radiation delivery methods can be used in the practice of this invention.

For tumor therapy, both α and β-particle emitters have been investigated. Alpha particles are particularly good cytotoxic agents because they dissipate a large amount of energy within one or two cell diameters. The n-particle emitters have relatively long penetration range (2-12 mm in the tissue) depending on the energy level. The long-range penetration is particularly important for solid tumors that have heterogeneous blood flow and/or receptor expression. The β-particle emitters yield a more homogeneous dose distribution even when they are heterogeneously distributed within the target tissue.

In a particular embodiment, therapeutically effective amounts of the compounds and compositions described herein are administered in combination with a therapeutically effective amount of radiation therapy to treat cancer (e.g., lung cancer, such as non-small cell lung cancer). The amount of radiation necessary can be determined by one of skill in the art based on known doses for a particular type of cancer. See, for example, Cancer Medicine 5$^{th}$ ed., Edited by R. C. Bast et al., July 2000, BC Decker.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXEMPLIFICATION

Abbreviations aq. Aqueous
CI Chemical ionization
DEA Diethylamine
DIPEA N,N-Diisopropyl ethylamine
DMF Dimethylformamide
EDTA ethylenediamine tetraacetic acid
EI electron impact ionization
equiv(s). equivalent(s)
EtOH Ethanol
Et Ethyl
h hour(s)
LC-MS liquid chromatography-mass spectrometry
LRMS low resolution mass spectrometry
min Minute(s)
NMR Nuclear magnetic resonance
PEG polyethylene glycol
RT, rt, r.t. Room temperature
SDS-PAGE Sodium dodecyl sulfate-polyacrylamide gel electrophoresis
T3P Propylphosphonic anhydride (available from Archimica)

Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "Advanced Organic Chemistry", March, 4th ed. McGraw Hill (1992) or, "Organic Synthesis", Smith, McGraw Hill, (1994). Techniques for purification of intermediates and final products include for example, straight and reversed phase chromatography on column or rotating plate, recrystallisation, distillation and liquid-liquid or solid-liquid extraction, which will be readily understood by the one skilled in the art. The definitions of substituents and groups are as in formula I except where defined differently. The term "room temperature" and "ambient temperature" shall mean, unless otherwise specified, a temperature between 16 and 25° C. The term "reflux" shall mean, unless otherwise stated, in reference to an employed solvent a temperature at or above the boiling point of named solvent.

It is understood that compounds for which a specific synthesis is not shown can be made in accordance with the general procedures disclosed herein.

Example 1

Synthetic Methods

Method A: Synthesis of Common Intermediates I and II

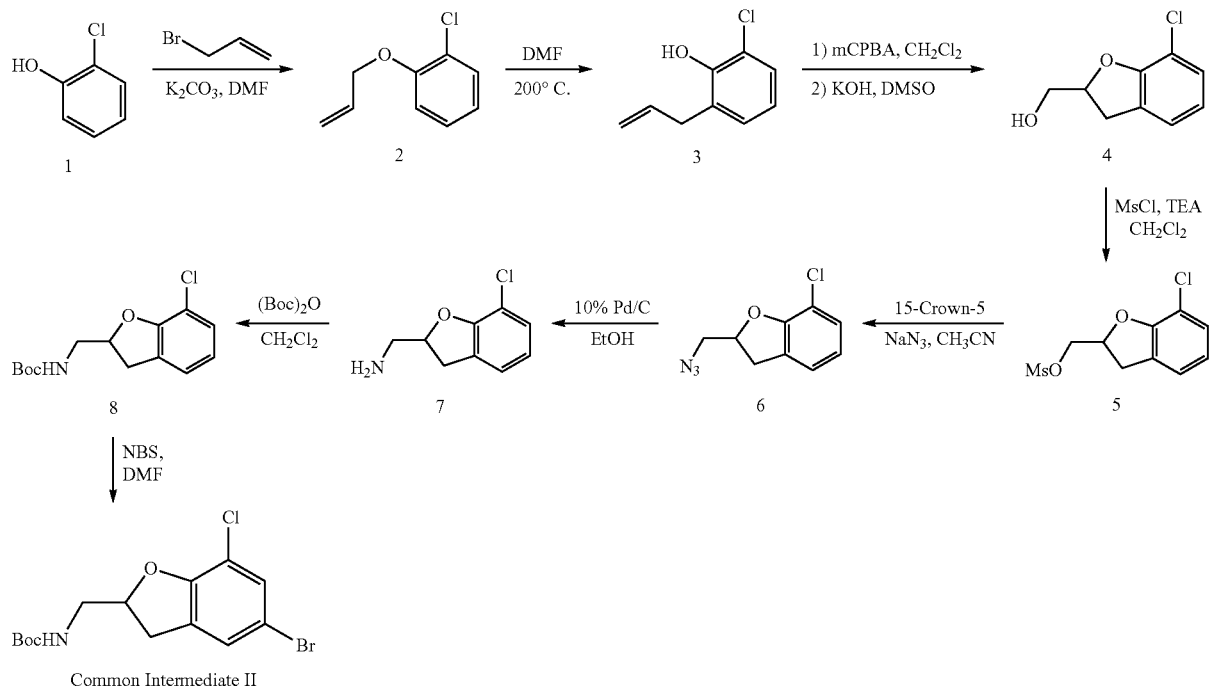

concentrated under reduced pressure to give 5 g of 1-(allyloxy)-2-chlorobenzene 2, which was used in the next step without further purification. $^{1}$H NMR (400 MHz, CDCl$_3$) δ 7.37-7.39 (d, J=6.4 Hz, 1H), 7.19-7.28 (m, 1H), 6.89-6.95 (m, 2H), 6.04-6.14 (m, 1H), 5.51-5.47 (d, J=17.2 Hz, 1H), 5.31-5.35 (d, J=14.8 Hz, 1H), 4.62-4.64 (m, 2H).

Synthesis of 1-(allyloxy)-2-chlorobenzene (2)

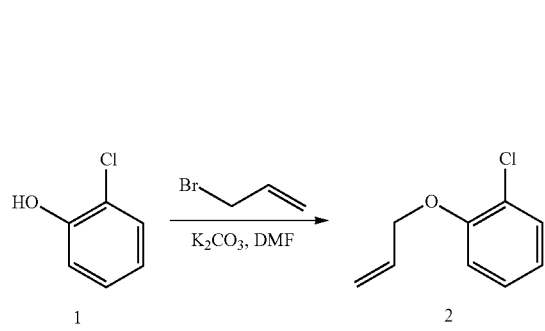

2-Chlorophenol 1 (5 g, 38.89 mmol) was dissolved in DMF (10 mL). K$_2$CO$_3$ (16.3 g, 116.68 mmol) and allyl bromide (9.41 g, 77.79 mmol) were added at 25° C. and the reaction mixture was stirred at 110° C. for 16 h. The reaction mixture was transferred into iced water and extracted with ethyl acetate (50 mL×3). The combined organic layers were washed with brine, dried over anhydrous Na$_2$SO$_4$, and Synthesis of 2-allyl-6-chlorophenol (3)

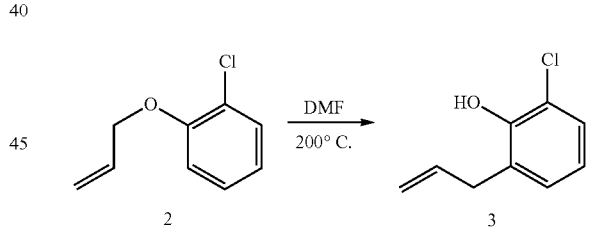

1-(Allyloxy)-2-chlorobenzene 2 (5 g, 29.65 mmol) was dissolved in DMF (5 mL) and the reaction mixture was heated at 200° C. for 15 h. The reaction mixture was cooled to room temperature, transferred into iced water and extracted with ethyl acetate (30 mL×3). The combined organic layers were washed with brine, dried over anhydrous Na$_2$SO$_4$ and concentrated under reduced pressure to give 5.3 g of crude 2-allyl-6-chlorophenol 3 which was purified by chromatography (0-3% ethyl acetate/n-hexane) to obtain 2.5 g of 2-allyl-6-chlorophenol 3 (50% yield). $^{1}$H NMR (400 MHz, CDCl$_3$) δ 7.20-7.23 (d, J=12.8 Hz, 1H), 7.06-7.08 (d, J=7.6 Hz, 1H), 6.86-6.81 (t, 1H), 5.97-6.07 (m, 1H), 5.09-5.14 (m, 2H), 3.95-3.96 (d, J=6.4 Hz, 2H).

Synthesis of (7-chloro-2,3-dihydrobenzofuran-2-yl)methanol (4)

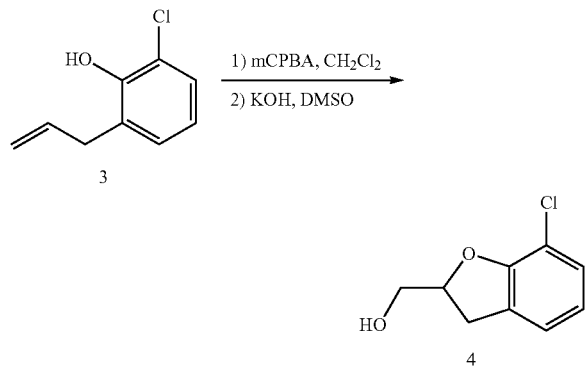

2-Allyl-6-chlorophenol 3 (0.4 g, 2.37 mmol) was dissolved in dichloromethane (4 mL). mCPBA (0.457 g, 3.3 mmol) was added at 0° C. and stirred at room temperature for 4 h. The reaction mixture was diluted with ethyl acetate (25 mL) and washed with saturated sodium bicarbonate solution, saturated sodium thiosulphate solution, followed by brine, dried over anhydrous $Na_2SO_4$, and concentrated under reduced pressure to give 0.4 g of the crude epoxy intermediate. The crude epoxy intermediate was then dissolved in DMSO (5 mL) and cooled to 0° C. where KOH (0.17 g, 3.0 mmol) in 1.5 mL water was added. The reaction mixture was allowed to warm to room temperature where it was stirred for 4 h. The reaction mixture was then transferred into iced water and extracted with ethyl acetate (25 mL×3). The combined organic layers were washed with brine, dried over anhydrous $Na_2SO_4$, and concentrated under reduced pressure to obtain 150 mg of the crude product which was purified by chromatography (0-30% ethyl acetate/n-hexane) to give 90 mg of (7-chloro-2,3-dihydrobenzofuran-2-yl) methanol 4 (20% yield). $^1$H NMR (400 MHz, $CDCl_3$) δ 7.13-7.15 (d, J=8 Hz, 1H), 7.07-7.09 (d, J=7.2 Hz, 1H), 6.79-6.83 (t, 1H), 5.00-5.06 (m, 1H), 3.94-3.97 (d, J=12 Hz, 1H), 3.77-3.80 (d, J=12 Hz, 1H), 3.30-3.36 (m, 1H), 3.15-3.20 (m, 1H). LCMS: m/z 183.07 [M−H]$^-$, $t_R$=5.65 min.

Synthesis of (7-chloro-2,3-dihydrobenzofuran-2-yl)methyl methanesulfonate (5)

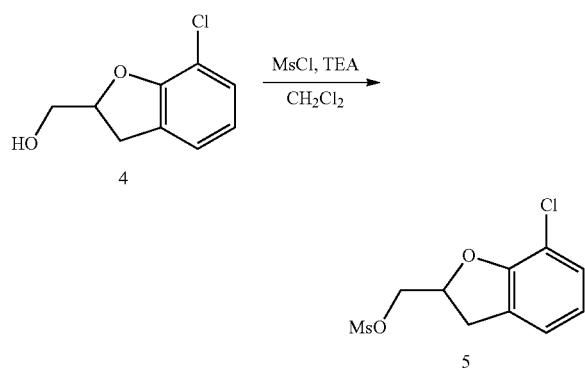

(7-Chloro-2,3-dihydrobenzofuran-2-yl)methanol 4 (4 g, 21.67 mmol) was dissolved in dichloromethane (40 mL). Methane sulfonyl chloride (3.72 g, 32.50 mmol) and triethylamine (2.85 g, 28.17 mmol) were added at 0° C. and the reaction mixture was allowed to warm to room temperature where it was stirred for 4 h. The reaction mixture was transferred into iced water and extracted with dichloromethane (200 mL×3). The combined organic layers were washed with brine, dried over anhydrous $Na_2SO_4$, and concentrated under reduced pressure to give 5 g of crude (7-chloro-2,3-dihydrobenzofuran-2-yl)methyl methanesulfonate 5, which was used in the next step without further purification. $^1$H NMR (400 MHz, $CDCl_3$) δ 7.15-7.17 (d, J=8 Hz, 1H), 7.09-7.11 (d, J=6.4 Hz, 1H), 6.83-6.85 (t, 1H), 5.14-5.20 (m, 1H), 4.43-4.52 (m, 2H), 3.29-3.49 (m, 1H), 3.11-3.20 (m, 2H), 3.03 (s, 3H). LCMS: m/z 280.06 [M+18]$^+$, $t_R$=1.90 min.

Synthesis of 2-(azidomethyl)-7-chloro-2,3-dihydrobenzofuran (6)

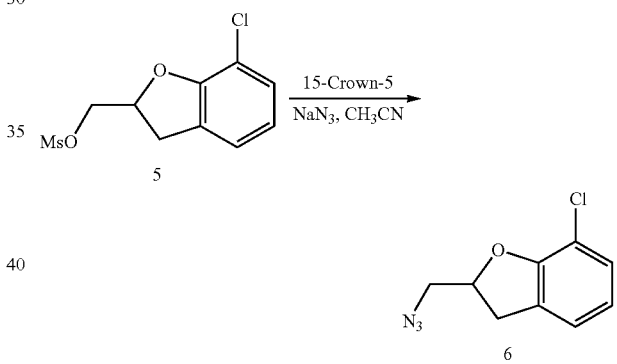

(7-Chloro-2,3-dihydrobenzofuran-2-yl)methyl methanesulfonate 5 (0.5 g, 1.9 mmol) was dissolved in acetonitrile (2.5 mL). Sodium azide (0.247 g, 3.81 mmol) and 15-crown-5 (15 mg) were added at room temperature. The reaction mixture was refluxed at 80° C. for 8 h, cooled to room temperature, transferred into iced water, and extracted with ethyl acetate (30 mL×3). The combined organic layers were washed with brine, dried over anhydrous $Na_2SO_4$, and concentrated under reduced pressure to give 0.5 g of the crude product, which was purified by chromatography (0-10% ethyl acetate/n-hexane) to obtain 0.2 g of 2-(azidomethyl)-7-chloro-2,3-dihydrobenzofuran 6 (50% yield). $^1$H NMR (400 MHz, $CDCl_3$) δ 7.17-7.19 (d, J=10.4 Hz, 1H), 7.05-7.07 (d, J=8.4 Hz, 1H), 6.81-6.85 (t, 1H), 5.03-5.11 (m, 1H), 3.59-3.63 (dd, $J_1$=4.4 Hz, $J_2$=4 Hz, 1H), 3.50-3.54 (dd, $J_1$,$J_2$=5.6 Hz, 1H), 3.21-3.42 (m, 1H), 3.01-3.19 (m, 1H).

Synthesis of (7-chloro-2,3-dihydrobenzofuran-2-yl)methanamine (7)

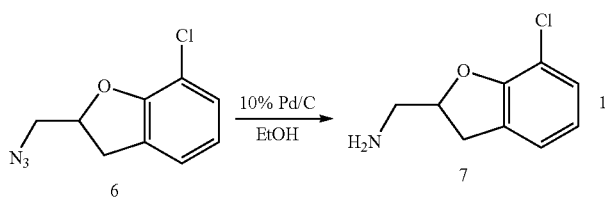

2-(Azidomethyl)-7-chloro-2,3-dihydrobenzofuran 6 (3.4 g, 0.95 mmol) was dissolved in ethanol (10 mL). 10% Pd/C (50% wet (60 mg)) was added and hydrogen gas was purged at room temperature for 1 h. The reaction mixture was filtered and the filtrate was concentrated under reduced pressure to give 0.15 g of the crude (7-chloro-2,3-dihydrobenzofuran-2-yl)methanamine 7, which was used without further purification in the next step. $^1$H NMR (400 MHz, CDCl$_3$) δ 7.12-7.14 (d, J=8 Hz, 1H), 7.06-7.07 (d, J=7.2 Hz, 1H), 6.81-6.85 (t, 1H), 4.90-4.97 (m, 1H), 3.29-3.39 (m, 1H), 2.94-3.09 (m, 3H). LCMS: m/z 184.01 [M+H]$^+$, t$_R$=0.46 min.

Synthesis of tert-butyl (7-chloro-2,3-dihydrobenzofuran-2-yl)methylcarbamate (8)

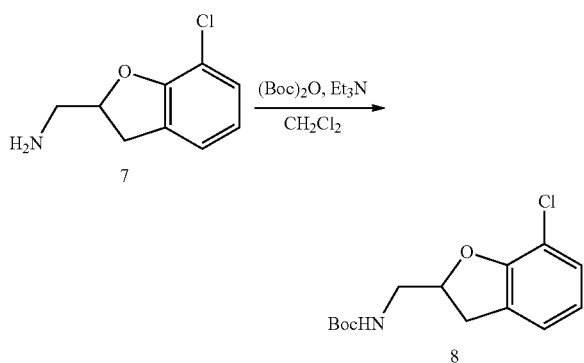

(7-Chloro-2,3-dihydrobenzofuran-2-yl)methanamine 7 (0.15 g, 0.816 mmol) was dissolved in dichloromethane (10 mL) and boc anhydride (0.196 mg, 0.898 mmol) was added at 0° C. Triethylamine (82.66 mg, 0.816 mmol) was added and the reaction mixture was stirred at room temperature for 4 h. The reaction mixture was transferred into iced water and extracted with dichloromethane (15 mL×3). The combined organic layers were washed with brine, dried over anhydrous Na$_2$SO$_4$, and concentrated under reduced pressure to give 0.2 g of crude tert-butyl (7-chloro-2,3-dihydrobenzofuran-2-yl)methylcarbamate 8 which was used without further purification in the next step. $^1$H NMR (400 MHz, CDCl$_3$) δ 7.12-7.14 (d, J=8 Hz, 1H), 7.06-7.07 (d, J=7.2 Hz, 1H), 6.81-6.85 (t, 1H), 4.90-4.97 (m, 1H), 3.29-3.39 (m, 1H), 2.94-3.09 (m, 3H), 1.49 (s, 9H). LCMS: m/z 228.07 [M−56]$^-$, t$_R$=2.28.

Synthesis of tert-butyl (5-bromo-7-chloro-2,3-dihydrobenzofuran-2-yl)methylcarbamate (Common Intermediate II)

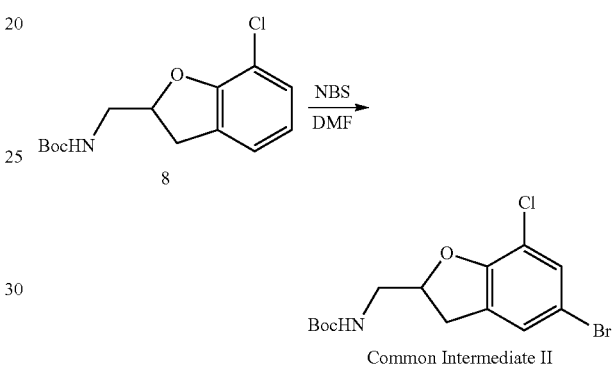

tert-Butyl(7-chloro-2,3-dihydrobenzofuran-2-yl)methylcarbamate 8 (0.20 g, 0.704 mmol) was dissolved in DMF (4 mL). NBS (0.150 mg, 0.845 mmol) was added at room temperature and stirred for 12 h. The reaction mixture was transferred into iced water and extracted with ethyl acetate (25 mL×3). The combined organic layers were washed with brine, dried over anhydrous Na$_2$SO$_4$, and concentrated under reduced pressure to give 0.21 g of the crude tert-butyl(5-bromo-7-chloro-2,3-dihydrobenzofuran-2-yl)methylcarbamate (Common Intermediate II), which was used in the next step without further purification. $^1$H NMR (400 MHz, CDCl$_3$) δ 7.21 (s, 1H), 7.18 (s, 1H), 4.97-5.02 (m, 1H), 3.59-3.63 (m, 1H), 3.30-3.43 (m, 2H), 3.02-3.08 (m, 1H), 1.47 (s, 9H). LCMS: m/z 306 [M−56]$^-$, t$_R$=2.54 min.

Method B: Synthesis of Common Intermediates I and II

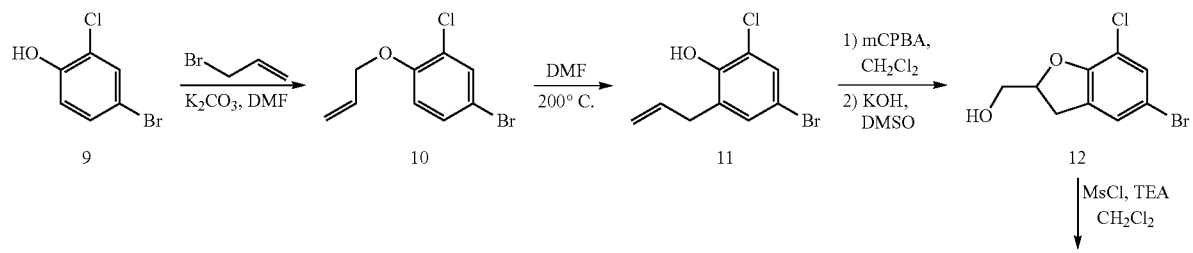

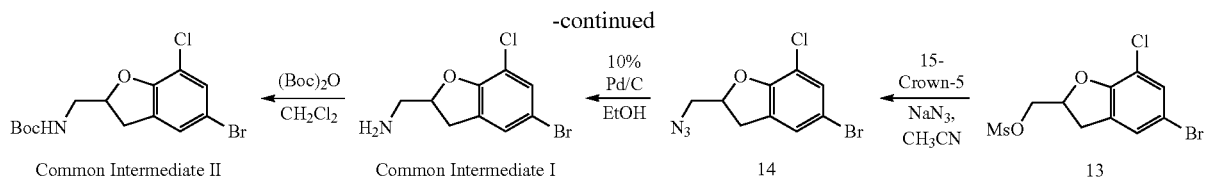

Synthesis of 1-(allyloxy)-4-bromo-2-chlorobenzene (10)

Synthesis of (5-bromo-7-chloro-2,3-dihydrobenzofuran-2-yl)methanol (12)

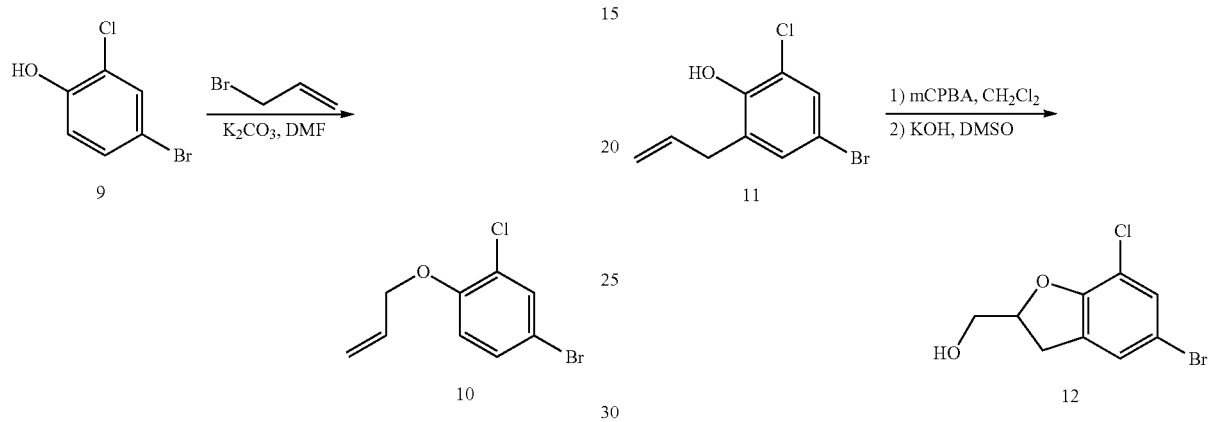

Intermediate 10 was synthesized similar to intermediate 2 as described in Method A. (45% yield). ¹H NMR (400 MHz, CDCl₃) δ 7.5-7.52 (m, 1H), 7.3-7.33 (dd, J=2.4 Hz, J=8.8 Hz, 1H), 6.79-6.81 (d, J=8.8 Hz, 1H), 6.01-6.1 (m, 1H), 5.32-5.49 (m, 2H), 4.62-4.64 (m, 2H).

Intermediate 12 was synthesized similar to intermediate 4 as described in Method A. (42% yield). ¹H NMR (400 MHz, CDCl₃) δ 6.79-7.19 (m, 2H), 5.01-5.07 (m, 1H), 4.13-4.14 (m, 2H), 3.92-3.96 (m, 1H), 3.29-3.35 (m, 1H), 3.14-3.21 (m, 1H). LCMS: m/z 308.69 [M+45]⁺, $t_R$=2.0 min.

Synthesis of 2-allyl-4-bromo-6-chlorophenol (11)

Synthesis of (5-bromo-7-chloro-2,3-dihydrobenzofuran-2-yl)methyl methanesulfonate (13)

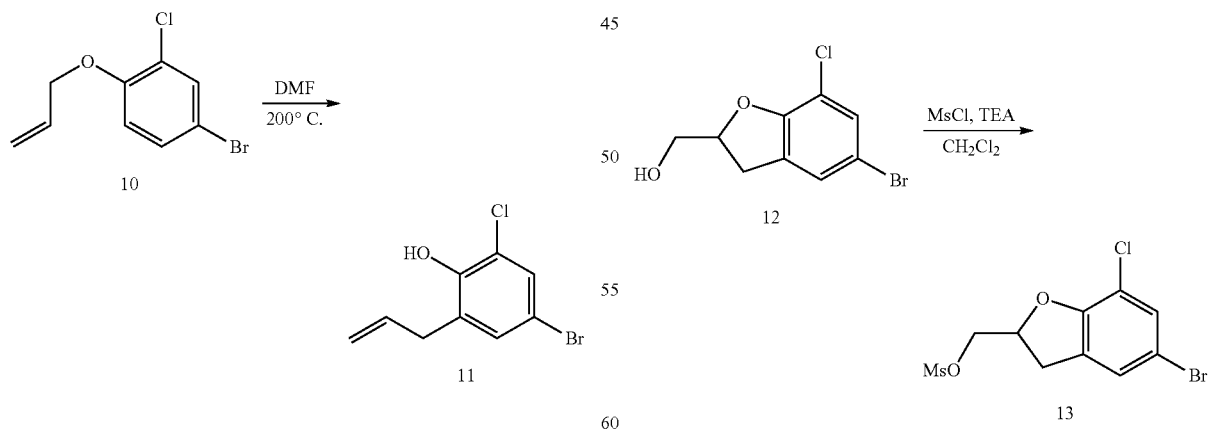

Intermediate 11 was synthesized similar to intermediate 3 as described in Method A. (50% yield). ¹H NMR (400 MHz, CDCl₃) δ 7.17-7.36 (d, 2H), 5.91-6.05 (m, 1H), 5.09-5.16 (m, 2H), 3.41-3.46 (m, 2H). LCMS: m/z 245.29 [M+H]⁺, $t_R$=2.45 min.

Intermediate 13 was synthesized similar to intermediate 5 as described in Method A. (62% yield). ¹H NMR (400 MHz, CDCl₃) δ 7.11-7.31 (m, 2H), 5.13-5.2 (m, 1H), 4.41-4.51 (m, 2H), 3.42-3.48 (m, 1H), 3.22-3.27 (m, 1H), 3.11 (s, 3H). LCMS: m/z 386.9 [M+45]⁺, $t_R$=2.25 min.

Synthesis of 2-(azidomethyl)-5-bromo-7-chloro-2,3-dihydrobenzofuran (14)

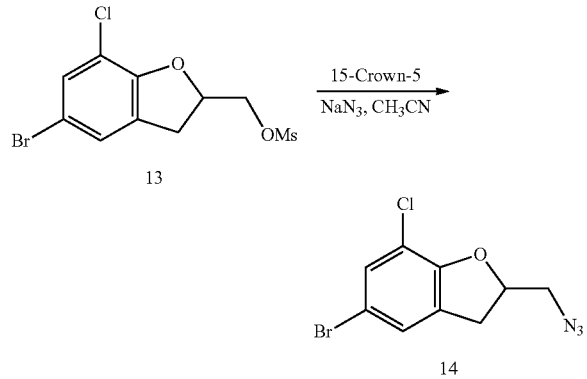

Intermediate 14 was synthesized similar to intermediate 6 as described in Method A. (54% yield). $^1$H NMR (400 MHz, DMSO-d6) δ 7.49-7.53 (d, 2H), 5.13-5.19 (m, 1H), 3.70-3.74 (d, 1H), 3.46-3.59 (d, 1H), 3.40-3.46 (m, 1H), 3.04-3.09 (d, 1H).

Synthesis of (5-bromo-7-chloro-2,3-dihydrobenzofuran-2-yl)methanamine (Common Intermediate I)

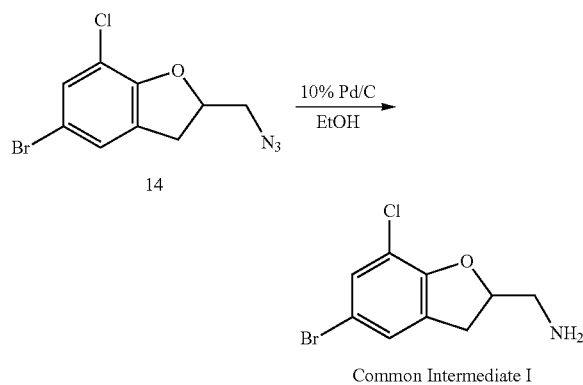

Common Intermediate I was synthesized similar to intermediate 7 as described in Method A. (50% yield). $^1$H NMR (400 MHz, DMSO-d$_6$) δ 7.29-7.35 (d, 2H), 4.90-4.92 (m, 1H), 3.29-3.39 (m, 1H), 2.94-3.09 (m, 3H). LCMS: m/z 264.07 [M+H]$^+$, $t_R$=1.25 min.

General Procedure 1—Suzuki Coupling

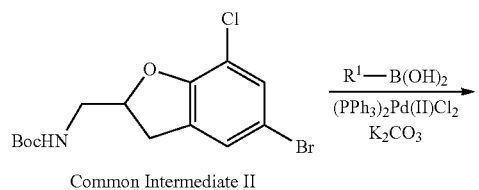

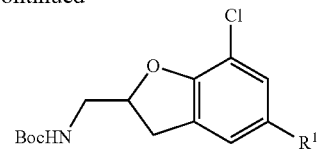

The Common Intermediate II (0.5 g, 1.38 mmol) was dissolved in dioxane (12 mL) and degassed for 5 min. Tetrakis(triphenylphosphine)palladium (0) (100 mg, 20 mol %) and the respective boronic acid R$^1$B(OH)$_2$ (2.07 mmol) were added at room temperature and stirred for 5 min. A degassed solution of K$_2$CO$_3$ (2.76 mmol) in 2 mL of water was added and the reaction mixture was irradiated under microwave for 30 min at 100° C. The reaction mixture was transferred into water and extracted with ethyl acetate (50 mL×3). The combined organic layers were washed with brine, dried over anhydrous Na$_2$SO$_4$, and concentrated under reduced pressure to give the crude product, which was purified by chromatography (0-50% ethyl acetate/n-hexane).

General Procedure 2—Removal of Boc Protecting Group

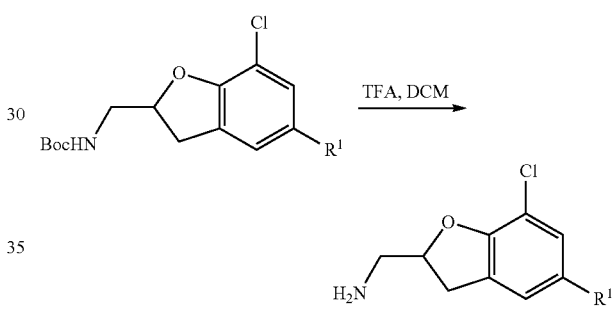

The Boc protected amine (1 eq) was dissolved in CH$_2$Cl$_2$ (2 mL for every 100 mg of the starting material). TFA (10 eq) was added at 0° C. The reaction mixture was stirred at room temperature for 12 h. The reaction mixture was diluted with CH$_2$Cl$_2$, neutralized with saturated sodium bicarbonate solution (150 mL), washed with water and brine, dried over anhydrous Na$_2$SO$_4$, and concentrated under reduced pressure to give the crude product, which was used without further purification in the next step.

General Procedure 3—Amide Bond Formation

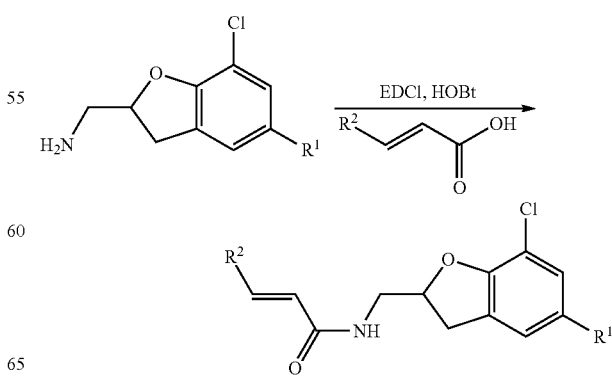

The primary amine (2.60 mmol) was dissolved in CH$_2$Cl$_2$ (20 mL) and the carboxylic acid (3.12 mmol) was added at 0° C. EDCl (3.12 mmol) and HOBt (3.12 mmol) were added to this reaction mixture at 0° C. followed by DIPEA (3.12 mmol) dropwise. The reaction mixture was allowed to warm to room temperature and stirred further for 4 h. The reaction mixture was transferred into water (100 mL) and extracted with CH$_2$Cl$_2$ (25 mL×3). The combined organic layers were washed with brine, dried over anhydrous Na$_2$SO$_4$ and concentrated under reduced pressure to give crude product which was purified by chromatography (methanol/CH$_2$Cl$_2$).

Synthesis of (E)-N-((7-chloro-5-p-tolyl-2,3-dihydrobenzofuran-2-yl)methyl)-3-(pyridin-3-yl) acrylamide (15)

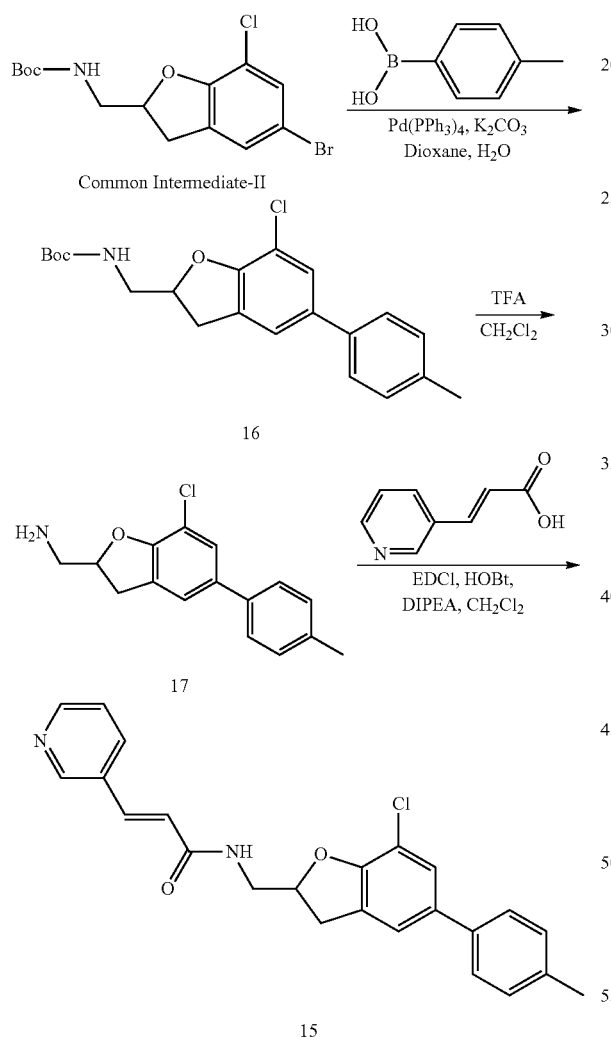

tert-Butyl (7-chloro-5-p-tolyl-2,3-dihydrobenzofuran-2-yl)methylcarbamate 16 was synthesized from common intermediate II using General Procedure 1. Yield (50%). $^1$H NMR (400 MHz, CDCl$_3$) δ 7.27-7.41 (m, 2H), 7.25 (s, 2H), 7.23 (s, 2H), 5.00-5.06 (m, 1H), 3.63-3.69 (m, 1H), 3.46-3.60 (m, 2H), 3.06-3.12 (m, 1H), 2.29 (s, 3H), 1.47 (s, 9H). LCMS: m/z 318.2 [M−56]$^+$, t$_R$=2.83 min.

(7-chloro-5-p-tolyl-2,3-dihydrobenzofuran-2-yl)methanamine 17 was synthesized using General Procedure 2. Yield (79%). $^1$H NMR (400 MHz, CDCl$_3$) δ 7.35-7.41 (m, 3H), 7.20-7.34 (m, 3H), 4.99 (s, 1H), 3.44-3.79 (m, 1H), 3.55-3.42 (m, 1H), 3.01-3.21 (m, 2H), 2.40 (s, 3H). LCMS: m/z 274.26 [M+H]$^+$, t$_R$=1.73 min.

(E)-N-((7-chloro-5-p-tolyl-2,3-dihydrobenzofuran-2-yl)methyl)-3-(pyridin-3-yl) acrylamide 15 was synthesized using General Procedure 3. Yield (48%). $^1$H NMR (400 MHz, DMSO-d$_6$) δ 8.77 (s, 1H), 8.53-8.56 (m, 2H), 7.98-8.00 (m, 1H), 7.43-7.53 (m, 6H), 7.24 (s, 1H), 7.22 (s, 1H), 6.28-6.86 (d, J=16 Hz, 1H), 5.05-5.09 (m, 1H), 3.57-3.63 (m, 2H), 3.39-3.54 (m, 1H), 3.07-3.13 (m, 1H), 2.32 (s, 3H). LCMS: m/z 405.15 [M+H]$^+$, t$_R$=2.24 min.

Synthesis of (E)-N-((7-chloro-5-(2-fluorophenyl)-2,3-dihydrobenzofuran-2-yl)methyl)-3-(pyridin-3-yl) acrylamide (18)

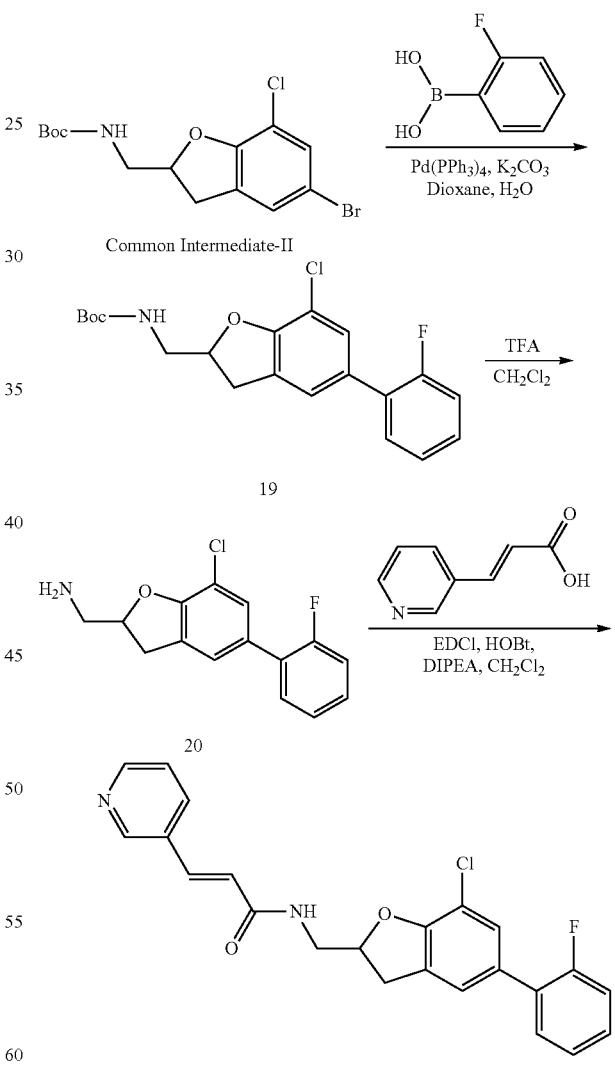

tert-Butyl (7-chloro-5-(2-fluorophenyl)-2,3-dihydrobenzofuran-2-yl)methylcarbamate 19 was synthesized using General Procedure 1. Yield (58%). $^1$H NMR (400 MHz, CDCl$_3$) δ 7.26-7.34 (m, 4H), 7.12-7.22 (m, 2H), 5.06 (s, 1H), 3.63-3.69 (m, 1H), 3.37-3.47 (m, 2H), 3.12-3.14 (m, 1H), 1.47 (s, 9H). LCMS: m/z 322.06 [M−56]⁺, t_R=2.65 min.

(7-chloro-5-(2-fluorophenyl)-2,3-dihydrobenzofuran-2-yl)methanamine 20 was synthesized using General Procedure 2. Yield (67%). ¹H NMR (400 MHz, DMSO-d₆) δ 7.23-7.52 (m, 6H), 4.98 (s, 1H), 3.15-4.04 (m, 4H). LCMS: m/z 278.26 [M+H]⁺, t_R=1.66 min.

(E)-N-((7-chloro-5-(2-fluorophenyl)-2,3-dihydrobenzofuran-2-yl)methyl)-3-(pyridin-3-yl)acrylamide 18 was synthesized using General Procedure 3. Yield (55%). ¹H NMR (400 MHz, DMSO-d₆) δ 8.77 (s, 1H), 8.55-8.57 (m, 2H), 7.99-8.00 (d, J=4.4 Hz, 1H), 7.25-7.53 (m, 8H), 6.82-6.86 (d, J=16 Hz, 1H), 5.06-5.13(m, 1H), 3.54-3.66 (m, 2H), 3.40-3.46 (m, 1H), 3.09-3.15 (m, 1H). LCMS: m/z 409.20 [M+H]⁺, t_R=2.22 min.

Synthesis of (E)-N-((7-chloro-5-(3,4,5-trifluorophenyl)-2,3-dihydrobenzofuran-2-yl)methyl)-3-(pyridin-3-yl)acrylamide (21)

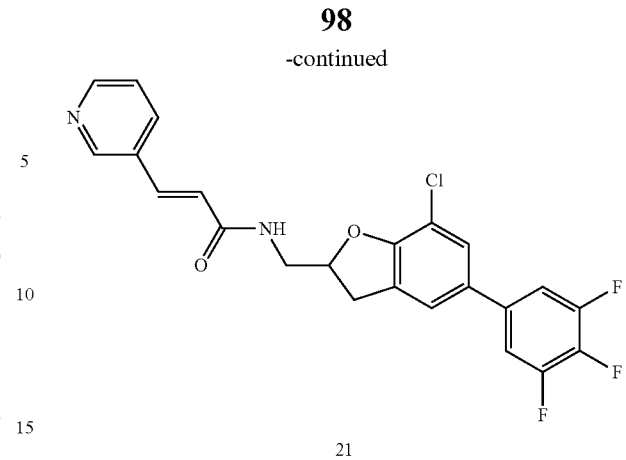

tert-Butyl (7-chloro-5-(3,4,5-trifluorophenyl)-2,3-dihydrobenzofuran-2-yl)methylcarbamate 22 was synthesized using General Procedure 1. Yield (70%). ¹H NMR (400 MHz, CDCl₃) δ 7.38 (s, 1H), 7.22 (s, 1H), 7.08-7.24 (m, 2H), 5.03-5.06 (m, 1H), 3.63-3.73 (m, 1H), 3.36-3.46 (m, 2H), 3.08-3.13 (m, 1H), 1.47 (s, 9H). LCMS: m/z 414.81 [M+H]⁺, t_R=1.93 min.

(7-chloro-5-(3,4,5-trifluorophenyl)-2,3-dihydrobenzofuran-2-yl)methanamine 23 was synthesized using General Procedure 2. Yield (90%). ¹H NMR (400 MHz, CDCl₃) δ 7.32 (s, 1H), 7.20 (s, 1H), 7.09-7.16 (m, 2H), 4.99-5.02 (m, 1H), 3.38-3.44 (m, 1H), 3.09-3.17 (m, 2H), 2.99-3.04 (m, 1H). LCMS: m/z 355.20 [M+41]⁺, t_R=1.81 min.

(E)-N-((7-chloro-5-(3,4,5-trifluorophenyl)-2,3-dihydrobenzofuran-2-yl)methyl)-3-(pyridin-3-yl)acrylamide 21 was synthesized using General Procedure 3. Yield (48%). ¹H NMR (400 MHz, DMSO-d₆) δ 8.77 (s, 1H), 8.53-8.56 (m, 2H), 7.98-8.00 (d, J=6.4 Hz, 1H), 7.60-7.70 (m, 3H), 7.49-7.52 (d, J=15.6 Hz, 1H), 7.43-7.47 (m, 1H), 6.81-6.85 (d, J=16 Hz, 1H), 5.08-5.10 (m, 1H), 3.55-3.64 (m, 2H), 3.46-3.95 (m, 1H), 3.08-3.32 (m, 1H). LCMS: m/z 445.19 [M+H]⁺, t_R=2.39 min.

Synthesis of (E)-N-((5-(5-acetylthiophen-2-yl)-7-chloro-2,3-dihydrobenzofuran-2-yl)methyl)-3-(pyridin-4-yl)acrylamide (24)

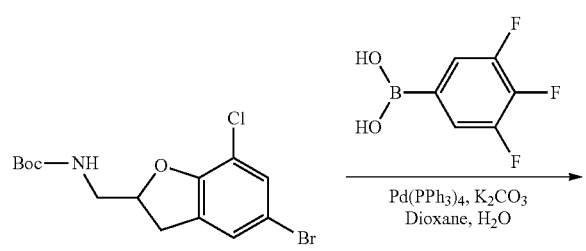

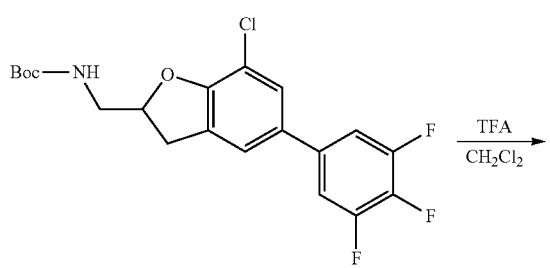

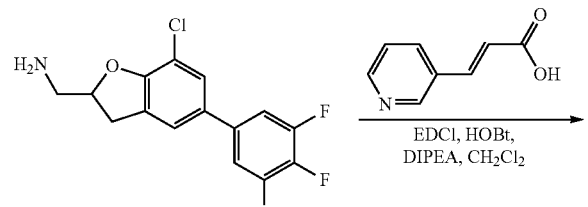

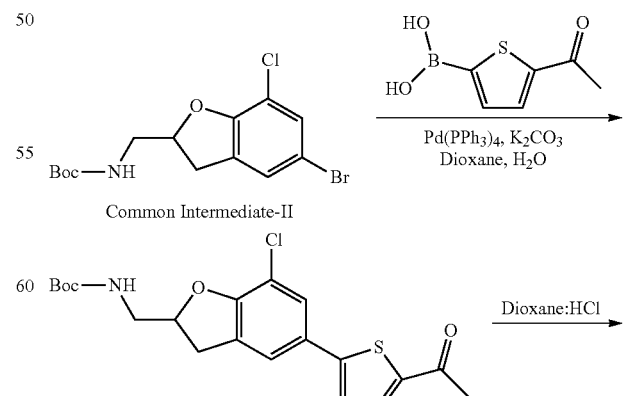

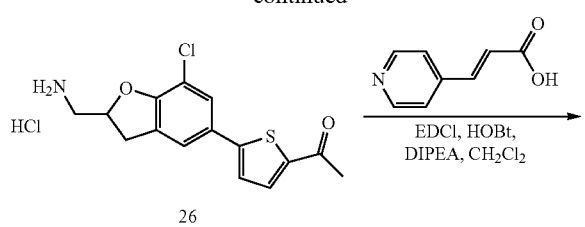

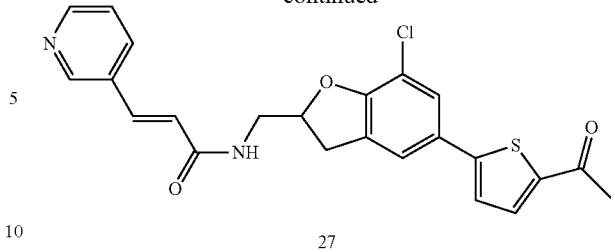

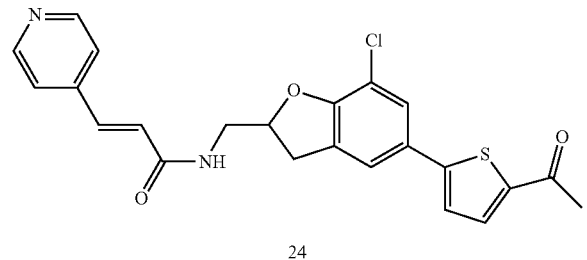

tert-Butyl (5-(5-acetylthiophen-2-yl)-7-chloro-2,3-dihydrobenzofuran-2-yl)methylcarbamate 25 was synthesized using General Procedure 1. Yield (46%). $^1$H NMR (400 MHz, CDCl$_3$) δ 7.63-7.64 (d, J=4 Hz, 1H), 7.45 (s, 1H), 7.35 (s, 1H), 7.19-7.20 (d, J=4 Hz, 1H), 5.02-5.08 (m, 1H), 3.62-3.67 (m, 1H), 3.35-3.46 (m, 2H), 3.07-3.13 (m, 1H), 2.55 (s, 3H) 1.46 (s, 9H). LCMS: m/z 408.15 [M+H]$^+$, $t_R$=2.43 min.

1-(5-(2-(aminomethyl)-7-chloro-2,3-dihydrobenzofuran-5-yOthiophen-2-yl)ethanone 26 was synthesized using General Procedure 2 (HCl was used instead of TFA). Yield (75%). $^1$H NMR (400 MHz, DMSO-d$_6$) δ 7.91-7.92 (d, J=4 Hz, 1H), 7.65-7.64 (d, J=4 Hz, 1H), 7.59 (s, 2H), 4.88-4.95 (m, 1H), 3.13-3.38 (m, 1H), 3.14-3.20 (m, 1H), 2.83-2.84 (d, J=4.8 Hz, 2H), 2.52 (s, 3H), 1.64 (bs, 2H). LCMS: m/z 308.16 [M+H]$^+$, $t_R$=1.32 min.

(E)-N-((5-(5-acetylthiophen-2-yl)-7-chloro-2,3-dihydrobenzofuran-2-yl)methyl)-3-(pyridin-4-yl)acrylamide 24 was synthesized using General Procedure 3. Yield (17.8%). $^1$H NMR (400 MHz, DMSO-d$_6$) δ 8.60-8.64 (q, 3H), 7.91-7.92 (d, J=4Hz, 1H), 7.58-7.71 (m, 3H), 7.40-7.53 (m, 3H), 6.92-6.96 (d, J=16 Hz, 1H), 5.09-5.11 (m, 1H), 4.37-4.39 (t, 1H), 3.56-3.65 (m, 2H), 3.40-3.47 (m, 3H), 3.08-3.14 (dd, $J_1$=7.6 Hz, $J_2$=8.8 Hz , 1H). LCMS: m/z 439.14 [M+H]$^+$, $t_R$=1.769 min.

Synthesis of (E)-N-((5-(5-acetylthiophen-2-yl)-7-chloro-2,3-dihydrobenzofuran-2-yl)methyl)-3-(yridine-3-yl)acrylamide (27)

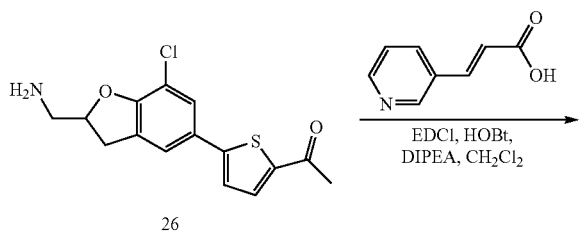

(E)-N-((5-(5-acetylthiophen-2-yl)-7-chloro-2,3-dihydrobenzofuran-2-yl)methyl)-3-(pyridin-3-yl)acrylamide 27 was synthesized using General Procedure 3. Yield (48%). $^1$H NMR (400 MHz, CDCl$_3$) δ 8.78 (bs, 1H), 8.61 (bs, 1H), 7.84-7.86 (d, J=8 Hz, 1H), 7.65-7.69 (d, J=15.6 Hz, 1H), 7.63-7.64 (d, J=4 Hz, 1H), 7.45 (s, 1H), 7.35-7.38 (m, 2H), 7.18-7.19 (d, J=4 Hz, 1H), 6.56-6.59 (d, J=15.6 Hz, 1H), 6.33-6.36 (m, 1H), 3.95-4.01 (m, 1H), 3.67-3.73 (m, 1H), 3.42-3.51 (m, 1H), 3.11-3.17 (m, 1H), 2.57 (s, 3H). LCMS: m/z 439.14 [M+H]$^+$, $t_R$=1.82 min.

Synthesis of (E)-N-((5-(5-acetylthiophen-2-yl)-7-chloro-2,3-dihydrobenzofuran-2-yl)methyl)-3-(pyridine-1-oxide-3-yl)acrylamide (28)

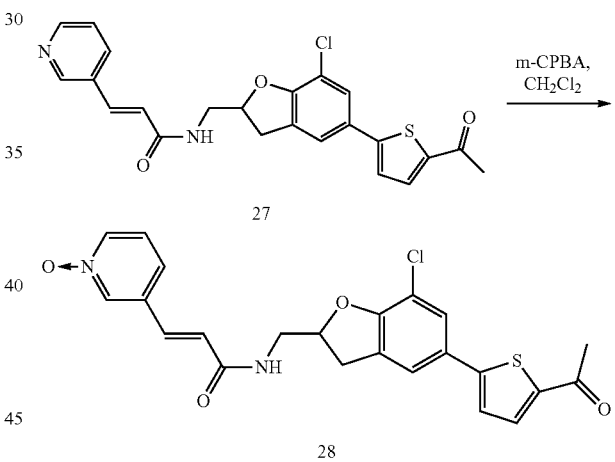

(E)-N-((5-(5-acetylthiophen-2-yl)-7-chloro-2,3-dihydrobenzofuran-2-yl)methyl)-3-(pyridin-3-yl) acrylamide 27 (0.075 g, 0.17 mmol) in DCM (5 mL) and m-CPBA (0.035 g, 0.20 mmol) were added at 0° C. The reaction mixture was allowed to warm to room temperature and stirred further for about 1.5 h. The reaction mixture was transferred into water (50 mL) and extracted with ethyl acetate (20 mL×3). The combined organic layers were washed with sat. bicarbonate and brine solution, dried over anhydrous Na$_2$SO$_4$ and concentrated under reduced pressure to afford 0.050 g of crude which was purified by column chromatography (60/120 silica gel, 0-30% ethyl acetate/hexane gradient). Fractions containing required compound were concentrated under reduced pressure to obtain 0.022 g of (E)-N-((5-(5-acetylthiophen-2-yl)-7-chloro-2,3-dihydrobenzofuran-2-yl) methyl)-3-(pyridine-1-oxide-3-yl)acrylamide 28. Yield (28%). $^1$H NMR (400 MHz, DMSO-d$_6$) δ 8.59-8.56 (brs, 1H), 8.49 (s, 1H), 8.21-8.19 (d, J=6.4 Hz, 1H), 7.93-7.92 (d, J=4 Hz, 1H), 7.67 (s, 1H), 7.64-7.59 (m, 2H), 7.55-7.53 (d, J=8 Hz, 1H), 7.41-7.39 (m, 2H), 6.87-6.83 (d, J=16 Hz, 1H), 5.14-5.07 (m, 1H), 3.64-3.55 (m, 2H), 3.47-3.40 (m, 1H), 3.14-3.08 (m, 1H), 2.56 (s, 3H). LCMS: m/z 455.11 [M+H]$^+$, t$_R$=1.776 min.

Synthesis of (E)-N-((7-chloro-5-phenyl-2,3-dihydrobenzofuran-2-yl)methyl)-3-(pyridin-3-yl)acrylamide (29)

(4-(2-(aminomethyl)-7-chloro-2,3-dihydrobenzofuran-5-yl)phenyl)(morpholino)-methanone 31 was synthesized using General Procedure 2. Yield (80%). $^1$H NMR (400 MHz, CDCl$_3$) δ 7.65-7.71 (m, 1H), 7.50-7.57 (m, 2H), 7.28-7.50 (m, 2H), 7.36-7.37 (d, J=1.6 Hz, 1H), 4.99-5.01 (t, 1H), 3.70-3.80 (m, 5H), 3.39-3.59 (m, 2H), 3.03-3.16 (m, 2H). LCMS: m/z 373.3 [M+H]$^+$, t$_R$=0.96 min.

tert-Butyl (7-chloro-5-(4-(morpholine-4-carbonyl)phenyl)-2,3-dihydrobenzofuran-2-yl)methylcarbamate 30 was synthesized using General Procedure 1. Yield (63%). $^1$H NMR (400 MHz, CDCl$_3$) δ 7.66-7.71 (m, 1H), 7.60-7.54 (m, 2H), 7.47-7.52 (m, 3H), 7.37-7.38 (d, J=2 Hz, 1H), 5.02-5.08 (m, 1H), 3.54-3.78 (m, 2H), 3.55-3.67 (m, 2H), 3.42-3.49 (m, 1H), 3.10-3.16 (m, 1H), 1.47 (s, 9H). LCMS: m/z 473.3 [M+H]$^+$, t$_R$=2.14 min.

(E)-N-((7-chloro-5-phenyl-2,3-dihydrobenzofuran-2-yl)methyl)-3-(pyridin-3-yl)acrylamide 29 was synthesized using General Procedure 3. Yield (40%) $^1$H NMR (400 MHz, DMSO-d$_6$) δ 8.77 (s, 1H), 8.55-8.57 (m, 2H), 7.98-8.00 (t, 1H), 7.68-7.70 (d, 2H), 7.53-7.55 (m, 2H), 7.43-7.49 (m, 3H), 6.82-6.86 (d, J=15.6 Hz, 1H), 5.09 (s, 1H), 3.56-3.64 (m, 2H), 3.40-3.47 (m, 2H), 3.09-3.15 (m, 1H). LCMS: m/z 504.3 [M+H]$^+$, t$_R$=1.61 min.

Synthesis of (E)-N-((7-chloro-5-(3,5-dichlorophenyl)-2,3-dihydrobenzofuran-2-yl)methyl)-3-(pyridin-3-yl)acrylamide (32)

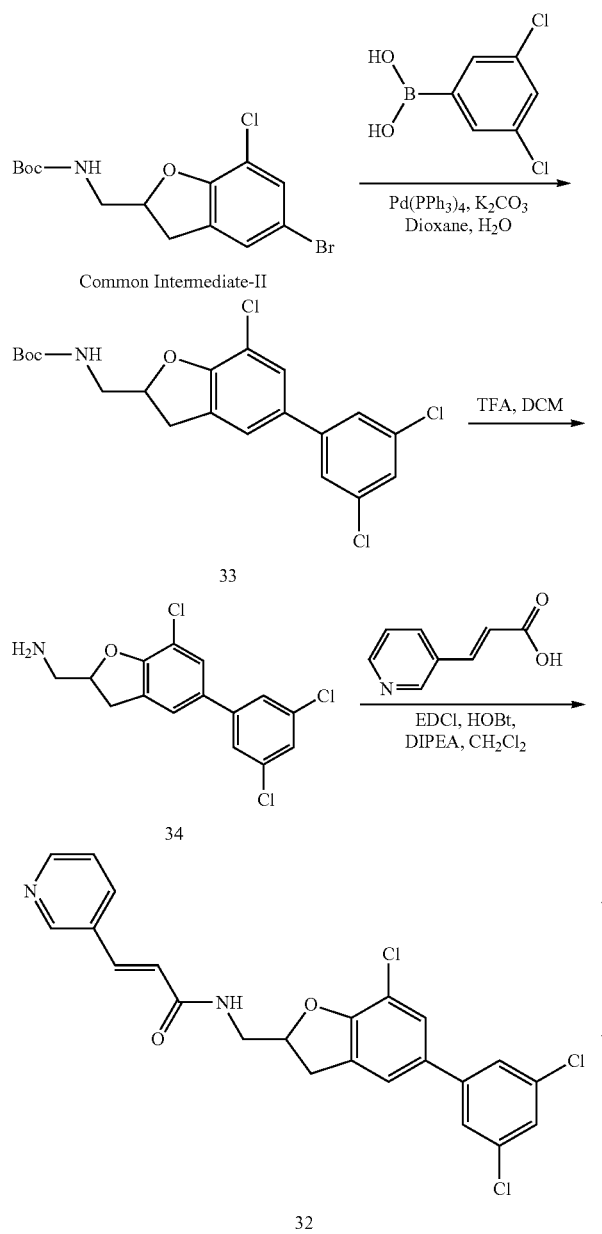

Synthesis of (E)-N-((7-chloro-5-(3,5-dimethylisoxazol-4-yl)-2,3-dihydrobenzofuran-2-yl)methyl)-3-(pyridin-3-yl)acrylamide (35)

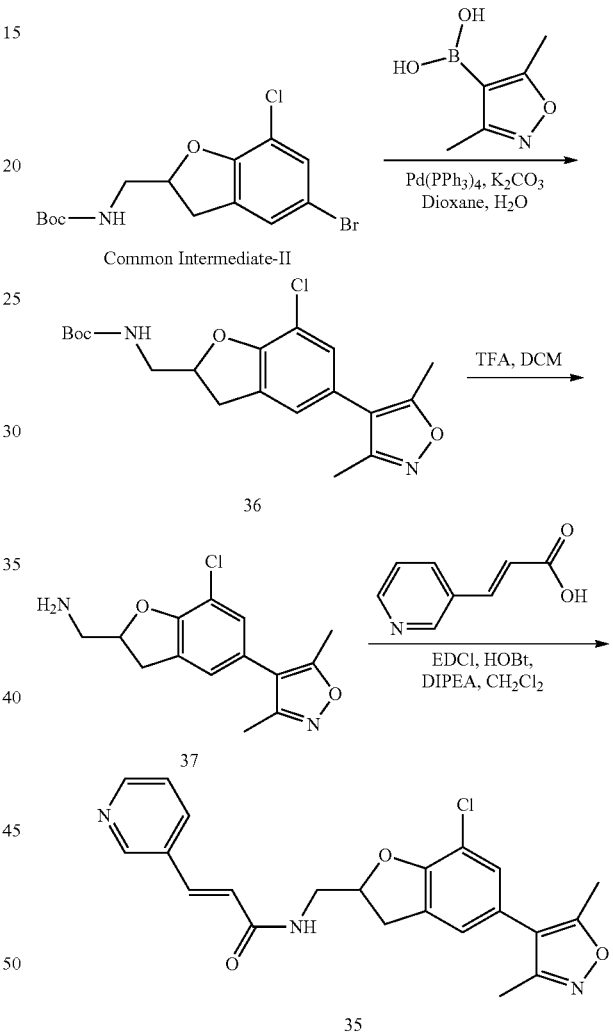

tert-Butyl (7-chloro-5-(3,5-dichlorophenyl)-2,3-dihydrobenzofuran-2-yl)methyl carbamate 33 was synthesized using General Procedure 1. Yield (56%). $^1$H NMR (400 MHz, CDCl$_3$) δ 7.44-7.52 (m, 1H), 7.32-7.43 (m, 4H), 5.03-5.06 (t, 1H), 3.64-3.73 (m, 1H), 3.36-3.46 (m, 2H), 3.07-3.16 (m, 1H), 1.42 (s, 9H). LCMS: m/z 372.2 [M−57]$^+$, $t_R$=3.03 min.

(7-chloro-5-(3,5-dichlorophenyl)-2,3-dihydrobenzofuran-2-yl)methanamine 34 was synthesized using General Procedure 2. Yield (75%). LCMS: m/z 328.2 [M+H]$^+$, $t_R$=1.95 min.

(E)-N-((7-chloro-5-(3,5-dichlorophenyl)-2,3-dihydrobenzofuran-2-yl)methyl)-3-(pyridin-3-yl)acrylamide 32 was synthesized using General Procedure 3. Yield (13%). $^1$H NMR (400 MHz, DMSO-d$_6$) δ 8.77 (s, 1H), 8.55-8.57 (m, 2H), 7.98-8.00 (m, 1H), 7.72 (s, 2H), 7.62-7.66 (m, 2H), 7.53-7.55 (m, 1H), 7.43-7.46 (m, 1H), 6.27-6.86 (d, J=16 Hz, 1H), 5.08-5.10 (t, 1H), 3.55-3.65 (m, 2H), 3.35-3.45 (m, 1H), 3.08-3.14 (m, 1H). LCMS: m/z 461.2 [M+H]$^+$, $t_R$=2.65 min.

tert-Butyl (7-chloro-5-(3,5-dimethylisoxazol-4-yl)-2,3-dihydrobenzofuran-2-yl)methylcarbamate 36 was synthesized using General Procedure 1. Yield (67%). $^1$H NMR (400 MHz, CDCl$_3$) δ 7.01 (s, 1H), 6.93 (s, 1H), 5.03-5.05 (m, 1H), 3.63-3.66 (m, 1H), 3.35-3.46 (m, 2H), 3.07-3.11 (m, 1H), 2.39 (s, 3H), 2.29 (s, 3H), 1.47 (s, 9H). LCMS: m/z 379.15 [M+H]$^+$, $t_R$=2.46 min.

(7-chloro-5-(3,5-dimethylisoxazol-4-yl)-2,3-dihydrobenzofuran-2-yl)methanamine 37 was synthesized using General Procedure 2. Yield (90%). $^1$H NMR (400 MHz, CDCl$_3$) δ 7.05 (s, 1H), 6.96 (s, 1H), 4.99-5.01 (m, 1H), 3.36-3.42 (m, 1H), 3.10-3.17 (m, 2H), 3.00-3.05 (m, 1H), 2.39 (s, 3H), 2.25 (s, 3H). LCMS: m/z 279.26 [M+H]$^+$, $t_R$=1.25 min.

(E)-N-((7-chloro-5-(3,5-dimethylisoxazol-4-yl)-2,3-dihydrobenzofuran-2-yl)methyl)-3-(pyridin-3-yl)acrylamide 35 was synthesized using General Procedure 3. Yield (52%). $^1$H NMR (400 MHz, DMSO-d$_6$) δ 8.77 (s, 1H), 8.53-8.57 (m, 2H), 7.98-8.00 (d, J=8 Hz, 1H), 7.49-7.53 (d, J=15.6 Hz, 1H), 7.44-7.47 (m, 1H), 7.20 (s, 2H), 6.82-6.86 (d, J=16 Hz, 1H), 5.04-5.11 (m, 1H), 3.54-3.65 (m, 2H), 3.37-3.44 (m, 1H), 2.67-3.13 (m, 1H), 2.40 (s, 3H), 2.09 (s, 3H). LCMS: m/z 410.30 [M+H]$^+$, $t_R$=1.83 min.

N-((5-(5-acetylthiophen-2-yl)-7-chloro-2,3-dihydrobenzofuran-2-yl)methyl)cinnamamide (38)

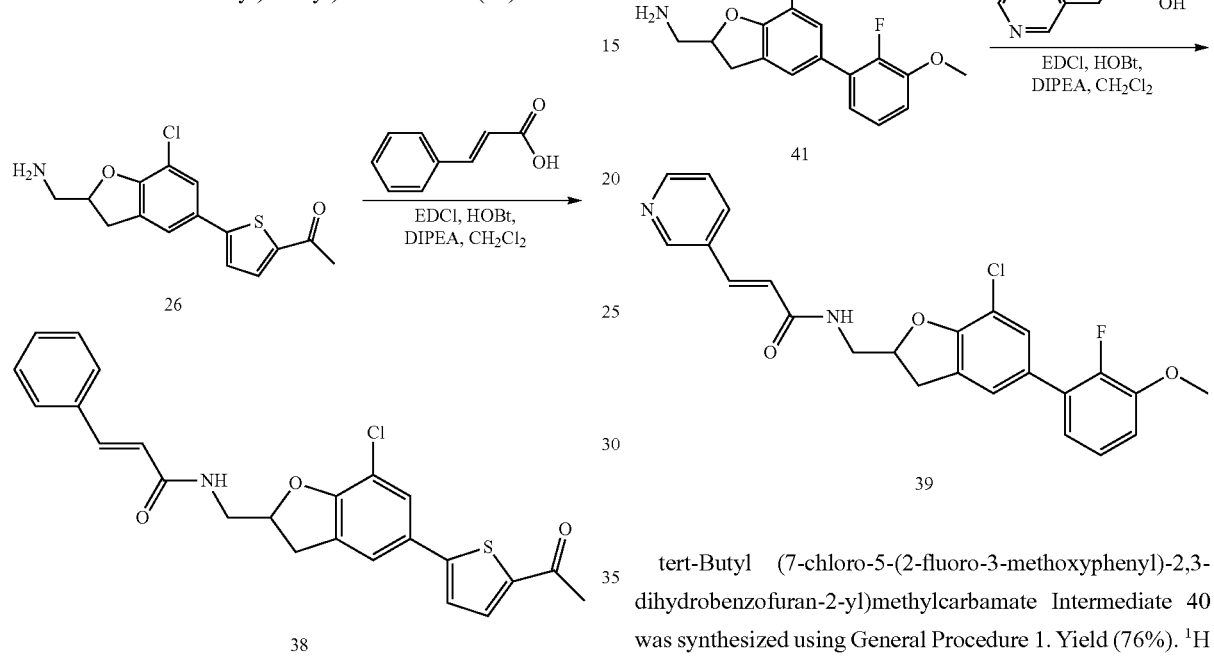

N-((5-(5-acetylthiophen-2-yl)-7-chloro-2,3-dihydrobenzofuran-2-yl)methyl)cinnamamide 38 was synthesized using General Procedure 3. Yield (55%). $^1$H NMR (400 MHz, DMSO d$_6$) δ 8.46-8.49 (m, 1H), 7.91-7.92 (d, J=2 Hz, 1H), 7.56-7.66 (m, 4H), 7.38-7.44 (m, 4H), 6.70-6.74 (d, J=15.6 Hz, 1H), 5.08 (m, 1H), 3.56-3.63 (m, 2H), 3.40-3.46 (m, 1H), 3.08-3.14 (m, 1H), 2.57 (s, 3H). LCMS: m/z 438.31 [M+H]$^+$, $t_R$=2.32 min.

Synthesis of (E)-N-((7-chloro-5-(2-fluoro-3-methoxyphenyl)-2,3-dihydrobenzofuran-2-yl)methyl)-3-(pyridin-3-yl)acrylamide (39)

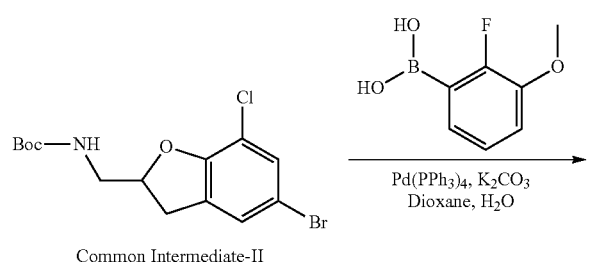

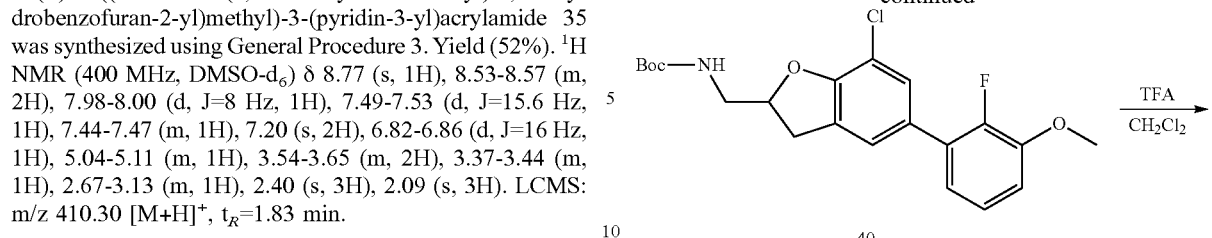

tert-Butyl (7-chloro-5-(2-fluoro-3-methoxyphenyl)-2,3-dihydrobenzofuran-2-yl)methylcarbamate Intermediate 40 was synthesized using General Procedure 1. Yield (76%). $^1$H NMR (400 MHz, CDCl$_3$) δ 7.33 (s, 1H), 7.09-7.13 (m, 1H), 6.92-6.94 (m, 1H), 6.94-6.97 (m, 2H), 5.01-5.08 (m, 1H), 3.94 (s, 3H), 3.63-3.68 (m, 1H), 3.36-3.47 (m, 2H), 3.07-3.13 (m, 1H), 1.47 (s, 9H). LCMS: m/z 352.08 [M−56]$^+$, $t_R$=2.56 min.

(7-chloro-5-(2-fluoro-3-methoxyphenyl)-2,3-dihydrobenzofuran-2-yl)methanamine 41 was synthesized using General Procedure 2. Yield (85%). LCMS: m/z 308.01 [M+H]$^+$, $t_R$=1.58 min.

(E)-N-((7-chloro-5-(2-fluoro-3-methoxyphenyl)-2,3-dihydrobenzofuran-2-yl)methyl)-3-(pyridin-3-yl)acrylamide 39 was synthesized using General Procedure 3. Yield (38%). $^1$H NMR (400 MHz, DMSO-d$_6$) δ 8.77 (s, 1H), 8.54-8.56 (m, 2H), 7.98-8.00 (d, J=8 Hz, 1H), 7.49-7.53 (d, J=15.6 Hz, 1H), 7.43-7.47 (m, 1H), 7.34 (s, 1H), 7.33 (s, 1H), 7.12-7.20 (m, 2H), 6.98-7.02 (m, 1H), 6.82-6.86 (d, J=15.6 Hz, 1H), 5.06-5.12 (m, 1H), 3.68 (s, 3H), 3.54-3.66 (m, 2H), 3.32-3.46 (m, 1H), 3.08-3.14 (m, 1H). LCMS: m/z 439.11 [M+H]$^+$, $t_R$=2.05 min.

Synthesis of (E)-N-((7-chloro-5-(furan-2-yl)-2,3-dihydrobenzofuran-2-yl)methyl)-3-(pyridin-3-yl)acrylamide (42)

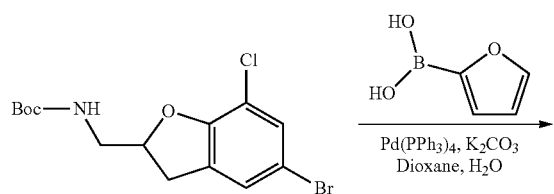

Common Intermediate-II

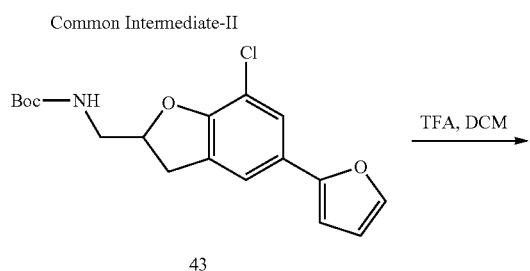

43

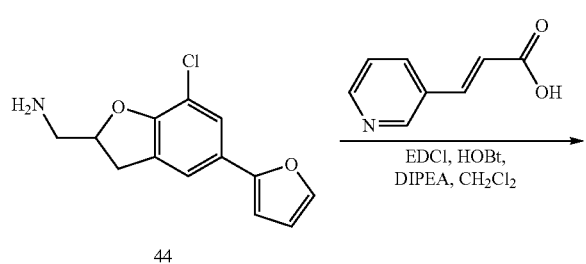

44

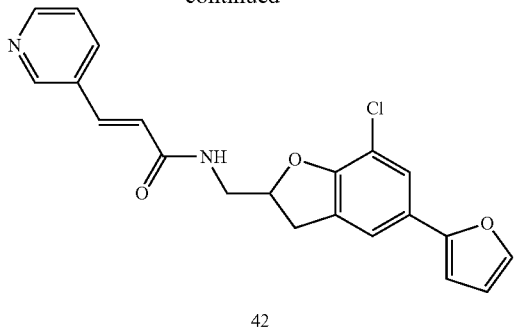

42 tert-Butyl (7-chloro-5-(furan-2-yl)-2,3-dihydrobenzofuran-2-yl)methyl carbamate 43 was synthesized using General Procedure 1. Yield (62%). $^1$H NMR (400 MHz, CDCl$_3$) δ 7.28-7.49 (m, 3H), 6.45-6.52 (m, 2H), 4.99-5.03 (m, 2H), 3.61-3.65 (m, 1H), 3.29-3.44 (m, 2H), 3.03-3.09 (m, 1H), 1.23 (s, 1H). LCMS: m/z 293.9 [M−56]$^+$, t$_R$=2.53 min.

(7-chloro-5-(furan-2-yl)-2,3-dihydrobenzofuran-2-yl)methanamine 44 was synthesized using General Procedure 2. Yield (71%). $^1$H NMR (400 MHz, DMSO-d$_6$) δ 7.43-7.62 (m, 3H), 6.27-6.77 (m, 2H), 6.27 (s, 1H), 5.05 (s, 2H), 2.99-3.15 (m, 2H).

(E)-N-((7-chloro-5-(furan-2-yl)-2,3-dihydrobenzofuran-2-yl)methyl)-3-(pyridin-3-yl)acrylamide 45 was synthesized using General Procedure 3. Yield (42%). $^1$H NMR (400 MHz, DMSO-d$_6$) δ 8.77 (s, 1H), 8.55 (s, 2H), 7.98-8.01 (d, J=7.6 Hz, 1H), 7.69 (s, 1H), 7.45-7.53 (m, 3H), 6.81-6.87 (m, 2H), 6.56 (s, 1H), 5.07 (s, 1H), 3.58-3.59 (d, J=5.6 Hz, 2H), 3.04-3.12 (m, 2H). LCMS: m/z 381.04 [M+H]$^+$, t$_R$=1.99 min.

Synthesis of (E)-N-((5-(5-acetylthiophen-2-yl)-7-chloro-2,3-dihydrobenzofuran-2-yl)methyl)-3-(6-chloropyridine-3-yl)acrylamide (45)

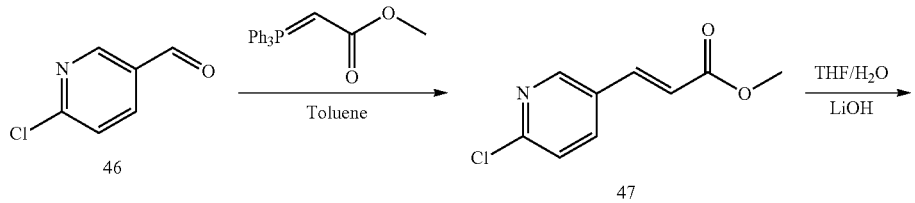

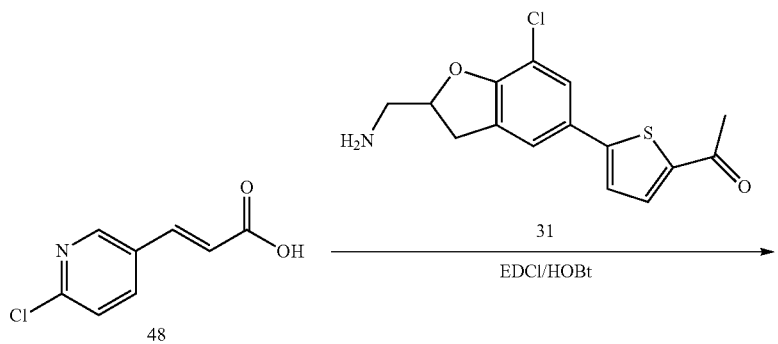

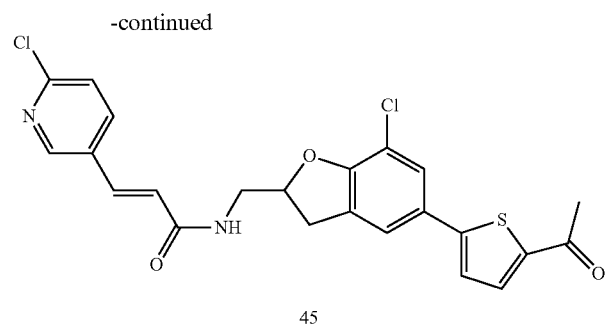

45

Methyl-3-(6-chloropyridin-3-yl)acrylate 47: 6-Chloronicotinaldehyde (1 g, 7.09 mmol) in toluene (10 mL) and (methoxycarbonylmethylene)triphenylphosphorane (2.84 g, 8.51 mmol) were added at 0° C. Then reaction mixture was stirred at 110° C. for 3 h, monitored by TLC. The reaction mixture was transferred into water (150 mL) and compound was extracted with ethyl acetate (50 mL×3). The combined organic layers were washed with brine solution, dried over anhydrous $Na_2SO_4$ and concentrated under reduced pressure to obtain 0.6 g of crude methyl-3-(6-chloropyridin-3-yl)acrylate 47. Yield (43%). $^1$H NMR (400 MHz, DMSO-$d_6$, ppm) δ 8.76-8.76 (s, 1H), 8.29-8.27 (d, J=10.8 Hz, 1H), 7.73-7.69 (d, J=16 Hz, 1H), 7.61-7.55 (d, J=24.8 Hz, 1H), 6.87-6.83 (d, J=16 Hz, 1H), 3.75 (s, 3H). LCMS: m/z 197.73 [M+H]$^+$, $t_R$=1.727 min.

3-(6-chloropyridine-3-yl)acrylic acid 48: Methyl-3-(6-chloropyridin-3-yl) acrylate 47 (0.500 g, 2.53 mmol) in THF:$H_2O$ (5:5) (10 mL) and LiOH (0.12 g, 5.076 mmol) was added at 0° C. Then reaction mixture was stirred at rt for 4 h and monitored by TLC. The reaction mixture was transferred into water and neutralize with dil. HCl and compound was extracted with ethyl acetate (50 mL×3). The combined organic layers were washed with sat. sodium bicarbonate and brine solution, dried over anhydrous $Na_2SO_4$ and concentrated under reduced pressure to obtain 0.3 g of crude 3-(6-chloropyridine-3-yl) acrylic acid 48. Yield (64.6%). $^1$H NMR (400 MHz, DMSO-$d_6$, ppm) δ 12.64 (s, 1H), 8.73-8.72 (s, 1H), 8.26-8.24 (d, J=10.8 Hz, 1H), 7.65-7.45 (m, 2H), 6.75-6.71 (d, J=16.4 Hz, 1H). LCMS: m/z 183.76 [M+H]$^+$, $t_R$=1.204 min.

(E)-N-((5-(5-acetylthiophen-2-yl)-7-chloro-2,3-dihydrobenzofuran-2-yl)methyl)-3-(6-chloropyridin-3-yl)acrylamide 45 was synthesized using General Procedure 3. Yield (31%). $^1$H NMR (400 MHz, CDCl$_3$, ppm) δ 8.63-8.54 (m, 2H), 8.08-8.05 (d, J=10.8, 1H), 7.93-7.92 (d, J=4 Hz, 1H), 7.66-7.49 (m, 5H), 6.86-6.82 (d, J=16 Hz, 1H), 5.14-5.07 (m, 1H), 3.66-3.54 (m, 1H), 3.46-3.41 (m, 1H), 3.14-3.08 (m, 1H), 2.53 (s, 3H). LCMS: m/z 472.97 [M+H]$^+$, $t_R$=2.218 min.

Synthesis of (E)-N-((5-(3,5-bis(trifluoromethyl)phenyl)-7-chloro-2,3-dihydrobenzofuran-2-yl)methyl)-3-(pyridin-3-yl)acrylamide (49)

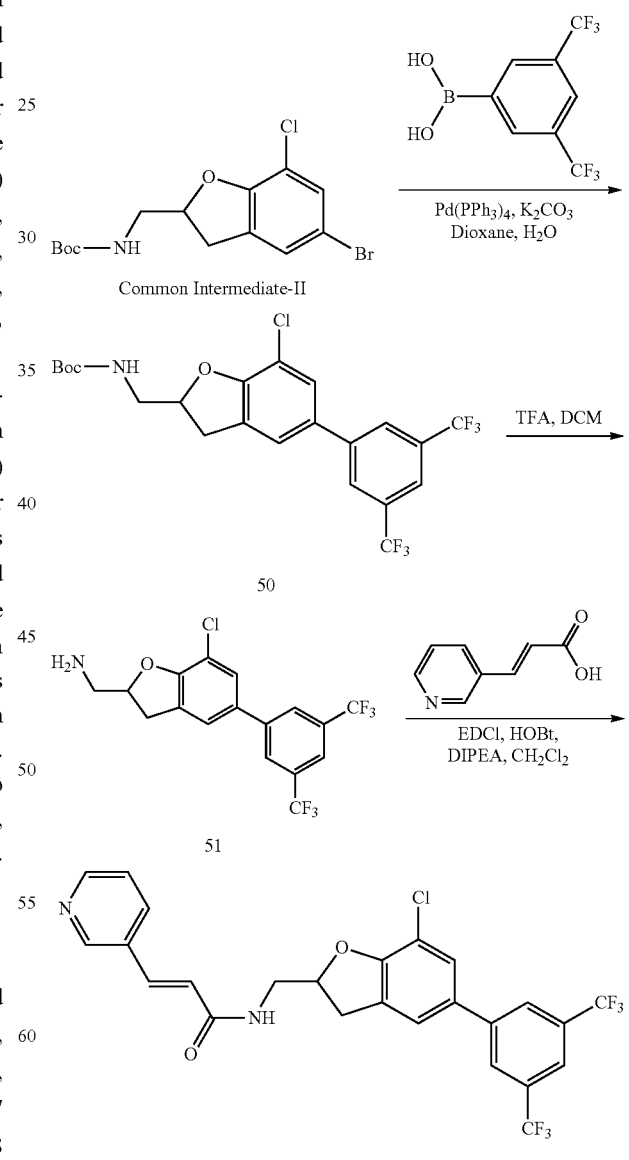

tert-Butyl (5-(3,5-bis(trifluoromethyl)phenyl)-7-chloro-2,3-dihydrobenzofuran-2-yl)methylcarbamate 50 was synthesized using General Procedure 1. Yield (48%). $^1$H NMR (400 MHz, CDCl$_3$) δ 7.84-7.98 (m, 3H), 7.49 (s, 1H), 7.28-7.40 (m, 2H), 5.03-5.11 (m, 1H), 3.65-3.73 (m, 1H), 3.40-3.48 (m, 2H), 3.11-3.17 (m, 1H), 1.44 (s, 9H). LCMS: m/z 540.43 [M+45]$^+$, $t_R$=2.95 min.

(5-(3,5-bis(trifluoromethyl)phenyl)-7-chloro-2,3-dihydrobenzofuran-2-yl)methanamine 51 was synthesized using General Procedure 2. Yield (79%). $^1$H NMR (400 MHz, CDCl$_3$) δ 8.31 (s, 2H), 8.10 (s, 1H), 7.97 (s, 1H), 7.74 (s, 1H), 4.91-4.98 (m, 1H), 3.13-3.22 (m, 1H), 2.82-2.91 (m, 2H), 2.33 (bs, 2H). LCMS: m/z 437.34 [M+41]$^+$, $t_R$=2.00 min.

(E)-N-((5-(3,5-bis(trifluoromethyl)phenyl)-7-chloro-2,3-dihydrobenzofuran-2-yl)methyl)-3-(pyridin-3-yl)acrylamide 49 was synthesized using General Procedure 3. Yield (40%). $^1$H NMR (400 MHz, DMSO-d$_6$) δ 8.76-8.77 (s, 1H), 8.55-8.58 (m, 2H), 8.32 (s, 2H), 7.97-8.03 (m, 2H), 7.83 (s, 1H), 7.70 (s, 1H), 7.43-7.53 (m, 2H), 6.82-6.86 (d, J=16 Hz, 1H), 5.09-5.16 (m, 1H), 3.55-3.67 (m, 2H), 3.42-3.49 (m, 1H), 3.10-3.16 (m, 1H). LCMS: m/z 527.28 [M+H]$^+$, $t_R$=2.52 min.

Synthesis of (E)-ethyl 3-(7-chloro-2-((3-(pyridin-3-yl)acrylamido)methyl)-2,3-dihydrobenzofuran-5-yl)benzoate (52)

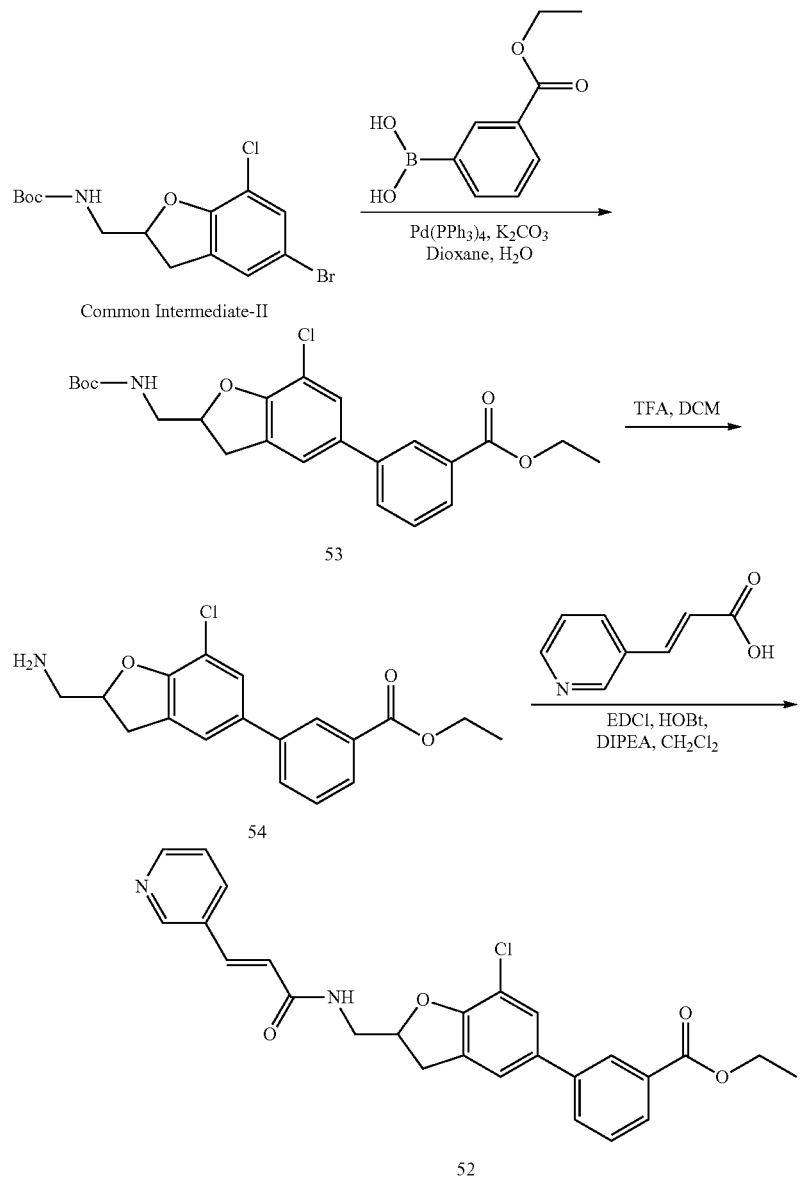

Ethyl 3-(2-((tert-butoxycarbonylamino)methyl)-7-chloro-2,3-dihydrobenzofuran-5-yl)benzoate 53 was synthesized using General Procedure 1. Yield (43%). $^1$H NMR (400 MHz, CDCl$_3$) δ 8.18 (s, 1H), 8.00-8.02 (m, 1H), 7.68-7.70 (m, 1H), 7.48-7.52 (t, J=7.6 Hz, 1H), 7.41 (s, 1H), 7.33 (s, 1H), 5.05-5.09 (m, 1H), 4.40-4.46 (m, 2H), 3.63-3.72 (m, 1H), 3.38-3.47 (m, 2H), 3.09-3.015 (m, 1H), 1.40-1.47 (m, 12H). LCMS: m/z 374.4 [M–57]⁺, $t_R$=2.88 min.

Ethyl 3-(2-(aminomethyl)-7-chloro-2,3-dihydrobenzofuran-5-yl)benzoate 54 was synthesized using General Procedure 2. Yield (72%). ¹H NMR (400 MHz, CDCl₃) δ 8.18 (s, 1H), 8.00-8.02 (d, J=7.6 Hz, 1H), 7.68-7.70 (d, J=6.8 Hz, 1H), 7.47-7.54 (t, J=10.8 Hz, 1H), 7.40 (s, 1H), 7.33 (s, 1H), 5.01 (bs, 1H), 4.40-4.45 (m, 2H), 3.40-3.51 (m, 1H), 3.01-3.17 (m, 3H), 1.41-1.44 (m, 3H). LCMS: m/z 373.15 [M+41]⁺, $t_R$=1.80 min.

(E)-ethyl 3-(7-chloro-2-((3-(pyridin-3-yl)acrylamido)methyl)-2,3-dihydrobenzofuran-5-yl)benzoate 52 was synthesized using General Procedure 3. Yield (30%). ¹H NMR (400 MHz, DMSO-d₆) δ 8.77 (s, 1H), 8.55-8.57 (m, 2H), 8.11 (s, 1H), 7.98-8.01 (m, 1H), 7.89-7.92 (m, 2H), 7.43-7.60 (m, 5H), 6.82-6.86 (d, J=15.6 Hz, 1H), 5.08-5.10 (m, 1H), 4.32-4.37 (m, 2H), 3.56-3.65 (m, 2H), 3.37-3.48 (m, 1H), 3.10-3.16 (m, 1H), 1.32-1.34 (t, 3H). LCMS: m/z 463.29 [M+H]⁺, $t_R$=2.17 min.

Synthesis of (E)-N-((7-chloro-5-(4-chloro-2-fluorophenyl)-2,3-dihydrobenzofuran-2-yl)methyl)-3-(pyridin-3-yl)acrylamide (55)

tert-Butyl (7-chloro-5-(4-chloro-2-fluorophenyl)-2,3-dihydrobenzofuran-2-yl)methylcarbamate 56 was synthesized using General Procedure 1. Yield (50%). LCMS: m/z 356.10 [M–56]⁺, $t_R$=2.83 min.

(7-chloro-5-(4-chloro-2-fluorophenyl)-2,3-dihydrobenzofuran-2-yl)methanamine 57 was synthesized using General Procedure 2. Yield (92%). ¹H NMR (400 MHz, CDCl₃) δ 7.26-7.37 (m, 2H), 7.14-7.22 (m, 3H), 4.97-5.01 (m, 1H), 3.37-3.44 (m, 1H), 3.08-3.16 (m, 2H), 2.99-3.04 (m, 1H). LCMS: m/z 353.20 [M+41]⁺, $t_R$=1.87 min.

(E)-N-((7-chloro-5-(4-chloro-2-fluorophenyl)-2,3-dihydrobenzofuran-2-yl)methyl)-3-(pyridin-3-yl)acrylamide 55 was synthesized using General Procedure 3. Yield (42.37%) ¹H NMR (400 MHz, DMSO-d₆) δ 8.77 (s, 1H), 8.54-8.56 (m, 2H), 7.98-8.00 (d, J=8 Hz, 1H), 7.31-7.67 (m, 6H), 6.82-6.86 (d, J=16 Hz, 1H), 5.06-5.13 (m, 1H), 3.54-3.66 (m, 2H), 3.35-3.46 (m, 1H), 3.08-3.14 (m, 1H). LCMS: m/z 443.24 [M+H]⁺, $t_R$=2.45 min.

Synthesis of (E)-N-((7-chloro-5-(3-(hydroxymethyl)phenyl)-2,3-dihydrobenzofuran-2-yl)methyl)-3-(pyridin-3-yl)acrylamide (58)

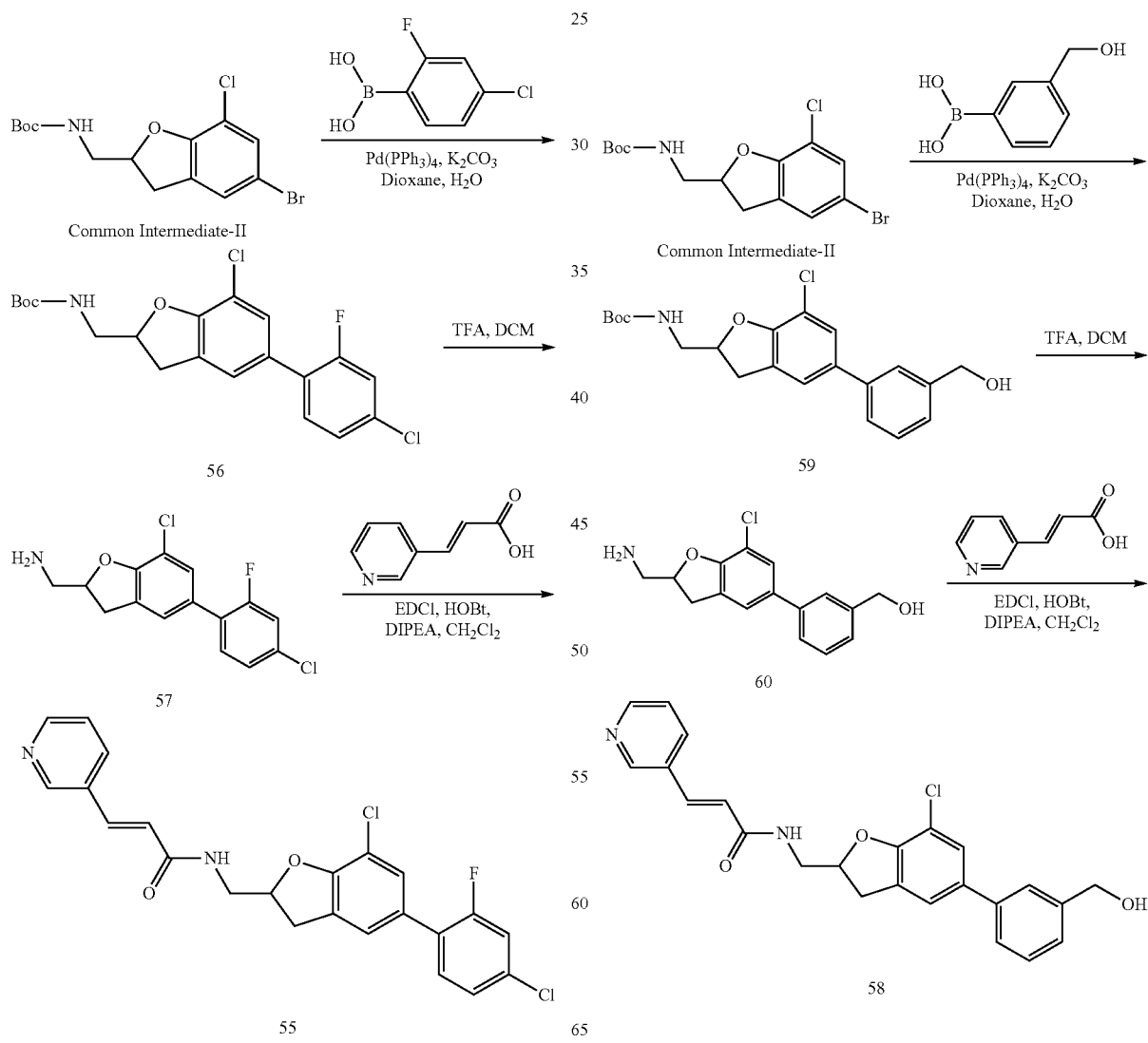

tert-butyl (7-chloro-5-(3-(hydroxymethyl)phenyl)-2,3-dihydrobenzofuran-2-yl)methylcarbamate 59 was synthesized using General Procedure 1. Yield (43%). $^1$H NMR (400 MHz, CDCl$_3$) δ 7.53 (s, 1H), 7.42-7.48 (m, 2H), 7.38-7.40 (m, 1H), 7.33-7.34 (m, 1H), 7.30 (s, 2H), 5.01-5.07 (m, 1H), 3.63-3.69 (m, 1H), 3.36-3.46 (m, 2H), 3.07-3.13 (m, 1H), 1.47 (s, 9H). LCMS: m/z 334.10 [M−57]$^+$, t$_R$=2.34 min.

(3-(2-(aminomethyl)-7-chloro-2,3-dihydrobenzofuran-5-yl)phenyl)methanol 60 was synthesized using General Procedure 2. Yield (59%). LCMS: m/z 290.16 [M+H]+, t$_R$=1.25 min.

(E)-N-((7-chloro-5-(3-(hydroxymethyl)phenyl)-2,3-dihydrobenzofuran-2-yl)methyl)-3-(pyridin-3-yl)acrylamide 56 was synthesized using General Procedure 3. Yield (46%). $^1$H NMR (400 MHz, DMSO-d$_6$) δ 8.78 (s, 1H), 8.54-8.77 (m, 2H), 8.00-8.02 (d, J=8 Hz, 1H), 7.53-7.56 (d, J=4.4 Hz, 1H), 7.45-7.49 (m, 1H), 7.35-7.39 (t, 1H), 7.23-7.28 (s, 1H), 6.83-6.87 (d, J=16 Hz, 1H,), 5.04-5.11 (m, 1H) 4.54 (s, 2H), 3.54-3.64 (m, 2H), 3.39-3.45 (m, 1H), 3.07-3.11 (m, 1H). LCMS: m/z 421.33 [M+H]$^+$, t$_R$=1.67 min.

Synthesis of (E)-N-((7-chloro-5-(5-fluoro-2-methoxyphenyl)-2,3-dihydrobenzofuran-2-yl)methyl)-3-(pyridin-3-yl)acrylamide (61)

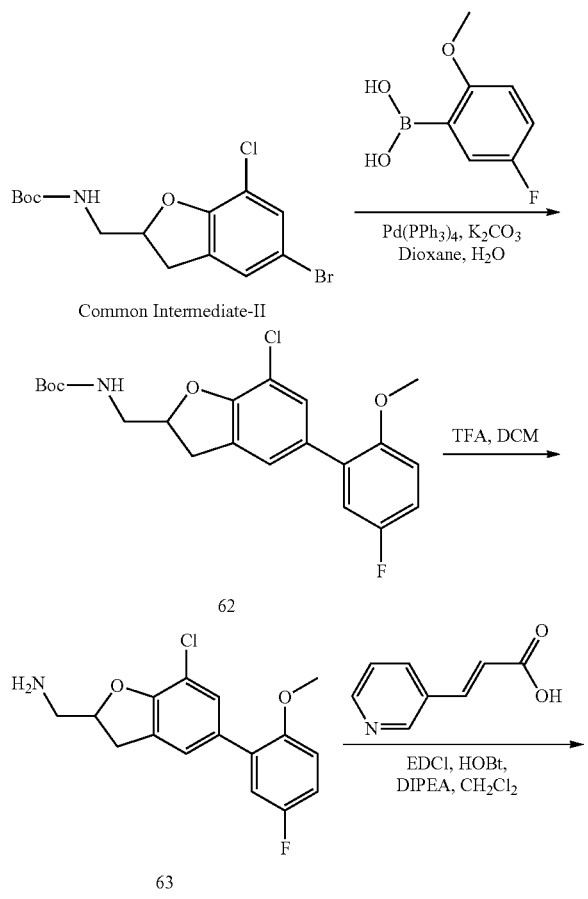

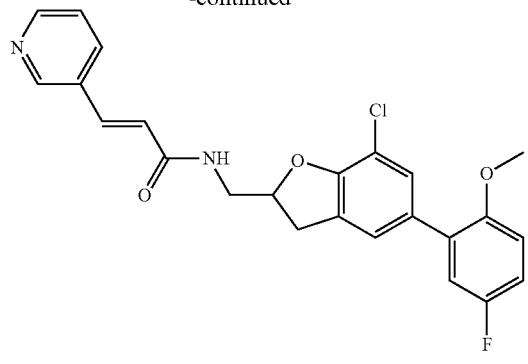

61 tert-butyl (7-chloro-5-(5-fluoro-2-methoxyphenyl)-2,3-dihydrobenzofuran-2-yl)methylcarbamate 62 was synthesized using General Procedure 1. Yield (64%). $^1$H NMR (400 MHz, CDCl$_3$) δ 7.30 (s, 1H), 7.22 (s, 1H), 6.91-7.02 (m, 2H), 6.87-6.90 (m, 1H), 5.00-5.06 (m, 1H), 3.80 (s, 3H), 3.62-3.72 (m, 2H), 3.34-3.46 (m, 2H), 3.06-3.11 (m, 1H), 1.44 (s, 9H). LCMS: m/z 352.1 [M−56]$^+$, t$_R$=2.63 min.

(7-chloro-5-(5-fluoro-2-methoxyphenyl)-2,3-dihydrobenzofuran-2-yl) methanamine 63 was synthesized using General Procedure 2. Yield (75%). $^1$H NMR (400 MHz, CDCl$_3$) δ 7.31 (s, 1H), 7.30 (s, 1H), 6.96-7.22 (m, 2H), 6.88-6.91 (m, 2H), 4.96-5.00 (m, 1H), 4.11-4.22 (m, 1H), 3.37-3.43 (m, 1H), 3.08 (s, 3H), 3.00-3.37 (m, 2H). LCMS: m/z 308.01 [M+H]$^+$, t$_R$=1.68 min.

(E)-N-((7-chloro-5-(5-fluoro-2-methoxyphenyl)-2,3-dihydrobenzofuran-2-yl)methyl)-3-(pyridin-3-yl)acrylamide 61 was synthesized using General Procedure 3. Yield (70%). $^1$H NMR (400 MHz, CDCl$_3$) δ 8.77 (s, 1H), 8.51-8.56 (m, 2H), 7.97-8.00 (m, 1H), 7.48-7.52 (d, J=15.6 Hz, 1H), 7.43-7.46 (m, 1H), 7.30 (s, 2H), 7.07-7.16 (m, 3H), 6.82-6.86 (d, J=16 Hz, 1H), 5.05-5.07 (m, 1H), 3.73 (s, 3H), 3.55-3.64 (m, 2H), 3.36-3.43 (m, 1H), 3.06-3.12 (m, 1H). LCMS: m/z 439.01 [M+H]$^+$, t$_R$=2.17 min.

Synthesis of (E)-N-((7-chloro-5-(4-(dimethylamino)phenyl)-2,3-dihydro benzofuran-2-yl)methyl)-3-(pyridin-3-yl)acrylamide (64)

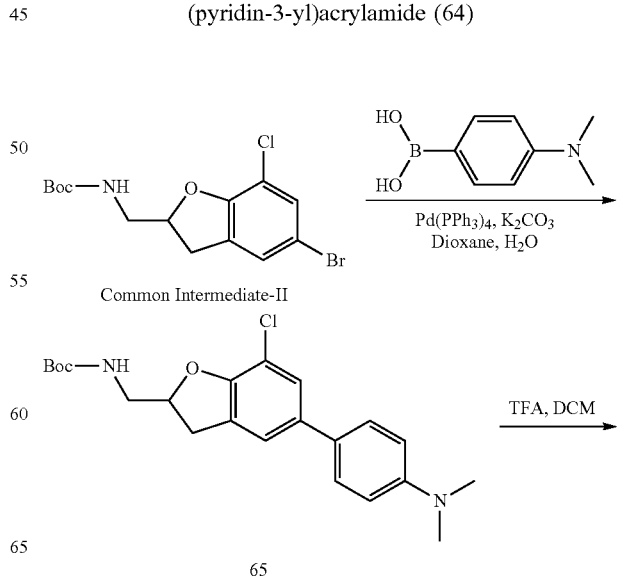

-continued

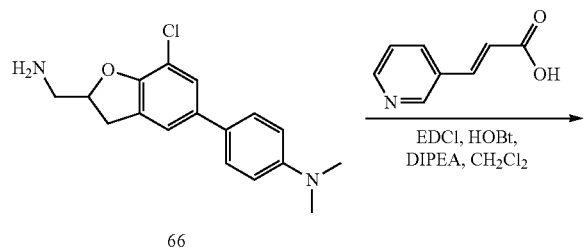

66

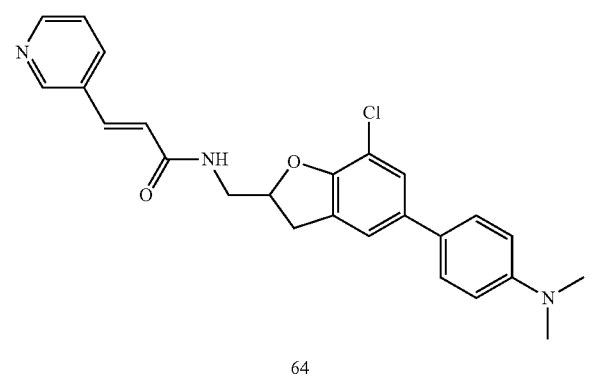

64 tert-butyl (7-chloro-5-(4-(dimethylamino)phenyl)-2,3-dihydrobenzofuran-2-yl) methylcarbamate 65 was synthesized using General Procedure 1. Yield (50%). $^1$H NMR (400 MHz, CDCl$_3$) δ 7.41 (s, 1H), 7.39 (s, 1H), 7.32 (s, 1H), 7.24 (s, 1H), 6.81 (s, 1H), 6.79 (s, 1H), 4.98-5.06 (m, 1H), 3.62-3.68 (m, 1H), 3.34-3.51 (m, 2H), 3.02-3.11 (m, 1H), 3.00 (s, 6H), 1.44 (s, 9H).

4-(2-(aminomethyl)-7-chloro-2,3-dihydrobenzofuran-5-yl)-N,N-dimethylaniline 66 was synthesized using General Procedure 2. Yield (79%). LCMS: m/z 302.9 [M+H]$^+$, t$_R$=1.38 min.

(E)-N-((7-chloro-5-(4-(dimethylamino)phenyl)-2,3-dihydrobenzofuran-2-yl) methyl)-3-(pyridin-3-yl)acrylamide 64 was synthesized using General Procedure 3. Yield (40%). $^1$H NMR (400 MHz, DMSO-d$_6$) δ 8.75 (s, 1H), 8.54-8.60 (m, 2H), 7.99-8.01 (d, J=7.6 Hz, 1H), 7.33-7.51 (m, 6H), 6.74-6.84 (m, 3H), 5.03 (s, 1H), 3.56-3.62 (m, 2H), 3.36-3.42 (m, 1H), 3.04-3.10 (m, 1H), 2.90 (s, 6H). LCMS: m/z 434.11 [M+H]$^+$, t$_R$=2.06 min.

Synthesis of (E)-N-((5-(5-acetylthiophen-2-yl)-7-chloro-2,3-dihydrobenzofuran-2-yl)methyl)-3-(6-methylpyridin-3-yl)acrylamide (67)

-continued

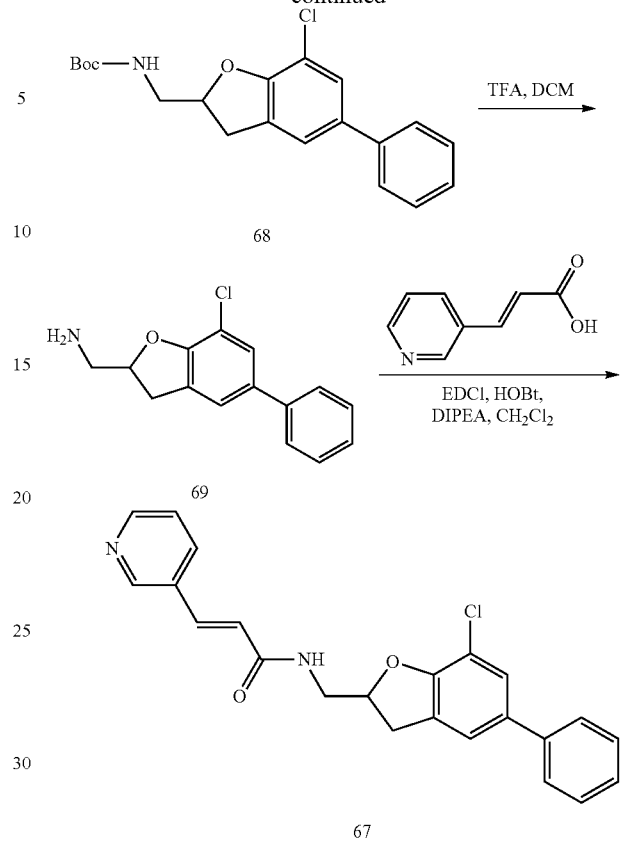

tert-Butyl (7-chloro-5-phenyl-2,3-dihydrobenzofuran-2-yl)methylcarbamate 68 was synthesized using General Procedure 1. Yield (61%). $^1$H NMR (400 MHz, CDCl$_3$) δ 7.48-7.52 (m, 2H), 7.41-7.45 (m, 2H), 7.29-7.38 (m, 3H), 5.02-5.05 (m, 1H), 3.63-3.66 (m, 1H), 3.37-3.47 (m, 2H), 3.08-3.13 (m, 1H), 1.42 (s, 9H). LCMS: m/z 304.21 [M−57]$^+$, t$_R$=2.68 min.

(7-chloro-5-phenyl-2,3-dihydrobenzofuran-2-yl)methanamine 69 was synthesized using General Procedure 2. Yield (97%). LCMS: m/z 260.22 [M+H]$^+$, t$_R$=1.59 min.

(E)-N-((7-chloro-5-phenyl-2,3-dihydrobenzofuran-2-yl)methyl)-3-(pyridin-3-yl)acrylamide 67 was synthesized using General Procedure 3. Yield (20%). $^1$H NMR (400 MHz, DMSO-d$_6$) δ 8.77 (s, 1H), 8.55-8.57 (m, 2H), 7.98-8.01 (m, 1H), 7.60-7.62 (m, 2H), 7.40-7.53 (m, 5H), 7.30-7.34 (m, 1H), 6.82-6.86 (d, J=16 Hz, 1H), 5.06-5.09 (m, 1H), 3.55-3.64 (m, 2H), 3.35-3.46 (m, 1H), 3.07-3.14 (m, 1H). LCMS: m/z 391.15 [M+H]$^+$, t$_R$=2.08 min.

Synthesis of (E)-N-((7-chloro-5-(pyridin-3-yl)-2,3-dihydrobenzofuran-2-yl)methyl)-3-(pyridin-3-yl)acrylamide (70)

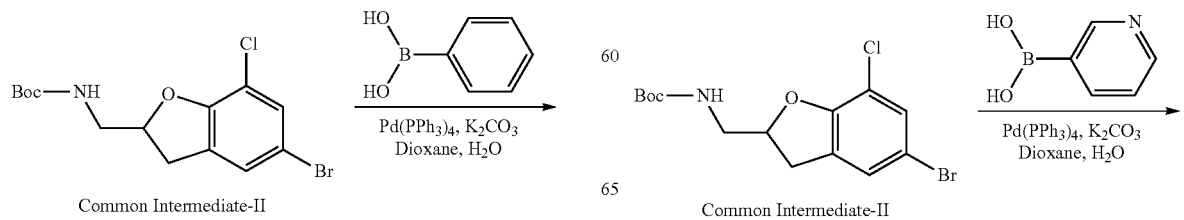

119

-continued

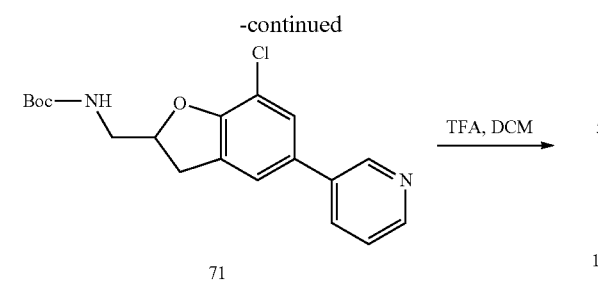

71

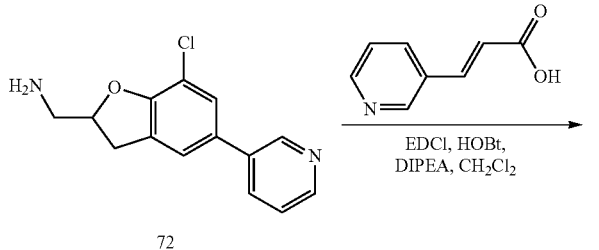

72

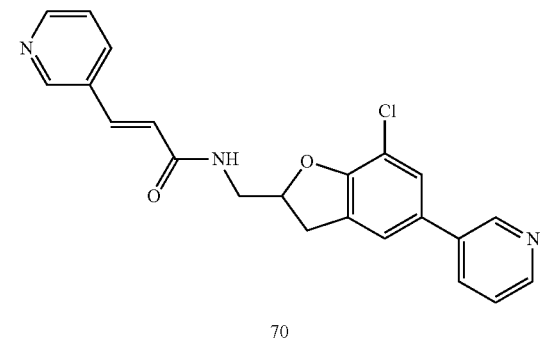

70 tert-Butyl (7-chloro-5-(pyridin-3-yl)-2,3-dihydrobenzofuran-2-yl)methylcarbamate 70 was synthesized using General Procedure 1. Yield (60%). LCMS: m/z 361.20 [M+H]$^+$, $t_R$=2.10 min.

(7-Chloro-5-(pyridin-3-yl)-2,3-dihydrobenzofuran-2-yl) methanamine 71 was synthesized using General Procedure 2. Yield (82%). $^1$H NMR (400 MHz, CDCl$_3$) δ 8.78 (s, 1H), 8.57-8.60 (m, 1H), 7.78-7.81 (m, 1H), 7.34-7.38 (m, 2H), 7.25 (s, 1H), 4.97-5.04 (m, 1H), 3.05-3.18 (m, 1H), 3.00-3.03 (m, 2H), 2.98-3.02 (m, 1H). LCMS: m/z 261.27 [M+H]$^+$, $t_R$=2.40 min.

(E)-N-((7-chloro-5-(pyridin-3-yl)-2,3-dihydrobenzofuran-2-yl)methyl)-3-(pyridin-3-yl)acrylamide 70 was synthesized using General Procedure 3. Yield (40%). $^1$H NMR (400 MHz, DMSO-d$_6$) δ 8.85 (s, 1H), 8.77 (s, 1H), 8.52-8.56 (m, 3H), 7.98-8.05 (m, 2H), 7.59 (s, 2H), 7.49-7.53 (d, J=15.6 Hz, 1H), 7.43-7.47 (m, 2H), 6.82-6.86 (d, J=15.6 Hz, 1H), 5.06-5.13 (m, 1H), 3.55-3.66 (m, 2H), 3.35-3.47 (m, 1H), 3.10-3.16 (m, 1H). LCMS: m/z [M+H]$^+$392.2, $t_R$=1.29 min.

120

Synthesis of (E)-N-((7-chloro-5-(2,3-difluorophenyl)-2,3-dihydrobenzo furan-2-yl)methyl)-3-(pyridin-3-yl)acrylamide (73)

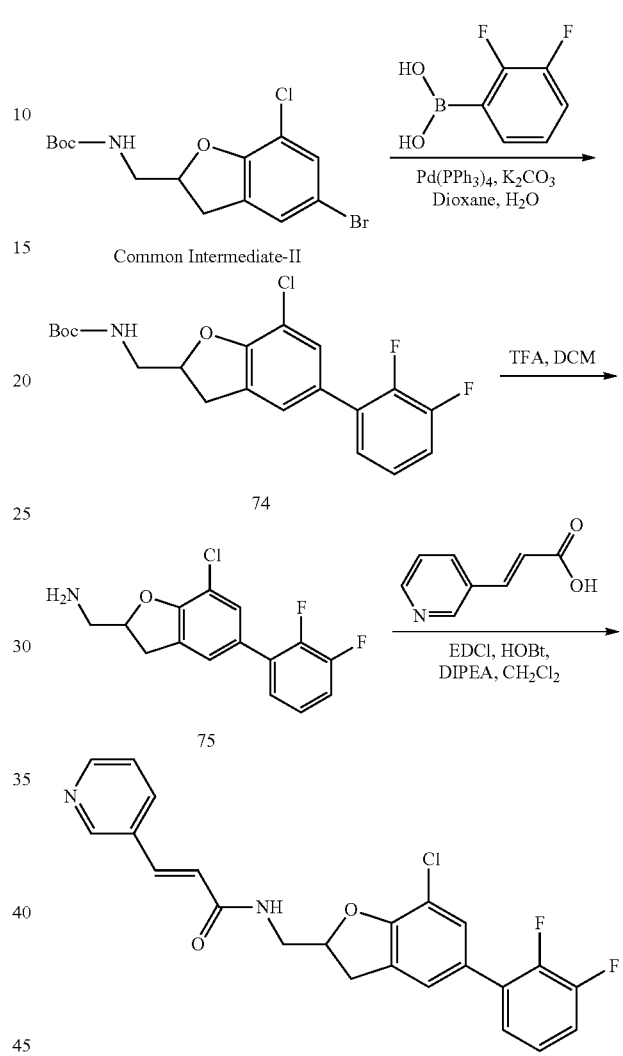

tert-Butyl (7-chloro-5-(2,3-difluorophenyl)-2,3-dihydrobenzofuran-2-yl)methyl carbamate 74 was synthesized using General Procedure 1. Yield (51%). $^1$H NMR (400 MHz, CDCl$_3$) δ 7.36 (s, 1H), 7.25-7.27 (m, 1H), 7.10-7.18 (m, 3H), 5.02-5.09 (m, 1H), 3.63-3.736 (m, 1H), 3.37-3.47 (m, 2H), 2.19-3.14 (m, 1H), 1.47 (s, 9H). LCMS: m/z 340.10 [M−57]$^+$, $t_R$=2.81 min.

(7-Chloro-5-(2,3-difluorophenyl)-2,3-dihydrobenzofuran-2-yl)methanamine 75 was synthesized using General Procedure 2. Yield (80%). LCMS: m/z 296.2 [M+H]$^+$, $t_R$=1.69 min.

(E)-N-((7-chloro-5-(2,3-difluorophenyl)-2,3-dihydrobenzofuran-2-yl)methyl)-3-(pyridin-3-yl)acrylamide 73 was synthesized using General Procedure 3. Yield (15%). $^1$H NMR (400 MHz, DMSO-d$_6$) δ 8.77 (s, 1H), 8.54-8.57 (m, 2H), 7.98-8.01 (m, 1H), 7.38-7.53 (m, 5H), 7.24-7.34 (m, 2H), 6.82-6.86 (d, J=15.6Hz, 1H), 5.09-5.12 (m, 1H), 3.55-3.67 (m, 2H), 3.41-3.47 (m, 1H), 3.09-3.18 (m, 1H). LCMS: m/z 427.39 [M+H]$^+$, $t_R$=2.11 min.

Synthesis of (E)-ethyl 3-(7-chloro-2-((3-(pyridin-3-yl)acrylamido)methyl)-2,3-dihydrobenzofuran-5-yl)benzoic acid (76)

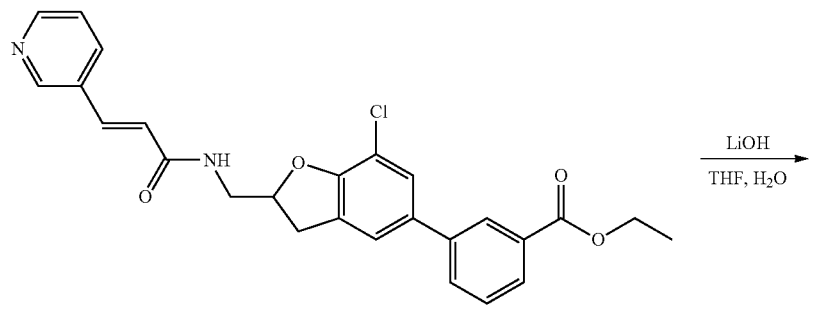

(E)-ethyl-3-(7-chloro-2-((3-(pyridin-3-yl)acrylamido)methyl)-2,3-dihydrobenzofuran-5-yl) benzoate 52 (0.15 g, 0.32 mmol) was dissolved in THF/H$_2$O (1:1) and LiOH.6H$_2$O (0.05 g, 1.29 mmol) was added at 0° C. The reaction mixture was allowed to warm to room temperature where it was stirred for 16 h. The reaction mixture was transferred into dilute HCl solution until pH~2, extracted with ethyl acetate (20 mL×3), dried over anhydrous Na$_2$SO$_4$, and concentrated under reduced pressure to obtain 0.04 g of pure (E)-3-(7-chloro-2-((3-(pyridin-3-yl)acrylamido)methyl)-2,3-dihydrobenzofuran-5-yl)benzoic acid 76. 29% yield. $^1$H NMR (400 MHz, DMSO-d$_6$) δ 8.95 (s, 1H), 8.71-8.72 (d, J=4.8 Hz, 1H), 8.35-8.37 (d, J=8.4 Hz, 1H), 8.11 (s, 1H), 7.86-7.90 (m, 2H), 7.75-7.78 (m, 1H), 7.52-7.60 (m, 4H), 6.96-7.00 (d, J=16 Hz, 1H), 5.06-5.13 (m, 1H), 3.54-3.67 (m, 2H), 3.37-3.50 (m, 1H), 3.11-3.17 (m, 1H). LCMS: m/z 435.54 [M+H]$^+$, t$_R$=1.74 min.

Synthesis of (E)-N-((7-chloro-5-(5-(methylsulfonyl)pyridin-3-yl)-2,3-dihydrobenzofuran-2-yl)methyl)-3-(pyridin-3-yl)acrylamide (77)

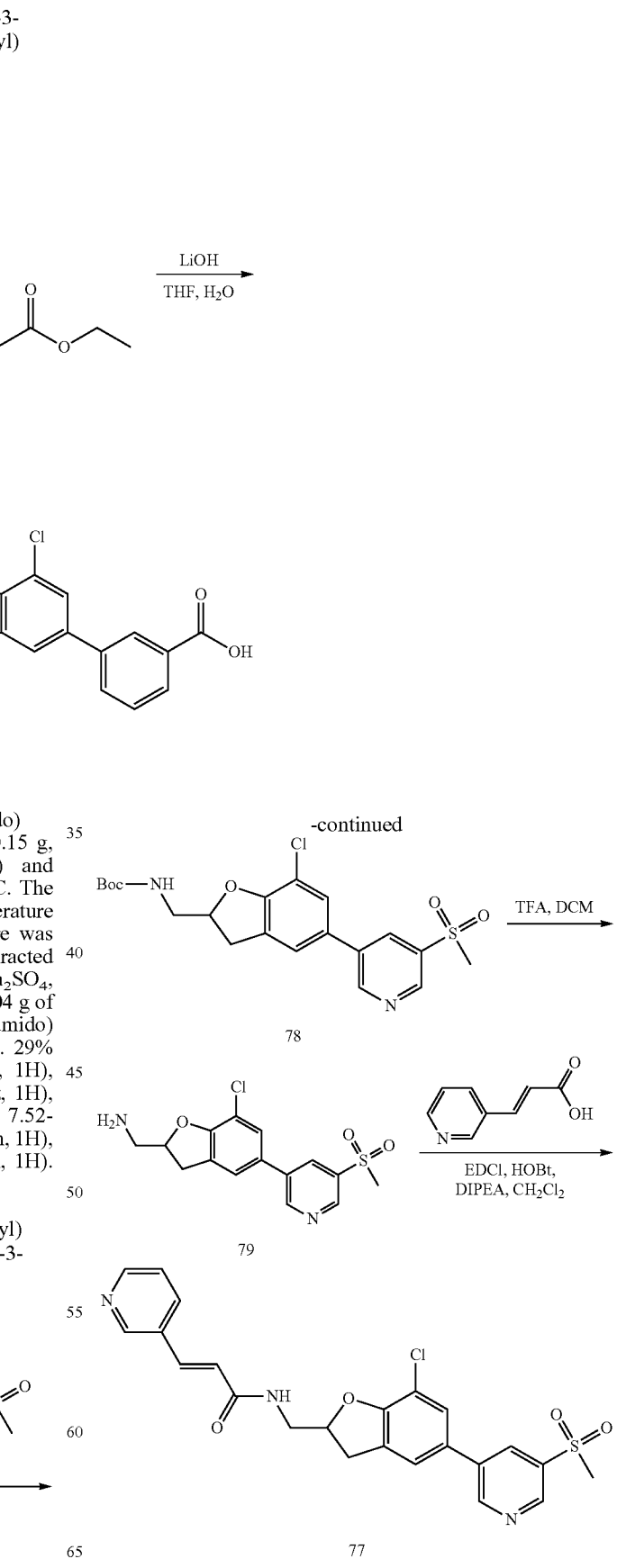

tert-Butyl (7-chloro-5-(5-(methylsulfonyl)pyridin-3-yl)-2, dihydrobenzofuran-2-yl)methylcarbamate 78 was synthesized using General Procedure 1. Yield (45%). LCMS: m/z 439.11 [M+H]$^+$, $t_R$=2.06 min.

(7-chloro-5-(5-(methylsulfonyl)pyridin-3-yl)-2,3-dihydrobenzofuran-2-yl)methanamine 79 was synthesized using General Procedure XX. Yield (30%). LCMS: m/z 279 [M−59]$^+$, $t_R$=1.87 min.

(E)-N-((7-chloro-5-(5-(methylsulfonyl)pyridin-3-yl)-2,3-dihydrobenzofuran-2-yl)methyl)-3-(pyridin-3-yl)acrylamide 77 was synthesized using General Procedure 3. Yield (30%). $^1$H NMR (400 MHz, DMSO-d$_6$) δ 9.20-9.21 (d, J=2.4 Hz, 1H), 8.98-8.99 (d, J=2 Hz, 1H), 8.77-8.78 (d, J=2 Hz, 1H), 8.51-8.58 (m, 3H), 7.98-8.01 (d, J=8 Hz, 1H), 7.80 (s, 1H), 7.75 (s, 1H), 7.53 (s, 1H), 7.49-7.53 (d, J=16 Hz, 1H), 7.43-7.47 (m, 1H), 6.82-6.86 (d, J=16 Hz, 1H), 5.13-5.14 (m, 1H), 3.43-3.49 (m, 2H), 3.36 (s, 1H), 3.12-3.15 (m, 1H). LCMS: m/z 515.91 [M+45]$^+$, $t_R$=1.47 min.

Synthesis of (E)-N-((7-chloro-5-(3-(methylsulfonyl)phenyl)-2,3-dihydrobenzofuran-2-yl)methyl)-3-(pyridin-3-yl)acrylamide (80)

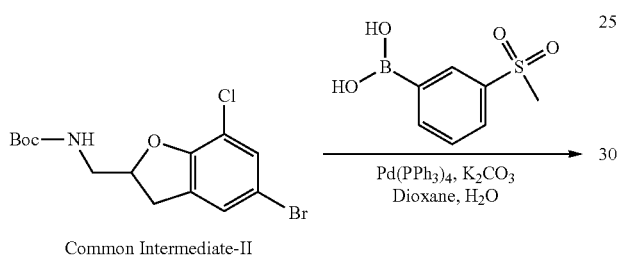

Common Intermediate-II

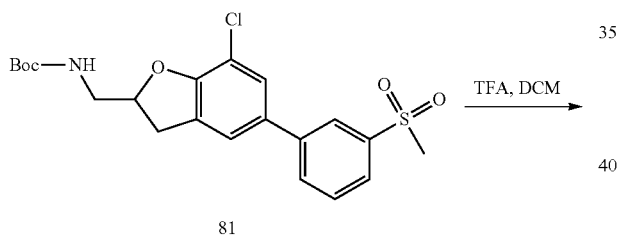

81

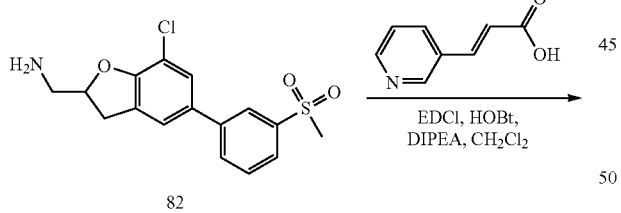

82

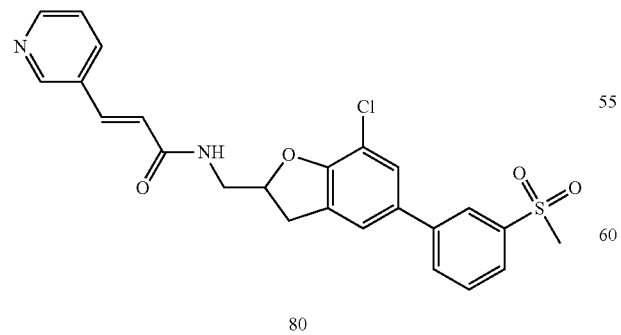

80 tert-Butyl(7-chloro-5-(3-(methylsulfonyl)phenyl)-2,3-dihydrobenzofuran-2-yl)methylcarbamate 81 was synthesized using General Procedure 1. Yield (83%). $^1$H NMR (400 MHz, CDCl$_3$) δ 8.08 (s, 1H), 7.89-7.92 (m, 1H), 7.78-7.81 (m, 1H), 7.64-7.66 (t, J=3.6 Hz, 1H), 7.41 (s, 1H), 7.33 (s, 1H), 5.04-5.08 (m, 1H), 3.64-3.70 (m, 1H), 3.38-3.51 (m, 2H), 3.06-3.15 (m, 4H), 1.43 (s, 9H). LCMS: m/z 457.2 [M+18]$^+$, $t_R$=2.26 min.

Ethyl 3-(2-(aminomethyl)-7-chloro-2,3-dihydrobenzofuran-5-yl)benzoate 82 was synthesized using General Procedure 2. Yield (97%). $^1$H NMR (400 MHz, CDCl$_3$, ppm) δ=8.11 (s, 1H), 7.98-8.01 (m, 1H), 7.85-7.87 (m, 1H), 7.68-7.87 (t, J=8 Hz, 1H), 7.62-7.64 (d, J=6.4 Hz, 2H), 4.93-5.00 (m, 1H), 3.39-3.68 (m, 1H), 3.26 (s, 3H), 3.12-3.23 (m, 1H), 2.92-2.95 (m, 2H). LCMS: m/z 381.13 [M+41]$^+$, $t_R$=1.34 min.

(E)-N-((7-chloro-5-(3-(methylsulfonyl)phenyl)-2,3-dihydrobenzofuran-2-yl)methyl)-3-(pyridin-3-yl)acrylamide 80 was synthesized using General Procedure 3. Yield (80%). $^1$H NMR (400 MHz, DMSO-d$_6$) δ 8.77 (s, 1H), 8.54-8.59 (m, 2H), 8.11 (s, 1H), 7.98-8.00 (m, 2H), 7.84-7.87 (m, 1H), 7.64-7.72 (m, 3H), 7.43-7.55 (m, 3H), 6.82-6.86 (d, J=16 Hz, 1H), 5.10-5.12 (m, 1H), 3.55-3.65 (m, 2H), 3.43-3.48 (m, 1H), 3.29 (s, 1H), 3.11-3.18 (m, 1H). LCMS: m/z 469.15 [M+H]$^+$, $t_R$=1.71 min.

Synthesis of (E)-N-((7-chloro-2,3-dihydrobenzofuran-2-yl)methyl)-3-(pyridin-3-yl)acrylamide (83)

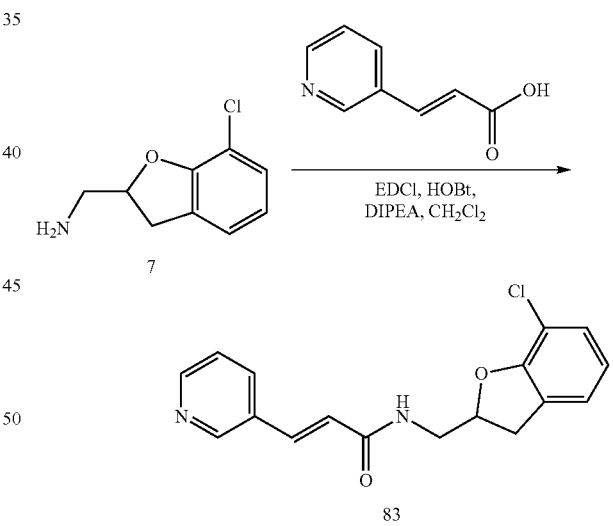

(E)-N-((7-chloro-2,3-dihydrobenzofuran-2-yl)methyl)-3-(pyridin-3-yl)acrylamide 83 was synthesized using General Procedure 3. Yield (40%). $^1$H NMR (400 MHz, CDCl$_3$) δ 8.76 (s, 1H), 8.59-8.60 (d, J=3.6 Hz, 1H), 7.82-7.83 (d, J=7.6 Hz, 1H), 7.63-7.67 (d, J=15.6 Hz, 1H), 7.32-7.35 (m, 1H), 7.05-7.16 (m, 2H), 6.77-6.91 (m, 1H), 6.52-6.55 (d, J=15.6 Hz, 1H), 6.31 (bs, 1H), 5.04-5.11 (m, 1H), 3.94-4.00 (m, 1H), 3.61-3.76 (m, 1H), 3.33-3.44 (m, 1H), 3.03-3.10 (m, 1H). LCMS: m/z 315.76 [M+H]$^+$, $t_R$=1.57 min.

Synthesis of (E)-N-((5-(2-aminophenyl)-7-chloro-2,3-dihydrobenzofuran-2-yl)methyl)-3-(pyridin-3-yl)acrylamide (84)

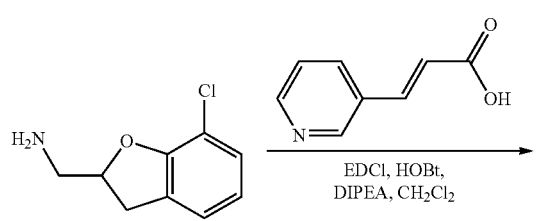

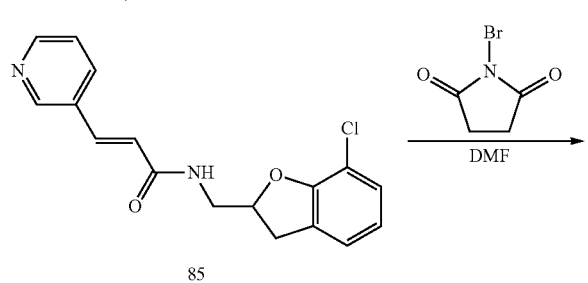

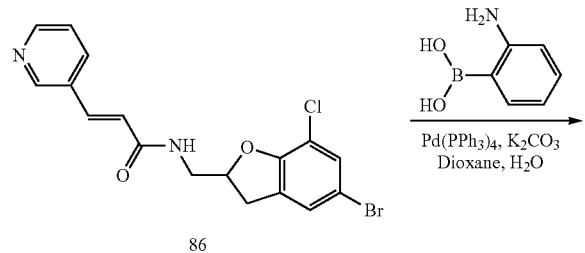

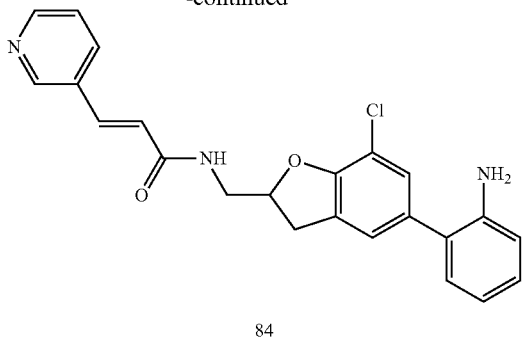

(E)-N-((7-chloro-2,3-dihydrobenzofuran-2-yl)methyl)-3-(pyridin-3-yl)acrylamide 85 was synthesized using General Procedure 3. Yield (40%) $^1$H NMR (400 MHz, CDCl$_3$) δ 8.76 (s, 1H), 8.59-8.60 (d, J=3.6 Hz, 1H), 7.82-7.83 (d, J=7.6 Hz, 1H), 7.63-7.67 (d, J=15.6 Hz, 1H), 7.32-7.35 (m, 1H), 7.05-7.16 (m, 2H), 6.77-6.91 (m, 1H), 6.52-6.55 (d, J=15.6 Hz, 1H), 6.31 (bs, 1H), 5.04-5.11 (m, 1H), 3.94-4.00 (m, 1H), 3.61-3.76 (m, 1H), 3.33-3.44 (m, 1H), 3.03-3.10 (m, 1H). LCMS: m/z 315.76 [M+H]$^+$, $t_R$=1.57 min.

(E)-N-((5-bromo-7-chloro-2,3-dihydrobenzofuran-2-yl)methyl)-3-(pyridin-3-yl)acrylamide 86 was been synthesized using conditions described in the last step in Method A (conversion of 8 to Common Intermediate II). Yield (15%). LCMS: m/z 395.30 [M+H]$^+$, $t_R$=1.91 min.

(E)-N-((5-(2-aminophenyl)-7-chloro-2,3-dihydrobenzofuran-2-yl)methyl)-3-(pyridin-3-yl)acrylamide 84 was synthesized using General Procedure 1. Yield (15%). $^1$H NMR (400 MHz, DMSO-d$_6$) δ 8.78 (s, 1H), 8.54-8.57 (t, 2H), 7.99-8.01 (d, J=8 Hz, 1H), 7.53 (s, 1H), 7.44-7.49 (m, 1H), 7.20 (s, 1H), 7.15 (s, 1H), 7.03(s, 1H), 6.93-6.95 (d, J=7.2 Hz, 1H), 6.83-6.87 (d, J=16 Hz, 1H), 6.72-6.74 (d, J=8 Hz, 1H), 6.58-6.61 (t, 1H), 5.03-5.09 (m, 1H), 4.82 (bs, 2H), 3.55-3.63 (m, 2H), 3.34-3.43 (m, 1H), 3.06-3.12 (m, 1H). LCMS: m/z 406.15 [M+H]$^+$, $t_R$=2.89 min.

Synthesis of (E)-N-((5-(5-acetylthiophen-2-yl)-7-fluoro-2,3-dihydrobenzofuran-2-yl)methyl)-3-(pyridin-3-yl)acrylamide (87)

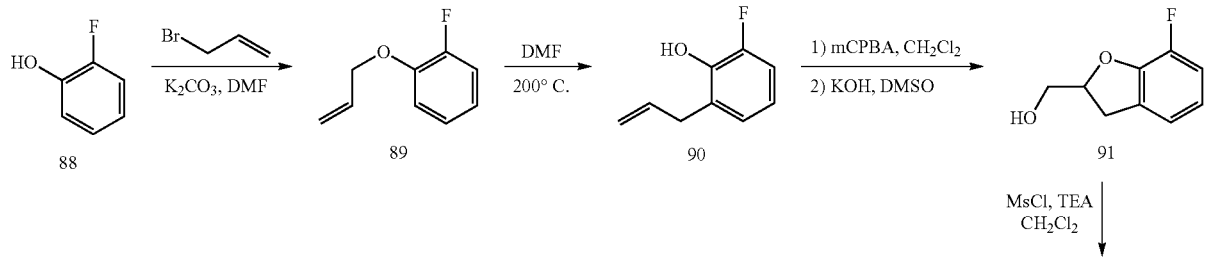

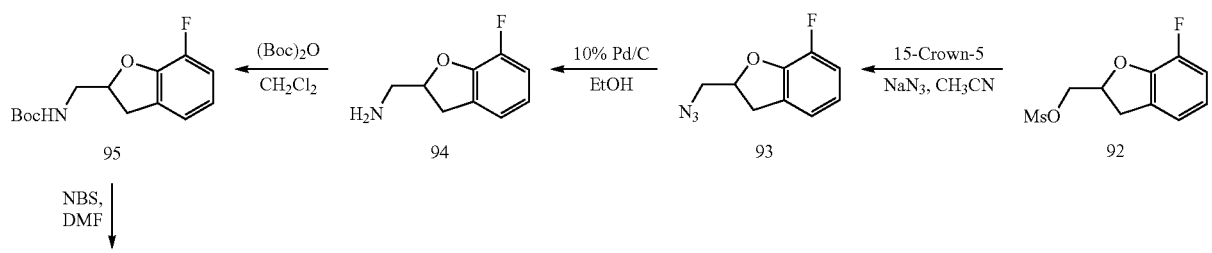

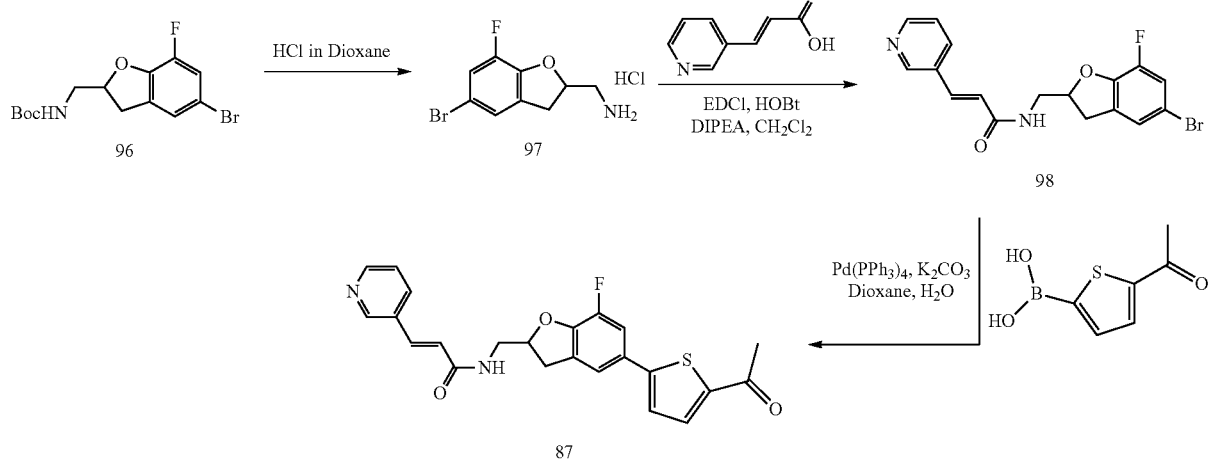

1-(Allyloxy)-2-fluorobenzene 89 was synthesized using conditions described in the first step in Method A (conversion of 1 to 2). Yield (88%). ¹H NMR (400 MHz, CDCl₃) δ 6.91-7.13 (m, 4H), 6.06-6.13 (m, 1H), 5.43-5.48 (m, 1H), 5.31-5.34 (m, 1H), 4.63-4.64 (m, 2H). LC: $t_R$=2.263 min.

2-Allyl-6-fluorophenol 90 was synthesized using conditions described in the second step in Method A (conversion of 2 to 3). Yield (50%). LCMS: m/z 151.13 [M−H]⁻, $t_R$=6.932 min.

(7-Fluoro-2,3-dihydrobenzofuran-2-yl)methanol 91 was synthesized using conditions described in the third step in Method A (conversion of 3 to 4). Yield (60%). ¹H NMR (400 MHz, CDCl₃) δ 6.88-6.99 (m, 2H), 6.76-6.84 (m, 1H), 4.99-5.05 (m, 1H), 3.89-3.93 (m, 1H), 3.76-3.80 (m, 1H), 3.26-3.33 (m, 1H), 3.08-3.15 (m, 1H). LCMS: m/z 168.7 [M+H]⁺, $t_R$=1.299 min.

(7-Fluoro-2,3-dihydrobenzofuran-2-yl)methyl methanesulfonate 92 was synthesized using conditions described in the fourth step in Method A (conversion of 4 to 5). Yield (76%). ¹H NMR (400 MHz, DMSO-d₆) δ 7.01-7.06 (m, 2H), 6.81-6.86 (m, 1H), 5.16-5.23 (m, 1H), 4.50-4.53 (m, 1H), 4.38-4.42 (m, 1H), 3.20-3.48 (m, 1H), 3.04-3.08 (m, 1H), 2.51 (s, 3H).

2-(Azidomethyl)-7-fluoro-2,3-dihydrobenzofuran 93 was synthesized using conditions described in the fifth step in Method A (conversion of 5 to 6). Yield (51%). ¹H NMR (400 MHz, DMSO-d₆) δ 7.01-7.07 (m, 2H), 6.81-6.89 (m, 1H), 5.09-5.16 (m, 1H), 3.69-3.79 (m, 1H), 3.54-3.61 (m, 1H), 3.32-3.39 (m, 1H), 3.01-3.06 (m, 1H).

(7-Fluoro-2,3-dihydrobenzofuran-2-yl)methanamine 94 was synthesized using conditions described in the sixth step in Method A (conversion of 6 to 7). Yield (65%). ¹H NMR (400 MHz, DMSO-d₆) δ 7.00-7.27 (m, 2H), 6.79-6.84 (m, 1H), 4.90-4.97 (m, 1H), 4.39 (br, 2H), 3.31-3.35 (m, 1H), 3.04-3.17 (m, 2H), 2.89-2.99 (m, 1H). LCMS: m/z 168.05 [M+H]⁺, $t_R$=4.913 min.

tert-Butyl (7-fluoro-2,3-dihydrobenzofuran-2-yl)methylcarbamate 95 was synthesized using conditions described in the seventh step in Method A (conversion of 7 to 8). Yield (55%). ¹H NMR (400 MHz, CDCl₃) δ 7.01-7.26 (m, 2H), 6.78-6.83 (m, 1H), 4.90-4.97 (m, 1H), 4.40 (br, 1H), 3.31-3.34 (m, 1H), 3.04-3.18 (m, 2H), 2.89-2.99 (m, 1H), 1.49 (s, 9H). LCMS: m/z 211.9 [M−56]⁺ and 167.9 [M−100]⁺, $t_R$=2.187 min.

tert-Butyl (5-bromo-7-fluoro-2,3-dihydrobenzofuran-2-yl)methylcarbamate 96 was synthesized using conditions described in the last step in Method A (conversion of 8 to Common Intermediate II). Yield (65%). LCMS: m/z 289.9 [M−56]⁺, $t_R$=2.461 min.

(5-Bromo-7-fluoro-2,3-dihydrobenzofuran-2-yl)methanamine hydrochloride 97 was synthesized using General Procedure 2. Yield (62%). LCMS: m/z 168.06 [M+H]⁺, $t_R$=1.32 min.

(E)-N-((5-bromo-7-fluoro-2,3-dihydrobenzofuran-2-yl)methyl)-3-(pyridin-3-yl)acrylamide 98 was synthesized using General Procedure 3. Yield (45%). ¹H NMR (400 MHz, MeOD) δ 8.78 (s, 1H), 8.58-8.59 (d, J=4.4 Hz, 1H), 8.11-8.13 (t, 1H), 7.61-7.65 (d, J=15.6 Hz, 1H), 7.53-7.56 (m, 1H), 7.19-7.23 (m, 2H), 6.82-6.86 (d, J=15.2 Hz, 1H), 5.14-5.18 (m, 1H), 3.69-3.79 (m, 2H), 3.38-3.49 (m, 1H), 3.11-3.17 (m, 1H). LCMS: m/z 422.9 [M−46]⁻, $t_R$=1.801 min.

(E)-N-((5-(5-acetylthiophen-2-yl)-7-fluoro-2,3-dihydrobenzofuran-2-yl)methyl)-3-(pyridin-3-yl)acrylamide 87 was synthesized using General Procedure 1. Yield (48%). ¹H NMR (400 MHz, DMSO-d₆) δ 8.75 (s, 1H), 8.51-8.55 (m, 2H), 7.96-7.98 (d, J=8 Hz, 1H), 7.89-7.90 (d, J=4 Hz, 1H), 7.42-7.55 (m, 5H), 6.79-6.83 (d, J=16 Hz, 1H), 5.08-5.15 (m, 1H), 3.31-3.34 (m, 1H), 3.57-3.60 (m, 2H), 3.04-3.08 (m, 1H), 2.61 (s, 3H). LCMS: m/z 423.1 [M+H]⁺, $t_R$=1.82 min.

(E)-N-((5-(5-acetylthiophen-2-yl)-2,3-dihydrobenzofuran-2-yl)methyl)-3-(pyridin-3-yl)acrylamide (292) was synthesized in a manner similar to that described for Compound 87 using the appropriate reagents. ¹H NMR (400 MHz, DMSO-d₆) δ 8.77 (s, 1H), 8.56 (m, 2H), 8.00 (m, 1H), 7.98 (m, 1H), 7.90 (s, 1H), 7.46 (m, 4H), 6.85 (m, 1H), 6.79 (m, 1H), 4.99 (m, 1H), 3.55 (m, 2H), 3.3 (m, 1H), 3.02 (m, 1H), 2.5 (s, 3H). LCMS: m/z 405.0 [M+H]⁺, $t_R$=1.76 min.

Synthesis of (E)-N-((5-(5-acetylfuran-2-yl)-7-chloro-2,3-dihydrobenzofuran-2-yl)methyl)-3-(pyridin-3-yl)acrylamide (99)

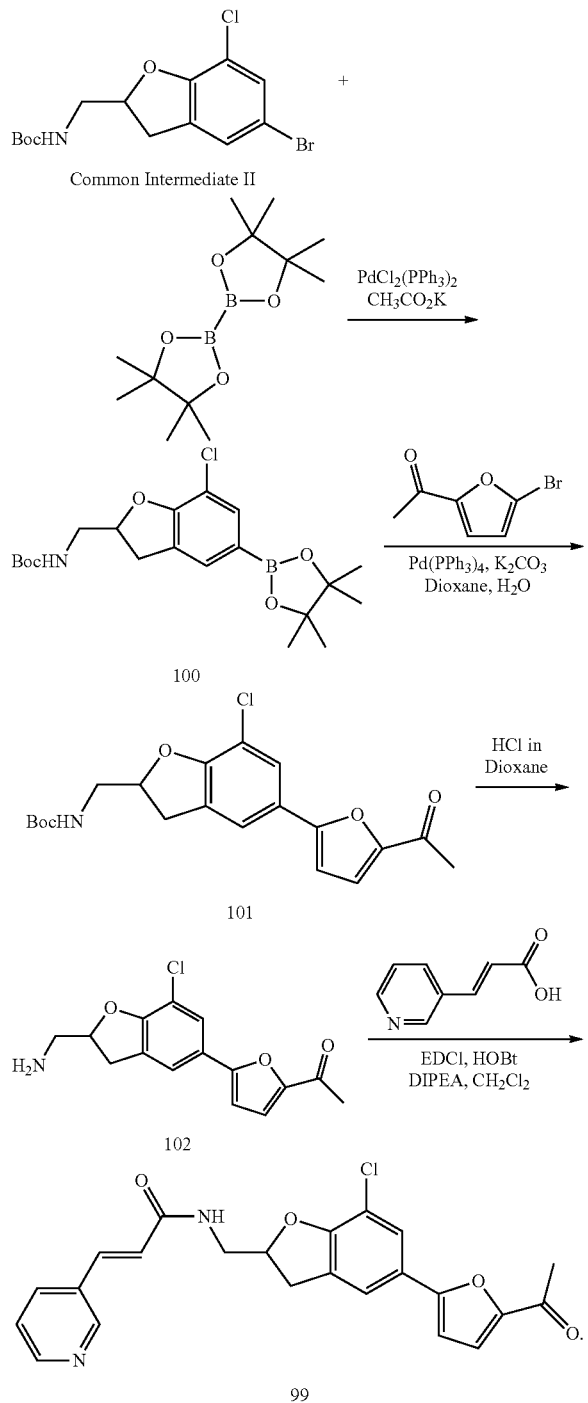

tert-Butyl (7-chloro-5-(4,4,5,5-tetramethyl-1,3,2-dioxaborolan-2-yl)-2,3-dihydrobenzofuran-2-yl)methylcarbamate 100 was synthesized using General Procedure 1. Yield (44%). LCMS: m/z 353.97 [M–56]+, $t_R$=2.769 min.

tert-Butyl (5-(5-acetylfuran-2-yl)-7-chloro-2,3-dihydrobenzofuran-2-yl)methylcarbamate 101 was synthesized using General Procedure 1. Yield (42%). $^1$H NMR (400 MHz, DMSO-d$_6$) δ 7.13-7.70 (m, 4H), 4.92-5.05 (m, 1H), 3.59-3.63 (m, 1H), 3.30-3.43 (m, 2H), 3.02-3.08 (m, 1H), 2.48 (s, 3H), 1.38 (m, 9H). LCMS: m/z 336.0 [M–56]+, $t_R$=2.314 min.

1-(5-(2-(Aminomethyl)-7-chloro-2,3-dihydrobenzofuran-5-yl)furan-2-yl)ethanone 102 was synthesized using General Procedure 2. Yield (60%). $^1$H NMR (400 MHz, DMSO-d$_6$) δ 8.20 (s, 2H, exchangeable), 7.17-7.75 (m, 6H, 2H exchangeable), 5.19-5.21 (m, 1H), 3.24-3.58 (m, 4H), 2.49 (s, 3H). LCMS: m/z 218.84 [M+H]+, $t_R$=1.005 min.

(E)-N-((5-(5-Acetylfuran-2-yl)-7-chloro-2,3-dihydrobenzofuran-2-yl)methyl)-3-(pyridin-3-yl)acrylamide 99 was synthesized using General Procedure 3. Yield (47%). $^1$H NMR (400 MHz, DMSO-d$_6$) δ 8.76 (s, 1H), 8.55-8.56 (m, 2H), 7.89-8.00 (d, J=7.6 Hz, 1H), 7.70-7.72 (d, J=7.6 Hz, 2H), 7.44-7.55 (m, 3H), 7.14-7.15 (d, J=4 Hz, 2H), 6.81-6.85 (d, J=15.6 Hz, 1H), 5.10-5.13 (m, 1H), 3.42-3.62 (m, 3H), 3.09-3.17 (m, 1H), 2.45 (s, 3H). LCMS: m/z 423.00 [M+H]+, $t_R$=1.713 min.

Synthesis of (E)-N-((5-(5-acetylthiophen-2-yl)-7-chloro-2,3-dihydrobenzofuran-2-yl)methyl)-3-(pyridin-2-yl)acrylamide (103)

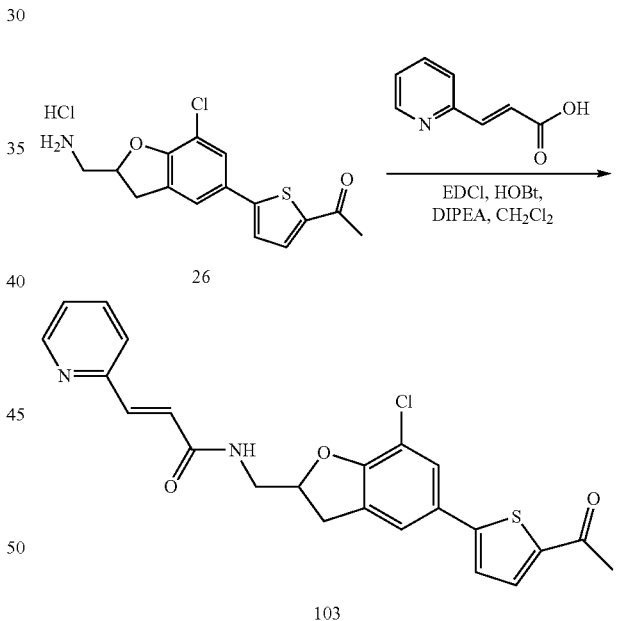

(E)-N-((5-(5-Acetylthiophen-2-yl)-7-chloro-2,3-dihydrobenzofuran-2-yl)methyl)-3-(pyridin-2-yl)acrylamide 103 was synthesized using General Procedure 3. Yield (17.6%). $^1$H NMR (400 MHz, DMSO) δ 8.59-8.64 (m, 2H), 7.90-7.91 (d, J=4 Hz, 1H), 7.81-7.85 (t, 1H), 7.57-7.64 (m, 4H), 7.45-7.49 (d, J=15.6 Hz, 1H), 7.34-7.37 (q, 1H), 7.11-7.15 (d, J=15.6 Hz, 1H), 5.09-5.11 (m, 1H), 3.50-3.75 (m, 2H), 3.39-3.45 (m, 1H), 3.05-3.11 (m, 1H), 2.52 (s, 3H). LCMS: m/z 439.06 [M+H]+, $t_R$=2.018 min.

Synthesis of (E)-N-((5-(5-acetylthiophen-2-yl)-7-chloro-2,3-dihydrobenzofuran-2-yl)methyl)-3-(2-aminopyrimidin-5-yl)acrylamide (104)

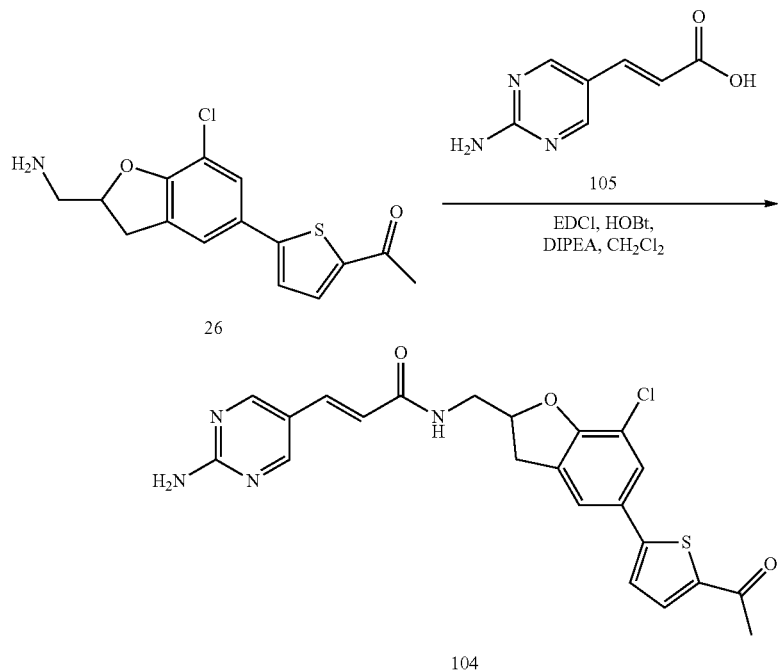

To a suspension of 26 (52 mg, 0.15 mmol) and 105 (25 mg, 0.15 mmol) in DMF (1 mL)/DCM (1 mL) was added EDCI (58 mg, 2 eq), HOBT (40 mg, 2 eq) and iPr$_2$NEt (100 uL) at room temperature and the mixture was stirred at room temperature for overnight. The reaction mixture was the diluted with DCM and washed with water, and brine. The organic layer was dried over Na$_2$SO$_4$, filtered, and concentrated. The resulting residue was purified by prep-HPLC to yield the product 104 (15%). $^1$H NMR (300 MHz, DMSO-d6) δ 8.43 (S, 2H); 8.30 (t, 1H); 7.89 (d, 1H); 7.5-7.63 (m, 4H); 7.25 (d, 1H); 7.0-7.15 (m, 1H); 6.53 (d, 1H); 5.0-5.1 (m, 1H); 3.2-3.6 (m, 2H); 2.95-3.18 (m, 2H); 2.5 (s, 3H). LCMS: m/z 454.88 [M+H]$^+$, t$_R$7.02 min.

Synthesis of (E)-N-((5-(5-acetylthiophen-2-yl)-7-chloro-2,3-dihydrobenzofuran-2-yl)methyl)-3-(2-aminopyridin-3-yl)acrylamide (106)

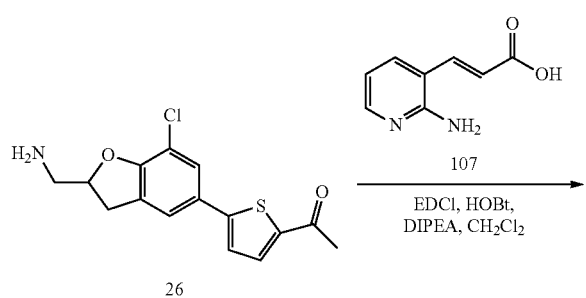

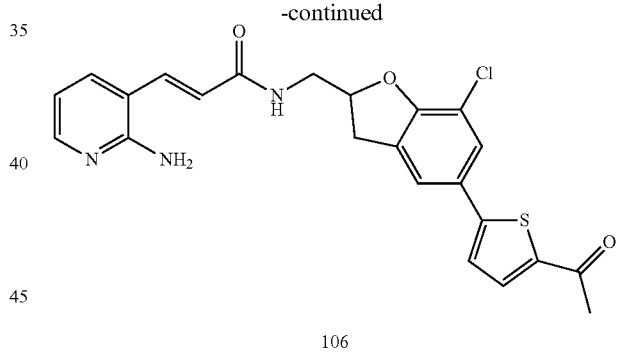

To a suspension of 26 (52 mg, 0.15 mmol) and 107 (25 mg, 0.15 mmol) in DMF (1 mL)/DCM (1 mL) was added EDCI (58 mg, 2 eq), HOBT (40 mg, 2 eq) and iPr$_2$NEt (100 uL) at room temperature and the mixture was stirred at room temperature for overnight. The reaction mixture was the diluted with DCM and washed with water, and brine. The organic layer was dried over Na$_2$SO$_4$, filtered, and concentrated. The resulting residue was purified by prep-HPLC to yield the product 106 (44%). $^1$H NMR (300 MHz, DMSO-d6) δ 8.36-8.38 (m, 1H); 7.9-7.95 (m, 2H); 7.67-7.64 (m, 5H); 6.52-6.59 (m, 2H); 6.18 (s, 2H); 5.0-5.15 (m, 1H); 3.2-3.6 (m, 2H); 3.0-3.18 (m, 2H); 2.5 (s, 3H). LCMS: m/z 453.99 [M+H]$^+$, t$_R$ 6.77 min.

133

Synthesis of (E)-N-((5-(5-acetylthiophen-2-yl)-7-chloro-2,3-dihydrobenzofuran-2-yl)methyl)-3-(4-aminopyridin-3-yl)acrylamide (108)

134

Synthesis of (E)-N-((5-(5-acetylthiophen-2-yl)-7-chloro-2,3-dihydrobenzofuran-2-yl)methyl)-3-(2-aminophenyl)acrylamide (110)

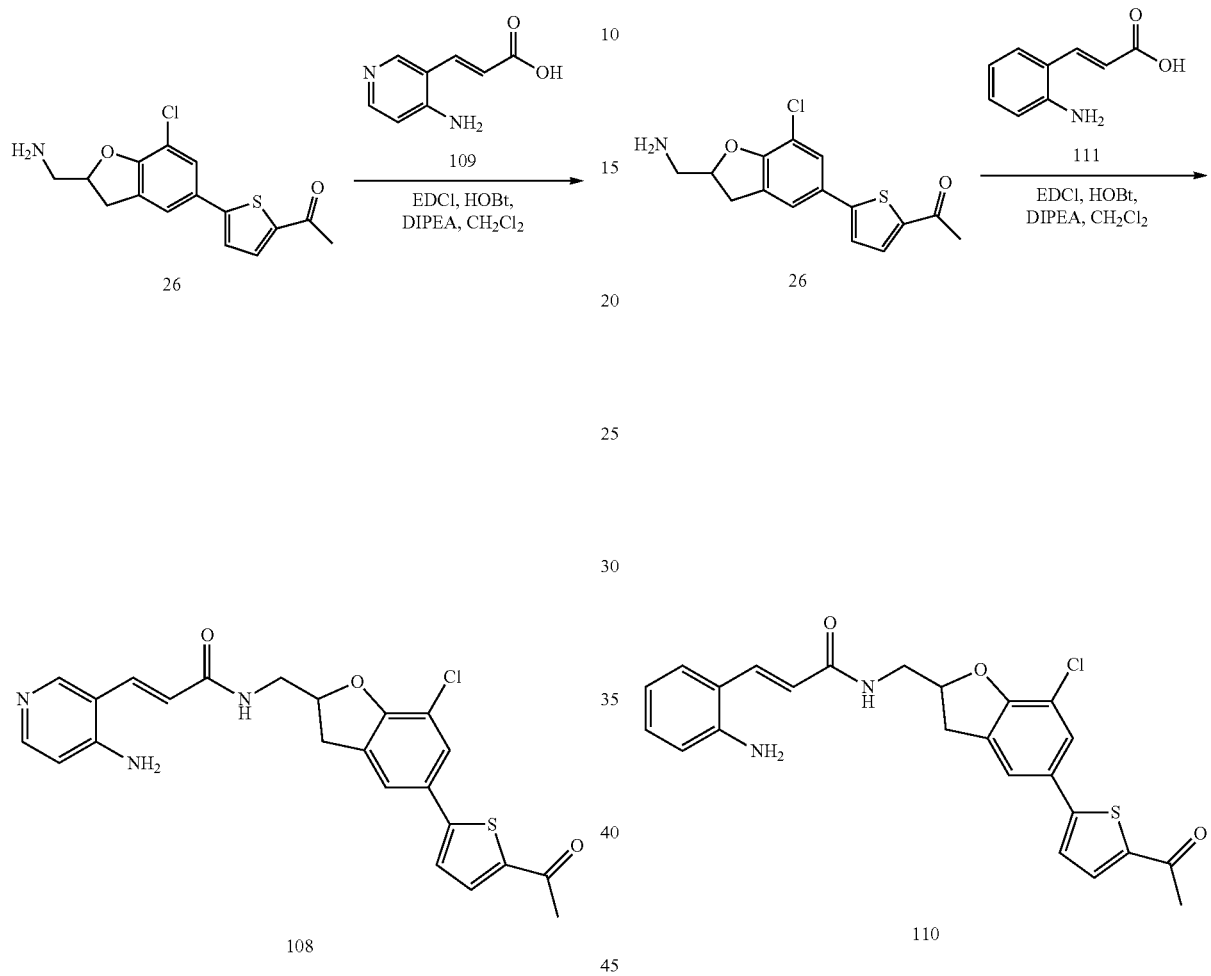

To a suspension of 25 (52 mg, 0.15 mmol) and 109 (25 mg, 0.15 mmol) in DMF (1 mL)/DCM (1 mL) was added EDCI (58 mg, 2 eq), HOBT (40 mg, 2 eq) and iPr₂NEt (100 uL) at room temperature and the mixture was stirred at room temperature for overnight. The reaction mixture was the diluted with DCM and washed with water, and brine. The organic layer was dried over $Na_2SO_4$, filtered, and concentrated. The resulting residue was purified by prep-HPLC to yield the product 108 (26%). $^1$H NMR (300 MHz, DMSO-d6) δ 8.37 (t, 1H); 8.25 (s, 1H); 7.9-7.93 (m, 2H); 7.55-7.64 (m, 4H); 7.54-7.59 (m, 2H); 6.39 (s, 2H); 5.04-5.15 (m, 1H); 3.4-3.6 (m, 2H); 3.04-3.18 (m, 2H); 2.5 (s, 3H). LCMS: m/z 454.06 [M+H]⁺, $t_R$ 6.67 min.

To a suspension of 26 (52 mg, 0.15 mmol) and 111 (25 mg, 0.15 mmol) in DMF (1 mL)/DCM (1 mL) was added EDCI (58 mg, 2 eq), HOBT (40 mg, 2 eq) and iPr₂NEt (100 uL) at room temperature and the mixture was stirred at room temperature for overnight. The reaction mixture was the diluted with DCM and washed with water, and brine. The organic layer was dried over $Na_2SO_4$, filtered, and concentrated. The resulting residue was purified by prep-HPLC to yield the product 110 (40%). $^1$H NMR (300 MHz, DMSO-d6) δ 8.33 (t, 1H); 7.80 (d, 1H); 7.56-7.66 (m, 6H); 7.28 (d, 1H); 6.99-7.05 (m, 1H); 6.68 (d, 1H); 6.44-6.56 (m, 2H); 5.40 (s, 1H); 5.04-5.12 (m, 1H); 3.4-3.6 (m, 2H); 3.04-3.18 (m, 2H); 2.5 (s, 3H). LCMS: m/z 452.88 [M+H]⁺, $t_R$ 7.44 min.

Synthesis of (E)-N-((5-(5-acetylthiophen-2-yl)-7-chloro-2,3-dihydrobenzofuran-2-yl)methyl)-3-(4-cyanophenyl)acrylamide (112)

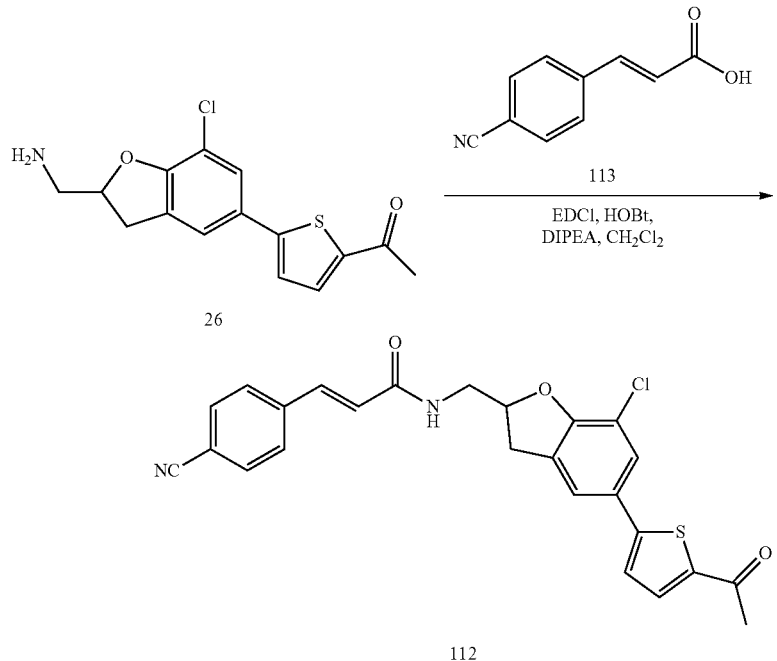

To a suspension of 26 (10 mg, 0.029 mmol) and 113 (5 mg, 0.029 mmol) in DMF (0.5 mL)/DCM (1 mL) was added EDCI (11 mg, 2 eq), HOBT (8 mg, 2 eq) and iPr$_2$NEt (20 uL) at room temperature and the mixture was stirred at room temperature for overnight. The reaction mixture was the diluted with DCM and washed with water, and brine. The organic layer was dried over Na$_2$SO$_4$, filtered, and concentrated. The resulting residue was purified by prep-HPLC to yield the product 112 (33%). LCMS: m/z 462.95 [M+H]$^+$, t$_R$ 8.19 min.

Synthesis of (E)-N-((5-(5-acetylthiophen-2-yl)-7-chloro-2,3-dihydrobenzofuran-2-yl)methyl)-3-(4-aminophenyl)acrylamide (114)

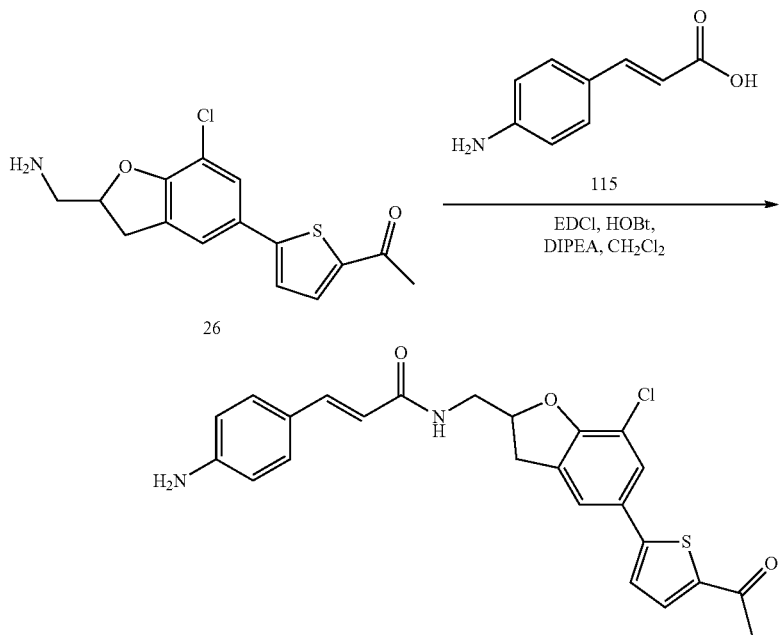

To a suspension of 26 (52 mg, 0.15 mmol) and 115 (25 mg, 0.15 mmol) in DMF (1 mL)/DCM (1 mL) was added EDCI (58 mg, 2 eq), HOBT (40 mg, 2 eq) and iPr2NEt (100 uL) at room temperature and the mixture was stirred at room temperature for overnight. The reaction mixture was the diluted with DCM and washed with water, and brine. The organic layer was dried over $Na_2SO_4$, filtered, and concentrated. The resulting residue was purified by prep-HPLC to yield the product 114 (26%). $^1$H NMR (300 MHz, DMSO-d6) δ 8.19 (t, 1H); 7.90 (d, 1H); 7.56-7.63 (m, 4H); 7.2-7.24 (m, 3H); 6.62-6.55 (m, 2H); 6.34 (d, 1H); 5.57 (s, 1H); 5.04-5.12 (m, 1H); 3.4-3.6 (m, 2H); 3.04-3.18 (m, 2H); 2.5 (s, 3H). LCMS: m/z 452.94 [M+H]$^+$, $t_R$ 7.07 min.

Synthesis of (E)-N-((5-(5-acetylthiophen-2-yl)-7-chloro-2,3-dihydrobenzofuran-2-yl)methyl)-3-(6-aminopyridin-3-yl)acrylamide (116)

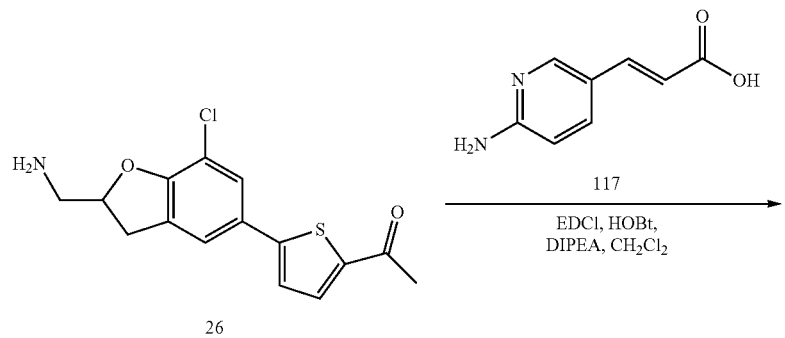

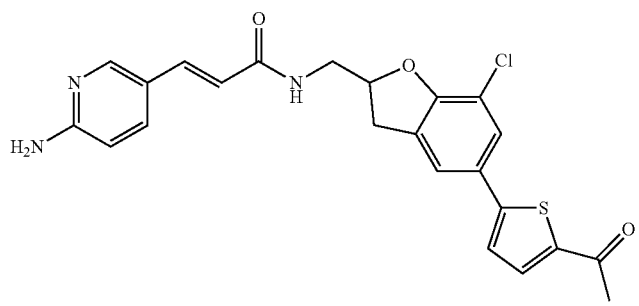

116

To a suspension of 26 (52 mg, 0.15 mmol) and 117 (26 mg, 0.15 mmol) in DMF (1 mL)/DCM (1 mL) was added EDCI (58 mg, 2 eq), HOBT (40 mg, 2 eq) and iPr2NEt (100 uL) at room temperature and the mixture was stirred at room temperature for overnight. The reaction mixture was the diluted with DCM and washed with H2O, and brine. The organic layer was dried over $Na_2SO_4$, filtered, and concentrated. The resulting residue was purified by prep-HPLC to yield the product 116 (35%). $^1$H NMR (300 MHz, DMSO-d6) δ 8.26 (t, 1H); 8.07 (d, 1H); 7.89 (d, 1H); 7.55-7.67 (m, 4H); 7.30 (d, 1H); 6.70 (s, 2H); 6.53 (d, 1H); 6.42 (d, 1H); 5.02-5.12 (m, 1H); 3.4-3.62 (m, 2H); 3.02-3.12 (m, 2H); 2.5 (s, 3H). LCMS: m/z 453.99 [M+H]$^+$, $t_R$ 6.74 min.

Chiral Separation of 116: Preparation of (S,E)-N-((5-(5-acetylthiophen-2-yl)-7-chloro-2,3-dihydrobenzofuran-2-yl)methyl)-3-(6-aminopyridin-3-yl)acrylamide and (R,E)-N-((5-(5-acetylthiophen-2-yl)-7-chloro-2,3-dihydrobenzofuran-2-yl)methyl)-3-(6-aminopyridin-3-yl)acrylamide Compound 116 was subjected to chiral separation employing Supercritical Fluid Chromatography to give single enantiomers, 308 and 309 with a chemical purity of greater than 99% and an ee of greater than or equal to 99%. The conditions of the separation were as follows:

| Preparative Method: | Analytical Method: |
|---|---|
| column: OJ-H (2 × 25 cm) | column: OJ-H (25 × 0.46 cm) |
| 35% isopropanol(0.1% DEA)/$CO_2$, | 40% isopropanol(DEA)/$CO_2$, |

-continued

| Preparative Method: | Analytical Method: |
|---|---|
| 100 bar | 100 bar |
| 60 mL/min, 220 nm | 3 mL/min, 220 and 254 nm |
| injection volume: 0.5 mL, | |
| 5 mg/mL 1:1 DCM:methanol | |

The absolute configuration of Compounds 308 and 309 has not been determined. Therefore, Compound 308, as used herein, refers to the compound with a retention time of 5.78 minutes in the supercritical fluid chromatographic method employed to separate it from its enantiomer, Compound 309. Conversely, Compound 309, as used herein, refers to the compound with a retention time of 6.67 minutes in the supercritical fluid chromatographic method employed to separate it from its enantiomer, Compound 308. Compound 308: Chiral purity: greater than 99%; $t_R$ 5.78 min. Compound 309: Chiral purity: 99%; $t_R$ 6.67 min.

(S,E)-N-((5-(5-acetylthiophen-2-yl)-7-chloro-2,3-dihydrobenzofuran-2-yl)methyl)-3-(6-aminopyridin-3-yl)acrylamide and (R,E)-N-((5-(5-acetylthiophen-2-yl)-7-chloro-2,3-dihydrobenzofuran-2-yl)methyl)-3-(6-aminopyridin-3-yl)acrylamide can be depicted as follows:

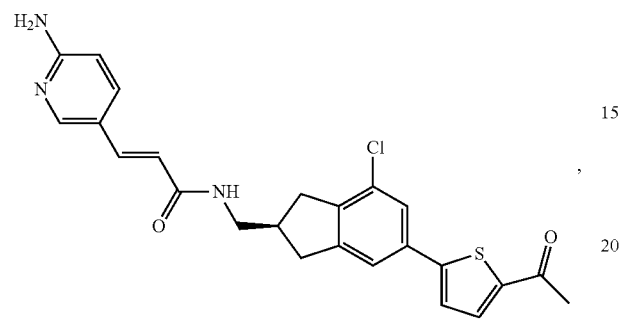

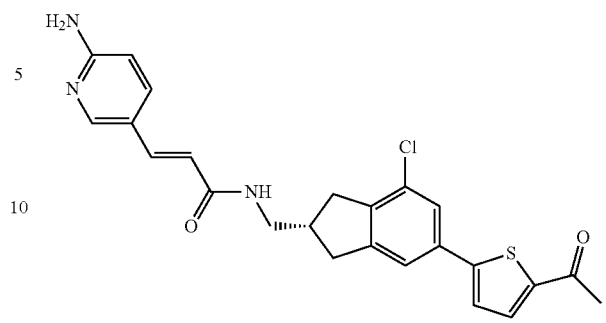

Synthesis of (E)-N-((5-(5-acetylthiophen-2-yl)-7-chloro-2,3-dihydrobenzofuran-2-yl)methyl)-3-(6-amino-2-methylpyridin-3-yl)acrylamide (118)

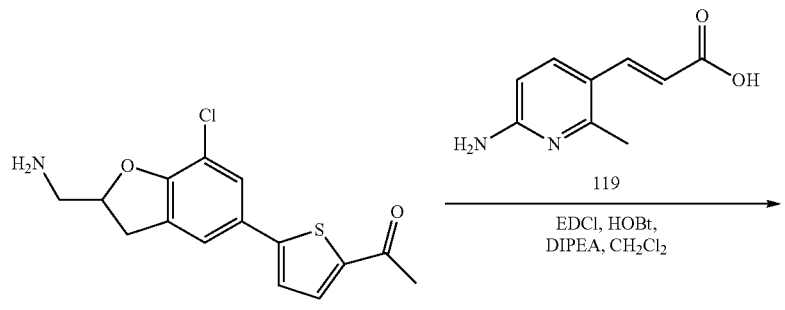

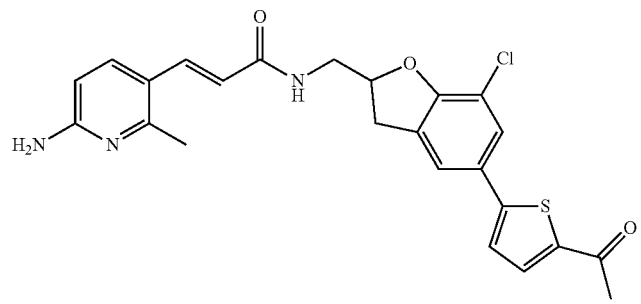

To a suspension of 26 (52 mg, 0.15 mmol) and 119 (26 mg, 0.15 mmol) in DMF (1 mL)/DCM (1 mL) was added EDCI (58 mg, 2 eq), HOBT (40 mg, 2 eq) and iPr$_2$NEt (100 uL) at room temperature and the mixture was stirred at room temperature for overnight. The reaction mixture was the diluted with DCM and washed with water, and brine. The organic layer was dried over Na$_2$SO4, filtered, and concentrated. The resulting residue was purified by prep-HPLC to yield the product 118 (26%). $^1$H NMR (300 MHz, DMSO-d6) δ 8.28 (t, 1H); 7.89 (d, 1H); 7.49-7.63 (m, 6H); 6.40 (s, 1H); 6.3-6.35 (m, 2H); 5.02-5.12 (m, 1H); 3.4-3.62 (m, 2H); 3.02-3.12 (m, 2H); 2.5 (s, 3H); 2.34 (s, 3H). LCMS: m/z 468.05 [M+H]$^+$, t$_R$ 6.80 min.

Synthesis of (E)-N-((5-(5-acetylthiophen-2-yl)-7-chloro-2,3-dihydrobenzofuran-2-yl)methyl)-3-(2-chloro-3,5-dihydroimidazo [1,2-a]pyridin-3-yl)acrylamide (120)

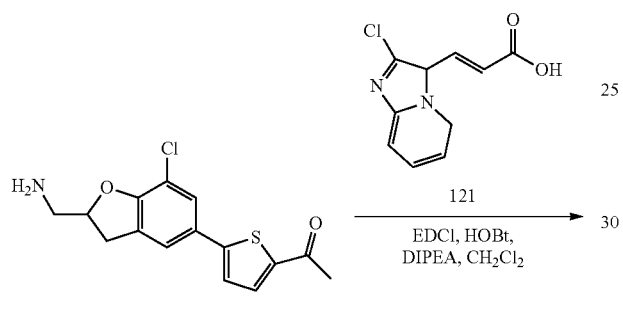

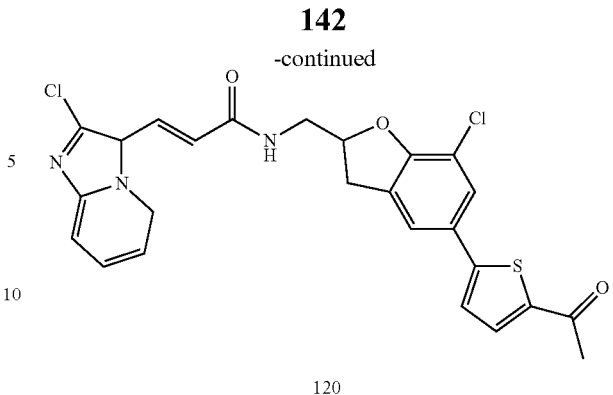

120

(E)-N-((5-(5-Acetylthiophen-2-yl)-7-chloro-2,3-dihydrobenzofuran-2-yl)methyl)-3-(2-chloro-3,5-dihydroimidazo [1,2-a]pyridin-3-yl)acrylamide 120 was prepared according to General Procedure 1 starting with acid 121 (34 mg, 0.15 mmol) (40% yield). $^1$H NMR (300 MHz, DMSO-d6) δ 8.71 (d, 1H); 8.5 (t, 1H); 7.89 (d, 1H); 7.72 (d, 1H); 7.42-7.66 (m, 5H); 7.16 (t, 1H); 6.96 (d, 1H); 5.04-5.12 (m, 1H); 3.4-3.62 (m, 2H); 3.04-3.18 (m, 2H); 2.5 (s, 3H); 2.30 (s, 3H). LCMS: m/z 515.96 [M+H]$^+$, t$_R$ 7.96 min.

Chiral Separation of 27: Preparation of (S,E)-N-((5-(5-acetylthiophen-2-yl)-7-chloro-2,3-dihydrobenzofuran-2-yl)methyl)-3-(pyridin-2-yl)acrylamide and (R,E)-N-((5-(5-acetylthiophen-2-yl)-7-chloro-2,3-dihydrobenzofuran-2-yl)methyl)-3-(pyridin-2-yl)acrylamide

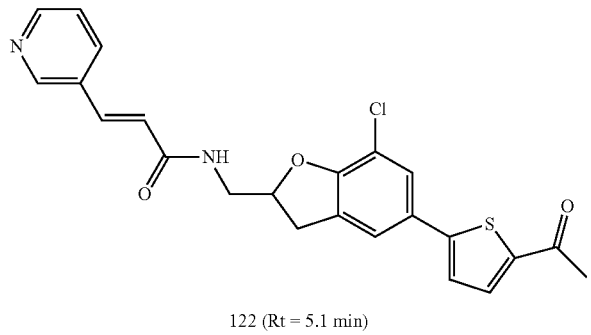

122 (Rt = 5.1 min)

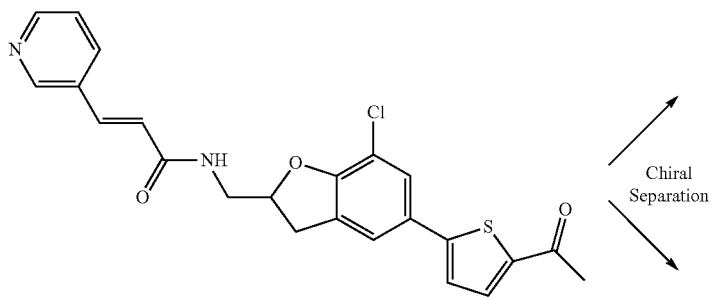

27

Chiral Separation

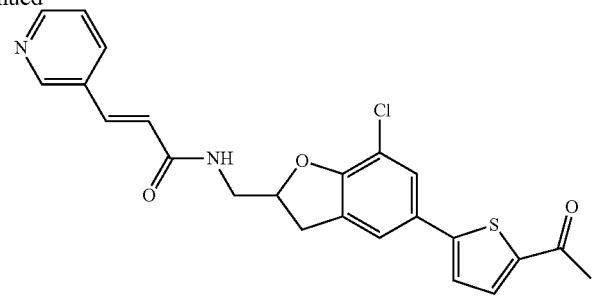

123 (Rt = 5.6 min)

Compound 27 was subjected to chiral separation employing Supercritical Fluid Chromatography to give single enantiomers, 122 and 123 with a chemical purity of greater than 99% and an ee of greater than 99%. The conditions of the separation were as follows:

| Preparative Method: | Analytical Method: |
|---|---|
| column: AS-H (2 × 25 cm) | column: AS-H (25 × 0.46 cm) |
| 25% methanol(0.1% DEA)/CO$_2$, | 40% methanol(DEA)/CO$_2$, |
| 100 bar | 100 bar |
| 70 mL/min, 220 nm | 3 mL/min, 220 and 254 nm |
| inj vol.: 0.5 mL, 10 mg/mL methanol | |

The absolute configuration of Compounds 122 and 123 has not been determined. Therefore, Compound 122, as used herein, refers to the compound with a retention time of 5.1 minutes in the supercritical fluid chromatographic method employed to separate it from its enantiomer, Compound 123. Conversely, Compound 123, as used herein, refers to the compound with a retention time of 5.6 minutes in the supercritical fluid chromatographic method employed to separate it from its enantiomer, Compound 122. Compound 122: Chiral purity: 100%; $t_R$ 5.1 min. Compound 123: Chiral purity: 99.7%; $t_R$ 5.6 min (S,E)-N-((5-(5-acetylthiophen-2-yl)-7-chloro-2,3-dihydrobenzofuran-2-yl)methyl)-3-(pyridin-2-yl)acrylamide and (R,E)-N-((5-(5-acetylthiophen-2-yl)-7-chloro-2,3-dihydrobenzofuran-2-yl)methyl)-3-(pyridin-2-yl)acrylamide can be depicted as follows:

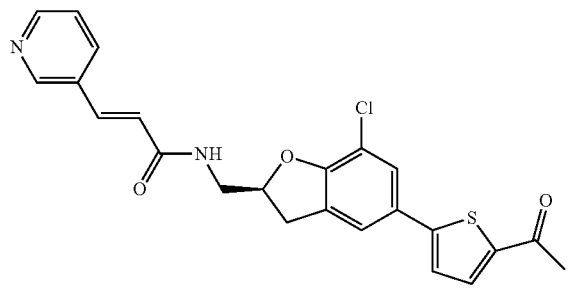

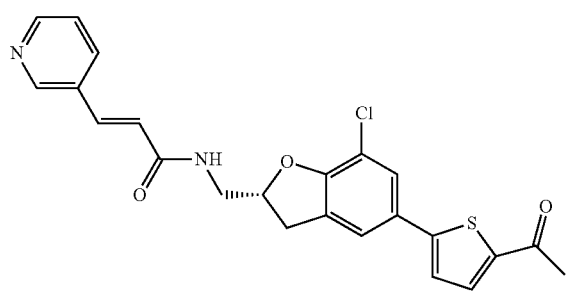

Synthesis of (E)-N-((7-chloro-5-(5-(1-hydroxyethyl)thiophen-2-yl)-2,3-dihydrobenzofuran-2-yl)methyl)-3-(pyridin-3-yl)acrylamide (124)

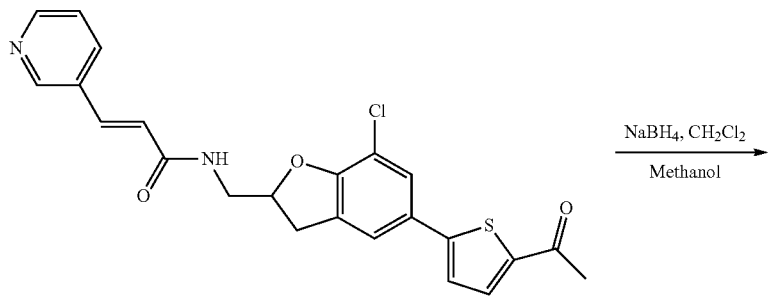

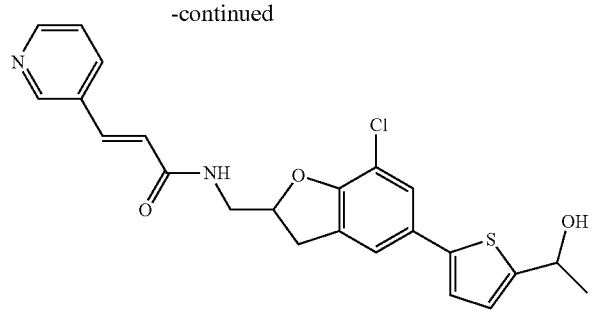

124

(E)-N-((5-(5-acetylthiophen-2-yl)-7-chloro-2,3-dihydrobenzofuran-2-yl)methyl)-3-(pyridin-4-yl)acrylamide (27) (0.050 g, 0.113 mmol) was dissolved in dichloromethane (2.5 mL) and methanol (0.5 mL) at 0° C. and sodium borohydride (2.16 g, 0.057 mmol) was added portion wise. The reaction mixture was stirred at room temperature for 3 h. The reaction mixture was transferred into iced water and extracted with ethyl acetate (50 mL×3). The combined organic layers were washed with brine, dried over anhydrous $Na_2SO_4$, and concentrated under reduced pressure to give the crude product which was purified by chromatography (0-5% MeOH/$CH_2Cl_2$) to give 15 mg of (E)-N-((7-chloro-5-(5-(1-hydroxyethypthiophen-2-yl)-2,3-dihydrobenzofuran-2-yl)methyl)-3-(pyridin-3-yl)acrylamide (124) (29% yield). $^1$H NMR (400 MHz, DMSO-$d_6$) δ 8.76-8.78 (d, J=2 Hz, 1H), 8.52-8.56 (m, 2H), 7.98-8.00 (d, J=8 Hz, 1H), 7.42-7.52 (m, 3H), 7.23-7.24 (d, J=3.6 Hz, 1H), 6.81-6.88 (m, 2H), 5.57-5.58 (d, J=4.8 Hz, 1H), 5.06-5.09 (t, 1H), 4.89-4.94 (q, 1H), 3.53-3.62 (m, 2H), 3.37-3.53 (m, 1H), 3.05-3.18 (m, 1H), 1.41-1.43 (d, J=6 Hz, 3H). LCMS: m/z 423.34 [M−17], $t_R$=1.83 min.

Synthesis of (E)-N-((5-(5-acetylthiophen-2-yl)-7-chloro-2,3-dihydrobenzofuran-2-yl)methyl)-N-methyl-3-(pyridin-3-yl)acrylamide (125)

(E)-N-((5-(5-acetylthiophen-2-yl)-7-chloro-2,3-dihydrobenzofuran-2-yl)methyl)-3-(pyridin-3-yl) acrylamide (27) (0.2 g, 0.45 mmol) was dissolved in $CH_2Cl_2$ (5 mL) and NaH (60%) (0.054 g, 1.3 mmol) was added at 0° C. and stirred for 2 h at 0° C. Methyl iodide (0.129 g, 0.91 mmol) was added and the reaction mixture was allowed to warm to room temperature where it was further stirred for 3 h. The reaction mixture was transferred into iced water (50 mL) and extracted with ethyl acetate (25 mL×3). Combined organic layers were dried over $Na_2SO_4$ and concentrated under reduced pressure to give the crude product, which was purified by chromatography to give 10 mg of (E)-N-((5-(5-acetylthiophen-2-yl)-7-chloro-2,3-dihydrobenzofuran-2-yl) methyl)-N-methyl-3-(pyridin-3-yl)acrylamide (125) (5% yield). $^1$H NMR (400 MHz, DMSO-$d_6$) δ 8.81-8.89 (d, J=35.6 Hz, 1H), 8.51-8.56 (m, 1H), 8.00-8.21 (m, 1H), 7.92-7.93 9 (d, J=7.2 Hz, 1H), 7.57-7.62 (m, 2H), 7.50-7.53 (d, J=14.8 Hz, 1H), 7.35-7.41 (d, J=22 Hz, 1H), 5.22-5.25 (m, 1H), 3.74-3.86 (m, 1H), 3.43-3.53 (m, 1H), 3.28 (s, 3H), 3.01 (s, 3H). LCMS: m/z 453.3 [M+H]$^+$, $t_R$=1.91 min.

Synthesis of (E)-ethyl 4-(7-chloro-2-((3-(pyridin-3-yl)acrylamido)methyl)-2,3-dihydrobenzofuran-5-yl)benzoate (128)

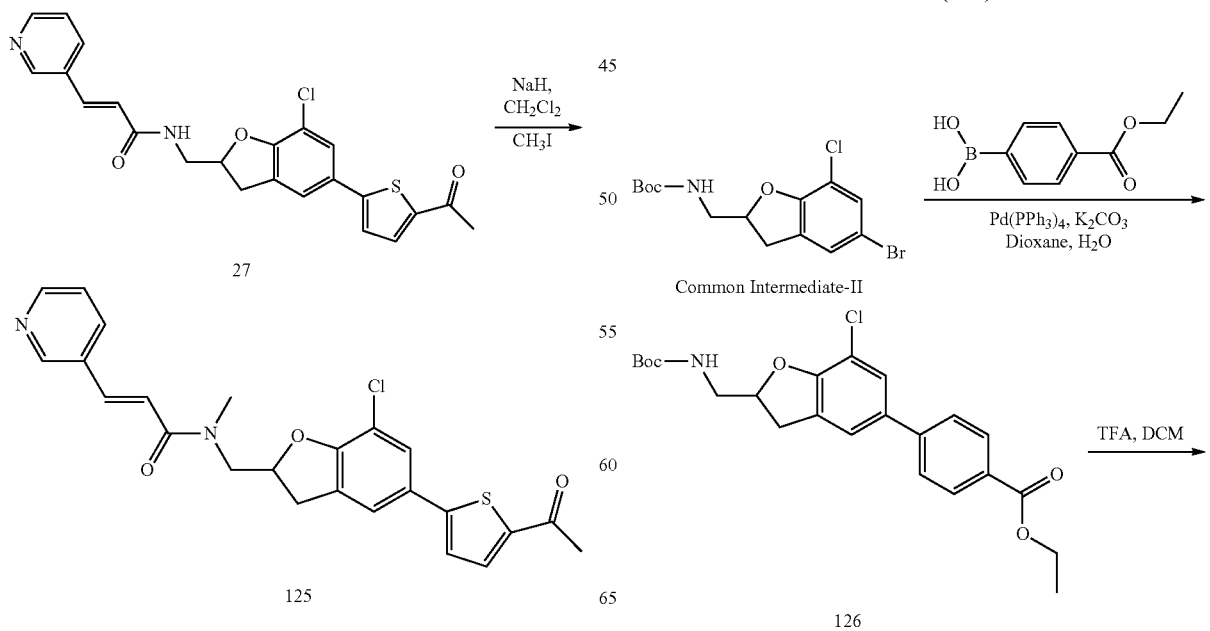

148

Synthesis of (E)-4-(7-chloro-2-((3-(pyridin-3-yl)acrylamido)methyl)-2,3-dihydrobenzofuran-5-yl)benzoic acid (129)

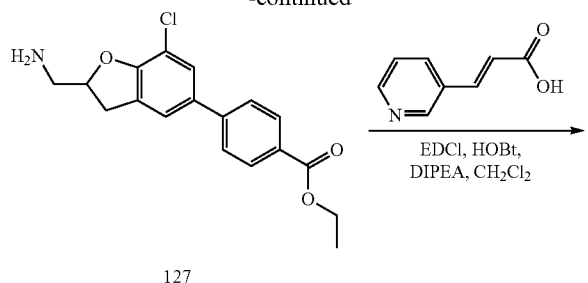

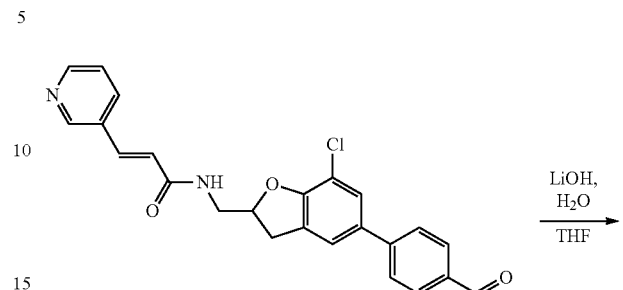

Ethyl 4-(2-(((tert-butoxycarbonyl)amino)methyl)-7-chloro-2,3-dihydrobenzofuran-5-yl)benzoate 126 was synthesized using General Procedure 1. Yield (45%). $^1$H NMR (400 MHz, CDCl$_3$) δ 8.00 (s, 1H), 7.98 (s, 1H), 7.80 (s, 1H), 7.78 (s, 1H), 7.58 (s, 2H), 4.95-4.99 (m, 1H), 4.24-4.36 (m, 2H), 3.37-3.43 (m, 1H), 3.22-3.32 (m, 2H), 3.07-3.13 (m, 1H), 1.39 (s, 9H), 1.27-1.36 (m, 3H). LCMS: m/z 376.09 [M−56]$^+$, $t_R$=2.71 min.

Ethyl 4-(2-(aminomethyl)-7-chloro-2,3-dihydrobenzofuran-5-yl)benzoate 127 was synthesized using General Procedure 2. Yield (80%). $^1$H NMR (400 MHz, CDCl$_3$) δ 7.97-7.99 (d, 2H), 7.54-7.81 (t, 2H), 7.55-7.63 (t, 2H), 4.94 (s, 1H), 4.22-4.32 (m, 2H), 3.35-3.42 (m, 1H), 3.12-3.16 (m, 1H), 2.86 (s, 2H), 1.25-1.32 (m, 3H). LCMS: m/z 332.0 [M+H]$^+$, $t_R$=1.75 min.

(E)-ethyl 4-(7-chloro-2-((3-(pyridin-3-yl)acrylamido)methyl)-2,3-dihydrobenzofuran-5-yl)benzoate 128 was synthesized using General Procedure 3. Yield (43%). $^1$H NMR (400 MHz, DMSO-d$_6$) δ 8.82 (s, 1H), 8.57-8.62 (m, 2H), 8.03-8.06 (m, 3H), 7.83-7.85 (m, 2H), 7.65 (s, 2H), 7.54-7.58 (d, J=16 Hz, 1H), 7.49-7.52 (m, 1H), 6.91-6.87 (d, J=16 Hz, 1H), 5.16 (s, 1H), 4.36-4.41 (m, 2H), 3.61-3.70 (m, 2H), 3.44-3.54 (m, 1H), 3.16-3.22 (m, 1H), 1.37-1.41 (t, 3H). LCMS: m/z 463.1 [M+H]$^+$, $t_R$=2.22 min.

(E)-ethyl 4-(7-chloro-2-((3-(pyridin-3-yl)acrylamido)methyl)-2,3-dihydrobenzofuran-5-yl)benzoate 128 (0.15 g, 0.32 mmol) was dissolved in THF/H$_2$O (1:1) and LiOH.6H$_2$O (0.05 g, 1.29 mmol) was added at 0° C. The reaction mixture was allowed to warm to room temperature where it was stirred for 16 h. The reaction mixture was transferred into dilute HCl solution until pH~2, extracted with ethyl acetate (20 mL×3), dried over anhydrous Na$_2$SO$_4$, and concentrated under reduced pressure to obtain 0.04 g of pure (E)-4-(7-chloro-2-((3-(pyridin-3-yl)acrylamido)methyl)-2,3-dihydrobenzofuran-5-yl)benzoic acid 129. (73% yield). $^1$H NMR (400 MHz, DMSO-d$_6$) δ 8.98 (s, 1H), 8.75 (s, 1H), 8.73 (s, 1H), 8.40-8.42 (d, J=7.6 Hz, 1H), 7.98 (s, 2H), 7.75-7.82 (m, 3H), 7.57-7.61 (m, 3H), 6.96-7.00 (d, J=16 Hz, 1H), 5.11 (s, 1H), 3.56-3.65 (m, 2H), 3.42-3.48 (m, 1H), 3.11-3.17 (m, 1H). LCMS: m/z 435.1 [M+H]$^+$, $t_R$=1.67 min.

(E)-N-((5-(5-acetylthiophen-2-yl)-7-methyl-2,3-dihydrobenzofuran-2-yl)methyl)-3-(pyridin-3-yl)acrylamide (138)

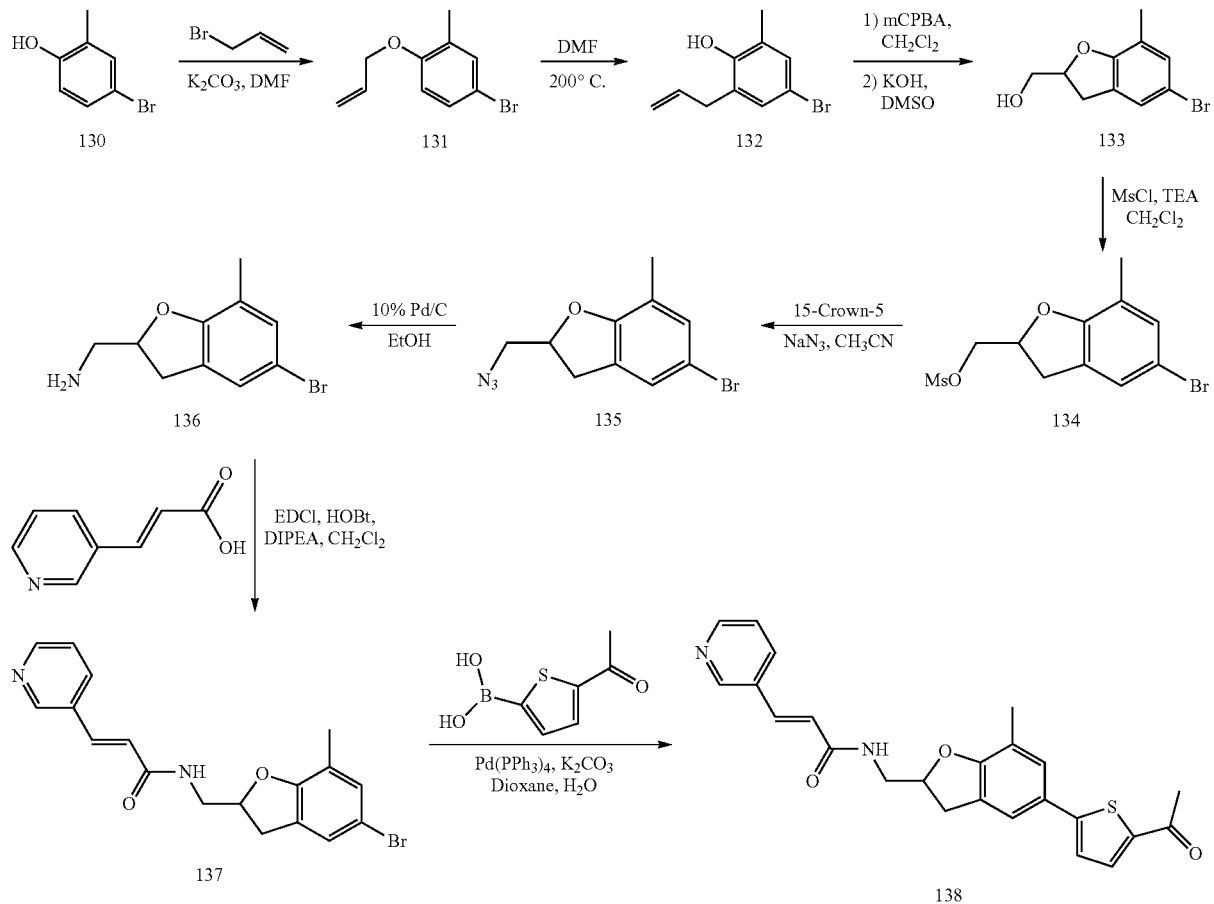

1-(Allyloxy)-4-bromo-2-methylbenzene 131 was synthesized using conditions described in the first step in Method B (conversion of 9 to 10) starting from 4-bromo-2-methylphenol (130). Yield (83%). $^1$H NMR (400 MHz, CDCl$_3$) δ 7.24-7.29 (m, 1H), 6.69-6.71 (d, J=8 Hz, 1H), 6.02-6.12 (m, 1H), 5.46-5.47 (d, J=4 Hz, 1H) 5.41-5.42 (d, J=4 Hz, 1H), 4.53-4.55 (m, 2H) 2.24 (s, 3H).

2-Allyl-4-bromo-6-methylphenol 132 was synthesized using conditions described in the second step in Method B (conversion of 10 to 11). Yield (30%). $^1$H NMR (400 MHz, CDCl$_3$) δ 8.58 (s, 1H) 7.13-7.14 (d, J=4 Hz, 1H), 7.03-7.04 (d, J=4 Hz, 1H), 5.87-5.97 (m, 1H), 5.01-5.08 (m, 2H), 3.31-3.37 (m, 2H), 2.16 (s, 3H).

(5-Bromo-7-methyl-2,3-dihydrobenzofuran-2-yl)methanol 133 was synthesized using conditions described in the third step in Method B (conversion of 11 to 12). Yield (69%). $^1$H NMR (400 MHz, CDCl$_3$) δ 7.17-7.18 (d, J=4 Hz, 1H), 7.09-7.10 (d, J=4 Hz, 1H), 4.89-4.96 (m, 1H), 3.86-3.89 (m, 1H), 3.73-3.78 (m, 1H), 3.21-3.29 (m, 1H), 3.02-3.08 (m, 1H), 2.21 (s, 3H).

(5-Bromo-7-methyl-2,3-dihydrobenzofuran-2-yl)methyl methanesulfonate 134 was synthesized using conditions described in the fourth step in Method B (conversion of 12 to 13). Yield (89%). $^1$H NMR (400 MHz, CDCl$_3$-d$_6$) δ 7.17-7.18 (d, J=4 Hz, 1H), 7.09-7.10 (d, J=4 Hz, 1H), 5.03-5.10 (m, 1H), 4.37-4.45 (m, 2H), 3.33-3.41 (m, 1H), 3.09-3.11 (m, 1H), 3.04-3.08 (m, 3H), 2.2 (s, 3H).

2-(Azidomethyl)-5-bromo-7-methyl-2,3-dihydrobenzofuran 135 was synthesized using conditions described in the fifth step in Method B (conversion of 13 to 14). Yield (70%). $^1$H NMR (400 MHz, DMSO-d$_6$) δ 7.17-7.18 (d, J=4 Hz, 1H), 7.09-7.10 (d, J=4 Hz, 1H), 4.99-5.08 (m, 1H), 3.62-3.63 (m, 1H), 3.28-3.34 (m, 1H), 2.91-3.01 (m, 1H), 2.10 (s, 3H).

(5-Bromo-7-methyl-2,3-dihydrobenzofuran-2-yl)methanamine 136 was synthesized using conditions described in the sixth step in Method B (conversion of 14 to Common Intermediate I). Yield (69%). $^1$H NMR (400 MHz, DMSO-d$_6$) δ 7.15-7.16 (d, J=4 Hz, 1H), 7.98-7.99 (d, J=4 Hz, 1H), 4.76 (m, 1H), 3.16-4.37 (m, 2H), 2.91-3.14 (m, 2H), 2.75-2.76 (d, J=4 Hz, 2H), 2.33 (s, 3H). LCMS: m/z 243.89 [M+H]$^+$, t$_R$=1.321 min.

(E)-N-((5-Bromo-7-methyl-2,3-dihydrobenzofuran-2-yl)methyl)-3-(pyridin-3-yl)acrylamide 137 was synthesized using General Procedure 3. Yield (76%). $^1$H NMR (400 MHz, CDCl$_3$) δ 8.76-8.77 (d, J=4 Hz, 1H), 8.55-8.57 (m, 1H), 8.44-8.47 (t, 1H), 7.97-8.00 (d, J=Hz, 1H), 7.44-7.48 (m, 2H), 7.21 (s, 1H), 7.13 (s, 1H), 4.97-4.99 (d, J=6.8 Hz, 1H), 3.49-3.55 (m, 2H),2.48-3.31 (m, 1H), 2.93-2.2.98 (m, 1H), 2.20 (s,3H). LCMS: m/z 374.93 [M+H]$^+$ t$_R$=1.945 min.

(E)-N-((5-(5-Acetylthiophen-2-yl)-7-methyl-2,3-dihydrobenzofuran-2-yl)methyl)-3-(pyridin-3-yl)acrylamide 138 was synthesized using General Procedure 1. Yield (7%). $^1$H NMR (400 MHz, DMSO-d$_6$) δ 8.77 (s, 1H), 8.56 (s, 1H), 7.99-8.00 (d, J=2 Hz, 1H), 7.89-7.90 (d, J=2 Hz, 1H), 7.41-7.52 (m, 5H), 6.80-6.84 (d, J=16 Hz, 1H), 4.93-5.00 (m, 1H), 3.49-3.58 (m, 2H), 3.25-3.36 (m, 1H), 2.98-3.03 (m, 1H), 2.51 (s, 3H), 2.20 (s, 3H). LCMS: m/z 419.05 [M+H]$^+$, $t_R$=1.858 min.

Synthesis of (E)-N-((5-(5-acetylthiophen-2-yl)-7-chloro-2,3-dihydrobenzofuran-2-yl)methyl)-3-(2-chloropyridin-3-yl)acrylamide (142)

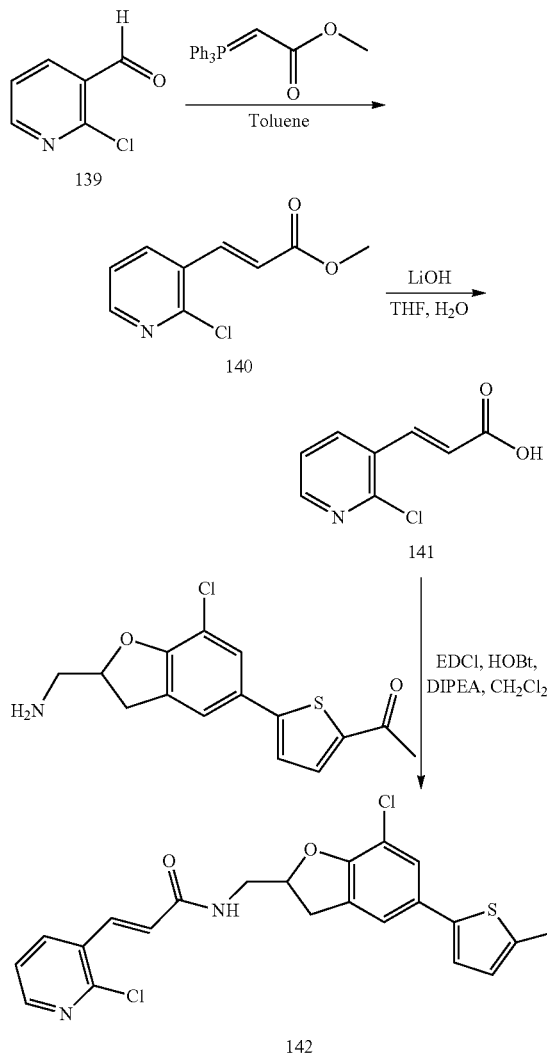

6-Chloronicotinaldehyde 139 (1 g, 7.09 mmol) and (methoxycarbonylmethylene)triphenyl phosphorane (3.18 g, 9.60 mmol) were added in toluene (10 mL) at 0° C. The reaction mixture was stirred at 110° C. for 3 h. The reaction mixture was diluted with water (150 mL) and extracted with ethyl acetate (50 mL×3). The combined organic layers were washed with brine, dried over anhydrous Na$_2$SO$_4$, and concentrated under reduced pressure to give 1.8 g of crude product, which was purified by chromatography to give 0.99 g of methyl-3-(2-chloropyridin-3-yl) acrylate 140. Yield (71%). $^1$H NMR (400 MHz, DMSO-d$_6$) δ 8.47-8.41 (m, 2H), 7.84-7.80 (d, J=16 Hz, 1H), 7.54-7.51 (m, 1H), 6.87-6.83 (d, J=16 Hz, 1H), 3.77 (s, 3H). LCMS: m/z 197.78 [M+H]$^+$, $t_R$=1.652 min.

Methyl-3-(6-chloropyridin-3-yl) acrylate 140 (0.84 g, 4.26 mmol) was dissolved in THF: H$_2$O (1:1) (10 mL) and LiOH.H$_2$O (0.43 g, 10.06 mmol) was added at 0° C. The reaction mixture was stirred at room temperature for 4 h. The reaction mixture was transferred into iced water, quenched with dilute HCl, and extracted with ethyl acetate (50 mL×3). The combined organic layers were washed with saturated sodium bicarbonate, brine, dried over anhydrous Na$_2$SO$_4$, and concentrated under reduced pressure to give 0.3 g of crude product, which was purified by chromatography to give 0.99 g of 3-(6-chloropyridine-3-yl) acrylic acid 141. Yield (77%), $^1$H NMR (400 MHz, DMSO-d$_6$) δ=12.71 (s, 1H), 8.45-8.44 (d, J=6.4 Hz, 1H), 8.41-8.37 (d, J=12.8 Hz, 1H); 7.79-7.75 (d, J=16 Hz, 1H), 7.56-7.49 (m, 1H). LCMS: m/z 183.76 [M+H]$^+$, $t_R$=0.825 min.

(E)-N-((5-(5-acetylthiophen-2-yl)-7-chloro-2,3-dihydrobenzofuran-2-yl)methyl)-3-(2-chloropyridin-3-yl)acrylamide 142 was prepared according to General Procedure 3. Yield (26%), $^1$H NMR (400 MHz, DMSO-d$_6$) δ 8.670-8.641 (m, 1H), 8.434-8.418 (d, J=6.4,1H), 8.156-8.132 (d, J=9.6 Hz, 1H), 7.928-7.918 (d, J=4 Hz, 1H), 7.681-7.585 (m, 4H), 7.533-7.502 (m, 1H), 6.877-6.817 (d, J=24 Hz, 1H), 5.134-5.099 (m, 1H), 3.650-3.563 (m, 2H), 3.473-3.410 (s, 1H), 3.147-3.087 (m, 1H), 2.530-2.502 (s, 3H). LCMS: m/z 473.02 [M+H]$^+$, $t_R$=2.177 min.

Synthesis of (E)-N-((5-(5-acetylthiophen-2-yl)-7-chloro-2,3-dihydrobenzofuran-2-yl)methyl)-3-(6-methylpyridin-3-yl)acrylamide (146)

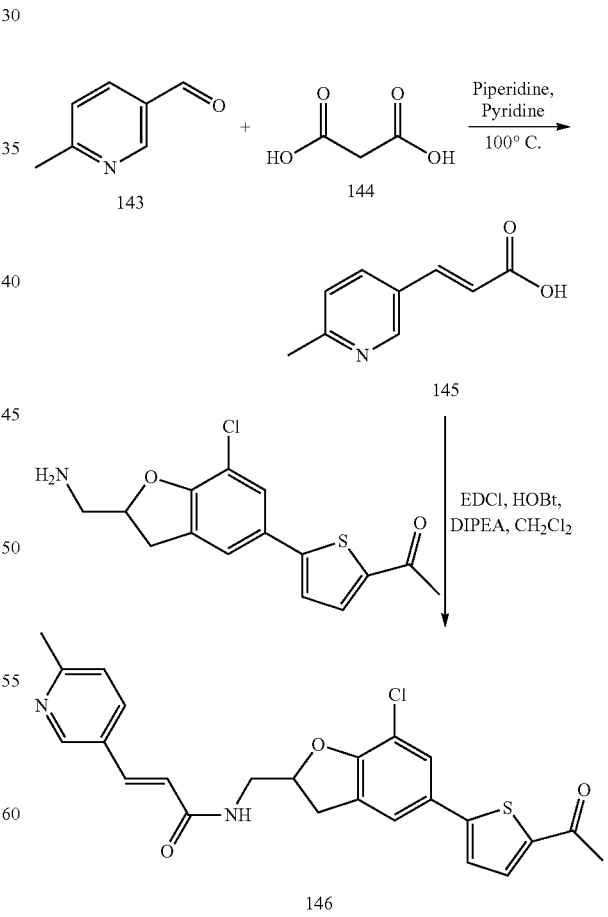

6-Methylnicotinaldehyde 143 (0.5 g, 4.13 mmol) and malonic acid 144 (0.515 g, 4.95 mmol) were dissolved in pyridine at room temperature. Piperidine (50 mg) was added and the reaction mixture was refluxed for 2 h at 100° C. The reaction mixture was concentrated under reduced pressure, quenched with water, and extracted with ethyl acetate (25 mL×3). The combined organic layers was washed with brine, dried over anhydrous Na₂SO₄, and concentrated under reduced pressure to give 450 mg of the crude product, which was purified by trituration using diethyl ether to give (E)-3-(6-methylpyridin-3-yl)acrylic acid 145 (300 mg, 45% yield). $^1$H NMR (400 MHz, DMSO-d$_6$) δ 12.1 (bs, 1H, D$_2$O exchangeable), 8.71 (s, 1H), 8.05-8.07 (t, 1H), 7.55-7.63 (m, 1H), 7.28-7.33 (m, 1H), 6.58-6.65 (m, 1H), 2.50 (s, 3H). LCMS m/z 163.80 [M+H]$^+$, $t_R$=2.356 min.

(E)-N-((5-(5-Acetylthiophen-2-yl)-7-chloro-2,3-dihydrobenzofuran-2-yl)methyl)-3-(6-methylpyridin-3-yl)acrylamide 146 was synthesized using General Procedure 3 with 42% yield. $^1$H NMR (400 MHz, DMSO-d$_6$) δ 8.62-8.63 (d, J=2 Hz, 1H), 8.48-8.51 (t, 1H), 7.86-7.92 (m, 2H), 7.58-7.66 (m, 3H), 7.45-7.49 (d, J=16 Hz, 1H), 7.29-7.32 (d, J=8 Hz, 1H), 6.75-6.79 (d, J=15.6 Hz, 1H), 5.08-5.12 (m, 1H), 3.45-3.63 (m, 2H), 3.40-3.46 (m, 1H), 3.08-3.18 (m, 1H), 2.52 (s, 3H), 2.48 (s, 3H). LCMS: m/z 453.11 [M+H]$^+$, $t_R$=1.813 min.

Synthesis of (E)-N-((5-(5-acetylthiophen-2-yl)-7-chloro-2,3-dihydrobenzofuran-2-yl)methyl)-3-(3,5-dimethylisoxazol-4-yl)acrylamide (147)

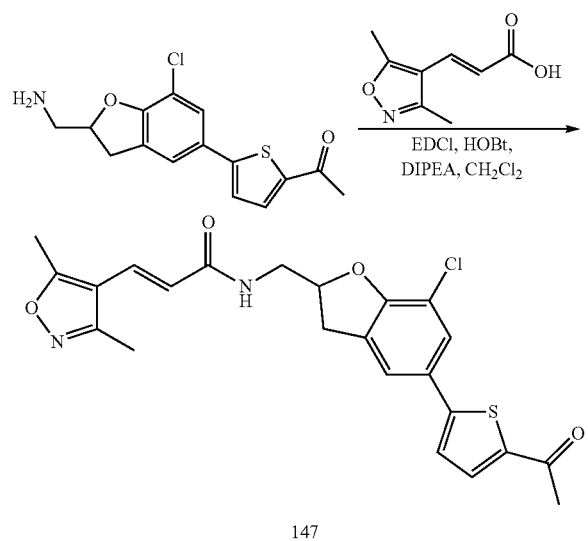

147

(E)-N-((5-(5-Acetylthiophen-2-yl)-7-chloro-2,3-dihydrobenzofuran-2-yl)methyl)-3-(3,5-dimethylisoxazol-4-yl)acrylamide 147 was prepared according to General Procedure 3 (30% yield). $^1$H NMR (300 MHz, DMSO-d6) δ 8.5 (t, 1H); 7.89 (d, 1H); 7.55-7.63 (m, 3H); 7.21 (d, 1H); 6.49 (d, 1H); 5.02-5.12 (m, 1H); 3.4-3.62 (m, 2H); 3.02-3.12 (m, 2H); 2.5 (s, 3H); 2.30 (s, 3H); 2.30 (s, 6H). LCMS: m/z 457.89 [M+H]$^+$, $t_R$ 9.30 min.

Synthesis of (E)-N-((5-(5-acetylthiophen-2-yl)-7-chloro-2,3-dihydrobenzofuran-2-yl)methyl)-3-(2-methylthiazol-5-yl)acrylamide (148)

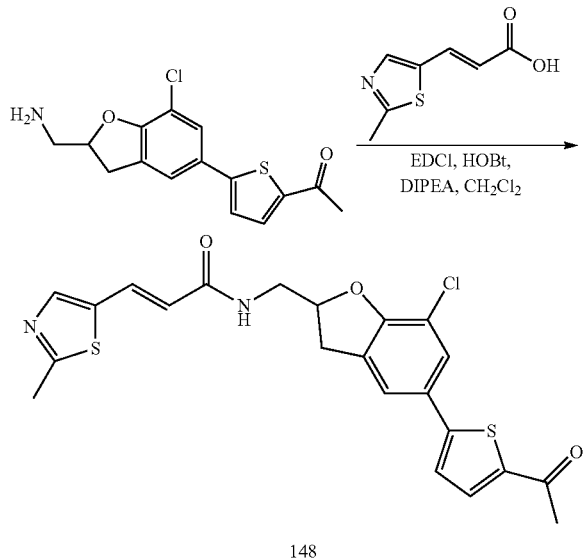

148

(E)-N-((5-(5-Acetylthiophen-2-yl)-7-chloro-2,3-dihydrobenzofuran-2-yl)methyl)-3-(2-methylthiazol-5-yl)acrylamide 148 was prepared according to General Procedure 3 (28% yield). 1H NMR (300 MHz, DMSO-d6) δ 8.46 (t, 1H); 7.87-7.89 (m, 2H); 7.55-7.63 (m, 4H); 6.38 (d, 1H); 5.02-5.12 (m, 1H); 3.4-3.62 (m, 2H); 3.02-3.12 (m, 2H); 2.64 (s, 3H); 2.5 (s, 3H). LCMS: m/z 459.91 [M+H]$^+$, $t_R$ 8.12 min.

Synthesis of (E)-N-((5-(5-acetylthiophen-2-yl)-7-chloro-2,3-dihydrobenzofuran-2-yl)methyl)-3-(1-methyl-1H-pyrazol-4-yl)acrylamide (149)

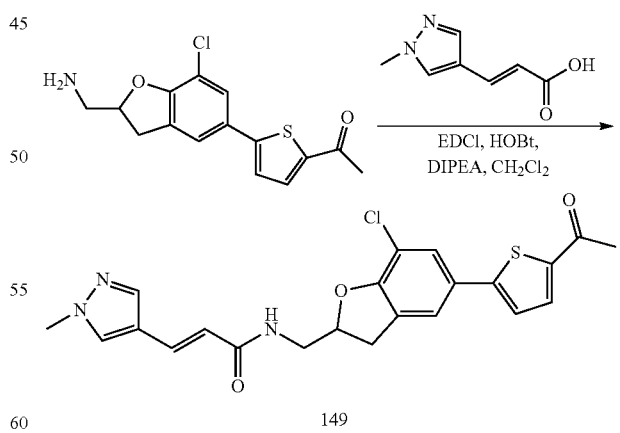

149

(E)-N-((5-(5-Acetylthiophen-2-yl)-7-chloro-2,3-dihydrobenzofuran-2-yl)methyl)-3-(1-methyl-1H-pyrazol-4-yl) acrylamide 149 was prepared according to General Procedure 3 (31% yield). $^1$H NMR (300 MHz, DMSO-d$_6$) δ 8.30 (t, 1H); 7.88-7.95 (m, 2H); 7.56-7.66 (m, 4H); 7.28 (d, 1H);

6.33 (d, 1H); 5.04-5.12 (m, 1H); 3.81 (s, 3H); 3.4-3.6 (m, 2H); 3.04-3.18 (m, 2H); 2.5 (s, 3H). LCMS: m/z 441.92 [M+H]$^+$, $t_R$ 7.49 min.

Synthesis of (E)-N-((5-(5-acetylthiophen-2-yl)-7-chloro-2,3-dihydrobenzofuran-2-yl)methyl)-3-(5-methylfuran-2-yl)acrylamide (150)

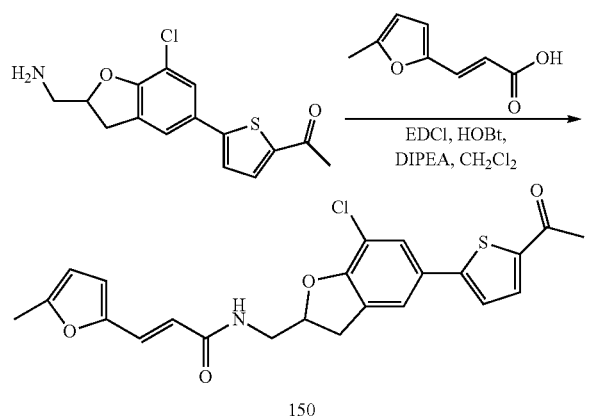

(E)-N-((5-(5-Acetylthiophen-2-yl)-7-chloro-2,3-dihydrobenzofuran-2-yl)methyl)-3-(5-methylfuran-2-yl)acrylamide 150 was prepared according to General Procedure 3 (28% yield). $^1$H NMR (300 MHz, DMSO-d6) δ 8.40 (m, 1H); 7.90 (d, 1H); 7.56-7.63 (m, 3H); 7.16 (d, 1H); 6.48 (s, 1H); 6.38 (d, 1H); 6.20 (s, 1H); 5.04-5.12 (m, 1H); 3.81 (s, 3H); 3.4-3.6 (m, 2H); 3.04-3.18 (m, 2H); 2.5 (s, 3H); 2.30 (s, 3H). LCMS: m/z 441.89 [M+H]$^+$, $t_R$ 8.27 min.

Synthesis of (E)-N-((5-(5-acetylthiophen-2-yl)-7-chloro-2,3-dihydrobenzofuran-2-yl)methyl)-3-(quinoxalin-2-yl)acrylamide (151)

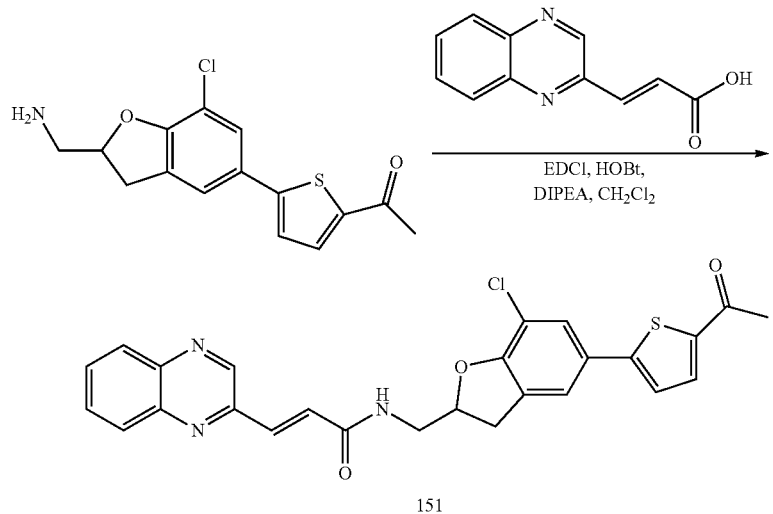

(E)-N-((5-(5-Acetylthiophen-2-yl)-7-chloro-2,3-dihydrobenzofuran-2-yl)methyl)-3-(quinoxalin-2-yl)acrylamide 151 was prepared according to General Procedure 3 (30% yield). $^1$H NMR (300 MHz, DMSO-d6) δ 9.18 (s, 1H); 8.82 (m, 1H); 8.04-8.08 (m, 2H); 7.55-7.90 (m, 7H); 7.42 (d, 1H); 5.08-5.18 (m, 1H); 3.4-3.6 (m, 2H); 3.04-3.18 (m, 2H); 2.5 (s, 3H); 2.30 (s, 3H). LCMS: m/z 489.97 [M+H]$^+$, $t_R$ 8.35 min.

Synthesis of (E)-N-((5-(5-acetylthiophen-2-yl)-7-chloro-2,3-dihydrobenzofuran-2-yl)methyl)-3-(3-methylthiophen-2-yl)acrylamide (152)

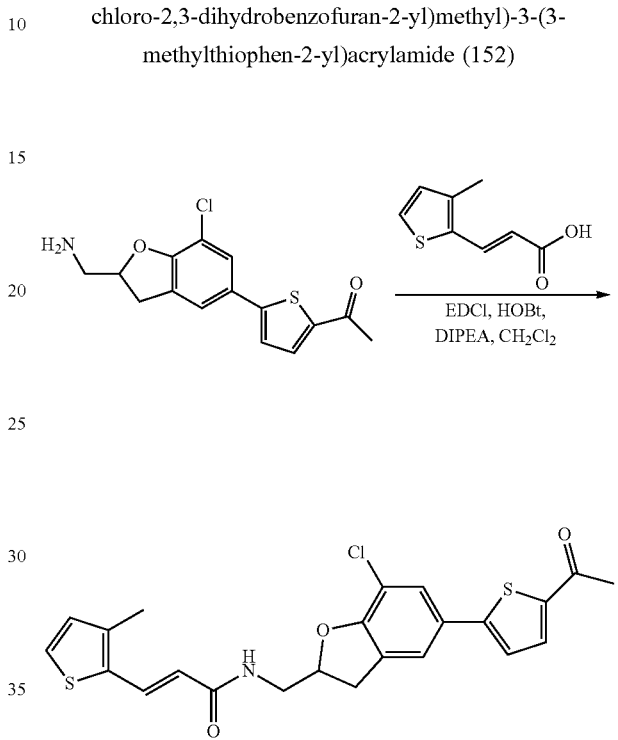

(E)-N-((5-(5-Acetylthiophen-2-yl)-7-chloro-2,3-dihydrobenzofuran-2-yl)methyl)-3-(quinoxalin-2-yl)acrylamide 152 was prepared according to General Procedure 3 (30% yield). LCMS: m/z 457.86 [M+H]$^+$, $t_R$ 8.38 min.

Synthesis of (E)-N-((5-(5-acetylthiophen-2-yl)-7-chloro-2,3-dihydrobenzofuran-2-yl)methyl)-3-(1H-pyrrol-3-yl)acrylamide (153)

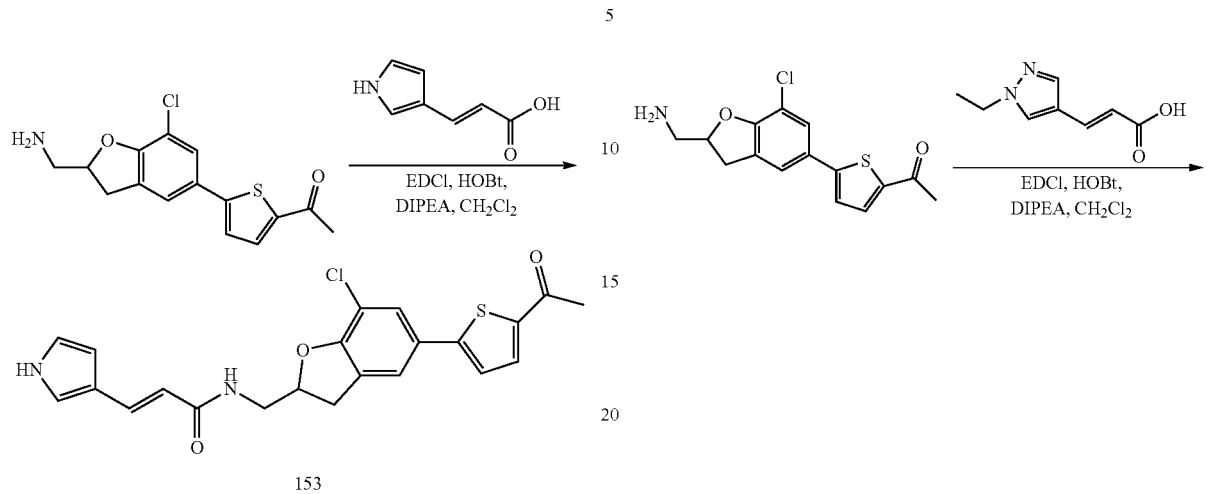

(E)-N-((5-(5-Acetylthiophen-2-yl)-7-chloro-2,3-dihydrobenzofuran-2-yl)methyl)-3-(1H-pyrrol-3-yl)acrylamide 153 was prepared according to General Procedure 3 (30% yield). LCMS: m/z 427.94 [M+H]$^+$, $t_R$ 6.60 min.

Synthesis of (E)-N-((5-(5-acetylthiophen-2-yl)-7-chloro-2,3-dihydrobenzofuran-2-yl)methyl)-3-(5-chloro-1-isobutyl-3-methyl-1H-pyrazol-4-yl)acrylamide (154)

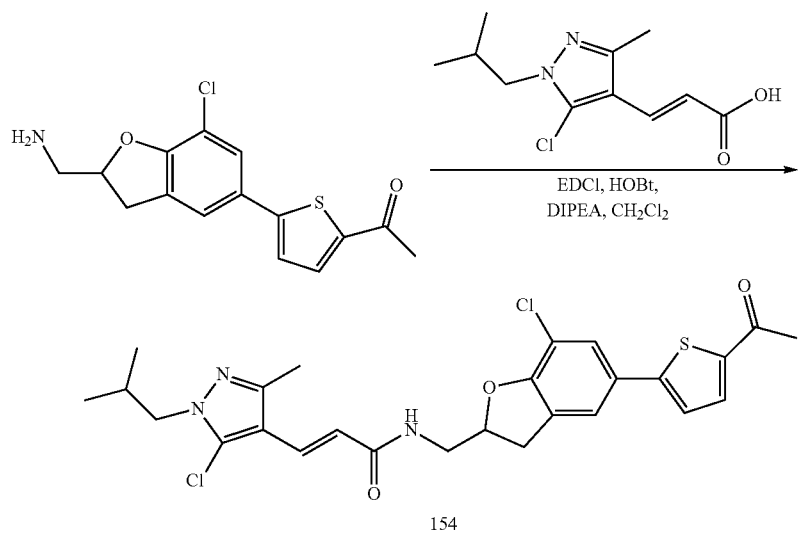

(E)-N-((5-(5-Acetylthiophen-2-yl)-7-chloro-2,3-dihydrobenzofuran-2-yl)methyl)-3-(5-chloro-1-isobutyl-3-methyl-1H-pyrazol-4-yl)acrylamide 154 was prepared according to General Procedure 3 (39% yield). $^1$H NMR (300 MHz, DMSO-d6) δ 8.45 (t, 1H); 7.89 (d, 1H); 7.55-7.63 (m, 3H); 7.23 (d, 1H); 6.55 (d, 1H); 5.02-5.12 (m, 1H); 3.87 (d, 2H); 3.4-3.6 (m, 2H); 2.96-3.12 (m, 2H); 2.5 (s, 3H); 2.27 (s, 3H); 2.04-2.15 (m, 1H); 0.83 (d, 6H). LCMS: m/z 531.91 [M+H]$^+$, $t_R$ 8.67 min.

Synthesis of (E)-N-((5-(5-acetylthiophen-2-yl)-7-chloro-2,3-dihydrobenzofuran-2-yl)methyl)-3-(1-ethyl-1H-pyrazol-4-yl)acrylamide (155)

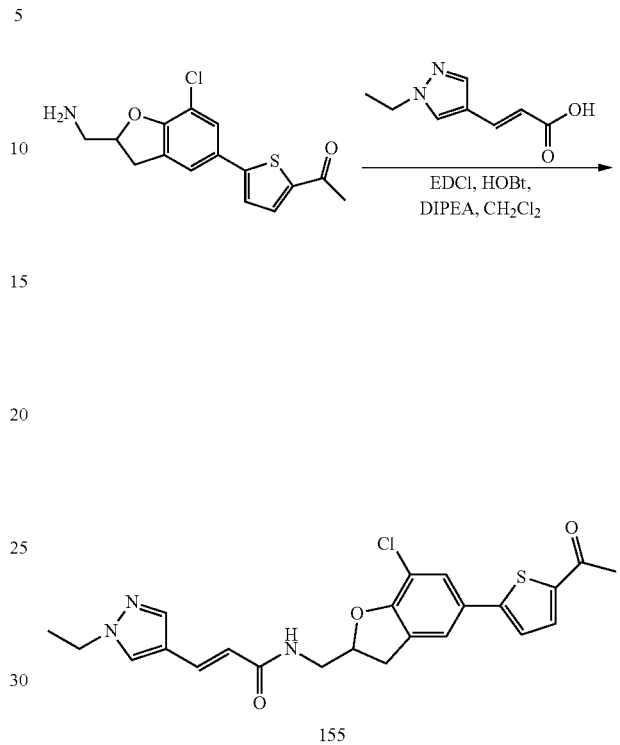

(E)-N-((5-(5-Acetylthiophen-2-yl)-7-chloro-2,3-dihydrobenzofuran-2-yl)methyl)-3-(1-ethyl-1H-pyrazol-4-yl)acrylamide 155 was prepared according to General Procedure 3 (38% yield). $^1$H NMR (300 MHz, DMSO-d6) δ 8.27 (t, 1H); 7.99 (s, 1H); 7.89 (d, 1H); 7.55-7.67 (m, 4H); 7.30 (d, 1H); 6.33 (d, 1H); 5.0-5.12 (m, 1H); 4.10 (q, 4H); 3.4-3.62 (m, 2H); 3.0-3.12 (m, 2H); 2.5 (s, 3H); 1.34 (t, 3H). LCMS: m/z 455.89 [M+H]$^+$, $t_R$ 10.03 min.

Synthesis of (E)-N-((5-(5-acetylthiophen-2-yl)-7-chloro-2,3-dihydrobenzofuran-2-yl)methyl)-3-(1,3-dimethyl-1H-pyrazol-4-yl)acrylamide (156)

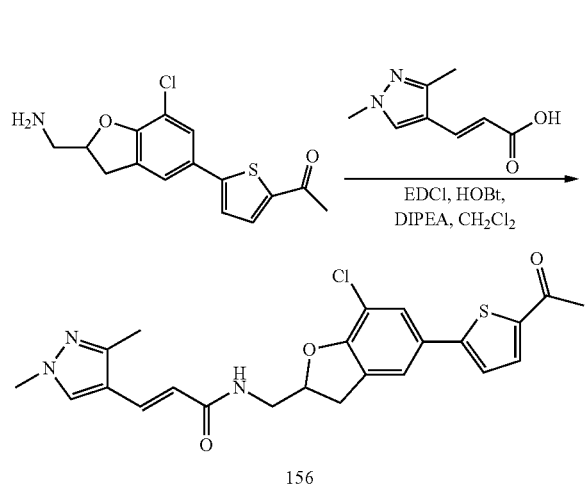

(E)-N-((5-(5-Acetylthiophen-2-yl)-7-chloro-2,3-dihydrobenzofuran-2-yl)methyl)-3-(1,3-dimethyl-1H-pyrazol-4-yl)acrylamide 156 was prepared according to General Procedure 3 (41% yield). $^1$H NMR (300 MHz, DMSO-d6) δ 8.28 (t, 1H); 7.85-7.90 (m, 2H); 7.55-7.64 (m, 3H); 7.28 (d, 1H); 6.25 (d, 1H); 5.0-5.12 (m, 1H); 3.73 (s, 3H); 3.34-3.62 (m, 2H); 3.0-3.12 (m, 2H); 2.5 (s, 3H); 2.21 (s, 3H). LCMS: m/z 455.89 [M+H]$^+$, $t_R$ 9.93 min.

Synthesis of (E)-N-((5-(5-acetylthiophen-2-yl)-7-chloro-2,3-dihydrobenzofuran-2-yl)methyl)-3-(1,5-dimethyl-1H-pyrazol-4-yl)acrylamide (157)

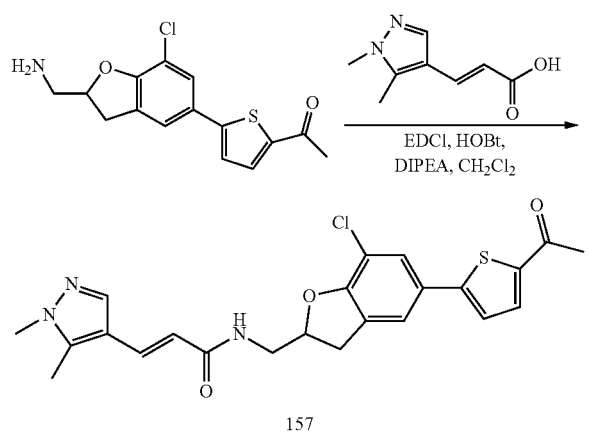

(E)-N-((5-(5-acetylthiophen-2-yl)-7-chloro-2,3-dihydrobenzofuran-2-yl)methyl)-3-(1,5-dimethyl-1H-pyrazol-4-yl)acrylamide 157 was prepared according to General Procedure 3 (44% yield). $^1$H NMR (300 MHz, DMSO-d6) δ 8.25 (t, 1H); 7.90 (d, 1H); 7.55-7.63 (m, 5H); 7.26 (d, 1H); 6.30 (d, 1H); 5.0-5.12 (m, 1H); 3.71 (s, 3H); 3.34-3.62 (m, 2H); 3.02-3.12 (m, 2H); 2.5 (s, 3H); 2.29 (s, 3H). LCMS: m/z 455.93 [M+H]$^+$, $t_R$ 9.95 min.

Synthesis of (E)-N-((5-(5-acetylthiophen-2-yl)-7-chloro-2,3-dihydrobenzofuran-2-yl)methyl)-3-(2-methylthiazol-4-yl)acrylamide (159)

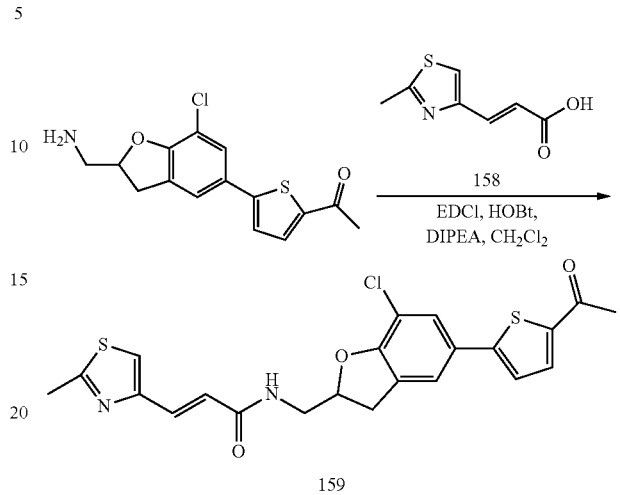

(E)-N-((5-(5-Acetylthiophen-2-yl)-7-chloro-2,3-dihydrobenzofuran-2-yl)methyl)-3-(2-methylthiazol-4-yl)acrylamide 159 was prepared according to General Procedure 3 starting with (E)-3-(2-methylthiazol-4-yl)acrylic acid 158 (28% yield). $^1$H NMR (300 MHz, DMSO-d6) δ 8.44 (t, 1H); 8.17 (s, 1H); 7.90 (d, 1H); 7.55-7.63 (m, 3H); 7.03-7.11 (m, 2H); 5.0-5.12 (m, 1H); 3.71 (s, 3H); 3.34-3.62 (m, 2H); 3.18 (s, 3H); 3.02-3.12 (m, 2H); 2.5 (s, 6H). LCMS: m/z 499.93 [M+H]$^+$, $t_R$ 7.42 min.

Synthesis of (E)-N-((5-(5-acetylthiophen-2-yl)-7-chloro-2,3-dihydrobenzofuran-2-yl)methyl)-3-(5-chloro-1,3-dimethyl-1H-pyrazol-4-yl)acrylamide (160)

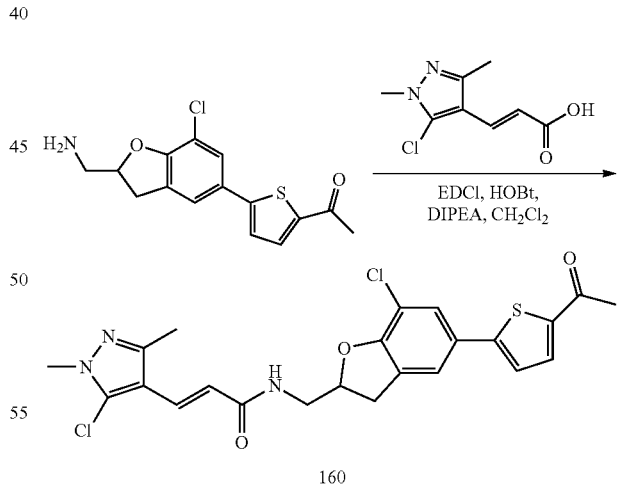

(E)-N-((5-(5-acetylthiophen-2-yl)-7-chloro-2,3-dihydrobenzofuran-2-yl)methyl)-3-(5-chloro-1,3-dimethyl-1H-pyrazol-4-yl)acrylamide 160 was prepared according to General Procedure 3 (28% yield). $^1$H NMR (300 MHz, DMSO-d6) δ 8.45 (t, 1H); 7.89 (d, 1H); 7.55-7.63 (m, 3H); 7.32 (d, 1H); 6.5 (d, 1H); 5.0-5.12 (m, 1H); 3.72 (s, 3H); 3.34-3.62 (m, 2H); 2.92-3.12 (m, 2H); 2.5 (s, 6H); 2.25 (s, 3H). LCMS: m/z 489.93 [M+H]$^+$, $t_R$ 8.07 min.

161

Synthesis of (E)-N-((5-(5-acetylthiophen-2-yl)-7-chloro-2,3-dihydrobenzofuran-2-yl)methyl)-3-(2,6-dimethylimidazo[2,1-b]thiazol-5-yl)acrylamide (161)

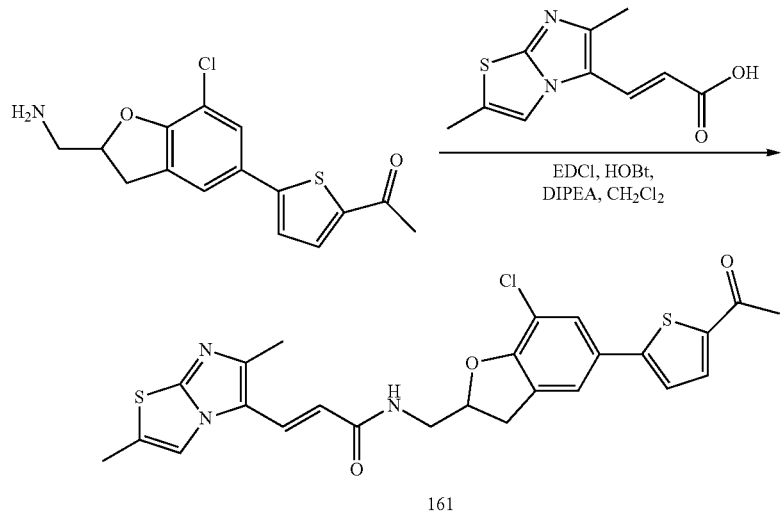

(E)-N-((5-(5-Acetylthiophen-2-yl)-7-chloro-2,3-dihydrobenzofuran-2-yl)methyl)-3-(2,6-dimethylimidazo[2,1-b]thiazol-5-yl)acrylamide 161 was prepared according to General Procedure 3 (28% yield). $^1$H NMR (300 MHz, DMSO-d6) δ 8.17 (t, 1H); 7.89 (d, 1H); 7.86 (d, 1H); 7.63 (d, 1H); 7.69 (m. 1H); 7.55 (d, 1H); 7.45 (d, 1H); 6.45 (d, 1H); 5.0-5.12 (m, 1H); 3.72 (s, 3H); 3.34-3.62 (m, 2H); 2.92-3.12 (m, 2H); 2.5 (s, 6H); 2.25 (s, 3H); 2.33 (s, 3H). LCMS: m/z 512.04 [M+H]$^+$, $t_R$ 9.53 min.

162

Synthesis of 1-(5-(7-chloro-2-(((E)-3-(pyridin-3-yl)acrylamido)methyl)-2,3-dihydrobenzofuran-5-yl)thiophen-2-yl)ethyl 5-((3aS,4S,6aR)-2-oxohexahydro-1H-thieno[3,4-d]imidazol-4-yl)pentanoate (162)

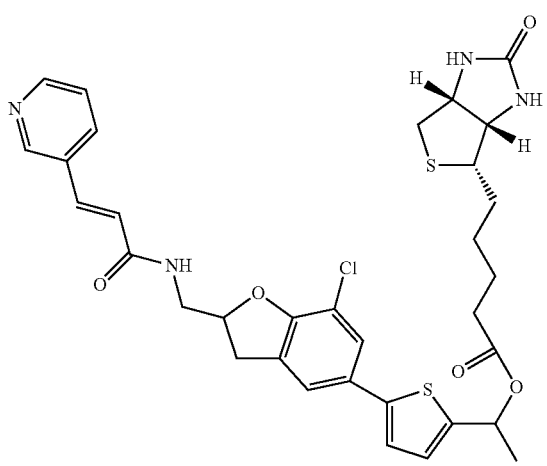

1-(5-(7-chloro-2-(((E)-3-(pyridin-3-yl)acrylamido) methyl)-2,3-dihydrobenzofuran-5-yl)thiophen-2-yl)ethyl 5-((3aS,4S,6aR)-2-oxohexahydro-1H-thieno[3,4-d]imidazol-4-yl)pentanoate 162 was prepared according to General Procedure 3 (13% yield). $^1$H NMR (400 MHz, DMSO-d$_6$) δ 8.77 (s, 1H), 8.52-8.56 (m, 2H), 7.97-8.00 (m, 1H), 7.44-7.52 (m, 4H), 7.29-7.30 (m, 1H), 7.07-7.08 (d, J=4 Hz, 1H), 6.81-6.85 (d, J=4 Hz, 1H), 6.43 (s, 1H), 6.36 (s, 1H), 6.04-6.06 (m, 1H), 5.12 (m, 1H), 4.26 (m, 1H), 4.09-4.10 (m, 1H), 3.56-3.60 (m, 2H), 3.03-3.11 (m, 2H), 2.76-2.80 (m, 1H), 2.54-2.57 (m, 2H), 2.30-2.34 (t, 2H), 1.51-1.58 (m, 5H), 1.30-1.43 (m, 4H). LCMS: m/z 667.43 [M]$^+$, t$_R$=1.99 min.

Synthesis of (E)-N-((5-(5-acetylthiophen-2-yl)-7-chloro-2,3-dihydrobenzofuran-2-yl)methyl)-3-(3-chlorothiophen-2-yl)acrylamide (163)

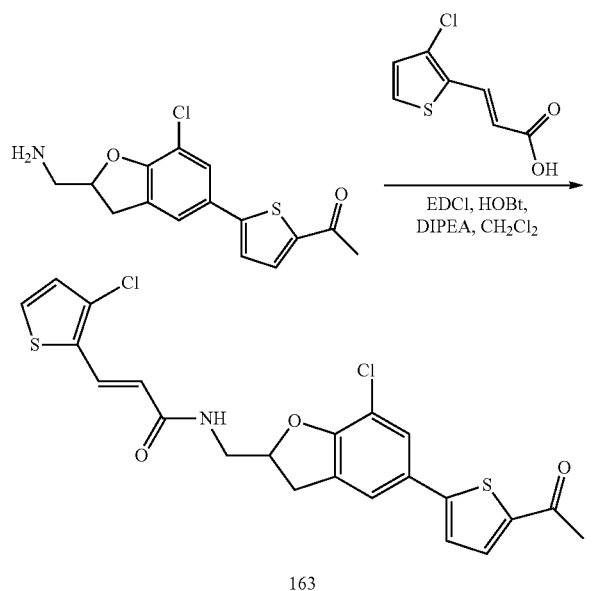

(E)-N-((5-(5-Acetylthiophen-2-yl)-7-chloro-2,3-dihydrobenzofuran-2-yl)methyl)-3-(3-chlorothiophen-2-yl)acrylamide 163 was prepared according to General Procedure 3 (25% yield). $^1$H NMR (400 MHz, DMSO-d6) δ 8.5 (bs, 1H), 7.91-7.92 (d, J=4 Hz, 1H), 7.76-7.77 (d, J=5.6 Hz, 1H), 7.65-7.66 (d, J=1.6 Hz, 1H), 7.58-7.61 (m, 2H), 7.54(S, 1H), 7.18-7.19 (d, J=5.2 Hz, 1H), 6.56-6.60 (d, J=15.2 Hz, 1H), 5.09 (m, 1H), 3.56-3.61 (m, 2H), 3.41-3.44 (m, 1H), 3.06-3.12 (m, 1H), 2.5 (s, 3H). LCMS: m/z 479.9 [M+H]$^+$, t$_R$=2.40 min.

Synthesis of (E)-N-((5-(5-acetylthiophen-2-yl)-7-chloro-2,3-dihydrobenzofuran-2-yl)methyl)-3-(1-methyl-1H-imidazol-2-yl)acrylamide (164)

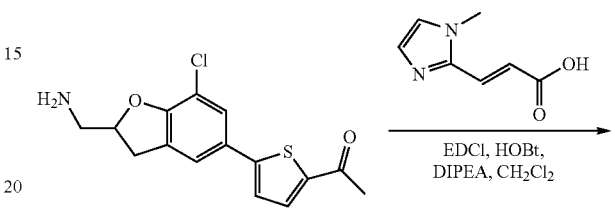

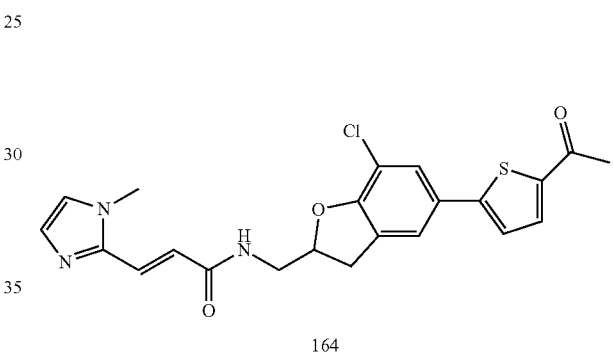

(E)-N-((5-(5-acetylthiophen-2-yl)-7-chloro-2,3-dihydrobenzofuran-2-yl)methyl)-3-(1-methyl-1H-imidazol-2-yl)acrylamide 164 was prepared according to General Procedure 3 (28% yield). $^1$H NMR (400 MHz, DMSO-d6) δ 8.61 (s, 1H), 7.91-7.92 (d, J=4 Hz, 1H), 7.58-7.65 (m, 3H), 7.33-7.37 (d, J=16 Hz, 1H), 7.26 (s, 1H), 7.00(S, 1H), 7.85-7.89 (d, J=16 Hz, 1H), 5.09 (m, 1H), 3.74 (s, 3H), 3.56-3.61 (m, 2H), 3.41-3.44 (m, 1H), 3.08-3.13 (m, 1H), 2.5 (s, 3H). LCMS: m/z 442.01 [M+H]$^+$, t$_R$=1.63 min.

Synthesis of (E)-N-((4-(5-acetylthiophen-2-yl)-7-chloro-2,3-dihydrobenzofuran-2-yl)methyl)-3-(pyridin-3-yl)acrylamide (173)

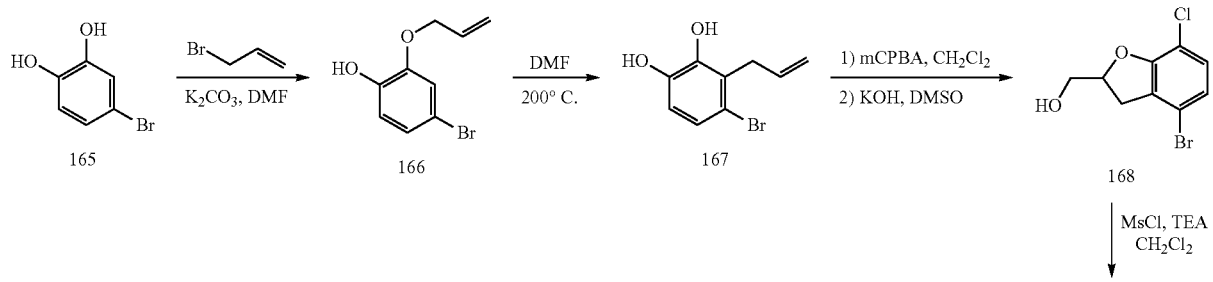

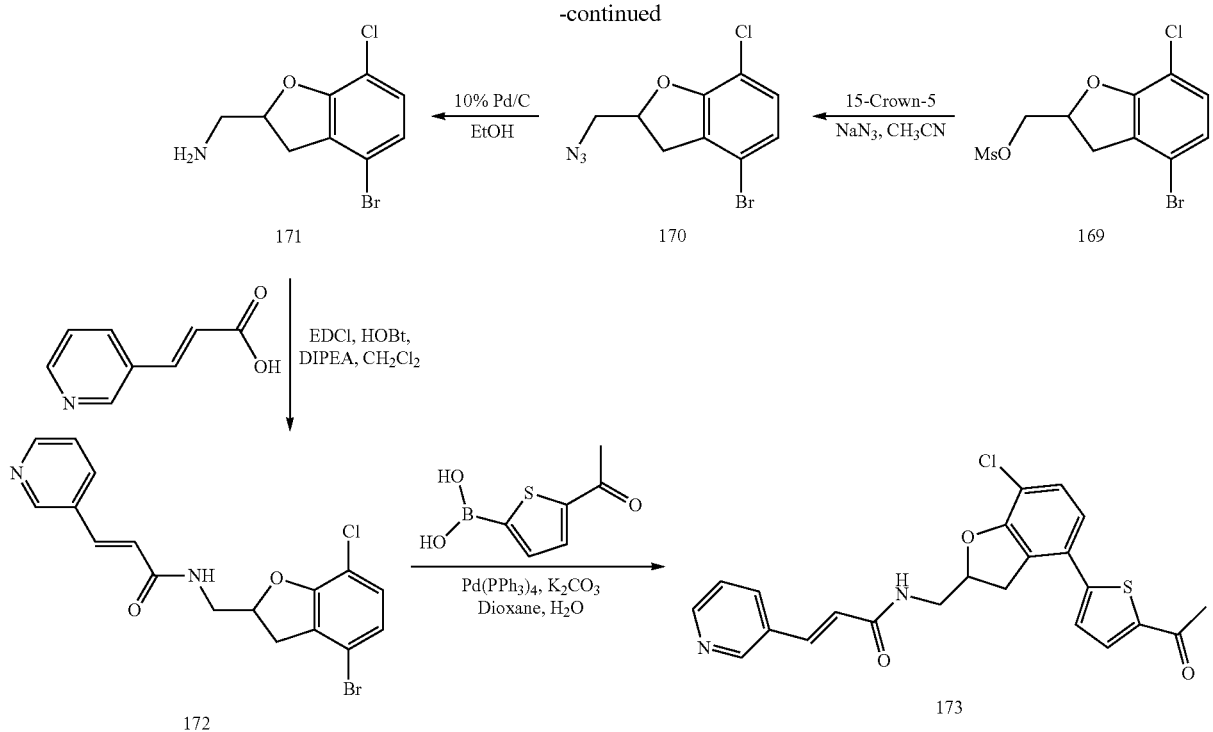

2-(Allyloxy)-4-bromo-1-chlorobenzene 166 was synthesized using conditions described in the first step in Method B (conversion of 9 to 10) starting from 5-bromo-2-chlorophenol 165. Yield (78%). $^1$H NMR (400 MHz, CDCl$_3$) δ 7.03-7.28 (m, 3H), 6.02-6.12 (m, 1H), 5.47-5.52 (m, 1H), 5.34-5.38 (m, 1H), 4.60-4.63 (m, 2H). LC: $t_R$=2.56 min.

2-Allyl-3-bromo-6-chlorophenol 167 was synthesized using conditions described in the second step in Method B (conversion of 10 to 11). Yield (55%). LCMS: m/z 247.08 [M−H]$^−$, $t_R$=2.443 min.

(4-Bromo-7-chloro-2,3-dihydrobenzofuran-2-yl)methanol 168 was synthesized using conditions described in the third step in Method B (conversion of 11 to 12). Yield (50%). LCMS: m/z 262.8 [M−H]$^−$, $t_R$=1.92 min.

(4-Bromo-7-chloro-2,3-dihydrobenzofuran-2-yl)methyl methanesulfonate 169 was synthesized using conditions described in the fourth step in Method B (conversion of 12 to 13). Yield (62%). $^1$H NMR (400 MHz, DMSO-d$_6$) δ 7.19-7.21 (d, J=8.8 Hz, 1H), 7.07-7.09 (d, J=8.4 Hz, 1H), 5.25-5.32 (m, 1H), 4.54-4.57 (dd, J$_1$=2.8 Hz, J2 =8.8 Hz, 1H), 4.44-4.49 (dd, J$_1$=6 Hz, J$_2$=5.6 Hz, 1H), 3.33-3.46 (dd, J$_1$=2.8 Hz, J$_2$=8.8 Hz, 1H), 3.24 (s, 3H), 3.07-3.12 (dd, J$_1$=2.8 Hz, J$_2$=8.8 Hz, 1H). LCMS: m/z 359.9 [M+18]$^+$, $t_R$=2.176 min.

2-(Azidomethyl)-4-bromo-7-chloro-2,3-dihydrobenzofuran 170 was synthesized using conditions described in the fifth step in Method B (conversion of 13 to 14). Yield (61%). $^1$H NMR (400 MHz, CDCl$_3$) δ 7.03-7.05 (d, J=7.6 Hz, 1H), 6.97-6.99 (d, J=8.4 Hz, 1H), 5.09-5.15 (m, 1H), 3.63-3.67 (dd, J$_1$=4 Hz, J$_2$=9.2 Hz, 1H), 3.51-3.56 (dd, J$_1$=5.2 Hz, J$_2$=8 Hz, 1H), 3.37-3.43 (dd, J$_1$=9.6 Hz, J$_2$=6 Hz, 1H), 3.11-3.17 (dd, J$_1$=7.2 Hz, J$_2$=9.2 Hz, 1H). LCMS: m/z 288.2 [M+H]$^+$, $t_R$=2.22 min.

(7-Chloro-2,3-dihydrobenzofuran-2-yl)methanamine 171 was synthesized using conditions described in the sixth step in Method B (conversion of 14 to Common Intermediate I). Yield (45%). $^1$H NMR (400 MHz, DMSO-d$_6$) δ 8.009 (br, 2H, exchangeable), 7.21-7.23 (d, J=8.8 Hz, 1H), 7.10-7.12 (d, J=78.8 Hz, 1H), 5.15-5.22 (m, 1H), 3.40-3.47 (dd, J$_1$=9.2 Hz, J$_2$=9.6 Hz, 1H), 3.21-3.34 (m, 2H), 3.10-3.17 (dd, J$_1$=8 Hz, J$_2$=8.4 Hz, 1H). LCMS: m/z 263.87 [M+H]$^+$, $t_R$=1.12 min.

(E)-N-((4-Bromo-7-chloro-2,3-dihydrobenzofuran-2-yl)methyl)-3-(pyridin-3-yl)acrylamide 172 was synthesized using General Procedure 3. Yield (52%). $^1$H NMR (400 MHz, MeOD) δ 8.73 (s, 1H), 8.53-8.54 (d, J=3.6 Hz, 1H), 8.06-8.09 (m, 1H), 7.58-7.62 (d, J=16 Hz, 1H), 7.48-7.51 (m, 1H), 7.07-7.09 (d, J=8.4 Hz, 1H), 6.98-7.01 (d, J=8.8 Hz, 1H), 6.82-6.87 (d, J=16 Hz, 1H), 5.10-5.17 (m, 1H), 3.70-3.72 (m, 2H), 3.36-3.42 (m, 1H), 3.14-3.15 (m, 1H). LCMS: m/z 394.99 [M+H]$^+$, $t_R$=1.909 min.

(E)-N-((4-(5-Acetylthiophen-2-yl)-7-chloro-2,3-dihydrobenzofuran-2-yl)methyl)-3-(pyridin-3-yl)acrylamide 173 was synthesized using General Procedure 1. Yield (48%). $^1$H NMR (400 MHz, DMSO-d$_6$) δ 8.77 (s, 1H), 8.55-8.56 (m, 2H), 7.99-8.01 (m, 2H), 7.58-7.59 (d, J=4 Hz, 1H), 7.48-7.52 (d, J=16 Hz, 1H), 7.43-7.46 (m, 1H), 7.32-7.36 (d, J=8.4 Hz, 1H), 7.26-7.29 (d, J=8.4 Hz, 1H), 6.80-6.84 (d, J=16 Hz, 1H), 5.10-5.15 (m, 1H), 3.64-3.69 (m, 2H), 3.53-3.63 (m, 1H), 3.28-3.39 (m, 1H), 2.56 (s, 3H). LCMS: m/z 439.11 [M+H]$^+$, $t_R$=1.930 min.

Synthesis of (E)-N-((5-(5-acetylthiophen-2-yl)-7-chloro-2,3-dihydrobenzofuran-2-yl)methyl)-3-(2,6-dimethylpyridin-3-yl)acrylamide (174)

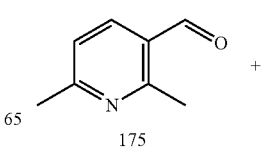

167

-continued

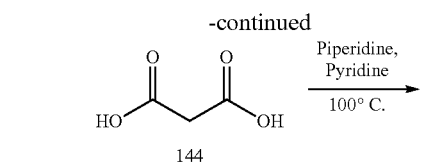

168

Synthesis of (E)-N-((5-(5-acetylthiophen-2-yl)-7-chloro-2,3-dihydrobenzofuran-2-yl)methyl)-3-(2-ethyl-4-methyl-1H-imidazol-5-yl)acrylamide (177)

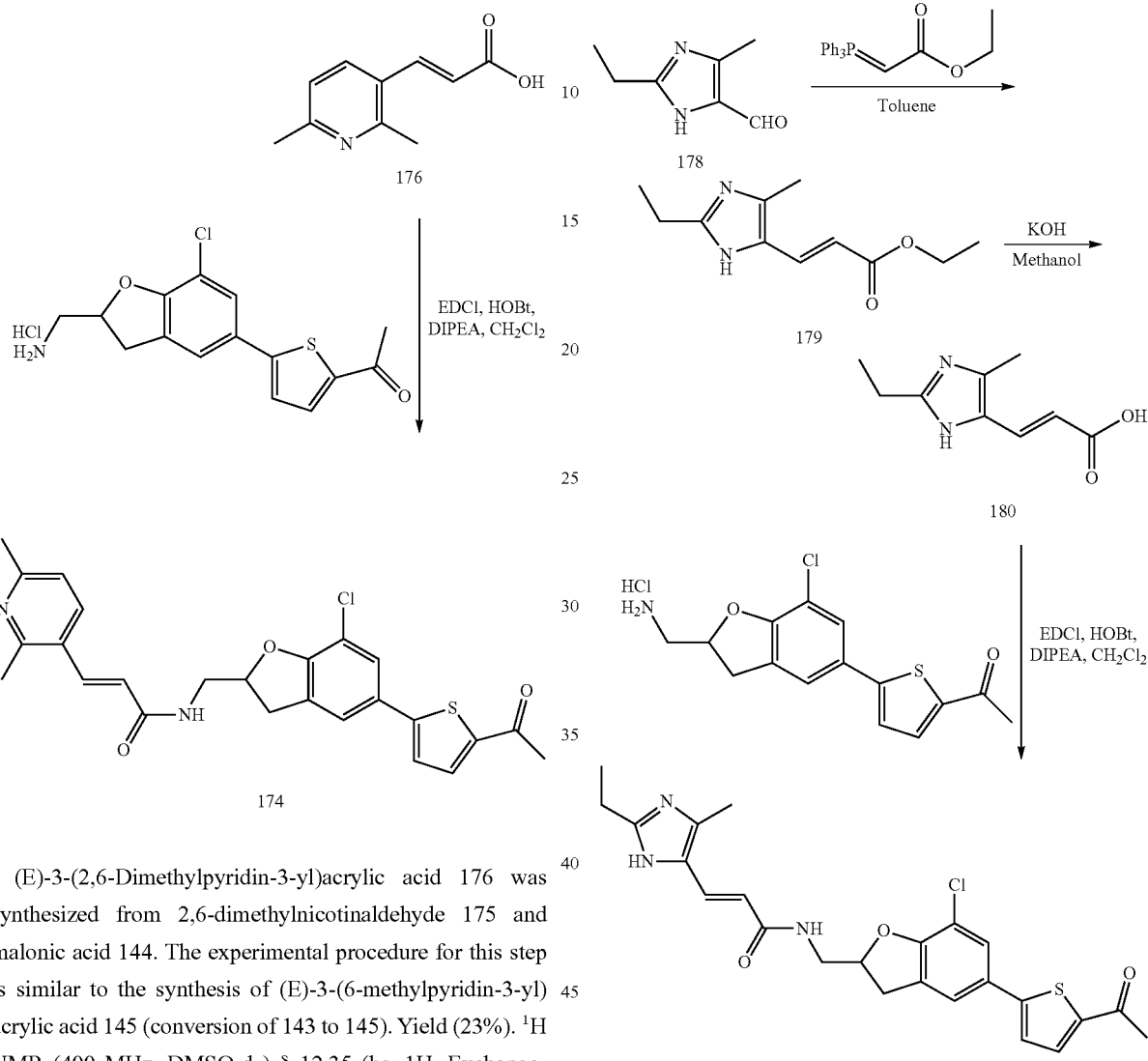

(E)-3-(2,6-Dimethylpyridin-3-yl)acrylic acid 176 was synthesized from 2,6-dimethylnicotinaldehyde 175 and malonic acid 144. The experimental procedure for this step is similar to the synthesis of (E)-3-(6-methylpyridin-3-yl) acrylic acid 145 (conversion of 143 to 145). Yield (23%). $^1$H NMR (400 MHz, DMSO-$d_6$) δ 12.35 (bs, 1H, Exchangeable), 8.58-8.59 (d, J=1.6 Hz, 1H), 7.98-8.01 (d, J=8 Hz, 1H), 7.72-7.79 (m, 1H), 7.38-7.39 (m, 1H), 7.12-7.17 (m, 1H), 6.46-6.49 (d, J=15.6 Hz, 1H), 2.51 (s, 3H), 2.45 (m, 3H). LCMS m/z 178.2 [M+H]$^+$.

(E)-N-((5-(5-Acetylthiophen-2-yl)-7-chloro-2,3-dihydrobenzofuran-2-yl)methyl)-3-(2,6-dimethylpyridin-3-yl) acrylamide (174) was synthesized using General Procedure 3 with 45% yield. $^1$H NMR (400 MHz, DMSO-$d_6$) δ 8.50 (t, 1H), 7.90 (d, J=4.4 Hz, 1H), 7.78 (d, J=8 Hz, 1H), 7.58-7.66 (m, 4H), 7.14 (d, J=8 Hz, 1H), 6.62 (d, J=15.6 Hz, 1H), 5.07-5.14 (m, 1H), 3.52-3.65 (m, 2H), 3.38-3.46 (m, 1H), 3.08-3.14 (m, 1H), 2.50 (s, 6H), 2.43 (s, 3H). LCMS m/z 467.12 [M+H]$^+$, $t_R$=1.72 min.

2-Ethyl-4-methyl-1H-imidazole-5-carbaldehyde 178 (0.5 g, 3.6 mmol) was dissolved in toluene (20 mL). (Carbethoxymethylene)triphenylphosphorane (1.70 g, 4.89 mmol) was added at 25° C. and the reaction mixture was stirred at 110° C. for 4 h. The reaction mixture was concentrated under reduced pressure and purified by silica gel chromatography (0-4% Methanol/CH$_2$Cl$_2$) to give (E)-ethyl 3-(2-ethyl-4-methyl-1H-imidazol-5-yl) acrylate (179). Yield (0.4 g, 53%). LCMS: m/z 208.53 [M+H]$^+$, $t_R$=0.429 min.

(E)-Ethyl-3-(2-ethyl-4-methyl-1H-imidazol-5-yl) acrylate (179) (0.4 g, 1.9 mmol) was dissolved in methanol (10 mL). Potassium hydroxide (0.21 g, 3.8 mmol) was added at 25° C. and stirred for 4 h. The reaction mixture was distilled and the residue was transferred into iced water, acidified with dil. HCl (pH~2) and extracted with ethyl acetate (15 mL×3). The combined organic layers was washed with brine, dried over anhydrous Na$_2$SO$_4$, and concentrated under reduced pressure to give (E)-3-(2-ethyl-4-methyl-1H-imidazol-5-yl)acrylic acid (180). Yield (0.5 g, 45%). $^1$H NMR (400 MHz, DMSO-d$_6$) δ 12.67 (s, 1H), 7.43 (d, J=16 Hz, 1H), 6.59 (d, J=16 Hz, 1H), 2.90-2.96 (m, 2H), 2.38 (s, 3H), 1.30-1.34 (t, 3H). LCMS: m/z 180.81 [M+H]$^+$, t$_R$=2.37 min.

(E)-N-((5-(5-acetylthiophen-2-yl)-7-chloro-2,3-dihydrobenzofuran-2-yl)methyl)-3-(2-ethyl-4-methyl-1H-imidazol-5-yl)acrylamide 177 was synthesized using General Procedure 3 with 15% yield. $^1$H NMR (400 MHz, DMSO-d$_6$) δ 8.26 (t, 1H), 8.14 (s, 1H), 7.91 (d, J=4 Hz, 1H), 7.64 (d, 1H), 7.58-7.60 (m, 2H), 7.26 (d, J=15.2 Hz, 1H), 6.39 (s, 1H), 5.04-5.11 (m, 1H), 3.55-3.61 (m, 1H), 3.41-3.50 (m, 2H), 3.08-3.13 (m, 1H), 2.52-2.59 (m, 5H), 2.20 (s, 3H), 3.18 (t, 3H). LCMS: m/z 470.07 [M+H]$^+$, t$_R$=1.67 min.

Synthesis of (E)-N-((5-(5-acetylthiophen-2-yl)-7-chloro-2,3-dihydrobenzofuran-2-yl)methyl)but-2-enamide (181)

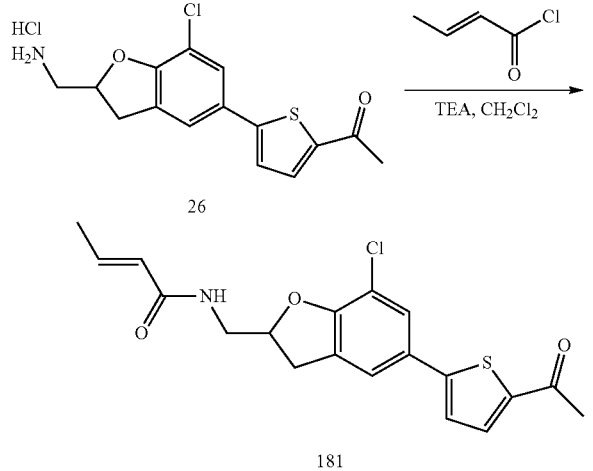

1-(5-(2-(Aminomethyl)-7-chloro-2,3-dihydrobenzofuran-5-yl)thiophen-2-yl)ethanone 26 (0.1 g, 0.32 mmol) was dissolved in CH$_2$Cl$_2$ (10 mL) and cooled to 0° C. Triethylamine (0.2 mL, 0.48 mmol) and crotonyl chloride (0.04 g, 0.38 mmol) were added at 0° C., then allowed to warm to room temperature and stirred at room temperature for 2 h. The reaction mixture was transferred into iced water (50 mL) and extracted with ethyl acetate (20 mL×3). The combined organic layers were washed with brine, dried over anhydrous Na$_2$SO$_4$, and concentrated under reduced pressure. The crude product was purified by silica gel chromatography (0-3% Methanol/CH$_2$Cl$_2$) to give (E)-N-((5-(5-acetylthiophen-2-yl)-7-chloro-2,3-dihydrobenzofuran-2-yl)methyl)but-2-enamide 181. Yield (0.017 g, 14%). $^1$H NMR (400 MHz, DMSO) δ 8.26 (t, 1H), 7.92 (d, J=4 Hz, 1H), 7.66 (d, J=1.6 Hz, 1H), 7.59 (m, 2H), 6.62-6.69 (m, 1H), 5.97 (q, 1H), 5.01-5.08 (m, 1H), 3.43-3.53 (m, 3H), 3.03-3.09 (m, 1H), 2.53 (s, 3H), 1.79 (d, J=8.4 Hz, 3H). LCMS: m/z 375.93 [M+H]$^+$, t$_R$=2.07 min.

Synthesis of (E)-N-((5-(5-acetylthiophen-2-yl)-7-chloro-2,3-dihydrobenzofuran-2-yl)methyl)-3-(2-methylpyridin-3-yl)acrylamide (182)

To a solution of 2-methyl-pyridine 3-carbaldehyde 183 (0.5g, 4.1 mmol) in pyridine (2.5 mL) was added malonic acid 144 (0.65g, 6.1 mmol) and catalytic piperidine (0.2 mL). The reaction mixture was refluxed at 100° C. for 3 h and concentrated under reduced pressure. The residue was diluted with water and the solid precipitate was filtered to give (E)-3-(2-methylpyridin-3-yl) acrylic acid 184. Yield (0.47 g, 71%). $^1$H NMR (400 MHz, DMSO-d$_6$) δ 12.6 (s, 1H), 8.45 (dd, J$_1$=1.6 Hz, J$_2$=4.8 Hz, 1H), 8.09 (dd, J$_1$=1.6 Hz, J$_2$=8 Hz, 1H), 7.76 (d, J=16 Hz, 1H), 7.27-7.30 (m, 1H), 6.53 (d, J=16 Hz, 1H), 2.58 (s, 3H). LCMS: m/z 163.75 [M+H]$^-$, t$_R$=0.755 min.

(E)-N-((5-(5-Acetylthiophen-2-yl)-7-chloro-2,3-dihydrobenzofuran-2-yl)methyl)-3-(2-methylpyridin-3-yl)acrylamide 182 was synthesized using General Procedure 3 with 9% yield. $^1$H NMR (400 MHz, DMSO-d$_6$) δ 8.5 (bs, 1H), 8.42 (d, J=3.6 Hz, 1H), 7.92 (d, J=4 Hz, 1H), 7.89 (d, J=8 Hz, 1H), 7.58-7.66 (m, 4H), 7.27-7.30 (m, 1H), 6.66 (d, J=15.6 Hz, 1H), 5.11 (m, 1H), 3.60 (m, 2H), 3.4-3.47 (m, 1H), 3.09-3.15 (m, 1H), 2.57 (s, 3H), 2.51 (s, 3H). LCMS: m/z 453.03 [M+H]$^+$, t$_R$=1.74 min.

Synthesis of (E)-N-((5-(5-acetylthiophen-2-yl)-7-chloro-2,3-dihydrobenzofuran-2-yl)methyl)-3-(2,5-dimethyl-1H-pyrrol-3-yl)acrylamide (185)

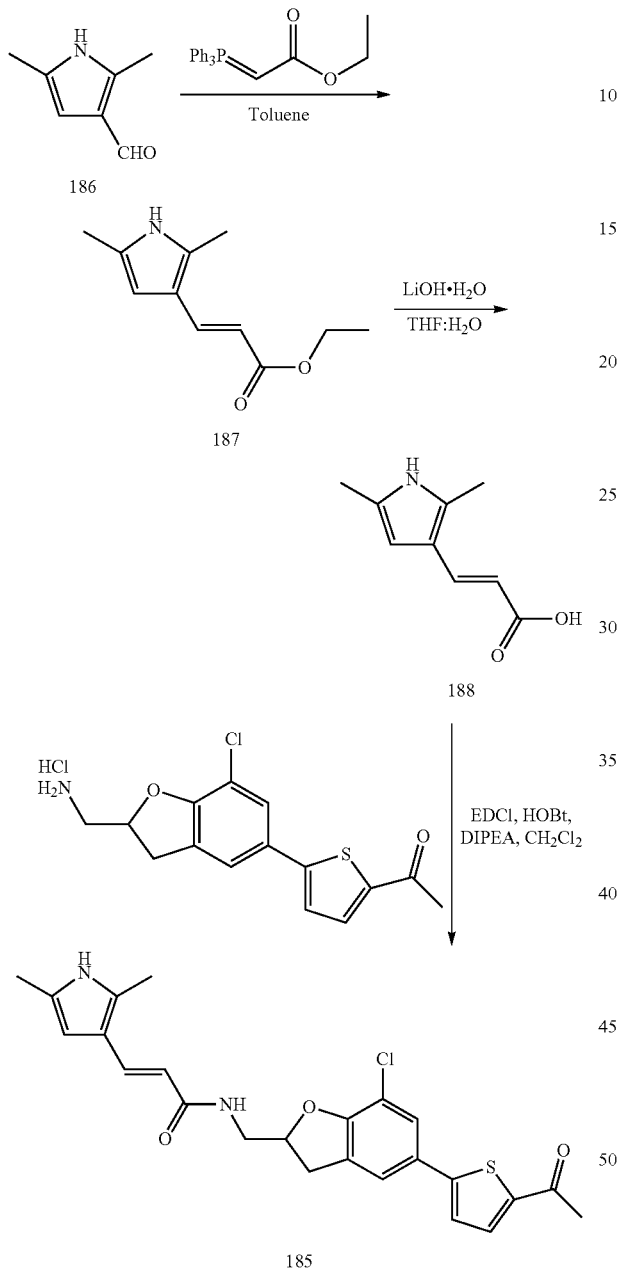

(E)-Ethyl 3-(2,5-dimethyl-1H-pyrrol-3-yl)acrylate 187 was synthesized from 2,5-dimethyl-1H-pyrrole-3-carbaldehyde 186. The experimental procedure for this step was similar to the synthesis of (E)-ethyl 3-(2-ethyl-4-methyl-1H-imidazol-5-yl) acrylate 179 (conversion of 178 to 179). Yield (79%). $^1$H NMR (400 MHz, DMSO-$d_6$) δ 10.82 (s, 1H), 7.49 (d, J=15.2 Hz, 1H), 6.00 (s, 1H), 5.84 (d, J=15.6 Hz, 1H), 3.63 (s, 3H), 2.22 (s, 3H), 2.10 (s, 3H). LCMS: m/z 179.8 [M+H]$^+$, $t_R$=1.76 min.

(E)-3-(2,5-dimethyl-1H-pyrrol-3-yl)acrylic acid 188 was synthesized from (E)-ethyl 3-(2,5-dimethyl-1H-pyrrol-3-yl) acrylate 187. The experimental procedure for this step was similar to the synthesis of (E)-3-(2-ethyl-4-methyl-1H-imidazol-5-yl)acrylic acid 180 (conversion of 179 to 180) with the following exception. Lithium hydroxide was used instead of potassium hydroxide. Yield (69%). $^1$H NMR (400 MHz, DMSO-$d_6$) δ 11.65 (s, 1H), 10.77 (s, 1H), 7.43 (d, J=15.2 Hz, 1H), 5.96 (s, 1H), 5.75 (d, J=15.6 Hz, 1H), 2.21 (s, 3H), 2.10 (s, 3H). LCMS: m/z 165.75 [M+H]$^+$, $t_R$=0.98 min.

(E)-N-((5-(5-Acetylthiophen-2-yl)-7-chloro-2,3-dihydrobenzofuran-2-yl)methyl)-3-(2,5-dimethyl-1H-pyrrol-3-yl) acrylamide 185 was synthesized using General Procedure 3 with 18% yield. $^1$H NMR (400 MHz, DMSO-$d_6$) δ 10.64 (s, 1H), 8.08 (t, 1H), 7.91-7.92 (d, J=4 Hz, 1H), 7.65 (s, 1H), 7.58-7.63 (m, 2H), 7.28-7.32 (d, J=15.2 Hz, 1H), 5.99-6.03 (d, J=15.2 Hz, 1H), 5.82 (s, 1H), 5.02-5.06 (m, 1H), 3.4-3.59 (m, 3H), 3.07-3.13 (m, 1H), 2.5 (s, 3H), 2.23 (s, 3H), 2.10 (s, 3H). LCMS: m/z 454.97 [M+H]$^+$, $t_R$=2.16 min.

Synthesis of (E)-N-((5-(5-acetylthiophen-2-yl)-7-chloro-2,3-dihydrobenzofuran-2-yl)methyl)-3-(1-methyl-1H-indol-3-yl)acrylamide (189)

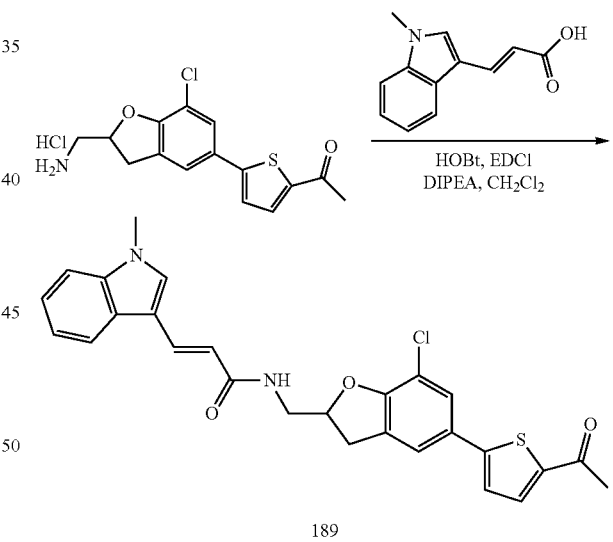

(E)-N-((5-(5-Acetylthiophen-2-yl)-7-chloro-2,3-dihydrobenzofuran-2-yl)methyl)-3-(1-methyl-1H-indol-3-yl) acrylamide 189 was synthesized using General Procedure 3 with 43% yield. $^1$H NMR (400 MHz, DMSO-$d_6$) δ 8.26 (t, 1H), 7.91-7.93 (m, 2H), 7.77 (s, 1H), 7.59-7.67 (m, 4H), 7.52 (d, J=8 Hz, 1H), 7.19-7.29 (m, 2H), 6.70 (d, J=15.6 Hz, 1H), 5.08-5.11 (m, 1H), 3.81 (s, 3H), 3.56-3.64 (m, 1H), 3.48-3.56 (m, 2H), 3.10-3.16 (m, 1H), 2.52 (s, 3H). LCMS: m/z 491.1 [M+H]$^+$, $t_R$=2.35 min.

Synthesis of (E)-N-((5-(5-acetylthiophen-2-yl)-7-chloro-2,3-dihydrobenzofuran-2-yl)methyl)-3-(benzo[d]thiazol-2-yl)acrylamide (190)

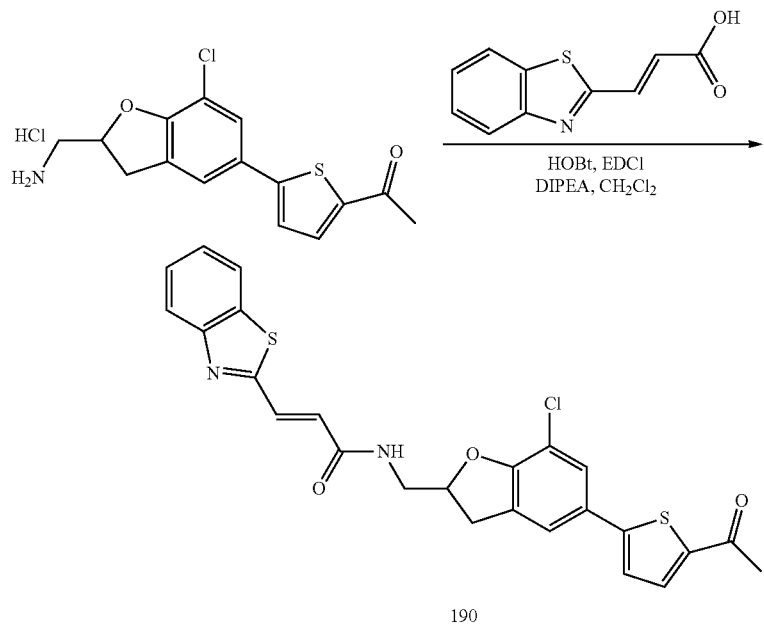

(E)-N-((5-(5-Acetylthiophen-2-yl)-7-chloro-2,3-dihydrobenzofuran-2-yl)methyl)-3-(benzo[d]thiazol-2-yl)acrylamide 190 was synthesized using General Procedure 3 with 40% yield. $^1$H NMR (400 MHz, DMSO-$d_6$) δ 8.84 (t, 1H), 8.16 (d, J=7.6 Hz, 1H), 8.05 (d, J=7.6 Hz, 1H), 7.92 (d, J=4 Hz, 1H), 7.49-7.67 (m, 5H), 7.17 (d, J=15.6 Hz, 1H), 5.11-5.13 (m, 1H), 3.61-3.65 (m, 2H), 3.40-3.49 (m, 1H), 3.09-3.15 (m, 1H), 2.53 (s, 3H). LCMS: m/z 494.92 [M+H]$^+$, $t_R$=2.34 min.

Synthesis of (E)-N-((5-(5-acetylthiophen-2-yl)-7-chloro-2,3-dihydrobenzofuran-2-yl)methyl)-3-(1-ethyl-1H-imidazol-2-yl)acrylamide (191)

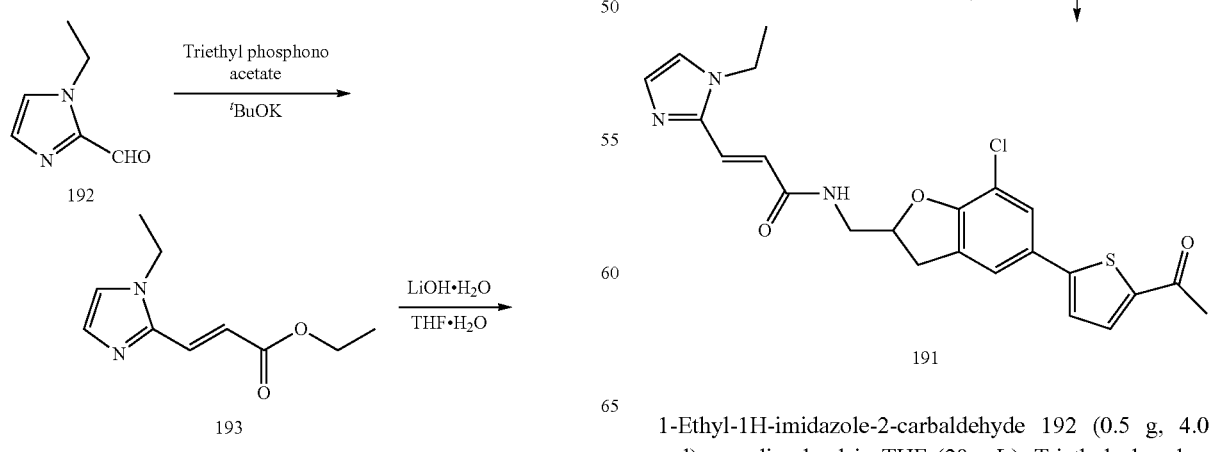

1-Ethyl-1H-imidazole-2-carbaldehyde 192 (0.5 g, 4.0 mmol) was dissolved in THF (20 mL). Triethyl phosphonoacetate (1.62 g, 7.2 mmol) and potassium-t-butoxide (0.81 g, 7.2 mmol) were added at 25° C. and the reaction mixture was stirred for 15 min. The reaction mixture was transferred into iced water and extracted with ethyl acetate (15 mL×3). The combined organic layers were washed with brine, dried over anhydrous $Na_2SO_4$ and concentrated under reduced pressure. The crude product was purified by silica gel chromatography (0-2% methanol/dichloromethane) to give (E)-ethyl 3-(1-ethyl-1H-imidazol-2-yl) acrylate 193. Yield: 0.6 g (77%). LCMS: m/z 195.88 [M+H]$^+$, $t_R$=2.49 min.

(E)-3-(1-ethyl-1H-imidazol-2-yl) acrylic acid 194 was synthesized from (E)-ethyl 3-(1-ethyl-1H-imidazol-2-yl) acrylate 193. The experimental procedure for this step was similar to the synthesis of (E)-3-(2-ethyl-4-methyl-1H-imidazol-5-yl)acrylic acid 180 (conversion of 179 to 180). Lithium hydroxide was used instead of potassium hydroxide. Yield: 58%. $^1$H NMR (400 MHz, DMSO-$d_6$) δ 7.82 (s, 1H), 7.64 (s, 1H), 7.53 (d, J=15.6 Hz, 1H), 7.14 (d, J=15.6 Hz, 1H), 4.28-4.33 (m, 2H), 1.33-1.37 (m, 3H). LCMS: m/z 166.75 [M+H]$^+$, $t_R$=0.62 min.

(E)-N-((5-(5-acetylthiophen-2-yl)-7-chloro-2,3-dihydrobenzofuran-2-yl)methyl)-3-(1-ethyl-1H-imidazol-2-yl) acrylamide 191 was synthesized using General Procedure 3 with 4% yield. $^1$H NMR (400 MHz, DMSO-$d_6$) δ 8.61 (t, 1H), 7.91 (d, J=4 Hz, 1H), 7.58-7.66 (m, 3H), 7.35 (d, 2H), 7.02 (s, 1H) 6.89 (d, J=15.2 Hz, 1H), 5.10-5.11 (m, 1H), 4.09-4.15 (m, 2H), 3.50-3.63 (m, 2H), 3.34-3.46 (m, 1H), 3.08-3.14 (m, 1H), 2.50-2.55 (m, 3H), 1.24-1.31 (m, 3H). LCMS: m/z 456.01 [M+H]$^+$, $t_R$=1.76 min.

Synthesis of (E)-N-((5-(5-acetylthiophen-2-yl)-7-chloro-2,3-dihydrobenzofuran-2-yl)methyl)-2-cyano-3-(pyridin-3-yl)acrylamide (195)

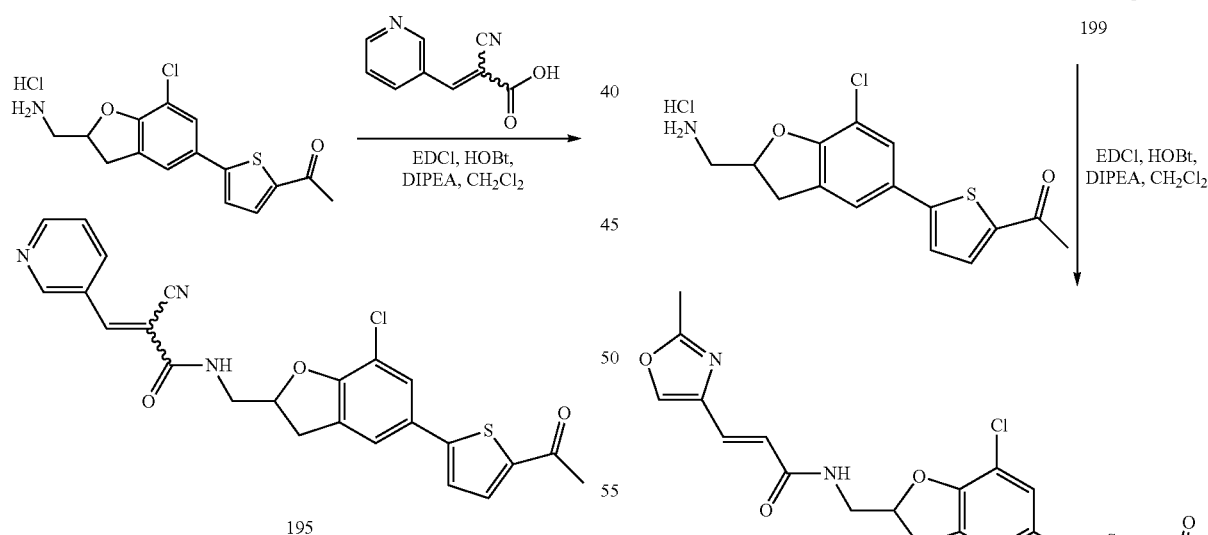

195

(E)-N-((5-(5-Acetylthiophen-2-yl)-7-chloro-2,3-dihydrobenzofuran-2-yl)methyl)-2-cyano-3-(pyridin-3-yl)acrylamide 195 was synthesized using General Procedure 3 with 4% yield. $^1$H NMR (400 MHz, DMSO-$d_6$) δ 8.97 (d, J=1.6 Hz, 1H), 8.88 (t, 1H), 8.74 (d, J=3.6 Hz, 1H), 8.38 (d, J=8.4 Hz, 1H), 8.22 (s, 1H) 7.93 (d, J=4 Hz, 1H), 7.58-7.60 (m, 3H), 7.51-7.52 (m, 1H), 5.12-5.17 (m, 1H), 3.57-3.66 (m, 2H), 3.37-3.50 (m, 1H), 3.14-3.20 (m, 1H), 2.51-2.53 (m, 3H). LCMS: m/z 463.97 [M+H]$^+$, $t_R$=2.11 min.

Synthesis of (E)-N-((5-(5-acetylthiophen-2-yl)-7-chloro-2,3-dihydrobenzofuran-2-yl)methyl)-3-(2-methyloxazol-4-yl)acrylamide (196)

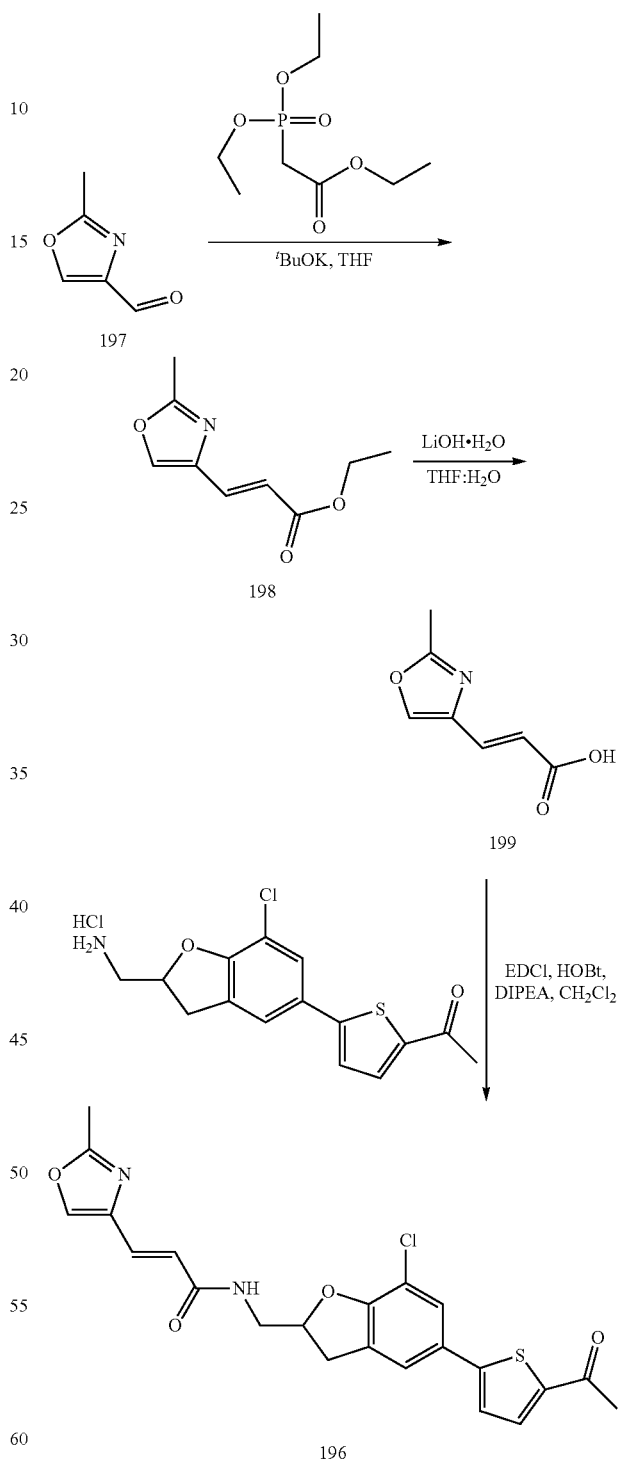

(E)-Ethyl 3-(2-methyloxazol-4-yl) acrylate 198 was synthesized from 2-methyloxazole-4-carbaldehyde 197. The experimental procedure for this step is similar to the synthesis of (E)-ethyl 3-(1-ethyl-1H-imidazol-2-yl) acrylate 193 (conversion of 192 to 193). Yield (81%). $^1$H NMR (400

MHz, DMSO) δ 8.33 (s, 1H), 7.50 (d, J=16 Hz, 1H), 6.38 (d, J=16 Hz, 1H), 4.15 (t, 2H), 2.44 (s, 3H), 1.25 (t, 3H). LCMS: m/z 181.76 [M+H]+ $t_R$=1.551 min.

(E)-3-(2-methyloxazol-4-yl) acrylic acid 199 was synthesized from (E)-ethyl 3-(2-methyloxazol-4-yl) acrylate 198. The experimental procedure for this step was similar to the synthesis of (E)-3-(2-ethyl-4-methyl-1H-imidazol-5-yl) acrylic acid 180 (conversion of 179 to 180) with the following exception. Lithium hydroxide was used instead of potassium hydroxide. Yield (32%). $^1$H NMR (400 MHz, DMSO-d6) δ 12.44 (bs, 1H), 8.29 (s, 1H), 7.42 (d, J=16 Hz, 1H), 6.33 (d, J=16 Hz, 1H), 2.44 (s, 3H). LCMS: m/z 153.74 [M+H]+, $t_R$=0.52 min.

(E)-N-((5-(5-Acetylthiophen-2-yl)-7-chloro-2,3-dihydrobenzofuran-2-yl)methyl)-3-(2-methyloxazol-4-yl)acrylamide 196 was synthesized using General Procedure 3 with 28% yield. $^1$H NMR (400 MHz, DMSO-d6) δ 8.53 (t, 1H), 8.21 (s, 1H), 7.92 (d, J=4 Hz, 1H), 7.65 (d, J=4 Hz, 1H), 7.59 (t, 2H), 7.29 (d, J=16 Hz, 1H), 6.69 (d, J=16 Hz, 1H), 5.08 (m, 1H), 3.49-3.62 (m, 2H), 3.35-3.43 (m, 1H), 3.06-3.12 (m, 1H), 2.42 (s, 3H), 2.33 (s, 3H). LCMS: m/z 442.96 [M+H]+, $t_R$=2.078 min.

Synthesis of (E)-N-((5-(5-acetylthiophen-2-yl)-7-chloro-2,3-dihydrobenzofuran-2-yl) methyl)-3-(benzo[b]thiophen-3-yl) acrylamide (200)

(E)-N-((5-(5-Acetylthiophen-2-yl)-7-chloro-2,3-dihydrobenzofuran-2-yl) methyl)-3-(benzo[b]thiophen-3-yl) acrylamide 200 was synthesized using General Procedure 3 with 33% yield. $^1$H NMR (400 MHz, DMSO-d$_6$) δ 8.53-8.56 (m, 1H), 8.17 (s, 1H), 7.92-8.13 (m, 2H), 7.91(s, 1H), 7.72-7.76 (m, 1H), 7.62-7.66 (m, 1H), 7.58-7.59 (m, 2H), 7.44-7.53 (m, 2H), 6.87-6.91 (m, 1H), 5.10-5.13 (m, 1H), 3.58-3.67 (m, 2H), 3.42-3.48 (m, 1H), 3.10-3.16 (m, 1H), 2.50-2.52 (m, 3H). LCMS: m/z 493.97 [M+H]+, $t_R$=2.58 min.

Synthesis of (E)-N-((5-(5-acetylthiophen-2-yl)-7-chloro-2,3-dihydrobenzofuran-2-yl)methyl)-3-(1-phenyl-1H-imidazol-2-yl)acrylamide (201)

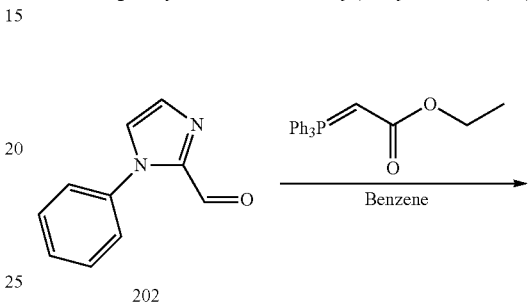

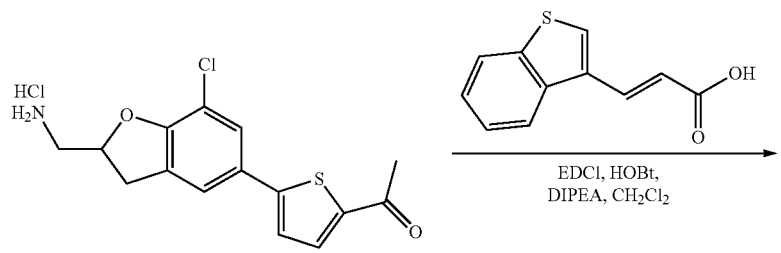

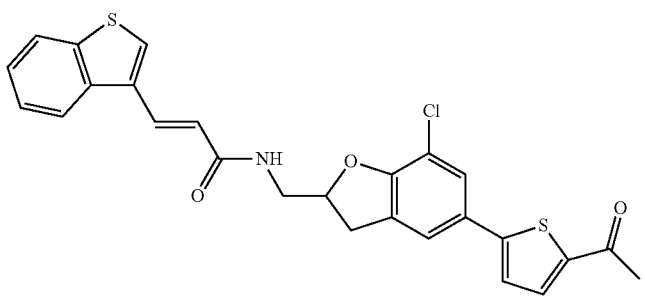

-continued

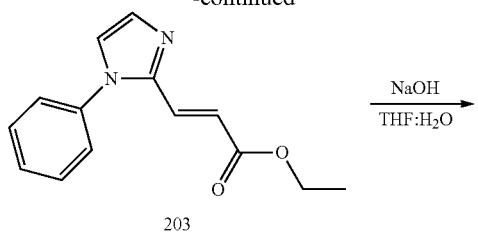

(E)-Ethyl 3-(1-phenyl-1H-imidazol-2-yl)acrylate 203 was synthesized from 1-phenyl-1H-imidazole-2-carbaldehyde 202. The experimental procedure for this step was similar to the synthesis of (E)-ethyl 3-(2-ethyl-4-methyl-1H-imidazol-5-yl) acrylate 179 (conversion of 178 to 179). Benzene was used as the solvent instead of toluene. Yield (80%). $^1$H NMR (400 MHz, CDCl$_3$) 7.48-7.56 (m, 3H), 7.36 (s, 1H), 7.29-7.33 (m, 3H), 7.20 (s, 1H), 6.30 (d, J=15.6 Hz, 1H), 4.18-4.24 (m, 2H), 1.27-1.30 (m, 3H). LCMS: m/z 243.91 [M+H]$^+$, t$_R$=1.66 min.

(E)-3-(1-phenyl-1H-imidazol-2-yl)acrylic acid 204 was synthesized from (E)-ethyl 3-(1-phenyl-1H-imidazol-2-yl) acrylate 203. The experimental procedure for this step was similar to the synthesis of (E)-3-(2-ethyl-4-methyl-1H-imidazol-5-yl)acrylic acid 180 (conversion of 179 to 180). Sodium hydroxide was used instead of potassium hydroxide. Yield (69%). $^1$H NMR (400 MHz, DMSO-d$_6$) δ 8.09 (d, J=8 Hz, 1H), 7.94 (d, J=12.8 Hz, 1H), 7.63-7.68 (m, 5H), 7.20 (dd, J$_2$=16 Hz, 1H), 7.05 (dd, J$_1$, J$_2$=16 Hz, 1H).

(E)-N-((5-(5-acetylthiophen-2-yl)-7-chloro-2,3-dihydrobenzofuran-2-yl)methyl)-3-(1-phenyl-1H-imidazol-2-yl) acrylamide 201 was synthesized using General Procedure 3 with 25% yield. $^1$H NMR (400 MHz, DMSO-d$_6$) δ 8.66 (s, 1H), 7.92 (s, 1H), 7.57-7.65 (m, 6H), 7.44-7.46 (m, 2H), 7.22 (s, 1H), 7.05 (d, J=16 Hz, 1H), 6.96 (d, J=16 Hz, 1H), 5.06 (s, 1H), 3.43-3.55 (m, 4H), 3.04-3.10 (m, 1H), 2.51 (s, 3H). LCMS: m/z 503.98 [M+H]$^+$, t$_R$=2.05 min

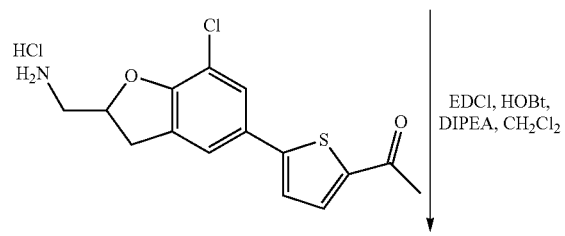

Synthesis of (E)-N-((5-(5-acetylthiophen-2-yl)-7-chloro-2,3-dihydrobenzofuran-2-yl)methyl)-3-(2-tert-butylthiazol-5-yl)acrylamide (205)

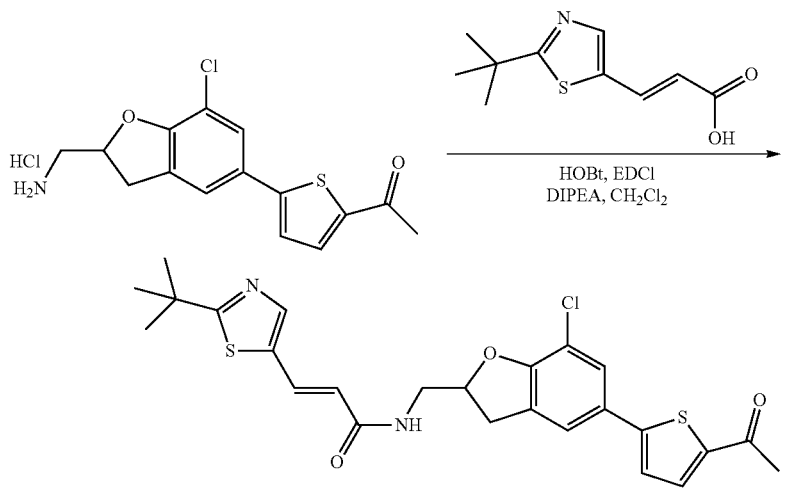

(E)-N-((5-(5-Acetylthiophen-2-yl)-7-chloro-2,3-dihydrobenzofuran-2-yl)methyl)-3-(2-tert-butylthiazol-5-yl)acrylamide 205 was synthesized using General Procedure 3 with 41% yield. $^1$H NMR (400 MHz, DMSO-d$_6$) δ 8.48 (t, 1H), 7.92 (d, J=5.6 Hz, 1H), 7.59-7.66 (m, 4H), 6.42 (d, J=15.2 Hz, 1H), 5.05-5.12 (m, 1H), 3.51-3.63 (m, 2H), 3.39-3.46 (m, 1H), 3.06-3.12 (m, 1H), 2.53 (s, 3H), 1.38 (s, 9H). LCMS: m/z 501.03 [M+H]$^+$, t$_R$=2.42 min.

Synthesis of (E)-N-((5-(5-acetylthiophen-2-yl)-7-chloro-2,3-dihydrobenzofuran-2-yl)methyl)-3-(2-(4-fluorophenyl)thiazol-4-yl)acrylamide (206)

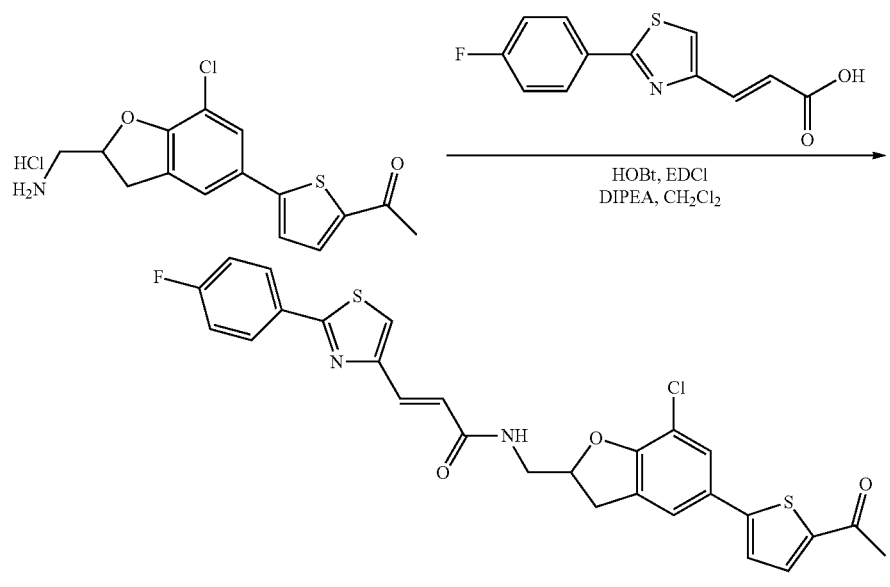

206

(E)-N-((5-(5-Acetylthiophen-2-yl)-7-chloro-2,3-dihydrobenzofuran-2-yl)methyl)-3-(2-(4-fluorophenyl)thiazol-4-yl)acrylamide was synthesized using General Procedure 3 with 41% yield. Yield (41%). $^1$H NMR (400 MHz, DMSO-d$_6$) δ 8.61 (t, 1H), 8.01-8.04 (m, 3H), 7.65 (d, J=4 Hz, 1H), 7.58-7.67 (m, 3H), 7.48 (d, J=15.6 Hz, 1H), 7.37-7.41 (m, 2H), 6.99 (d, J=15.2 Hz, 1H), 5.09-5.11 (m, 1H), 3.53-3.65 (m, 2H), 3.38-3.48 (m, 1H), 3.09-3.15 (m, 1H), 2.52 (s, 3H). LCMS: m/z 538.93 [M+H]$^+$, t$_R$=7.24 min.

Synthesis of (E)-N-((5-(4-acetylcyclopenta-1,3-dienyl)-7-chloro-2,3-dihydrobenzofuran-2-yl)methyl)-3-(thiazol-2-yl)acrylamide (207)

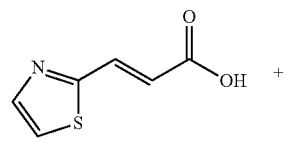

+

207

(E)-N-((5-(4-Acetylcyclopenta-1,3-dienyl)-7-chloro-2,3-dihydrobenzofuran-2-yl)methyl)-3-(thiazol-2-yl)acrylamide 207 was synthesized using General Procedure 3 with 41% yield. $^1$H NMR (400 MHz, DMSO-d$_6$) δ 8.72 (t, 1H), 7.95 (d, J=3.2 Hz, 1H), 7.92 (d, J=4 Hz, 1H), 7.86 (d, J=3.2 Hz, 1H), 7.55-7.66 (m, 4H), 6.98 (d, J=15.6 Hz, 1H), 5.08-5.11 (m, 1H), 3.55-3.67 (m, 2H), 3.44 (dd, J$_1$=7.2 Hz, J$_2$=9.2 Hz, 1H), 3.10 (dd, J$_1$=8 Hz, J$_2$=8.4 Hz, 1H), 2.51 (s, 3H). LCMS: m/z 445.02 [M+H]$^+$, t$_R$=2.08 min.

Synthesis of (E)-N-((5-(5-acetylthiophen-2-yl)-7-chloro-2,3-dihydrobenzofuran-2-yl)methyl)-3-(1-(4-fluorophenyl)-3,5-dimethyl-1H-pyrazol-4-yl)acrylamide (208)

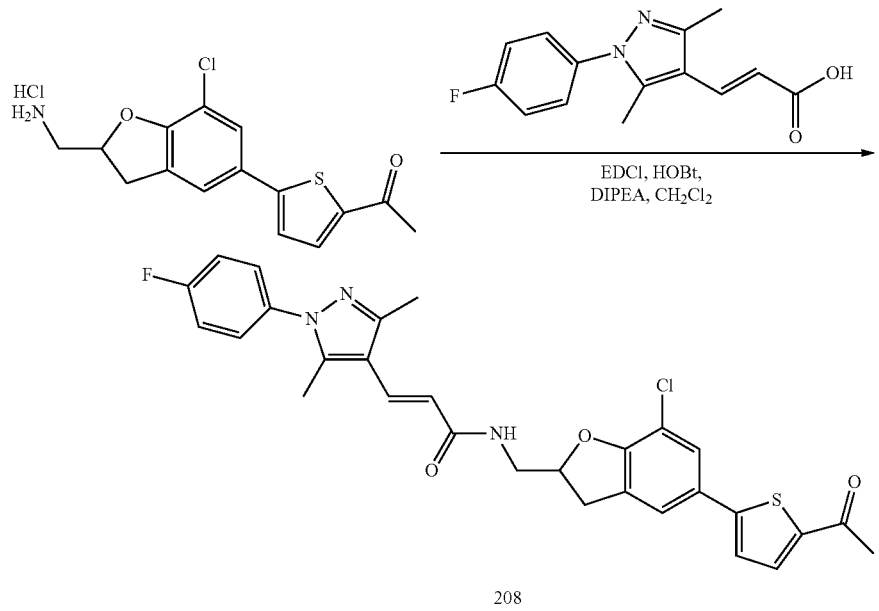

208

(E)-N-((5-(5-acetylthiophen-2-yl)-7-chloro-2,3-dihydrobenzofuran-2-yl)methyl)-3-(1-(4-fluorophenyl)-3,5-dimethyl-1H-pyrazol-4-yl)acrylamide 208 was synthesized using General Procedure 3 with 17% yield. $^1$H NMR (400 MHz, DMSO-$d_6$) δ 8.40 (s, 1H), 7.91 (d, J=3.6 Hz, 1H), 7.56-7.66 (m, 5H), 7.35-7.41 (m, 3H), 6.42 (d, J=16.4 Hz, 1H), 5.09 (m, 1H), 3.57-3.59 (m, 2H), 3.39-3.46 (m, 1H), 3.09-3.15 (m, 1H), 2.51 (s, 3H), 2.33-2.34 (m, 6H). LCMS: m/z 550.09 [M+H]$^+$, $t_R$=2.45 min.

Synthesis of (E)-N-((5-(5-acetylthiophen-2-yl)-7-chloro-2,3-dihydrobenzofuran-2-yl)methyl)-3-(1-(4-chlorophenyl)-2,5-dimethyl-1H-pyrrol-3-yl)acrylamide (209)

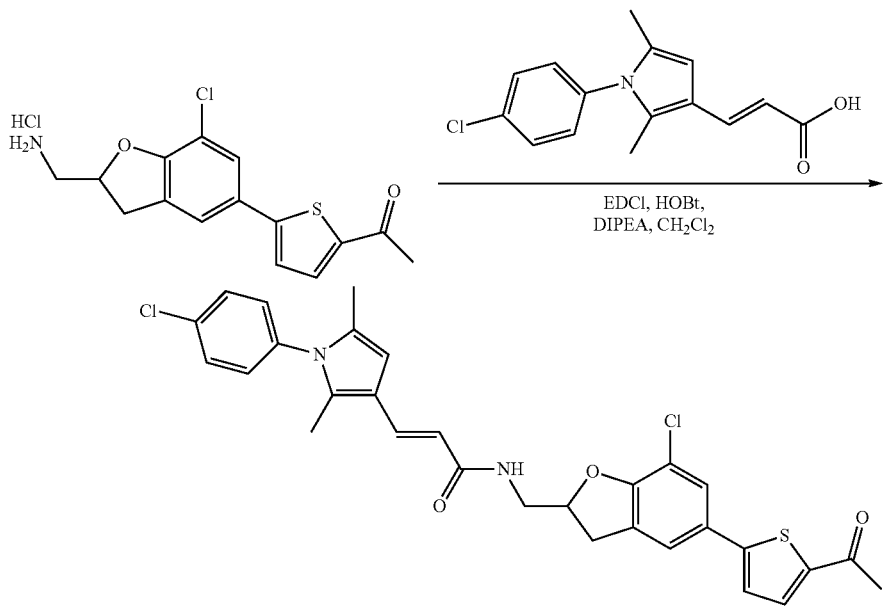

209

(E)-N-((5-(5-acetylthiophen-2-yl)-7-chloro-2,3-dihydrobenzofuran-2-yl)methyl)-3-(1-(4-chlorophenyl)-2,5-dimethyl-1H-pyrrol-3-yl)acrylamide 209 was synthesized using General Procedure 3 with 31% yield. $^1$H NMR (400 MHz, DMSO-$d_6$) δ 8.18 (t, 1H), 7.92 (d, J=4.4 Hz, 1H), 7.65 (d, 1H), 7.58-7.61 (m, 4H), 7.36-7.38 (m, 3H), 6.13-6.20 (m, 2H), 5.80 (m, 1H), 3.48-3.60 (m, 2H), 3.38-3.44 (m, 1H), 3.08-3.14 (m, 1H), 2.05-2.53 (m, 3H), 2.04 (s, 3H), 1.96 (s, 3H). LCMS: m/z 565.24 [M+H]$^+$, $t_R$=2.85 min.

Synthesis of (E)-N-((5-(5-acetylthiophen-2-yl)-7-chloro-2,3-dihydrobenzofuran-2-yl)methyl)-3-(5-(N,N-dimethylsulfamoyl)pyridin-3-yl)acrylamide (210)

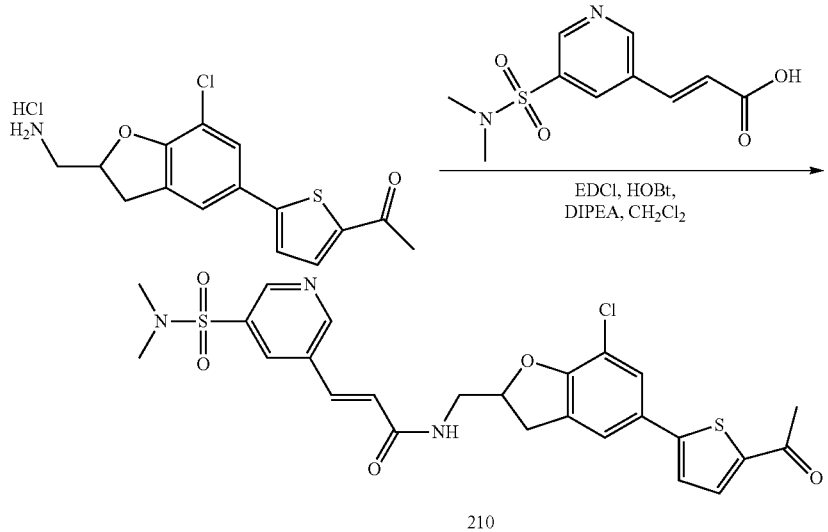

210

(E)-N-((5-(5-Acetylthiophen-2-yl)-7-chloro-2,3-dihydrobenzofuran-2-yl)methyl)-3-(5-(N,N-dimethylsulfamoyl)pyridin-3-yl)acrylamide 210 was synthesized using General Procedure 3 with 48% yield. $^1$H NMR (400 MHz, DMSO-$d_6$) δ 9.08 (d, 1H), 8.87 (d, J=2 Hz, 1H), 8.53-8.56 (m, 1H), 8.30 (s, 1H), 7.91 (d, J=4 Hz, 1H), 7.58-7.66 (m, 4H), 7.02 (d, J=16 Hz, 1H), 5.07-5.14 (m, 1H), 3.57-3.67 (m, 2H), 3.37-3.47 (m, 1H), 3.08-3.14 (m, 1H), 2.69 (s, 6H), 2.52 (s, 3H). LCMS: m/z 545.99 [M+H]$^+$, $t_R$=2.27 min.

Synthesis of (E)-N-((5-(5-acetylthiophen-2-yl)-7-chloro-2,3-dihydrobenzofuran-2-yl)methyl)-3-(5-chloro-3-methyl-1-phenyl-1H-pyrazol-4-yl)acrylamide (211)

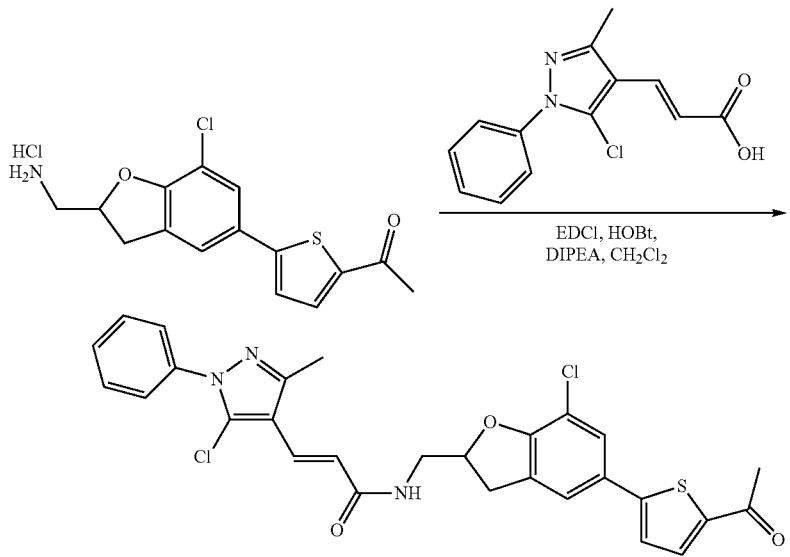

211

(E)-N-((5-(5-Acetylthiophen-2-yl)-7-chloro-2,3-dihydrobenzofuran-2-yl)methyl)-3-(5-chloro-3-methyl-1-phenyl-1H-pyrazol-4-yl)acrylamide 211 was synthesized using General Procedure 3 with 32% yield. $^1$H NMR (400 MHz, DMSO-d$_6$) δ 8.54-8.56 (m, 1H), 7.91 (d, J=4 Hz, 1H), 7.66 (s, 1H), 7.53-7.61 (m, 6H), 7.50-7.52 (m, 1H), 7.33 (d, J=16 Hz, 1H), 6.68 (d, J=16 Hz, 1H), 5.10 (m, 1H), 3.57-3.61 (m, 2H), 3.34-3.39 (m, 1H), 3.08-3.14 (m, 1H), 2.51 (s, 3H), 2.39 (s, 3H). LCMS: m/z 552.0 [M+H]$^+$, t$_R$=2.58 min.

Synthesis of (E)-N-((5-(5-acetylthiophen-2-yl)-7-chloro-2,3-dihydrobenzofuran-2-yl)methyl)-3-(4-methyl-1H-imidazol-5-yl)acrylamide (212)

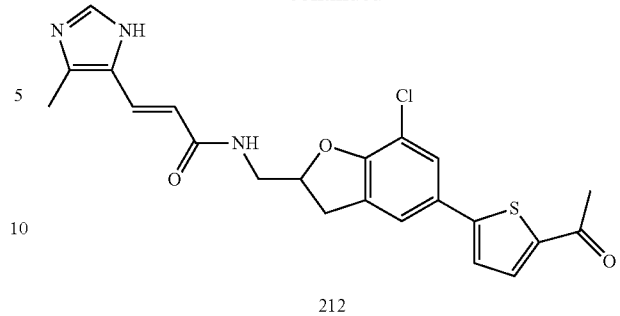

212

(E)-N-((5-(5-acetylthiophen-2-yl)-7-chloro-2,3-dihydrobenzofuran-2-yl)methyl)-3-(4-methyl-1H-imidazol-5-yl)acrylamide 212 was synthesized using General Procedure 3 with 48% yield. $^1$H NMR (400 MHz, DMSO-d$_6$) δ 12.2 (s, 1H), 8.32-8.35 (m, 1H), 7.91 (d, J=4 Hz, 1H), 7.58-7.72 (m, 4H), 7.32 (d, J=15.2 Hz, 1H), 6.46 (d, J=15.2 Hz, 1H), 5.04-5.09 (m, 1H), 3.60-3.62 (m, 1H), 3.51-3.58 (m, 2H), 3.08-3.14 (m, 1H), 2.50 (s, 3H), 2.25 (s, 3H). LCMS: m/z 442.16 [M+H]$^+$, t$_R$=1.86 min.

Synthesis of (E)-N-((5-(5-acetylthiophen-2-yl)-7-chloro-2,3-dihydrobenzofuran-2-yl)methyl)-3-(1-methyl-1H-pyrrol-3-yl)acrylamide (213)

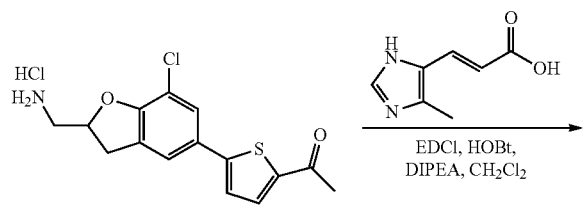

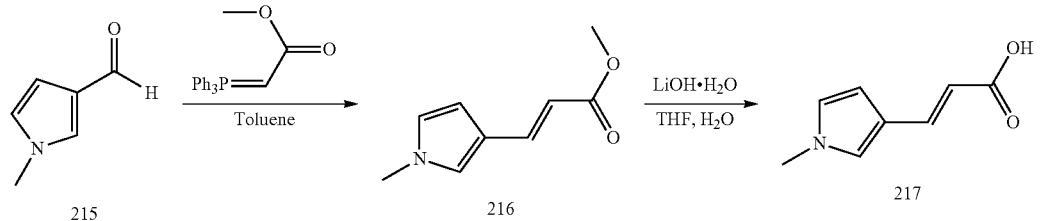

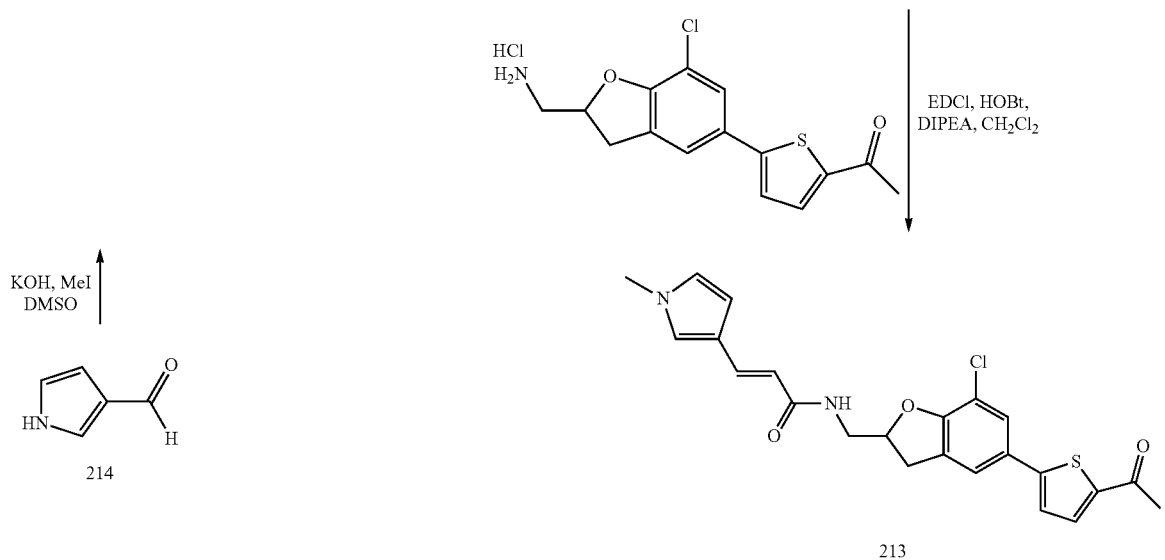

To a solution of pyrrole 3-carbaldehyde 214 (0.5 g, 5.2 mmol) in DMSO (2.5 mL) was added KOH (0.29 g, 5.2 mmol) and stirred for 30 min. Methyl iodide (0.39 mL, 6.2 mmol) was added at 0° C. and the reaction mixture was stirred at room temperature for 18 h. Reaction mixture was transferred into iced water (25 mL) and extracted with ethyl acetate (3×10 mL). Organic layer was dried over anhydrous Na$_2$SO$_4$ and concentrated under reduced pressure to give 1-methyl-1H-pyrrole-3-carbaldehyde 215. Yield (0.43 g, 75%). $^1$H NMR (400 MHz, DMSO-d$_6$) δ 9.62 (s, 1H), 7.59 (s, 1H), 6.88 (d, J=4.4 Hz, 1H), 6.44 (d, J=4.4 Hz, 1H), 3.69 (s, 3H). LCMS: m/z 109.6 [M+H]$^+$, t$_R$=1.31 min.

acrylamide 213 was synthesized using General Procedure 3 with 24% yield. $^1$H NMR (400 MHz, DMSO-d$_6$) δ 8.16 (t, J=5.6 Hz, 1H), 7.91 (d, J=4 Hz, 1H), 7.58-7.65 (m, 3H), 7.29 (d, J=15.2 Hz, 1H), 7.04 (s, 1H), 6.73 (d, J=4.4 Hz, 1H), 6.22 (d, J=2 Hz, 1H), 6.18 (d, J=15.6 Hz, 1H), 5.06 (m, 1H), 3.6 (s, 3H), 3.41-3.56 (m, 3H), 3.06-3.12 (m, 1H), 2.56 (s, 3H). LCMS: m/z 441.01 [M+H]$^+$, t$_R$=2.30 min.

Synthesis of 1-(5-(2-(aminomethyl)-7-chloro-2,3-dihydrobenzofuran-4-yl)thiophen-2-yl)ethanone hydrochloride (218)

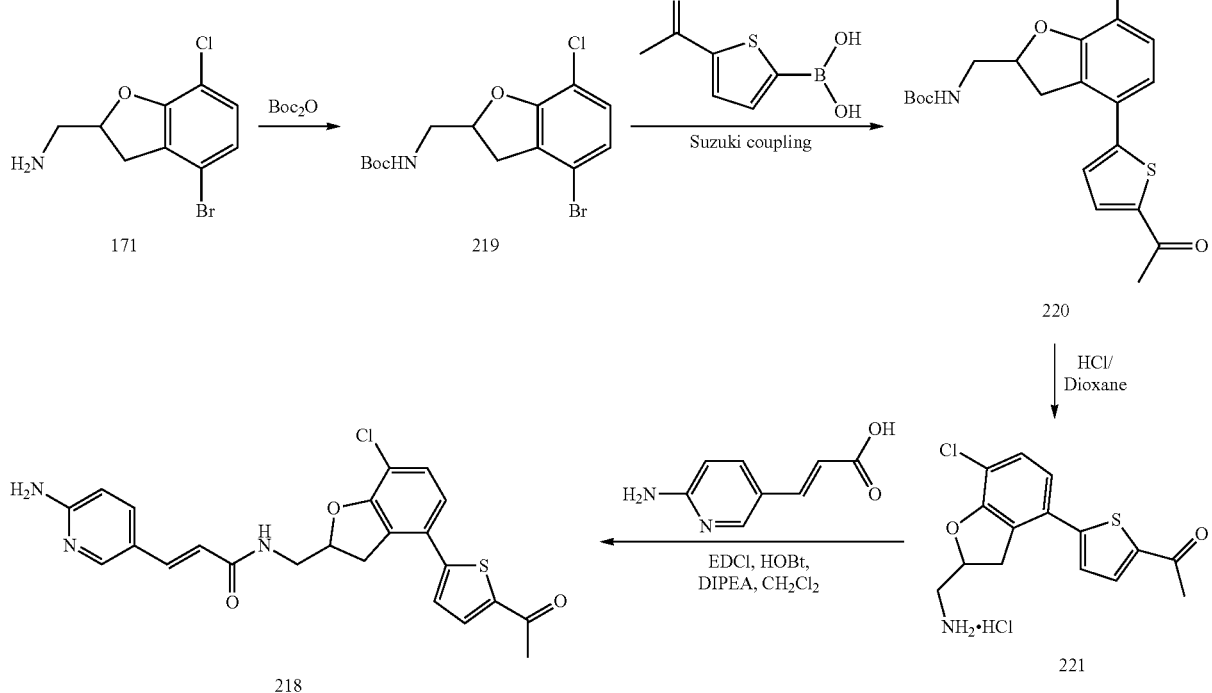

(E)-Methyl 3-(1-methyl-1H-pyrrol-3-yl)acrylate 216 was synthesized from 1-methyl-1H-pyrrole-3-carbaldehyde 215. The experimental procedure for this step was similar to the synthesis of (E)-ethyl 3-(2-ethyl-4-methyl-1H-imidazol-5-yl) acrylate 179 (conversion of 178 to 179). Methyl 2-(triphenylphosphoranylidene)acetate was used instead of ethyl 2-(triphenylphosphoranylidene)acetate. Yield (47%). $^1$H NMR (400 MHz, DMSO-d$_6$) δ 7.51 (d, J=15.6 Hz, 1H), 7.19 (s, 1H), 6.77 (d, J=4.4 Hz, 1H), 6.42 (d, J=4.4 Hz, 1H), 6.06 (d, J=15.6 Hz, 1H), 3.65 (s, 3H), 3.61 (s, 3H). LCMS: m/z 165.8 [M+H]$^+$, t$_R$=2.08 min.

(E)-3-(1-Methyl-1H-pyrrol-3-yl)acrylic acid 217 was synthesized from (E)-methyl 3-(1-methyl-1H-pyrrol-3-yl) acrylate 216. The experimental procedure for this step was similar to the synthesis of (E)-3-(2-ethyl-4-methyl-1H-imidazol-5-yl)acrylic acid 180 (conversion of 179 to 180). Lithium hydroxide was used instead of potassium hydroxide. Yield (88%). $^1$H NMR (400 MHz, DMSO-d$_6$) δ 11.81 (s, 1H), 7.41 (d, J=16 Hz, 1H), 7.14 (s, 1H), 6.75 (d, J=4.4 Hz, 1H), 6.38 (d, J=4.4 Hz, 1H), 5.96 (d, J=15.6 Hz, 1H), 3.65 (s, 3H). LCMS: m/z 151.7 [M+H]$^+$, t$_R$=1.78 min.

(E)-N-((5-(5-acetylthiophen-2-yl)-7-chloro-2,3-dihydrobenzofuran-2-yl)methyl)-3-(1-methyl-1H-pyrrol-3-yl)

tert-Butyl ((4-bromo-7-chloro-2,3-dihydrobenzofuran-2-yl)methyl)carbamate was 219 was synthesized from (4-bromo-7-chloro-2,3-dihydrobenzofuran-2-yl)methanamine 171. The experimental procedure for this step was similar to the synthesis of tent-butyl ((7-chloro-2,3-dihydrobenzofuran-2-yl)methyl)carbamate 8 (conversion of 7 to 8; Method A). Yield (23%). $^1$H NMR (400 MHz, CDCl$_3$) δ 7.03 (d, J=8.4Hz, 1H), 6.95 (d, J=8.8Hz, 1H), 5.0-5.05 (m, 2H), 3.61-3.65 (m, 1H), 3.31-3.45 (m, 2H), 3.0-3.06 (m, 1H), 1.47 (s, 9H). LCMS: m/z 307.7 [M−56]$^+$, t$_R$=2.69 min.

tert-Butyl ((4-(5-acetylthiophen-2-yl)-7-chloro-2,3-dihydrobenzofuran-2-yl)methyl)carbamate 220 was synthesized using General Procedure 1. Yield (22%). LCMS: m/z 352.1 [M−56]$^+$, t$_R$=2.62 min.

1-(5-(2-(Aminomethyl)-7-chloro-2,3-dihydrobenzofuran-4-yl)thiophen-2-yl)ethanone hydrochloride 221 was synthesized from ((4-(5-acetylthiophen-2-yl)-7-chloro-2,3-dihydrobenzofuran-2-yl)methyl)carbamate 220 using General Procedure 2. HCl in dioxane was used instead of TFA. Yield (21%). LCMS: m/z 308 [M+H]$^+$, t$_R$=1.83 min.

1-(5-(2-(aminomethyl)-7-chloro-2,3-dihydrobenzofuran-4-yl)thiophen-2-yl)ethanone hydrochloride 218 was synthesized using General Procedure 3 with 37% yield. $^1$H NMR (400 MHz, DMSO-$d_6$) δ 8.28 (t, 1H), 8.06 (d, J=2Hz, 1H), 7.99 (d, J=4Hz, 1H), 7.57-7.62 (m, 2H), 7.26-7.33 (m, 3H), 6.39-6.48 (m, 4H), 5.09-5.11 (m, 1H), 3.59-3.67 (m, 2H), 3.48-3.54 (m, 1H), 3.27-3.31 (m, 1H), 2.56 (s, 3H). LCMS: m/z 454.31 [M+H]$^+$, $t_R$=2.05 min.

Synthesis of (E)-N-((5-(5-acetylthiophen-2-yl)-7-chloro-2,3-dihydrobenzofuran-2-yl)methyl)-4-(pyridin-3-yl)but-2-enamide (222)

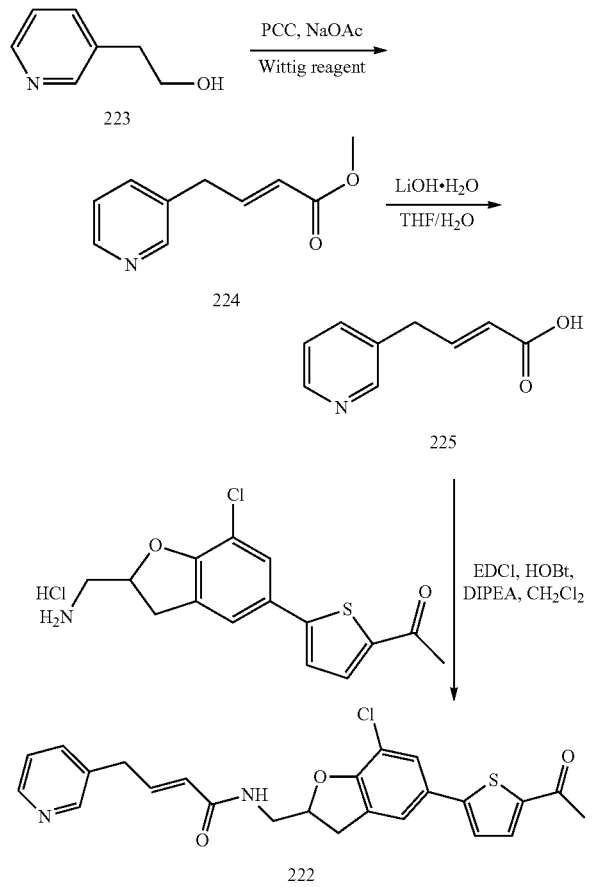

Pyridinium chlorochromate (1.75 g, 8.1 mmol) and sodium acetate (0.66 g, 8.1 mmol) were dissolved in dichloromethane (20 mL). 2-(Pyridin-3-yl)ethanol (0.5 g, 4.0 mmol) and (carbethoxy methylene)-triphenyl phosphorane (2.12 g, 6.09 mmol) were added at 0° C. and the reaction mixture was warmed to room temperature and stirred for 10 h. The reaction mixture was transferred into iced water and extracted with ethyl acetate (15 mL×3). The combined organic layers were washed with brine, dried over anhydrous Na$_2$SO$_4$ and concentrated under reduced pressure. The crude product was purified by silica gel chromatography (0-2% methanol/dichloromethane) to give of (E)-methyl 4-(pyridin-3-yl)but-2-enoate 224. Yield (0.1 g, 13%). LCMS: m/z 192.07 [M+H]$^+$, $t_R$=1.60 min.

(E)-4-(Pyridin-3-yl)but-2-enoic acid 225 was synthesized from (E)-methyl 4-(pyridin-3-yl)but-2-enoate 224 similar to the synthesis of (E)-3-(2-ethyl-4-methyl-1H-imidazol-5-yl) acrylic acid 180 (conversion of 179 to 180). Lithium hydroxide was used instead of potassium hydroxide. Yield (47%).

$^1$H NMR (400 MHz, DMSO-$d_6$) δ 12.47 (s, 1H), 8.59 (s, 1H), 8.43 (d, J=4 Hz, 1H), 7.88-7.90 (m, 1H), 7.34-7.37 (m, 1H), 6.42-6.51 (m, 2H), 3.22-3.23 (m, 2H). LCMS: m/z 164.02 [M+H]$^+$, $t_R$=3.56 min.

(E)-N-((5-(5-Acetylthiophen-2-yl)-7-chloro-2,3-dihydrobenzofuran-2-yl)methyl)-4-(pyridin-3-yl)but-2-enamide 222 was synthesized using General Procedure 3 with 22% yield. $^1$H NMR (400 MHz, DMSO-$d_6$) δ 8.55 (d, 1H), 8.40-8.41 (m, 1H), 8.30-8.33 (m, 1H), 7.91 (d, J=4 Hz, 1H), 7.81-7.83 (m, 1H), 7.56-7.58 (m, 3H), 7.31-7.33 (m, 1H), 6.44-6.47 (m, 2H), 5.03-5.06 (m, 1H), 3.41-3.51 (m, 4H), 3.10-3.13 (m, 2H), 2.51 (s, 3H). LCMS: m/z 453.16 [M+H]$^+$, $t_R$=2.08 min.

Synthesis of (E)-3-(6-aminopyridin-3-yl)-N-((7-chloro-5-(4-(3,3-difluoroazetidine-1-carbonyl)phenyl)-2,3-dihydrobenzofuran-2-yl)methyl)acrylamide (226)

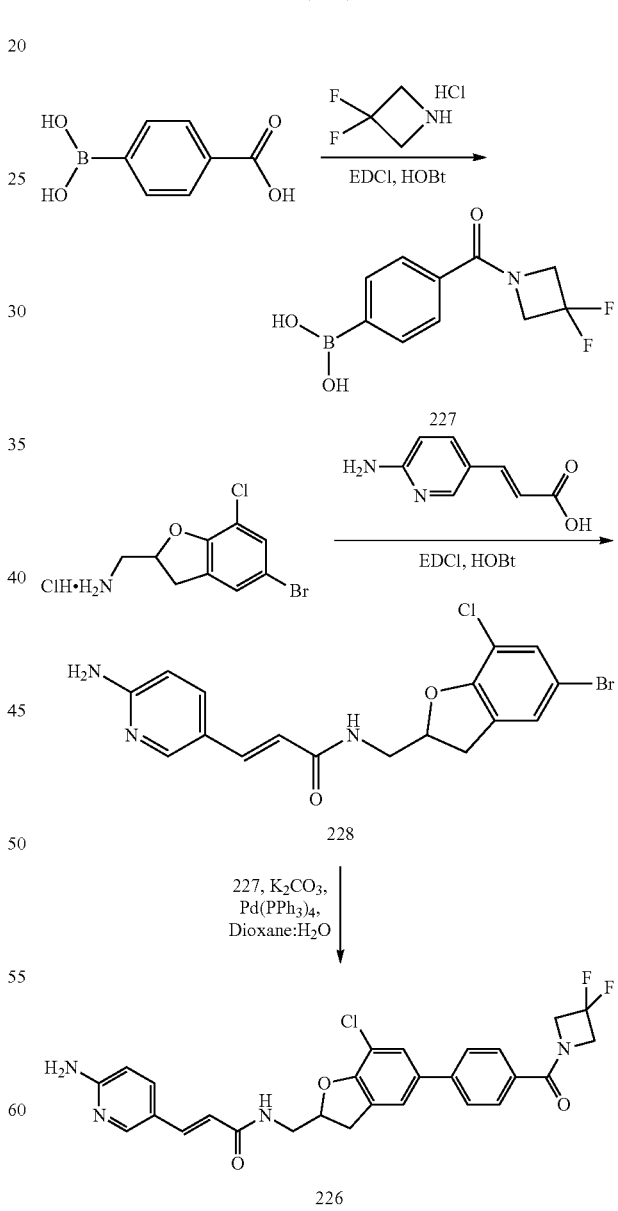

(4-(3,3-Difluoroazetidine-1-carbonyl)phenyl)boronic acid 227 was synthesized using General Procedure 3 with 72% yield. ¹H NMR (400 MHz, DMSO-d₆) δ 8.26 (bs, 1H), 7.95 (br, 1H), 7.83-7.88 (m, 2H), 7.64-7.74 (m, 2H), 4.77 (bs, 2H), 4.49 (bs, 2H). LCMS: m/z 242 [M+H]⁺, $t_R$=1.76 min.

(E)-3-(6-aminopyridin-3-yl)-N-((5-bromo-7-chloro-2,3-dihydrobenzofuran-2-yl)methyl)acrylamide 228 was synthesized using General Procedure 3 with 50% yield. ¹H NMR (400 MHz, DMSO-d₆) δ 8.23 (t, 1H), 8.06 (d, J=2Hz, 1H), 7.57-7.60 (m, 1H), 7.36-7.43 (m, 2H), 7.30 (d, J=15.6Hz, 1H), 6.38-6.47 (m, 4H), 5.01-5.04 (m, 1H), 3.45-3.56 (m, 2H), 3.28-3.39 (m, 1H), 3.01-3.12 (m, 1H). LCMS: m/z 409.9 [M+H]⁺, $t_R$=1.98 min.

(E)-3-(6-Aminopyridin-3-yl)-N-((7-chloro-5-(4-(3,3-difluoroazetidine-1-carbonyl)phenyl)-2,3-dihydrobenzofuran-2-yl)methyl)acrylamide 226 was synthesized using General Procedure 1. Yield (39%). ¹H NMR (400 MHz, DMSO-d₆) δ 8.28 (t, 1H), 8.07 (d, J=2 Hz, 1H), 7.71-7.76 (m, 4H), 7.57-7.60 (m, 3H), 7.30 (d, J=16 Hz, 1H), 6.41-6.47 (m, 4H), 5.06-5.09 (m, 1H), 4.78-4.82 (m, 2H), 4.49-4.52 (m, 2H), 3.51-3.60 (m, 2H), 3.38-3.45 (m, 1H), 3.08-3.14 (m, 1H). LCMS: m/z 525.19 [M+H]⁺, $t_R$=1.91 min.

Synthesis of (E)-N-((5-(5-acetylthiophen-2-yl)-7-chloro-2,3-dihydrobenzofuran-2-yl)methyl)-3-(1H-1,2,4-triazol-1-yl)acrylamide (229)

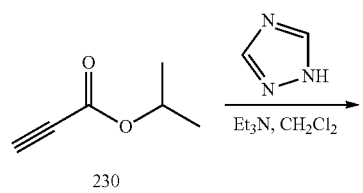

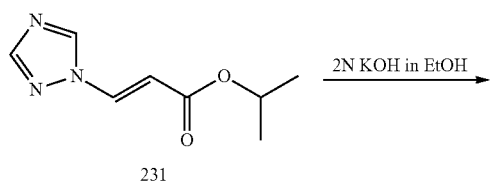

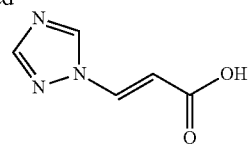

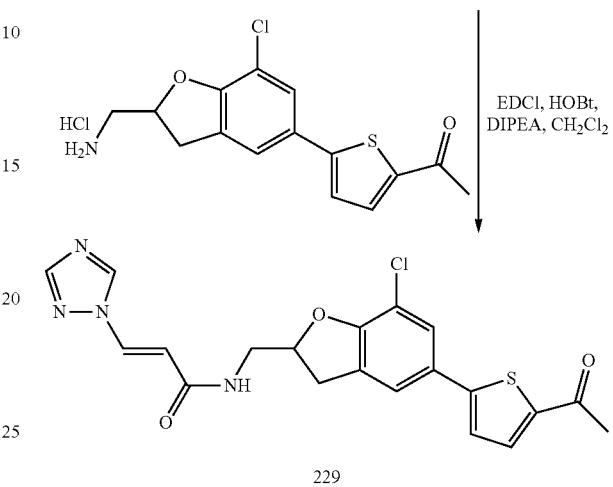

1H-1,2,4-triazole (1 g, 14.5 mmol) was dissolved in dichloromethane (20 mL) and isopropyl propiolate 230 (2.43 g, 21.7 mmol) and Et₃N (3.9 mL, 29.0 mmol) were added at 25° C. The reaction mixture was stirred for 4 h. The reaction mixture was concentrated under reduced pressure and the crude product was purified by silica gel chromatography (5-10% ethyl acetate:hexane gradient) to give (E)-isopropyl 3-(1H-1,2,4-triazol-1-yl)acrylate 231. Yield (0.8 g, 30%). ¹H NMR (400 MHz, CDCl₃) δ 8.36 (s, 1H), 8.09 (s, 1H), 8.01 (d, J=14.8 Hz, 1H), 6.59 (d, J=14 Hz, 1H), 5.13-5.20 (m, 1H), 1.33 (d, 6H). LCMS: m/z 182.11 [M+1]⁺, $t_R$=1.88 min.

(E)-isopropyl 3-(1H-1,2,4-triazol-1-yl)acrylate 231 (0.5 g, 2.74 mmol) was dissolved in ethanol (10 mL) and 2N KOH in ethanol (10 mL) was added at 25° C. The reaction mixture was stirred for 4 h. The reaction mixture was acidified by HCl in dioxane, and the reaction mixture was concentrated under reduced pressure to give (E)-3-(1H-1,2,4-triazol-1-yl)acrylic acid 232 Yield (150 mg, 39%). ¹H NMR (400 MHz, DMSO-d₆) δ 12.65 (bs, 1H), 9.00 (s, 1H), 8.26 (s, 1H), 8.23 (d, J=14 Hz, 1H), 6.39 (d, J=13.6 Hz, 1H). LCMS m/z 140.01 [M]⁺, $t_R$=1.42 min.

(E)-N-((5-(5-acetylthiophen-2-yl)-7-chloro-2,3-dihydrobenzofuran-2-yl)methyl)-3-(1H-1,2,4-triazol-1-yl)acrylamide 229 was synthesized using General Procedure 3 with 37% yield. ¹H NMR (400 MHz, DMSO-d₆) δ 8.94 (s, 1H), 8.67 (t, 1H), 8.23 (s, 1H), 8.15 (d, J=14.4 Hz, 1H), 7.92 (d, J=4 Hz, 1H), 7.66 (s, 1H), 7.61 (s, 1H), 7.58 (d, J=4 Hz, 1H), 6.76 (d, J=14 Hz, 1H), 5.09 (m, 1H), 3.56-3.63 (m, 2H), 3.39-3.48 (m, 1H), 3.05-3.11 (m, 1H), 2.52 (s, 3H). LCMS: m/z 429.15 [M+H]⁺, $t_R$=2.13 min.

Synthesis of (E)-4-(2-((3-(6-aminopyridin-3-yl)acrylamido)methyl)-7-chloro-2,3-dihydro benzofuran-5-yl)-N,N-dimethylbenzamide (233)

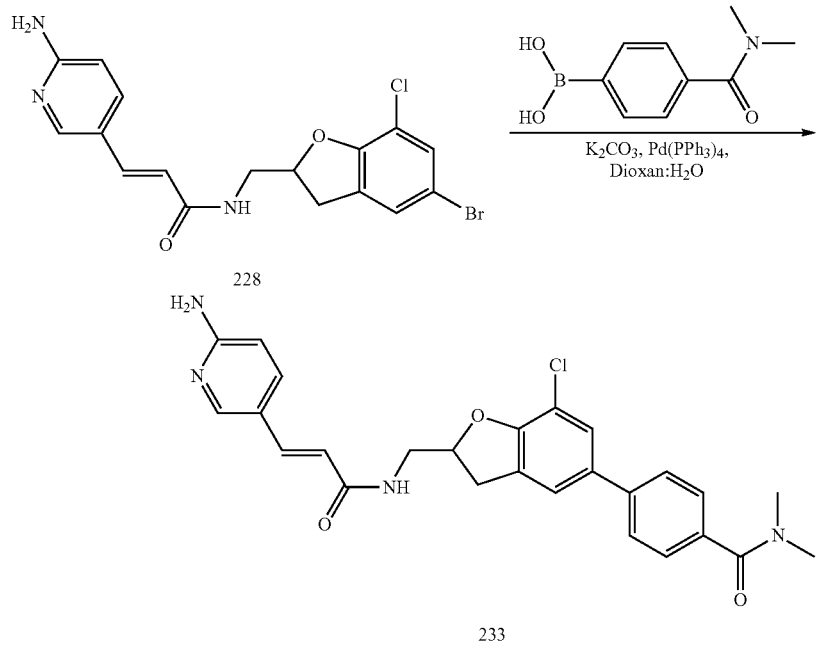

(E)-4-(2-((3-(6-aminopyridin-3-yl)acrylamido)methyl)-7-chloro-2,3-dihydrobenzofuran-5-yl)-N,N-dimethylbenzamide 233 was synthesized using General Procedure 1. Yield (12%). $^1$H NMR (400 MHz, DMSO-d$_6$) δ 8.28 (t, 1H), 8.07 (d, J=2 Hz, 1H), 7.67 (d, J=8.4 Hz, 2H), 7.54-7.61 (m, 3H), 7.45 (d, J=8 Hz, 2H), 7.31 (d, J=15.6 Hz, 1H), 6.41-6.47 (m, 4H), 5.06 (m, 1H), 3.51-3.59 (m, 2H), 3.38-3.45 (m, 1H), 3.08-3.14 (m, 1H), 2.97 (d, J=13.6 Hz, 6H). LCMS: m/z 477.26 [M+H]$^+$, t$_R$=1.87 min.

Synthesis of (E)-3-(6-aminopyridin-3-yl)-N-((7-chloro-5-(4-(piperidine-1-carbonyl) phenyl)-2,3-dihydrobenzofuran-2-yl)methyl)acrylamide (234)

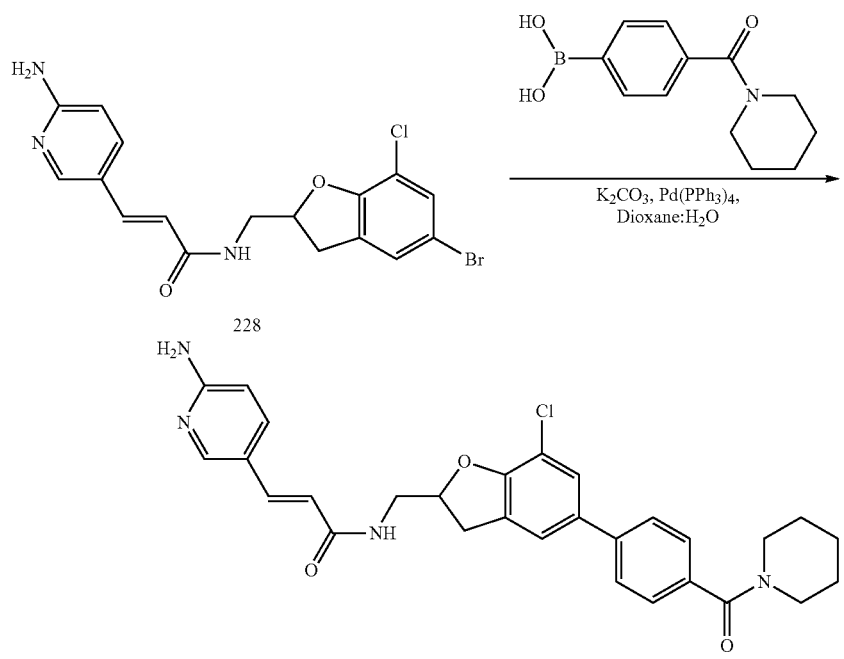

(E)-3-(6-aminopyridin-3-yl)-N-((7-chloro-5-(4-(piperidine-1-carbonyl) phenyl)-2,3-dihydrobenzofuran-2-yl)methyl)acrylamide 234 was synthesized using General Procedure 1. Yield (23%). $^1$H NMR (400 MHz, DMSO-d$_6$) δ 8.27 (t, 1H), 8.07 (d, J=2 Hz, 1H), 7.67 (d, J=8.4 Hz, 2H), 7.53-7.61 (m, 3H), 7.41 (d, J=8.4 Hz, 2H), 7.31 (d, J=15.6 Hz, 1H), 6.41-6.48 (m, 4H), 5.04-5.08 (m, 1H), 3.49-3.61 (m, 4H), 3.38-3.45 (m, 2H), 3.08-3.14 (m, 1H), 1.52-1.63 (m, 7H). LCMS: m/z 517.32 [M+H]$^+$, $t_R$=2.09 min.

Synthesis of (E)-N-((7-chloro-5-(3,5-dimethylisoxazol-4-yl)-2,3-dihydrobenzofuran-2-yl)methyl)-3-(pyridazin-3-yl)acrylamide (235)

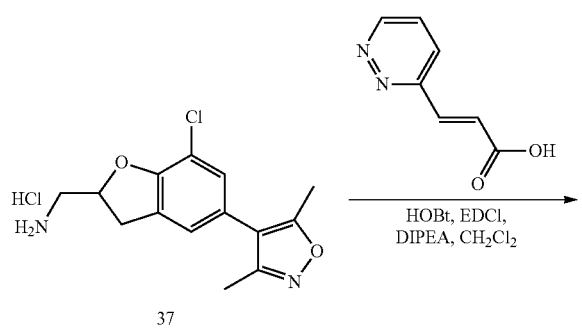

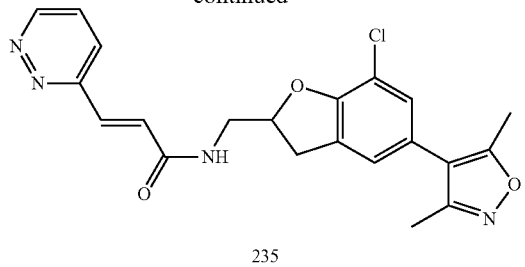

(E)-N-((7-Chloro-5-(3,5-dimethylisoxazol-4-yl)-2,3-dihydrobenzofuran-2-yl)methyl)-3-(pyridazin-3-yl)acrylamide 235 was synthesized using General Procedure 3 with 43% yield. $^1$H NMR (400 MHz, DMSO-d$_6$) δ 9.19 (d, J=6.4 Hz, 1H), 8.77 (t, 1H), 7.91-7.94 (m, 1H), 7.74-7.77 (m, 1H), 7.62 (d, J=16 Hz, 1H), 7.29 (d, J=16 Hz, 1H) 7.20 (s, 2H), 5.08 (s, 1H), 3.59-3.64 (m, 2H), 3.40-3.46 (m, 1H), 3.09-3.15 (m, 1H), 2.35 (s, 3H), 2.19 (s, 3H). LCMS: m/z 411.19 [M+H]$^+$, $t_R$=2.11 min.

Synthesis of (E)-N-((7-chloro-5-(4-(morpholine-4-carbonyl)phenyl)-2,3-dihydrobenzofuran-2-yl)methyl)-3-(pyridazin-3-yl)acrylamide (236)

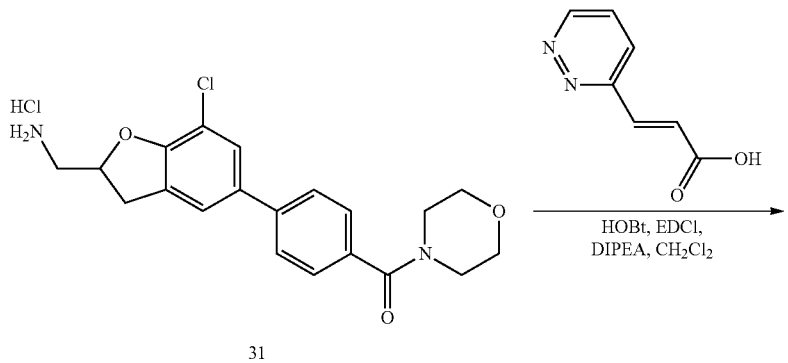

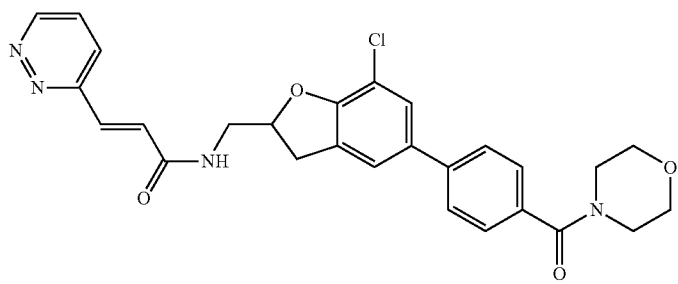

(E)-N-((7-chloro-5-(4-(morpholine-4-carbonyl)phenyl)-2,3-dihydrobenzofuran-2-yl)methyl)-3-(pyridazin-3-yl)acrylamide 236 was synthesized using General Procedure 3 with 31% yield. $^1$H NMR (400 MHz, DMSO-$d_6$) δ 9.19 (t, 1H), 8.76-8.79 (m, 1H), 7.91-7.96 (m, 1H), 7.38-7.77 (m, 1H), 7.70 (s, 1H), 7.68 (s, 1H), 7.63 (d, J=16 Hz, 1H), 7.55 (s, 1H), 7.54 (s, 1H), 7.47 (s, 1H), 7.45 (s, 1H), 7.29 (d, J=16 Hz, 1H), 5.11 (m, 1H), 3.57-4.02 (m, 8H), 3.34-3.51 (m, 3H), 3.11-3.17 (m, 1H). LCMS: m/z 505.17 [M+H]$^+$, $t_R$=2.03 min.

Synthesis of (E)-3-(6-aminopyridin-3-yl)-N-((7-chloro-5-(4-(4-methylpiperazine-1-carbonyl)phenyl)-2,3-dihydrobenzofuran-2-yl)methyl)acrylamide (237)

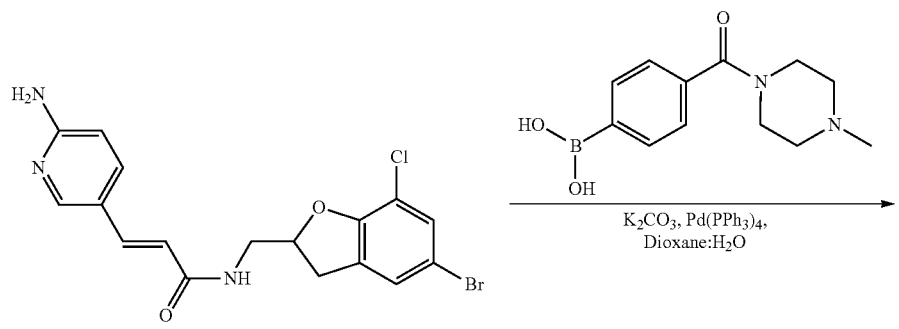

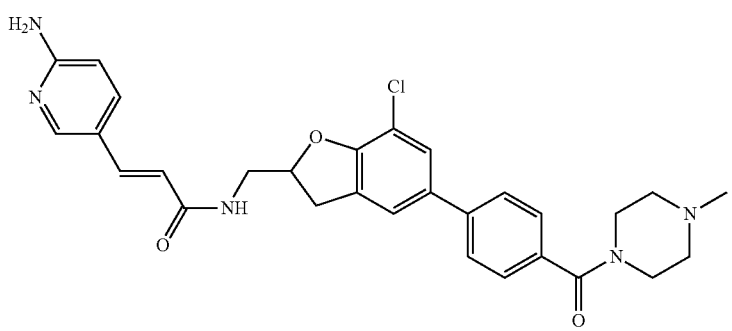

(E)-3-(6-aminopyridin-3-yl)-N-((7-chloro-5-(4-(4-methylpiperazine-1-carbonyl)phenyl)-2,3-dihydrobenzofuran-2-yl)methyl)acrylamide 237 was synthesized using General Procedure 1. Yield (34%). $^1$H NMR (400 MHz, DMSO-$d_6$) δ 8.35 (t, 1H), 8.06 (d, J=2 Hz, 1H), 7.68 (d, J=8.4 Hz, 2H), 7.58-7.60 (m, 1H), 7.53 (d, J=3.6 Hz, 2H), 7.42 (d, J=8.4 Hz, 2H), 7.30 (d, J=15.6 Hz, 1H), 6.42-6.48 (m, 4H), 5.05-5.06 (m, 1H), 3.48-3.65 (m, 4H), 3.36-3.44 (m, 3H), 3.06-3.15 (m, 1H), 2.29-2.33 (m, 4H), 2.18 (s, 3H). LCMS: m/z 532.3 [M+H]$^+$, $t_R$=1.82 min.

Synthesis of (E)-3-(6-aminopyridin-3-yl)-N-((7-chloro-5-(3-methyl-4-(morpholine-4-carbonyl)phenyl)-2,3-dihydrobenzofuran-2-yl)methyl)acrylamide (238)

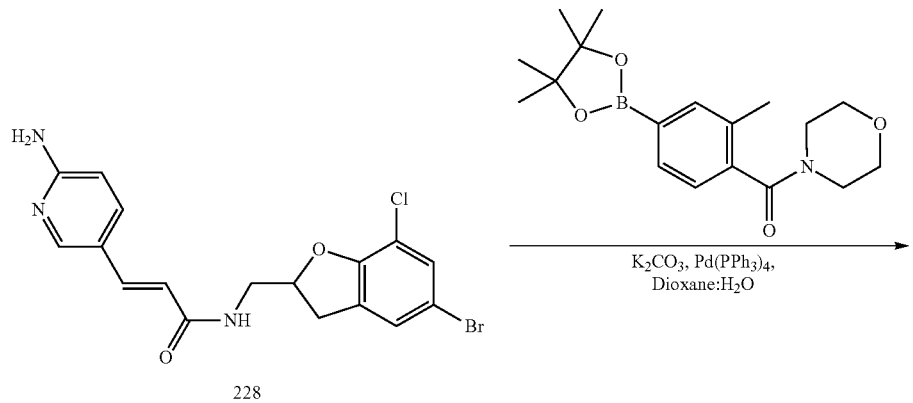

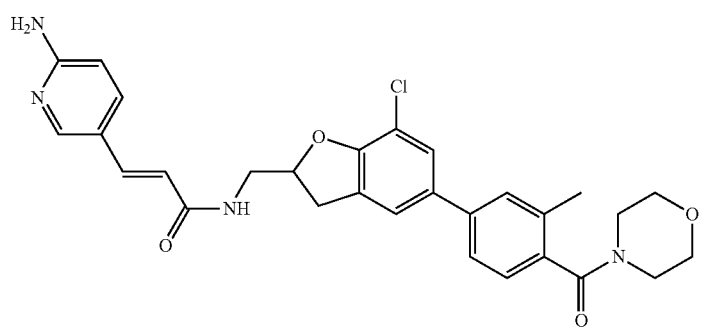

(E)-3-(6-aminopyridin-3-yl)-N-((7-chloro-5-(3-methyl-4-(morpholine-4-carbonyl)phenyl)-2,3-dihydrobenzofuran-2-yl)methyl)acrylamide 238 was synthesized using General Procedure 1. Yield (27%). $^1$H NMR (400 MHz, DMSO-$d_6$) δ 8.27 (bs, 1H), 8.07 (bs, 1H), 7.52-7.60 (m, 5H), 7.23-7.43 (m, 2H), 6.43-6.45 (m, 3H), 5.77 (s, 1H), 5.06 (bs, 1H), 3.66 (bs, 3H), 3.51-3.58 (m, 3H), 3.42 (m, 3H), 3.17 (m, 3H), 2.27 (s, 3H). LCMS: m/z 533.24 [M+H]$^+$, $t_R$=1.83 min.

Synthesis of (E)-3-(6-aminopyridin-3-yl)-N-((7-chloro-5-(3-(morpholine-4-carbonyl) phenyl)-2,3-dihydrobenzofuran-2-yl)methyl)acrylamide (239)

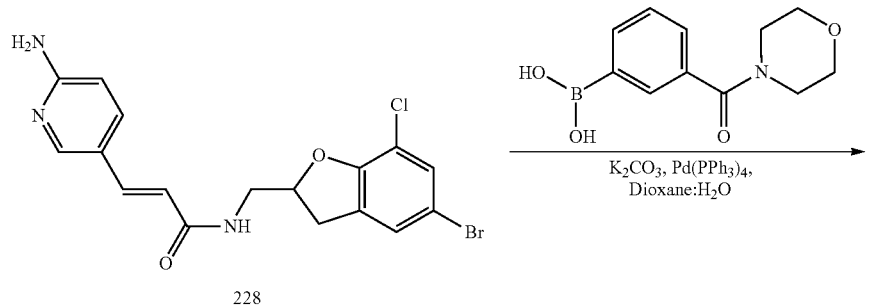

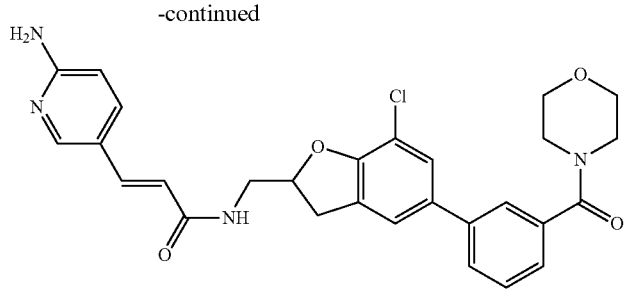

239

(E)-3-(6-aminopyridin-3-yl)-N-((7-chloro-5-(3-(morpholine-4-carbonyl)phenyl)-2,3-dihydrobenzofuran-2-yl)methyl)acrylamide 239 was synthesized using General Procedure 1. Yield (20%). $^1$H NMR (400 MHz, DMSO-d$_6$) δ 8.28 (t, 1H), 8.06 (d, J=2 Hz, 1H), 7.71 (d, J=7.2 Hz, 1H), 7.58-7.62 (m, 2H), 7.48-7.54 (m, 3H), 7.29-7.35 (m, 2H), 6.41-6.47 (m, 4H), 5.07 (m, 1H), 3.51-3.65 (m, 8H), 3.35-3.44 (m, 2H), 3.09-3.13 (m, 2H). LCMS: m/z 519.24 [M+H]$^+$, t$_R$=2.24 min.

Synthesis of N-((5-(5-acetylthiophen-2-yl)-7-chloro-2,3-dihydrobenzofuran-2-yl)methyl)-2-(pyridin-3-ylmethyl)acrylamide (240)

Ethyl acetate in Hexane) to give diethyl 2-(pyridin-3-ylmethyl)malonate 243. Yield (1.2 g, 39%). $^1$H NMR (400 MHz, DMSO-d$_6$) δ 8.42-8.44 (m, 2H), 7.66-7.68 (m, 1H), 7.30-7.33 (m, 1H), 4.05-4.08 (m, 4H), 3.91 (t, 1H), 3.10 (d, J=8 Hz, 2H), 1.08-1.12 (m, 6H). LCMS: m/z 253.16 [M+H]$^+$, t$_R$=1.89 min.

To a solution of diethyl 2-(pyridin-3-ylmethyl)malonate 243 (1.2 g, 4.8 mmol) in 1,4-dioxane (12 mL) was added a solution of KOH (0.58 g, 10 mmol) in water (2 mL) and stirred for 6 h at room temperature, acidified to pH 6 using dilute HCl and concentrated under reduced pressure. The resulting residue was refluxed in MeOH (15 mL) and filtered. The filtrate was concentrated under reduced pressure to give 2-(pyridin-3-ylmethyl)malonic acid 244. Yield

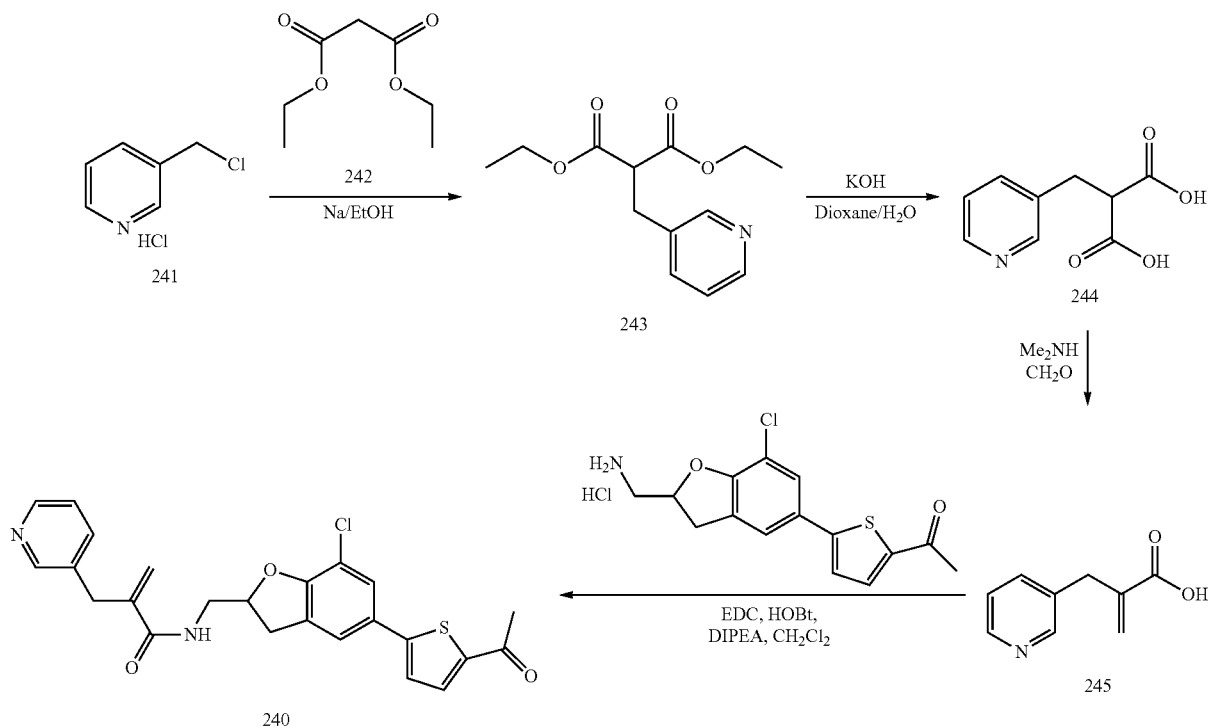

To a solution of sodium metal (0.69 g, 30 mmol) in EtOH (25 mL) was added diethyl malonate 242 (3.15 mL, 20 mmol) at 50° C. and stirred for 30 min. 3-chloromethyl pyridine hydrochloride 241 (2 g, 12 mmol) was added in small portions and the reaction mixture was refluxed for 2 h, and then concentrated under reduced pressure. The crude product was purified by silica gel chromatography (0-60%

(0.75 g, 80%). $^1$H NMR (400 MHz, DMSO-d$_6$) δ 8.38 (d, J=8.4 Hz, 2H), 7.60 (d, J=7.2 Hz, 1H), 7.25-7.28 (m, 1H), 3.37-3.42 (m, 1H), 3.09 (d, J=6 Hz, 2H).

Dimethylamine (0.43 mL, 3.8 mmol) was added to 2-(pyridin-3-ylmethyl)malonic acid 244 (0.75 g, 3.8 mmol) at 10° C. followed by formaldehyde (0.31 mL, 3.8 mmol). The reaction mixture was stirred at room temperature for 20 h. The reaction mixture was concentrated under reduced pressure and the residue was heated at 125° C. to give 2-(pyridin-3-ylmethyl)acrylic acid 245. Yield (0.3 g, 48%). $^1$H NMR (400 MHz, DMSO-$d_6$) δ 8.4 (s, 1H), 8.37 (d, J=4.4 Hz, 1H), 7.59 (d, J=7.6 Hz, 1H), 7.25-7.28 (m, 1H), 5.77 (bs, 1H), 5.08 (bs, 1H), 3.52 (s, 2H). LCMS: m/z 164 [M+H]$^+$, $t_R$=3.66 min.

3.28-3.33 (m, 1H), 2.97-3.03 (m, 1H), 2.53 (s, 3H). LCMS: m/z 453.17 [M+H]$^+$, $t_R$=1.96 min.

Synthesis of (E)-3-(6-aminopyridin-3-yl)-N-((7-chloro-5-(4-(piperazine-1-carbonyl)phenyl)-2,3-dihydrobenzofuran-2-yl)methyl)acrylamide dihydrochloride (246)

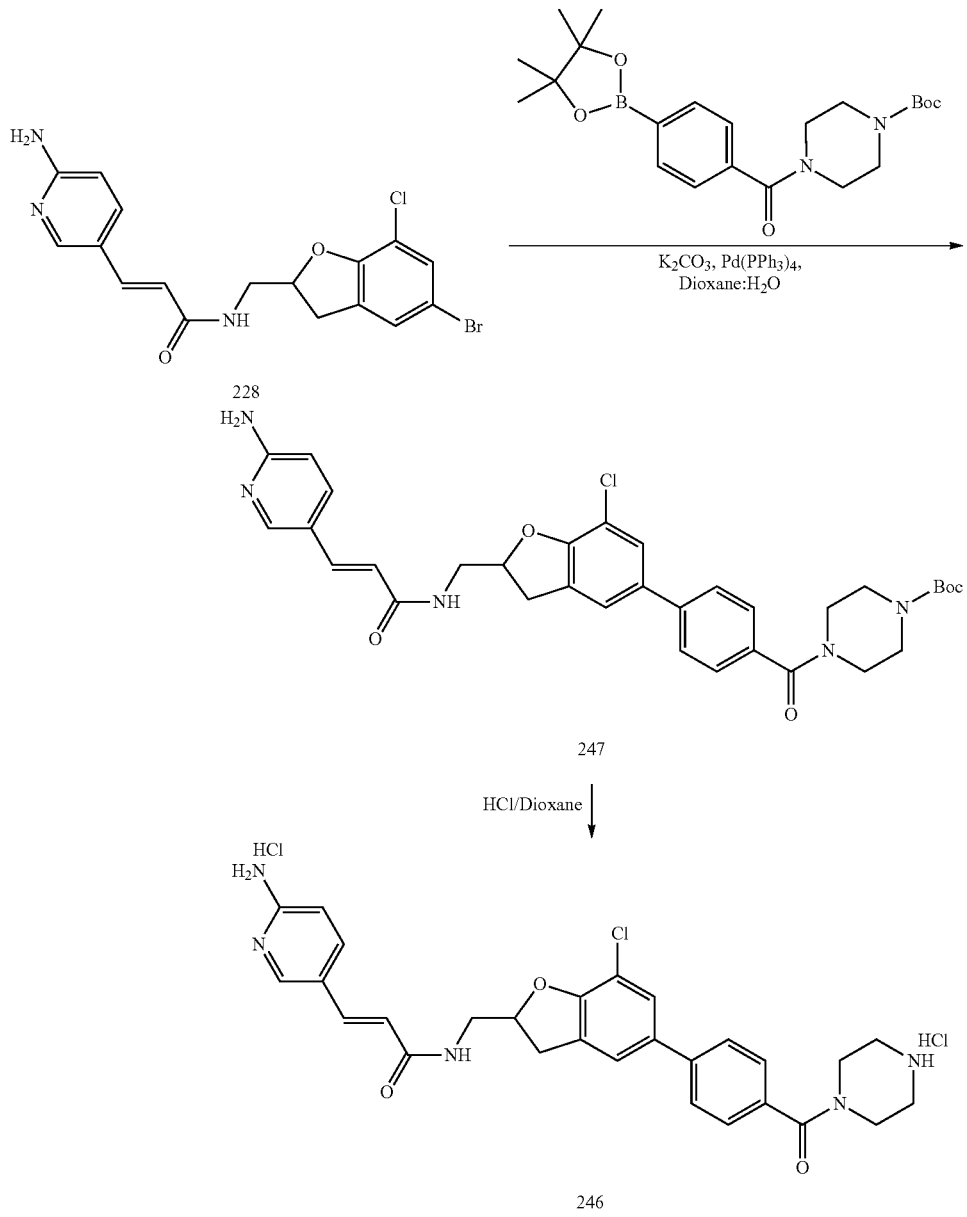

N-((5-(5-acetylthiophen-2-yl)-7-chloro-2,3-dihydrobenzofuran-2-yl)methyl)-2-(pyridin-3-ylmethyl)acrylamide 240 was synthesized using General Procedure 3 with 10% yield. $^1$H NMR (400 MHz, DMSO-$d_6$) δ 8.37-8.43 (m, 3H), 7.92 (d, J=4 Hz, 1H), 7.64 (d, J=1.6 Hz, 1H), 7.29-7.59 (m, 3H), 7.26-7.28 (m, 1H), 5.7 (s, 1H), 5.36 (s, 1H), 4.98-5.05 (m, 1H), 3.61 (s, 2H), 3.46-3.52 (m, 1H), 3.37-3.42 (m, 1H), (E)-tert-Butyl 4-(4-(2-((3-(6-aminopyridin-3-yl)acrylamido)methyl)-7-chloro-2,3-dihydrobenzofuran-5-yl)benzoyl)piperazine-1-carboxylate 247 was synthesized using General Procedure 1. Yield (49%). $^1$H NMR (400 MHz, DMSO-$d_6$) δ 8.27 (t, 1H), 8.07 (s, 1H), 7.69 (d, J=8 Hz, 2H), 7.58-7.61 (m, 1H), 7.55 (d, J=2.8 Hz, 2H), 7.46 (d, J=8 Hz, 2H), 7.32 (d, J=15.6 Hz, 1H), 6.41-6.48 (m, 4H), 5.07 (m, 1H), 3.54-3.62 (m, 5H), 3.34-3.51 (m, 6H), 3.13 (m, 1H), 1.41(s, 9H). LCMS: m/z 618.36 [M]$^+$, $t_R$=2.40 min.

(E)-3-(6-aminopyridin-3-yl)-N-((7-chloro-5-(4-(piperazine-1-carbonyl)phenyl)-2,3-dihydrobenzofuran-2-yl)methyl)acrylamide dihydrochloride 246 was synthesized using General Procedure 2. HCl in dioxane was used instead of TFA. Yield (62%). $^1$H NMR (400 MHz, DMSO-$d_6$) δ 9.25 (s, 2H), 8.52 (t, 1H), 8.20-8.26 (m, 3H), 8.07 (d, J=9.2 Hz, 1H), 7.72 (d, J=8 Hz, 2H), 7.51-7.60 (m, 4H), 7.41 (d, J=16 Hz, 1H), 7.0 (d, J=9.2 Hz, 1H), 6.63 (d, J=15.6 Hz, 1H), 5.0 (m, 1H), 3.38-3.73 (m, 8H), 3.13-3.17 (m, 5H). LCMS: m/z 518.24 [M+H]$^+$, $t_R$=1.61 min.

Synthesis of (E)-3-(6-aminopyridin-3-yl)-N-((7-chloro-5-(6-(morpholine-4-carbonyl)pyridin-3-yl)-2,3-dihydrobenzofuran-2-yl)methyl)acrylamide (248)

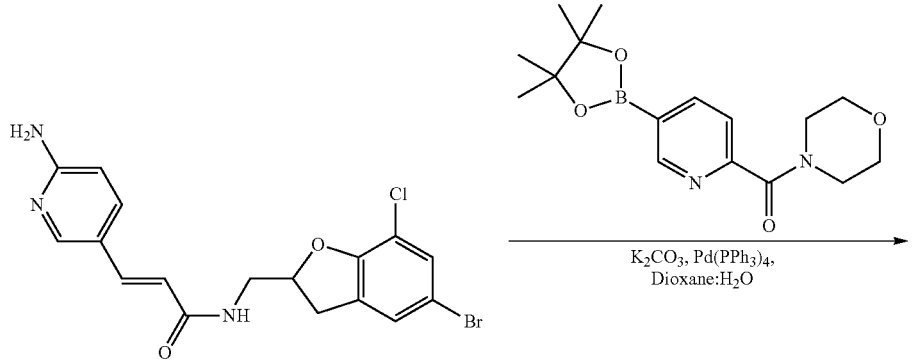

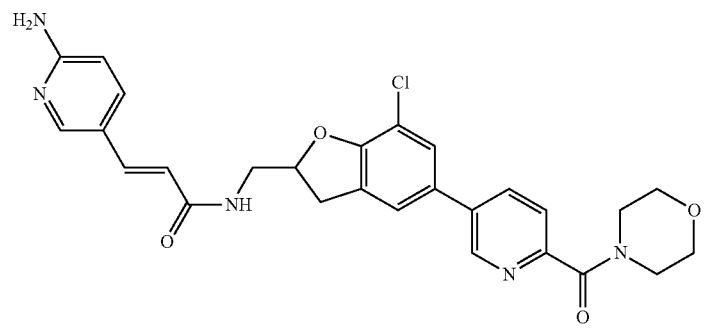

(E)-3-(6-aminopyridin-3-yl)-N-((7-chloro-5-(6-(morpholine-4-carbonyl)pyridin-3-yl)-2,3-dihydrobenzofuran-2-yl)methyl)acrylamide 248 was synthesized using General Procedure 1. Yield (44%). $^1$H NMR (400 MHz, DMSO-$d_6$) δ 8.93 (d, J=2.4 Hz, 1H), 8.55 (d, J=1.6 Hz, 1H), 8.29 (t, 1H), 8.07-8.08 (m, 2H), 7.65 (d, J=8 Hz, 2H), 7.58-7.61 (m, 1H), 7.30 (d, J=15.6 Hz, 1H), 6.41-6.48 (m, 4H), 5.08 (m, 1H), 3.51-3.67 (m, 8H), 3.36-3.45 (m, 3H), 3.09-3.15 (m, 1H). LCMS: m/z 520.29 [M+H]$^+$, $t_R$=1.71 min.

Synthesis of (E)-3-(6-aminopyridin-3-yl)-N-((7-chloro-4-(4-(morpholine-4-carbonyl) phenyl)-2,3-dihydrobenzofuran-2-yl)methyl)acrylamide (250)

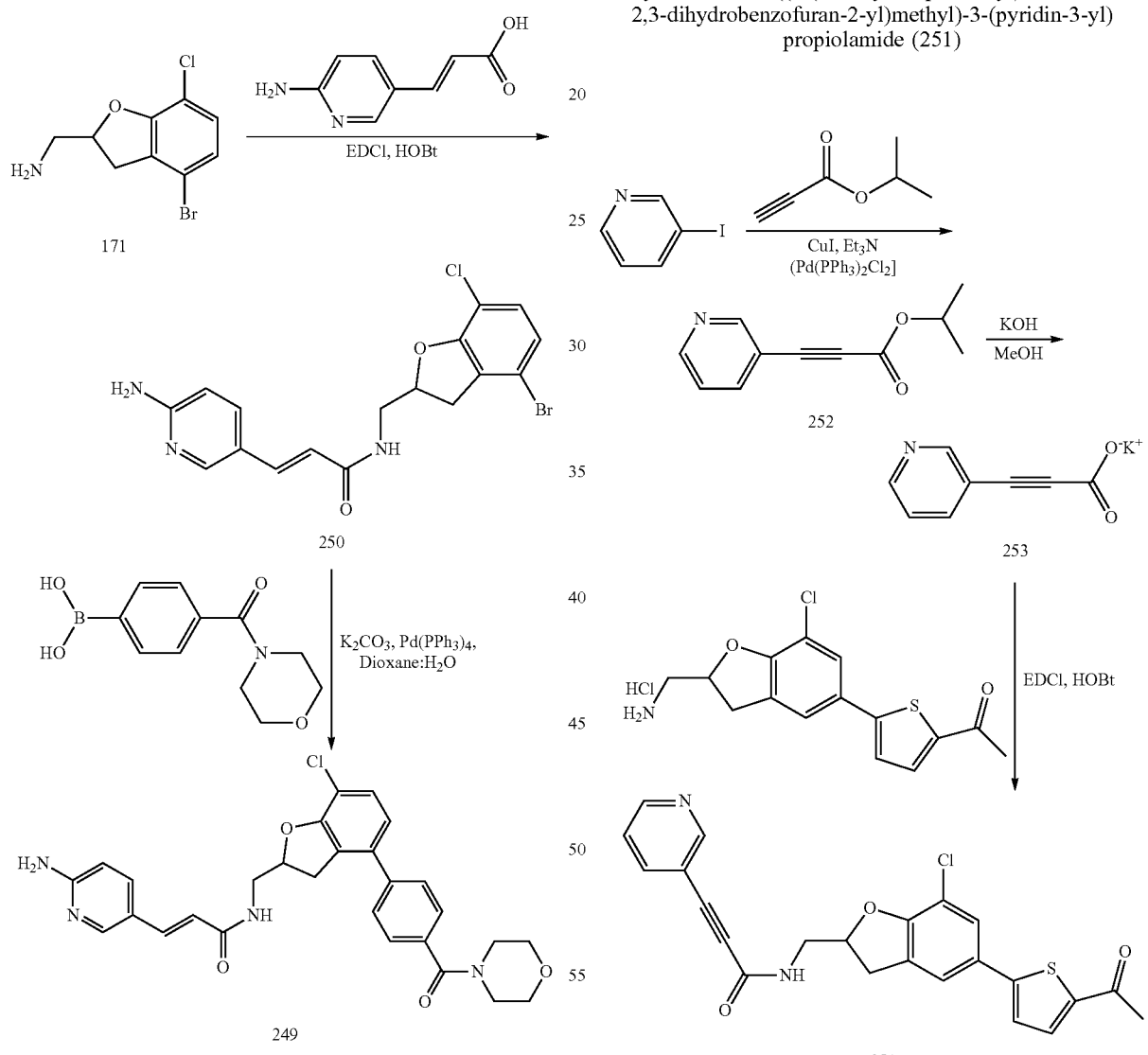

(E)-3-(6-Aminopyridin-3-yl)-N-((4-bromo-7-chloro-2,3-dihydrobenzofuran-2-yl)methyl)acrylamide 250 was synthesized using General Procedure 3 with 50% yield. LCMS: m/z 410.0 [M+H]$^+$, $t_R$=1.95 min.

(E)-3-(6-aminopyridin-3-yl)-N-((7-chloro-4-(4-(morpholine-4-carbonyl)phenyl)-2,3-dihydrobenzofuran-2-yl)methyl)acrylamide 249 was synthesized using General Procedure 1. Yield (16%). $^1$H NMR (400 MHz, DMSO-$d_6$) δ 8.25 (t, 1H), 8.06 (d, J=2 Hz, 1H), 7.59 (d, J=8 Hz, 3H), 7.50 (d, J=8 Hz, 2H), 7.27-7.33 (m, 2H), 6.97 (d, J=8.4 Hz, 1H), 6.38-6.47 (m, 4H), 5.01-5.03 (m, 1H), 3.53-3.72 (m, 6H), 3.34-3.50 (m, 5H), 3.12-3.18 (m, 1H). LCMS: m/z 519.29 [M+H]$^+$, $t_R$=1.92 min.

(E)-3-(6-aminopyridin-3-yl)-N-((7-(tert-butyl)-4-(4-(morpholine-4-carbonyl)phenyl)-2,3-dihydrobenzofuran-2-yl)methyl)acrylamide (355) was synthesized in a manner similar to that used to synthesize Compound 249 using the appropriate reagents. $^1$H NMR (400 MHz, DMSO-$d_6$) δ 8.14 (t, 1H), 8.06 (s, 1H), 7.60 (m, 1H), 7.58 (d, 2H), 7.47 (m, 2H), 7.26 (d, 1H), 7.14 (d, 1H), 6.96 (d, 1H), 6.36-6.47 (m, 4H), 4.89 (1H), 3.30-3.62 (m, 9H), 3.28 (s, 1H), 3.05 (dt, 1H), 1.25 (s, 9H). LCMS: m/z 541.5 [M+H]$^+$, $t_R$=2.01 min.

Synthesis of N-((5-(5-acetylthiophen-2-yl)-7-chloro-2,3-dihydrobenzofuran-2-yl)methyl)-3-(pyridin-3-yl)propiolamide (251)

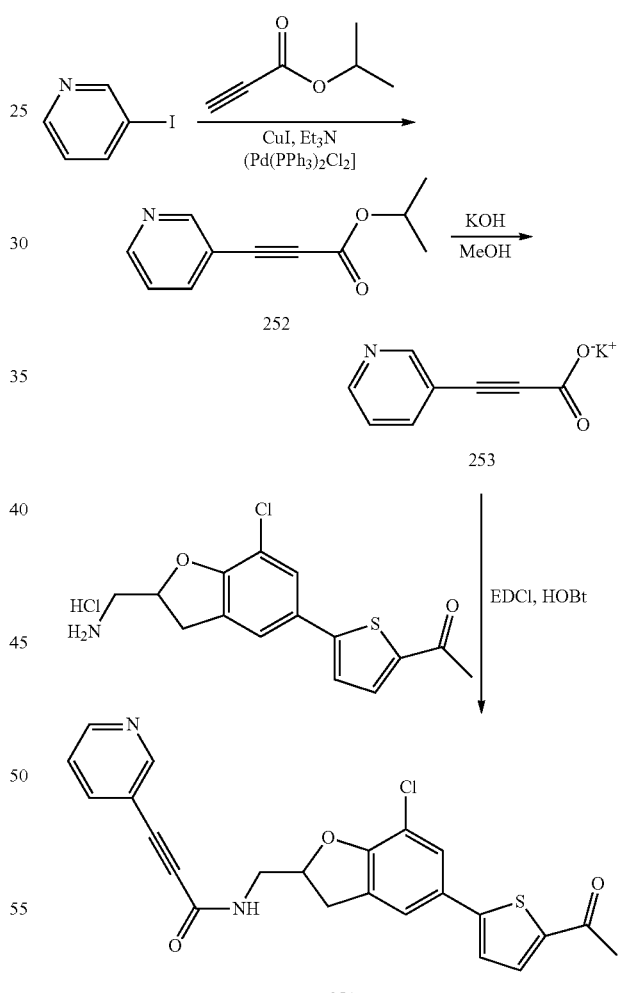

To a solution of 3-iodopyridine (6.0 g, 29.2 mmol) in dry DMF (60 mL) was added isopropyl propiolate (8.0 g, 73.0 mmol) followed by CuI (0.8 g, 4.3 mmol) and Et$_3$N (8.78 g, 87.0 mmol) (8.5 mL). The reaction mixture was stirred at 25° C. for 15 min and [Pd(PPh$_3$)$_2$Cl$_2$] (1.0 g, 1.4 mmol) was added. After stirring 6 h at 25° C., the reaction mixture was diluted with EtOAc (250 mL) and washed with brine (500 mL), concentrated under reduced pressure and purified by silica gel chromatography (0-6% ethyl acetate/n-hexane) to give isopropyl 3-(pyridin-3-yl) propiolate 252. Yield (2 g, 42%). ¹H NMR (400 MHz, CDCl₃) δ 8.85-8.86 (s, 1H), 8.72 (t, 1H), 8.12 (t, 1H), 7.51-7.54 (m, 1H), 5.05-5.11 (m, 1H), 1.21-1.27 (s, 6H).

To a solution of isopropyl 3-(pyridin-3-yl) propiolate 252 (0.8g, 5.9 mmol) in MeOH (10 mL) was added a solution of KOH in MeOH (1 eq., 1N, 4.2 mL). The reaction mixture was stirred at 25° C. for 4 h, concentrated under reduced pressure to give potassium 3-(pyridin-3-yl) propiolate 253. (Yield (0.5 g, 97%). ¹H NMR (400 MHz, DMSO-d₆) δ 8.57 (s, 1H), 8.50-8.56 (t, 1H), 7.79-7.81 (t, 1H), 7.37-7.40 (m, 1H). LCMS: m/z 147 [M+H]⁺ 148.0, $t_R$=1.55 min.

N-((5-(5-Acetylthiophen-2-yl)-7-chloro-2,3-dihydrobenzofuran-2-yl)methyl)-3-(pyridin-3-yl) propiolamide 251 was synthesized using General Procedure 3 with the yield of 46%. ¹H NMR (400 MHz, DMSO-d₆) δ 9.27-9.29 (t, 1H), 8.72 (s, 1H), 8.67-8.68 (d, J=4 Hz, 1H), 8.02-8.04 (d, J=8 Hz, 1H), 7.92-7.93 (d, J=4 Hz, 1H), 7.58-7.67 (m, 4H), 5.05-5.08 (m, 1H), 3.49-3.60 (m, 2H), 3.35-3.46 (m, 1H), 3.03-3.13 (m, 1H), 2.53 (s, 3H). LCMS: m/z 437.12 [M+H]⁺, $t_R$=2.05 min.

General Procedure 4—Heck Reaction

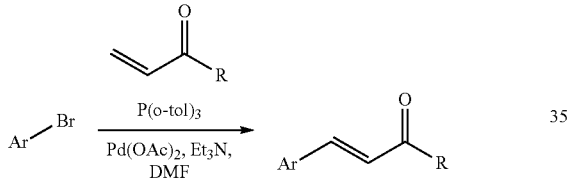

An aryl bromide (1 eq.) was dissolved in 1:1 mixture of DMF:H₂O (1:10 loading ratio). The acrylate (1.5 eq.), Pd(OAc)₂ (1 mol %), Tri(o-tolyl) phosphine (1 mol %) and triethylamine (2 eq.) were added at room temperature. The reaction mixture was heated at 80° C. for 4 h, transferred into iced water (10 mL) and extracted with ethyl acetate (3×15 mL). The combined organic layers were washed with brine, dried over anhydrous Na₂SO₄ and concentrated under reduced pressure to give the crude product which was purified by silica gel chromatography (2% MeOH in CH₂Cl₂) to give the desired product.

Synthesis of (E)-N-((5-(5-acetylthiophen-2-yl)-7-chloro-2,3-dihydrobenzofuran-2-yl)methyl)-3-(pyrimidin-5-yl)acrylamide (254)

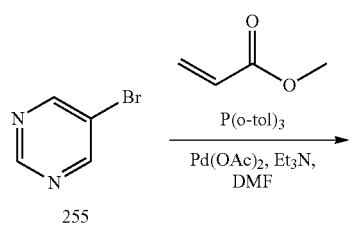

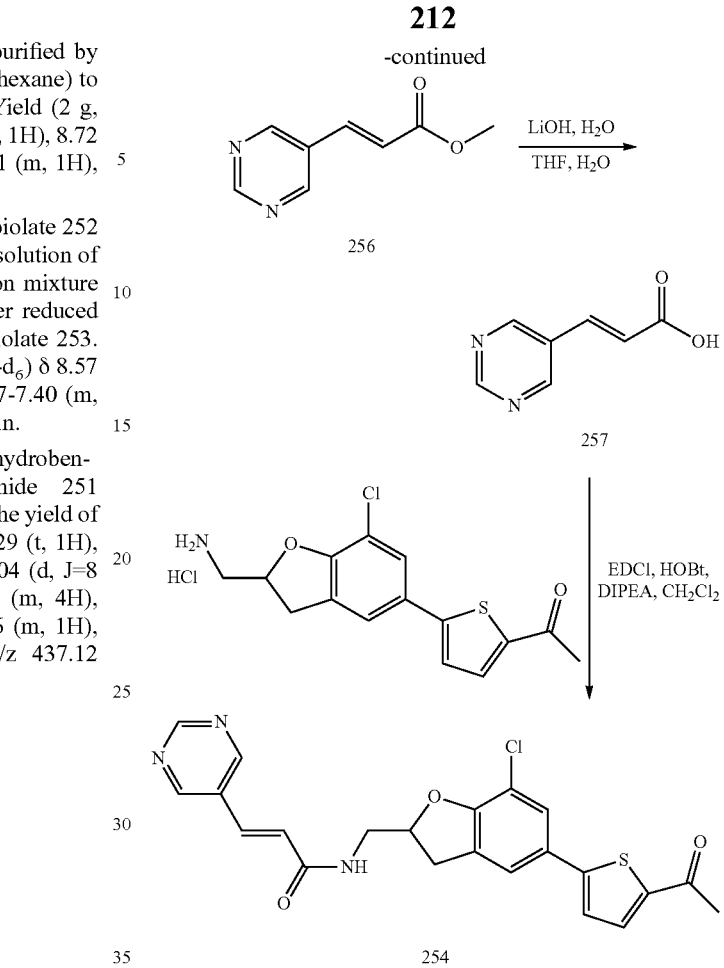

(E)-Methyl 3-(pyrimidin-5-yl) acrylate 256 was synthesized using General Procedure 4. Yield (48%). ¹H NMR (400 MHz, DMSO-d₆) δ 9.20 (t, 3H), 7.72 (d, J=16 Hz, 1H), 6.75 (d, J=16 Hz, 1H), 3.76 (s, 3H). LCMS: m/z 164.80 [M+H]⁺, $t_R$=0.53 min.

(E)-3-(Pyrimidin-5-yl) acrylic acid 257 was synthesized from (E)-methyl 3-(pyrimidin-5-yl) acrylate 256. The experimental procedure for this step was similar to the synthesis of (E)-3-(2-ethyl-4-methyl-1H-imidazol-5-yl) acrylic acid 180 (conversion of 179 to 180). Lithium hydroxide was used instead of potassium hydroxide. Yield (58%). ¹H NMR (400 MHz, DMSO-d₆) δ 12.73 (s, 1H), 9.16 (d, 3H), 7.61 (d, J=16 Hz, 1H), 7.84 (d, J=16 Hz, 1H), LCMS: m/z 150.74 [M+H]⁺, $t_R$=2.43 min.

(E)-N-((5-(5-acetylthiophen-2-yl)-7-chloro-2,3-dihydrobenzofuran-2-yl)methyl)-3-(pyrimidin-5-yl)acrylamide 254 was synthesized using General Procedure 3 with 6% yield. ¹H NMR (400 MHz, DMSO-d₆) δ 9.16 (s, 1H), 9.03 (s, 2H), 8.63 (t, 1H), 7.93 (d, J=4 Hz, 1H), 7.66-7.56 (m, 3H), 7.50 (d, J=16 Hz, 1H), 6.91-6.95 (m, 1H), 5.08-5.15 (m, 1H), 3.55-3.66 (m, 2H), 3.41-3.47 (m, 1H) 3.08-3.18 (m, 1H), 2.53 (s, 3H). LCMS: m/z 439.95 [M+H]⁺, $t_R$=1.90 min.

Synthesis of (E)-N-((5-(5-acetylthiophen-2-yl)-7-chloro-2,3-dihydrobenzofuran-2-yl)methyl)-3-(pyrazin-2-yl)acrylamide (258)

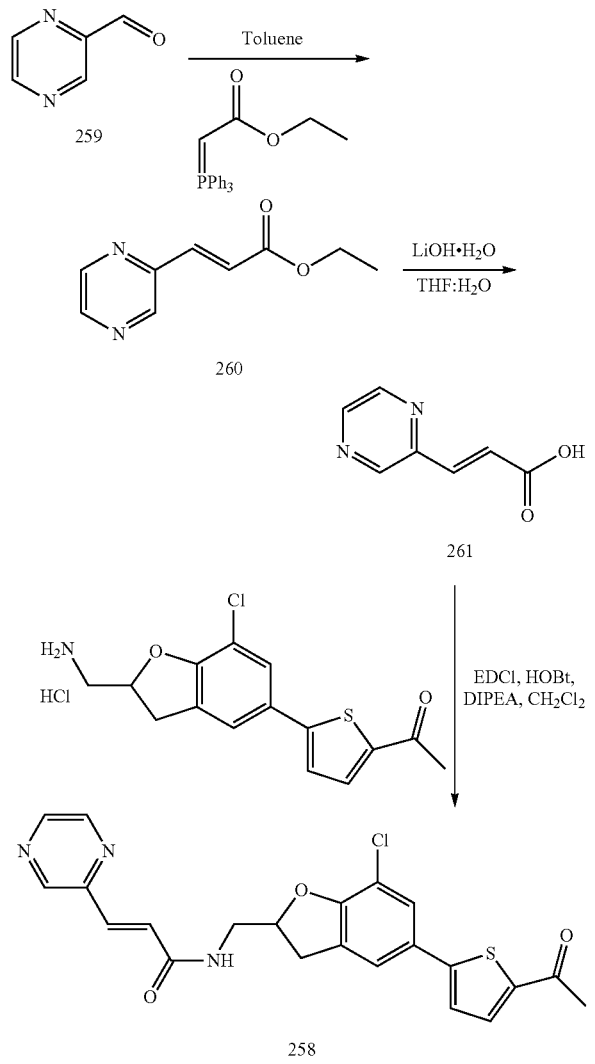

Pyrazine-2-carbaldehyde 259 (0.2 g, 1.8 mmol) and (carbethoxymethyl)triphenyl phosphorane (0.77 g, 2.2 mmol) were dissolved in toluene (5 mL) and the reaction mixture was stirred at 110° C. for 12 h. The reaction mixture was concentrated under reduced pressure and purified by silica gel chromatography (0-3% ethyl acetate/n-hexane) to give (E)-ethyl 3-(pyrazin-2-yl) acrylate 260. Yield (0.25 g, 76%). $^1$H NMR (400 MHz, CDCl$_3$) δ 8.69 (s, 1H), 8.63 (t, 1H), 8.56 (d, J=2.4 Hz, 1H), 7.71 (d, J=15.6 Hz, 1H), 7.05 (d, J=15.6 Hz, 1H), 4.30 (q, 2H), 1.37 (t, 3H). LCMS: m/z 178.81 [M−H]$^+$, t$_R$=1.35 min.

(E)-Ethyl 3-(pyrazin-2-yl) acrylate 260 (0.25 g, 1.4 mmol) and LiOH.H$_2$O (0.29 g, 7.0 mmol) were added to a mixture of THF:water (1:1, 200 mL). After stirring for 4 h, the reaction mixture was transferred to iced water, acidified with dil. HCl and extracted with ethyl acetate (10 mL×3). The combined organic layers were washed with brine, dried over anhydrous Na$_2$SO$_4$ and concentrated under reduced pressure to give (E)-3-(pyrazin-2-yl)acrylic acid 261. Yield (0.13 g, 50%). $^1$H NMR (400 MHz, DMSO-d$_6$) δ 12.80 (s, 1H), 8.97 (s, 1H), 8.68 (d, J=21.2 Hz, 2H), 7.68 (d, J=16 Hz, 1H), 6.93 (d, J=16 Hz, 1H). LCMS: m/z 150.74 [M+H]$^+$, t$_R$=2.47 min.

(E)-N-((5-(5-acetylthiophen-2-yl)-7-chloro-2,3-dihydrobenzofuran-2-yl)methyl)-3-(pyrazin-2-yl)acrylamide 258 was synthesized using General Procedure 3 with 22% yield. $^1$H NMR (400 MHz, CDCl$_3$) δ 8.67 (s, 1H), 8.62 (s, 1H), 8.57 (s, 1H), 7.71 (d, J=15.2 Hz, 1H), 7.64 (d, J=4 Hz, 1H), 7.48 (s, 1H), 7.36 (s, 1H), 7.20 (d, J=4 Hz, 1H), 7.13 (d, J=15.2 Hz, 1H), 3.96-4.02 (m, 1H), 3.68-3.74 (m, 2H), 3.44-3.50 (m, 1H), 3.11-3.17 (m, 1H), 2.57 (s, 3H). LCMS: m/z 440.01 [M+H]$^+$, t$_R$=1.95 min.

Synthesis of (E)-N-((5-(5-acetylthiophen-2-yl)-7-chloro-2,3-dihydrobenzofuran-2-yl)methyl)-2-methyl-3-(pyridin-3-yl) acrylamide (262)

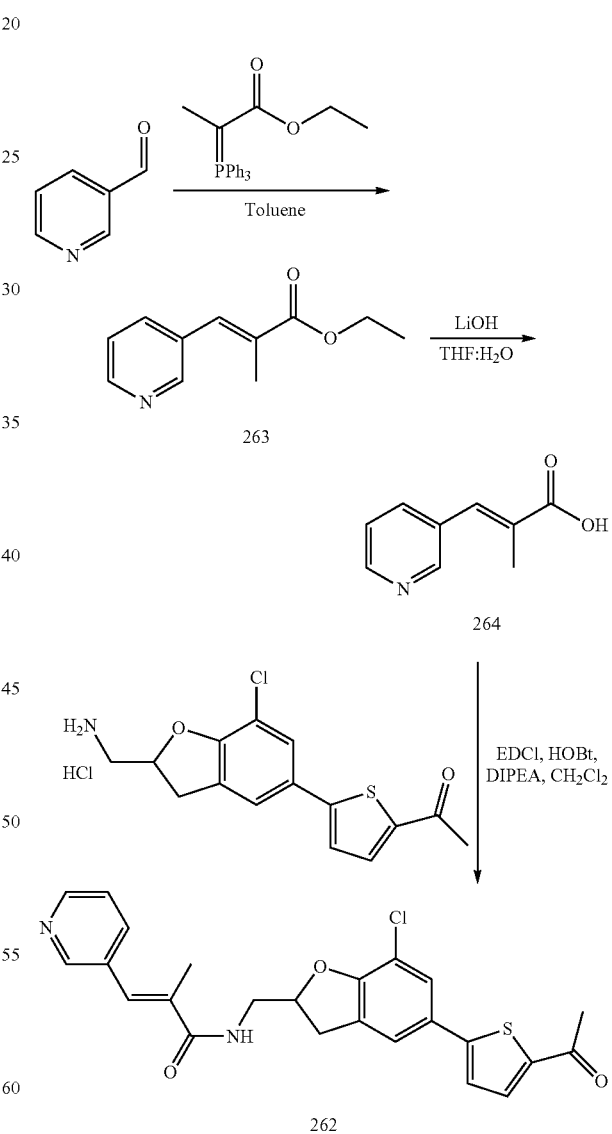

(E)-Ethyl 2-methyl-3-(pyridin-3-yl)acrylate 263 was synthesized from nicotinaldehyde. The experimental procedure for this step was similar to the synthesis of (E)-ethyl 3-(2-ethyl-4-methyl-1H-imidazol-5-yl) acrylate 179 (conversion of 178 to 179). Ethyl 2-(triphenylphosphoranylidene)propanoate was used instead of ethyl 2-(triphenylphosphoranylidene)acetate. Yield (80%), $^1$H NMR (400 MHz, DMSO-$d_6$) δ 8.67 (d, 1H), 8.55 (q, 1H), 7.93-7.90 (m, 1H), 7.61 (s, 1H), 7.49-7.45 (m, 1H), 4.20 (q, 2H), 2.05 (s, 3H), 1.29 (m, 3H) LCMS: m/z 192.8 [M+H]$^+$, $t_R$=0.87 min.

(E)-2-methyl-3-(pyridin-3-yl)acrylic acid 264 was synthesized from (E)-ethyl 2-methyl-3-(pyridin-3-yl)acrylate 263. The experimental procedure for this step was similar to the synthesis of (E)-3-(2-ethyl-4-methyl-1H-imidazol-5-yl) acrylic acid 180 (conversion of 179 to 180). Lithium hydroxide was used instead of potassium hydroxide. Yield (45%), $^1$H NMR (400 MHz, DMSO-$d_6$) δ 12.707 (s, 1H), 8.67-8.67 (d, 1H), 8.55-8.54 (q, 1H); 7.92-7.89 (m, 1H), 7.60 (s 1H) 7.49-7.45 (m, 1H), 2.00 (s, 3H) LCMS: m/z 163.75 [M+H]$^+$, $t_R$=2.34 min.

(E)-N-((5-(5-acetylthiophen-2-yl)-7-chloro-2,3-dihydrobenzofuran-2-yl)methyl)-2-methyl-3-(pyridin-3-yl) acrylamide 262 was synthesized using General Procedure 3 with 26% yield. $^1$H NMR (400 MHz, DMSO-$d_6$) δ 8.57 (d, 1H), 8.51 (dd, 1H), 8.44 (t, 1H), 7.93 (d, 1H), 7.80 (d, 1H), 7.67 (d, 1H), 7.62 (s, 1H), 7.60 (d, 1H), 7.42 (q, 1H), 7.11 (s, 1H), 5.15-5.11 (m, 1H), 3.61-3.35 (m, 3H), 3.20-3.14 (m, 1H), 2.51 (s, 3H), 2.02 (s, 3H). LCMS: m/z 453.0 [M+H]$^+$, $t_R$=1.88 min.

Synthesis of PEGylated Compound 246 and
Resin-immobilized PEGylated Compound 246

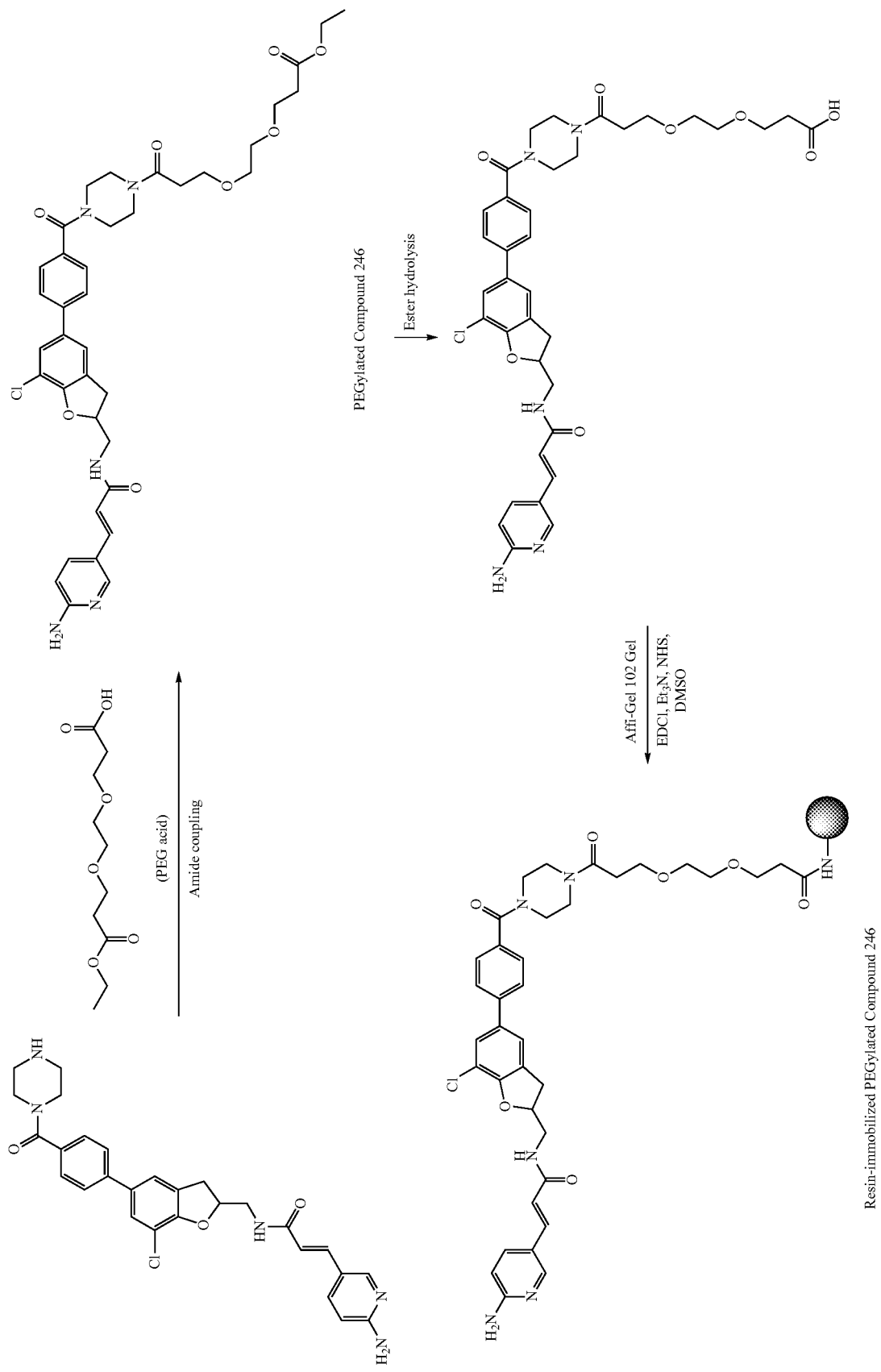

PEGylated Compound 246 (also referred to herein as Compound 354) was synthesized from Compound 246 using General Procedure 3.

Resin-immobilized PEGylated Compound 246 was synthesized from PEGylated Compound 246 in two steps. In the first step, PEGylated Compound 246 was hydrolyzed using an experimental procedure similar to that used for the synthesis of Compound 264 from Compound 263 described above. A representative procedure for the synthesis of Resin-immobilized PEGylated Compound 246 from the carboxylic acid depicted above is described in Shao-En Ong et al. *PNAS,* 2009, 16(12), 4617-4622.

(E)-N-((5-(5-Acetylthiophen-2-yl)-7-chloro-2,3-dihydrobenzofuran-2-yl)methyl)-3-(thiazol-4-yl)acrylamide (272)

was allowed to cool to room temperature, transferred into iced water and extracted with ethyl acetate (3×50 mL). The combined organic layers were washed with brine, dried over anhydrous Na$_2$SO$_4$, and concentrated under reduced pressure to give the crude product, which was purified by silica gel chromatography (0-10% ethyl acetate/n-hexane) to obtain (E)-methyl 3-(thiazol-4-yl)acrylate (373). (Yield: 1.1 g, 90%). $^1$H NMR (400 MHz, DMSO-d$_6$) δ 8.85 (s, 1H), 7.71 (d, J=15.6 Hz, 1H), 7.51 (s, 1H), 6.82 (d, J=15.6 Hz, 1H), 3.83 (s, 3H).

(E)-3-(Thiazol-4-yl)acrylic acid (374) was synthesized similar to 3-(6-chloropyridine-3-yl)acrylic acid (48) (Conversion of 47 to 48). (Yield: 1 g, 82%). $^1$H NMR (400 MHz, CDCl$_3$) δ 8.90 (s, 1H), 7.79 (d, J=16 Hz, 1H), 7.58 (s, 1H), 6.84 (d, J=15.6 Hz, 1H). LCMS: m/z 155.7 [M+H]$^+$, t$_R$=2.54 min.

(E)-N-((5-(5-Acetylthiophen-2-yl)-7-chloro-2,3-dihydrobenzofuran-2-yl)methyl)-3-(thiazol-4-yl)acrylamide

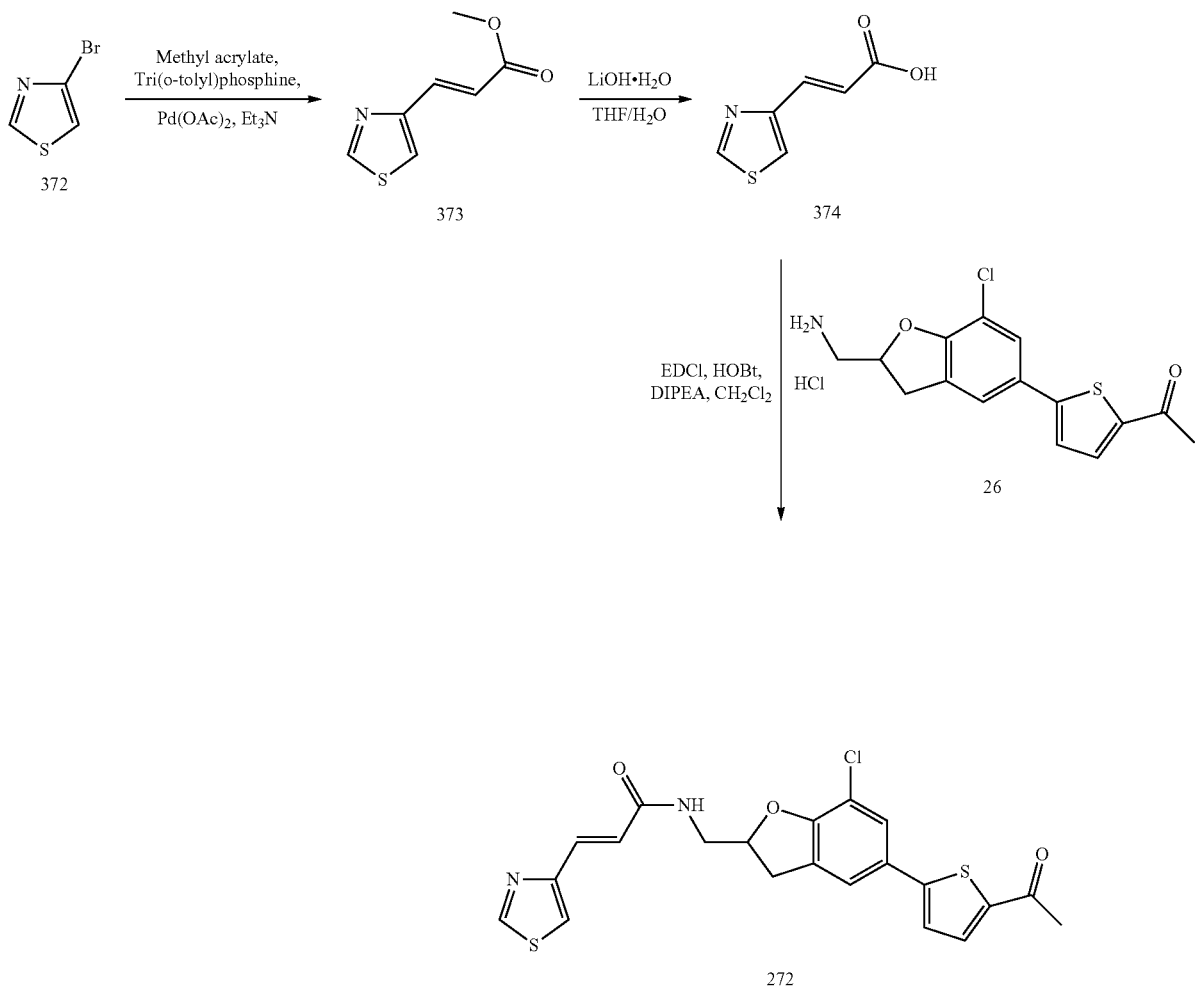

(E)-Methyl 3-(thiazol-4-yl)acrylate (373): 4-bromothiazole (0.75 g, 4.57 mmol) was dissolved in DMF (10 mL) at room temperature and degassed using N$_2$ for 5 min. Methyl acrylate (2 mL, 18.2 mmol), tri(o-tolyl)phosphine (2.2 g, 9.1 mmol), palladium acetate (0.01 g, 1 mol %) and triethylamine (2 mL, 13.5 mmol) were added and degassed again using N2 for 15 min. The reaction mixture was irradiated under microwave for 60 min at 120° C. The reaction mixture (272) was synthesized using general procedure 3. (Yield: 6.6 mg, 18%). $^1$H NMR (400 MHz, DMSO-d$_6$) δ 9.16 (s, 1H), 8.59-8.62 (m, 1H), 7.96 (s, 1H), 7.88 (s, 1H), 7.54-7.62 (m, 3H), 7.49 (d, J=15.6 Hz, 1H), 6.92 (d, J=15.2 Hz, 1H), 5.06-5.13 (m, 1H), 3.50-3.64 (m, 2H), 3.38-3.45 (m, 1H), 3.07-3.11 (m, 1H), 2.51 (s, 3H). LCMS: m/z 445.11 [M+H]$^+$, t$_R$=2.01 min.

Synthesis of (E)-N-((5-(5-acetylthiophen-2-yl)-7-chloro-2,3-dihydrobenzofuran-2-yl) methyl)-3-(pyridazin-4-yl)acrylamide (273)

(273) was synthesized using General Procedure 3. (Yield: 28%). ¹H NMR (400 MHz, DMSO-d$_6$) δ 9.40 (s, 1H), 9.26-9.28 (dd, J$_1$=1.2 Hz, J$_2$=4 Hz, 1H), 8.69-8.72 (m, 1H),

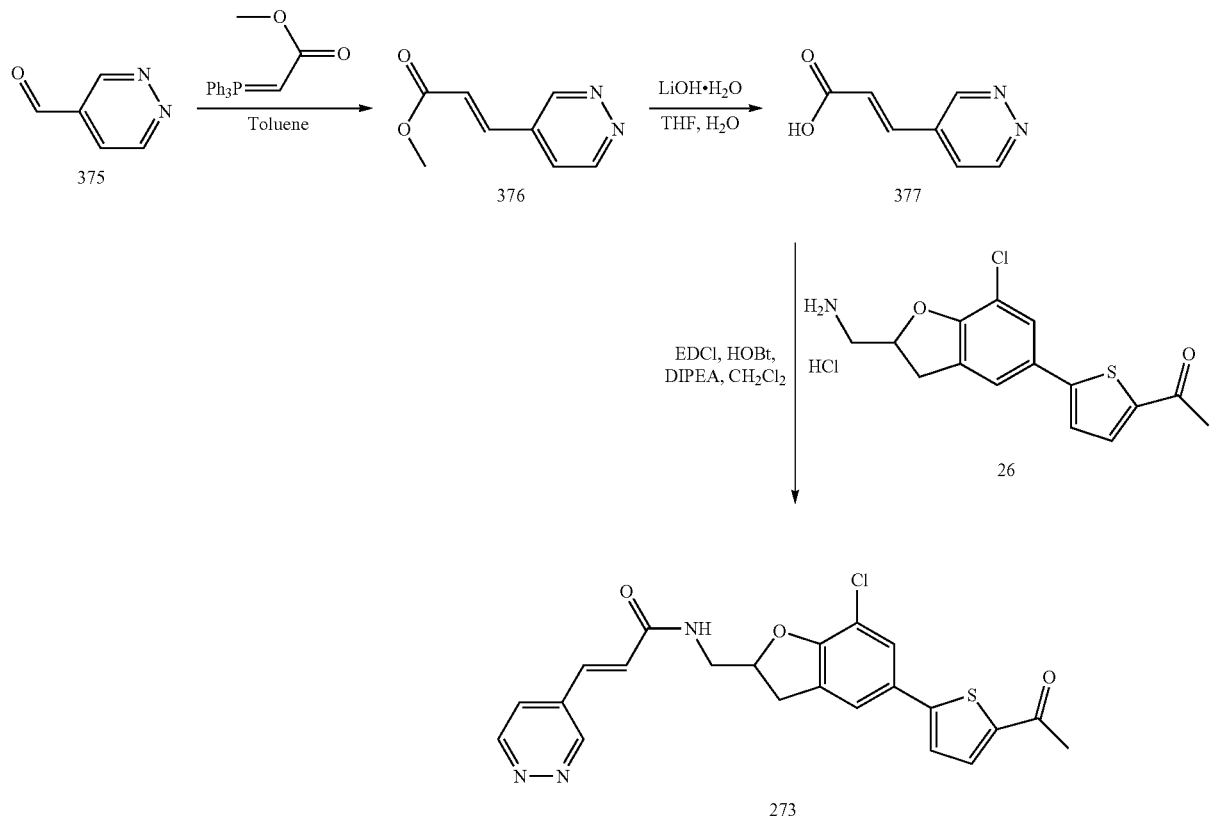

(E)-Methyl 3-(pyridazin-4-yl) acrylate (376) was synthesized similar to methyl-3-(6-chloropyridin-3-yl)acrylate (47) (conversion of 46 to 47). (Yield: 69%). ¹H NMR (400 MHz, DMSO-d$_6$) δ 9.58 (s, 1H), 9.25-9.33 (m, 1H), 8.00-8.02 (m, 1H), 7.58 (d, J=16 Hz, 1H), 7.12 (d, J=16.4 Hz, 1H), 3.78 (s, 3H). LCMS: m/z 164.50 [M]$^+$, t$_R$=2.53 min.

(E)-3-(Pyridazin-4-yl) acrylic acid (377) was synthesized similar to 3-(6-chloropyridine-3-yl)acrylic acid (48) (conversion of 47 to 48). (Yield: 49%). LCMS: m/z 150.8 [M$^+$]$^+$, t$_R$=0.27 min.

(E)-N-((5-(5-Acetylthiophen-2-yl)-7-chloro-2,3-dihydrobenzofuran-2-yl)methyl)-3-(pyridazin-4-yl)acrylamide 7.92 (d, J=4 Hz, 1H), 7.81-7.83 (m, 1H), 7.67 (s, 1H), 7.58-7.62 (m, 2H), 7.48 (d, J=16 Hz, 1H), 7.08 (d, J=16 Hz, 1H), 5.09-5.15 (m, 1H), 3.57-3.65 (m, 2H), 3.38-3.51 (m, 1H), 3.11 (dd, J$_1$=8 Hz, J$_2$=8.4 Hz, 1H), 2.53 (s, 3H). LCMS: m/z 440.01 [M]$^+$, t$_R$=1.83 min.

Synthesis of (E)-N-((5-(5-acetylthiophen-2-yl)-7-chloro-2,3-dihydrobenzofuran-2-yl)methyl)-3-(1-ethyl-1H-pyrazol-5-yl)acrylamide (274)

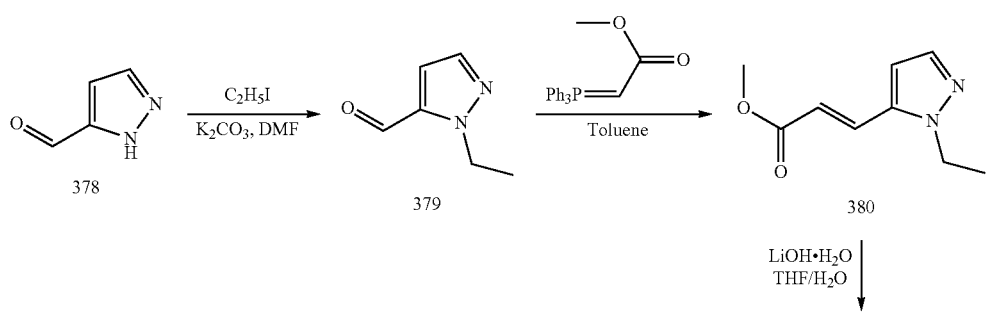

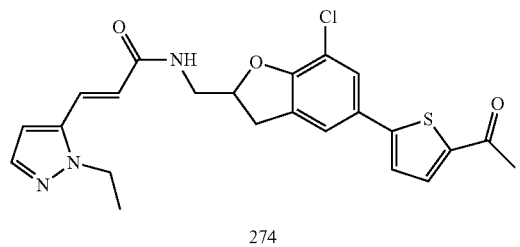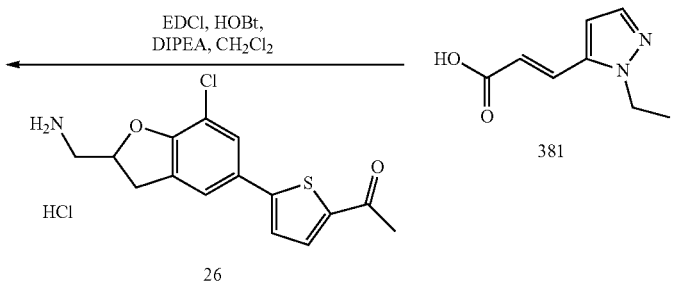

1-Ethyl-1H-pyrazole-5-carbaldehyde (379): 1H-Pyrazole-5-carbaldehyde 378 (0.25 g, 2.6 mmol) was dissolved in DMF (10 mL) at room temperature followed by addition of ethyl iodide (0.8 g, 5.2 mmol) and $K_2CO_3$ (1 g, 7.8 mmol) and stirred for 4 h. The reaction mixture was transferred into iced water and extracted with ethyl acetate (3×25 mL). The combined organic layers were washed with brine, dried over anhydrous $Na_2SO_4$, and concentrated under reduced pressure to give crude product which was purified by silica gel chromatography (0-10% Ethyl acetate/hexane) to obtain 1-ethyl-1H-pyrazole-5-carbaldehyde 379. (Yield: 0.3 g, 94%). $^1$H NMR (400 MHz, $CDCl_3$) δ 9.96 (s, 1H), 7.46 (d, J=1.6 Hz, 1H), 6.79 (d, J=2.4 Hz, 1H), 4.24-4.30 (m, 2H), 1.52-1.56 (m, 3H). LCMS: m/z 124.7 $[M+H]^+$, $t_R$=2.61 min.

(E)-Methyl 3-(1-ethyl-1H-pyrazol-5-yl)acrylate 380 was synthesized similar to methyl-3-(6-chloropyridin-3-yl)acrylate (47) (conversion of 46 to 47). (Yield: 70%). $^1$H NMR (400 MHz, $CDCl_3$) δ 7.69 (d, J=16 Hz, 1H), 7.39 (d, J=2.4 Hz, 1H), 6.50 (d, J=2 Hz, 1H), 6.42 (d, J=16 Hz, 1H), 4.13-4.29 (m, 2H), 3.74 (s, 3H), 1.51-1.54 (m, 3H). LCMS: m/z 180.8 $[M+H]^+$, $t_R$=1.47 min.

(E)-3-(1-Ethyl-1H-pyrazol-5-yl)acrylic acid 381 was synthesized similar to 3-(6-chloropyridine-3-yl)acrylic acid (48) (Conversion of 47 to 48). (Yield: 59%). $^1$H NMR (400 MHz, $CDCl_3$) δ 12.25 (bs, 1H), 7.79 (s, 1H), 7.42 (d, J=16 Hz, 1H), 6.71 (s, 1H), 6.38 (d, J=16 Hz, 1H), 4.12-4.27 (m, 2H), 1.35-1.38 (m, 3H). LCMS: m/z 167.05 $[M+H]^+$, $t_R$=2.52 min.

(E)-N-((5-(5-Acetylthiophen-2-yl)-7-chloro-2,3-dihydrobenzofuran-2-yl)methyl)-3-(1-ethyl-1H-pyrazol-5-yl)acrylamide 274 was synthesized using General Procedure 3. (Yield: 32%). $^1$H NMR (400 MHz, DMSO-$d_6$) δ 8.43-8.45 (m, 1H), 7.92 (d, J=4 Hz, 1H), 7.76 (d, J=2.4 Hz, 1H), 7.65 (d, J=2.4 Hz, 1H), 7.58-7.61 (m, 2H), 7.31 (d, J=15.6 Hz, 1H), 6.60 (d, J=15.6 Hz, 1H), 6.49 (s, 1H), 5.06-5.10 (m, 1H), 4.11-4.17 (m, 2H), 3.52-3.61 (m, 2H), 3.35-3.45 (m, 1H), 3.10 (dd, $J_1$=7.2 Hz, $J_2$=8.8 Hz, 1H), 2.52 (s, 3H), 1.35-1.39 (m, 3H). LCMS: m/z 456.06 $[M]^+$, $t_R$=2.06 min.

Synthesis of (E)-N-((7-chloro-5-methyl-2,3-dihydrobenzofuran-2-yl)methyl)-3-(pyridin-3-yl)acrylamide (275)

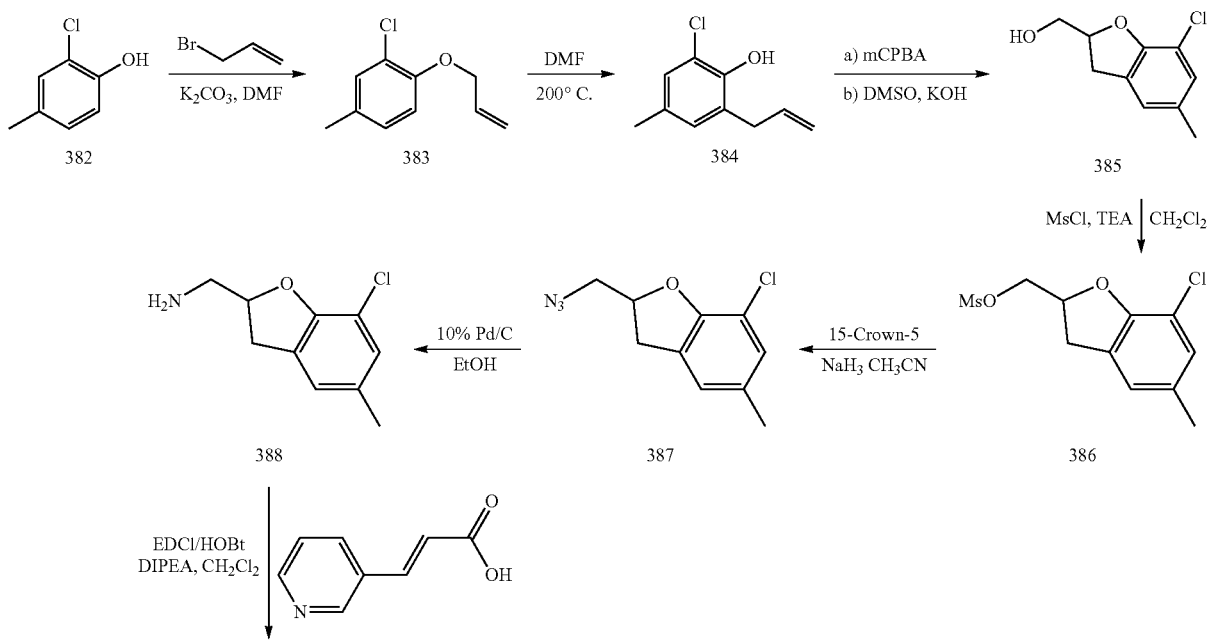

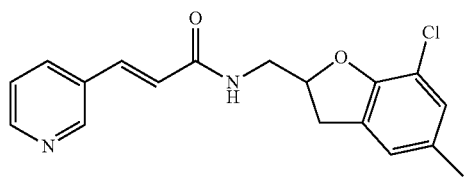

275

Synthesis of 1-(allyloxy)-2-chloro-4-methylbenzene (383): 2-Chloro-4-methylphenol 382 (15 g, 105.2 mmol) was dissolved in DMF (75 mL) at room temperature. $K_2CO_3$ (43.62 g, 315.6 mmol) and allyl bromide (25.30 g, 210.4 mmol) were added and heated at 110° C. for 1.5 h. The reaction mixture was allowed to cool to room temperature, transferred into iced water and extracted with ethyl acetate (3×500 mL). The combined organic layers were washed with brine solution, dried over anhydrous $Na_2SO_4$ and concentrated under reduced pressure to give 1-(allyloxy)-2-chloro-4-methylbenzene 383. The crude product was used for next step without further purification. $^1$H NMR (400 MHz, $CDCl_3$) δ 7.20 (d, J=1.6 Hz, 1H), 6.99-7.01 (m, 1H), 6.82 (d, J=8.4 Hz, 1H), 6.04-6.13 (m, 1H), 5.44-5.50 (m, 1H), 5.30-5.33 (m, 1H), 4.59-4.61 (m, 2H), 2.29 (s, 3H).

Synthesis of 2-allyl-6-chloro-4-methylphenol (384): 1-(Allyloxy)-2-chloro-4-methylbenzene 383 (19 g, 104.0 mmol) was dissolved in DMF (20 mL) at room temperature and heated at 220° C. for 15 h. The reaction mixture was allowed to cool to room temperature, transferred into iced water and extracted with ethyl acetate (3×500 mL). The combined organic layers were washed with brine solution, dried over anhydrous $Na_2SO_4$ and concentrated under reduced pressure to give 2-allyl-6-chloro-4-methylphenol (384). The crude product was used for next step without further purification. $^1$H NMR (400 MHz, $CDCl_3$) δ 7.03 (s, 1H), 6.86 (s, 1H), 5.96-6.06 (m, 1H), 5.47 (s, 1H), 5.09-5.14 (m, 2H), 3.41 (d, J=6.4 Hz, 2H), 2.20 (s, 3H). LCMS: m/z 181.13 [M−H], $t_R$=6.77 min.

Synthesis of (7-chloro-5-methyl-2,3-dihydrobenzofuran-2-yl)methanol (385): 2-Allyl-6-chloro-4-methylphenol (384) (17.5 g, 95.81 mmol) was dissolved in dichloromethane (350 mL) at room temperature. m-CPBA (41.33 g, 143.3 mmol) was added to the reaction mixture and stirred for 2 h at room temperature. The reaction mixture was transferred into iced water and extracted with $CH_2Cl_2$ (3×500 mL). The combined organic layer were washed with saturated sodium bicarbonate solution (200 mL), saturated sodium thiosulphate solution (200 mL) followed by brine solution (200 mL) respectively, dried over anhydrous $Na_2SO_4$ and concentrated under reduced pressure to give 18.5 g of crude epoxy intermediate. The crude epoxy intermediate was dissolved in DMSO (95 mL) at room temperature. The reaction mixture was cooled to 5° C. and a solution of KOH (7.31 g, 130.3 mmol) in 30 mL water was added drop wise by maintaining temperature at 5° C. and stirred for 1.5 h. The reaction mixture was allowed to warm to room temperature, transferred into iced water and extracted with ethyl acetate (3×500 mL). The combined organic layers were washed with brine solution, dried over anhydrous $Na_2SO_4$ and concentrated under reduced pressure to give (7-chloro-5-methyl-2,3-dihydrobenzofuran-2-yl)methanol (385). The crude product was used for next step without further purification. $^1$H NMR (400 MHz, $CDCl_3$) δ 6.95 (s, 1H), 6.89 (s, 1H), 4.97-5.03 (m, 1H), 3.92-3.95 (m, 1H), 3.74-3.79 (m, 1H), 3.25-3.32 (m, 1H), 3.10-3.16 (m, 1H), 2.27 (s, 3H).

Synthesis of (7-chloro-5-methyl-2,3-dihydrobenzofuran-2-yl)methyl methanesulfonate (386): (7-Chloro-5-methyl-2,3-dihydrobenzofuran-2-yl)methanol 385 (1.0 g, 5.03 mmol) was dissolved in dichloromethane (10 mL) at room temperature and cooled to 10° C. Methane sulphonyl chloride (0.58 mL, 7.55 mmol) was added dropwise followed by addition of triethylamine (0.917 g, 9.06 mmol). The reaction mixture was allowed to warm to room temperature and stirred for 2 h. The reaction mixture was transferred into iced water and extracted with $CH_2Cl_2$ (3×50 mL). The combined organic layers were washed with brine, dried over anhydrous $Na_2SO_4$ and concentrated under reduced pressure to afford (7-chloro-5-methyl-2,3-dihydrobenzofuran-2-yl)methyl methane sulfonate 386. The crude product was used for next step without further purification. $^1$H NMR (400 MHz, $CDCl_3$) δ 6.97 (s, 1H), 6.90 (s, 1H), 5.09-5.16 (m, 1H), 4.40-4.50 (m, 2H), 3.38-3.44 (m, 1H), 3.12-3.15 (m, 1H), 3.11 (s, 3H), 2.28 (s, 3H).

Synthesis of 2-(azidomethyl)-7-chloro-5-methyl-2,3-dihydrobenzofuran (387): (7-Chloro-5-methyl-2,3-dihydrobenzofuran-2-yl)methyl methane sulfonate 386 (1.3 g, 4.69 mmol) was dissolved in acetonitrile (10 mL) at room temperature. Sodium azide (0.610 g, 9.39 mmol) and 15-crown-5 (0.055 g, 0.24 mmol) was added and heated at 95° C. for 15 h. The reaction mixture was allowed to cool to room temperature, transferred into iced water and extracted with ethyl acetate (3×30 mL). The combined organic layers were washed with brine solution, dried over anhydrous $Na_2SO_4$ and concentrated under reduced pressure to give crude product. The crude product was purified by silica gel column chromatography (0-10% ethyl acetate/n-hexane) to obtain 2-(azidomethyl)-7-chloro-5-methyl-2,3-dihydrobenzofuran (387). (Yield: 0.75 g, 72%). $^1$H NMR (400 MHz, $CDCl_3$) δ 6.97 (s, 1H), 6.89 (s, 1H), 5.05-5.08 (m, 1H), 3.57-3.61 (m, 1H), 3.48-3.53 (m, 1H), 3.34-3.40 (m, 1H), 3.07-3.13 (m, 1H), 2.26 (s, 3H).

Synthesis of (7-chloro-5-methyl-2,3-dihydrobenzofuran-2-yl)methanamine (388): 2-(Azidomethyl)-7-chloro-5-methyl-2,3-dihydrobenzofuran 387 (0.75 g, 3.35 mmol) was dissolved in ethanol (12 mL) and degassed with $N_2$ gas. 10% Pd/C (50% wet, 75 mg) was added. $H_2$ gas was purged to the reaction mixture for 2 h. The reaction mixture was filtered through celite bed and filtrate was concentrated under reduced pressure to give (7-chloro-5-methyl-2,3-dihydrobenzofuran-2-yl)methanamine 388. The crude product was used for next step without further purification. $^1$H NMR (400 MHz, $CDCl_3$) δ 6.94 (s, 2H), 4.75-4.79 (m, 1H), 3.20-3.26 (m, 1H), 2.97-3.06 (m, 1H), 2.76-2.81 (m, 2H), 2.18 (s, 3H), 1.72-1.86 (m, 2H). LCMS m/z 197.83 [M+H]$^+$: $t_R$: 0.93 min.

Synthesis of (E)-N-((7-chloro-5-methyl-2,3-dihydrobenzofuran-2-yl)methyl)-3-(pyridin-3-yl)acrylamide (275): (7-Chloro-5-methyl-2,3-dihydrobenzofuran-2-yl)methanamine 388 (0.2 g, 1.01 mmol) was dissolved in dichloromethane (12 mL) at room temperature. (E)-3-(pyridin-3-yl)acrylic acid (0.181 g, 1.21 mmol), EDCl (0.232 g, 1.21 mmol), HOBt (0.164 g, 1.21 mmol) and DIPEA (0.52 mL, 3.03 mmol) were added and stirred for 1 h at room temperature. The reaction mixture was transferred into iced water and extracted with CH$_2$Cl$_2$ (3×25 mL). The combined organic layers were washed with brine solution, dried over anhydrous Na$_2$SO$_4$ and concentrated under reduced pressure to give crude product. The crude product was purified by silica gel column chromatography (0-3% methanol/CH$_2$Cl$_2$) to obtain of (E)-N-((7-chloro-5-methyl-2,3-dihydrobenzofuran-2-yl)methyl)-3-(pyridin-3-yl)acrylamide 275. (Yield: 0.15 g, 45%). $^1$H NMR (400 MHz, CDCl$_3$) δ 8.77 (d, J=1.6 Hz, 1H), 8.49-8.56 (m, 2H), 7.98-8.0 (m, 1H), 7.44-7.52 (m, 2H), 6.99 (s, 2H), 6.82 (d, J=15.6 Hz, 1H), 4.93-5.0 (m, 1H), 3.51-3.57 (m, 2H), 3.28-3.32 (m, 1H), 2.97-3.02 (m, 1H), 2.21 (s, 3H). LCMS m/z 328.96 [M+H]$^+$: t$_R$: 1.86 min.

Synthesis of (E)-N-((5-(5-acetylthiophen-2-yl)-7-chloro-2,3-dihydrobenzo furan-2-yl)methyl)-3-(6-chloroimidazo[2,1-b]thiazol-5-yl)acrylamide (276)

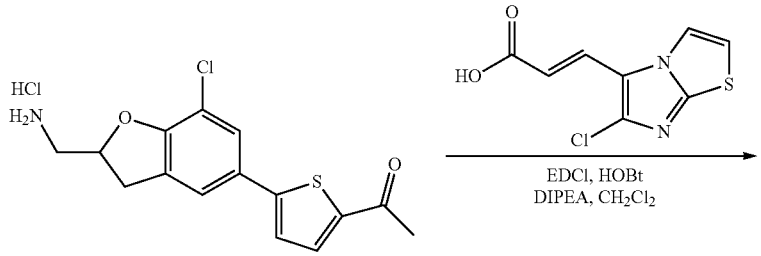

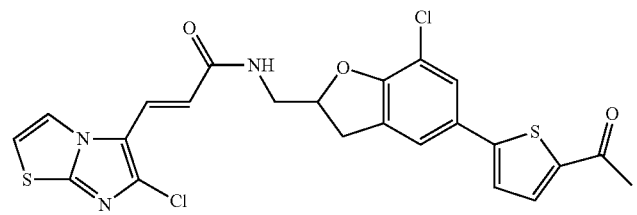

(E)-N-((5-(5-Acetylthiophen-2-yl)-7-chloro-2,3-dihydrobenzofuran-2-yl) methyl)-3-(6-chloroimidazo[2,1-b]thiazol-5-yl)acrylamide 276 was synthesized using General Procedure 3. Yield (21%). $^1$H NMR (400 MHz, DMSO-d$_6$) δ 8.36 (s, 1H), 8.21-8.22 (d, J=4.4 Hz, 1H), 7.91-7.92 (d, J=3.6 Hz, 1H), 7.58-7.66 (m, 4H), 7.48-7.52 (d, J=16 Hz, 1H), 6.77-6.81 (d, J=16 Hz, 1H), 5.01-5.18 (m, 1H), 3.63 (s, 2H), 3.40-3.47 (m, 1H), 3.08-3.14 (m, 1H), 2.55(s, 3H). LCMS: m/z 517.88 [M+H]$^+$, t$_R$=2.17 min.

Synthesis of (E)-N-((5-(5-acetylthiophen-2-yl)-7-chloro-2,3-dihydrobenzo furan-2-yl)methyl)-3-(5-methylisoxazol-3-yl)acrylamide (277)

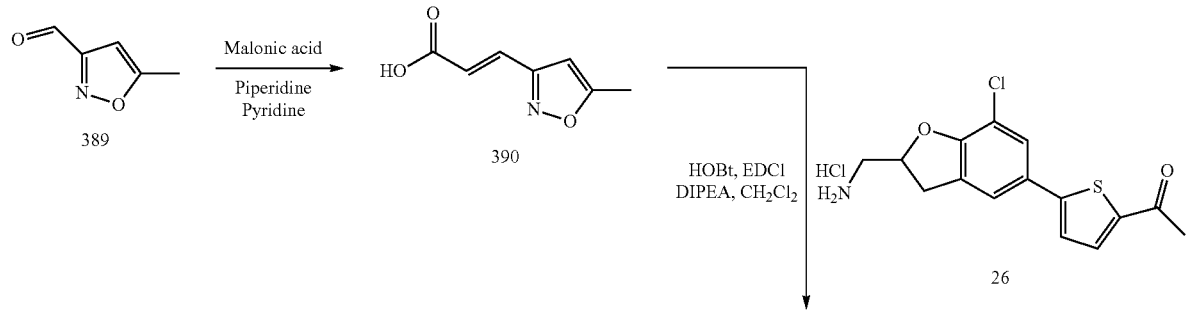

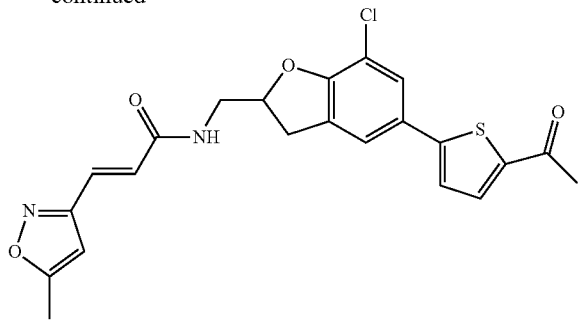

277

(E)-3-(5-Methylisoxazol-3-yl) acrylic acid 390 was synthesized similar to (E)-3-(6-methylpyridin-3-yl)acrylic acid 145 (conversion of 143 to 145). Yield (21%). $^1$H NMR (400 MHz, DMSO-d$_6$) δ 12.89 (bs, 1H), 7.37-7.40 (d, J=16 Hz, 1H), 6.76 (s, 1H), 6.67-6.71 (d, J=16 Hz, 1H), 2.43 (s, 3H). LCMS: m/z 153.56 [M+1]$^+$, t$_R$=0.81 min.

(E)-N-((5-(5-Acetylthiophen-2-yl)-7-chloro-2,3-dihydrobenzofuran-2-yl)methyl-3-(5-methylisoxazol-3-yl)acrylamide 277 was synthesized using General Procedure 3. Yield (21%). $^1$H NMR (400 MHz, DMSO-d$_6$) δ 8.60-8.71 (t, 1H), 7.92-7.93 (d, J=4.0 Hz, 1H), 7.65 (s, 1H), 7.61 (s, 1H), 7.58-7.59 (d, J=4.0 Hz, 1H), 7.28-7.32 (d, J=16 Hz, 1H), 6.79-6.83 (d, J=16 Hz, 1H), 6.51 (s, 1H), 5.02-5.12 (m, 1H), 3.55-3.63 (m, 2H), 3.37-3.46 (m, 1H), 3.07-3.13 (m, 1H), 2.53 (s, 3H), 2.43 (s, 3H). LCMS: m/z 442.96 [M+H]$^+$, t$_R$=2.16 min.

Synthesis of (E)-N-((5-(5-acetylthiophen-2-yl)-7-chloro-2,3-dihydrobenzofuran-2-yl)methyl)-3-(1H-imidazol-2-yl)acrylamide (278)

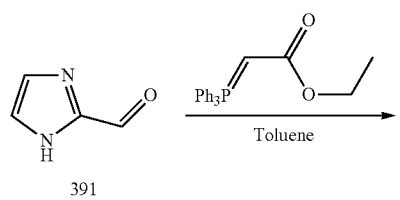

391

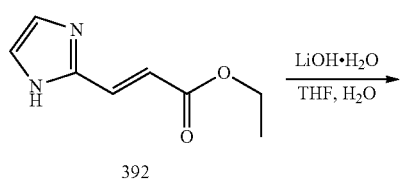

392

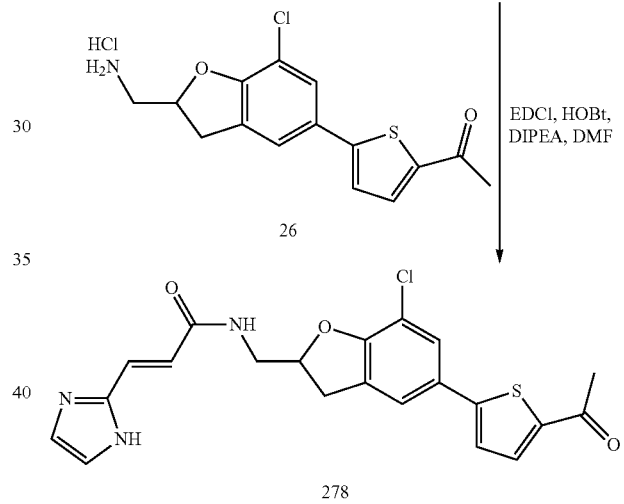

278

(E)-Methyl 3-(1H-imidazol-2-yl) acrylate 392 was synthesized similar to methyl-3-(6-chloropyridin-3-yl)acrylate (47) (conversion of 46 to 47). Yield (35%). $^1$H NMR (400 MHz, DMSO-d$_6$) δ 12.73 (s, 1H), 7.37-7.41 (d, J=16 Hz, 1H), 7.13 (s, 2H), 6.53-6.57 (d, J=16 Hz, 1H), 4.16-4.21 (q, 2H), 1.24-1.27 (t, 3H). LCMS: m/z 166.75 [M+H]$^+$ t$_R$=2.448 min.

(E)-3-(1H-Imidazol-2-yl) acrylic acid 393 was synthesized similar to 3-(6-chloropyridine-3-yl)acrylic acid (48) (Conversion of 47 to 48). Yield (42%). $^1$H NMR (400 MHz, DMSO-d$_6$) δ 15.48 (bs, 1H), 13.23 (bs, 1H), 7.61-7.81 (s, 2H), 7.48-7.52 (d, J=16.4 Hz, 1H), 7.18-7.22 (d, J=16.4 Hz, 1H). LCMS: m/z 139.02 [M+H]$^+$, t$_R$=1.922 min.

(E)-N-((5-(5-Acetylthiophen-2-yl)-7-chloro-2,3-dihydrobenzofuran-2-yl)methyl)-3-(1H-imidazol-2-yl)acrylamide 278 was synthesized using General Procedure 3. Yield (7%). $^1$H NMR (400 MHz, DMSO-d$_6$) δ 13.25 (bs, 1H), 8.57-8.59 (t, 1H), 7.92-7.93 (d, J=4 Hz, 1H), 7.58-7.65 (m, 3H), 7.25-7.29 (d, J=16 Hz, 2H), 7.16-7.18 (d, J=8 Hz, 1H), 6.74-6.77(d, J=12 Hz, 1H), 5.08-5.11 (t, 1H), 3.55-3.62 (m, 2H), 3.46-3.52 (m, 1H), 3.12-3.44 (m, 1H), 2.51 (s, 3H). LCMS: m/z 427.95 [M+H]⁺, $t_R$=1.637 min.

Synthesis of (E)-N-((5-(5-acetylthiophen-2-yl)-7-chloro-2,3-dihydrobenzofuran-2yl)methyl)-3-(pyridazin-3-yl)acrylamide (279)

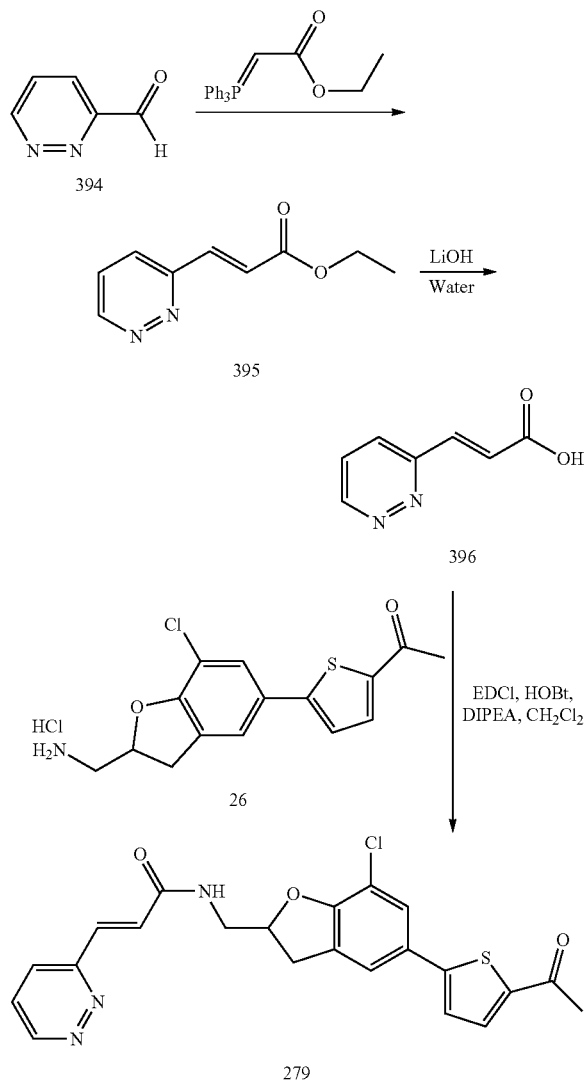

Synthesis of (E)-ethyl 3-(pyridazin-3-yl) acrylate (395): Triethylphosphano Acetate (3.73 g, 16.6 mmol) and KO′Bu (1.82 g, 16.6 mmol) were dissolved in THF (20 mL). Pyridazine-3-carbaldehyde (1.0 g, 9.2 mmol) was added and stirred at room temperature for 15 min. The reaction mixture was transferred into water (100 mL) and extracted with EtOAc (25 mL×3). The combined organic layers were washed with brine, dried over anhydrous Na₂SO₄ and concentrated under reduced pressure to give (E)-ethyl 3-(pyridazin-3-yl)acrylate, which was used in next step without further purification. Yield (1.6 g, 98%), LCMS: m/z 178.8 [M+H]⁺, $t_R$=1.78 min.

Synthesis of (E)-3-(pyridazin-3-yl) acrylic acid (396): (E)-Ethyl 3-(pyridazin-3-yl) acrylate 395 (1.6 g, 9.2 mmol) was dissolved in THF (20 mL). A solution of LiOH (0.8 g, 18.51 mmol) in water (10 mL) was added at 25° C. and the reaction mixture was stirred at 25° C. for 4 h. The reaction mixture was concentrated under reduced pressure and neutralized with dilute HCl to obtain product (E)-3-(pyridazin-3-yl) acrylic acid 396. Yield (0.5 g). ¹H NMR (400 MHz, DMSO-d₆) δ 12.8 (s, 1H, D₂O exchangeable), 9.2 (t, 1H), 8.13-8.15 (t, 1H), 7.71-7.79 (m, 2H), 6.99-7.03 (d, J=16 Hz, 1H). LCMS: m/z 150.7 found 151.0 [M+H]⁺, $t_R$=1.6 min.

Synthesis of (E)-N-((5-(5-acetylthiophen-2-yl)-7-chloro-2,3-dihydrobenzofuran-2-yl)methyl)-3-(pyridazin-3-yl) acrylamide (279): (E)-N-((5-(5-Acetylthiophen-2-yl)-7-chloro-2,3-dihydrobenzofuran-2-yl)methyl)-3-(pyridazin-3-yl)acrylamide 279 was synthesized using General Procedure 3. Yield (88%). ¹H NMR (400 MHz, DMSO-d₆) δ 9.18-9.20 (t, 1H), 8.76-8.79 (t, 1H), 7.91-7.93 (m, 2H), 7.73-7.76 (m, 1H), 7.65 (m, 1H), 7.58-7.61 (m, 2H), 7.26-7.30 (d, J=16 Hz, 1H), 5.11 (m, 1H), 3.55-3.68 (m, 2H), 3.41-3.48 (m, 1H), 3.09-3.18 (m, 1H), 2.51 (s, 3H): LCMS: m/z 440.2 [M+H]⁺, $t_R$=2.13 min.

Chiral Separation of 279: Preparation of (S,E)-N-((5-(5-acetylthiophen-2-yl)-7-chloro-2,3-dihydrobenzofuran-2-yl)methyl)-3-(pyridazin-3-yl)acrylamide and (R,E)-N-((5-(5-acetylthiophen-2-yl)-7-chloro-2,3-dihydrobenzofuran-2-yl)methyl)-3-(pyridazin-3-yl)acrylamide Compound 279 was subjected to chiral separation employing HPLC to give single enantiomers, 317 and 318. The conditions of the separation were as follows:

| Mobile Phase: (A) | 0.1% FA IN N-HEPTANE |
|---|---|
| Mobile Phase: (B) | 0.1% FA IN ETOH |
| Wave length: | 346 nm |
| Flow Rate: | 1.00 ml/min |
| Column ID: | Chiral PaK - IA (250*4.6, 5u) |
| Gradient: | Gradient |

| % T | % B |
|---|---|
| 0.01 | 25.00 |
| 15.00 | 90.00 |
| 30.00 | 90.00 |
| 30.01 | 25.00 |
| 35.00 | 25.00 |

The absolute configuration of Compounds 317 and 318 has not been determined. Therefore, Compound 317, as used herein, refers to the compound with a retention time of 16.53 minutes in the HPLC method employed to separate it from its enantiomer, Compound 318. Conversely, Compound 318, as used herein, refers to the compound with a retention time of 30.13 minutes in the HPLC method employed to separate it from its enantiomer, Compound 317.

Compound 317: ¹H NMR (400 MHz, DMSO-d₆) δ 9.19 (dd, J₁=1.6 Hz, J₂=1.2 Hz, 1H), 8.77 (t, J=5.8 Hz, 1H), 7.93-7.91 (m, 2H), 7.76-7.73 (m, 1H), 7.66-7.58 (m, 4H), 7.28 (d, J=15.6 Hz, 1H), 5.17-5.11 (m, 1H), 3.68-3.55 (m, 2H), 3.48-3.44 (m, 1H), 3.15-3.09 (m, 1H), 2.51 (s, 3H). LCMS: m/z 440.12 [M+H]⁺, $t_R$=2.06 min. Chiral purity: >99%; $t_R$ 16.53 min.

Compound 318: ¹H NMR (400 MHz, DMSO-d₆) δ 9.19 (dd, J₁=1.6 Hz, J₂=1.2 Hz, 1H), 8.77 (t, J=5.8 Hz, 1H), 7.93-7.91 (m, 2H), 7.76-7.73 (m, 1H), 7.66-7.58 (m, 4H), 7.28 (d, J=15.6 Hz, 1H), 5.17-5.11 (m, 1H), 3.68-3.55 (m, 2H), 3.48-3.44 (m, 1H), 3.15-3.09 (m, 1H), 2.51 (s, 3H). LCMS: m/z 440.12 [M+H]⁺, $t_R$=2.06 min. Chiral purity: >99%; $t_R$ 30.13 min.

233
(S,E)-N-((5-(5-acetylthiophen-2-yl)-7-chloro-2,3-dihydrobenzofuran-2-yl)methyl)-3-(pyridazin-3-yl)acrylamide and (R,E)-N-((5-(5-acetylthiophen-2-yl)-7-chloro-2,3-dihydrobenzofuran-2-yl)methyl)-3-(pyridazin-3-yl)acrylamide can be depicted as follows:
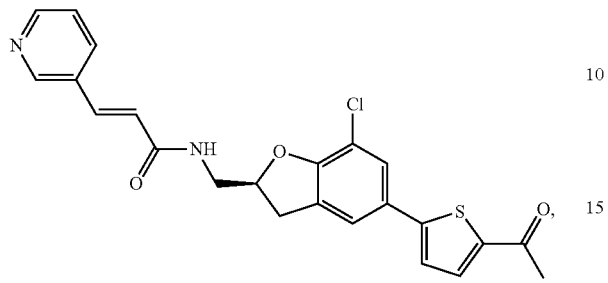
234
-continued
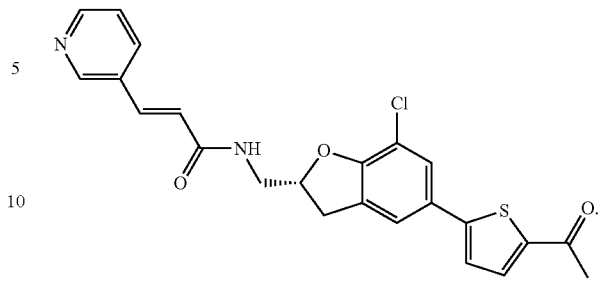
(E)-N-((5-(5-acetylthiophen-2-yl)-7-chloro-2,3-dihydrobenzofuran-2-yl)methyl)-3-(5-methylpyridin-3-yl)acrylamide (280)
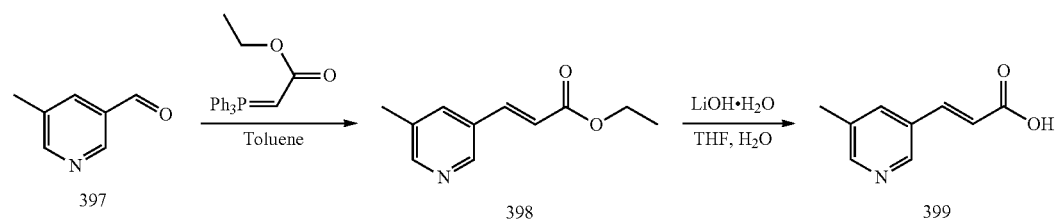
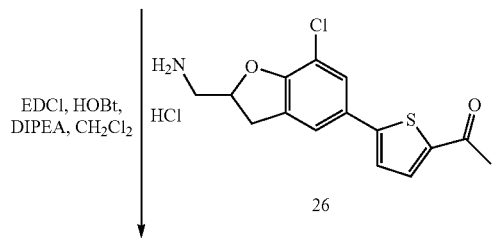
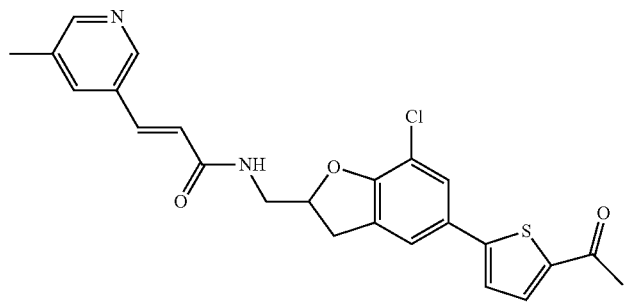
280

5-Methylnicotinaldehyde 397 (0.3 g, 2.4 mmol) was dissolved in THF (20 mL). Triethyl phosphonoacetate (1.0 g, 4.4 mmol) and potassium-t-butoxide (0.5 g, 4.4 mmol) was added at 25° C. and stirred 15 min. The reaction mixture was transferred into iced water and extracted with ethyl acetate (15 mL×3). The combined organic layers were washed with brine, dried over anhydrous $Na_2SO_4$ and concentrated under reduced pressure. The crude product was purified by column chromatography (0-2% methanol/dichloromethane) to obtain (E)-ethyl 3-(5-methylpyridin-3-yl) acrylate 398. Yield (0.4 g, 84%). LCMS: m/z 191.8 $[M+H]^+$, $t_R$=1.17 min.

(E)-3-(5-Methylpyridin-3-yl) acrylic acid 399 was synthesized similar to 3-(6-chloropyridine-3-yl)acrylic acid 48 (Conversion of 47 to 48). Yield (29%). $^1$H NMR (400 MHz, DMSO-$d_6$) δ 12.54 (s, 1H), 8.64 (s, 1H), 8.43 (s, 1H), 8.00 (s, 1H), 7.57-7.61 (d, J=16, 1H), 6.64-6.68 (d, J=16, 1H), 2.32 (s, 3H), LCMS: m/z 164.05 $[M-H]^+$, $t_R$=0.96 min.

(E)-N-((5-(5-Acetylthiophen-2-yl)-7-chloro-2,3-dihydrobenzofuran-2-yl)methyl)-3-(5-methylpyridin-3-yl)acrylamide 280 was synthesized using using General Procedure 3. Yield (22%). $^1$H NMR (400 MHz, DMSO-$d_6$) δ 8.49-8.56 (m, 2H), 8.40 (s, 1H), 7.91-7.92 (d, J=4 Hz, 1H), 7.79 (s, 1H), 7.58-7.61 (m, 2H), 6.79-6.83(d, J=16, 1H), 7.44-7.48 (d, J=16, 1H), 5.10 (m, 1H), 3.57-3.62 (m, 2H), 3.40-3.46 (m, 1H), 3.12-3.13 (m, 1H), 2.51-2.52 (m, 3H), 2.32 (s, 3H). LCMS: m/z 452.97 $[M+H]^+$, $t_R$=1.93 min.

Synthesis of (E)-N-((5-(5-acetylthiophen-2-yl)-7-chloro-2,3-dihydrobenzo furan-2-yl)methyl)-3-(1,2,3-thiadizol-5-yl)acrylamide (281)

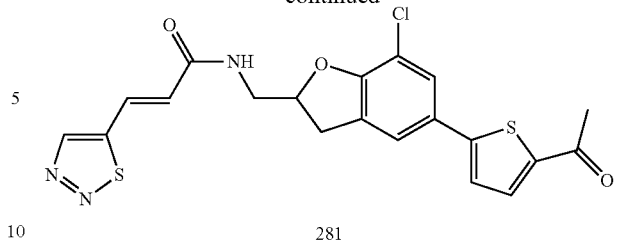

(E)-Ethyl 3-(1,2,3-thiadiazol-5-yl) acrylate 401 was synthesized similar to methyl-3-(6-chloropyridin-3-yl)acrylate 47 (conversion of 46 to 47). Yield (30%). $^1$H NMR (400 MHz, $CDCl_3$) 8.61 (s, 1H), 7.93-7.97 (d, J=16 Hz, 1H), 7.02-7.06 (d, J=15.6 Hz, 1H), 4.29-4.35 (q, 2H), 1.36-1.39 (t, 3H). LCMS: m/z 184.82 $[M+H]^+$, $t_R$=1.616 min.

(E)-3-(1,2,3-Thiadiazol-5-yl)acrylic acid 402: (E)-ethyl 3-(1,2,3-thiadiazol-5-yl) acrylate (401) (0.5 g, 4.3859 mmol) was dissolved in methanol (5 mL). 5% aqueous solution of sodium hydroxide (0.107 g, 2.67 mmol) was added at 25° C. and the reaction mixture was stirred at 25° C. for 4 h. The reaction mixture was diluted with ethyl acetate and the aq. layer was acidified with dil. HCl (pH=2) and removed. The organic layer was washed with brine, dried over anhydrous $Na_2SO_4$ and concentrated under reduced pressure to obtain (E)-3-(1,2,3-thiadiazol-5-yl)acrylic acid 402. Yield (0.2 g, 48%). $^1$H NMR (400 MHz, DMSO-$d_6$) δ 9.57 (s, 1H), 7.90-7.94 (d, J=16 Hz, 1H), 6.90-6.94 (d, J=15.6 Hz, 1H).

(E)-N-((5-(5-Acetylthiophen-2-yl)-7-chloro-2,3-dihydrobenzo furan-2-yl)methyl)-3-(1,2,3-thiadiazol-5-yl)acrylamide 281 was synthesized using General Procedure 3. Yield (12%). $^1$H NMR (400 MHz, DMSO-$d_6$) δ 9.38 (s, 1H), 8.73-8.76 (t, 1H), 7.91-7.92 (d, J=4 Hz, 1H), 7.75-7.79 (d, J=15.6 Hz, 1H), 7.58-7.61 (m, 2H), 7.20-7.24 (d, J=15.6 Hz, 1H), 5.10-5.13 (m, 1H), 3.56-3.66 (m, 2H), 3.41-3.48 (m, 1H), 3.09-3.15 (m, 1H), 2.57 (s, 3H). LCMS: m/z 445.96 $[M+H]^+$, $t_R$=2.084 min.

Synthesis of (Z)-N-((5-(5-acetylthiophen-2-yl)-7-chloro-2,3-dihydrobenzofuran-2-yl) methyl)-3-(pyridin-3-yl)but-2-enamide (282)

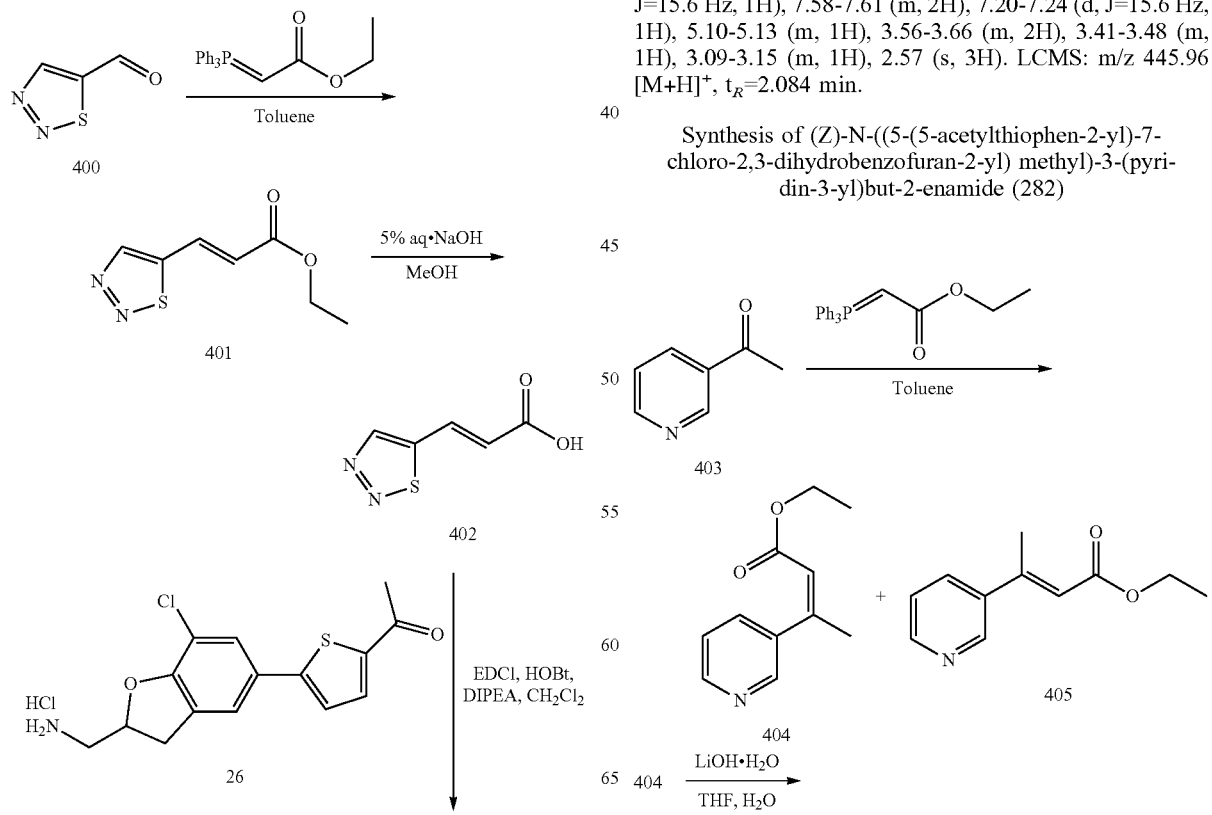

237

-continued

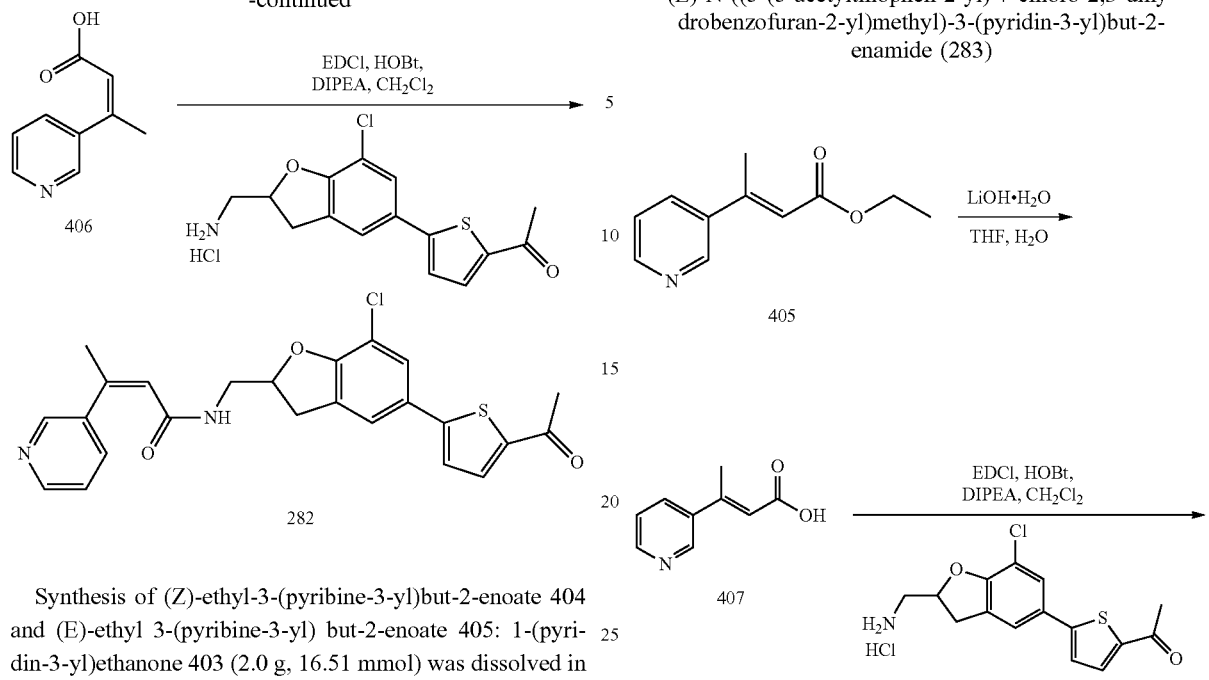

Synthesis of (Z)-ethyl-3-(pyribine-3-yl)but-2-enoate 404 and (E)-ethyl 3-(pyribine-3-yl) but-2-enoate 405: 1-(pyridin-3-yl)ethanone 403 (2.0 g, 16.51 mmol) was dissolved in toluene (20 mL) at room temperature. (Carbethoxymethylene) triphenyiphosphorane (8.63 g, 24.77 mmol) was added and stirred at room temperature for 1 h. The reaction mixture was transferred into iced water and extracted with ethyl acetate (3×200 mL). The combined organic layers were washed with brine, dried over anhydrous $Na_2SO_4$, and concentrated under reduced pressure. The crude product was purified by silica gel chromatography (0-50% ethyl acetate/n-hexane) to give (Z)-ethyl 3-(pyribine-3-yl)but-2-enoate 404 and (E) ethyl 3-(pyribine-3-yl)but-2-enoate 405.

404: Yield (0.9 g, 29%). $^1$H NMR (400 MHz, DMSO-$d_6$) δ 8.79 (s, 1H), 8.78-8.59 (m, 2H), 8.02-7.99 (m, 1H), 7.46-7.43 (m, 1H), 6.24 (s, 1H), 4.19-4.13 (m, 1H), 2.53 (s, 3H), 1.25 (t, J=16 Hz, 3H). LCMS: m/z 192.12 [M+H]$^+$, $t_R$=1.25 min.

405: Yield (0.8 g, 26%). $^1$H NMR (400 MHz, DMSO-$d_6$) δ 8.51-8.42 (m, 1H), 8.42 (d, J=2.4 Hz, 1H), 7.69-7.66 (m, 1H), 7.40-7.37 (m, 1H), 6.07 (s, 1H), 3.96-3.91 (m, 2H), 2.18 (s, 3H), 1.03 (t, J=16 Hz, 3H). LCMS: m/z 191.77 [M+H]$^+$, $t_R$=1.69 min.

(Z) 3-(Pyribine-3-yl)but-2-enoic acid 406 was synthesized similar to 3-(6-chloropyridine-3-yl)acrylic acid 48 (Conversion of 47 to 48). Yield (0.2 g, 47%). $^1$H NMR (400 MHz, DMSO-$d_6$) δ 12.43 (s, 1H), 8.76-8.75 (m, 1H), 8.59-8.58 (m, 1H), 7.99-7.96 (m, 1H), 7.46-7.43 (m, 1H), 6.18 (s, 1H), 2.51 (s, 3H). LCMS: m/z 163.75 [M+H]$^+$, $t_R$=2.38 min.

(Z)-N-((5-(5-Acetylthiophen-2-yl)-7-chloro-2,3-dihydrobenzofuran-2-yl)methyl)-3-(pyridin-3-yl)but-2-enamide 282 was synthesized using General Procedure 3. Yield (0.03 g, 26%). $^1$H NMR (400 MHz, DMSO-$d_6$) δ 8.71 (s, 1H), 8.59 (d, J=6 Hz, 1H), 8.41 (t, J=5.6 Hz, 1H) 7.93-7.88 (m, 2H), 7.66-7.58 (m, 3H), 7.45-7.42 (m, 1H), 6.35 (s, 1H), 5.09 (m, 1H), 3.59-3.50 (m, 2H), 3.46-3.50 (m, 1H), 3.14-3.08 (m, 1H), 2.53 (s, 6H). LCMS: m/z 453.0 [M+H]$^+$, $t_R$=1.95 min.

238

(E)-N-((5-(5-acetylthiophen-2-yl)-7-chloro-2,3-dihydrobenzofuran-2-yl)methyl)-3-(pyridin-3-yl)but-2-enamide (283)

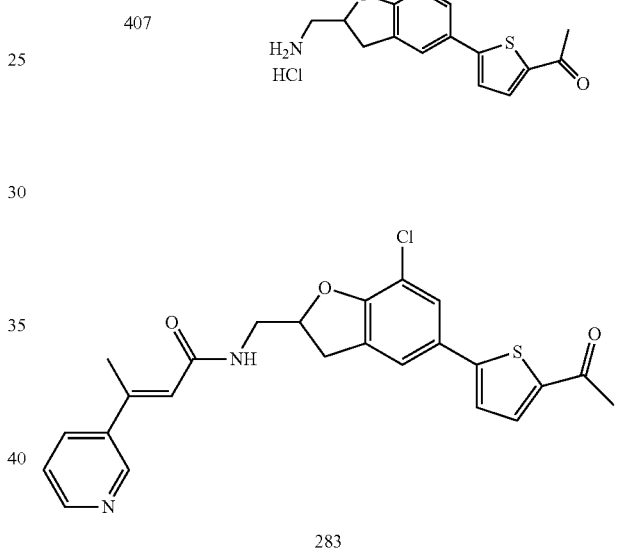

(E) 3-(Pyribine-3-yl)but-2-enoic acid 407 was synthesized similar to 3-(6-chloropyridine-3-yl)acrylic acid 48 (Conversion of 47 to 48). Yield (0.2 g, 47%). $^1$H NMR (400 MHz, DMSO-$d_6$) δ 12.10 (s, 1H), 8.48 (d, J=6.4 Hz, 1H), 8.42 (d, J=1.6 Hz, 1H), 7.69-7.66 (m, 1H), 7.39-7.35 (m, 1H), 6.00 (s, 1H), 2.16 (s, 3H). LCMS: m/z 163.75 [M+H]$^+$, $t_R$=2.36 min.

(E)-N-((5-(5-Acetylthiophen-2-yl)-7-chloro-2,3-dihydrobenzofuran-2-yl)methyl)-3-(pyridin-3-yl)but-2-enamide 283 was synthesized using General Procedure 3. Yield (0.03 g, 26%). $^1$H NMR (400 MHz, DMSO-$d_6$) δ 8.44 (d, J=3.2 Hz, 1H), 8.41 (s, 1H) 8.38 (t, J=5.6 Hz 1H), 7.92 (d, J=4 Hz, 1H), 7.64-7.58 (m, 4H), 7.34-7.31 (m, 1H), 6.09 (s, 1H), 4.69-4.92 (m, 1H), 3.44-3.34 (m, 3H), 3.01-2.95 (m, 1H), 2.53 (s, 3H), 2.11 (s, 3H). LCMS: m/z 453.0 [M+H]$^+$, $t_R$=1.82 min.

(E)-N-((5-(5-acetylthiophen-2-yl)-7-chloro-2,3-dihydrobenzofuran-2-yl)methyl)-3-(5-chloro-1-(4-fluorophenyl)-3-methyl-1H-pyrazol-4-yl)acrylamide (284)

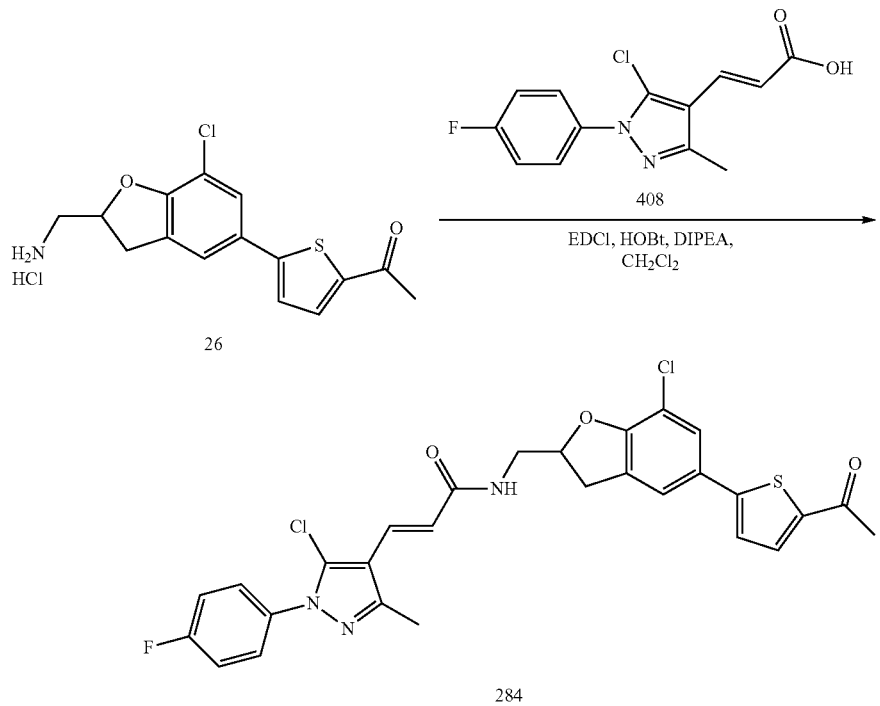

(E)-N-((5-(5-Acetylthiophen-2-yl)-7-chloro-2,3-dihydrobenzofuran-2-yl)methyl)-3-(5-chloro-1-(4-fluorophenyl)-3-methyl-1H-pyrazol-4-yl)acrylamide 284 was synthesized using General Procedure 3. Yield (0.03 g, 50%). $^1$H NMR (400 MHz, DMSO-$d_6$) δ 8.55 (t, J=5.6 Hz, 1H), 7.93 (d, J=4 Hz, 1H), 7.66-7.75 (m, 4H), 7.44 (t, J=8.8 Hz, 2H), 7.32 (d, J=16 Hz, 1H), 6.68 (d, J=16.4 Hz, 1H), 5.11-5.09 (m, 1H) 3.61-3.57 (m, 2H), 3.46-3.40 (m, 2H), 3.14-3.08 (m, 1H), 2.53 (s, 3H), 2.39 (s, 3H). LCMS: m/z 570.08 [M+H]$^+$, $t_R$=2.49 min.

Synthesis of (E)-N-((5-(5-acetylthiophen-2-yl)-7-chloro-2,3-dihydrobenzo furan-2-yl)methyl)-3-(2,5-dimethyl-1-(thiazol-2-yl)-1H-pyrrol-3-yl)acrylamide (285)

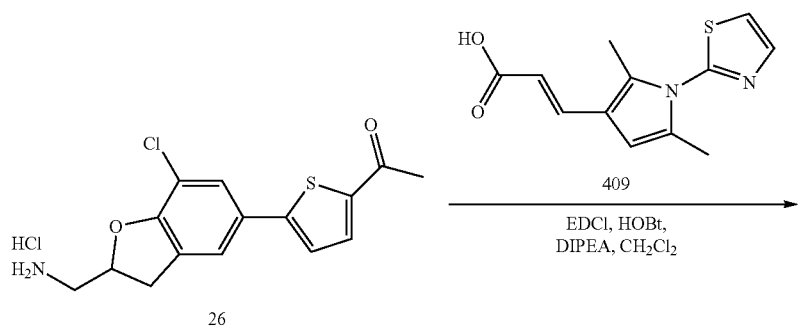

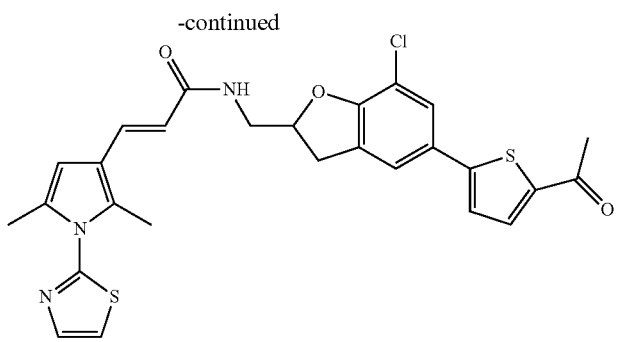

285

(E)-N-((5-(5-Acetylthiophen-2-yl)-7-chloro-2,3-dihydrobenzofuran-2-yl)methyl)-3-(2,5-dimethyl-1-(thiazol-2-yl)-1H-pyrrol-3-yl)acrylamide 285 was synthesized using General Procedure 3. Yield (29%). $^1$H NMR (400 MHz, DMSO-$d_6$) δ 8.26 (bs, 1H), 7.92-7.93 (m, 2H), 7.87-7.88 (d, J=3.6 Hz, 1H), 7.65 (s, 1H), 7.58-7.61 (m, 2H), 7.35-7.39 (d, J=15.6 Hz, 1H), 6.23-6.27 (d, J=15.6 Hz, 1H), 6.19 (s, 1H), 5.06-5.08 (m, 1H), 3.49-3.59 (m, 2H), 3.41-3.45 (m, 1H), 3.08-3.14 (m, 1H), 2.51 (s, 3H), 2.18 (s, 3H), 2.10 (s, 3H). LCMS: m/z 538.04 [M+H]$^+$, $t_R$=2.34 min.

Synthesis of (E)-N-((5-(5-acetylthiophen-2-yl)-7-chloro-2,3-dihydrobenzofuran-2-yl)methyl)-2-cyano-3-(furan-3-yl) acrylamide (286)

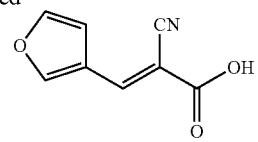

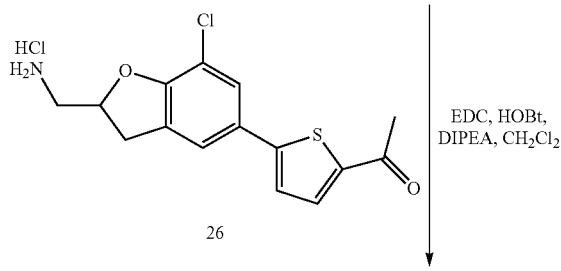

(E)-2-Cyano-3-(furan-3-yl) acrylic acid 412 was synthesized similar to 3-(6-chloropyridine-3-yl)acrylic acid 48 (Conversion of 47 to 48). Yield (38%). $^1$H NMR (400 MHz, DMSO) δ 13.83 (s, 1H), 8.55(s, 1H), 8.29 (s, 1H), 7.97-7.96 (m, 1H), 7.19-7.18 (m, 1H). LCMS: m/z 161.8 [M+H]$^-$, $t_R$=0.79 min.

(E)-N-((5-(5-Acetylthiophen-2-yl)-7-chloro-2,3-dihydrobenzofuran-2-yl)methyl)-2-cyano-3-(furan-3-yl) acrylamide 286 was synthesized using General Procedure 3. Yield (2%). $^1$H NMR (400 MHz, DMSO) δ 8.67-8.70 (m, 1H), 8.46 (s, 1H), 8.13 (s, 1H), 7.92-7.95 (m, 1H), 7.51-7.66 (m, 4H), 7.16 (s, 1H), 5.09-5.16 (m, 1H), 3.32-3.63 (m, 2H), 2.53-3.18 (m, 2H), 2.50-2.51 (m, 3H). LCMS: m/z 452.97 [M+H]$^+$, $t_R$=2.33 min.

Synthesis of (E)-N-((5-(5-acetylthiophen-2-yl)-7-chloro-2,3-dihydrobenzo furan-2-yl)methyl)-3-(2-methyl-7-(trifluoromethyl)pyrazolo[1,5-a]pyrimidin-3-yl) acryl amide (287)

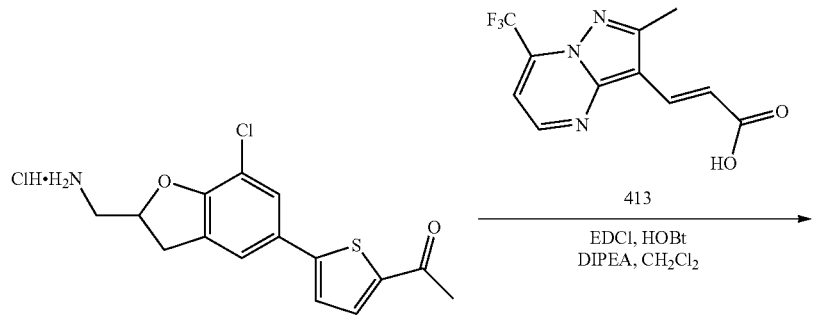

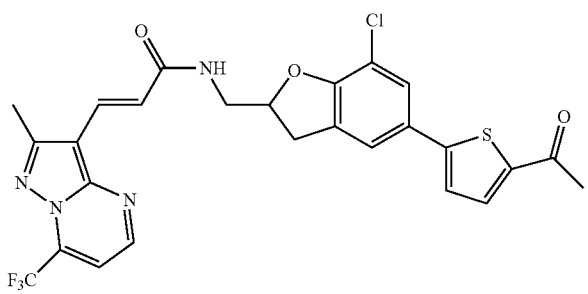

(E)-N-((5-(5-Acetylthiophen-2-yl)-7-chloro-2,3-dihydrobenzofuran-2-yl)methyl)-3-(2-methyl-7-(trifluoromethyl)pyrazolo[1,5-a]pyrimidin-3-yl)acrylamide 287 was synthesized using General Procedure 3. Yield (21%). $^1$H NMR (400 MHz, DMSO-$d_6$) δ 8.83-8.84 (d, J=4.4 Hz, 1H), 8.57-8.60 (t, 1H), 7.91-7.92 (d, J=4.0 Hz, 1H), 7.58-7.67 (m, 5H), 7.04-7.08 (d, J=15.6 Hz, 1H), 5.07-5.14 (m, 1H), 3.51-3.66 (m, 2H), 3.34-3.47 (m, 1H), 3.10-3.16 (m, 1H), 2.60 (s, 3H), 2.52(s, 3H). LCMS: m/z 560.99 [M+H]$^+$, $t_R$=2.33 min.

Synthesis of (E)-N-((5-(5-acetylthiophen-2-yl)-7-chloro-2,3-dihydrobenzo furan-2-yl)methyl)-3-(2,5-dimethyl-1-(5-methylisoxazol-3-yl)-1H-pyrrol-3-yl) acrylamide (288)

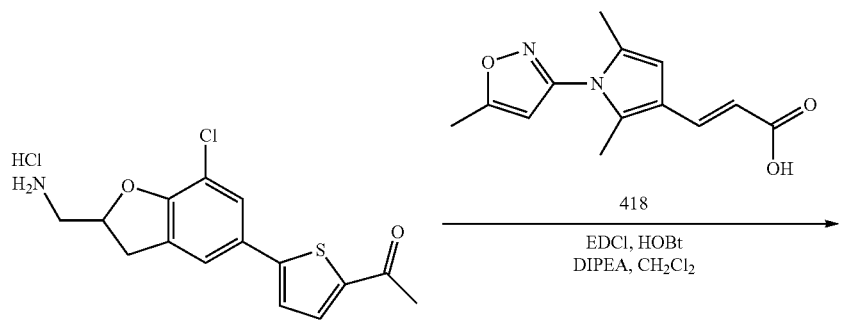

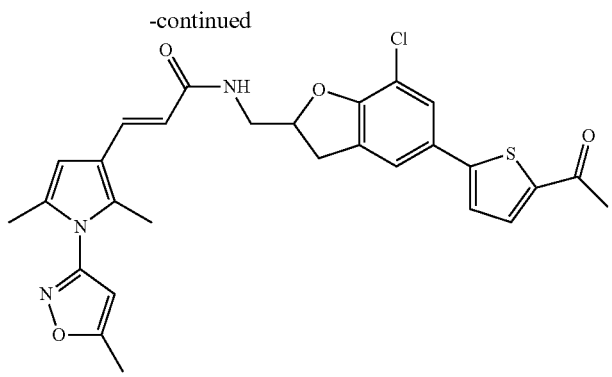

288

(E)-N-((5-(5-Acetylthiophen-2-yl)-7-chloro-2,3-dihydrobenzofuran-2-yl)methyl-3-(2,5-dimethyl-1-(5-methylisoxazol-3-yl)-1H-pyrrol-3-yl)acrylamide 288 was synthesized using General Procedure 3. Yield (21%). $^1$H NMR (400 MHz, DMSO-d$_6$) δ 8.23-8.26 (t, 1H), 7.91-7.92 (d, J=4.0 Hz, 1H), 7.65 (s, 1H), 7.61 (s, 1H), 7.58-7.59 (d, J=4.0 Hz, 1H), 7.35-7.39 (d, J=15.6 Hz, 1H), 6.65 (s, 1H), 6.21-7.25 (d, J=15.6 Hz, 1H), 6.18 (s, 1H), 5.01-5.11 (m, 1H), 3.48-3.61 (m, 2H), 3.35-3.44 (m, 1H), 3.08-3.14 (m, 1H), 2.50(s, 6H), 2.19 (s, 3H), 2.12 (s, 3H). LCMS: m/z 536.03 [M+H]$^+$, t$_R$=2.37 min.

Synthesis of (E)-N-((5-(5-acetylthiophen-2-yl)-7-chloro-2,3-dihydrobenzofuran-2-yl)methyl)-3-(1-isopropyl-6-oxo-6,7-dihydro-1H-pyrazolo[3,4-b]pyridin-5-yl)acrylamide (289)

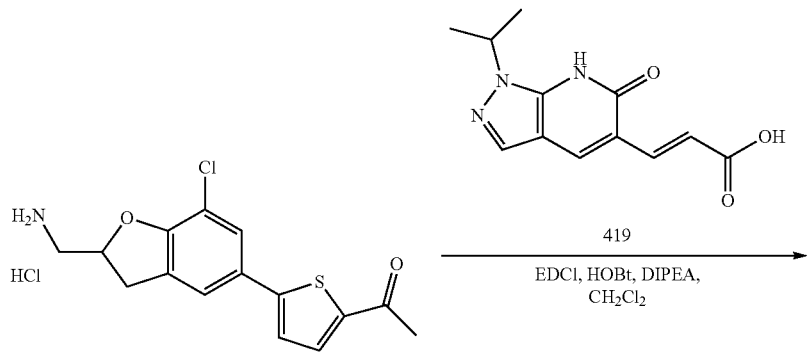

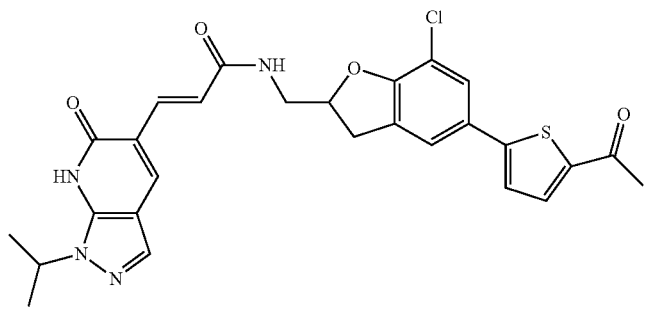

289

(E)-N-((5-(5-Acetylthiophen-2-yl)-7-chloro-2,3-dihydrobenzofuran-2-yl)methyl)-3-(1-isopropyl-6-oxo-6,7-dihydro-1H-pyrazolo[3,4-b]pyridin-5-yl)acrylamide 289 was synthesized using General Procedure 3. Yield (4 mg, 13%). $^1$H NMR (400 MHz, DMSO-d$_6$) δ 12.55-12.75 (bs, 1H), 8.46-8.49 (m, 1H), 8.21 (s, 1H), 7.91 (d, J=4 Hz, 1H), 7.85 (s, 1H), 7.66 (d, J=12 Hz, 1H), 7.61 (s, 1H), 7.58 (d, J=4 Hz, 1H), 7.43 (s, 1H), 7.11-7.18 (m, 1H), 5.05-5.10 (m, 1H), 4.89-4.91 (m, 1H), 3.61-3.63 (m, 1H), 3.34-3.59 (m, 2H), 3.07-3.15 (m, 1H), 2.52 (s, 3H), 1.40 (d, J=8 Hz, 6H). LCMS: m/z 537.09 [M+H]$^+$, $t_R$=2.0 min.

(E)-N-((5-(5-acetylthiophen-2-yl)-7-chloro-2,3-dihydrobenzofuran-2-yl)methyl)-3-(isoxazol-5-yl)acrylamide (293)

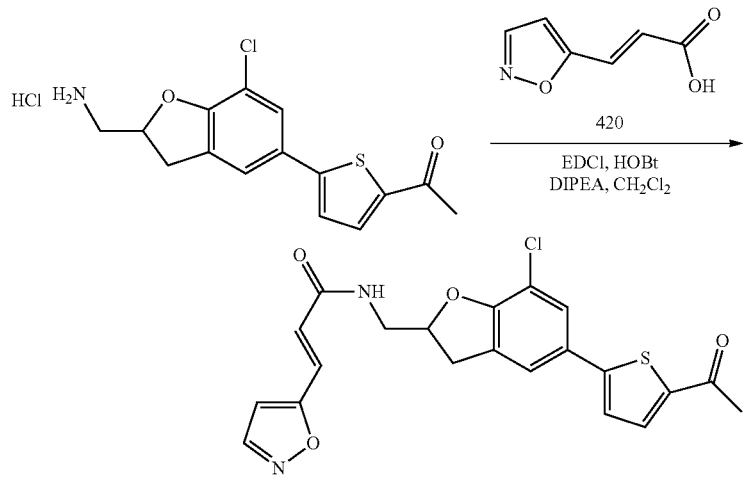

(E)-N-((5-(5-Acetylthiophen-2-yl)-7-chloro-2,3-dihydrobenzofuran-2-yl)methyl)-3-(isoxazol-5-yl)acrylamide 293 was synthesized using General Procedure 3. Yield (0.05 g, 40%). $^1$H NMR (400 MHz, DMSO-d$_6$) δ 8.77 (t, J=5.8 Hz, 1H), 8.65 (s, 1H), 7.92 (d, J=4.0 Hz, 2H), 7.66 (s, 1H), 7.61-7.58 (m, 2H), 7.42 (d, J=16.0 Hz, 1H), 6.86 (d, J=16.0 Hz, 1H), 6.82 (d, J=2.0 Hz, 1H), 5.12-5.08 (m, 1H), 3.65-3.58 (m, 2H), 3.47-3.40 (m, 1H), 2.52 (s, 3H). LCMS: m/z 428.95 [M]$^+$, $t_R$=2.23 min.

Synthesis of (E)-N-((5-(5-acetylthiophen-2-yl)-7-chloro-2,3-dihydrobenzofuran-2-yl)methyl)-3-(6-(methylamino)pyridin-3-yl)acrylamide (294)

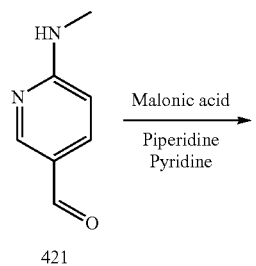

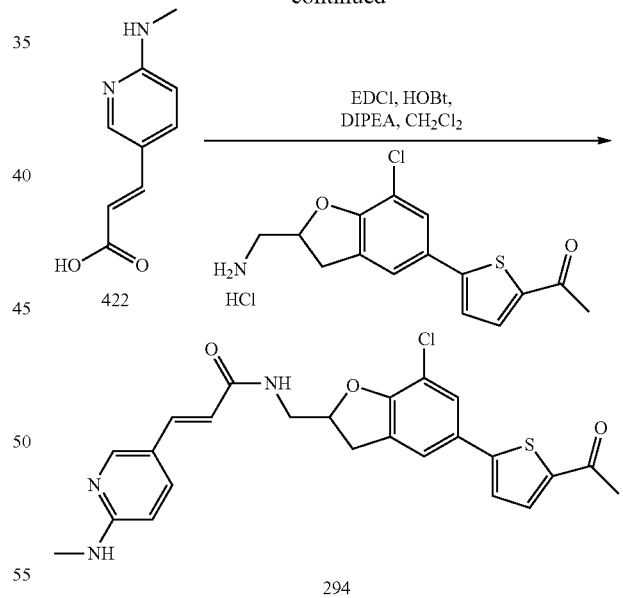

(E)-3-(6-(Methylamino)pyridin-3-yl)acrylic acid 422 was synthesized similar to (E)-3-(6-methylpyridin-3-yl)acrylic acid 145 (conversion of 143 to 145). Yield: (0.040 g, 30%). $^1$H NMR (400 MHz, DMSO-d$_6$) δ 12.04 (s, 1H), 8.19 (d, J=2 Hz, 1H), 7.58-7.78 (m, 1H), 7.45 (d, J=16 Hz, 1H), 7.12 (d, J=4.8 Hz, 1H), 6.47 (d, J=8.8 Hz, 1H), 6.22 (d, J=16 Hz, 1H), 2.80 (s, 3H). LCMS: m/z 178.8 [M]$^+$, $t_R$=0.62 min.

(E)-N-((5-(5-Acetylthiophen-2-yl)-7-chloro-2,3-dihydrobenzofuran-2-yl)methyl)-3-(6-(methylamino)pyridin-3-yl)acrylamide 294 was synthesized using General Procedure 3. Yield (0.040 g, 17%). $^1$H NMR (400 MHz, DMSO-d$_6$) δ 8.26-8.29 (m, 1H), 8.14 (s, 1H), 7.92 (d, J=4.0 Hz, 1H), 7.58-7.65 (m, 4H), 7.32 (d, J=15.6 Hz, 1H), 6.99-7.02 (m, 1H), 6.48 (d, J=8.4 Hz, 1H), 6.42 (d, J=15.6 Hz, 1H), 5.04-5.11 (m, 1H), 3.49-3.62 (m, 2H), 3.34-3.42 (m, 1H), 3.07-3.11 (m, 1H), 2.80 (d, J=4.8 Hz, 3H), 2.52 (s, 3H). LCMS: m/z 468.02 [M+1]$^+$, t$_R$=1.95 min.

Synthesis of (E)-N-((5-(5-acetylthiophen-2-yl)-7-chloro-2,3-dihydrobenzo furan-2-yl)methyl)-3-(6-(dimethylamino) pyridin-3-yl)acrylamide (295)

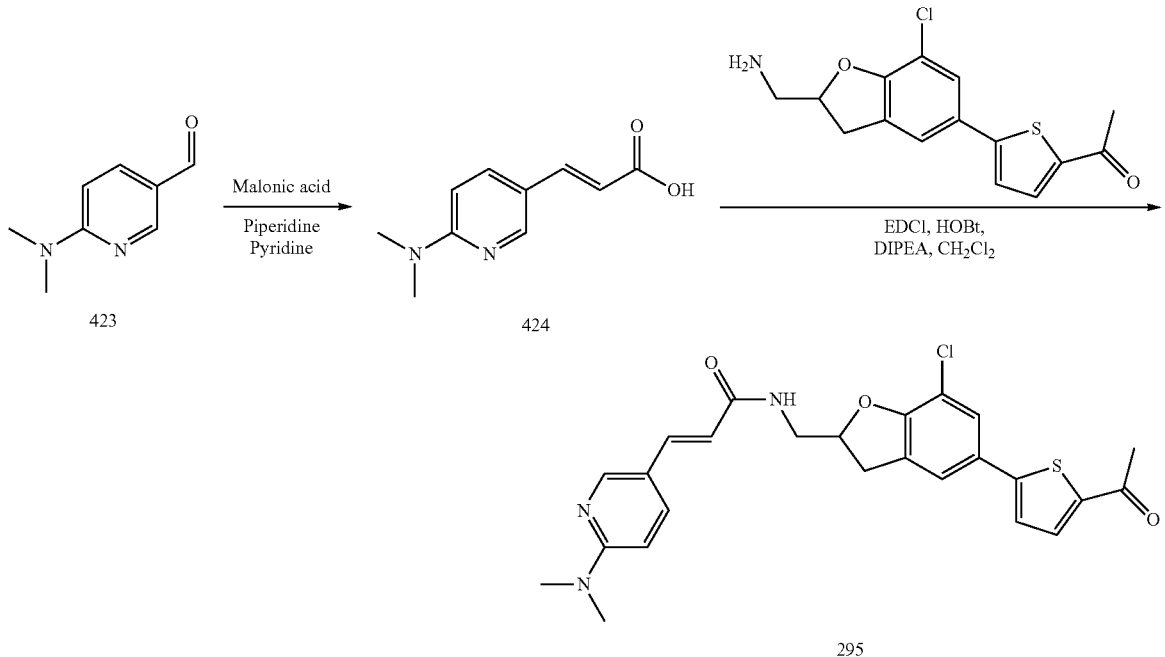

(E)-3-(6-(Dimethylamino)pyridin-3-yl) acrylic acid 424 was synthesized similar to (E)-3-(6-methylpyridin-3-yl) acrylic acid 145 (conversion of 143 to 145). Yield (21%). $^1$H NMR (400 MHz, DMSO-d$_6$) δ 12.08 (bs, 1H), 8.29-8.30 (d, J=2 Hz, 1H), 7.87-7.90 (m, 1H), 7.46-7.50 (d, J=16 Hz, 1H), 6.66-6.69 (d, J=9.2 Hz, 1H), 6.27-6.31 (d, J=16 Hz, 1H), 3.08 (s, 6H). LCMS: m/z 192.87 [M+H]$^+$, t$_R$=0.93 min.

(E)-N-((5-(5-acetylthiophen-2-yl)-7-chloro-2,3-dihydrobenzofuran-2-yl)methyl-3-(6-(dimethylamino)pyridin-3-yl)acrylamide 295 was synthesized using General Procedure 3. Yield 21%. $^1$H NMR (400 MHz, DMSO-d$_6$) δ 8.28-8.31 (t, 1H), 8.23-8.24 (d, J=2.4 Hz, 1H), 7.91-7.92 (d, J=4.4 Hz, 1H), 7.69-7.71 (d, J=9.2 Hz, 1H), 7.65 (s, 1H), 7.57-7.60 (m, 2H), 7.34-7.38 (d, J=15.6 Hz, 1H), 6.68-6.70 (d, J=8.8 Hz, 1H), 6.45-6.49 (d, J=16 Hz, 1H), 5.06-5.10 (m, 1H), 3.50-3.61 (m, 2H), 3.35-3.44 (m, 1H), 3.06-3.13 (m, 1H), 3.05 (s, 6H), 2.50-2.52 (m, 3H). LCMS: m/z 482.02 [M+H]$^+$, t$_R$=2.00 min.

Synthesis of (E)-N-((5-(5-acetylthiophen-2-yl)-7-chloro-2,3-dihydrobenzo furan-2-yl)methyl)-3-(6-methoxypyridin-3-yl)acrylamide (296)

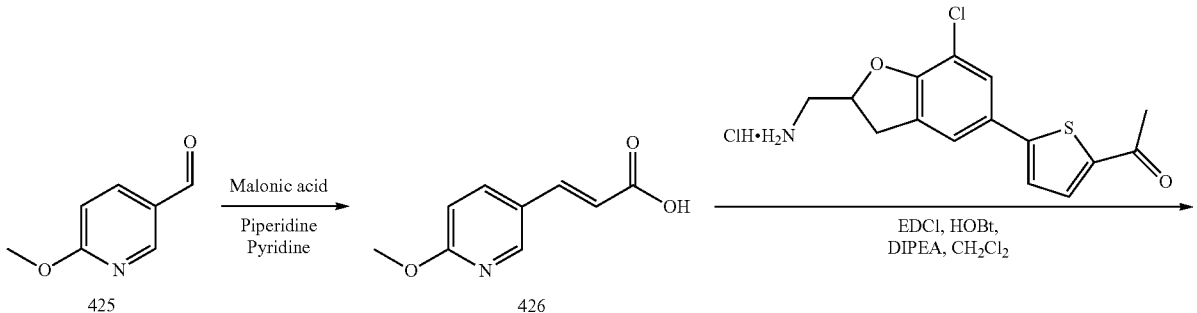

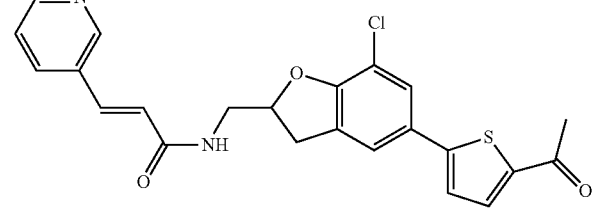

296

(E)-3-(6-Methoxypyridin-3-yl) acrylic acid 426 was synthesized similar to (E)-3-(6-methylpyridin-3-yl)acrylic acid 145 (conversion of 143 to 145). Yield (72%). $^1$H NMR (400 MHz, DMSO-$d_6$) δ 12.40 (s, 1H), 8.44 (s, 1H), 8.11-8.13 (m, 1H), 7.56-7.60 (d, J=16 Hz, 1H), 6.68-6.88 (d, J=8.8 Hz, 1H), 6.49-6.53 (d, J=16 Hz, 1H), 3.88 (s, 3H). LCMS: m/z 179.9 [M]$^+$, $t_R$=1.81 min.

(E)-N-((5-(5-Acetylthiophen-2-yl)-7-chloro-2,3-dihydrobenzofuran-2-yl)methyl)-3-(6-methoxypyridin-3-yl) acrylamide 296 was synthesized using General Procedure 3. Yield (31%). $^1$H NMR (400 MHz, DMSO-$d_6$) δ 8.42-8.45 (t, 1H), 8.36-8.37 (d, J=2.4 Hz, 1H), 7.91-7.96 (m, 2H), 7.65 (s, 1H), 7.58-7.60 (t, 2H), 7.44-7.47 (d, J=15.6 Hz, 1H), 6.87-6.89 (d, J=8.4 Hz, 1H), 6.26-6.66 (d, J=15.6 Hz, 1H), 5.09 (s, 1H), 3.88 (s, 3H), 3.55-3.60 (m, 2H), 3.39-3.46 (m, 1H), 3.07-3.13 (m, 1H), 2.51 (s, 3H). LCMS: m/z 469.02 [M+H]$^+$, $t_R$=2.35 min.

Synthesis of (E)-N-((5-(5-acetylthiophen-2-yl)-7-chloro-2,3-dihydrobenzofuran-2-yl)methyl)-3-(5-fluoropyridin-3-yl)acrylamide (298)

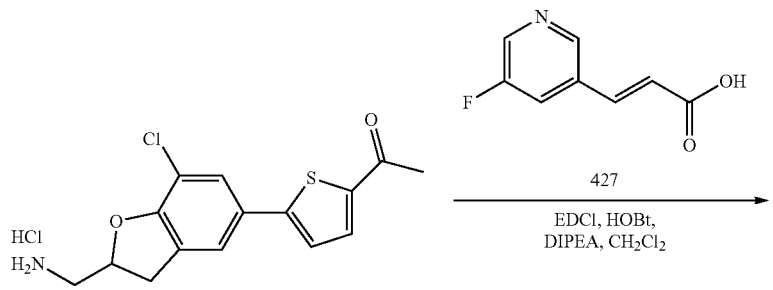

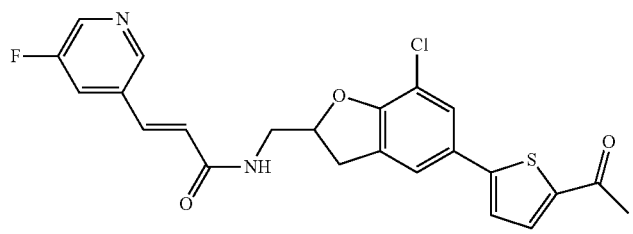

298

(E)-N-((5-(5-Acetylthiophen-2-yl)-7-chloro-2,3-dihydrobenzofuran-2-yl)methyl)-3-(6-aminopyridin-3-yl)acrylamide 298 was synthesized using General Procedure 3. Yield (15%). $^1$H NMR (400 MHz, DMSO-$d_6$) δ 8.67 (s, 1H), 8.57-8.58 (d, J=4 Hz, 1H), 8.54 (s, 1H), 7.95-7.97 (d, J=8 Hz, 1H), 7.91-7.94 (d, J=12 Hz, 1H), 7.66 (s, 2H), 7.51-7.55 (d, J=16 Hz, 1H), 6.85-6.90 (d, J=15.6 Hz, 1H), 5.07-5.14 (m, 1H), 3.54-3.64 (m, 2H), 3.39-3.47 (m, 1H), 3.08-3.14 (m, 1H), 2.52 (s, 3H). LCMS: m/z 457.01 [M+H]$^+$, $t_R$=2.22 min.

Synthesis of (Z)-N-((5-(5-acetylthiophen-2-yl)-7-chloro-2,3-dihydrobenzofuran-2-yl)methyl)-3-(pyridin-3-yl)acrylamide (299)

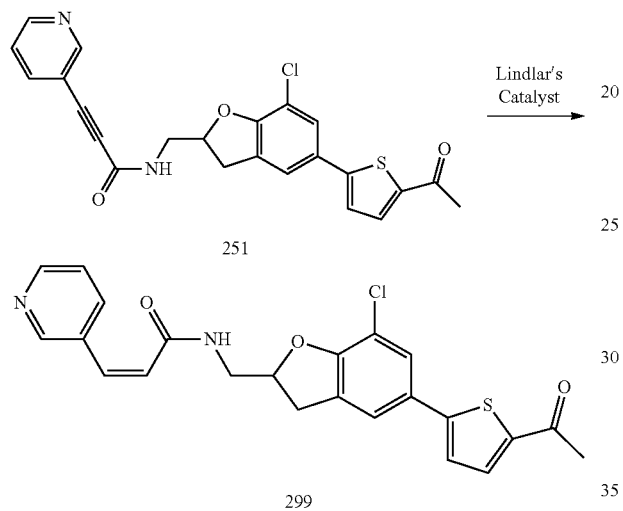

To a solution of N-((5-(5-acetylthiophen-2-yl)-7-chloro-2,3-dihydrobenzofuran-2-yl)methyl)-3-(pyridin-3-yl)propiolamide 251 (0.07 g, 0.16 mmol) in EtOAc (3 mL) was added K$_2$CO$_3$ (2.0 mg, 0.008 mmol) and Lindlar's Catalyst (2 mg, 0.016 mmol), stirred the reaction mixture at room temperature under H$_2$ atmosphere for overnight. Reaction mixture was filtered and the filtrate was concentrated under reduced pressure. The crude product was purified by semi-preparative HPLC. Fractions containing required compound were concentrated under reduced pressure to give (Z)-N-((5-(5-acetylthiophen-2-yl)-7-chloro-2,3-dihydrobenzofuran-2-yl)methyl)-3-(pyridin-3-yl)acrylamide 299. Yield (50%). $^1$H NMR (400 MHz, DMSO-$d_6$) δ 8.70 (d, J=2, 1H), 8.60-8.63 (t, 1H), 8.46-8.47 (m, 1H), 8.12-8.14 (d, J=8 Hz, 1H), 7.91-7.92 (d, J=4 Hz, 1H), 7.65 (s, 1H), 7.58-7.65 (m, 2H), 7.34-7.37 (m, 1H), 6.76-6.79 (d, J=12 Hz, 1H), 6.17-6.20 (d, J=12 Hz, 1H), 5.0 (m, 1H), 3.44-3.56 (m, 3H), 3.11 (m, 1H), 2.5 (s, 3H). LCMS: m/z 439.26 [M+H]$^+$, $t_R$=1.96 min.

Chiral Separation of 299: Preparation of (S,Z)-N-((5-(5-acetylthiophen-2-yl)-7-chloro-2,3-dihydrobenzofuran-2-yl)methyl)-3-(pyridin-3-yl)acrylamide and (R,Z)-N-((5-(5-acetylthiophen-2-yl)-7-chloro-2,3-dihydrobenzofuran-2-yl)methyl)-3-(pyridin-3-yl)acrylamide Compound 299 was subjected to chiral separation by HPLC to give single enantiomers, 312 and 313. The conditions of the separation were as follows:

| Mobile Phase: (A) | 0.1% FA in n-Heptane |
| Mobile Phase: (B) | 0.1% FA in n-IPA |
| Wave lenghth: | 246 nm |
| Flow Rate: | 1.00 ml/min |
| Column ID: | Chiral PaK AD-H (250*4.6, 5u) |
| Gradient: | |

| % T | % B |
|---|---|
| 0.01 | 60.00 |
| 15.00 | 85.00 |
| 20.00 | 85.00 |
| 20.01 | 60.00 |
| 25.00 | 60.00 |

The absolute configuration of Compounds 312 and 313 has not been determined. Therefore, Compound 312, as used herein, refers to the compound with a retention time of 9.55 minutes in the HPLC method employed to separate it from its enantiomer, Compound 313. Conversely, Compound 313, as used herein, refers to the compound with a retention time of 8.84 minutes in the HPLC method employed to separate it from its enantiomer, Compound 312.

(S,Z)-N-((5-(5-acetylthiophen-2-yl)-7-chloro-2,3-dihydrobenzofuran-2-yl)methyl)-3-(pyridin-3-yl)acrylamide and (R,Z)-N-((5-(5-acetylthiophen-2-yl)-7-chloro-2,3-dihydrobenzofuran-2-yl)methyl)-3-(pyridin-3-yl)acrylamide can be depicted as follows:

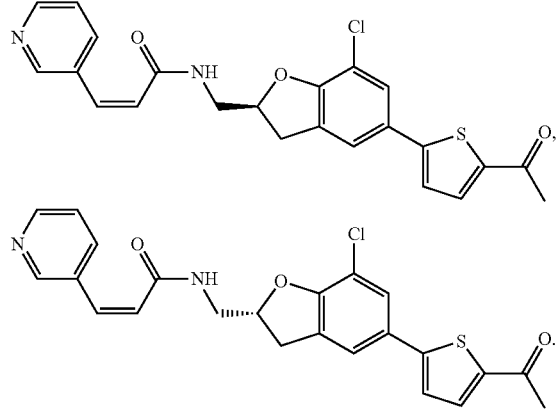

Synthesis of (E)-3-(6-aminopyridin-3-yl)-N-((7-chloro-5-(3,5-dimethylisoxazol-4-yl)-2,3-dihydrobenzofuran-2-yl)methyl)acrylamide (300)

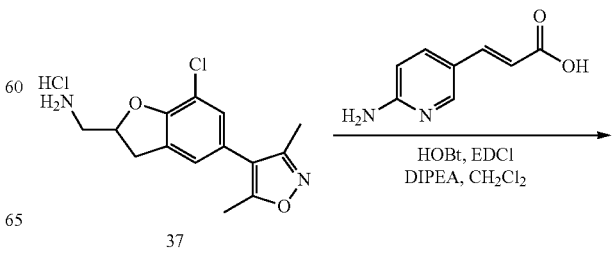

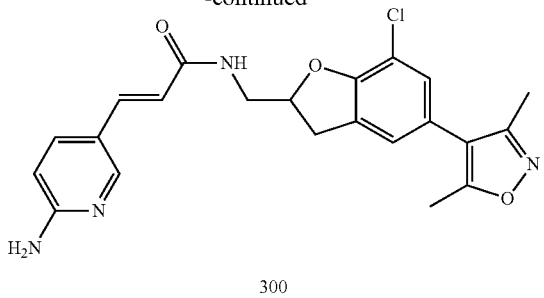

(E)-3-(6-Aminopyridin-3-yl)-N-((7-chloro-5-(3,5-dimethylisoxazol-4-yl)-2,3-dihydrobenzofuran-2-yl)methyl)

acrylamide 300 was synthesized using General Procedure 3. Yield (31%). $^1$H NMR (400 MHz, DMSO-$d_6$) δ 8.27 (s, 1H), 8.07 (s, 1H), 7.58-7.60 (d, J=8 Hz, 1H), 7.29-7.33 (d, J=15.6 Hz, 1H), 7.20 (s, 2H), 6.41-6.48 (m, 4H), 5.05 (s, 1H), 3.51-3.61 (m, 2H), 3.35-3.42 (m, 1H), 3.06-3.18 (m, 1H), 2.36 (s, 3H), 2.19 (s, 3H). LCMS: m/z 425.50 [M+H]$^+$, $t_R$=1.83 min.

Synthesis of (E)-N-((5-(5-acetylthiophen-2-yl)-7-chloro-2,3-dihydrobenzofuran-2-yl)methyl)-3-(2,5-dimethyl-1-phenyl-1H-pyrrol-3-yl)acrylamide (301)

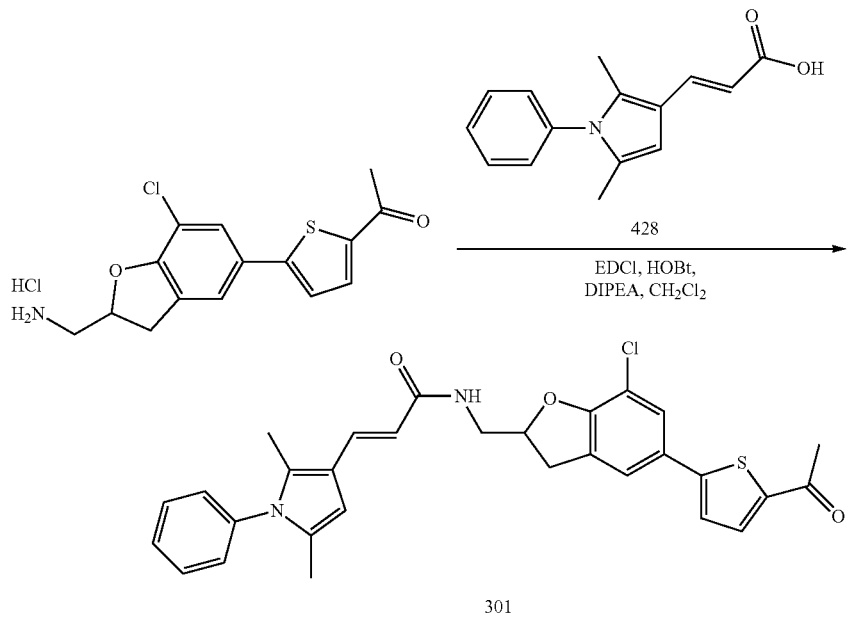

(E)-N-((5-(5-Acetylthiophen-2-yl)-7-chloro-2,3-dihydrobenzofuran-2-yl)methyl)-3-(2,5-dimethyl-1-phenyl-1H-pyrrol-3-yl)acrylamide 301 was synthesized using General Procedure 3. Yield (11%). $^1$H NMR (400 MHz, DMSO-$d_6$) δ 8.17-8.20 (t, 1H), 7.91-7.92 (d, J=4 Hz, 1H), 7.65-7.66 (d, J=2 Hz, 1H), 7.46-7.61 (m, 5H), 7.37-7.41 (d, J=15.2 Hz, 1H), 7.30-7.31 (d, 2H), 6.16-6.20 (d, J=15.2 Hz, 1H), 6.12 (s, 1H), 5.04-5.11 (m, 1H), 3.48-3.61 (m, 3H), 3.08-3.17 (m, 1H), 2.68-2.09 (d, 3H), 2.00 (s, 3H), 1.95 (s, 3H). LCMS: m/z 533.83 [M+H]$^+$, $t_R$=2.665 min.

Synthesis of (E)-3-(6-aminopyridin-3-yl)-N-((7-chloro-5-(4-(morpholine-4-carbonyl) phenyl)-2,3-dihydrobenzofuran-2-yl)methyl)acrylamide (302)

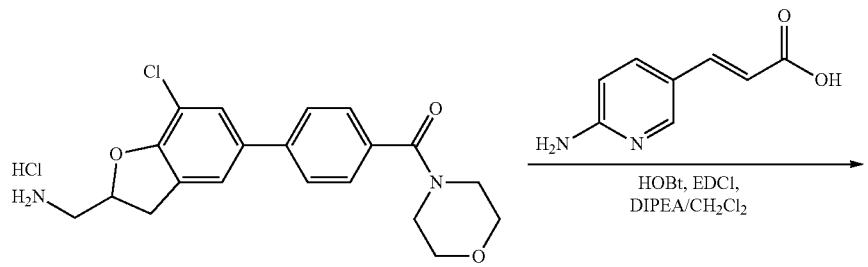

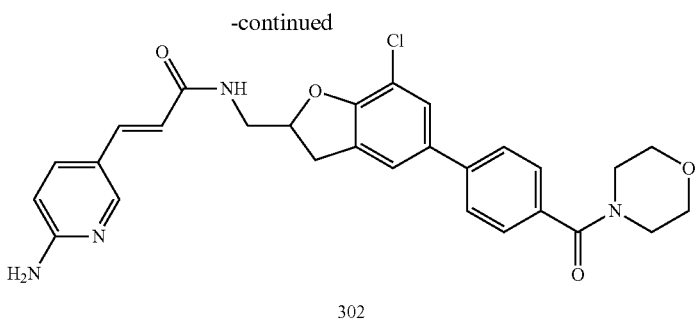

302

(E)-3-(6-Aminopyridin-3-yl)-N-((7-chloro-5-(4-(morpholine-4-carbonyl)phenyl)-2,3-dihydrobenzofuran-2-yl)methyl)acrylamide 302 was synthesized using General Procedure 3. Yield (31%). ¹H NMR (400 MHz, DMSO-d₆) δ 8.27-8.30 (t, 1H), 8.06 (s, 1H), 7.68-7.70 (d, J=8.4 Hz, 2H), 7.53-7.60 (m, 3H), 7.45-7.47 (d, J=8.4 Hz, 2H), 7.29-7.33 (d, J=15.6 Hz, 1H), 6.41-6.47 (m, 4H), 3.44-3.61 (m, 8H), 3.62-3.45 (m, 3H), 3.08-3.14 (m, 1H). LCMS: m/z 519.23 [M+H]⁺, $t_R$=1.76 min.

Synthesis of (E)-N-((5-(5-acetylthiophen-2-yloxy)-7-chloro-2,3-dihydro benzofuran-2-yl)methyl)-3-(pyridin-3-yl)acrylamide (303)

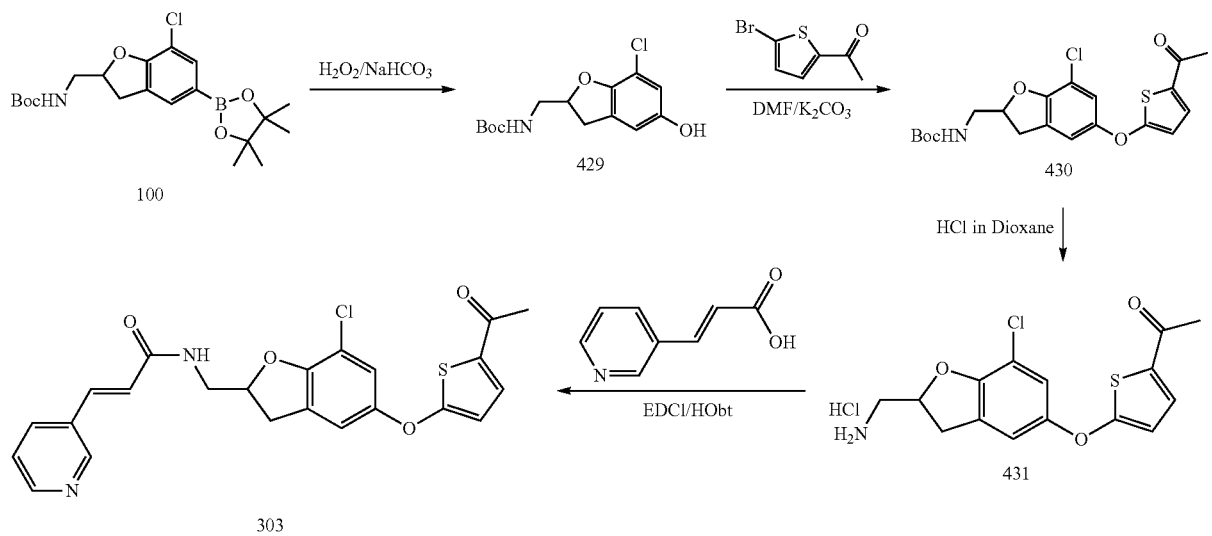

303

Synthesis of tert-butyl (7-chloro-5-hydroxy-2,3-dihydrobenzofuran-2-yl) methylcarbamate 429: tert-Butyl (7-chloro-5-(4,4,5,5-tetramethyl-1,3,2-dioxaborolan-2-yl)-2,3-dihydrobenzo furan-2-yl)methylcarbamate 100 (1.5 g, 3.6 mmol) was dissolved in acetonitrile (20 mL) at 0° C. Sodium bicarbonate (0.46 g, 5.5 mmol) and hydrogen peroxide (1.24 mL, 30%, 11.0 mmol) were added and stirred at 0° C. or 2 h. The reaction mixture was transferred into iced water and extracted with ethyl acetate (25 mL×3). The combined organic layers were washed with sodiumthiosulphate solution and brine, dried over anhydrous Na₂SO₄, and concentrated under reduced pressure. The crude product was purified by chromatography (0-20% ethyl acetate/n-hexane) to give tert-butyl (7-chloro-5-hydroxy-2,3-dihydrobenzofuran-2-yl) methyl carbamate 429. Yield (0.3 g, 34%). ¹H NMR (400 MHz, DMSO-d₆) δ 9.22 (s, 1H), 7.11-7.08 (m, 1H), 6.59-6.59 (s, 1H), 6.52-6.51 (s, 1H), 4.80-4.74 (m, 1H), 3.26-3.11 (m, 3H), 2.95-2.89 (m, 1H), 1.388-1.35 (s, 9H). LCMS: m/z 244.0 [M−56]⁺, $t_R$=2.147 min.

Synthesis of tert-butyl (5-(5-acetylthiophen-2-yloxy)-7-chloro-2,3-dihydrobenzofuran-2-yl) methyl carbamate 430: tert-Butyl (7-chloro-5-hydroxy-2,3-dihydrobenzofuran-2-yl) methylcarbamate 429 (0.2 g, 0.66 mmol) and 2-acetyl-5-bromothiophene (0.137 g, 0.66 mmol) were dissolved in DMF (3 mL). Potassium carbonate (0.217 g, 0.66 mmol) was added and stirred at 120° C. for 4 h. After cooling to room temperature, the reaction mixture was transferred into iced water and extracted with ethyl acetate (25 mL×3). The combined organic layers were washed with brine, dried over anhydrous Na₂SO₄, and concentrated under reduced pressure. The crude product was purified by chromatography (0-20% ethyl acetate/n-hexane) to give tert-butyl (5-(5-acetylthiophen-2-yloxy)-7-chloro-2,3-dihydrobenzofuran-2-yl) methylcarbamate 430. Yield (0.23 g, 82%). ¹H NMR (400 MHz, DMSO-d₆) δ 8.25-8.15 (m, 1H), 7.94-7.57 (m, 3H), 6.59-6.52 (d, 1H), 4.77-4.72 (m, 1H), 3.26-3.20 (m, 2H), 2.91-2.89 (m, 1H), 2.78-2.68 (m, 1H), 1.38 (m, 9H). LCMS: m/z 368.13 [M−56]⁺, $t_R$=2.594 min.

Synthesis of 1-(5-(2-(aminomethyl)-7-chloro-2,3-dihydrobenzofuran-5-yloxy)thiophen-2-yl) ethanone 431: 1-(5-(2-(Aminomethyl)-7-chloro-2,3-dihydrobenzofuran-5-yloxy)thiophen-2-yl) ethanone 431 was synthesized using General Procedure 2. Yield (60%). $^1$H NMR (400 MHz, DMSO-$d_6$) δ 7.79-7.78 (d, J=4.4 Hz, 1H), 7.28-7.25 (m, 1H), 7.0-6.97 (m, 1H), 6.65-6.64 (d, J=4.4 Hz, 1H) 6.58 (s, 1H), 5.70-5.15 (m, 1H), 3.50-3.36 (m, 2H), 3.24-3.16 (m, 2H), 2.48-2.45 (m, 3H). LCMS: m/z 324.2 [M+H]$^+$, $t_R$=1.853 min.

Synthesis of (E)-N-((5-(5-acetylthiophen-2-yloxy)-7-chloro-2,3-dihydrobenzofuran-2-yl)methyl)-3-(pyridin-3-yl)acrylamide 303: (E)-N-((5-(5-Acetylthiophen-2-yloxy)-7-chloro-2,3-dihydrobenzofuran-2-yl)methyl)-3-(pyridin-3-yl)acrylamide 303 was synthesized using General Procedure 3. Yield (16%). $^1$H NMR (400 MHz, DMSO-$d_6$) δ 8.77 (s, 1H), 8.57-8.51 (m, 2H), 8.01-7.98 (m, 1H), 7.75-7.74 (d, J=4.4 Hz, 1H), 7.52-7.44 (m, 2H), 7.23-7.20 (m, 2H), 6.85-6.81 (d, J=16 Hz, 1H), 6.62-6.60 (d, J=4.4Hz, 1H), 5.08 (m, 1H), 3.61-3.56 (m, 2H), 3.43-3.38 (m, 1H), 3.11-3.05 (m, 1H), 2.43 (s, 3H). LCMS: m/z 455.21 [M+H]$^+$, $t_R$=2.157 min.

Synthesis of (E)-N-((7-chloro-5-(5-(2-hydroxypropan-2-yl)thiophen-2-yl)-2,3-dihydrobenzofuran-2-yl)methyl)-3-(pyridine-3-yl) acrylamide (304)

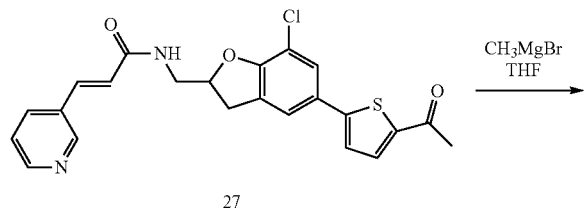

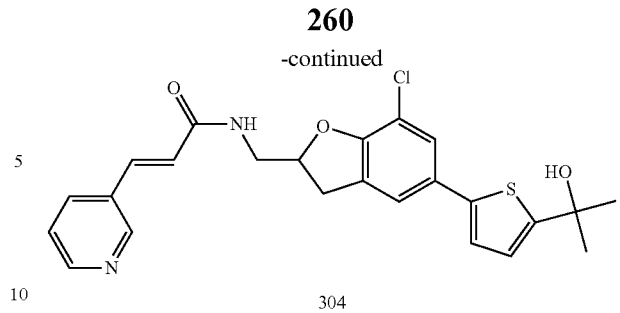

(E)-N-((5-(5-Acetylthiophen-2-yl)-7-chloro-2,3-dihydrobenzofuran-2-yl)methyl)-3-(pyridin-3-yl)acrylamide 27 (0.080 g, 0.18 mmol) was dissolved in THF (3 mL). Methyl magnesium bromide (3 M in THF, 0.12 ml, 0.36 mmol) was added at 25° C. and stirred for 2 h. The reaction mixture was transferred into saturated ammonium chloride solution (10 mL) and extracted with ethyl acetate (5 mL×3). The combined organic layers were washed with brine solution, dried over anhydrous $Na_2SO_4$ and concentrated under reduced pressure. The crude product was purified by column chromatography (60/120 silica gel, 0-10% methanol/dichloromethane gradient) to obtain 0.012 g of (E)-N-((7-chloro-5-(5-(2-hydroxypropan-2-yl)thiophen-2-yl)-2,3-dihydrobenzofuran-2-yl)methyl)-3-(pyridine-3-yl) acrylamide 304. Yield (0.012 g, 14.45%). $^1$H NMR (400 MHz, DMSO-$d_6$) δ 8.77 (s, 1H), 8.55 (s, 2H), 7.98-8.00 (d, J=8 Hz, 1H), 7.41-7.53 (m, 4H), 7.20 (s, 1H), 6.81-6.85 (m, 2H), 5.49 (s, 1H, $D_2O$ exchangeable), 5.06 (s, 1H), 3.57-3.59 (m, 2H), 3.39-3.43 (m, 1H), 3.05-3.11 (m, 1H), 1.50 (s, 6H): LCMS: m/z 437.1 [M−18]$^+$, $t_R$=2.061 min.

Synthesis of (E)-N-((7-(5-acetylthiophen-2-yl)-2,3-dihydrobenzofuran-2-yl)methyl)-3-(6-aminopyridin-3-yl) acrylamide (305)

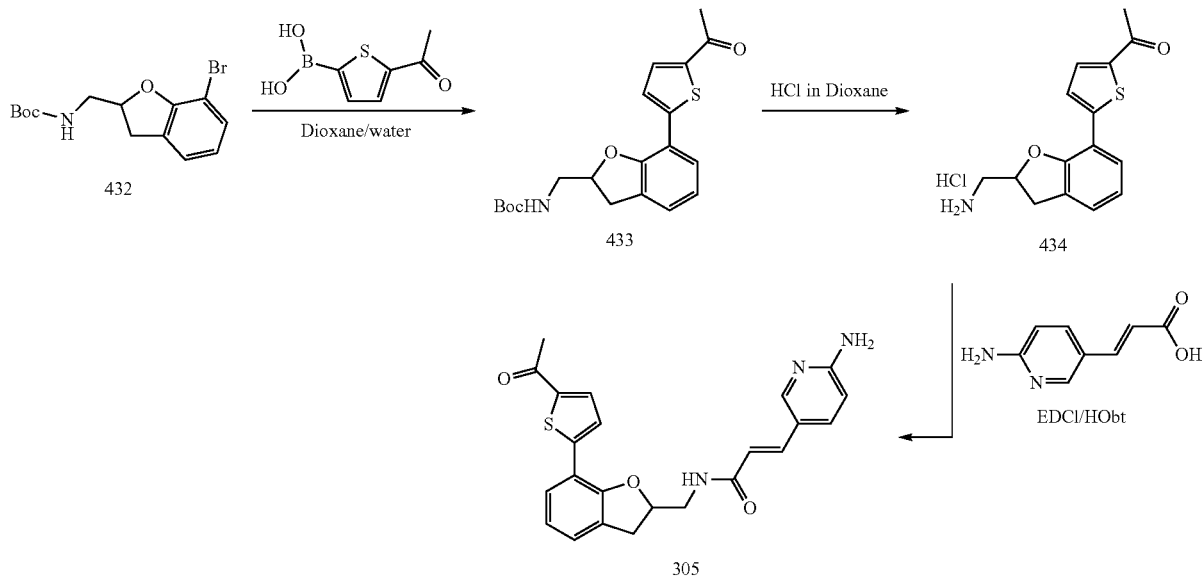

tert-Butyl (7-(5-acetylthiophene-2-yl)-2,3-dihydrobenzfuran-2-yl) methyl carbamate 433 was synthesized using General Procedure 1. Yield (46%). $^1$H NMR (400 MHz, DMSO-d$_6$) δ 7.96-7.97 (d, J=4 Hz, 1H), 7.91-7.92 (d, J=4 Hz, 1H), 7.65-7.66 (d, J=4 Hz, 1H), 7.55-7.56 (d, J=4 Hz, 1H), 7.19-7.26 (t, 1H), 6.91-6.95 (t, 1H), 4.94-4.98 (m, 1H), 3.33-3.34 (d, J=4 Hz, 1H), 3.30-3.31 (d, J=4 Hz, 1H), 3.02-3.03 (d, J=4 Hz, 1H), 2.50-2.51 (d, J=4 Hz, 1H), 2.51(s, 3H), 1.38 (s, 9H). LCMS: m/z 318 [M−56]$^-$, t$_R$=2.51 min.

1-(5-2-(Aminomethyl)-2,3-dihydrobenzfuran-7-yl)thiophen-2-yl)ethanone 434 was synthesized using General Procedure 2. Yield (50%). $^1$H NMR (400 MHz, DMSO-d$_6$) δ=7.91-7.92 (d, J=4 Hz, 1H), 7.81-7.82 (d, J=4 Hz, 1H), 7.47-7.65 (m, 2H), 7.53-7.55 (d, J=8 Hz, 1H), 7.28-7.30 (d, J=8 Hz, 1H), 6.97-7.01 (t, 1H), 5.17-5.21 (m, 1H), 3.38-3.46 (m, 1H), 3.25-3.30 (m, 1H), 3.16-3.21 (m, 1H), 3.06-3.12 (m, 1H), 2.52 (s, 3H). LCMS: m/z 274.13 [M+H]$^+$, t$_R$=1.81 min.

(E)-N-((7-(5-Acetylthiophen-2-yl)-2,3-dihydrobenzofuran-2-yl)methyl)-3-(6-aminopyridin-3-yl)acrylamide 305 was synthesized using General Procedure 3. Yield (20%). $^1$H NMR (400 MHz, DMSO-d$_6$) δ 8.24-8.27 (t, 1H), 8.07 (s, 1H), 7.92-7.93 (d, J=4 Hz, 1H), 7.75-7.76 (d, J=4 Hz, 1H), 7.55-7.61 (m, 2H), 7.24-7.33 (m, 2H), 6.91-6.95 (t, 1H), 6.40-6.48 (m, 4H), 5.08-5.10 (m, 1H), 3.57-3.60 (m, 1H), 3.46-3.50 (m, 1H), 3.33-3.36 (m, 1H), 3.01-3.07 (m, 1H), 2.52 (s, 3H). LCMS: m/z 420.20 [M+H]$^+$, t$_R$=1.92 min.

Synthesis of (E)-3-(6-aminopyridin-3-yl)-N-((7-chloro-5-(5-(1-hydroxyethyl) thiophen-2-yl)-2,3-dihydrobenzofuran-2-yl)methyl)acrylamide (306)

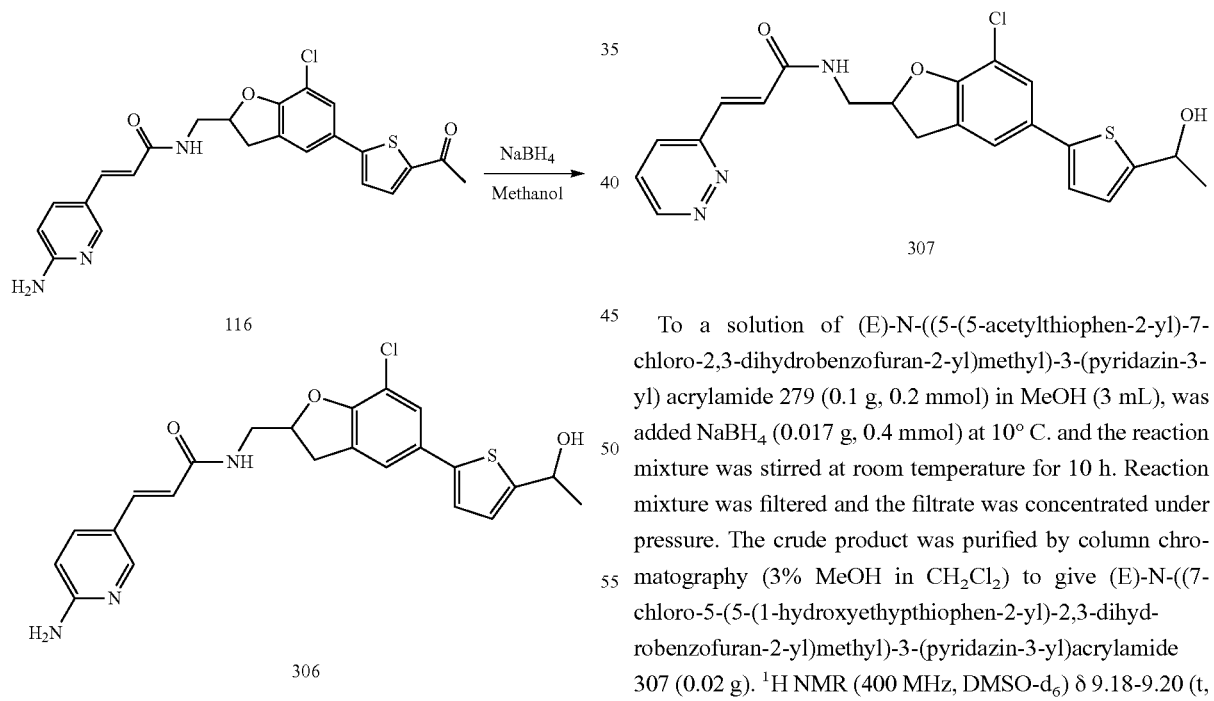

(E)-3-(6-Aminopyridin-3-yl)-N-((7-chloro-5-(5-(1-hydroxyethyl) thiophen-2-yl)-2,3-dihydrobenzofuran-2-yl) methyl)acrylamide 306 was synthesized similar to (E)-N-((7-chloro-5-(5-(1-hydroxyethypthiophen-2-yl)-2,3-dihydrobenzofuran-2-yl)methyl)-3-(pyridin-3-yl) acrylamide 124 (conversion of 27 to 124). Yield (30%). $^1$H NMR (400 MHz, DMSO-d$_6$) δ 8.27-8.28 (d, J=4 Hz, 1H), 8.07 (s, 1H), 7.59-7.61 (d, J=8 Hz, 1H), 7.42 (s, 2H), 7.29-7.33 (d, J=16 Hz, 1H), 7.23-7.24 (d, J=4 Hz, 1H), 6.87-6.88 (d, J=4 Hz, 1H), 6.41-6.48 (m, 4H), 5.58-5.59 (d, J=4 Hz, 1H), 5.03-5.10 (m, 1H), 4.90-4.92 (m, 1H), 3.48-3.59 (m, 2H), 3.35-3.41 (m, 1H), 3.04-3.10 (m, 1H), 1.41-1.43 (d, J=8 Hz, 3H). LCMS: m/z 456.16 [M+H]$^+$, t$_R$=1.9 min.

Synthesis of (E)-N-((5-(5-acetylthiophen-2-yl)-7-chloro-2,3-dihydrobenzofuran-2yl) methyl)-3-(pyridazin-3-yl) acrylamide (307)

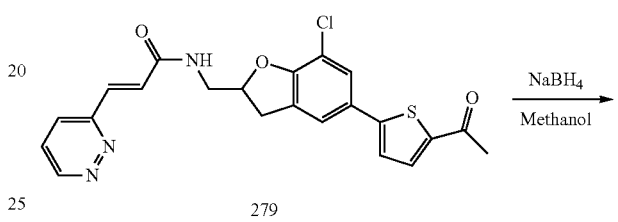

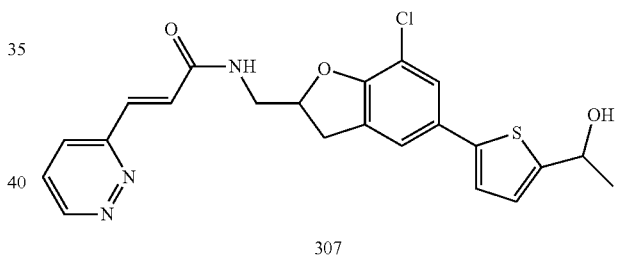

To a solution of (E)-N-((5-(5-acetylthiophen-2-yl)-7-chloro-2,3-dihydrobenzofuran-2-yl)methyl)-3-(pyridazin-3-yl) acrylamide 279 (0.1 g, 0.2 mmol) in MeOH (3 mL), was added NaBH$_4$ (0.017 g, 0.4 mmol) at 10° C. and the reaction mixture was stirred at room temperature for 10 h. Reaction mixture was filtered and the filtrate was concentrated under pressure. The crude product was purified by column chromatography (3% MeOH in CH$_2$Cl$_2$) to give (E)-N-((7-chloro-5-(5-(1-hydroxyethypthiophen-2-yl)-2,3-dihydrobenzofuran-2-yl)methyl)-3-(pyridazin-3-yl)acrylamide 307 (0.02 g). $^1$H NMR (400 MHz, DMSO-d$_6$) δ 9.18-9.20 (t, 1H), 8.76-8.78 (t, 1H), 7.91-7.93 (t, 1H), 7.73-7.77 (m, 1H), 7.60-7.64 (d, J=16 Hz, 1H), 7.43 (s, 2H), 7.23-7.31 (m, 2H), 6.86-6.88 (t, 1H), 5.59 (s, 1H), 5.08 (m, 1H), 4.89-4.92 (m, 1H), 3.55-3.65 (m, 2H), 3.35-3.42 (m, 1H), 3.0-3.12 (m, 1H), 1.41-1.43 (d, J=8 Hz, 3H). LCMS: 444.19 [M+H]$^+$, t$_R$=2.12 min.

Synthesis of (E)-N-((5-(5-acetylthiophen-2-yl)-7-chloro-2,3-dihydrobenzofuran-2-yl)methyl)-2-(pyridine-3-yl) ethenesulphonamide (310)

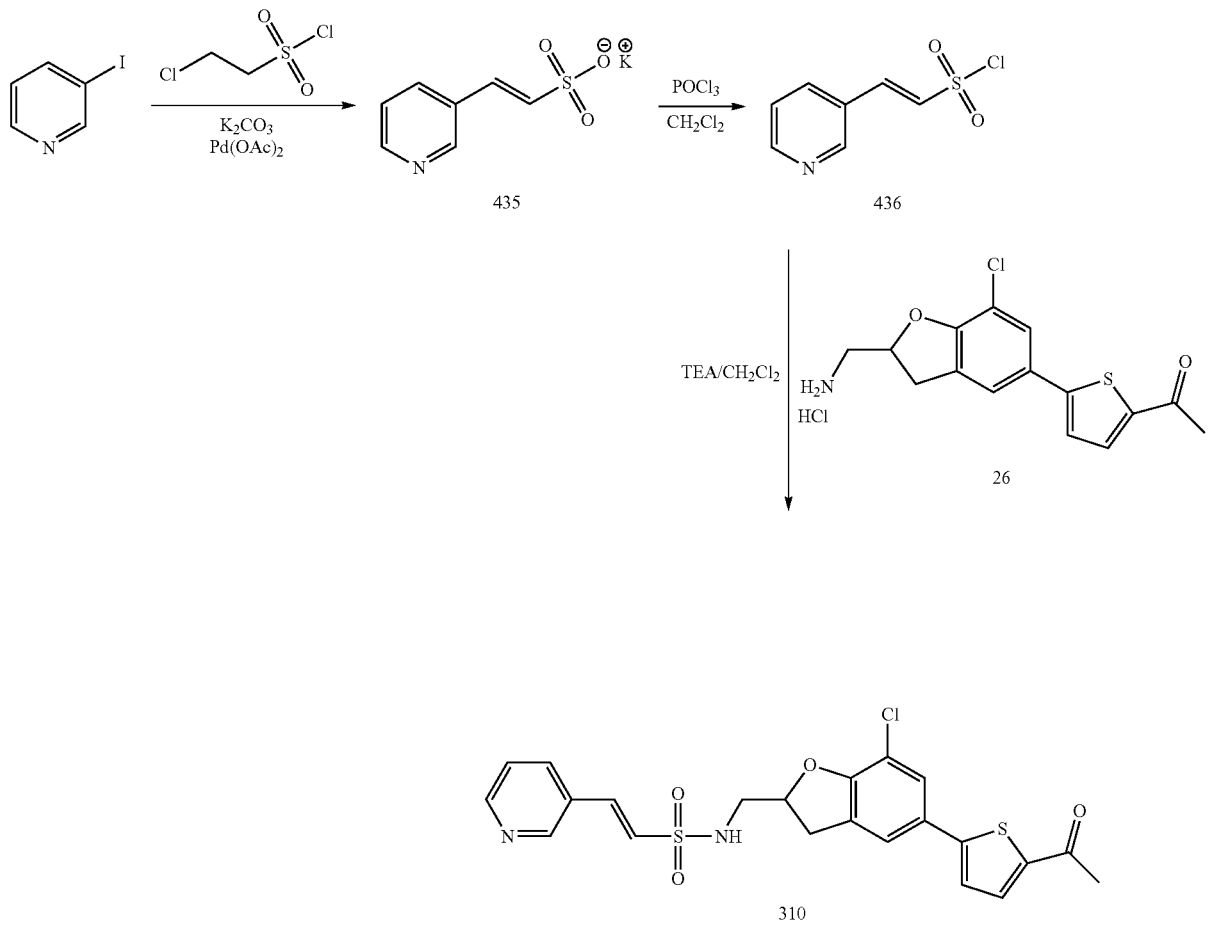

Synthesis of potassium (E)-2-(pyridine-3-yl) ethenesulphonate (435): Anhydrous potassium carbonate (1.009 g, 7.31 mmol), palladium(II) acetate (0.011 g, 0.049 mmol) and iodopyridine (0.5 g, 2.45 mmol) were added in water (10 mL) at room temperature. 2-Chloromethanesulfonyl chloride (0.281 ml, 2.45 mmol) was added to the reaction mixture dropwise. The vial was heated in a microwave for 10 min at 180° C. Pd(OAc)$_2$ (0.0055 g, 0.024 mmol,) was then added to the reaction mixture. The vial was resealed and heated in a microwave oven under the same conditions. The reaction mixture was filtered and washed with acetone. The crude solid was extracted with methanol/CH$_2$Cl$_2$ (20/80). The extract was concentrated under reduced pressure to give potassium (E)-2-(pyridine-3-yl) ethanesulphonate 435. Yield (0.4 g, 95%). $^1$H NMR (400 MHz, DMSO-d$_6$) δ 8.68 (s, 1H), 8.48-8.47 (d, J=5.6 Hz, 1H), 8.0-7.98 (d, J=8 Hz, 1H), 7.39-7.36 (m, 1H), 7.08-7.047 (d, J=16 Hz, 1H), 6.96-6.92 (d, J=16 Hz, 1H). LCMS: m/z 186.01 [M+H]$^+$, t$_R$=0.55 min.

Synthesis of (E)-2-(pyridin-3-yl) ethenesulphonyl chloride (436): Potassium (E)-2-(pyridine-3-yl) ethane sulphonate 435 (0.2 g, 1.081 mmol) was dissolved in POCl$_3$ (2 mL) and refluxed for 1 h. The reaction mixture was allowed to cool to room temperature and ice was added into the reaction mixture and extracted with ethyl acetate (3×10 mL), and washed with brine. The ethyl acetate layer was concentrated under reduced pressure to obtain (E)-2-(pyridin-3-yl) ethanesulphonyl chloride 436. Yield (0.21 g). The crude product was used in the next step without further purification.

Synthesis of (E)-N-((5-(5-acetylthiophen-2-yl)-7-chloro-2,3-dihydrobenzofuran-2-yl)methyl)-2-(pyridine-3-yl) ethenesulphonamide (310): 2-(Pyridin-3-yl)ethenesulphonyl chloride 436 (0.05 g, 0.27 mmol) was dissolved in dichloromethane (3 mL) and cooled to 0° C. 1-(5-(2-(aminomethyl)-7-chloro-2,3-dihydrobenzofuran-5-yl)thiophen-2-yl) ethanone 27 (0.07 g, 0.22 mmol) and triethyl amine (0.034 mL, 0.24 mmol) were added and stirred for 1 h. The reaction mixture was transferred into cold water and extracted with ethyl acetate (10 mL×3). The combined organic layers were washed with brine, dried over anhydrous Na$_2$SO$_4$, and concentrated under reduced pressure. The crude product was purified by chromatography (0-2% Methanol/CH$_2$Cl$_2$) to give (E)-N-((5-(5-acetylthiophen-2-yl)-7-chloro-2,3-dihydrobenzofuran-2-yl)methyl)-2-(pyridine-3-yl) ethenesulphonamide 310. Yield (0.035 g, 34%). $^1$H NMR (400 MHz, DMSO-d$_6$) δ 8.86 (s, 1H), 8.60-8.59 (d, J=4.4, 1H), 8.17-8.15 (d, J=8, 1H), 7.93-7.92 (d, J=4, 1H), 7.88-7.85 (m, 1H), 7.61-7.57 (m, 4H), 7.47-7.41 (m, 3H), 5.07 (m, 1H), 3.44-3.34 (m, 2H), 3.32-3.20 (m, 2H), 2.51 (s, 1H). LCMS: m/z 475.17 [M+H]$^+$, t$_R$=2.36 min.

Synthesis of (E)-N-((5-(5-acetylthiophen-2-yl)-7-chloro-2,3-dihydrobenzofuran-2-yl)methyl)-3-(6-hydroxypyridin-3-yl)acrylamide (311)

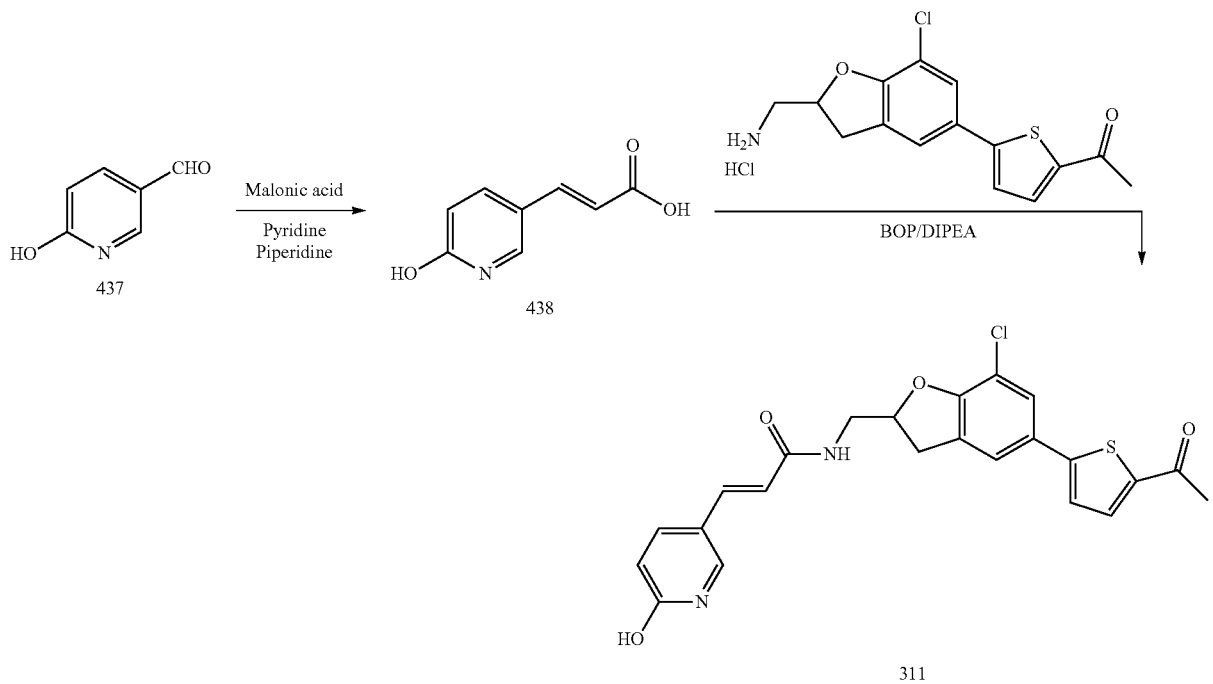

(E)-3-(6-Hydroxypyridin-3-yl) acrylic acid 438 was synthesized similar to (E)-3-(6-methylpyridin-3-yl)acrylic acid 145 (conversion of 143 to 145). Yield (45%). $^1$H NMR (400 MHz, DMSO-d$_6$) δ 7.76-7.79 (d, J=12 Hz, 1H), 7.57 (s, 1H), 7.06-7.10 (d, J=8 Hz, 1H), 6.13-6.17 (d, J=16 Hz, 2H). LCMS: m/z 166.05 [M+H]$^+$, t$_R$=0.76 min.

(E)-N-((5-(5-acetylthiophen-2-yl)-7-chloro-2,3-dihydrobenzofuran-2-yl)methyl)-3-(6-hydroxypyridin-3-yl)acrylamide 311 was synthesized using General Procedure 3. Yield (40%). $^1$H NMR (400 MHz, DMSO-d$_6$) δ 11.89 (s, 1H), 8.28-8.31 (t, 1H), 7.92-7.93 (d, J=4 Hz 1H), 7.58-7.72 (m, 5H), 7.30-7.34 (d, J=16 Hz 1H), 6.42 (s, 1H), 6.36-6.40 (d, J=16 Hz 1H), 5.08-5.12 (m, 1H), 3.51-3.62 (m, 2H), 3.38-3.45 (m, 1H), 3.07-3.13 (m, 1H), 2.52 (s, 3H). LCMS: m/z 455.11 [M+H]$^+$, t$_R$=2.11 min.

Synthesis of (E)-N-((5-(5-acetylfuran-2-yl)-7-chloro-2,3-dihydrobenzofuran-2-yl)methyl)-3-(pyridazin-3-yl)acrylamide (314)

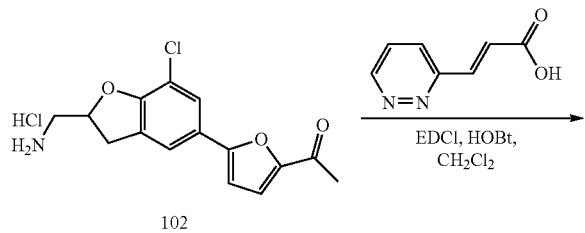

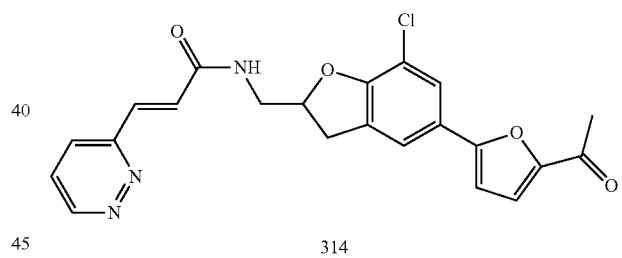

(E)-N-((5-(5-Acetylfuran-2-yl)-7-chloro-2,3-dihydrobenzofuran-2-yl)methyl)-3-(pyridazin-3-yl) acrylamide 314 was synthesized using General Procedure 3. Yield (21%). $^1$H NMR (400 MHz, DMSO-d$_6$) δ 9.20-9.18 (m, 1H), 8.79-8.76 (t, 1H), 7.93-7.91 (d, J=9.2 Hz, 1H), 7.76-7.70 (m, 3H), 7.64-7.60 (d, J=16 Hz, 1H), 7.54-7.53 (d, J=4 Hz, 1H), 7.30-7.26 (d, J=15.6 Hz, 1H), 7.14-7.13 (m, 1H), 5.17-5.10 (m, 1H), 3.69-3.56 (m, 2H), 3.50-3.43 (m, 1H), 3.17-3.11(m, 1H), 2.44 (s, 3H). LCMS: m/z 424.16 [M+H]$^+$, t$_R$=1.937 min.

Synthesis of (E)-3-(6-acetamidopyridin-3-yl)-N-((5-(5-acetylthiophen-2-yl)-7-chloro-2,3-dihydrobenzofuran-2-yl)methyl)acrylamide (315)

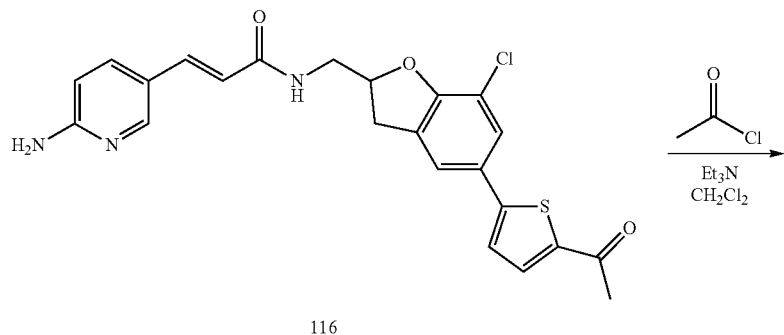

116

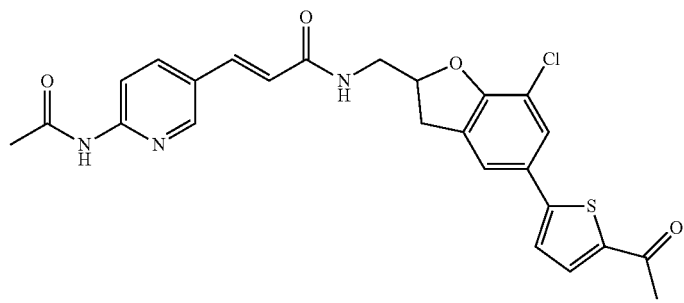

315

(E)-N-((5-(5-Acetylthiophen-2-yl)-7-chloro-2,3-dihydrobenzofuran-2-yl)methyl)-3-(6-amino pyridin-3-yl)acrylamide 116 (50 mg, 0.11 mmol) was dissolved in dichloromethane (10 mL) at room temperature. Acetyl chloride (12.97 mg, 0.165 mmol) and triethylamine (12.2 mg, 0.121 mmol) were added drop wise at 0° C. and stirred for 1 h. The reaction mixture was allowed to warm to room temperature, transferred into iced water and extracted with dichloromethane (3×20 mL). The combined organic layers were washed with brine, dried over anhydrous $Na_2SO_4$, and concentrated under reduced pressure to give crude product which was purified by silica gel chromatography (0-5% MeOH/$CH_2Cl_2$) to obtain (E)-N-((5-(5-acetylthiophen-2-yl)-7-chloro-2,3-dihydrobenzofuran-2-yl)methyl)-3-(6-aminopyridin-3-yl)acrylamide 315. Yield (6 mg, 11%). $^1$H NMR (400 MHz, DMSO-$d_6$) δ 10.67 (s, 1H), 8.44-8.49 (m, 2H), 8.12 (d, J=8 Hz, 1H), 7.91-7.99 (m, 2H), 7.58-7.66 (m, 3H), 7.44 (d, J=16 Hz, 1H), 6.72 (d, J=16 Hz, 1H), 5.08-5.10 (m, 1H), 3.54-3.64 (m, 2H), 3.40-3.46 (m, 1H), 3.08-3.14 (m, 1H), 2.51 (s, 3H), 2.33 (s, 3H). LCMS: m/z 496.02 [M+H]$^+$, $t_R$=7.28 min.

Synthesis of (E)-3-(6-aminopyridin-3-yl)-N-((5-bromo-7-chloro-2,3-dihydrobenzofuran-2-yl)methyl)acrylamide (316)

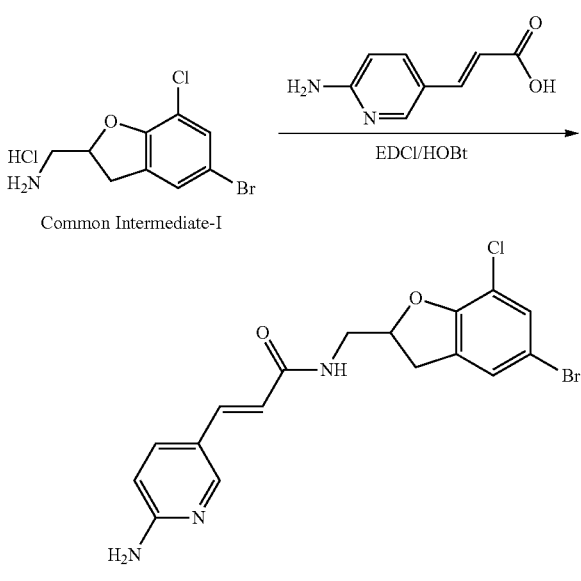

269

(E)-3-(6-Aminopyridin-3-yl)-N-(5-bromo-7-chloro-2,3-dihydrobenzofuran-2-yl)methyl) acrylamide 316 was synthesized using General Procedure 3. Yield (48%). $^1$H NMR (400 MHz, DMSO-$d_6$) δ 8.22-8.25 (t, 1H), 8.06-8.07 (d, J=4 Hz, 1H), 7.58-7.60 (d, $J_1J_2$=4 Hz, 1H), 7.39 -7.43 (d, J=12 Hz, 2H), 7.28-7.32 (d, J=16 Hz, 1H), 6.46-6.48 (d, J=8 Hz, 2H), 6.43 (s, 2H), 4.99-5.06 (m, 1H), 3.47-3.65 (m, 2H), 3.33-3.39 (m, 1H), 3.00-3.07 (m, 1H). LCMS: m/z 410.10 [M+H]$^+$, $t_R$=1.98 min.

Synthesis of (E)-N-((5-(5-acetylfuran-2-yl)-7-chloro-2,3-dihydro benzo furan-2-yl)methyl)-3-(6-aminopyridine-3-yl)acrylamide (319)

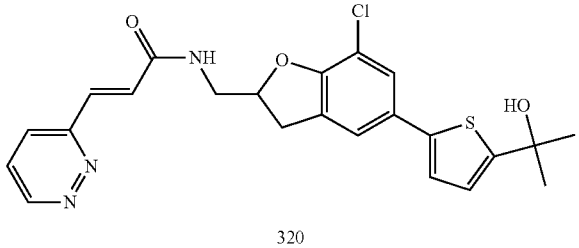

320

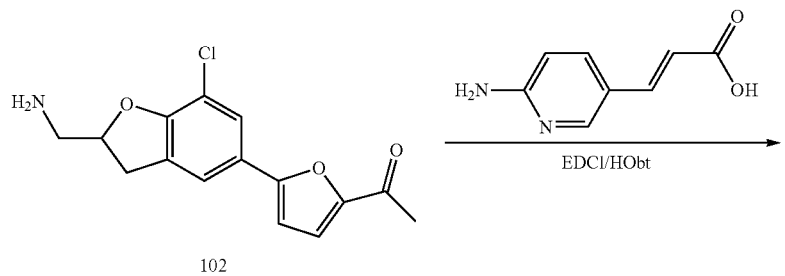

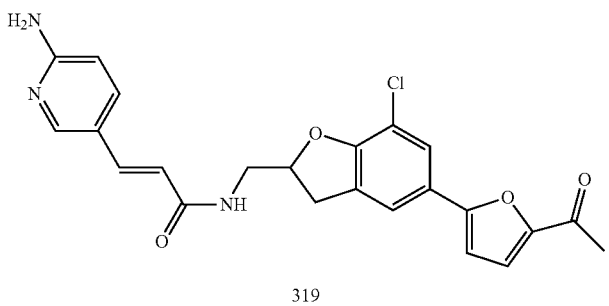

319

(E)-N-((5-(5-Acetylfuran-2-yl)-7-chloro-2,3-dihydrobenzofuran-2-yl)methyl)-3-(6-aminopyridine-3-yl)acrylamide 310 was synthesized using General Procedure 3. Yield (21%). $^1$H NMR (400 MHz, DMSO-$d_6$) δ 8.28-8.25 (m, 1H), 8.071 (s, 1H), 7.71-7.69 (d, 2H), 7.60-7.53 (m, 2H), 7.33-7.29 (d, J=15.6 Hz, 1H), 7.14-7.13 (d, J=3.6 Hz, 1H), 6.47-6.40 (m, 4H), 5.09 (m, 1H), 3.63-3.49 (m, 2H), 3.46-3.38 (m, 1H), 3.18-3.09 (m, 1H), 2.44 (s, 3H). LCMS: m/z 438.27 [M+H]$^+$, $t_R$=1.870 min.

Synthesis of (E)-N-((7-chloro-5-(5-(2-hydroxypropan-2-yl)thiophen-2-yl)-2,3-dihydrobenzofuran-2-yl)methyl)-3-(pyridazin-3-yl)acrylamide (320)

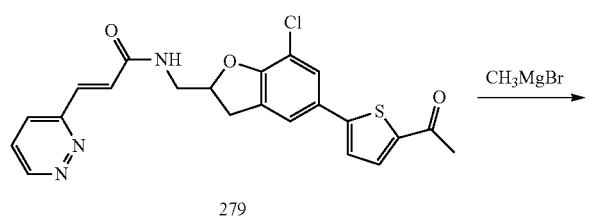

279

To a solution of E)-N-((5-(5-acetylthiophen-2-yl)-7-chloro-2,3-dihydrobenzofuran-2-yl)methyl)-3-(pyridazin-3-yl) acrylamide 279 (0.15 g, 0.3 mmol) in THF (3 mL) was added CH$_3$MgBr in THF (1.1 mmol) at 0° C. The reaction mixture was then heated at 60° C. for 10 h, transferred into saturated NH$_4$Cl solution and extracted with EtOAc. The organic layers were concentrated under reduced pressure. The crude product was purified by column chromatography (3% MeOH in CH$_2$Cl$_2$) to give (E)-N-((7-chloro-5-(5-(2-hydroxypropan-2-yl)thiophen-2-yl)-2,3-dihydrobenzofuran-2-yl) methyl)-3-(pyridazin-3-yl) acrylamide 320. Yield (7 mg). $^1$H NMR (400 MHz, DMSO) δ=9.18-9.20 (m, 1H), 8.75-8.78 (t, 1H), 7.91-7.93 (t, 1H), 7.73-7.77 (m, 1H), 7.60-7.64 (d, J=16 Hz, 1H), 7.41-7.42 (s, 2H), 7.27-7.31 (d, J=16 Hz, 1H), 7.20-7.21 (t, 1H), 6.85-6.86 (t, 1H), 5.48 (s, 1H), 5.08 (m, 1H), 3.54-3.65 (m, 2H), 3.34-3.45 (m, 1H), 3.06-3.12 (m, 1H), 1.50 (s, 6H).

(E)-3-(6-aminopyridin-3-yl)-N-((7-chloro-5-(5-(2-hydroxypropan-2-yl)thiophen-2-yl)-2,3-dihydrobenzofuran-2-yl)methyl)acrylamide (321)

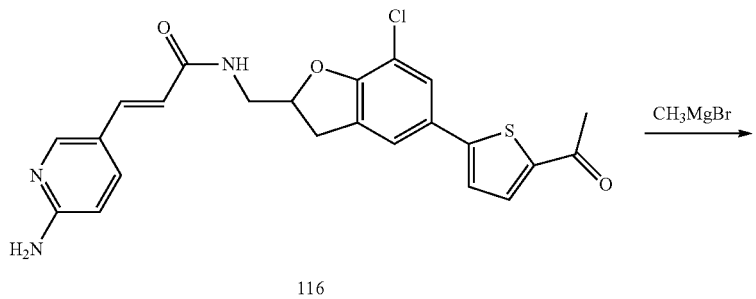

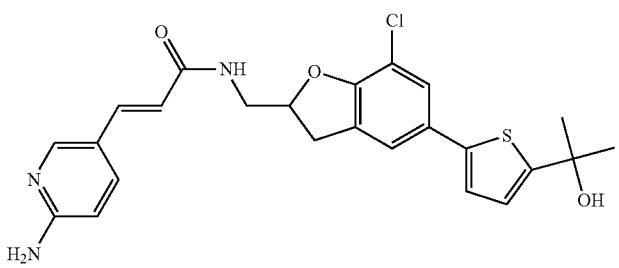

(E)-N-((5-(5-Acetylthiophen-2-yl)-7-chloro-2,3-dihydrobenzofuran-2-yl)methyl)-3-(6-aminopyridin-3-yl)acrylamide 116 (0.3 g, 0.66 mmol) was dissolved in THF (10 mL). Methyl magnesium bromide (0.47 g, 3.96 mmol) was added drop wise at 0° C. and the reaction mixture was heated at 70° C. for 10 h. The reaction mixture was transferred into ice water and extracted with ethyl acetate (3×50 mL). The combined organic layers were washed with brine, dried over anhydrous $Na_2SO_4$ and concentrated under reduced pressure. The crude product was purified by chromatography (0-5% methanol/dichloromethane) to give (E)-3-(6-aminopyridin-3-yl)-N-((7-chloro-5-(5-(2-hydroxypropan-2-yl)thiophen-2-yl)-2,3 dihydrobenzofuran-2-yl)methyl)acrylamide 321. Yield (0.03 g, 10%). $^1$H NMR (400 MHz, DMSO-$d_6$) δ 8.24-8.27 (t, 1H), 8.06-8.07 (d, 1H), 7.58-7.60 (dd, $J_1J_2$=2.4 Hz, 1H), 7.40-7.41 (d, 1H), 7.33 (s, 1H), 7.29 (s, 1H), 7.20-7.21 (d, J=3.6, 1H), 6.85-6.859 (d, J=3.6, 1H), 6.40-6.48 (m, 4H), 5.48 (s, 1H), 5.00-5.06 (m, 1H), 3.50-3.61 (m, 2H), 3.36-3.40 (m, 1H), 3.04-3.10 (m, 1H), 1.50 (s, 6H). LCMS: m/z 470.18 [M+H]$^+$, $t_R$=1.918 min.

Synthesis of (E)-N-((5-acetyl-3,4-dimethylthiophen-2-yl)-7-chloro-2,3-di hydrobenzofuran-2-yl) methyl)-3-(6-aminopyridin-3-yl) acrylamide (322)

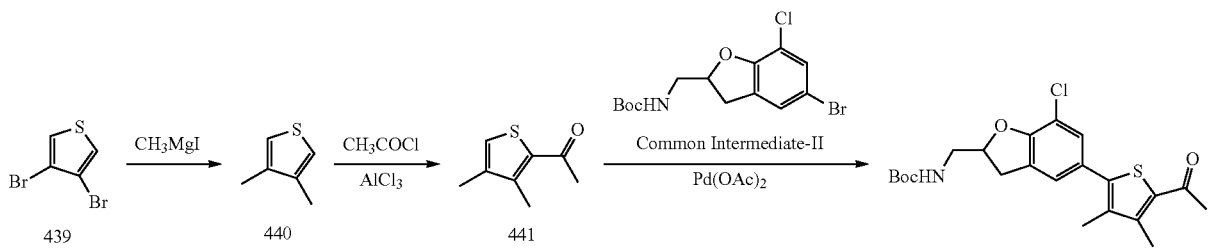

2 | HCl in Dioxane

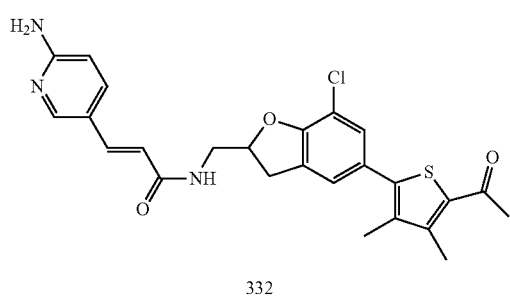

332

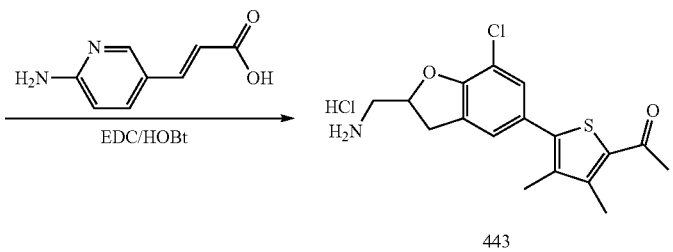

443

Synthesis of 3,4-dimethylthiophene (440): 3,4-Dibromothiophene 439 (3 g, 12.4 mmol) and [Ni(dpp)Cl$_2$] (0.047 g, 0.007 mmol) were dissolved in dry ether (3 mL). This mixture was added to methyl magnesium iodide (4.74 g, 2.88 mmol) and diethyl ether (10 mL) at 0° C. under N$_2$ atm. The reaction mixture was then refluxed for 20 h. After cooling to room temperature, the reaction was quenched with aqueous ammonium chloride solution (100 mL). The organic layer was extracted with diethyl ether (30 mL×3). The combined organic layer was washed with brine, dried over anhydrous Na$_2$SO$_4$ and concentrated under reduced pressure to obtain 3,4-dimethylthiophene 440. Yield (1.2 g, 86%). $^1$H NMR (400 MHz, CDCl$_3$) δ 6.9 (s, 2H), 2.22-2.19 (s, 6H).

Synthesis of 1-(3,4-dimethylthiophen-2-yl) ethanone (441): 3,4-Dimethylthiophene 440 (0.5 g, 4.4 mmol) and AlCl$_3$ (1.19 g, 8.9 mmol) were dissolved in dichloromethane at 0° C., acetyl chloride (0.34 g, 4.3 mmol) was added drop wise. After stirring at room temperature for 2-3 h, the reaction mixture was cooled to 30° C. and quenched with aqueous ammonium chloride solution (100 mL). The organic layer was extracted with diethyl ether (30 mL×3). The combined organic layer was washed with brine, dried over anhydrous Na$_2$SO$_4$ and concentrated under reduced pressure to obtain 1-(3,4-dimethylthiophen-2-yl) ethanone 441. Yield (0.34 g, 49%). $^1$H NMR (400 MHz, CDCl$_3$) δ 7.12 (s, 1H), 2.5 (s, 6H), 2.20 (s, 3H). LCMS: m/z 155.04 [M+H]$^+$, $t_R$=2.17 min.

Synthesis of tert-butyl (5-(5-acetyl-3,4-dimethylthiophen-2-yl)-7-chloro-2,3-dihydrobenzo furan-2-yl) methylcarbamate (442): tert-Butyl (5-bromo-7-chloro-2,3-dihydrobenzofuran-2-yl) methylcarbamate (0.5 g, 1.3 mmol), 1-(3,4-dimethylthiophen-2-yl) ethanone, Common Intermediate-II, (0.31 g, 2.06 mmol) and sodium acetate (0.21 g, 2.59 mmol) were dissolved in dimethylacetamide (5 mL) under N$_2$ atm. Pd(OAc)$_2$ (0.029 g, 0.12 mmol) was added and refluxed at 150° C. for 20 h. The reaction mixture was transferred into iced water and extracted with ethyl acetate (25 mL×3). The combined organic layers were washed with brine, dried over anhydrous Na$_2$SO$_4$, and concentrated under reduced pressure. The crude product was purified by chromatography (0-25% ethyl acetate/n-hexane) to give tert-butyl (5-(5-acetyl-3,4-dimethylthiophen-2-yl)-7-chloro-2,3-dihydrobenzo furan-2-yl) methyl carbamate 442. Yield (0.14 g, 23%). $^1$H NMR (400 MHz, DMSO-d$_6$) δ 7.28 (s, 2H), 7.18-7.15 (bs, 1H), 5.0-4.9 (m, 1H), 3.43-3.39 (m, 1H), 3.31-3.23 (m, 2H), 3.13-3.07 (m, 1H), 2.47 (s, 3H), 2.14 (s, 6H), 1.38-1.37 (s, 9H). LCMS: m/z 436.2 [M+H]$^+$, $t_R$=2.83 min.

Synthesis of 1-(5-(2-(aminomethyl)-7-chloro-2,3-dihydrobenzofuran-5-yl)-3,4-dimethyl thiophen-2-yl) ethanone (443): 1-(5-(2-(Aminomethyl)-7-chloro-2,3-dihydrobenzofuran-5-yl)-3,4-dimethyl thiophen-2-yl) ethanone 443 was synthesized using General Procedure 2. Yield (86%). $^1$H NMR (400 MHz, DMSO-d$_6$) δ 8.18 (s, 1H), 7.36-7.34 (m, 2H), 5.22-5.19 (m, 1H), 3.57-3.49 (m, 1H), 3.26-3.16 (m, 3H), 2.51 (s, 3H), 2.15 (s, 6H). LCMS: m/z 377.14 [M+H]$^+$, $t_R$=1.946 min.

Synthesis of (E)-N-((5-acetyl-3,4-dimethylthiophen-2-yl)-7-chloro-2,3-dihydrobenzofuran-2-yl) methyl)-3-(6-aminopyridin-3-yl) acrylamide (322): (E)-N-((5-Acetyl-3,4-dimethylthiophen-2-yl)-7-chloro-2,3-dihydrobenzofuran-2-yl) methyl)-3-(6-aminopyridin-3-yl) acrylamide 322 was synthesized using General Procedure 3. Yield (10%). $^1$H NMR (400 MHz, DMSO-d$_6$) δ 8.28-8.25 (t, 1H), 8.07-8.06 (d, 1H), 7.60-7.58 (d, J=10.8, 1H), 7.35-7.29 (m, 2H), 6.50-6.31 (m, 4H), 5.08-5.07 (m, 1H), 3.62-3.50 (m, 1H), 3.48-3.41 (m, 1H), 3.38-3.34 (m, 2H), 2.33 (s, 3H), 2.18 (s, 6H). LCMS: m/z 482.23[M+H]$^+$, $t_R$=2.175 min.

275
(E)-3-(6-aminopyridin-3-yl)-N-((7-chloro-5-(2-(morpholine-4-carbonyl)pyrimidin-5-yl)-2,3-dihydrobenzofuran-2-yl)methyl)acrylamide (323)

276
Synthesis of (E)-3-(6-aminopyridin-3-yl)-N-((7-chloro-5-(2-(morpholine-4-carbonyl) pyrimidin-5-yl)-2,3-dihydrobenzofuran-2-yl)methyl)acrylamide (323): (E)-3-(6-

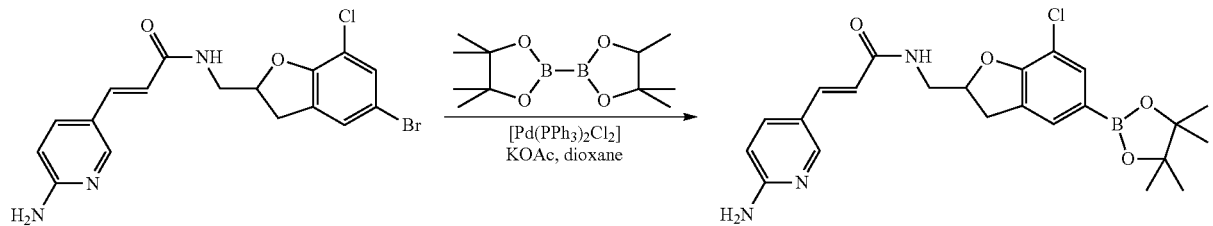

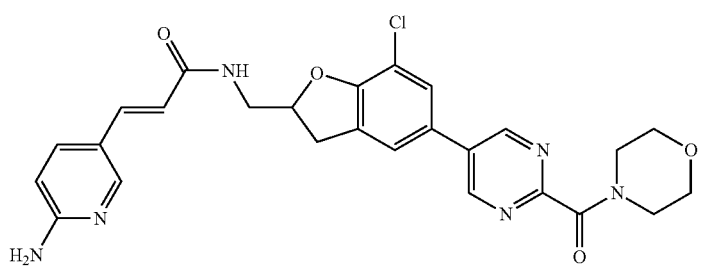

Synthesis of (E)-3-(6-aminopyridin-3-yl)-N-((7-chloro-5-(4,4,5,5-tetramethyl-1,3,2-dioxaborolan-2-yl)-2,3-dihydrobenzofuran-2-yl)methyl)acrylamide (444). (E)-3-(6-Aminopyridin-3-yl)-N-((5-bromo-7-chloro-2,3-dihydrobenzofuran-2-yl)methyl)acryl amide 316 (0.5 g, 1.22 mmol) was dissolved in 1,4-dioxane (5 mL) at room temperature. 4,4,4',4',5,5,5'-heptamethyl-2,2'-bi(1,3,2-dioxaborolane) (0.62 g, 2.44 mmol) and a solution of potassium acetate (0.24 g, 2.44 mmol) in water (2.0 mL) were added and degassed using $N_2$ for 15 min. Bis(triphenylphosphine)palladium(II) dichloride (0.08 g, 0.12 mmol) was added and the reaction mixture was irradiated under microwave for 40 min at 100° C. The reaction mixture was allowed to cool to room temperature, transferred into water and extracted with ethyl acetate (3×50 mL). The combined organic layers were washed with brine, dried over anhydrous $Na_2SO_4$, and concentrated under reduced pressure. The crude product was purified by silica gel chromatography (0-4% MeOH in $CH_2Cl_2$) to obtain (E)-3-(6-aminopyridin-3-yl)-N-((7-chloro-5-(4,4,5,5-tetramethyl-1,3,2-dioxaborolan-2-yl)-2,3-dihydrobenzofuran-2-yl)methyl)acrylamide 444. (Yield: 0.3 g, 55%). $^1$H NMR (400 MHz, DMSO-$d_6$) δ 8.24-8.25 (m, 1H), 8.06 (s, 1H), 7.58 (dd, $J_1$=2.4 Hz, $J_2$=2.4 Hz, 1H), 7.39-7.43 (m, 2H), 7.30 (d, J=16 Hz, 1H), 6.39-6.47 (m, 4H), 5.02-5.04 (m, 1H), 3.49-3.54 (m, 2H), 3.38-3.39 (m, 1H), 3.04-3.06 (m, 1H), 1.27 (s, 12H).

Aminopyridin-3-yl)-N-((7-chloro-5-(4,4,5,5-tetramethyl-1,3,2-dioxaborolan-2-yl)-2,3-dihydrobenzofuran-2-yl) methyl)acrylamide (444) (0.05 g, 0.10 mmol) was dissolved in 1,4-dioxane (2 mL) at room temperature and degassed using $N_2$ for 5 min. Tetrakis(triphenylphosphine) palladium (0) (20 mg, 0.02 mmol) and (5-bromopyrimidin-2-yl)(morpholino)methanone (0.05 g, 0.16 mmol) were added at room temperature and stirred for 5 min. Degassed solution of $K_2CO_3$ (30 mg, 0.21 mmol) in water (2 mL) was added and the reaction mixture was irradiated under microwave for 30 min at 100° C. The reaction mixture was transferred into water and extracted with ethyl acetate (3×20 mL). The combined organic layers were washed with brine, dried over anhydrous $Na_2SO_4$, and concentrated under reduced pressure to give the crude product which was purified by silica gel chromatography (0-5% MeOH in $CH_2Cl_2$) to obtain (E)-3-(6-aminopyridin-3-yl)-N-((7-chloro-5-(2-(morpholine-4-carbonyl)pyrimidin-5-yl)-2,3-dihydrobenzofuran-2-yl)methyl) acrylamide 323. Yield (10 mg, 18%). $^1$H NMR (400 MHz, DMSO-$d_6$) δ 9.18 (s, 2H), 8.28-8.31 (m, 1H), 8.07 (s, 1H), 7.77 (s, 1H), 7.72 (s, 1H), 7.58-7.60 (m, 1H), 7.29-7.33 (d, J=15.6 Hz, 1H), 6.40-6.40 (m, 4H), 5.10 (s, 1H), 3.68 (s, 4H), 3.41-3.61 (m, 5H), 3.14-3.25 (m, 3H). LCMS: m/z 521.24 [M+H]$^+$, $t_R$=1.70 min.

Synthesis of (E)-5-(2-((3-(6-aminopyridin-3-yl)acrylamido)methyl)-7-chloro-2,3-dihydro benzofuran-5-yl)-N,N-dimethylfuran-2-carboxamide (324)

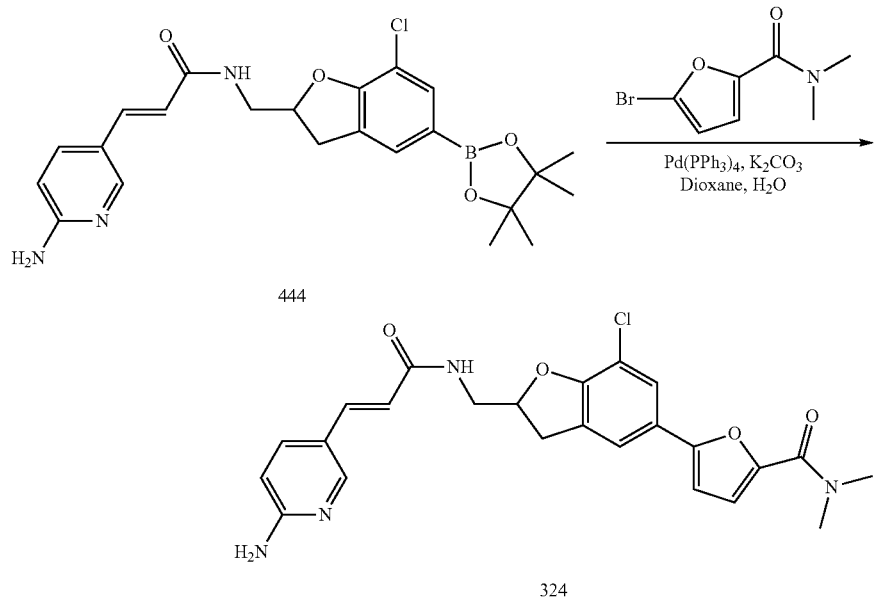

(E)-5-(2-((3-(6-Aminopyridin-3-yl)acrylamido)methyl)-7-chloro-2,3-dihydrobenzofuran-5-yl)-N,N-dimethylfuran-2-carboxamide 324 was synthesized using General Procedure 1. (Yield: 0.02 g, 20%). $^1$H NMR (400 MHz, DMSO-$d_6$) δ 8.27 (t, J=5.8 Hz, 1H), 8.06 (d, J=2 Hz, 1H), 7.61-7.57 (m, 3H), 7.31 (d, J=16 Hz, 1H), 7.09 (d, J=3.6 Hz, 1H), 7.02 (d, J=3.2 Hz, 1H), 6.47-6.40 (m, 4H), 5.07-5.05 (m, 1H), 3.60-3.48 (m, 2H), 3.45-3.38 (m, 2H), 3.26 (s, 3H), 3.18-3.01 (m, 3H). LCMS: m/z 467.19 [M+H]$^+$, $t_R$=1.75 min.

Synthesis of (E)-3-(6-aminopyridin-3-yl)-N-((7-chloro-5-(5-methyl-3-phenylisoxazol-4-yl)-2,3-dihydrobenzofuran-2-yl)methyl)acrylamide (325)

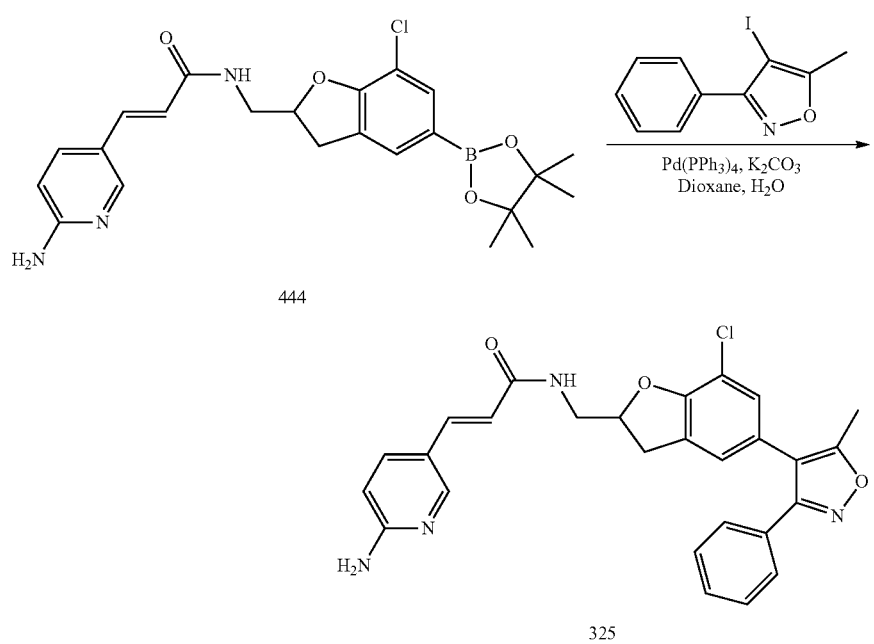

(E)-3-(6-Aminopyridin-3-yl)-N-((7-chloro-5-(5-methyl-3-phenylisoxazol-4-yl)-2,3-dihydrobenzofuran-2-yl)methyl)acrylamide 325 was synthesized using General Procedure 1. Yield (0.012 g, 11%). $^1$H NMR (400 MHz, DMSO-$d_6$) δ 8.24 (t, J=5.8 Hz, 1H), 8.07 (s, 1H), 7.60 (dd, $J_1$, $J_2$=2.0 Hz, 1H), 7.42-7.36 (m, 5H), 7.31 (d, J=15.6 Hz, 1H), 7.03 (d, J=7.2 Hz, 2H), 6.48-6.40 (m, 4H), 5.04-5.03 (m, 1H), 3.60-3.46 (m, 2H), 3.36-3.30 (m, 1H), 3.06-3.00 (m, 1H), 2.40 (s, 3H). LCMS: m/z 487.23 [M+H]$^+$, $t_R$=2.10 min.

(E)-3-(6-aminopyridin-3-yl)-N-((7-chloro-5-(5-chloro-6-(morpholine-4-carbonyl)pyridin-3-yl)-2,3-dihydrobenzofuran-2-yl)methyl)acrylamide (326)

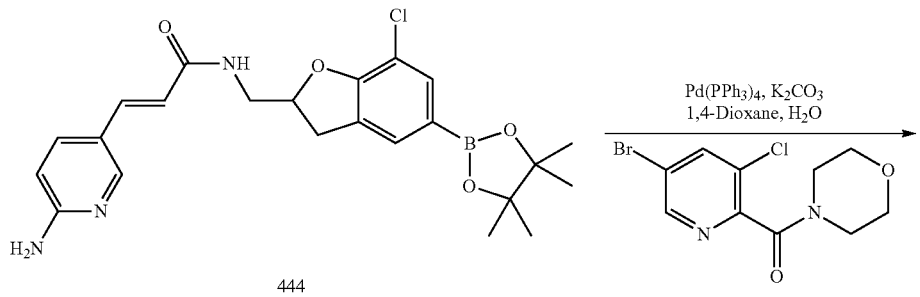

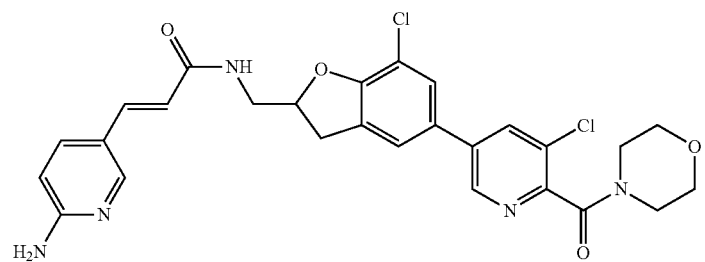

(E)-3-(6-Aminopyridin-3-yl)-N-((7-chloro-5-(5-chloro-6-(morpholine-4-carbonyl)pyridin-3-yl)-2,3-dihydrobenzofuran-2-yl)methyl)acrylamide 326 was synthesized using General Procedure 1. Yield (0.011 g, 18%). $^1$H NMR (400 MHz, DMSO-$d_6$) δ 8.86 (s, 1H), 8.34 (s, 1H), 8.27-8.30 (m, 1H), 8.07 (s, 1H), 7.73 (s, 1H), 7.69 (s, 1H), 7.58-7.60 (m, 1H), 7.31 (d, J=15.6 Hz, 1H), 6.40-6.47 (m, 4H), 5.07-5.11 (m, 1H), 3.68 (m, 4H), 3.44-3.66 (m, 6H), 3.05-3.06 (m, 2H). LCMS: m/z 554.20 [M+H]$^+$, $t_R$=1.80 min.

Synthesis of (E)-3-(6-aminopyridin-3-yl)-N-((7-chloro-5-(3-methyl-5-phenylisoxazol-4-yl)-2,3-dihydrobenzofuran-2-yl)methyl)acrylamide (327)

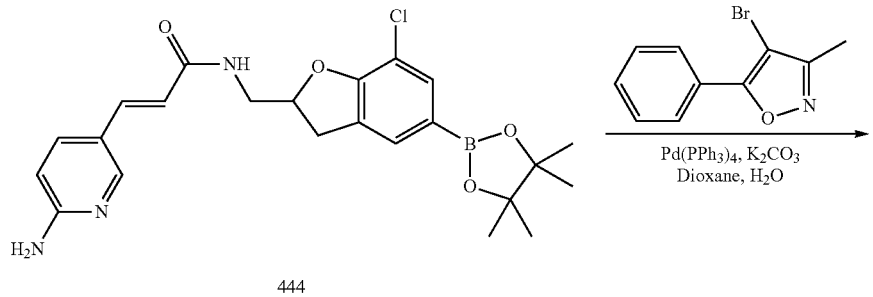

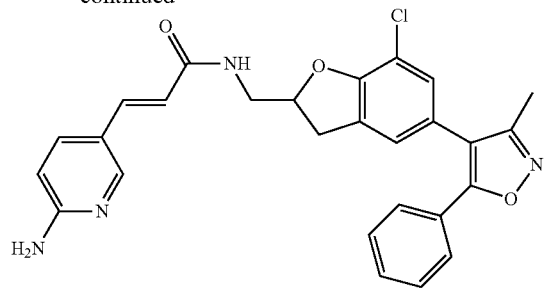
327
(E)-3-(6-Aminopyridin-3-yl)-N-((7-chloro-5-(3-methyl-5-phenylisoxazol-4-yl)-2,3-dihydrobenzofuran-2-yl)methyl)acrylamide 327 was synthesized using General Procedure 1. Yield (0.01 g, 10%). $^1$H NMR (400 MHz, DMSO-$d_6$) δ 8.24 (t, J=5.8 Hz, 1H), 8.07 (s, 1H), 7.60 (dd, $J_1$, $J_2$=2.0 Hz, 1H), 7.42-7.36 (m, 5H), 7.31 (d, J=15.6 Hz, 1H), 7.02 (d, J=7.2 Hz, 2H), 6.48-6.40 (m, 4H), 5.04-5.02 (m, 1H), 3.60-3.48 (m, 2H), 3.36-3.30 (m, 1H), 3.06-3.00 (m, 1H), 2.40 (s, 3H). LCMS: m/z 487.28 $[M+H]^+$, $t_R$=2.09 min.
(E)-3-(6-Aminopyridin-3-yl)-N-((7-chloro-5-(2,5-difluoro-4-(morpholine-4-carbonyl)phenyl-2,3-dihydrobenzofuran-2-yl)methyl)acrylamide (328)
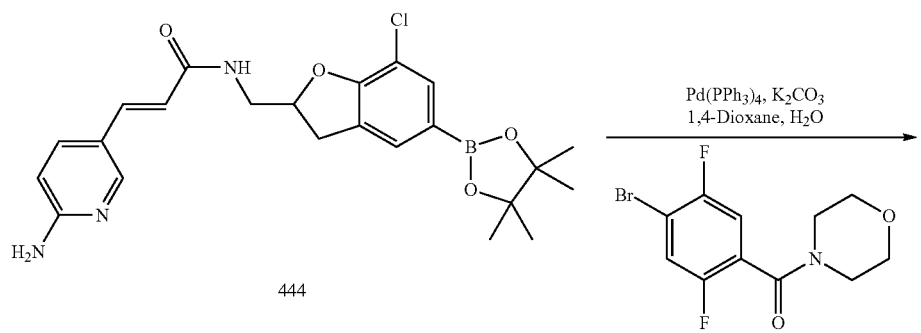
444
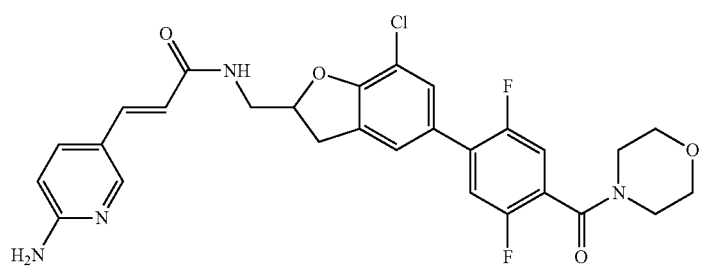
328

(E)-3-(6-Aminopyridin-3-yl)-N-((7-chloro-5-(2,5-difluoro-4-(morpholine-4-carbonyl)phenyl)-2,3-dihydrobenzofuran-2-yl)methyl)acrylamide 328 was synthesized using General Procedure 1. Yield (0.005 g, 16%). $^1$H NMR (400 MHz, DMSO-$d_6$) δ 8.27-8.30 (m, 1H), 8.07 (s, 1H), 7.51-7.61 (m, 2H), 7.44-7.46 (m, 2H), 7.31 (d, J=15.6 Hz, 1H), 6.41-6.48 (m, 4H), 5.05-5.12 (m, 1H), 3.53-3.65 (m, 7H), 3.88-3.45 (m, 1H), 3.30-3.31 (m, 2H), 3.08-3.18 (m, 2H). LCMS: m/z 555.35 [M+H]$^+$, $t_R$=1.89 min.

(E)-3-(6-Aminopyridin-3-yl)-N-((7-chloro-5-(5-fluoro-6-(morpholine-4-carbonyl)pyridin-3-yl)-2,3-dihydrobenzofuran-2-yl)methyl)acrylamide (329)

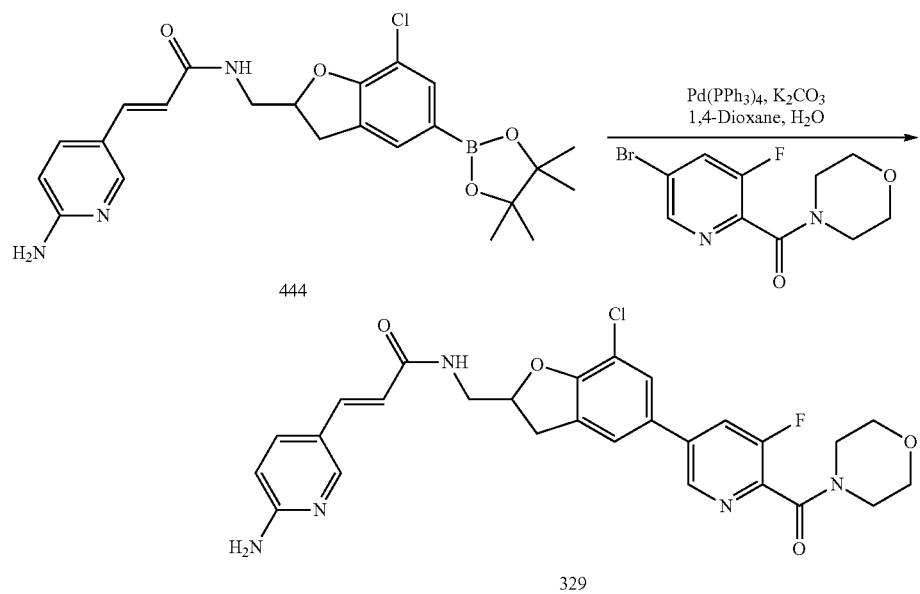

(E)-3-(6-Aminopyridin-3-yl)-N-((7-chloro-5-(5-fluoro-6-(morpholine-4-carbonyl)pyridin-3-yl)-2,3-dihydrobenzofuran-2-yl)methyl)acrylamide 329 was synthesized using General Procedure 1. Yield (0.07 g, 45%). $^1$H NMR (400 MHz, DMSO-$d_6$) δ 8.79 (s, 1H), 8.29 (s, 1H), 8.19 (d, J=10.4 Hz, 1H), 8.07 (s, 1H), 7.41 (s, 1H), 7.07 (s, 1H), 7.61 (s, 1H), 7.59 (s, 1H), 7.32 (d, J=16 Hz, 1H), 6.41-6.48 (m, 4H), 5.01 (s, 1H), 3.59-3.68 (m, 4H), 3.40-3.46 (m, 1H), 3.21-3.29 (m, 2H), 3.14-3.18 (m, 1H), 3.09 (s, 3H). LCMS: m/z 538.34 [M+H]$^+$, $t_R$=1.75 min.

(E)-3-(6-Aminopyridin-3-yl)-N-((7-chloro-5-(5-(morpholine-4-carbonyl)pyrimidin-2-yl)-2,3-dihydrobenzofuran-2-yl)methyl)acrylamide (330)

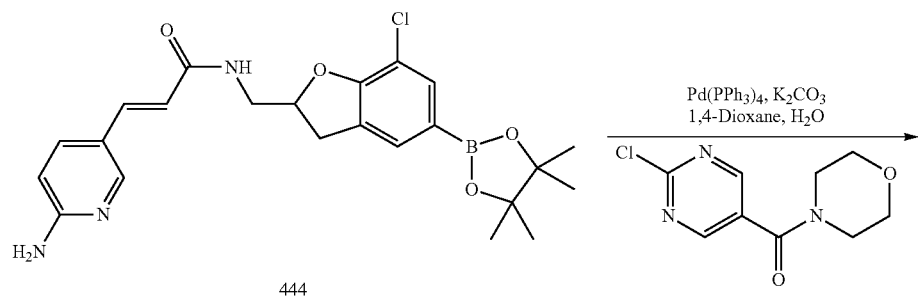

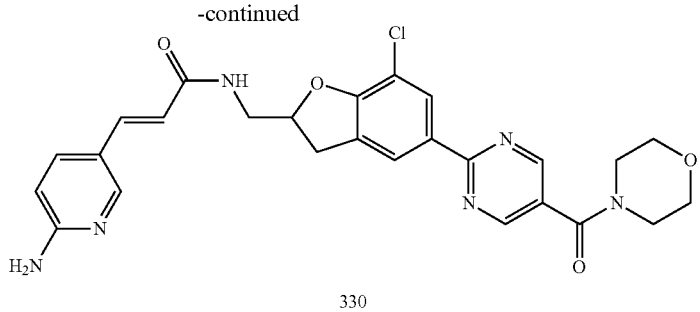

330

(E)-3-(6-Aminopyridin-3-yl)-N-((7-chloro-5-(5-(morpholine-4-carbonyl)pyrimidin-2-yl)-2,3-dihydrobenzofuran-2-yl)methyl)acrylamide (330) was synthesized using General Procedure 1. Yield (0.015 g, 26%). $^1$H NMR (400 MHz, DMSO-$d_6$) δ 8.67 (s, 2H), 8.27-8.29 (m, 1H), 8.22 (d, J=6 Hz, 2H), 8.07 (s, 1H), 7.57-7.60 (m, 1H), 7.31 (d, J=15.6 Hz, 1H), 6.40-6.47 (m, 4H), 5.14 (m, 1H), 3.34-3.65 (m, 10H), 3.11-3.16 (m, 2H). LCMS: m/z 521.24 [M+H]$^+$, $t_R$=1.77 min.

(E)-3-(6-Aminopyridin-3-yl)-N-((7-chloro-5-(6-(morpholine-4-carbonyl)pyridazin-3-yl)-2,3-dihydrobenzofuran-2-yl)methyl)acrylamide (331)

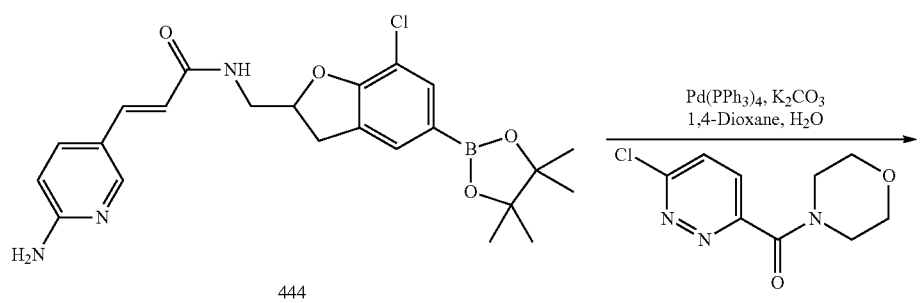

444

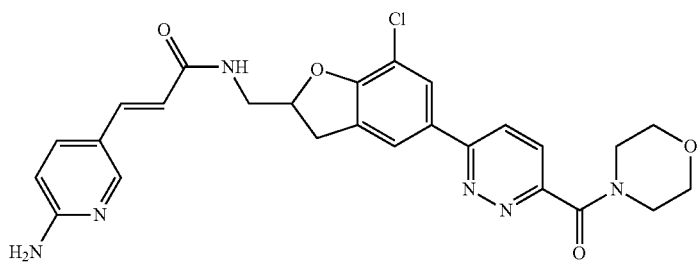

331

(E)-3-(6-Aminopyridin-3-yl)-N-((7-chloro-5-(6-(morpholine-4-carbonyl)pyridazin-3-yl)-2,3-dihydrobenzofuran-2-yl)methyl)acrylamide 331 was synthesized using General Procedure 1. (Yield: 0.021 g, 36%). $^1$H NMR (400 MHz, DMSO-$d_6$) δ 8.36 (d, J=8.8 Hz, 1H), 8.28-8.31 (m, 1H), 8.08 (d, J=10.4 Hz, 3H), 7.93 (d, J=8.8 Hz, 1H), 7.58-7.60 (m, 1H), 7.32 (d, J=15.6 Hz, 1H), 6.40-6.47 (m, 4H), 5.13 (m, 1H), 3.72 (s, 4H), 3.19-3.62 (m, 6H), 3.17-3.19 (m, 1H). LCMS: m/z 521.24 [M+H]$^+$, $t_R$=1.71 min.

(E)-3-(6-Aminopyridin-3-yl)-N-((7-chloro-5-(3,5-difluoro-4-(morpholine-4-carbonyl)phenyl)-2,3-dihydrobenzofuran-2-yl)methyl)acrylamide (332)

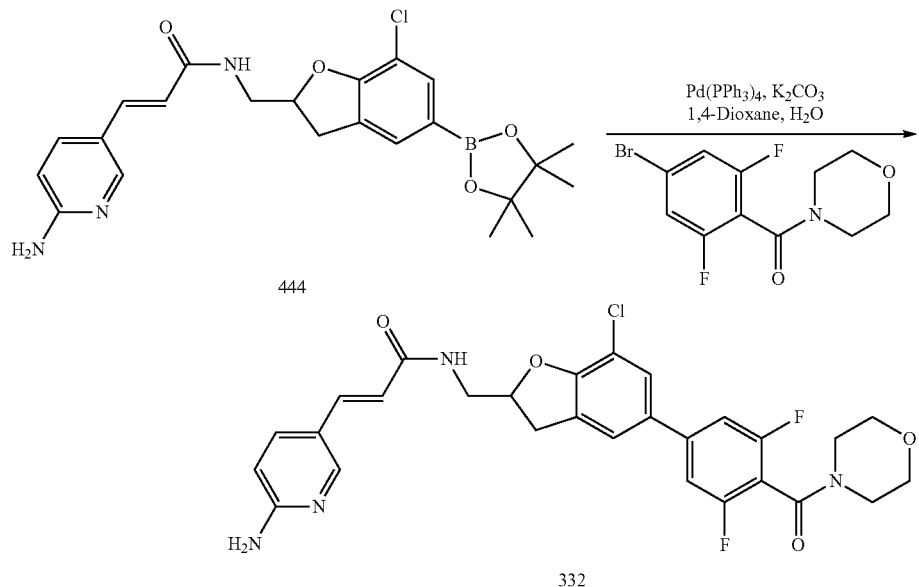

(E)-3-(6-Aminopyridin-3-yl)-N-((7-chloro-5-(3,5-difluoro-4-(morpholine-4-carbonyl)phenyl)-2,3-dihydrobenzofuran-2-yl)methyl)acrylamide 332 was synthesized using General Procedure 1. Yield (0.01 g, 9%). $^1$H NMR (400 MHz, DMSO-d$_6$) δ 8.27-8.30 (m, 1H), 8.07 (s, 1H), 7.56-7.68 (m, 5H), 7.31 (d, J=15.6 Hz, 1H), 6.41-6.49 (m, 4H), 5.05-5.12 (m, 1H), 3.62-3.67 (m, 4H), 3.58-3.60 (m, 4H), 3.08-3.51 (m, 4H). LCMS: m/z 555.89 [M+H]$^+$, t$_R$=1.86 min.

(E)-3-(6-Aminopyridin-3-yl)-N-((7-chloro-5-(5-(morpholine-4-carbonyl)pyridin-2-yl)-2,3-dihydrobenzofuran-2-yl)methyl)acrylamide (333)

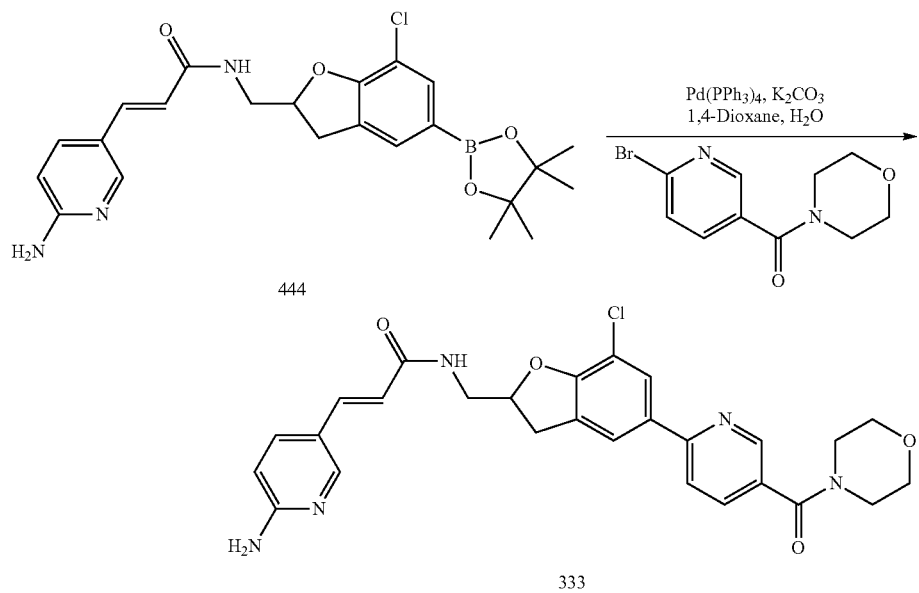

(E)-3-(6-Aminopyridin-3-yl)-N-((7-chloro-5-(5-(morpholine-4-carbonyl)pyridin-2-yl)-2,3-dihydrobenzofuran-2-yl)methyl)acrylamide (333) was synthesized using General Procedure 1. Yield (0.01 g, 8%). $^1$H NMR (400 MHz, DMSO-d$_6$) δ 8.65 (s, 1H), 8.27-8.30 (m, 1H), 8.06 (s, 1H), 7.98-8.02 (m, 3H), 7.88-7.90 (m, 1H), 7.57-7.60 (m, 1H), 7.31 (d, J=15.6 Hz, 1H), 6.40-6.47 (m, 4H), 5.10 (s, 1H), 3.51-3.64 (m, 10H), 3.10-3.17 (m, 2H). LCMS: m/z 520.78 [M+H]$^+$, t$_R$=1.71 min.

(E)-3-(7-Chloro-5-(4-(morpholine-4-carbonyl)phenyl)-2,3-dihydrobenzofuran-2-yl)-N-(pyridin-3-ylmethyl)acrylamide (334)

dissolved in toluene (20 mL) at room temperature. (Carbethoxymethylene)triphenylphosphorane (1.80 g, 5.17 mmol) was added to the reaction mixture and heated at 90° C. for 1 h. The reaction mixture was transferred into iced water and extracted with ethyl acetate (3×50 mL). The combined organic layers were washed with brine, dried over anhydrous Na$_2$SO$_4$, and concentrated under reduced pressure to give the crude product which was purified by silica gel chromatography (0-8% ethyl acetate/n-hexane) to obtain (E)-ethyl 3-(5-bromo-7-chloro-2,3-dihydrobenzofuran-2-yl)acrylate 446. Yield (0.6 g, 47%). $^1$H NMR (400 MHz, CDCl$_3$) δ 7.28 (s, 1H), 7.20-7.18 (m, 1H), 7.99 (dd, J$_1$, J$_2$=4.8 Hz, 1H), 6.15

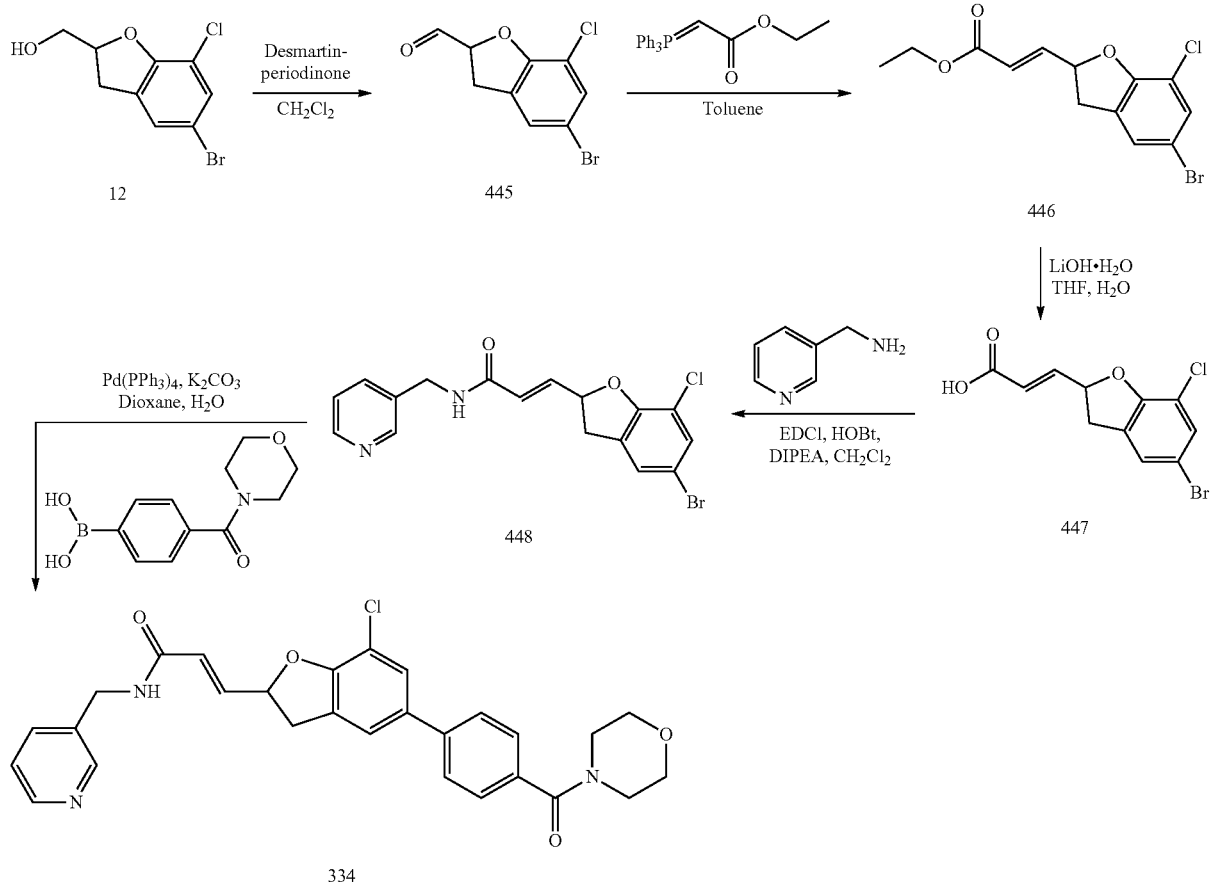

Synthesis of 5-bromo-7-chloro-2,3-dihydrobenzofuran-2-carbaldehyde (445): (5-Bromo-7-chloro-2,3-dihydrobenzofuran-2-yl)methanol (0.5 g, 1.89 mmol) was dissolved in dichloromethane (20 mL) at room temperature. Desmartin periodinane (1.2 g, 2.84 mmol) was added at 0° C. and stirred for 2 h. The reaction mixture was transferred into iced water and extracted with CH$_2$Cl$_2$ (3×50 mL). The combined organic layers were washed with brine, dried over anhydrous Na$_2$SO$_4$ and concentrated under reduced pressure to give crude 5-bromo-7-chloro-2,3dihydrobenzofuran-2-carbaldehyde 445 which was used in next reaction without further purification. Yield (1 g, 100%).

Synthesis of (E)-ethyl 3-(5-bromo-7-chloro-2,3-dihydrobenzofuran-2-yl)acrylate (446): 5-Bromo-7-chloro-2,3-dihydrobenzofuran-2-carbaldehyde (1.0 g, 3.83 mmol) was (d, J$_1$=2.0 Hz, J$_2$=1.2 Hz, 1H), 5.52-5.46 (m, 1H), 4.26-4.20 (m, 2H), 3.59-3.53 (m, 1H), 3.16-3.10 (m, 1H), 1.35-1.26 (m, 3H).

Synthesis of (E)-3-(5-bromo-7-chloro-2,3-dihydrobenzofuran-2-yl)acrylic acid (447): (E)-Ethyl 3-(5-bromo-7-chloro-2,3-dihydrobenzofuran-2-yl)acrylate 446 (0.5 g, 1.51 mmol) was added to a mixture of THF:Water (1:1, 20 mL) at room temperature. The reaction mixture was cooled to 0° C. and an ice cold lithium hydroxide solution (0.25 g in 2 mL water) was added to the reaction mixture. The reaction mixture was allowed to warm to room temperature and stirred for 5 h. The reaction mixture was transferred into iced water and pH was adjusted to 1-2 using 3M HCl solution (5 mL). The reaction mixture was then extracted with ethyl acetate (3×20 mL). The combined organic layers was washed with brine (50 mL), dried over anhydrous sodium sulfate and concentrated under reduced pressure to obtain (E)-3-(5-bromo-7-chloro-2,3-dihydrobenzofuran-2-yl) acrylic acid 447. Yield (0.3 g, 66%). $^1$H NMR (400 MHz, DMSO-$d_6$) δ 12.58 (s, 1H), 7.48-7.40 (m, 2H), 6.90 (dd, $J_1$, $J_2$=4.8 Hz, 1H), 5.97 (d, $J_1$=1.6 Hz, $J_2$=1.2 Hz, 1H), 5.64-5.59 (m, 1H), 3.62-3.55 (m, 1H), 3.19-3.13 (m, 1H).

Synthesis of (E)-3-(5-bromo-7-chloro-2,3-dihydrobenzofuran-2-yl)-N-(pyridin-3-ylmethyl)acrylamide (448): (E)-3-(5-Bromo-7-chloro-2,3-dihydrobenzofuran-2-yl)acrylic acid 447 (0.15 g, 0.49 mmol) was dissolved in dichloromethane (20 mL) at room temperature. Pyridin-3-ylmethanamine (0.05 g, 0.49 mmol), EDCI (0.11 g, 0.59 mmol), HOBt (0.08 g, 0.59 mmol) and DIPEA (0.17 mL, 0.99 mmol) were added to the reaction mixture and stirred for 1 h. The reaction mixture was transferred into iced water and extracted with ethyl acetate (3×50 mL). The combined organic layers were washed with brine, dried over anhydrous $Na_2SO_4$, and concentrated under reduced pressure. The crude product was purified by silica gel chromatography (0-3% MeOH in $CH_2Cl_2$) to obtain (E)-3-(5-bromo-7-chloro-2,3-dihydrobenzofuran-2-yl)-N-(pyridin-3-ylmethyl)acrylamide 448. Yield (0.15 g, 77%). $^1$H NMR (400 MHz, DMSO-$d_6$) δ 8.76 (t, J=5.8 Hz, 1H), 8.49-8.45 (m, 2H), 7.67-7.65 (m, 1H), 7.47 (d, J=1.6 Hz, 1H), 7.37-7.33 (m, 2H), 6.78 (dd, $J_1$, $J_2$=4.8 Hz, 1H), 6.20 (d, $J_1$, $J_2$=1.6 Hz, 1H), 5.63-5.58 (m, 1H), 4.36 (d, J=6 Hz, 2H), 3.61-3.54 (m, 1H), 3.15-3.13 (m, 1H). LCMS: m/z 395.29 [M+2], $t_R$=1.98 min.

Synthesis of (E)-3-(7-chloro-5-(4-(morpholine-4-carbonyl)phenyl)-2,3-dihydrobenzofuran-2-yl)-N-(pyridin-3-ylmethyl)acrylamide (334): (E)-3-(5-Bromo-7-chloro-2,3-dihydrobenzofuran-2-yl)-N-(pyridin-3-ylmethyl)acrylamide 448 (0.15 g, 0.38 mmol) was dissolved in 1,4-dioxane (2 mL) at room temperature and degassed using $N_2$ for 5 min. Tetrakis(triphenylphosphine) palladium (0) (0.02 g, 0.17 mmol) and 4-(morpholine-4-carbonyl)phenylboronic acid (0.13 g, 0.57 mmol) were added and degassed using $N_2$ for 5 min. The solution of degassed $K_2CO_3$ (0.1 g, 0.76 mmol) in 2 mL of water was added and the reaction mixture was irradiated under microwave for 30 min at 100° C. The reaction mixture was transferred into iced water and extracted with ethyl acetate (3×20 mL). The combined organic layers were washed with brine, dried over anhydrous $Na_2SO_4$, and concentrated under reduced pressure to give the crude product, which was purified by silica gel chromatography (0-5% MeOH in $CH_2Cl_2$) to obtain (E)-3-(7-chloro-5-(4-(morpholine-4-carbonyl)phenyl)-2,3-dihydrobenzofuran-2-yl)-N-(pyridin-3-ylmethyl)acrylamide 334. Yield (0.02 g, 10%). $^1$H NMR (400 MHz, DMSO-$d_6$) δ 8.79 (t, J=5.6 Hz, 1H), 8.49-8.46 (m, 2H), 7.81-7.65 (m, 3H), 7.56-7.55 (m, 2H), 7.48-7.46 (m, 2H), 7.37-7.34 (m, 1H), 6.82 (dd, $J_1$, $J_2$=4.8 Hz, 1H), 6.24 (d, $J_1$, $J_2$=1.2 Hz, 1H), 5.65-5.63 (m, 1H), 4.40-4.36 (m, 2H), 3.69-3.60 (m, 6H), 3.40-3.36 (m, 2H), 3.20-3.14 (m, 2H). LCMS: m/z 504.83 [M+H]$^+$, $t_R$=1.83 min.

Synthesis of (E)-3-(6-aminopyridin-3-yl)-N-((7-chloro-5-(4-(3,3-difluoroazetidine-1-carbonyl)-3,5-difluorophenyl)-2,3-dihydrobenzofuran-2-yl)methyl) acrylamide (335)

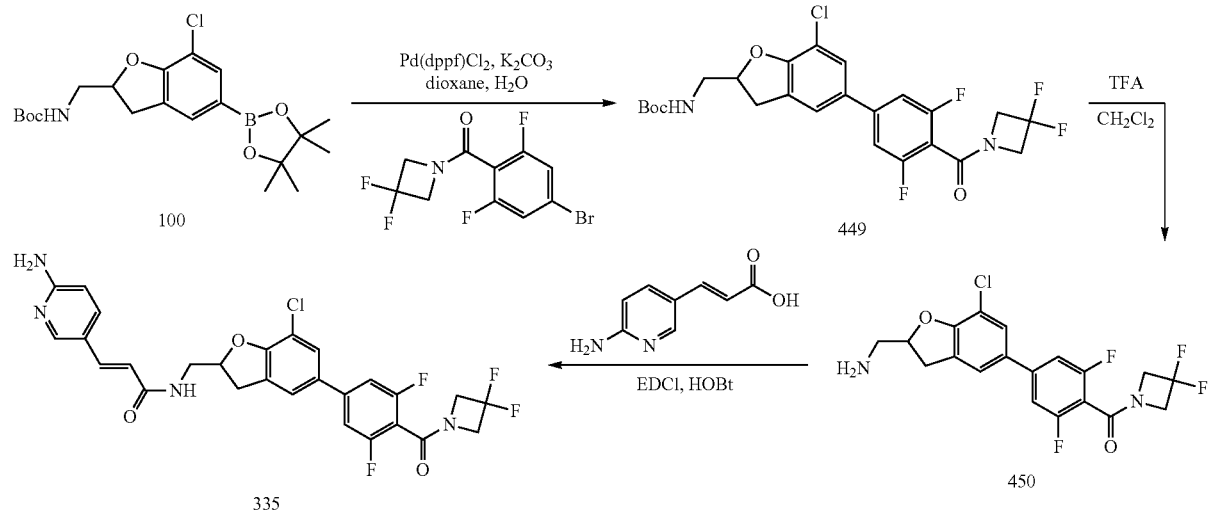

tert-Butyl (7-chloro-5-(4-(3,3-difluoroazetidine-1-carbonyl)-3,5-difluorophenyl)-2,3-dihydrobenzofuran-2-yl)methylcarbamate 449 was synthesized using General Procedure 1. Yield (100 mg, 60%). LCMS: m/z 515.0 [M+H]$^+$, $t_R$=1.91 min.

(4-(2-(Aminomethyl)-7-chloro-2,3-dihydrobenzofuran-5-yl)-2,6-difluorophenyl)(3,3-difluoroazetidin-1-yl)methanone 450 was synthesized using General Procedure 2. Yield (36 mg, 45%). LCMS: m/z 415.0 [M+H]$^+$, $t_R$=1.66 min.

(E)-3-(6-Aminopyridin-3-yl)-N-((7-chloro-5-(4-(3,3-difluoroazetidine-1-carbonyl)-3,5-difluorophenyl)-2,3-dihydrobenzofuran-2-yl)methyl)acrylamide 335 was synthesized using General Procedure 3. Yield (26 mg, 58%). $^1$H NMR (400 MHz, $CD_3OD$) δ 8.03 (s, 1H), 7.20 (dd, J=2 Hz, J=9 Hz, 1H), 7.51-7.35 (m, 5H), 6.60 (d, J=9 Hz, 1H), 6.45 (d, J=16 Hz, 1H), 5.13 (s, 1H), 4.60-4.48 (m, 4H), 3.70-3.68 (m, 2H), 3.49-3.45 (m, 1H), 3.21-3.15 (m, 1H). LCMS: m/z 561.2 [M+H]$^+$, $t_R$=1.69 min.

Synthesis of (E)-3-(6-aminopyridin-3-yl)-N-((7-chloro-5-(4-(3,3-difluoroazetidine-1-carbonyl)-3-fluorophenyl)-2,3-dihydrobenzofuran-2-yl)methyl)acrylamide (336)

robenzofuran-2-yl)methyl)acrylamide 336 was synthesized using General Procedure 3. Yield (21 mg, 36%, 2 steps). $^1$H NMR (400 MHz, DMSO-$d_6$) δ 8.49 (t, J=6 Hz, 1H), 8.19 (s, 1H), 8.07 (dd, J=2 Hz, J=10Hz, 1H), 7.58-7.66 (m, 5H), 7.41 (d, J=16 Hz, 1H), 6.97 (d, J=9 Hz, 1H), 6.76 (d, J=16 Hz,

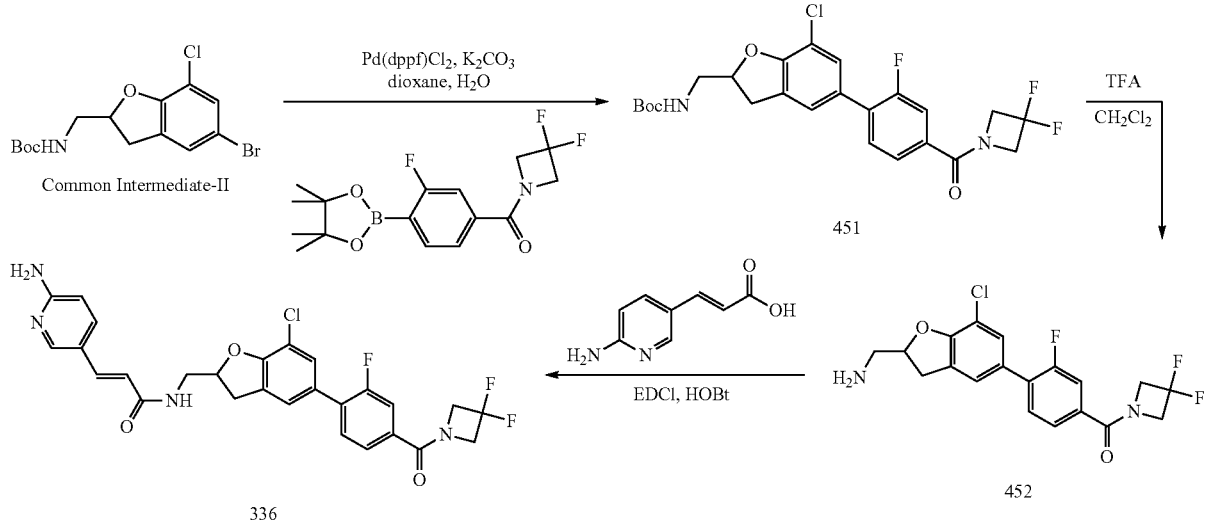

tert-Butyl(7-chloro-5-(4-(3,3-difluoroazetidine-1-carbonyl)-3-fluorophenyl)-2,3-dihydrobenzofuran-2-yl)methylcarbamate 451 was synthesized using General Procedure 1. Yield (54 mg, 38%). LCMS: m/z 497.0 [M+H]$^+$, $t_R$=1.02 min.

(4-(2-(Aminomethyl)-7-chloro-2,3-dihydrobenzofuran-5-yl)-2-fluorophenyl)(3,3-difluoroazetidin-1-yl)methanone 452 was synthesized using General Procedure 2. LCMS: m/z 397.0 [M+H]$^+$, $t_R$=0.75 min.

1H), 5.13-5.06 (m, 1H), 4.59-4.48 (m, 4H), 3.65-3.55 (m, 4H), 3.14-3.08 (m, 2H). LCMS: m/z 543.1 [M+H]$^+$, $t_R$=1.66 min.

Synthesis of ((E)-3-(6-aminopyridin-3-yl)-N-((7-chloro-5-(4-(3,3-difluoroazetidine-1-carbonyl)-2,3-difluorophenyl)-2,3-dihydrobenzofuran-2-yl)methyl)acrylamide (337)

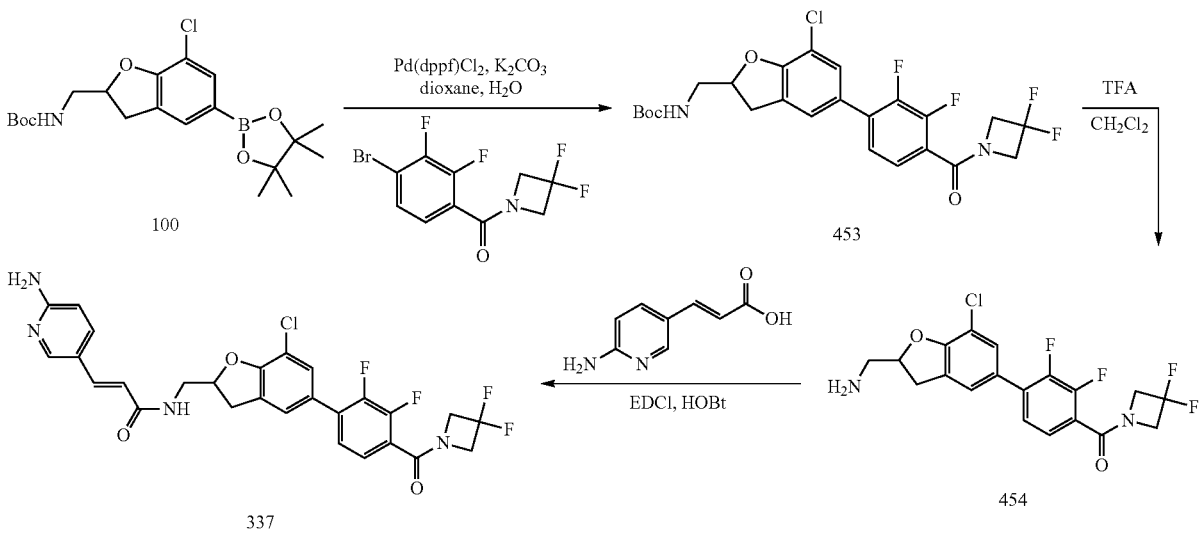

(E)-3-(6-Aminopyridin-3-yl)-N-((7-chloro-5-(4-(3,3-difluoroazetidine-1-carbonyl)-3-fluorophenyl)-2,3-dihydtert-Butyl (7-chloro-5-(4-(3,3-difluoroazetidine-1-carbonyl)-2,3-difluorophenyl)-2,3-dihydrobenzofuran-2-yl)methylcarbamate 453 was synthesized using General Procedure 1. Yield (55 mg, 48%). LCMS: m/z 515.1 [M+H]$^+$, $t_R$=1.05 min.

(4-(2-(Aminomethyl)-7-chloro-2,3-dihydrobenzofuran-5-yl)-2,3-difluorophenyl)(3,3-difluoroazetidin-1-yl)methanone 454 was synthesized using General Procedure 2. Yield (59 mg, 100%). LCMS: m/z 415.0 [M+H]$^+$, $t_R$=1.36 min.

((E)-3-(6-Aminopyridin-3-yl)-N-((7-chloro-5-(4-(3,3-difluoroazetidine-1-carbonyl)-2,3-difluorophenyl)-2,3-dihydrobenzofuran-2-yl)methyl)acrylamide 337 was synthesized using General Procedure 3. Yield (24 mg, 40%). $^1$H NMR (400 MHz, DMSO-d$_6$) δ 8.27 (t, J=6 Hz, 1H), 8.06 (d, J=2 Hz, 1H), 7.59 (dd, J=2 Hz, J=9 Hz, 1H), 7.48-7.40 (m, 4H), 7.31 (d, J=16 Hz, 1H), 6.48-6.41 (m, 4H), 5.10-5.08 (m, 1H), 4.64-4.50 (m, 4H), 3.62-3.39 (m, 3H), 3.15-3.09 (m, 1H). LCMS: m/z 561.2 [M+H]$^+$, $t_R$=1.39 min.

Synthesis of (E)-3-(6-aminopyridin-3-yl)-N-((7-chloro-5-(5-(3,3-difluoroazetidine-1-carbonyl)pyridin-2-yl)-2,3-dihydrobenzofuran-2-yl)methyl)acrylamide (338)

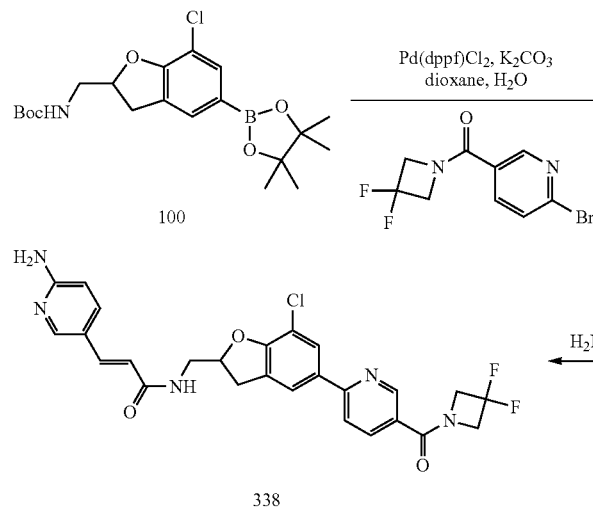
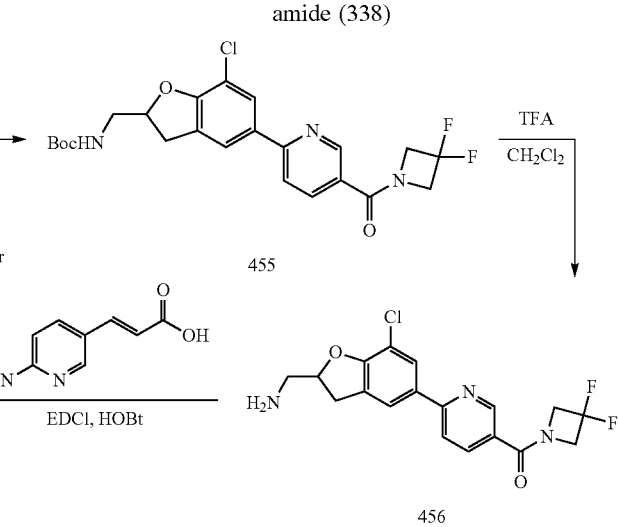

tert-Butyl (7-chloro-5-(5-(3,3-difluoroazetidine-1-carbonyl)pyridin-2-yl)-2,3-dihydrobenzofuran-2-yl)methylcarbamate 455 was synthesized using General Procedure 1. Yield (60 mg, 53%). LCMS: m/z 480.0 [M+H]$^+$, $t_R$=1.82 min.

(6-(2-(Aminomethyl)-7-chloro-2,3-dihydrobenzofuran-5-yl)pyridin-3-yl)(3,3-difluoroazetidin-1-yl)methanone 2,2,2-trifluoroacetate 456 was synthesized using General Procedure 2. Yield (66 mg, 100%). LCMS: m/z 380.0 [M+H]$^+$, $t_R$=1.27 min.

(E)-3-(6-Aminopyridin-3-yl)-N-((7-chloro-5-(5-(3,3-difluoroazetidine-1-carbonyl)pyridin-2-yl)-2,3-dihydrobenzofuran-2-yl)methyl)acrylamide 338 was synthesized using General Procedure 3. Yield (20 mg, 30%). $^1$H NMR (400 MHz, DMSO-d$_6$) δ 8.89 (d, J=2 Hz, 1H), 8.48 (t, J=6 Hz, 1H), 8.13-8.10 (m, 2H), 8.07-8.02 (m, 5H), 7.41 (d, J=16 Hz, 1H), 6.97 (d, J=9 Hz, 1H), 6.61 (d, J=16 Hz, 2H), 5.16-5.09 (m, 1H), 4.93-4.81 (m, 2H), 4.59-4.47 (m, 2H), 3.65-3.56 (m, 2H), 3.16-3.10 (m, 2H). LCMS: m/z 526.0 [M+H]$^+$, $t_R$=1.44 min.

Synthesis of (E)-3-(6-aminopyridin-3-yl)-N-((7-chloro-5-(5-(piperidine-1-carbonyl)pyridin-2-yl)-2,3-dihydrobenzofuran-2-yl)methyl)acrylamide (339)

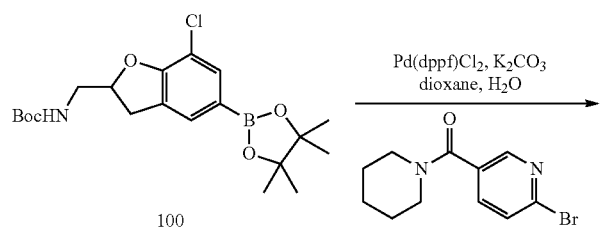

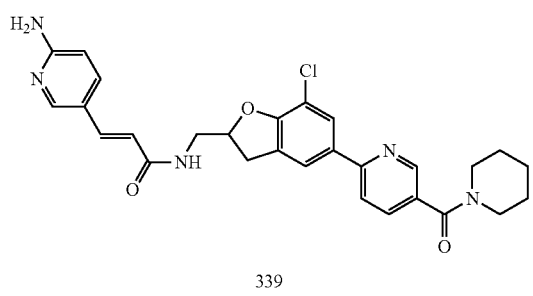
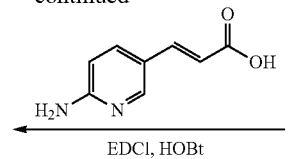

tert-Butyl (7-chloro-5-(5-(piperidine-1-carbonyl)pyridin-2-yl)-2,3-dihydrobenzofuran-2-yl)methylcarbamate 457 was synthesized using General Procedure 1. Yield (150 mg, 48%). LCMS: m/z 472.2 [M+H]$^+$, $t_R$=1.78 min.

(6-(2-(Aminomethyl)-7-chloro-2,3-dihydrobenzofuran-5-yl)pyridin-3-yl)(piperidin-1-yl)methanone 458 was synthesized using General Procedure 2. Yield (155 mg, 100%). LCMS: m/z 372.1 [M+H]$^+$, $t_R$=1.56 min.

(E)-3-(6-Aminopyridin-3-yl)-N-((7-chloro-5-(5-(piperidine-1-carbonyl)pyridin-2-yl)-2,3-dihydrobenzofuran-2-yl)methyl)acrylamide 339 was synthesized using General Procedure 3. Yield (58 mg, 35%). $^1$H NMR (400 MHz, DMSO-d$_6$) δ 8.61 (t, J=6 Hz, 1H), 8.29-8.25 (m, 1H), 8.01-7.96 (m, 4H), 7.85-7.83 (m, 1H), 7.59 (dd, J=2 Hz, J=9 Hz, 1H), 7.31 (d, J=16 Hz, 1H), 6.50-6.31 (m, 4H), 5.13-5.01 (m, 1H), 3.64-3.43 (m, 7H), 3.16-3.10 (m, 1H), 1.62-1.52 (m, 6H). LCMS: m/z 518.0 [M+H]$^+$, $t_R$=1.43 min.

Synthesis of (E)-3-(6-aminopyridin-3-yl)-N-((7-chloro-4-(4-(3,3-difluoroazetidine-1-carbonyl)phenyl)-2,3-dihydrobenzofuran-2-yl)methyl)acrylamide (340)

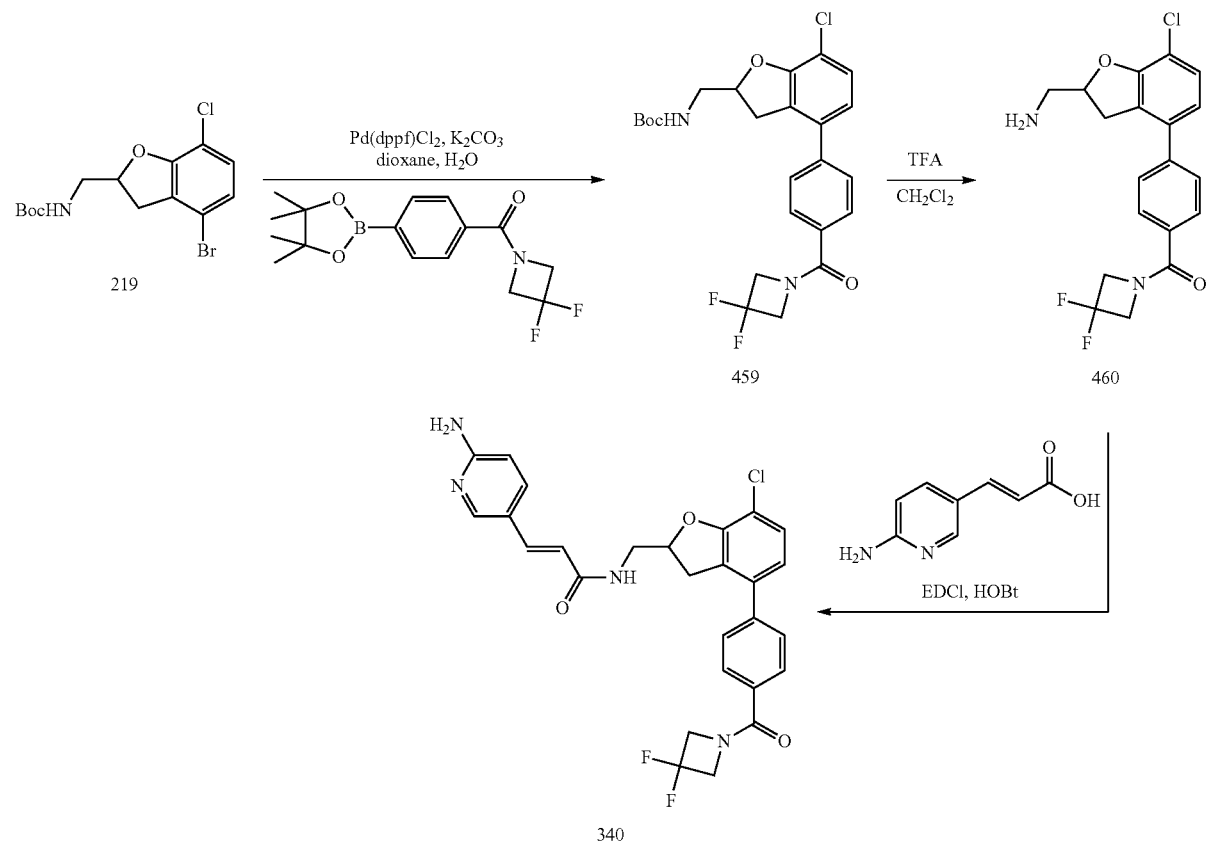

tert-Butyl (7-chloro-4-(4-(3,3-difluoroazetidine-1-carbonyl)phenyl)-2,3-dihydrobenzofuran-2-yl)methylcarbamate 459 was synthesized using General Procedure 1. Yield (120 mg, 45%). LCMS: m/z 501.0 [M+Na]$^+$, $t_R$=1.84 min.

(4-(2-(Aminomethyl)-7-chloro-2,3-dihydrobenzofuran-4-yl)phenyl)(3,3-difluoroazetidin-1-yl)methanone 460 was synthesized using General Procedure 2. Yield (80 mg, 84%). LCMS: m/z 379.1 [M+H]$^+$; $t_R$=1.30 min.

(E)-3-(6-Aminopyridin-3-yl)-N-((7-chloro-4-(4-(3,3-difluoroazetidine-1-carbonyl)phenyl)-2,3-dihydrobenzofuran-2-yl)methyl)acrylamide 340 was synthesized using General Procedure 3. Yield (80 mg, 73%). $^1$H NMR (400 MHz, CD$_3$OD) δ 8.04 (s, 1H), 7.82-7.78 (m, 2H), 7.73-7.71 (m, 1H), 7.65-7.60 (m, 2H), 7.41 (d, J=16 Hz, 1H), 7.26 (d, J=8 Hz, 1H), 6.94 (d, J=8 Hz, 1H), 6.60 (d, J=9 Hz, 1H), 6.44 (d, J=16 Hz, 1H), 5.09-5.05 (m, 1H), 4.87-4.56 (m, 4H), 3.69-3.66 (m, 2H), 3.52-3.46 (m, 1H), 3.25-3.19 (m, 1H). LCMS: m/z 525.0 [M+H]$^+$, t$_R$=1.66 min.

Synthesis of (E)-3-(6-aminopyridin-3-yl)-N-((7-chloro-4-(2-(3,3-difluoroazetidine-1-carbonyl)phenyl)-2,3-dihydrobenzofuran-2-yl)methyl)acrylamide (341)

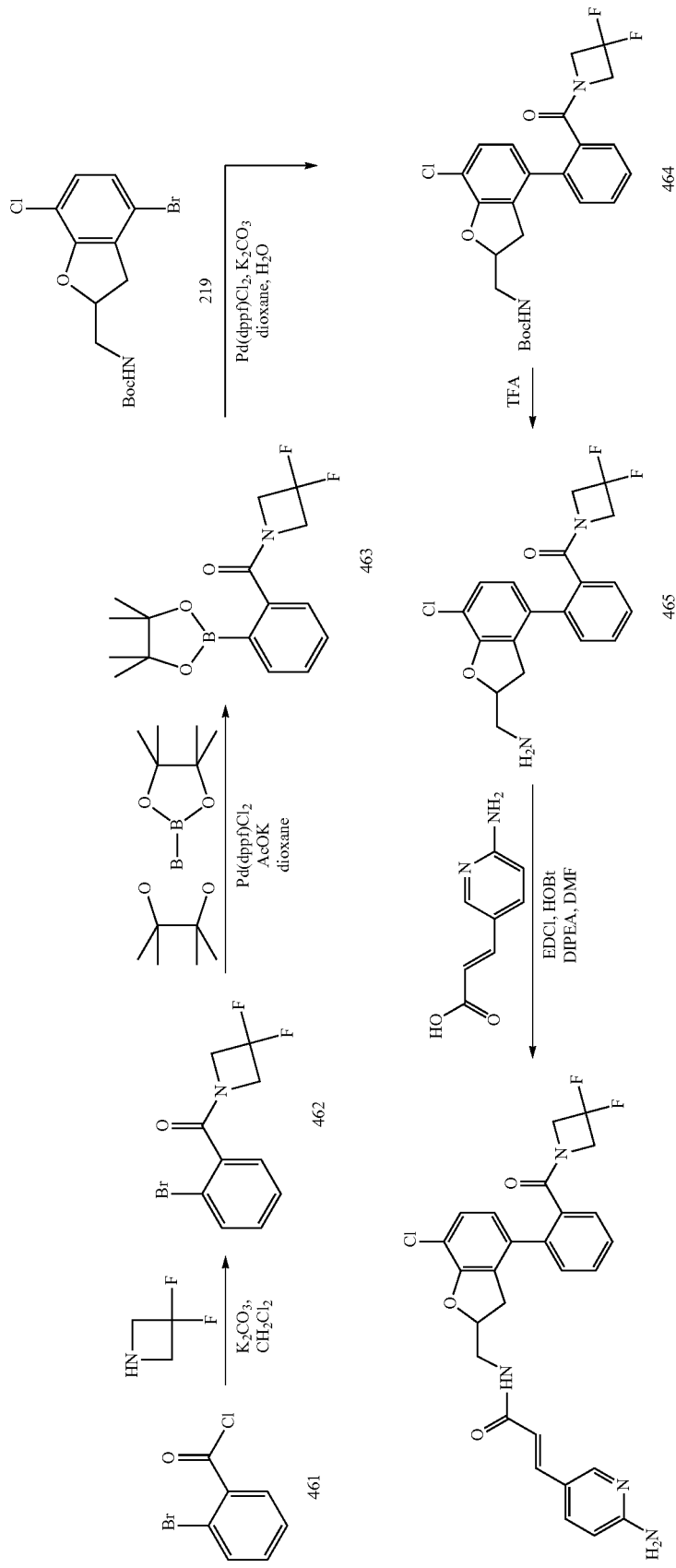

Synthesis of (2-bromophenyl)(3,3-difluoroazetidin-1-yl)methanone (462): 2-Bromobenzoyl chloride 461 (1 g, 4.6 mmol) and 3,3-difluoroazetidine hydrochloride (0.6 g, 4.6 mmol) were dissolved in dichloromethane (10 mL). Potassium carbonate (1.3 g, 9.1 mmol) was added. The reaction mixture was stirred at room temperature overnight. The reaction mixture was poured into 20 mL of water and extracted with EtOAc (20 mL×3). The combined organic layers were washed with brine, dried over anhydrous $Na_2SO_4$, and concentrated under reduced pressure to give the crude product, which was purified by silica gel chromatography (60% EtOAc/petroleum ether) to give (2-bromophenyl)(3,3-difluoroazetidin-1-yl)methanone 462 as white solid. Yield (1 g, 86%). LCMS: m/z 276.0 [M+H]$^+$, $t_R$=1.56 min.

Synthesis of (3,3-difluoroazetidin-1-yl)(2-(4,4,5,5-tetramethyl-1,3,2-dioxaborolan-2-yl)phenyl)methanone (463): A mixture of (2-bromophenyl)(3,3-difluoroazetidin-1-yl)methanone 462 (0.2 g, 0.7 mmol), 4,4,4',4',5,5,5',5'-octamethyl-2,2'-bi(1,3,2-dioxaborolane) (0.22 g, 0.9 mmol), Pd(dppf)Cl$_2$ (28 mg, 0.04 mmol) and potassium acetate (88 mg, 0.9 mmol) in dioxane (8 mL) was stirred at 90° C. under nitrogen atmosphere for 6 h. After cooling to room temperature, the mixture was filtered and the filtrate was concentrated under reduced pressure to give the crude product, which was purified by silica gel chromatography (50% EtOAc/petroleum ether) to give (3,3-difluoroazetidin-1(-yl)(2-(4,4,5,5-tetramethyl-1,3,2-dioxaborolan-2-yl)phenyl)methanone 463 as white solid. Yield (80 mg, 34%). LCMS: m/z 324.7 [M+H]$^+$; $t_R$=1.73 min.

tert-Butyl (7-chloro-4-(2-(3,3-difluoroazetidine-1-carbonyl)phenyl)-2,3-dihydrobenzofuran-2-yl)methylcarbamate 464 was synthesized using General Procedure 1. Yield (80 mg, 45%). LCMS: m/z 501.0 [M+Na]$^+$, $t_R$=1.79 min.

(2-(2-(Aminomethyl)-7-chloro-2,3-dihydrobenzofuran-4-yl)phenyl)(3,3-difluoroazetidin-1-yl)methanone 465 was synthesized using General Procedure 2. Yield (50 mg, 79%). LCMS: m/z 379.1 [M+H]$^+$; $t_R$=0.92 min.

(E)-3-(6-aminopyridin-3-yl)-N-((7-chloro-4-(2-(3,3-difluoroazetidine-1-carbonyl)phenyl)-2,3-dihydrobenzofuran-2-yl)methyl)acrylamide 341 was synthesized using General Procedure 3. Yield (50 mg, 71%). $^1$H NMR (400 MHz, CD$_3$OD) δ 8.08-8.05 (m, 1H), 7.91 (s, 1H), 7.49-7.28 (m, 5H), 7.10 (d, J=8 Hz, 1H), 6.94 (d, J=9 Hz, 1H), 6.64 (d, J=8 Hz, 1H), 6.51 (d, J=16 Hz, 1H), 5.0-4.94 (m, 1H), 4.22-4.16 (m, 2H), 4.06-4.02 (m, 2H), 3.56-3.46 (m, 2H), 3.30-3.22 (m, 2H). LCMS: m/z 525.0 [M+H]$^+$, $t_R$=1.26 min.

Synthesis of (E)-3-(6-aminopyridin-3-yl)-N-((7-chloro-5-(6-(piperazine-1-carbonyl)pyridin-3-yl)-2,3-dihydrobenzofuran-2-yl)methyl)acrylamide (342)

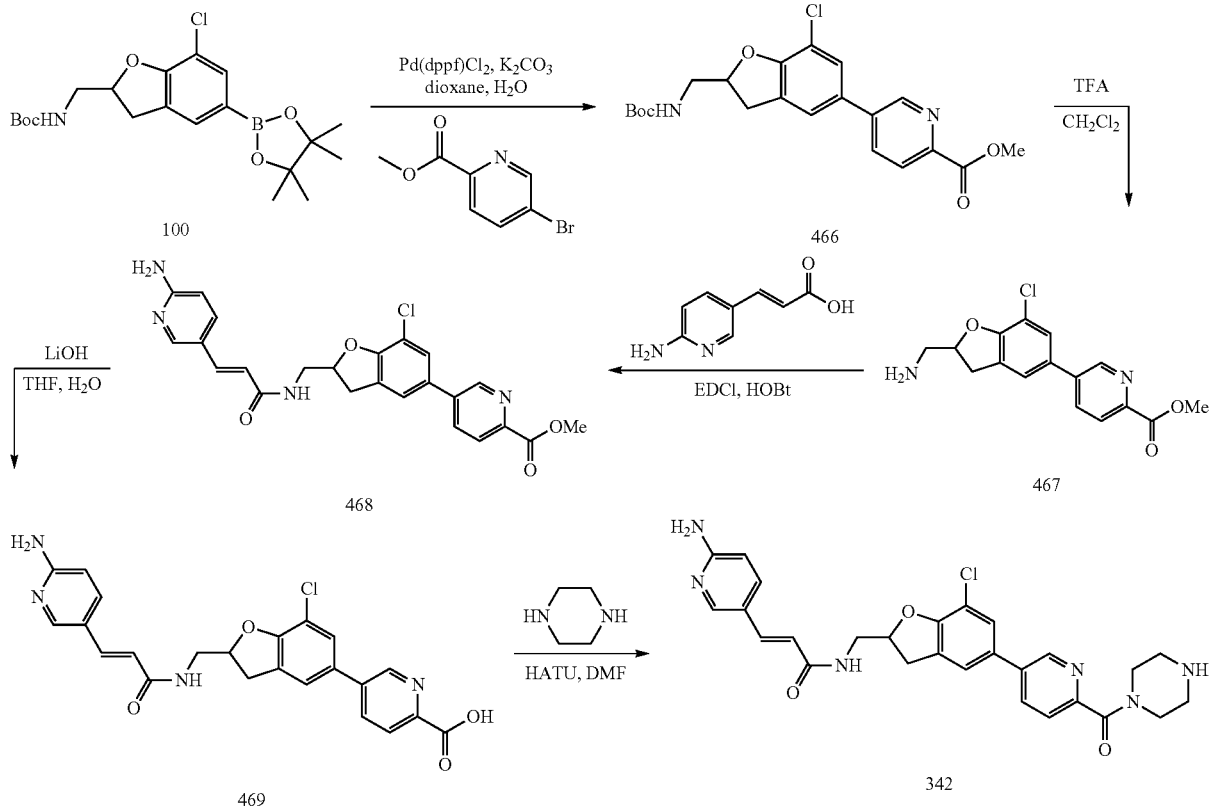

Methyl 5-(2-((tert-butoxycarbonylamino)methyl)-7-chloro-2,3-dihydrobenzofuran-5-yl)picolinate 466 was synthesized using General Procedure 1. Yield (180 mg, 78%). LCMS: m/z 419.1 [M+H]$^+$; $t_R$=1.18 min.

Methyl 5-(2-(aminomethyl)-7-chloro-2,3-dihydrobenzofuran-5-yl)picolinate 467 was synthesized using General Procedure 2. Yield (186 mg, 100%). LCMS: m/z 319.6 [M+H]$^+$; $t_R$=1.49 min.

(E)-Methyl 5-(2-((3-(6-aminopyridin-3-yl)acrylamido)methyl)-7-chloro-2,3-dihydrobenzofuran-5-yl)picolinate 468 was synthesized using General Procedure 3. Yield (100 mg, 50%). LCMS: m/z 464.7 [M+H]$^+$; $t_R$=1.19 min.

Synthesis of (E)-5-(2-((3-(6-aminopyridin-3-yl)acrylamido)methyl)-7-chloro-2,3-dihydrobenzofuran-5-yl)picolinic acid (469): (E)-methyl5-(2-((3-(6-aminopyridin-3-yl)acrylamido)methyl)-7-chloro-2,3-dihydrobenzofuran-5-yl)picolinate 468 (100 mg, 0.22 mmol) was dissolved in THF (0.8 mL), LiOH (20 mg, 0.44 mmol) and water (0.2 mL) were added to this mixture. The mixture was stirred at room temperature for 8 h. 1N HCl solution was added and adjusted to pH 6. The precipitate was collected by filtration to give (E)-5-(2-((3-(6-aminopyridin-3-yl)acrylamido)methyl)-7-chloro-2,3-dihydrobenzofuran-5-yl)picolinic acid 469. Yield (55 mg, 56%). LCMS: m/z 451.0 [M+H]$^+$; $t_R$=1.23 min.

(E)-3-(6-Aminopyridin-3-yl)-N-((7-chloro-5-(6-(piperazine-1-carbonyl)pyridin-3-yl)-2,3-dihydrobenzofuran-2-yl)methyl)acrylamide 342 was synthesized using General Procedure 3. Yield (13 mg, 23%). $^1$H NMR (400 MHz, CD$_3$OD) δ 8.84 (s, 1H), 8.23-8.17 (m, 2H), 8.05 (s, 1H), 7.81 (d, J=8 Hz, 1H), 7.55 (d, J=7 Hz, 2H), 7.47 (d, J=16 Hz, 1H), 7.12 (d, J=9 Hz, 1H), 6.66 (d, J=16 Hz, 1H), 5.17-5.14 (m, 1H), 4.04-3.96 (m, 4H), 3.78-3.65 (m, 2H), 3.55-3.39 (m, 4H), 3.22-3.16 (m, 2H). LCMS: m/z 519.2 [M+H]$^+$; $t_R$=1.36 min.

Synthesis of (E)-3-(6-aminopyridin-3-yl)-N-((7-chloro-5-(2-methyl-1,3-dioxoisoindolin-5-yl)-2,3-dihydrobenzofuran-2-yl)methyl)acrylamide (343)

tert-Butyl(7-chloro-5-(2-methyl-1,3-dioxoisoindolin-5-yl)-2,3-dihydrobenzofuran-2-yl)methylcarbamate 470 was synthesized using General Procedure 1. Yield (400 mg, 69%). LCMS: m/z 343.0 [M+H−100]$^+$; $t_R$=1.92 min.

5-(2-(Aminomethyl)-7-chloro-2,3-dihydrobenzofuran-5-yl)-2-methylisoindoline-1,3-dione 471 was synthesized using General Procedure 2. Yield (100 mg, 65%). LCMS: m/z 343.0 [M+H]$^+$; $t_R$=0.93 min.

(E)-3-(6-Aminopyridin-3-yl)-N-((7-chloro-5-(2-methyl-1,3-dioxoisoindolin-5-yl)-2,3-dihydrobenzofuran-2-yl)methyl)acrylamide 343 was synthesized using General Procedure 3. Yield (50 mg, 35%). $^1$H NMR (400 MHz, DMSO-d$_6$) δ 8.08-8.05 (m, 3H), 7.88 (d, J=8 Hz, 1H), 7.71-7.60 (m, 2H), 7.61-7.58 (m, 1H), 7.32 (d, J=16 Hz, 1H), 6.48-6.41 (m, 4H), 5.11-5.08 (m, 1H), 3.64-3.51 (m, 2H), 3.46-3.40 (m, 2H), 3.16-3.10 (m, 1H), 3.06 (s, 3H). LCMS: m/z 489.0 [M+H]$^+$; $t_R$=1.48 min.

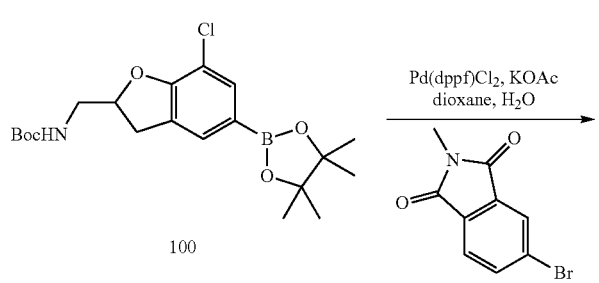
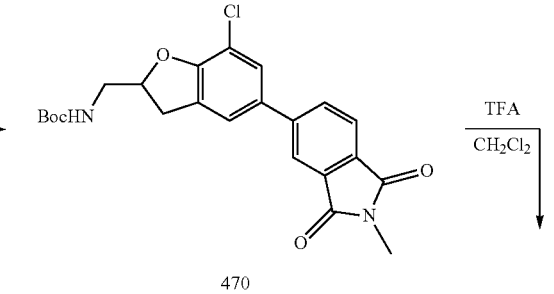
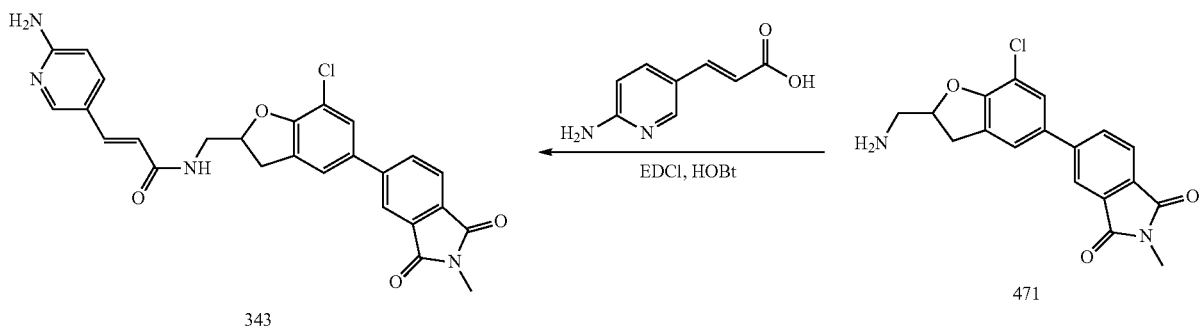

Synthesis of (E)-3-(6-aminopyridin-3-yl)-N-((7-chloro-4-(2-(morpholine-4-carbonyl)phenyl)-2,3-dihydrobenzofuran-2-yl)methyl)acrylamide (344)

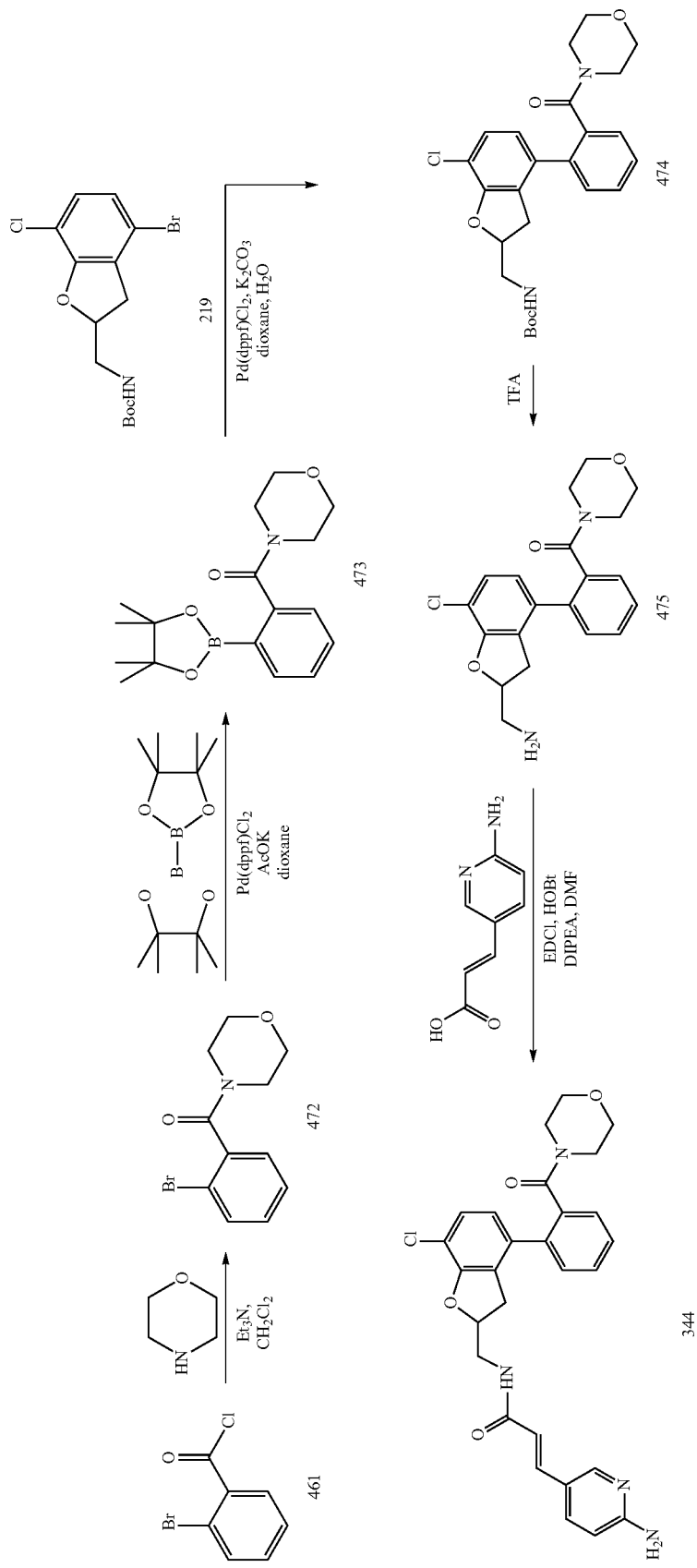

Synthesis of ((2-bromophenyl)(morpholino)methanone (472): 2-Bromobenzoyl chloride 461 (1 g, 4.6 mmol) and morpholine (0.4 g, 4.6 mmol) were dissolved in dichloromethane (10 mL). Triethylamine (0.9 g, 9.1 mmol) was added. The mixture was stirred at room temperature overnight, poured into 20 mL of water and extracted with EtOAc (20 mL×3). The combined organic layers were washed with brine, dried over anhydrous $Na_2SO_4$, and concentrated under reduced pressure to give the crude product, which was purified by silica gel chromatography (50% EtOAc/petroleum ether) to give ((2-bromophenyl)(morpholino)methanone 57 as white solid. Yield (1 g, 81%). LCMS: m/z 270.0 [M+H]$^+$; $t_R$=2.56 min.

Synthesis of morpholino(2-(4,4,5,5-tetramethyl-1,3,2-dioxaborolan-2-yl)phenyl)methanone (473): A mixture of ((2-bromophenyl)(morpholino)methanone 472 (0.2 g, 0.53 mmol), 4,4,4',4',5,5,5',5'-octamethyl-2,2'-bi(1,3,2-dioxaborolane) (0.13 g, 0.53 mmol), Pd(dppf)Cl$_2$ (20 mg, 0.03 mmol) and AcOK (78 mg, 0.8 mmol) in dioxane (5 mL) was stirred at 90° C. under nitrogen atmosphere for 6 h. After cooling to room temperature, the mixture was filtered and the filtrate was concentrated under reduced pressure to give the crude product, which was purified by silica gel chromatography (50% EtOAc/petroleum ether) to give morpholino (2-(4,4,5,5-tetramethyl-1,3,2-dioxaborolan-2-yl)phenyl) methanone 58 as white solid. Yield (60 mg, 36%). LCMS: m/z 318.1 [M+H]$^+$; $t_R$=1.64 min.

tert-Butyl (7-chloro-4-(2-(morpholine-4-carbonyl)phenyl)-2,3-dihydrobenzofuran-2-yl)methylcarbamate 474 was synthesized using General Procedure 1. Yield (80 mg, 36%). LCMS: m/z 495.7 [M+Na]$^+$, $t_R$=1.75 min.

(2-(2-(Aminomethyl)-7-chloro-2,3-dihydrobenzofuran-4-yl)phenyl)(morpholino)methanone (475) was synthesized using General Procedure 2. Yield (50 mg, 79%). LCMS: m/z 373.0 [M+H]$^+$; $t_R$=1.14 min.

(E)-3-(6-Aminopyridin-3-yl)-N-((7-chloro-4-(2-(morpholine-4-carbonyl)phenyl)-2,3-dihydrobenzofuran-2-yl) methyl)acrylamide 344 was synthesized using General Procedure 3. Yield (50 mg, 71%). $^1$H NMR (400 MHz, DMSO-d$_6$) δ 8.47-8.43 (m, 1H), 8.32-8.07 (m, 4H), 7.53-7.27 (m, 6H), 6.99 (d, J=9 Hz, 1H), 6.73 (d, J=8 Hz, 1H), 6.64-6.55 (m, 1H), 5.0 (s, 1H), 3.55-2.67 (m, 12H). LCMS: m/z 519.0 [M+H]$^+$, $t_R$=1.21 min.

Synthesis of (E)-3-(6-aminopyridin-3-yl)-N-((7-methoxy-5-(4-(morpholine-4-carbonyl)phenyl)-2,3-dihydrobenzofuran-2-yl)methyl)acrylamide (345)

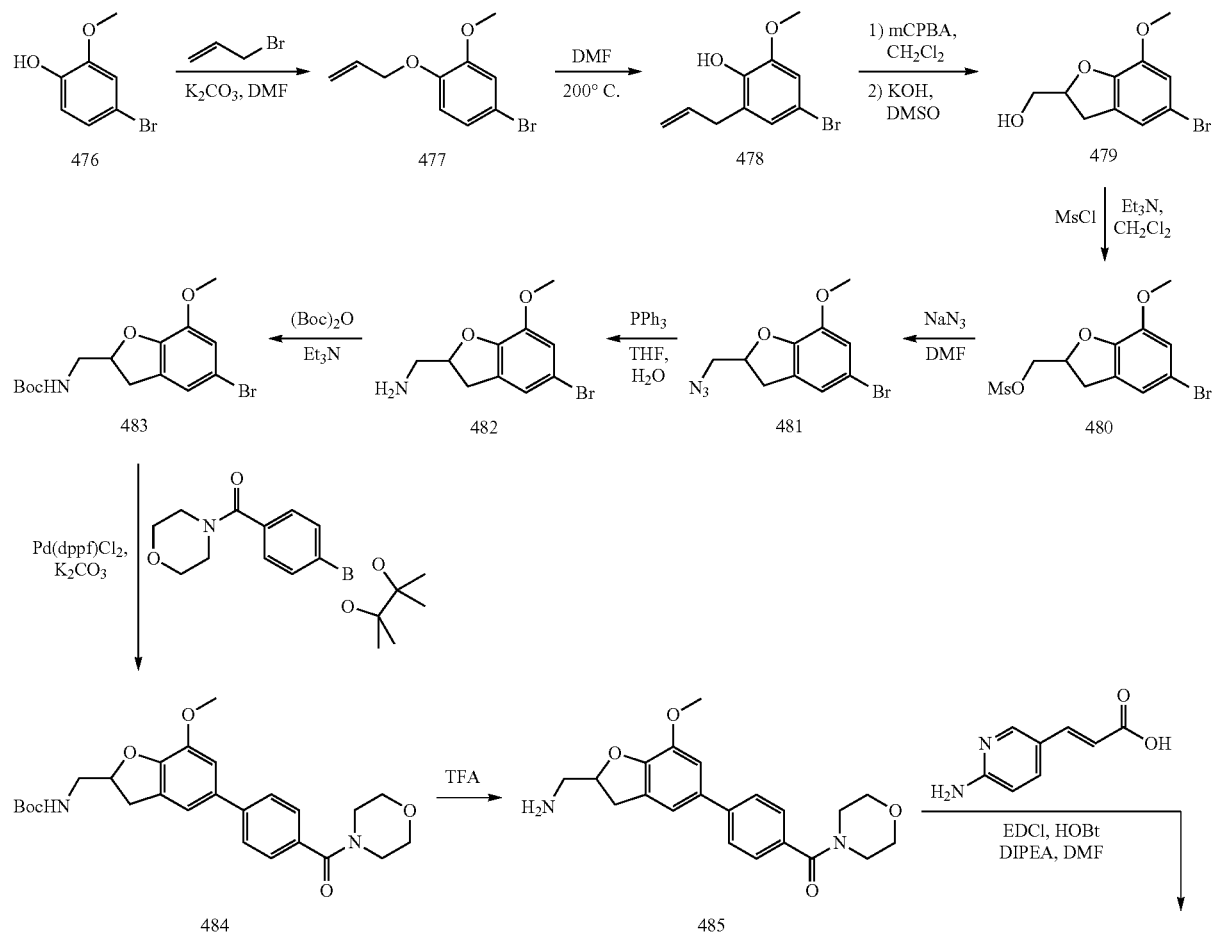

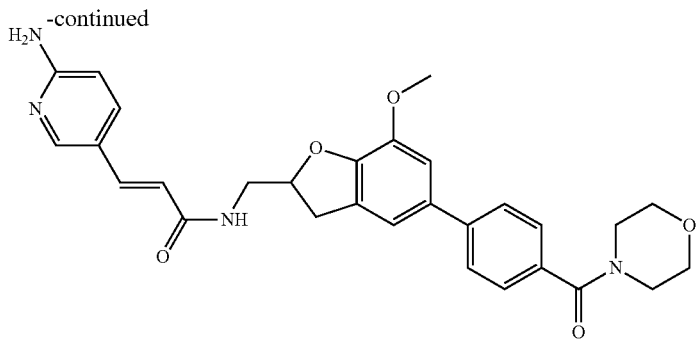

345

Synthesis of 1-(allyloxy)-4-bromo-2-methoxybenzene (477): 4-Bromo-2-methoxyphenol 476 (10 g, 50 mmol) was dissolved in DMF (200 mL). K$_2$CO$_3$ (21 g, 150 mmol) and allyl bromide (12 g, 100 mmol) were added at 25° C. and the reaction mixture was stirred at room temperature for 16 h. The reaction mixture was transferred into iced water and extracted with ethyl acetate (100 mL×3). The combined organic layers were washed with brine, dried over anhydrous Na$_2$SO$_4$, and concentrated under reduced pressure to give 1-(allyloxy)-4-bromo-2-methoxybenzene 477, which was used in the next step without further purification. Yied (11.1 g, 93%). LCMS: m/z 243.2 [M+H]$^+$; t$_R$=1.03 min.

Synthesis of 2-allyl-4-bromo-6-methoxyphenol (478): 1-(Allyloxy)-4-bromo-2-methoxybenzene 477 (7 g, 28.8 mmol) was dissolved in DMF (50 mL) and the reaction mixture was heated at 200° C. for 48 h. The reaction mixture was cooled to room temperature, transferred into iced water and extracted with ethyl acetate (70 mL×3). The combined organic layers were washed with brine, dried over anhydrous Na$_2$SO$_4$ and concentrated under reduced pressure. The crude product was purified by chromatography (0-3% ethyl acetate/petroleum ether) to obtain 2-allyl-4-bromo-6-methoxyphenol 478. Yield (6 g, 86%). LCMS: m/z 244.9 [M+H]$^+$; t$_R$=1.88 min.

Synthesis of (5-bromo-7-methoxy-2,3-dihydrobenzofuran-2-yl)methanol (479): 2-Allyl-4-bromo-6-methoxyphenol 478 (6 g, 24.7 mmol) was dissolved in dichloromethane (100 mL). mCPBA (5.1 g, 29.6 mmol) was added at 0° C. and stirred at room temperature for 4 h. The reaction mixture was diluted with ethyl acetate (150 mL) and washed with saturated sodium bicarbonate solution, saturated sodium thiosulphate solution, followed by brine. The resulting organic layer was dried over anhydrous Na$_2$SO$_4$, and concentrated under reduced pressure to give 2.4 g of the crude epoxy intermediate. The crude epoxy intermediate was then dissolved in DMSO (15 mL) and cooled to 0° C. A solution of KOH (624 mg, 10.1 mmol) in water (5 mL) was added. The reaction mixture was allowed to warm to room temperature and stirred for 4 h. The reaction mixture was then transferred into iced water and extracted with ethyl acetate (100 mL×3). The combined organic layers were washed with brine, dried over anhydrous Na$_2$SO$_4$, and concentrated under reduced pressure. The crude product was purified by silica gel chromatography (0-30% ethyl acetate/petroleum ether) to give (5-bromo-7-methoxy-2,3-dihydrobenzofuran-2-yl)methanol 479. Yield (900 mg, 12%). LCMS: m/z 258.9 [M+H]$^+$; t$_R$=1.59 min.

Synthesis of (5-bromo-7-methoxy-2,3-dihydrobenzofuran-2-yl)methyl methanesulfonate (480): (5-Bromo-7-methoxy-2,3-dihydrobenzofuran-2-yl)methanol 479 (900 mg, 3.5 mmol) was dissolved in dichloromethane (10 mL). Methane sulfonyl chloride (798 mg, 7 mmol) and triethylamine (1.1 g, 10.5 mmol) were added at 0° C. The reaction mixture was allowed to warm to room temperature and stirred for 4 h. The reaction mixture was transferred into iced water and extracted with dichloromethane (200 mL×3). The combined organic layers were washed with brine, dried over anhydrous Na$_2$SO$_4$, and concentrated under reduced pressure to give crude (5-bromo-7-methoxy-2,3-dihydrobenzofuran-2-yl)methyl methanesulfonate 75, which was used in the next step without further purification. LCMS: m/z 338.9 [M+H]$^+$; t$_R$=1.71 min.

Synthesis of 2-(azidomethyl)-5-bromo-7-chloro-2,3-dihydrobenzofuran (481): (5-Bromo-7-methoxy-2,3-dihydrobenzofuran-2-yl)methyl methanesulfonate 481 (1.4 g, 4.2 mmol) was dissolved in DMF (10 mL). Sodium azide (540 mg, 8.3 mmol) was added at room temperature. The reaction mixture was stirred at 80° C. for 2 h, cooled to room temperature, transferred into iced water, and extracted with ethyl acetate (50 mL×3). The combined organic layers were washed with brine, dried over anhydrous Na$_2$SO$_4$, and concentrated under reduced pressure to give 1.2 g of the crude product 2-(azidomethyl)-5-bromo-7-methoxy-2,3-dihydrobenzofuran 481, which was used in the next step without further purification.

Synthesis of (5-bromo-7-chloro-2,3-dihydrobenzofuran-2-yl)methanamine (482): 2-(Azidomethyl)-5-bromo-7-methoxy-2,3-dihydrobenzofuran 481 (1.2 g, 4.2 mmol) and PPh$_3$ (1.6 g, 6.3 mmol) were dissolved in THF (20 mL). The mixture was stirred at room temperature for 3 h. Water (5 mL) was added and the mixture was stirred at 55° C. for 3 h. The reaction mixture was transferred into iced water and extracted with dichloromethane (50 mL×3). The combined organic layers were washed with brine, dried over anhydrous Na$_2$SO$_4$, and concentrated under reduced pressure to give crude product which was purified by semi-preparative HPLC to give (5-bromo-7-methoxy-2,3-dihydrobenzofuran-2-yl)methanamine 482. Yield (700 mg, 64%). LCMS: m/z 258.1 [M+H]$^+$; t$_R$=1.53 min.

Synthesis of tert-butyl (5-bromo-7-methoxy-2,3-dihydrobenzofuran-2-yl)methylcarbamate (483): (5-Bromo-7-methoxy-2,3-dihydrobenzofuran-2-yl)methanamine 482 (700 mg, 2.7 mmol) was dissolved in dichloromethane (10 mL) and di-tert-butyl dicarbonate (708 mg, 3.3 mmol) was added at 0° C. Triethylamine (461 mg, 4.0 mmol) was added and the reaction mixture was stirred at room temperature for 4 h. The reaction mixture was transferred into iced water and extracted with dichloromethane (50 mL×3). The combined organic layers were washed with brine, dried over anhydrous Na$_2$SO$_4$, and concentrated under reduced pressure. The crude product was purified by chromatography (0-10% ethyl acetate/petroleum ether) to give tert-butyl (5-bromo-7-methoxy-2,3-dihydrobenzofuran-2-yl)methylcarbamate 483. Yield (500 mg, 51%). LCMS: m/z 381.1 [M+Na]$^+$; $t_R$=1.91 min.

Synthesis of tert-butyl (7-methoxy-5-(4-(morpholine-4-carbonyl)phenyl)-2,3-dihydrobenzofuran-2-yl)methylcarbamate (484): tert-Butyl (5-bromo-7-methoxy-2,3-dihydrobenzofuran-2-yl)methylcarbamate 483 (200 mg, 0.56 mmol) was dissolved in dioxane (40 mL) and H$_2$O (10 mL) and degassed for 5 min. Pd(dppf)Cl$_2$ (41 mg, 0.056 mol), K$_2$CO$_3$ (153 mg, 1.12 mmol) and morpholino(4-(4,4,5,5-tetramethyl-1,3,2-dioxaborolan-2-yl)phenyl)methanone (212 mg, 0.67 mmol) were added at room temperature and stirred for 5 min. Then, the reaction mixture was stirred at 80° C. for 2 h. The reaction mixture was transferred into water and extracted with ethyl acetate (50 mL×3). The combined organic layers were washed with brine, dried over anhydrous Na$_2$SO$_4$, and concentrated under reduced pressure. The crude product was purified by chromatography (0-40% ethyl acetate/petroleum ether) to give tert-butyl (7-methoxy-5-(4-(morpholine-4-carbonyl)phenyl)-2,3-dihydrobenzofuran-2-yl)methylcarbamate 484. Yield (140 mg, 54%). LCMS: m/z 469.3 [M+H]$^+$, $t_R$=1.74 min.

Synthesis of (4-(2-(aminomethyl)-7-methoxy-2,3-dihydrobenzofuran-5-yl)phenyl)(morpholino)methanone (485): tert-Butyl (7-methoxy-5-(4-(morpholine-4-carbonyl)phenyl)-2,3-dihydrobenzofuran-2-yl)methylcarbamate 484 (50 mg, 0.1 mmol) was dissolved in CH$_2$Cl$_2$ (5 mL). TFA (1 mL) was added to this mixture and the reaction mixture was stirred at room temperature for 0.5 h. This mixture was concentrated under reduced pressure to give (4-(2-(aminomethyl)-7-methoxy-2,3-dihydrobenzofuran-5-yl)phenyl)(morpholino)methanone 485. The crude product was used without further purification in the next step. Yield (39 mg, 100%). LCMS: m/z 369.3 [M+H]$^+$, $t_R$=1.37 min.

Synthesis of (E)-3-(6-aminopyridin-3-yl)-N-((7-methoxy-5-(4-(morpholine-4-carbonyl)phenyl)-2,3-dihydrobenzofuran-2-yl)methyl)acrylamide (345): (4-(2-(Aminomethyl)-7-methoxy-2,3-dihydrobenzofuran-5-yl)phenyl)(morpholino)methanone 485 (39 mg, 0.1 mmol) was dissolved in DMF (2 mL) and (E)-3-(6-aminopyridin-3-yl) acrylic acid (17 mg, 0.1 mmol), EDCI (23 mg, 0.12 mmol), HOBt (13 mg, 0.1 mmol), DIPEA (38 mg, 0.3 mmol)) were added at room temperature, stirred for 4 h, and purified without work-up by semi-preparative HPLC to obtain (E)-3-(6-aminopyridin-3-yl)-N-((7-methoxy-5-(4-(morpholine-4-carbonyl)phenyl)-2,3-dihydrobenzofuran-2-yl)methyl)acrylamide. Yield (14 mg, 26% yield). $^1$H NMR (400 MHz, CD3OD) δ 8.19 (dd, J=2 Hz, J=9 Hz, 1H), 8.03 (d, J=2 Hz, 1H), 7.68-7.66 (m, 2H), 7.49-7.41 (m, 3H), 7.14-7.04 (m, 3H), 6.63 (d, J=16 Hz, 1H), 5.07 (s, 1H), 3.93 (s, 3H), 3.78-3.32 (m, 11H), 3.13-3.10 (m, 1H). LCMS: m/z 515.3 [M+H]$^+$, $t_R$=1.48 min.

Synthesis of (E)-3-(6-aminopyridin-3-yl)-N-((5-(4-(morpholine-4-carbonyl)phenyl)-7-(trifluoromethyl)-2,3-dihydrobenzofuran-2-yl)methyl)acrylamide (346)

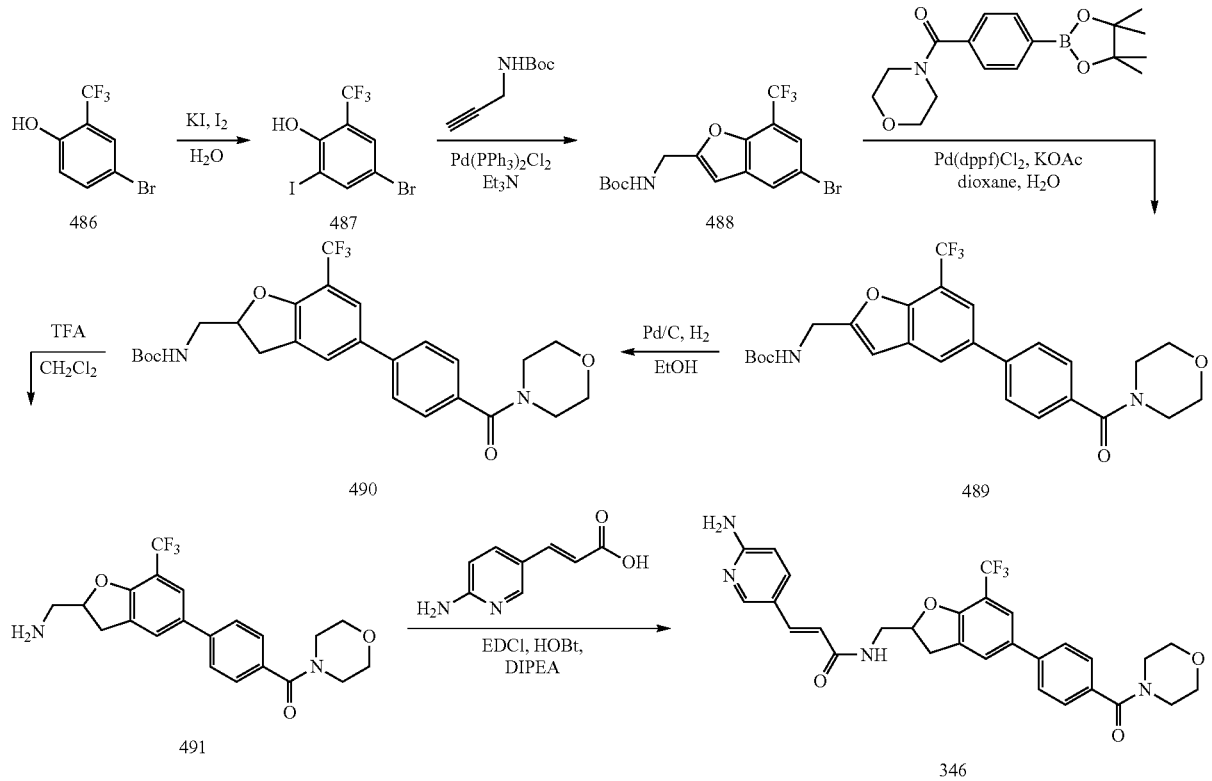

Synthesis of 4-Bromo-2-iodo-6-(trifluoromethyl) phenol (487): A mixture of 4-bromo-2-(trifluoromethyl)phenol 486 (8 g, 33.3 mmol), KI (16 g, 99.9 mmol), I$_2$ (8.5 g, 33.3 mmol) in NH$_4$OH (50 mL) and H$_2$O (50 mL) was stirred at 30° C. for 16 h. Concentrated HCl was added until pH~7. The mixture was extracted with EtOAc (100 mL×3). The combined organic layers were washed with brine, dried over anhydrous Na$_2$SO$_4$, and the solvents were removed under reduced pressure to give the crude product, which was purified by silica gel chromatography (20% EtOAc/petroleum ether) to give 4-bromo-2-iodo-6-(trifluoromethyl)phenol 487 as white solid. Yield (8 g, 67% yield). LCMS: m/z not found; $t_R$=1.53 min.

Synthesis of tert-Butyl (5-bromo-7-(trifluoromethyl)benzofuran-2-yl)methylcarbamate (488): A mixture of 4-bromo-2-iodo-6-(trifluoromethyl)phenol 487 (1 g, 2.7 mmol), tert-butyl prop-2-ynylcarbamate (500 mg, 3.2 mmol), Pd(PPh$_3$)$_2$Cl$_2$ (118 mg, 0.27 mmol), CuI (51 mg, 0.27 mmol) in Et$_3$N (20 mL) was stirred at 80° C. under nitrogen atmosphere for 2 h. The mixture was poured into iced water and extracted with EtOAc (50 mL×3). The combined organic layers were washed with brine, dried over anhydrous Na$_2$SO$_4$, and the solvents were removed under reduced pressure to give the crude product, which was purified by silica gel chromatography (20% EtOAc/petroleum ether) to give tert-butyl (5-bromo-7-(trifluoromethyl)benzofuran-2-yl)methylcarbamate 488 as white solid. Yield (600 mg, 57%). LCMS: m/z 417.9 [M+Na]$^+$; $t_R$=2.05 min.

Synthesis of tert-Butyl (5-(4-(morpholine-4-carbonyl)phenyl)-7-(trifluoromethyl)benzofuran-2-yl)methylcarbamate (489): tert-Butyl (5-(4-(morpholine-4-carbonyl)phenyl)-7-(trifluoromethyl)benzofuran-2-yl)methylcarbamate 489 was synthesized using General Procedure 1. Yield (120 mg, 47%). LCMS: m/z 505.0 [M+H]$^+$; $t_R$=1.86 min.

Synthesis of tert-Butyl (5-(4-(morpholine-4-carbonyl)phenyl)-7-(trifluoromethyl)-2,3-dihydrobenzofuran-2-yl)methylcarbamate (490): tert-Butyl (5-(4-(morpholine-4-carbonyl)phenyl)-7-(trifluoromethyl)benzofuran-2-yl)methylcarbamate 489 (120 mg, 0.24 mmol) was dissolved in ethanol (2 mL). 10% Pd/C (12 mg) was added and hydrogen gas was purged. The reaction mixture was stirred at room temperature for 1 h. The reaction mixture was filtered and the filtrate was concentrated under reduced pressure to give the crude tert-butyl (5-(4-(morpholine-4-carbonyl)phenyl)-7-(trifluoromethyl)-2,3-dihydrobenzofuran-2-yl)methylcarbamate 490, which was used without further purification in the next step. Yield (120 mg, 83%). LCMS: m/z 507.1 [M+H]$^+$; $t_R$=1.83 min.

Synthesis of (4-(2-(Aminomethyl)-7-(trifluoromethyl)-2,3-dihydrobenzofuran-5-yl)phenyl)(morpholino)methanone (491): (4-(2-(Aminomethyl)-7-(trifluoromethyl)-2,3-dihydrobenzofuran-5-yl)phenyl) (morpholino) methanone 491 was synthesized using General Procedure 2. Yield (100 mg, 100%). LCMS: m/z 407.1 [M+H]$^+$; $t_R$=1.29 min.

Synthesis of (E)-3-(6-aminopyridin-3-yl)-N-((5-(4-(morpholine-4-carbonyl)phenyl)-7-(trifluoromethyl)-2,3-dihydrobenzofuran-2-yl)methyl)acrylamide (346): (E)-3-(6-Aminopyridin-3-yl)-N-((5-(4-(morpholine-4-carbonyl)phenyl)-7-(trifluoromethyl)-2,3-dihydrobenzofuran-2-yl)methyl)acrylamide (346) was synthesized using General Procedure 3. Yield (65 mg, 59%). $^1$H NMR (400 MHz, DMSO-d$_6$) δ 8.43 (t, J=4 Hz, 1H), 8.27-8.18 (m, 2H), 8.08 (d, J=8 Hz, 1H), 7.87 (s, 1H), 7.72 (d, J=8 Hz, 2H), 7.65 (s, 1H), 7.49 (d, J=8 Hz, 2H), 7.41 (d, J=15 Hz, 1H), 6.98 (d, J=8 Hz, 1H), 6.61 (d, J=15 Hz, 1H), 5.17-5.11 (m, 1H), 3.71-3.31 (m, 12H), 3.13-3.07 (m, 1H). LCMS: m/z 553.1 [M+H]$^+$; $t_R$=1.39 min.

Synthesis of (E)-3-(6-aminopyridin-3-yl)-N-((7-hydroxy-5-(4-(morpholine-4-carbonyl)phenyl)-2,3-dihydrobenzofuran-2-yl)methyl)acrylamide (347)

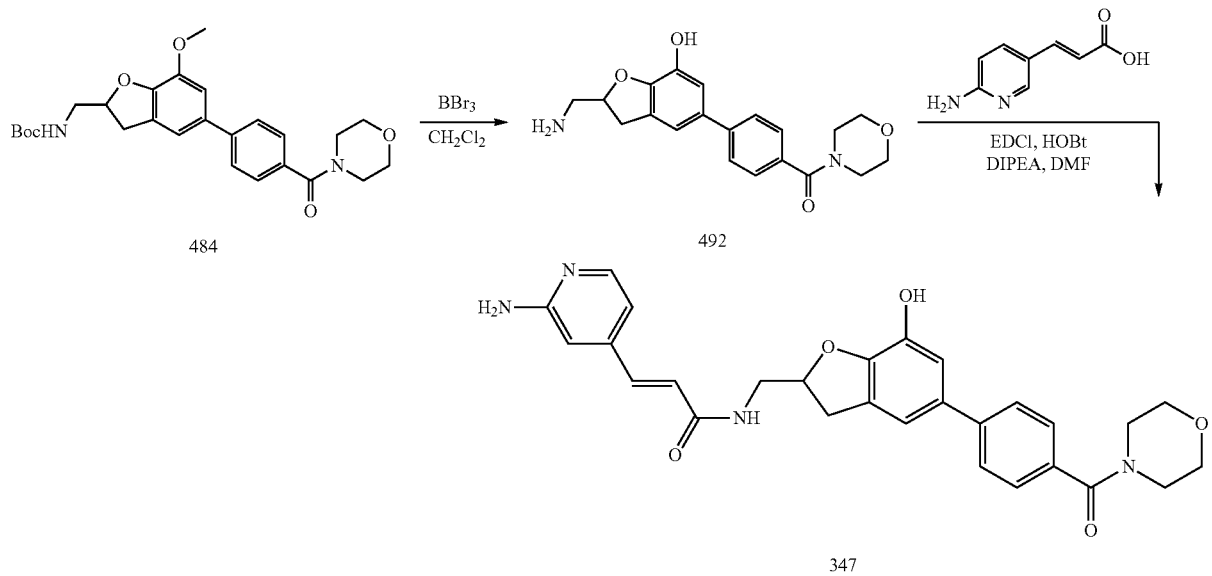

tert-Butyl (7-methoxy-5-(4-(morpholine-4-carbonyl)phenyl)-2,3-dihydrobenzofuran-2-yl)methylcarbamate 484 (80 mg, 0.17 mmol) was dissolved in CH$_2$Cl$_2$ (5 mL). BBr$_3$ (128 mg, 0.51 mmol) was added drop wise at 0° C. The reaction mixture was stirred at room temperature for 1 h and concentrated under reduced pressure to give the crude (4-(2-(aminomethyl)-7-hydroxy-2,3-dihydrobenzofuran-5-yl)phenyl)(morpholino)methanone 492, which was used without further purification in the next step. Yield (45 mg, 75%). LCMS: m/z 355.1 [M+H]$^+$, $t_R$=1.15 min.

(E)-3-(6-Aminopyridin-3-yl)-N-((7-hydroxy-5-(4-(morpholine-4-carbonyl)phenyl)-2,3-dihydrobenzofuran-2-yl)methyl)acrylamide 347 was synthesized using General Procedure 3. Yield (15 mg, 24%). $^1$H NMR (400 MHz, CD$_3$OD)

δ 8.20-8.17 (m, 1H), 8.02 (d, J=2 Hz, 1H), 7.62 (d, J=8 Hz, 2H), 7.47-7.41 (m, 3H), 7.06-6.95 (m, 3H), 6.65 (d, J=16 Hz, 1H), 4.88 (s, 1H), 3.37-3.30 (m, 12H). LCMS: m/z 501.1 [M+H]+, $t_R$=1.24 min.

Synthesis of (E)-3-(6-aminopyridin-3-yl)-N-((7-chloro-5-(4-(morpholine-4-carbonyl)phenyl)-3-oxo-2,3-dihydrobenzofuran-2-yl)methyl)acrylamide (348)

heated at 90° C. for 13 h. After cooling to room temperature, water (93 mL) and a 50 percent aqueous solution of sulfuric acid (46 mL) were sequentially added. The resulting mixture was stirred at room temperature for 2 h and extracted with ethyl acetate (100 mL×3). The combined organic layers were washed with 1 N aqueous solution of hydrochloric acid (50 mL×2) and dried over anhydrous $Na_2SO_4$. After removal of most of the solvents, the yellow solid was collected by filtration and dried in vacuum to give 5-bromo-3-chloro-2-hydroxybenzaldehyde 493. Yield (10.9 g, 58%). ¹H NMR

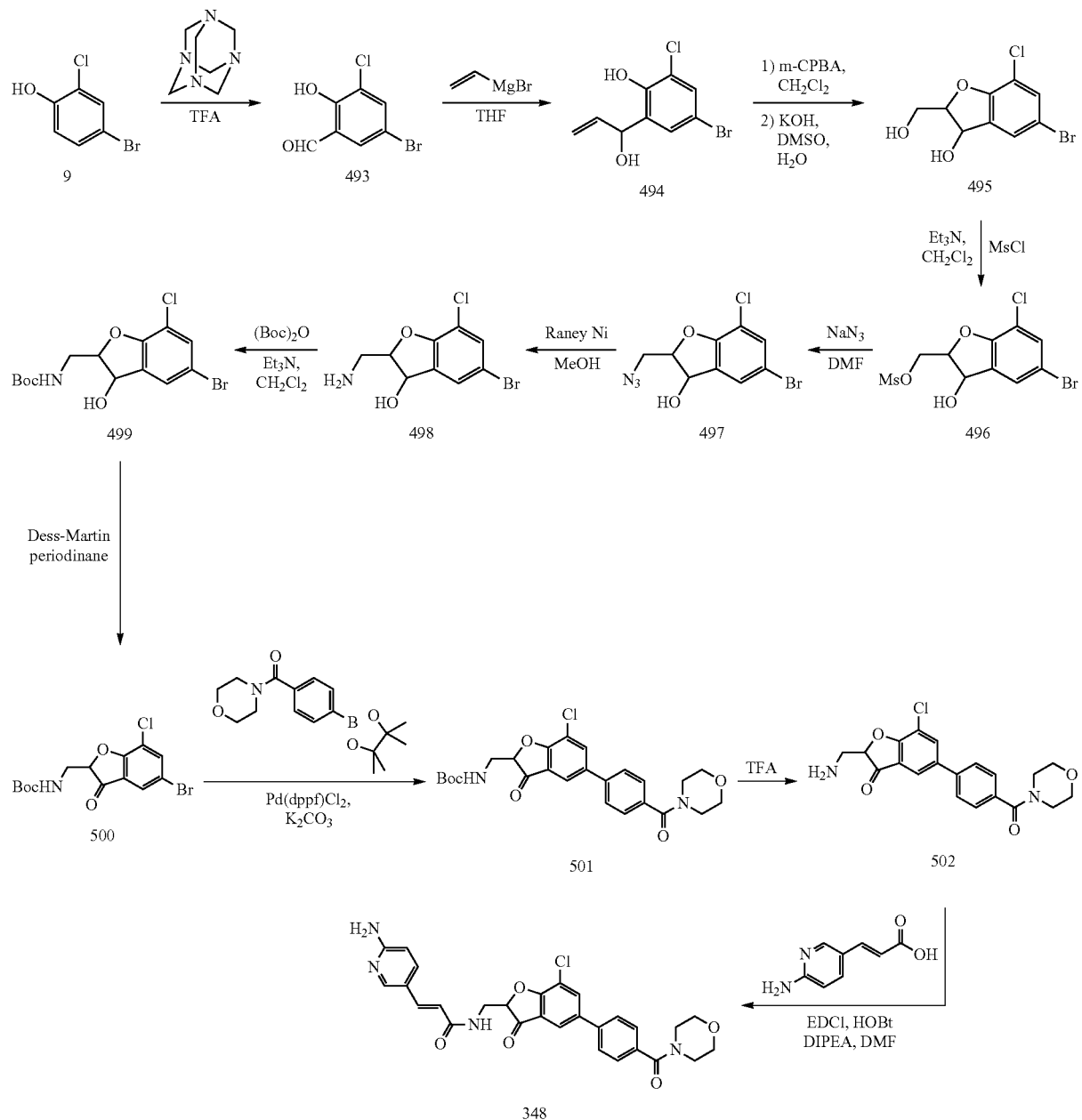

(400 MHz, DMSO-d₆) δ 11.2 (s, 1H), 10.1 (s, 1H), 7.99 (d, J=2 Hz, 1H), 7.83 (d, J=2 Hz, 1H).

Synthesis of 4-bromo-2-chloro-6-(1-hydroxyallyl)phenol (494): Vinylmagnesium bromide (99.5 mL, 159 mmol, 1.6 N in THF) was added to a stirred solution of 5-bromo-3-chloro-2-hydroxybenzaldehyde 493 (17 g, 72.3 mmol)

Synthesis of 5-bromo-3-chloro-2-hydroxybenzaldehyde (493): 4-Bromo-2-chlorophenol 9 (16.5 g, 80 mmol) was dissolved in trifluoroacetic acid (62 mL). Hexamethylenetetramine (22.4 g, 160 mmol) was added under nitrogen atmosphere in three portions over 20 min. The reaction mixture was stirred at room temperature for 20 min and then under nitrogen atmosphere at 0° C. The mixture was then stirred at 0° C. for 2 h, and quenched with NH$_4$Cl aqueous solution (100 mL). The resulting mixture was extracted with ethyl acetate (300 mL×3). The combined organic phases were washed with brine and dried over anhydrous Na$_2$SO$_4$ and concentrated. The residue was purified by silica gel chromatography (25% ethyl acetate/petroleum ether) providing 4-bromo-2-chloro-6-(1-hydroxyallyl)phenol 494. Yield (16.7 g, 88%). LCMS: m/z 248.9 [M−OH]$^+$, t$_R$=1.71 min.

Synthesis of 5-bromo-7-chloro-2-(hydroxymethyl)-2,3-dihydrobenzofuran-3-ol (495): 4-Bromo-2-chloro-6-(1-hydroxyallyl)phenol 494 (17.5 g, 66.5 mmol) was dissolved in dichloromethane (300 mL). m-CPBA (22.9 g, 133 mmol) was added at 0° C. and stirred at room temperature overnight. The reaction mixture was washed with saturated sodium bicarbonate solution, saturated sodium thiosulphate solution, brine, dried over anhydrous Na$_2$SO$_4$, and concentrated under reduced pressure. The crude epoxy intermediate was dissolved in DMSO (100 mL) and cooled to 0° C. A solution of KOH (4.4 g, 77.7 mmol) in water (30 mL) was added. The reaction mixture was allowed to warm to room temperature where it was stirred for 2 h. The reaction mixture was then transferred into iced water and extracted with ethyl acetate (100 mL×3). The combined organic layers were washed with brine, dried over anhydrous Na$_2$SO$_4$, and concentrated under reduced pressure to obtain the crude product which was purified by silica gel chromatography (0-30-50% ethyl acetate/petroleum ether) to 5-bromo-7-chloro-2-(hydroxymethyl)-2,3-dihydrobenzofuran-3-ol 495. Yield (9.1 g, 53%). LCMS: m/z 302.7 [M+Na]$^+$, t$_R$=1.48 min, 1.51 min.

Synthesis of (5-bromo-7-chloro-3-hydroxy-2,3-dihydrobenzofuran-2-yl)methyl methanesulfonate (496): 5-Bromo-7-chloro-2-(hydroxymethyl)-2,3-dihydrobenzofuran-3-ol 495 (5 g, 18 mmol) was dissolved in dichloromethane (100 mL). Triethylamine (2.2 g, 21.6 mmol) and methane sulfonyl chloride (2.3 g, 19.8 mmol) were added at 0° C. and the reaction mixture was stirred at 0° C. for 20 min. The reaction mixture was transferred into iced water and extracted with dichloromethane (50 mL×2). The combined organic layers were washed with brine, dried over anhydrous Na$_2$SO$_4$, and concentrated under reduced pressure. The crude product was purified by silica gel chromatography (20-33% ethyl acetate/petroleum ether) to give (5-bromo-7-chloro-3-hydroxy-2,3-dihydrobenzofuran-2-yl) methyl methanesulfonate 496. Yield (1.5 g, 24% yield). LCMS: m/z 378.5 [M+Na]$^+$, t$_R$=1.61 min.

Synthesis of 2-(azidomethyl)-5-bromo-7-chloro-2,3-dihydrobenzofuran-3-ol (497): (5-Bromo-7-chloro-3-hydroxy-2,3-dihydrobenzofuran-2-yl)methylmethanesulfonate 496 (1.8 g, 5 mmol) was dissolved in DMF (20 mL). Sodium azide (1 g, 15 mmol) and K$_2$CO$_3$ (1.4 g, 10 mmol) were added at room temperature. The reaction mixture was stirred at 80° C. overnight, cooled to room temperature, transferred into iced water, and extracted with ethyl acetate (40 mL×3). The combined organic layers were washed with brine, dried over anhydrous Na$_2$SO$_4$, and concentrated under reduced pressure to the crude product, which was purified by silica gel chromatography (25-50% ethyl acetate/petroleum ether) to obtain 2-(azidomethyl)-5-bromo-7-chloro-2,3-dihydrobenzofuran-3-ol 497 (0.95 g, 63% yield). LCMS: m/z 326.0 [M+Na]$^+$, t$_R$=1.75 min.

Synthesis of 2-(aminomethyl)-5-bromo-7-chloro-2,3-dihydrobenzofuran-3-ol (498): 2-(Azidomethyl)-5-bromo-7-chloro-2,3-dihydrobenzofuran-3-ol 497 (455 mg, 1.5 mmol) was dissolved in methanol (200 mL). Raney Ni (wet~400 mg) was added and hydrogen gas was purged at room temperature. The reaction mixture was stirred at room temperature for 4 h, filtered and the filtrate was concentrated under reduced pressure to give 2-(aminomethyl)-5-bromo-7-chloro-2,3-dihydrobenzofuran-3-ol 498, which was used without further purification in the next step. Yield (406 mg, 97%). LCMS: m/z 277.9 [M+H]$^+$, t$_R$=1.19 min.

Synthesis of tert-butyl (5-bromo-7-chloro-3-hydroxy-2,3-dihydrobenzofuran-2-yl)methylcarbamate 499: 2-(Aminomethyl)-5-bromo-7-chloro-2,3-dihydrobenzofuran-3-ol 498 (406 mg, 1.5 mmol) was dissolved in dichloromethane (15 mL). Di-tert-butyl dicarbonate (392 mg, 1.8 mmol) and triethylamine (227 mg, 2.25 mmol) was added at 0° C. and the reaction mixture was stirred at room temperature overnight. The reaction mixture was transferred into iced water and extracted with dichloromethane (15 mL×3). The combined organic layers were washed with brine, dried over anhydrous Na$_2$SO$_4$, and concentrated under reduced pressure to give crude product which was purified by silica gel chromatography (25-50% ethyl acetate/petroleum ether) to obtain tent-butyl (5-bromo-7-chloro-3-hydroxy-2,3-dihydrobenzofuran-2-yl)methylcarbamate 499. Yield (500 mg, 63%). LCMS: m/z 399.7 [M+Na]$^+$, t$_R$=1.82 min.

Synthesis of tert-butyl (5-bromo-7-chloro-3-oxo-2,3-dihydrobenzofuran-2-yl)methylcarbamate (500): tert-Butyl (5-bromo-7-chloro-3-hydroxy-2,3-dihydrobenzofuran-2-yl) methylcarbamate 499 (500 mg 1.3 mmol) was dissolved in dichloromethane (15 mL) and Dess-Martin periodinane (787 mg, 1.9 mmol) was added at 0° C. The reaction mixture was stirred at room temperature overnight, filtered and the filtrate was concentrated under reduced pressure to give the crude product, which was purified by silica gel chromatography (20% ethyl acetate/petroleum ether) to obtain tert-butyl (5-bromo-7-chloro-3-oxo-2,3-dihydrobenzofuran-2-yl)methylcarbamate 500. Yield (430 mg, 86% yield). LCMS: m/z 397.6 [M+Na]$^+$, t$_R$=1.84 min.

Synthesis of tert-butyl (7-chloro-5-(4-(morpholine-4-carbonyl)phenyl)-3-oxo-2,3-dihydrobenzofuran-2-yl)methylcarbamate (501): A mixture of tert-butyl (5-bromo-7-chloro-3-oxo-2,3-dihydrobenzofuran-2-yl)methylcarbamate 500 (160 mg, 0.42 mmol), morpholino(4-(4,4,5,5tetramethyl-1,3,2-dioxaborolan-2-yl)phenyl)methanone (161 mg, 0.51 mmol), Pd(dppf)Cl$_2$ (31 mg, 0.042 mmol) and K$_2$CO$_3$ (116 mg, 0.82 mmol) in dioxane (6 mL) and H$_2$O (0.6 mL) was stirred at 90 ° C. under nitrogen atmosphere for 3 h. The mixture was extracted with EtOAc (20 mL×3). The combined organic layers were washed with brine, dried over anhydrous Na$_2$SO$_4$, and the solvents were removed under reduced pressure to give the crude product, which was purified by silica gel chromatography (50%-100% EtOAc/petroleum ether) to give tert-butyl (7-chloro-5-(4-(morpholine-4-carbonyl)phenyl)-3-oxo-2,3-dihydrobenzofuran-2-yl)methylcarbamate 501 as a white solid. Yield (140 mg, 69%). LCMS: m/z 486.8 [M+H]$^+$; t$_R$=1.68 min.

Synthesis of 2-(aminomethyl)-7-chloro-5-(4-(morpholine-4-carbonyl)phenyl)benzofuran-3(2H)-one (502): tert-Butyl (7-chloro-5-(4-(morpholine-4-carbonyl)phenyl)-3-oxo-2,3-dihydrobenzofuran-2-yl)methylcarbamate 501 (90 mg, 0.19 mmol) was dissolved in CH$_2$Cl$_2$ (5 mL). TFA (1 mL) was added at 0° C. The reaction mixture was stirred at room temperature for 2 h, and concentrated under reduced pressure to give the crude 2-(aminomethyl)-7-chloro-5-(4-(morpholine-4-carbonyl)phenyl)benzofuran-3(2H)-one 502, which was used without further purification in the next step. Yield (100 mg, 100%). LCMS: m/z 386.9 [M+H]$^+$; t$_R$=1.13 min.

Synthesis of (E)-3-(6-aminopyridin-3-yl)-N-((7-chloro-5-(4-(morpholine-4-carbonyl)phenyl)-3-oxo-2,3-dihydrobenzofuran-2-yl)methyl)acrylamide (348): 2-(Aminomethyl)-7-chloro-5-(4-(morpholine-4-carbonyl)phenyl)benzofuran-3(2H)-one 502 (crude mixture from previous step, 0.19 mmol) was dissolved in DMF (2 mL) and (E)-3-(6-aminopyridin-3-yl)acrylic acid (36 mg, 0.22 mmol) was added at 0° C. EDCI (42 mg, 0.22 mmol) and HOBt (30 mg, 0.22 mmol) were added to this reaction mixture at 0° C. followed by DIPEA (48 mg, 0.37 mmol) dropwise. The reaction mixture was purified by semi-preparative HPLC to afford (E)-3-(6-aminopyridin-3-yl)-N-((7-chloro-5-(4-(morpholine-4-carbonyl)phenyl)-3-oxo-2,3-dihydrobenzofuran-2-yl)methyl)acrylamide 348. Yield (5 mg, 5%). $^1$H NMR (400 MHz, CD$_3$OD) 8.43-7.41 (m, 9H), 7.12-6.99 (m, 1H), 6.60-6.50 (m, 1H), 5.10-5.07 (m, 1H), 4.73-4.67 (m, 1H), 4.06-4.01 (m, 1H), 3.83-3.48 (m, 8H). LCMS: m/z 533.1 [M+H]$^+$; $t_R$=1.16 min.

Synthesis of (E)-3-(6-aminopyridin-3-yl)-N-((7-chloro-2-methyl-5-(4-(morpholine-4-carbonyl)phenyl)-2,3-dihydrobenzofuran-2-yl)methyl)acrylamide (349)

Synthesis of 4-Bromo-2-chloro-1-(2-methylallyloxy) benzene (503): 4-Bromo-2-chlorophenol 9 (5 g, 24.2 mmol) was dissolved in acetonitrile (100 mL). K$_2$CO$_3$ (6.7 g, 48.6 mmol) and allyl bromide (3.3 g, 24.2 mmol) were added at 25° C. and the reaction mixture was stirred at 25° C. for 16 h. The reaction mixture was transferred into iced water and extracted with ethyl acetate (100 mL×3). The combined organic layers were washed with brine, dried over anhydrous Na$_2$SO$_4$, and concentrated under reduced pressure to give 4-bromo-2-chloro-1-(2-methylallyloxy) benzene 503, which was used in the next step without further purification. Yield (5.5 g, 87%). LCMS: m/z 261.2 [M+H]$^+$, $t_R$=2.11 min.

Synthesis of 4-Bromo-2-chloro-6-(2-methylallyl)phenol (504): 4-Bromo-2-chloro-1-(2-methylallyloxy) benzene 503 (5.5 g, 21.1 mmol) was dissolved in DMF (50 mL) and heated at 200° C. for 60 h. The reaction mixture was cooled to room temperature, transferred into iced water and extracted with ethyl acetate (50 mL×3). The combined organic layers were washed with brine, dried over anhydrous Na$_2$SO$_4$ and concentrated under reduced pressure. The crude reaction mixture was purified by silica gel chromatography (10%-15% ethyl acetate/petroleum ether) to obtain 4-bromo-2-chloro-6-(2-methylallyl)phenol 504. Yield (2.2 g, 41%). LCMS: m/z 261.2 [M+H]$^+$, $t_R$=2.02 min.

Synthesis of (5-Bromo-7-chloro-2-methyl-2,3-dihydrobenzofuran-2-yl)methanol (505): 4-Bromo-2-chloro-6-(2-methylallyl)phenol 504 (2.0 g, 7.7 mmol) was dissolved in dichloromethane (20 mL). m-CPBA (1.84 g, 10.7 mmol) was added at 0° C. and stirred at room temperature for 4 h.

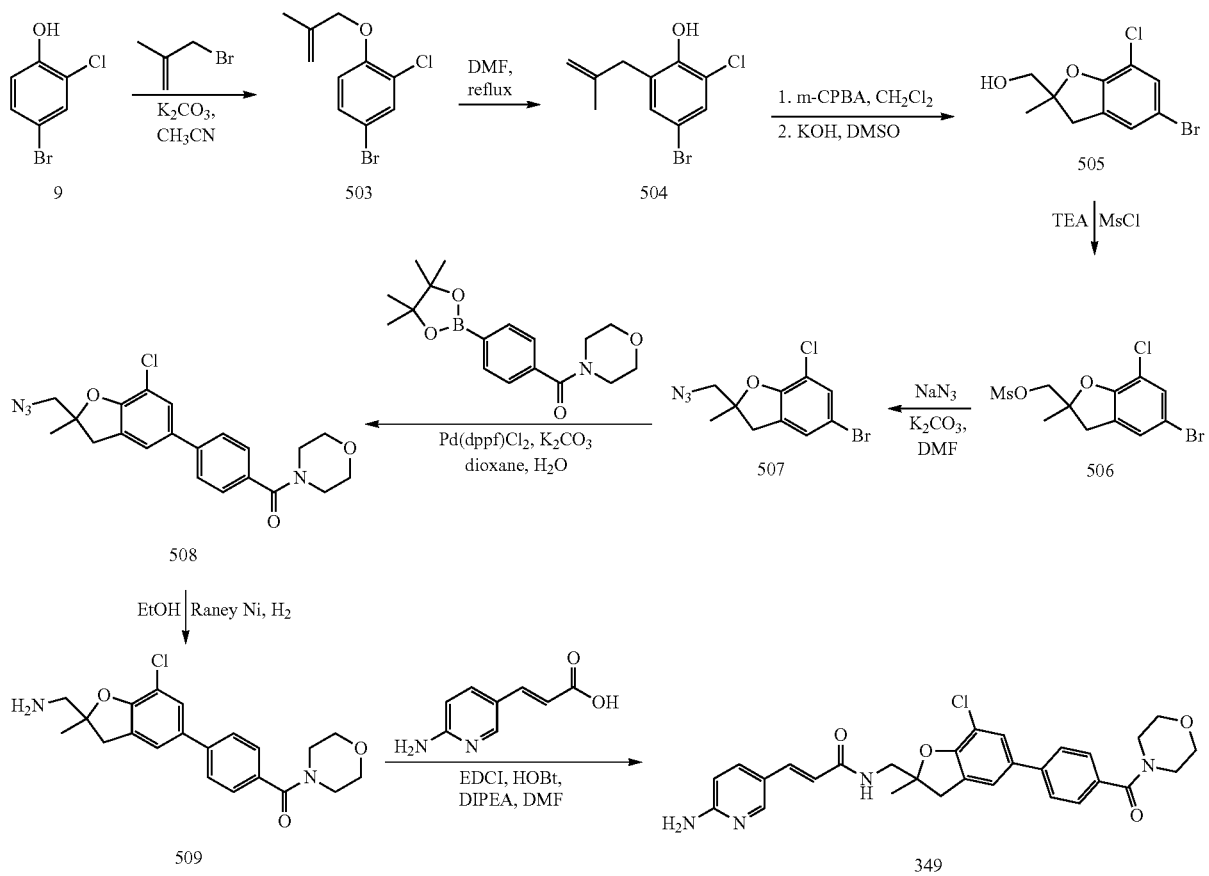

The reaction mixture was diluted with ethyl acetate (25 mL) and washed with saturated sodium bicarbonate solution, saturated sodium thiosulphate solution, brine, and dried over anhydrous Na$_2$SO$_4$. The organic layer was concentrated under reduced pressure to give 2.0 g of the crude epoxy intermediate. The crude epoxy intermediate was then dissolved in DMSO (30 mL) and cooled to 0° C. and a solution of KOH (0.86 g, 15.3 mmol) in water (7.5 mL) was added. The reaction mixture was allowed to warm to room temperature where it was stirred for 4 h. The reaction mixture was then transferred into iced water and extracted with ethyl acetate (50 mL×3). The combined organic layers were washed with brine, dried over anhydrous $Na_2SO_4$, and concentrated under reduced pressure to obtain the crude product which was purified by chromatography (0-30% ethyl acetate/petroleum ether) to give (5-bromo-7-chloro-2-methyl-2,3-dihydrobenzofuran-2-yl)methanol 505. Yield (1.06 g, 50%). LCMS: m/z 277.1 $[M+H]^-$, $t_R$=1.81 min.

Synthesis of (5-Bromo-7-chloro-2-methyl-2,3-dihydrobenzofuran-2-yl)methyl methanesulfonate (506): (5-Bromo-7-chloro-2-methyl-2,3-dihydrobenzofuran-2-yl) methanol 505 (276 mg, 1 mmol) was dissolved in dichloromethane (10 mL). Methane sulfonyl chloride (114 mg, 1 mmol) and triethylamine (202 mg, 2 mmol) were added at 0° C. and the reaction mixture was allowed to warm to room temperature where it was stirred for 4 h. The reaction mixture was transferred into iced water and extracted with dichloromethane (20 mL×3). The combined organic layers were washed with brine, dried over anhydrous $Na_2SO_4$, and concentrated under reduced pressure to give (5-bromo-7-chloro-2-methyl-2,3-dihydrobenzofuran-2-yl)methyl methanesulfonate 506 which was used in the next step without further purification. Yield (220 mg, 58%). LCMS: m/z 377.0 $[M+Na]^+$, $t_R$=1.85 min.

Synthesis of 2-(Azidomethyl)-5-bromo-7-chloro-2-methyl-2,3-dihydrobenzofuran (507): (5-Bromo-7-chloro-2-methyl-2,3-dihydrobenzofuran-2-yl)methylmethanesulfonate 506 (177 mg, 0.5 mmol) was dissolved in DMF (5 mL). Sodium azide (39 mg, 0.6 mmol) and $K_2CO_3$ (138 mg, 1 mmol) were added at room temperature. The reaction mixture was stirred at 80° C. for 16 h, cooled to room temperature, transferred into iced water, and extracted with ethyl acetate (20 mL×3). The combined organic layers were washed with brine, dried over anhydrous $Na_2SO_4$, and concentrated under reduced pressure to give 2-(azidomethyl)-5-bromo-7-chloro-2-methyl-2,3-dihydrobenzofuran 507. Yield (80 mg, 53%). LCMS: m/z 302.1 $[M+H]^+$, $t_R$=2.02 min.

Synthesis of (4-(2-(Azidomethyl)-7-chloro-2-methyl-2,3-dihydrobenzofuran-5-yl)phenyl)(morpholino)methanone (508): 2-(Azidomethyl)-5-bromo-7-chloro-2-methyl-2,3-dihydrobenzofuran 507 (120 mg, 0.4 mmol) and morpholino (4-(4,4,5,5-tetramethyl-1,3,2-dioxaborolan-2-yl)phenyl) methanone (127 mg, 0.4 mmol) was dissolved in dioxane (10 mL) and degassed for 5 min. $Pd(dppf)Cl_2$ (33 mg, 0.04 mmol) and $K_2CO_3$ (110 mg, 0.8 mmol) in water (1 mL) was added and the reaction mixture was stirred at 90° C. for 2 h. The reaction mixture was transferred into water and extracted with ethyl acetate (10 mL×3). The combined organic layers were washed with brine, dried over anhydrous $Na_2SO_4$, and concentrated under reduced pressure to give the crude product which was purified by silica gel chromatography (0-50% ethyl acetate/petroleum ether) to give (4-(2-(azidomethyl)-7-chloro-2-methyl-2,3-dihydrobenzofuran-5-yl)phenyl)(morpholino)methanone 508. Yield (100 mg, 61%). LCMS: m/z 412.9 $[M+H]^+$, $t_R$=1.85 min.

Synthesis of (4-(2-(Aminomethyl)-7-chloro-2-methyl-2,3-dihydrobenzofuran-5-yl)phenyl)(morpholino)methanone (509): (4-(2-(Azidomethyl)-7-chloro-2-methyl-2,3-dihydrobenzofuran-5-yl)phenyl)(morpholino)methanone (508) (40 mg, 0.1 mmol) was dissolved in ethanol (10 mL). Raney nickel (10 mg) was added and hydrogen gas was purged at room temperature for 1 h. The reaction mixture was filtered and the filtrate was concentrated under reduced pressure to give (4-(2-(aminomethyl)-7-chloro-2-methyl-2,3-dihydrobenzofuran-5-yl)phenyl)(morpholino)methanone 509, which was used without further purification in the next step. Yield (30 mg, 80%), LCMS: m/z 387.0 $[M+H]^+$, $t_R$=1.29 min.

Synthesis of (E)-3-(6-aminopyridin-3-yl)-N-((7-chloro-2-methyl-5-(4-(morpholine-4-carbonyl)phenyl)-2,3-dihydrobenzofuran-2-yl)methyl)acrylamide (349): (4-(2-(Aminomethyl)-7-chloro-2-methyl-2,3-dihydrobenzofuran-5-yl) phenyl)(morpholino)methanone 509 (20 mg, 0.05 mmol) was dissolved in DMF (5 mL) and (E)-3-(6-aminopyridin-3-yl)acrylic acid (8.5 mg, 0.05 mmol) was added at room temperature. EDCI (9.6 mg, 0.05 mmol), HOBt (7 mg, 0.05 mmol) and DIPEA (13 mg, 0.1 mmol) were added to this reaction mixture at room temperature. The reaction mixture was stirred at room temperature for 4 h. The reaction mixture was transferred into water (10 mL) and extracted with ethyl acetate (10 mL×3). The combined organic layers were washed with brine, dried over anhydrous $Na_2SO_4$ and concentrated under reduced pressure to give crude product which was purified by semi-preparative HPLC to obtain (E)-3-(6-aminopyridin-3-yl)-N-((7-chloro-2-methyl-5-(4-(morpholine-4-carbonyl)phenyl)-2,3-dihydrobenzofuran-2-yl)methyl)acrylamide 349. Yield (15 mg, 57% yield). $^1H$ NMR (400 MHz, $CD_3OD$) δ 8.05-7.88 (m, 2H), 7.54-7.27 (m, 7H), 6.92 (d, J=9 Hz, 1H), 6.51 (d, J=16 Hz, 1H), 3.66-3.39 (m, 10H), 3.28-3.01 (m, 2H), 1.43 (s, 3H). LCMS: m/z 533.0 $[M+H]^+$, $t_R$=1.42 min.

327

Synthesis of (E)-N-((6-aminopyridin-3-yl)methyl)-3-(7-chloro-5-(4-(morpholinosulfonyl)phenyl)-2,3-dihydrobenzofuran-2-yl)acrylamide (350)

328

(E)-tert-Butyl-5-(((3-(7-chloro-5-(4-(morpholinosulfonyl)phenyl)-2,3-dihydrobenzofuran-2-yl)acrylamido)methyl)pyridin-2-ylcarbamate 514 was synthesized using General

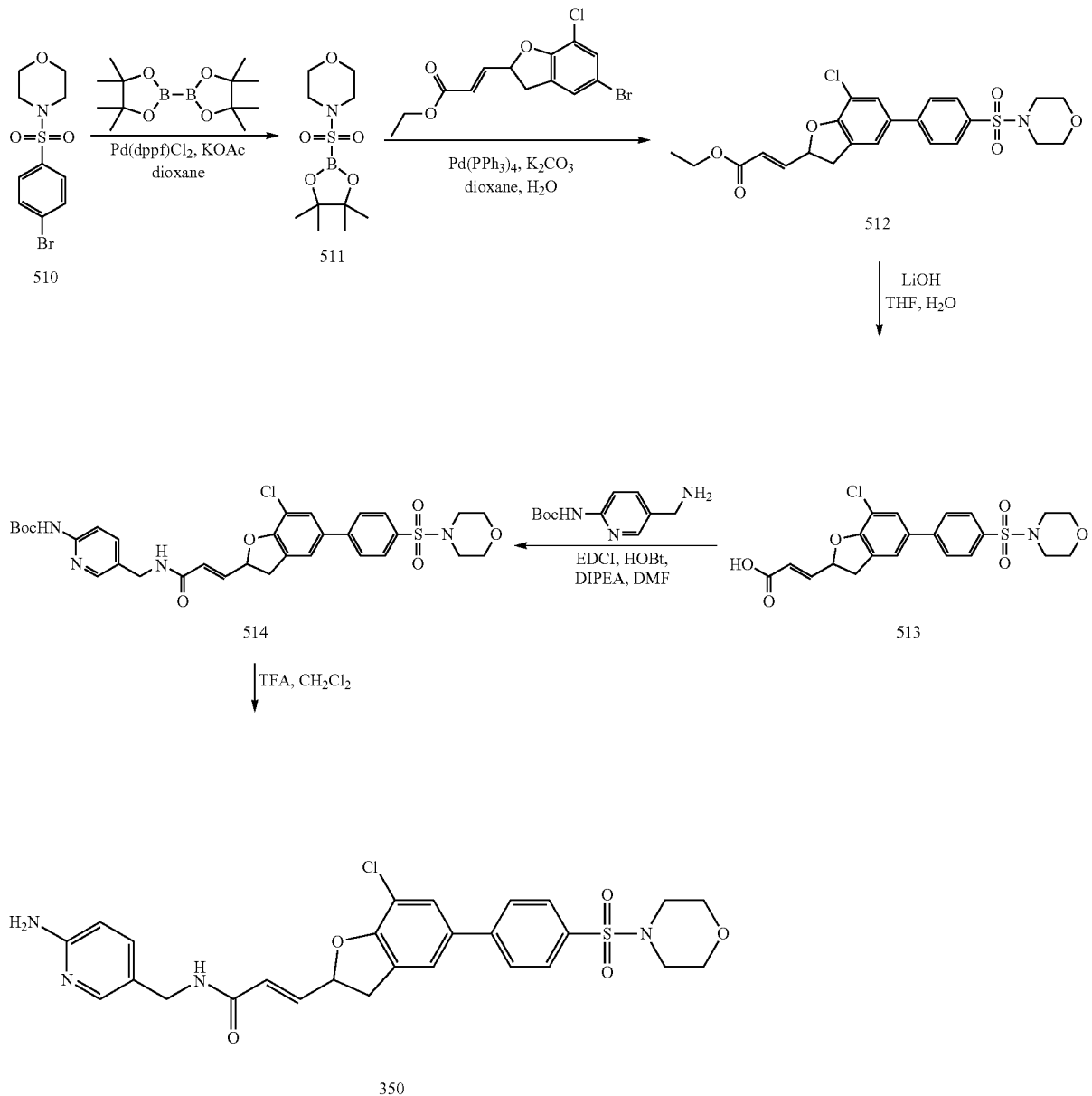

4-(4-(4,4,5,5-Tetramethyl-1,3,2-dioxaborolan-2-yl)phenylsulfonyl)morpholine 511 was synthesized using General Procedure 1. Yield (5.2 g, 75%). LCMS: m/z 354.0 [M+H]$^+$; $t_R$=1.89 min.

(E)-Ethyl 3-(7-chloro-5-(4-(morpholinosulfonyl)phenyl)-2,3-dihydrobenzofuran-2-yl)acrylate 512 was synthesized using General Procedure 1. Yield (140 mg, 49%). LCMS: m/z 478.0 [M+H]$^+$; $t_R$=1.94 min.

(E)-3-(7-Chloro-5-(4-(morpholinosulfonyl)phenyl)-2,3-dihydrobenzofuran-2-yl)acrylic acid 513 was synthesized similar to 3-(6-chloropyridine-3-yl)acrylic acid (48) (Conversion of 47 to 48). Yield (100 mg, 89%). LCMS: m/z 450.1 [M+H]$^+$; $t_R$=1.69 min.

Procedure 3. Yield (40 mg, 61%). LCMS: m/z 655.0 [M+H]$^+$; $t_R$=1.72 min.

(E)-N-((6-Aminopyridin-3-yl)methyl)-3-(7-chloro-5-(4-(morpholinosulfonyl)phenyl)-2,3-dihydrobenzofuran-2-yl)acrylamide 350 was synthesized using General Procedure 2. Yield (10 mg, 37%). $^1$H NMR (400 MHz, CD$_3$OD) δ 7.71-7.41 (m, 9H), 6.83-6.78 (m, 1H), 6.60 (d, J=9 Hz, 1H), 6.21-6.16 (m, 1H), 5.52-5.46 (m, 1H), 4.19 (s, 2H), 3.63-3.54 (m, 5H), 2.90-2.88 (m, 4H). LCMS: m/z 555.2 [M+H]$^+$; $t_R$=1.76 min.

Synthesis of (E)-N-((6-aminopyridin-3-yl)methyl)-3-(7-chloro-5-(4-(3,3-difluoroazetidine-1-carbonyl)phenyl)-2,3-dihydrobenzofuran-2-yl)acrylamide (351)

was synthesized using General Procedure 1. Yield (80 mg, 29%). LCMS: m/z 448.0 [M+H]$^+$; $t_R$=1.94 min.

(E)-3-(7-Chloro-5-(4-(3,3-difluoroazetidine-1-carbonyl)phenyl)-2,3-dihydrobenzofuran-2-yl)acrylic acid 517 was synthesized was synthesized similar to 3-(6-chloropyridine-

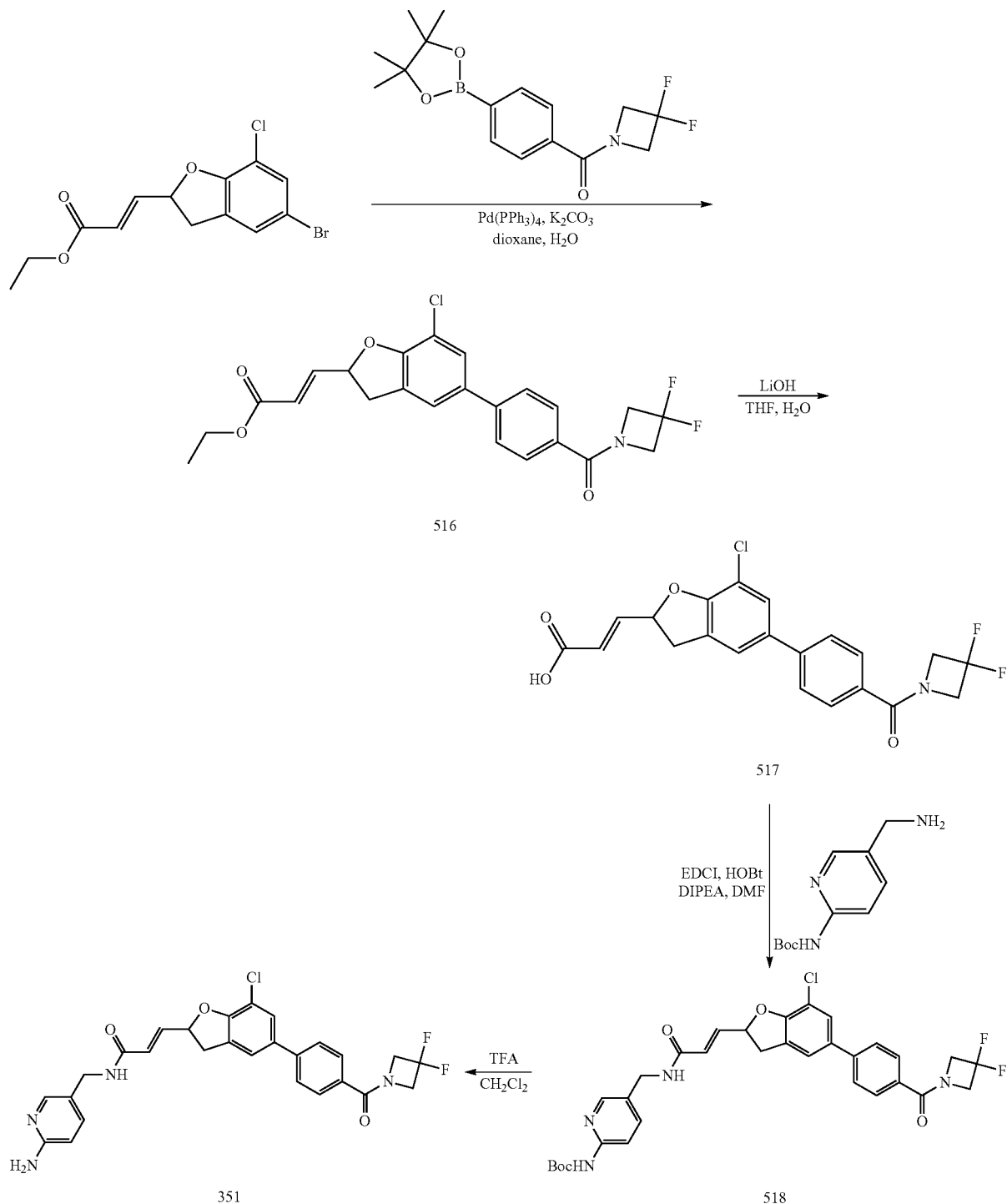

(E)-Ethyl3-(7-chloro-5-(4-(3,3-difluoroazetidine-1-carbonyl)phenyl)-2,3-dihydrobenzofuran-2-yl)acrylate 516

3-yl)acrylic acid (48) (Conversion of 47 to 48). Yield (60 mg, 65%). LCMS: m/z 420.0 [M+H]$^+$; $t_R$=1.68 min.

(E)-tert-Butyl5-((3-(7-chloro-5-(4-(3,3-difluoroazetidine-1-carbonyl)phenyl)-2,3-dihydrobenzofuran-2-yl)acrylamido)methyl)pyridin-2-ylcarbamate 518 was synthesized using General Procedure 3. Yield (40 mg, 60%). LCMS: m/z 625.1 [M+H]+; $t_R$=1.68 min.

(E)-N-((6-Aminopyridin-3-yl)methyl)-3-(7-chloro-5-(4-(3,3-difluoroazetidine-1-carbonyl)phenyl)-2,3-dihydrobenzofuran-2-yl)acrylamide 351 was synthesized using General Procedure 3. Yield (20 mg, 38%). $^1$H NMR (400 MHz, DMSO-d$_6$) δ 8.77-8.72 (m, 1H), 7.93-7.59 (m, 10H), 7.26-6.73 (m, 3H), 4.86-4.17 (m, 5H), 3.69-3.07 (m, 4H). LCMS: m/z 525.1 [M+H]+; $t_R$=1.30 min.

Synthesis of (E)-N-((6-aminopyridin-3-yl)methyl)-3-(7-chloro-4-(4-(3-fluoroazetidine-1-carbonyl)phenyl)-2,3-dihydrobenzofuran-2-yl)acrylamide (352)

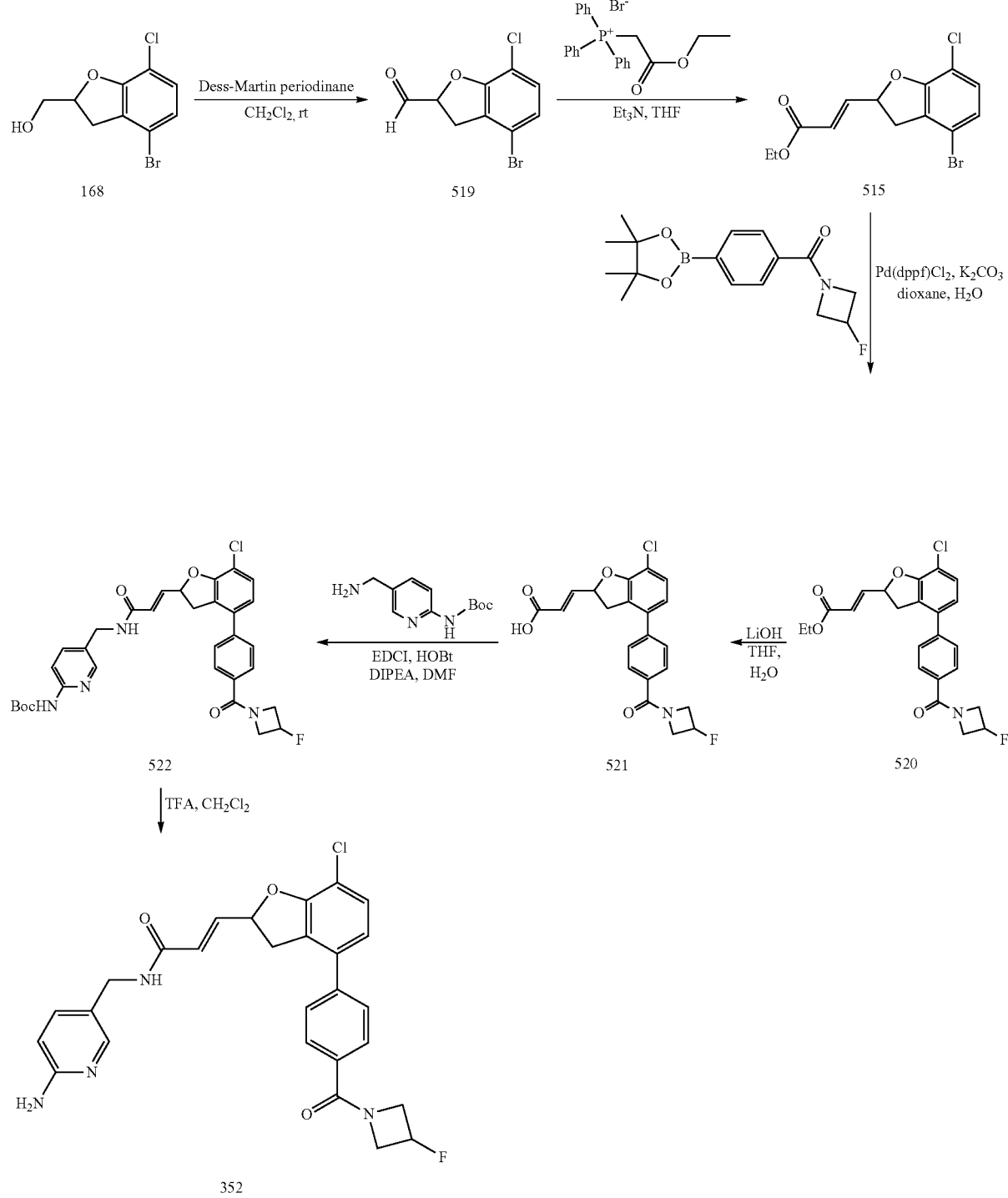

Synthesis of 4-bromo-7-chloro-2,3-dihydrobenzofuran-2-carbaldehyde (519): (4-Bromo-7-chloro-2, 3-dihydrobenzofuran-2-yl)methanol 168 (2.0 g, 7.6 mmol) was dissolved in CH$_2$Cl$_2$ (20 mL). Dess-Martin periodinane (4.7 g, 11.5 mmol) was added. The reaction mixture was stirred at room temperature for overnight. The mixture was filtrated and the filtrate was concentrated to get crude 4-bromo-7-chloro-2, 3-dihydrobenzofuran-2-carbaldehyde 519, which was used in the next step without further purification. Yield (795 mg, 40%). LCMS: m/z 261.0 [M+H]$^+$, t$_R$=1.31 min.

Synthesis of (E)-ethyl 3-(4-bromo-7-chloro-2,3-dihydrobenzofuran-2-yl)acrylate (515): 4-Bromo-7-chloro-2,3-dihydrobenzofuran-2-carbaldehyde (100 mg, 0.4 mmol) was dissolved in THF (5 mL). (2-Ethoxy-2-oxoethyl)triphenylphosphonium bromide (164 mg, 0.4 mmol) was added followed by triethylamine (40 mg, 0.4 mmol) at room temperature. The reaction mixture was stirred at room temperature for 3 h. The reaction mixture was poured into iced water and extracted with EtOAc (10 mL×3). The combined organic layers were washed with brine, dried over anhydrous Na$_2$SO$_4$. The solvents were removed under reduced pressure to give the crude product, which was purified by silica gel chromatography (0-20% EtOAc/petroleum ether) to give (E)-ethyl 3-(4-bromo-7-chloro-2,3-dihydrobenzofuran-2-yl)acrylate 515. Yield (60 mg, 50%). LCMS: m/z 331.0 [M+H]$^+$, t$_R$=1.98 min.

Synthesis of (E)-ethyl 3-(7-chloro-4-(4-(3-fluoroazetidine-1-carbonyl)phenyl)-2,3-dihydrobenzofuran-2-yl)acrylate (520): A mixture of (E)-ethyl 3-(4-bromo-7-chloro-2,3-dihydrobenzofuran-2-yl)acrylate 515 (200 mg, 0.6 mmol), (3-fluoroazetidin-1-yl)(4-(4,4,5,5-tetramethyl-1,3,2-dioxaborolan-2-yl)phenyl)methanone (240 mg, 0.8 mmol), Pd(dppf)Cl$_2$ (48 mg, 0.06 mmol) and potassium carbonate (165 mg, 1.2 mmol) in dioxane (10 mL) and H$_2$O (1 mL) was stirred at 85° C. under nitrogen atmosphere for 2 h. After cooling to room temperature, the mixture was filtered and the filtrate was concentrated under reduced pressure to give the crude product, which was purified by silica gel chromatography (40% EtOAc/petroleum ether) to give (E)-ethyl 3-(7-chloro-4-(4-(3-fluoroazetidine-1-carbonyl)phenyl)-2,3-dihydrobenzofuran-2-yl)acrylate as white solid 520. Yield (200 mg, 77%). LCMS: m/z 430.0 [M+H]$^+$, t$_R$=1.97 min.

Synthesis of (E)-3-(7-chloro-4-(4-(3-fluoroazetidine-1-carbonyl)phenyl)-2,3-dihydrobenzofuran-2-yl)acrylic acid (521): (E)-Ethyl 3-(7-chloro-4-(4-(3-fluoroazetidine-1-carbonyl)phenyl)-2,3-dihydrobenzofuran-2-yl)acrylate 520 (200 mg, 0.5 mmol) was dissolved in THF (15 mL). LiOH (40 mg, 0.9 mmol) and water (3 mL) was added to this mixture at room temperature. The reaction mixture was stirred at room temperature for 2 h. The reaction mixture was cooled to 0° C., acidified with dilute HCl to pH 6. The precipitate was collected by filtration to give crude (E)-3-(7-chloro-4-(4-(3-fluoroazetidine-1-carbonyl)phenyl)-2,3-dihydrobenzofuran-2-yl)acrylic acid 521 which was used without further purification in the next step. Yield (327 mg, 65%). LCMS: m/z 402.0 [M+H]$^+$; t$_R$=1.61 min.

Synthesis of (E)-tert-butyl 5-((3-(7-chloro-4-(4-(3-fluoroazetidine-1-carbonyl)phenyl)-2,3-dihydrobenzofuran-2-yl)acrylamido)methyl)pyridin-2-ylcarbamate (522): The crude (E)-3-(7-chloro-4-(4-(3-fluoroazetidine-1-carbonyl)phenyl)-2,3-dihydrobenzofuran-2-yl)acrylic acid 521 (120 mg, 0.3 mmol) was dissolved in N,N-dimethylformamide (10 mL) and tert-butyl 5-(aminomethyl)pyridin-2-ylcarbamate (68 mg, 0.3 mmol) was added at 0° C. EDCI (86 mg, 0.45 mmol) and HOBt (61 mg, 0.45 mmol) were added to this reaction mixture at 0° C. followed by DIPEA (58 mg, 0.5 mmol) dropwise. The reaction mixture was allowed to warm to room temperature and stirred for 4 h. The crude mixture was purified by semi-preparative HPLC without workup to afford (E)-tert-butyl 5-((3-(7-chloro-4-(4-(3-fluoroazetidine-1-carbonyl)phenyl)-2,3-dihydrobenzofuran-2-yl)acrylamido)methyl)pyridin-2-ylcarbamate 522. Yield (90 mg, 50%). LCMS: m/z 607.0 [M+H]$^+$, t$_R$=1.90 min.

Synthesis of (E)-N-((6-aminopyridin-3-yl)methyl)-3-(7-chloro-4-(4-(3-fluoroazetidine-1-carbonyl)phenyl)-2,3-dihydrobenzofuran-2-yl)acrylamide (352): (E)-tert-Butyl 5-((3-(7-chloro-4-(4-(3-fluoroazetidine-1-carbonyl)phenyl)-2,3-dihydrobenzofuran-2-yl)acrylamido)methyl)pyridin-2-ylcarbamate 522 (70 mg, 0.12 mmol) was dissolved in dichloromethane (5 mL). TFA (1 mL) was added at 0° C. The reaction mixture was stirred at room temperature for 2 h. The reaction mixture was concentrated under reduced pressure to give the crude product, which was purified by semi-preparative HPLC to give of (E)-N-((6-aminopyridin-3-yl)methyl)-3-(7-chloro-4-(4-(3-fluoroazetidine-1-carbonyl)phenyl)-2,3-dihydrobenzofuran-2-yl)acrylamide 352. Yield (18 mg, 31%). $^1$H NMR (400 MHz, CD$_3$OD) δ 7.73-7.70 (m, 1H), 7.62 (d, J=8 Hz, 3H), 7.44 (d, J=8 Hz, 2H), 7.15 (d, J=8 Hz, 1H), 6.85-6.74 (m, 3H), 6.17 (d, J=17 Hz, 1H), 5.42-5.23 (m, 2H), 4.56-4.20 (m, 6H), 3.60-3.53 (m, 1H), 3.08-3.02 (m, 1H). LCMS: m/z 507.2 [M+H]$^+$; t$_R$=1.73 min.

Synthesis of (E)-ethyl 3-(2-(3-(4-(4-(2-43-(6-aminopyridin-3-yl)acrylamido)methyl)-7-chloro-2,3-dihydrobenzofuran-5-yl)benzoyl)piperazin-1-yl)-3-oxopropoxy)ethoxy)propanoate (354)

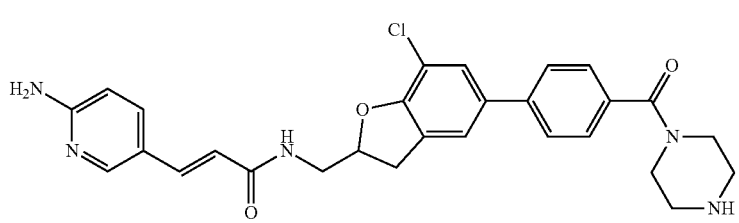 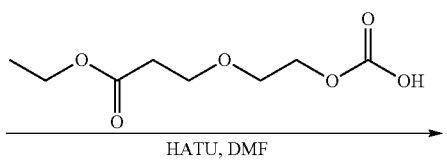

-continued

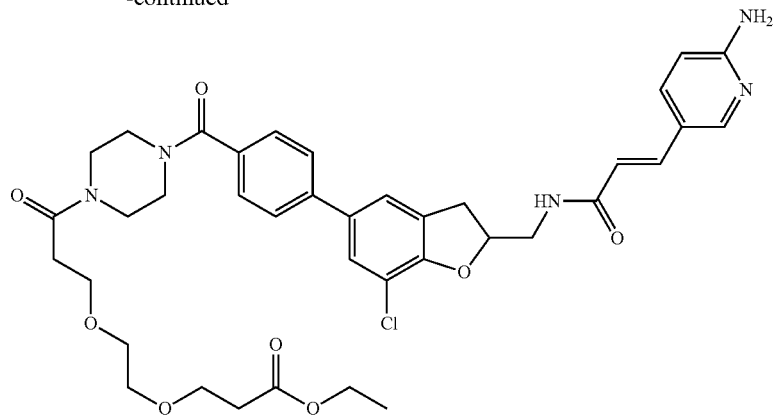

354

(E)-3-(6-aminopyridin-3-yl)-N-((7-chloro-5-(4-(piperazine-1-carbonyl)phenyl)-2,3-dihydrobenzofuran-2-yl)methyl)acrylamide 246 (200 mg, 0.34 mmol) was dissolved in DMF (2mL). 3-(2-(3-Ethoxy-3-oxopropoxy)ethoxy)propanoic acid (79 mg, 0.34 mmol) and HATU (62 mg, 0.51 mmol) were added. The mixture was stirred at room temperature for 2 h. The crude mixture was purified by semi-preparative HPLC without workup to give (E)-ethyl 3-(2-(3-(4-(4-(2-(((3-(6-aminopyridin-3-yl)acrylamido)methyl)-7-chloro-2,3-dihydrobenzofuran-5-yl)benzoyl)piperazin-1-yl)-3-oxopropoxy)ethoxy)propanoate 354. Yield (123 mg, 50%). $^1$H NMR (400 MHz, DMSO-$d_6$) δ 8.27 (t, J=6 Hz, 1H), 8.08 (d, J=2 Hz, 1H), 7.70 (d, J=8 Hz, 2H), 7.59 (dd, J=2 Hz, J=8 Hz, 1H), 7.54 (d, J=3 Hz, 2H), 7.47 (d, J=8 Hz, 2H), 7.31 (d, J=16 Hz, 1H), 6.48-6.41 (m, 4H), 5.10-5.03 (m, 1H), 4.08-4.02 (m, 2H), 3.64-3.38 (m, 19H), 3.14-3.08 (m, 1H), 2.59 (s, 2H), 1.17 (t, J=7 Hz, 3H). LCMS: m/z 734.1 [M+H]$^+$; $t_R$=1.56 min.

Synthesis of (E)-N-((6-aminopyridin-3-yl)methyl)-3-(7-chloro-5-(3-(morpholino-sulfonyl)phenyl)-2,3-dihydrobenzofuran-2-yl)acrylamide (357)

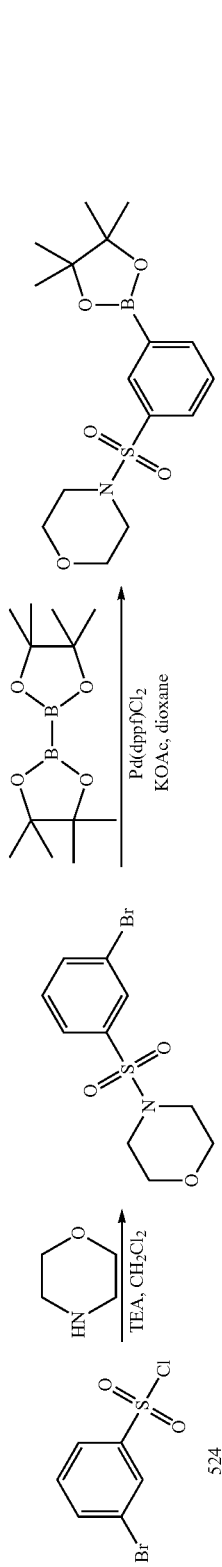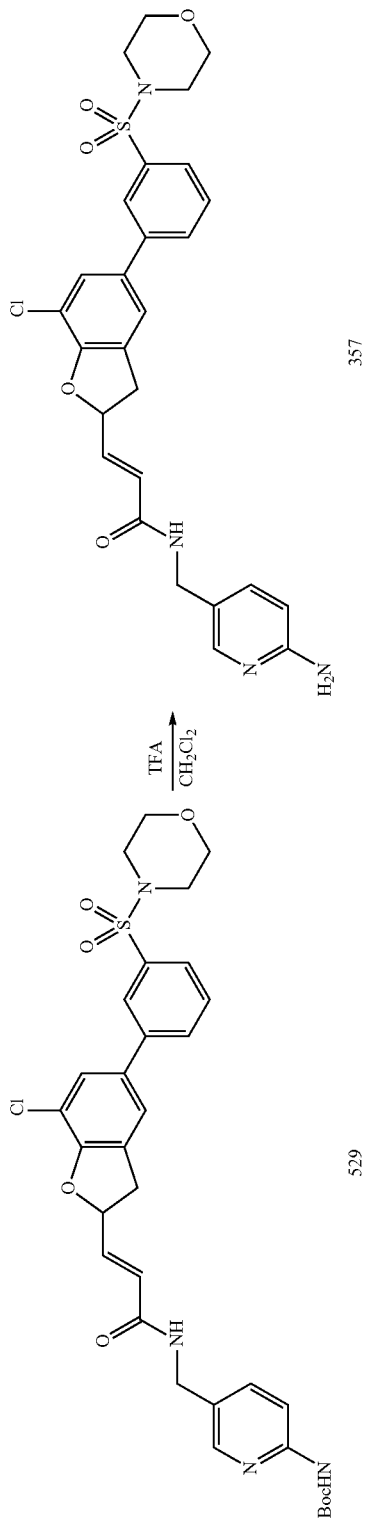

Synthesis of 4-(3-bromophenylsulfonyl)morpholine (525): Morpholine (3.4 g, 39.1 mmol) was dissolved in CH$_2$Cl$_2$ (20 mL). Et$_3$N (7.9 g, 78.3 mmol) and 3-bromobenzene-1-sulfonyl chloride 524 (10 g, 39.1 mmol) were added at 0° C. The resulting mixtue was then allowed to warm to room temperature and stirred for 10 h. The mixture was washed with H$_2$O (10 mL×2), dried over anhydrous Na$_2$SO$_4$ and concentrated under reduced pressure to give 4-(3-bromophenylsulfonyl)morpholine 525 as a white solid, which was used without further purification in the next step. Yield (11.7 g, 97%). LCMS: m/z 306.0 [M+H]$^+$; t$_R$=1.82 min.

Synthesis of 4-(3-(4,4,5,5-tetramethyl-1,3,2-dioxaborolan-2-yl) phenylsulfonyl)morpholine (526): A mixture of 4-(3-bromophenylsulfonyl)morpholine 525 (7.0 g, 22.9 mmol), 4,4,4',4',5,5,5',5'-octamethyl-2,2'-bi(1,3,2-dioxaborolane) (7.0 g, 27.4 mmol), Pd(dppf)Cl$_2$ (1.7 g, 2.3 mmol) and KOAc (4.5 g, 45.7 mmol) in dioxane (20 mL) was stirred at 90° C. under nitrogen atmosphere for 3 h. The reaction mixture was cooled to room temperature and water (10 mL) was added. The resulting mixture was extracted with EtOAc (20 mL×3). The combined organic layers were washed with brine, dried over anhydrous Na$_2$SO$_4$ and concentrated under reduced pressure to give the crude product, which was purified by silica gel chromatography (40% EtOAc/petroleum ether) to give 4-(3-(4,4,5,5-tetramethyl-1,3,2-dioxaborolan-2-yl) phenylsulfonyl)morpholine 526 as a white solid. Yield (5.6 g, 69%). LCMS: m/z 354.1 [M+H]$^+$; t$_R$=1.15 min.

Synthesis of (E)-ethyl 3-(7-chloro-5-(3-(morpholinosulfonyl)phenyl)-2,3-dihydrobenzofuran-2-yl)acrylate (527): (E)-Ethyl 3-(7-chloro-5-(3-(morpholinosulfonyl)phenyl)-2,3-dihydrobenzofuran-2-yl)acrylate 178 was synthesized using General Procedure 1. Yield (260 mg, 72%). LCMS: m/z 478.1 [M+H]$^+$; t$_R$=1.89 min.

Synthesis of (E)-3-(7-chloro-5-(3-(morpholinosulfonyl)phenyl)-2,3-dihydrobenzofuran-2-yl)acrylic acid (528): (E)-Ethyl 3-(7-chloro-5-(3-(morpholinosulfonyl)phenyl)-2,3-dihydrobenzofuran-2-yl)acrylate 527 (120 mg, 0.25 mmol) was dissolved in THF (8 mL). LiOH (32 mg, 0.75 mmol) and water (2 mL) were added to this mixture. The mixture was stirred at room temperature for 2 h. 1N HCl solution was added and adjusted to pH 6. The white precipitate was collected by filtration to give (E)-3-(7-chloro-5-(3-(morpholinosulfonyl)phenyl)-2,3-dihydrobenzofuran-2-yl) acrylic acid 528. Yield (110 mg, 97%). LCMS: m/z 450.0 [M+H]$^+$; t$_R$=1.61 min.

Synthesis of (E)-tert-butyl 5-((3-(7-chloro-5-(3-(morpholinosulfonyl)phenyl)-2,3-dihydrobenzofuran-2-yl)acrylamido)methyl)pyridin-2-ylcarbamate (529): (E)-3-(7-Chloro-5-(3-(morpholinosulfonyl)phenyl)-2,3-dihydrobenzofuran -2-yl)acrylic acid 528 (crude mixture from previous step, 0.25 mmol) was dissolved in DMF (5 mL) and tert-butyl 5-(aminomethyl)pyridin-2-ylcarbamate (55 mg, 0.25 mmol) was added at 0° C. EDCI (94 mg, 0.49 mmol) and HOBt (66 mg, 0.49 mmol) were added to this reaction mixture at 0° C. followed by DIPEA (63 mg, 0.49 mmol) dropwise. The reaction mixture was allowed to warm to room temperature and stirred further for 4 h. The reaction mixture was transferred into water (20 mL) and extracted with EtOAc (25 mL×3). The combined organic layers were washed with brine, dried over anhydrous Na$_2$SO$_4$ and concentrated under reduced pressure to give crude (E)-tert-butyl 5-((3-(7-chloro-5-(3-(morpholinosulfonyl)phenyl)-2,3-dihydrobenzofuran-2-yl)acrylamido)methyl)pyridin-2-ylcarbamate 529 as a yellow oil. Yield (137 mg, 84%). LCMS: m/z 655.2 [M+H]$^+$; t$_R$=1.08 min.

Synthesis of (E)-N-((6-aminopyridin-3-yl)methyl)-3-(7-chloro-5-(3-(morpholinosulfonyl)phenyl)-2,3-dihydrobenzofuran-2-yl) acrylamide (357): (E)-tert-Butyl 5-((3-(7-chloro-5-(3-(morpholinosulfonyl)phenyl)-2,3-dihydrobenzofuran-2-yl)acrylamido)methyl)pyridin-2-ylcarbamate 528 (160 mg, 0.24 mmol) was dissolved in CH$_2$Cl$_2$ (5 mL). TFA (1 mL) was added at 0° C. The reaction mixture was stirred at room temperature for 2 h. The reaction mixture was concentrated under reduced pressure to give the crude product which was purified by semi-preparative HPLC to afford (E)-N-((6-aminopyridin-3-yl)methyl)-3-(7-chloro-5-(3-(morpholinosulfonyl)phenyl)-2,3-dihydrobenzofuran-2-yl) acrylamide 357. Yield (40 mg, 30%). $^1$H NMR (400 MHz, CD$_3$OD) δ 7.92-7.98 (m, 4H), 7.80-7.71 (m, 5H), 7.64 (d, J=2 Hz, 1H), 7.44-7.23 (m, 4H), 7.02 (d, J=9 Hz, 1H), 6.20 (d, J=15 Hz, 1H), 4.37 (s, 2H), 3.74 (t, J=5 Hz, 4H), 3.03 (t, J=5 Hz, 4H). LCMS: m/z 555.2 [M+H]$^+$; t$_R$=1.46 min.

Synthesis of (E)-N-((6-aminopyridin-3-yl)methyl)-3-(7-chloro-5-(4-((R)-3-fluoropyrrolidine-1-carbonyl)phenyl)-2,3-dihydrobenzofuran-2-yl)acrylamide (358)

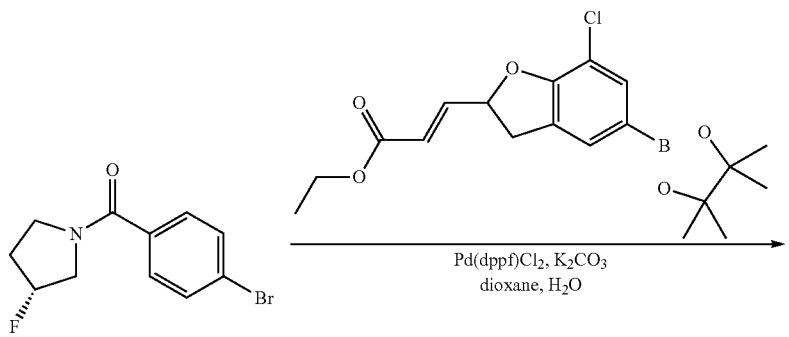

529

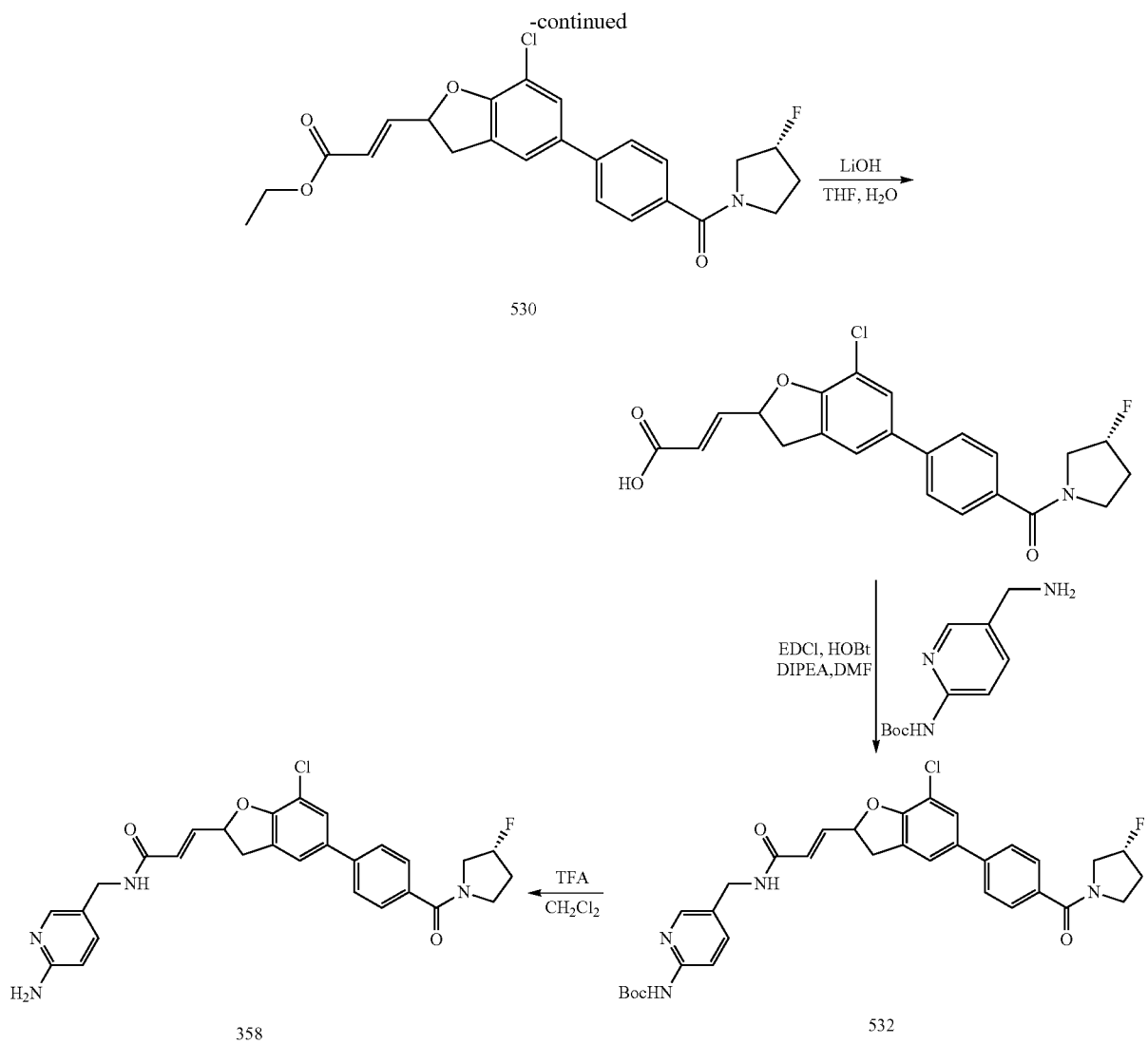

(E)-Ethyl-3-(7-chloro-5-(4-((R)-3-fluoropyrrolidine-1-carbonyl)phenyl)-2,3-dihydrobenzofuran-2-yl)acrylate 530 was synthesized using General Procedure 1. Yield (80 mg, 36%). LCMS: m/z 444.0 [M+H]$^+$; $t_R$=1.88 min.

(E)-3-(7-Chloro-5-(4-((R)-3-fluoropyrrolidine-1-carbonyl)phenyl)-2,3-dihydrobenzofuran-2-yl)acrylic acid 531 was synthesized similar to (E)-3-(7-chloro-5-(3-(morpholinosulfonyl)phenyl)-2,3-dihydrobenzofuran-2-yl) acrylic acid 528 (conversion of 527 to 528). Yield (60 mg, 80%). LCMS: m/z 416.1 [M+H]$^+$; $t_R$=1.62 min.

tert-Butyl 5-(((E)-3-(7-chloro-5-(4-((R)-3-fluoropyrrolidine-1-carbonyl)phenyl)-2,3-dihydrobenzofuran-2-yl)acrylamido)methyl)pyridin-2-ylcarbamate 532 was synthesized using General Procedure 3. Yield (35 mg, 60%). LCMS: m/z 621.3 [M+H]$^+$; $t_R$=1.65 min.

(E)-N-((6-Aminopyridin-3-yl)methyl)-3-(7-chloro-5-(4-((R)-3-fluoropyrrolidine-1-carbonyl)phenyl)-2,3-dihydrobenzofuran-2-yl)acrylamide 358 was synthesized using General Procedure 2. Yield (65 mg, 95%). $^1$H NMR (400 MHz, DMSO-d$_6$) δ 8.80-8.77 (m, 1H), 8.20 (s, 2H), 7.84-7.52 (m, 7H), 6.99-6.79 (m, 2H), 6.25-6.20 (m, 1H), 5.65-5.06 (m, 2H), 4.23-4.16 (m, 2H), 3.69-3.12 (m, 7H), 2.16-2.05 (m, 2H). LCMS: m/z 521.2 [M+H]$^+$; $t_R$=1.29 min.

Synthesis of (E)-N-((6-aminopyridin-3-yl)methyl)-3-(7-chloro-5-(4-((S)-3-fluoro pyrrolidine-1-carbonyl)phenyl)-2,3-dihydrobenzofuran-2-yl)acrylamide (359)

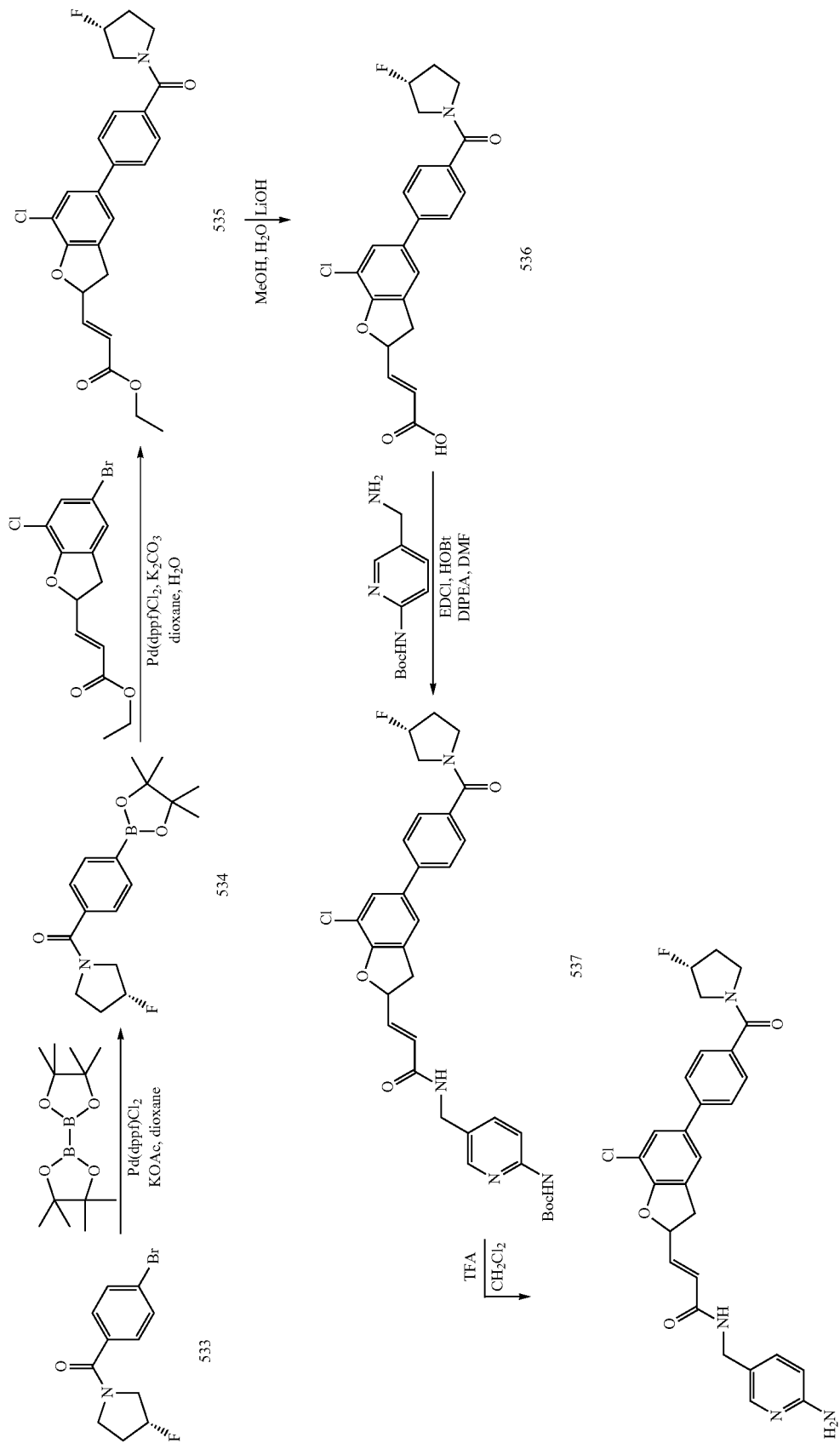

(S)-(3-Fluoropyrrolidin-1-yl)(4-(4,4,5,5-tetramethyl-1,3,2-dioxaborolan-2-yl)phenyl)methanone 534 was synthesized using General Procedure 1. Yield (922 mg, 97%). LCMS: m/z 320.7 [M+H]$^+$; $t_R$=1.10 min.

(E)-Ethyl 3-(7-chloro-5-(4-((S)-3-fluoropyrrolidine-1-carbonyl)phenyl)-2,3-dihydrobenzofuran-2-yl)acrylate 535 was synthesized using General Procedure 1. Yield (152 mg, 81%). LCMS: m/z 444.1 [M+H]$^+$; $t_R$=1.18 min.

(E)-3-(7-Chloro-5-(4-((S)-3-fluoropyrrolidine-1-carbonyl)phenyl)-2,3-dihydrobenzofuran-2-yl)acrylic acid 536 was synthesized similar to (E)-3-(7-chloro-5-(3-(morpholinosulfonyl)phenyl)-2,3-dihydrobenzofuran-2-yl) acrylic acid 528 (conversion of 527 to 528). Yield (140 mg, 98%). LCMS: m/z 416.1 [M+H]$^+$; $t_R$=1.59 min.

tert-Butyl 5-(((E)-3-(7-chloro-5-(4-((S)-3-fluoropyrrolidine-1-carbonyl)phenyl)-2,3-dihydrobenzofuran-2-yl)acrylamido)methyl)pyridin-2-ylcarbamate 537 was synthesized using General Procedure 3. Yield (200 mg, 95%). LCMS: m/z 621.3 [M+H]$^+$; $t_R$=1.83 min.

(E)-N-((6-Aminopyridin-3-yl)methyl)-3-(7-chloro-5-(4-((S)-3-fluoropyrrolidine-1-carbonyl)phenyl)-2,3-dihydrobenzofuran-2-yl)acrylamide 359 was synthesized using General Procedure 2. Yield (100 mg, 59%). $^1$H NMR (400 MHz, DMSO-d$_6$) δ 9.96 (s, 1H), 8.66 (s, 1H), 8.04-7.59 (m, 11H), 7.30-7.21 (m, 2H), 6.98 (d, J=9 Hz, 1H), 6.21-6.17 (m, 1H), 5.47-5.25 (m, 1H), 4.25 (d, J=6 Hz, 2H), 3.89-3.44 (m, 4H), 2.20-2.05 (m, 2H). LCMS: m/z 521.2 [M+H]$^+$; $t_R$=1.30 min.

Synthesis of (E)-N-((6-aminopyridin-3-yl)methyl)-3-(7-chloro-5-(2-(morpholinosulfonyl)phenyl)-2,3-dihydrobenzofuran-2-yl)acrylamide (360)

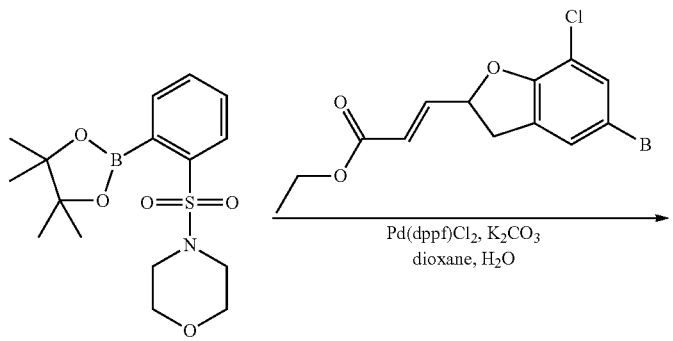

538

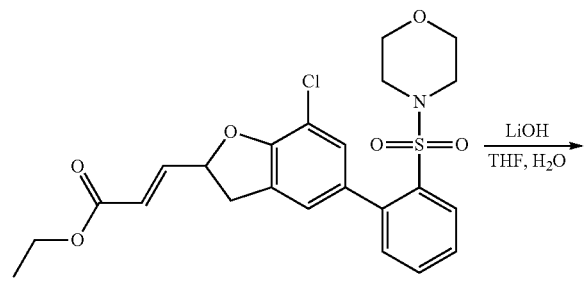

539

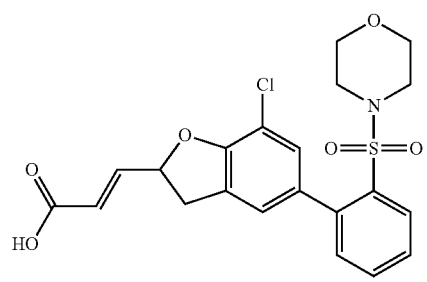

540

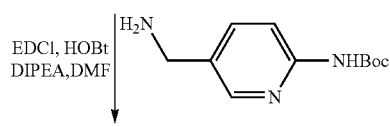

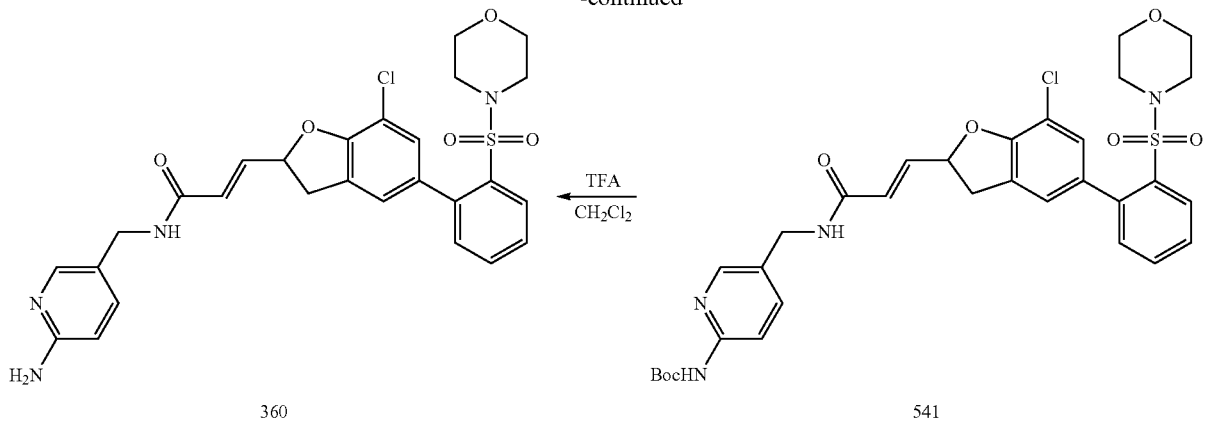

(E)-Ethyl 3-(7-chloro-5-(2-(morpholinosulfonyl)phenyl)-2,3-dihydrobenzofuran-2-yl)acrylate 539 was synthesized using General Procedure 1. Yield (120 mg, 37%). LCMS: m/z 478.1 [M+H]$^+$; $t_R$=1.89 min.

(E)-3-(7-Chloro-5-(2-(morpholinosulfonyl)phenyl)-2,3-dihydrobenzofuran-2-yl)acrylic acid 540 was synthesized similar to (E)-3-(7-chloro-5-(3-(morpholinosulfonyl)phenyl)-2,3-dihydrobenzofuran-2-yl)acrylic acid 528 (conversion of 527 to 528). Yield (110 mg, 97%). LCMS: m/z 450.0 [M+H]$^+$; $t_R$=1.60 min.

(E)-tert-Butyl 5-((3-(7-chloro-5-(2-(morpholinosulfonyl)phenyl)-2,3-dihydrobenzofuran-2-yl)acrylamido)methyl)pyridin-2-ylcarbamate 541 was synthesized using General Procedure 3. Yield (160 mg, 85%). LCMS: m/z 655.2 [M+H]$^+$; $t_R$=1.09 min.

(E)-N-((6-Aminopyridin-3-yl)methyl)-3-(7-chloro-5-(2-(morpholinosulfonyl)phenyl)-2,3-dihydrobenzofuran-2-yl)acrylamide 360 was synthesized using General Procedure 2. Yield (30 mg, 22%). $^1$H NMR (400 MHz, CD$_3$OD) δ 8.15-8.10 (m, 1H), 7.94-7.90 (m, 1H), 7.79-7.70 (m, 2H), 7.64-7.56 (m, 2H), 7.47-7.28 (m, 4H), 7.12-6.99 (m, 2H), 6.16 (d, J=15 Hz, 1H), 4.36 (s, 2H), 3.52-3.38 (m, 5H), 2.86-2.79 (m, 4H). LCMS: m/z 555.2 [M+H]$^+$; $t_R$=1.43 min.

Synthesis of (E)-N-((6-aminopyridin-3-yl)methyl)-3-(7-chloro-5-(4-(3-fluoro azetidine-1-carbonyl)phenyl)-2,3-dihydrobenzofuran-2-yl)acrylamide (361)

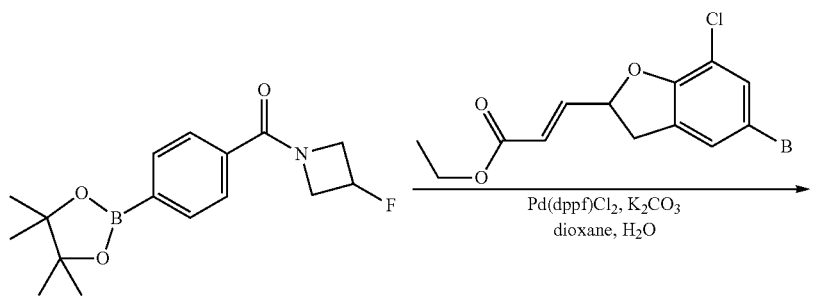

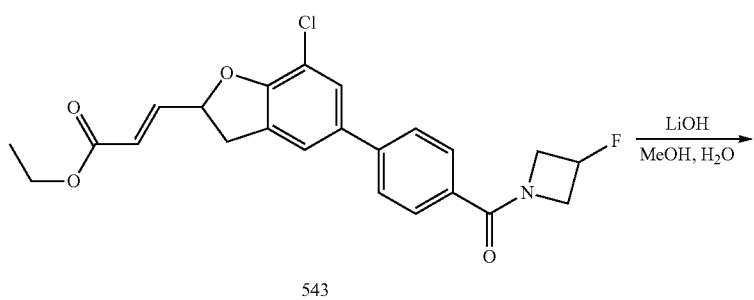

-continued

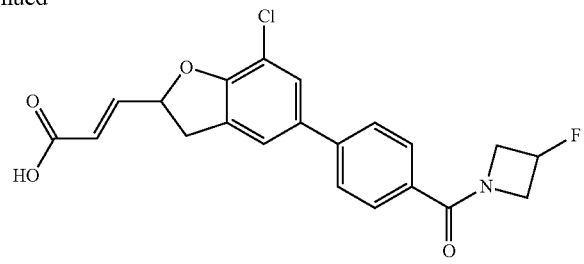

544

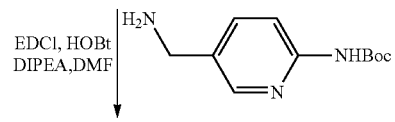

EDCl, HOBt
DIPEA, DMF

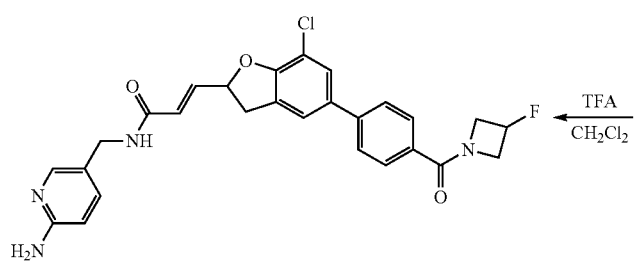

361

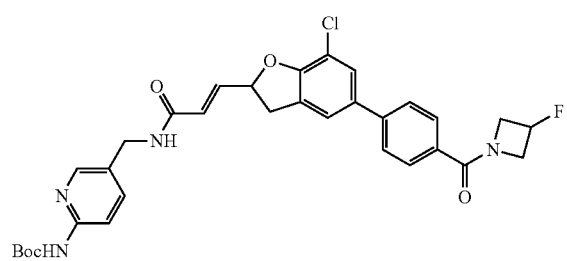

545

(E)-Ethyl 3-(7-chloro-5-(4-(3-fluoroazetidine-1-carbonyl)phenyl)-2,3-dihydrobenzofuran-2-yl)acrylate 543 was synthesized using General Procedure 1. Yield (60 mg, 43%). LCMS: m/z 430.1 [M+H]$^+$; $t_R$=1.79 min.

(E)-3-(7-Chloro-5-(4-(3-fluoroazetidine-1-carbonyl)phenyl)-2,3-dihydrobenzofuran-2-yl)acrylic acid 544 was synthesized similar to (E)-3-(7-chloro-5-(3-(morpholinosulfonyl)phenyl)-2,3-dihydrobenzofuran-2-yl)acrylic acid 528 (conversion of 527 to 528). Yield (60 mg, 78%). LCMS: m/z 402.0 [M+H]$^+$; $t_R$=1.56 min.

(E)-tert-Butyl 5-((3-(7-chloro-5-(4-(3-fluoroazetidine-1-carbonyl)phenyl)-2,3-dihydrobenzofuran-2-yl)acrylamido)methyl)pyridin-2-ylcarbamate 545 was synthesized using General Procedure 3. Yield (60 mg, 66%). LCMS: m/z 607.2 [M+H]$^+$; $t_R$=1.94 min.

(E)-N-((6-Aminopyridin-3-yl)methyl)-3-(7-chloro-5-(4-(3-fluoroazetidine-1-carbonyl)phenyl)-2,3-dihydrobenzofuran-2-yl)acrylamide 361 was synthesized using General Procedure 2. Yield (10 mg, 20%). $^1$H NMR (400 MHz, DMSO-$d_6$) δ 8.58-8.34 (m, 1H), 7.80-7.53 (m, 8H), 7.30-7.26 (m, 1H), 6.39 (d, J=8 Hz, 1H), 5.82 (d, J=8 Hz, 2H), 5.63-5.35 (m, 1H), 5.09-5.01 (m, 1H), 4.63-4.29 (m, 3H), 4.13-4.59 (m, 4H), 3.23-3.15 (m, 1H), 2.47-2.26 (m, 1H). LCMS: m/z 507.2 [M+H]$^+$; $t_R$=1.68 min.

Synthesis of (E)-N-((6-aminopyridin-3-yl)methyl)-3-(7-chloro-5-(4-(3,3-dimethylazetidine-1-carbonyl)phenyl)-2,3-dihydrobenzofuran-2-yl)acrylamide
(362)

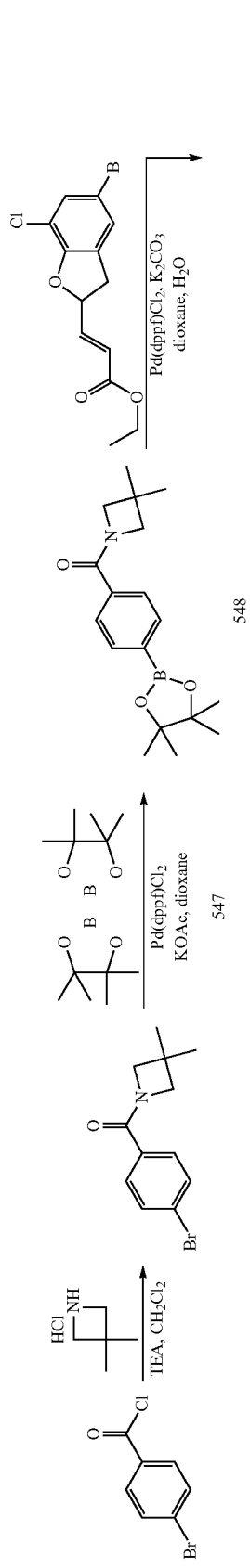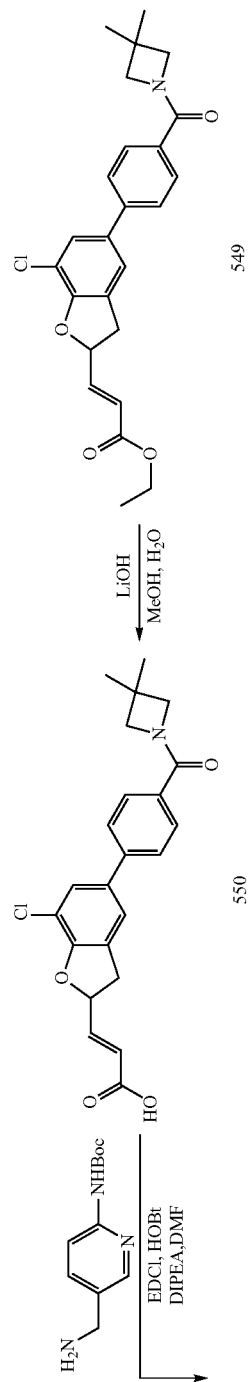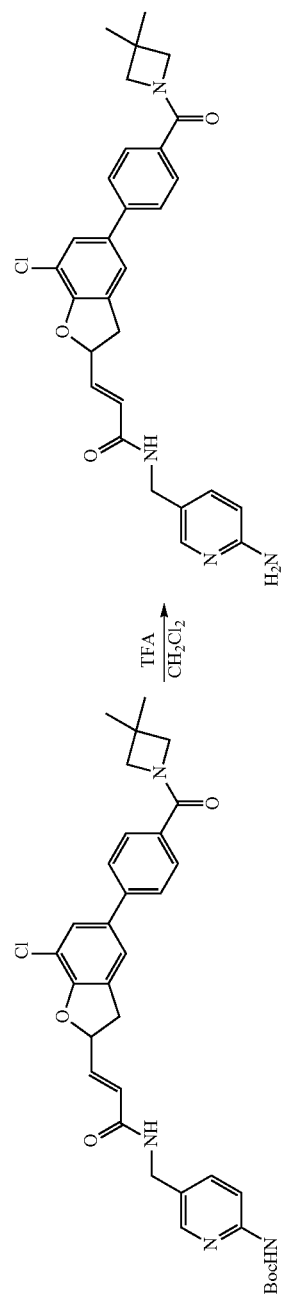

(4-Bromophenyl)(3,3-dimethylazetidin-1-yl)methanone (547): 3,3-Dimethylazetidine hydrochloride (500 mg, 4.1 mmol) was dissolved in $CH_2Cl_2$ (20 mL). The mixture was cooled to 0° C. and degassed. $Et_3N$ (410 mg, 8.3 mmol) and 4-bromobenzoyl chloride (900 mg, 4.1 mmol) were added to this mixture. The resulting mixtue was then allowed to warm to room temperature and stirred for 10 h. The mixture was washed with $H_2O$ (10 mL×2), dried over anhydrous $Na_2SO_4$ and concentrated under reduced pressure to give the product (4-bromophenyl)(3,3-dimethylazetidin-1-yl)methanone 230 as white solid, which was used without further purification in the next step. Yield (1.2 g, 88% yield). LCMS: m/z 268.0 $[M+H]^+$; $t_R$=1.68 min.

(3,3-Dimethylazetidin-1-yl)(4-(4,4,5,5-tetramethyl-1,3,2-dioxaborolan-2-yl)phenyl)methanone 548 was synthesized using General Procedure 1. Yield (400 mg, 78%). LCMS: m/z 316.1 $[M+H]^+$; $t_R$=2.01 min.

(E)-Ethyl 3-(7-chloro-5-(4-(3,3-dimethylazetidine-1-carbonyl)phenyl)-2,3-dihydrobenzofuran-2-yl)acrylate 549 was synthesized using General Procedure 1. Yield (140 mg, 75%). LCMS: m/z 440.2 $[M+H]^+$; $t_R$=1.83 min.

(E)-3-(7-Chloro-5-(4-(3,3-dimethylazetidine-1-carbonyl)phenyl)-2,3-dihydrobenzofuran-2-yl)acrylic acid 550 was synthesized similar to (E)-3-(7-chloro-5-(3-(morpholinosulfonyl)phenyl)-2,3-dihydrobenzofuran-2-yl)acrylic acid 528 (conversion of 527 to 528). Yield (120 mg, 91%). LCMS: m/z 412.1 $[M+H]^+$; $t_R$=1.09 min.

(E)-tert-Butyl 5-((3-(7-chloro-5-(4-(3,3-dimethylazetidine-1-carbonyl)phenyl)-2,3-dihydrobenzofuran-2-yl)acrylamido)methyl)pyridin-2-ylcarbamate 551 was synthesized using General Procedure 3. Yield (180 mg, 84%). LCMS: m/z 617.3 $[M+H]^+$; $t_R$=1.10 min.

(E)-N-((6-Aminopyridin-3-yl)methyl)-3-(7-chloro-5-(4-(3,3-dimethylazetidine-1-carbonyl)phenyl)-2,3-dihydrobenzofuran-2-yl)acrylamide 362 was synthesized using General Procedure 2. Yield (70 mg, 55%). $^1$H NMR (400 MHz, DMSO-$d_6$) δ 9.98 (s, 1H), 8.66 (s, 1H), 7.90-7.68 (m, 11H), 7.28-7.25 (m, 2H), 6.98 (d, J=9 Hz, 1H), 6.20-6.17 (m, 1H), 4.25 (d, J=6 Hz, 2H), 3.75 (s, 2H), 3.39 (s, 2H), 1.26 (s, 6H). LCMS: m/z 517.3 $[M+H]^+$; $t_R$=1.70 min.

Synthesis of (E)-N-((6-aminopyridin-3-yl)methyl)-3-(7-chloro-5-(4-(3,3-difluoroazetidin-1-ylsulfonyl)phenyl)-2,3-dihydrobenzofuran-2-yl)acrylamide (363)

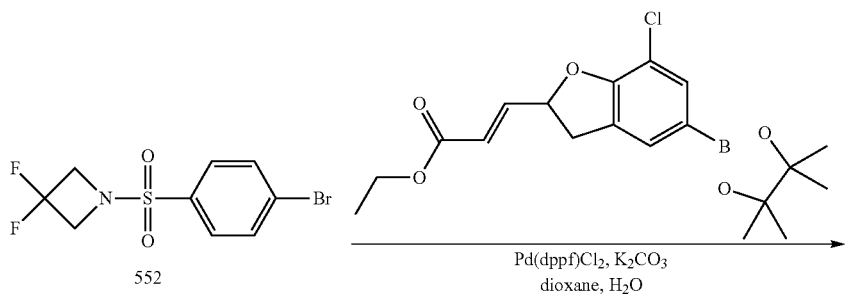

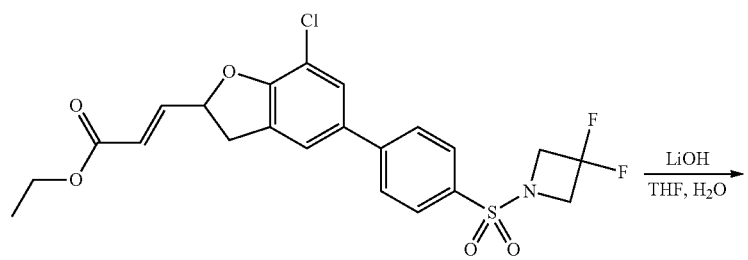

-continued

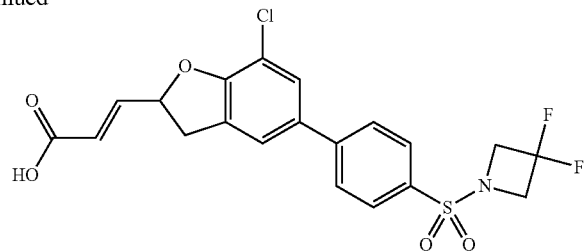

554

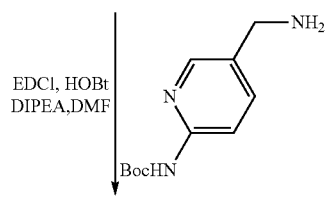

EDCl, HOBt
DIPEA,DMF

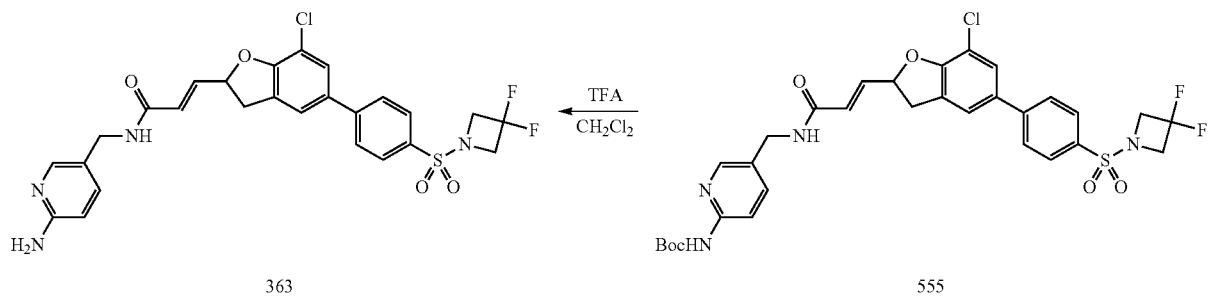

363      555

(E)-Ethyl 3-(7-chloro-5-(4-(3,3-difluoroazetidin-1-ylsulfonyl)phenyl)-2,3-dihydrobenzofuran-2-yl)acrylate 553 was synthesized General Procedure 1. Yield (50 mg, 41%). LCMS: m/z 484.1 [M+H]⁺; $t_R$=1.97 min.

(E)-3-(7-Chloro-5-(4-(3,3-difluoroazetidin-1-ylsulfonyl)phenyl)-2,3-dihydrobenzofuran-2-yl)acrylic acid 554 was synthesized similar to (E)-3-(7-chloro-5-(3-(morpholinosulfonyl)phenyl)-2,3-dihydrobenzofuran-2-yl)acrylic acid 528 (conversion of 527 to 528). Yield (30 mg, 67%). LCMS: m/z 456.1 [M+H]⁺; $t_R$=1.76 min.

(E)-tert-Butyl 5-((3-(7-chloro-5-(4-(3,3-difluoroazetidin-1-ylsulfonyl)phenyl)-2,3-dihydrobenzofuran-2-yl)acrylamido)methyl)pyridin-2-ylcarbamate 555 was synthesized using General Procedure 3. Yield (40 mg, 42%).LCMS: m/z 661.2 [M+H]⁺; $t_R$=1.75 min.

(E)-N-((6-Aminopyridin-3-yl)methyl)-3-(7-chloro-5-(4-(3,3-difluoroazetidin-1-ylsulfonyl)phenyl)-2,3-dihydrobenzofuran-2-yl)acrylamide 363 was synthesized using General Procedure 2. Yield (12 mg, 36%). ¹H NMR (400 MHz, CD₃OD) δ 7.95-7.85 (m, 6H), 7.56-7.43 (m, 4H), 6.93-6.90 (m, 1H), 6.57-6.27 (m, 2H), 5.59 (s, 1H), 4.28-4.19 (m, 7H), 3.70-3.64 (m, 1H), 3.22-3.16 (m, 1H). LCMS: m/z 561.2 [M+H]⁺; $t_R$=1.36 min.

Synthesis of (E)-N-((6-aminopyridin-3-yl)methyl)-3-(7-chloro-4-(4-(morpholinosulfonyl)phenyl)-2,3-dihydrobenzofuran-2-yl)acrylamide (364)

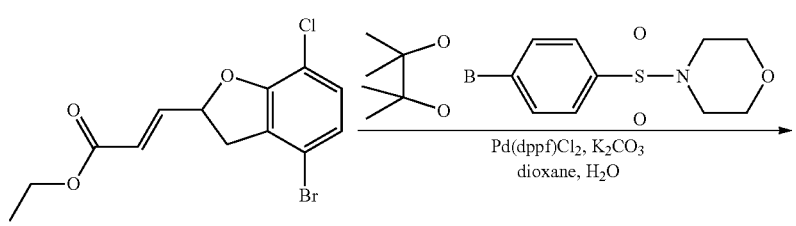

515

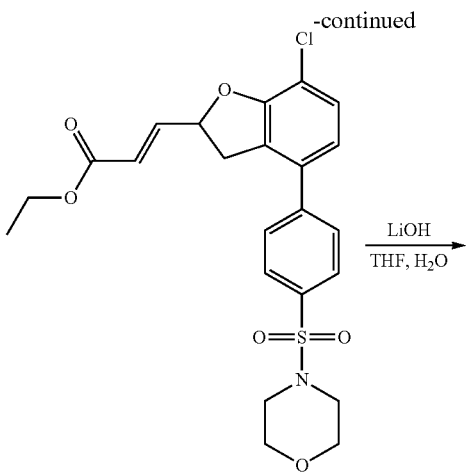

556

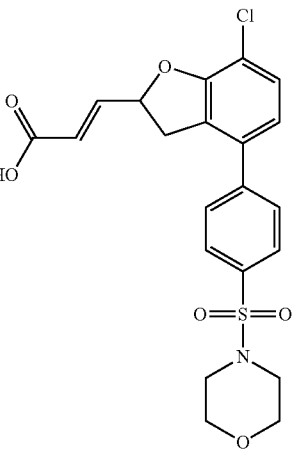

557

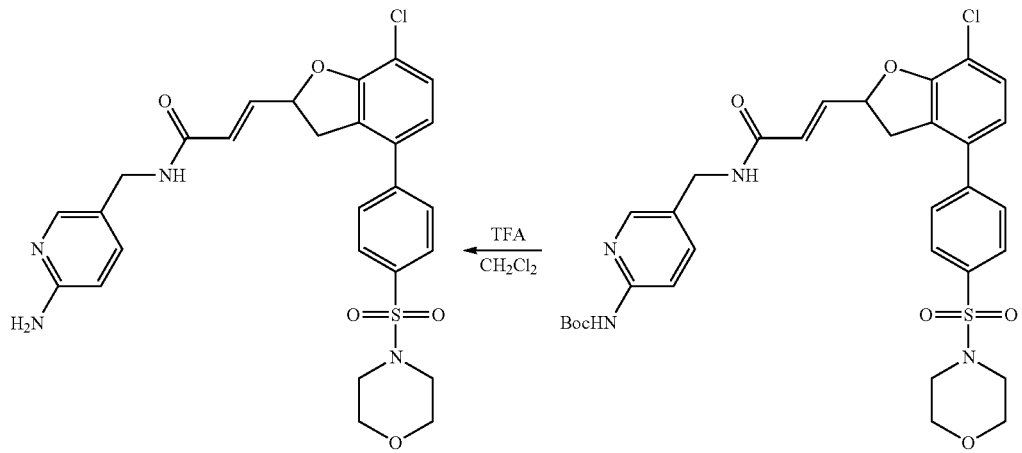

364                                                     558

(E)-Ethyl 3-(7-chloro-4-(4-(morpholinosulfonyl)phenyl)-2,3-dihydrobenzofuran-2-yl)acrylate 556 was synthesized using General Procedure 1. Yield (150 mg, 42%). LCMS: m/z 478.0 [M+H]$^+$, $t_R$=1.89 min.

(E)-3-(7-Chloro-4-(4-(morpholinosulfonyl)phenyl)-2,3-dihydrobenzofuran-2-yl)acrylic acid (557): (E)-ethyl 3-(7-chloro-4-(4-(morpholinosulfonyl)phenyl)-2,3-dihydrobenzofuran-2-yl)acrylate 556 (200 mg, 0.42 mmol) was dissolved in THF (10 mL). LiOH (36 mg, 0.84 mmol) and water (2 mL) were added to this mixture. The mixture was stirred at room temperature for 2 h. 1N HCl solution was added and adjusted to pH 6. (E)-3-(7-chloro-4-(4-(morpholinosulfonyl)phenyl)-2,3-dihydrobenzofuran-2-yl) acrylic acid 557 was collected by filtration. Yield (120 mg, 64% yield). LCMS: m/z 450.0 [M+H]$^+$; $t_R$=1.68 min.

(E)-tert-Butyl 5-((3-(7-chloro-4-(4-(morpholinosulfonyl)phenyl)-2,3-dihydrobenzofuran-2-yl)acrylamido)methyl)pyridin-2-ylcarbamate 558 was synthesized using General Procedure 3. Yield (120 mg, 68%). LCMS: m/z 655.0 [M+H]$^+$, $t_R$=1.63 min.

(E)-N-((6-Aminopyridin-3-yl)methyl)-3-(7-chloro-4-(4-(morpholinosulfonyl)phenyl)-2,3-dihydrobenzofuran-2-yl) acrylamide 364 was synthezied using General Procedure 2. Yield (38 mg, 45%). $^1$H NMR (400 MHz, CD$_3$OD) δ 8.72-8.70 (m, 1H), 7.92-7.80 (m, 7H), 7.39 (d, J=8 Hz, 1H), 7.08 (d, J=8 Hz, 1H), 6.93 (d, J=10 Hz, 1H), 6.81-6.76 (m, 1H), 6.20 (d, J=15 Hz, 1H), 5.63-5.60 (m, 1H), 4.20 (d, J=6 Hz, 2H), 3.75-3.60 (m, 6H), 3.29-3.22 (m, 1H), 2.92-2.90 (m, 1H). LCMS: m/z 555.0 [M+H]$^+$; $t_R$=1.36 min.

359
Synthesis of (E)-3-(6-aminopyridin-3-yl)-N-((7-chloro-3,3-dideutero-5-(4-(morpholine-4-carbonyl)phenyl)-2,3-dihydrobenzofuran-2-yl)methyl)acrylamide (365)
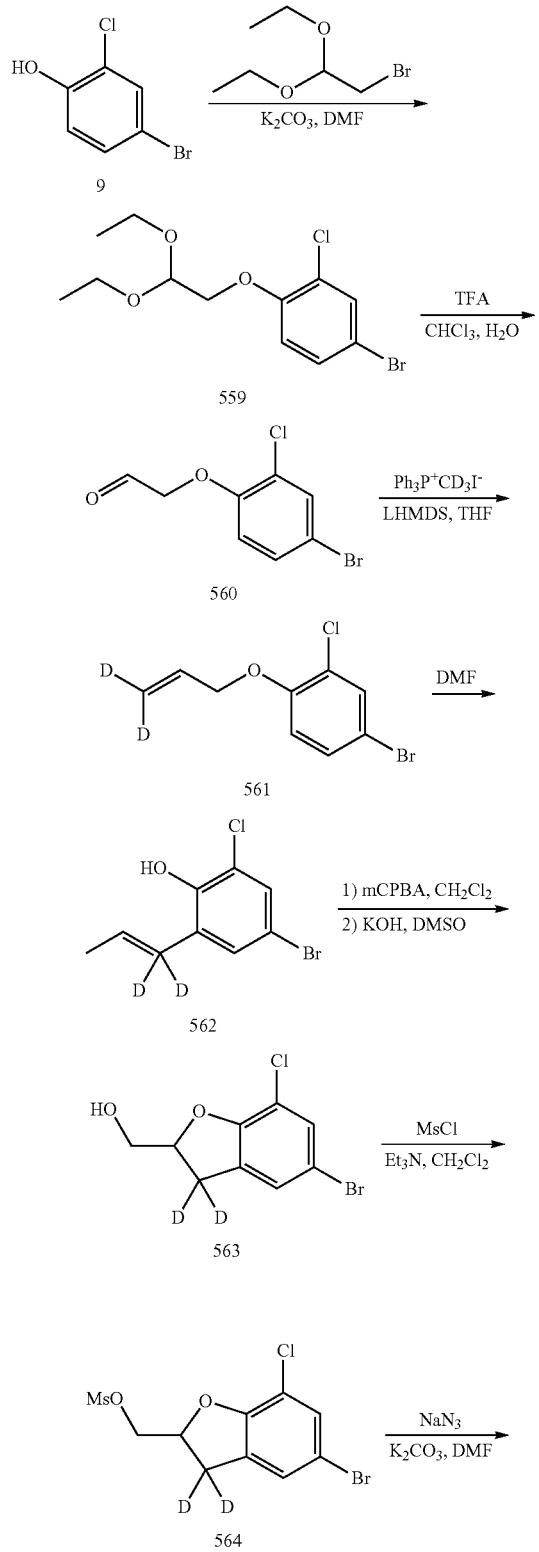
360
-continued
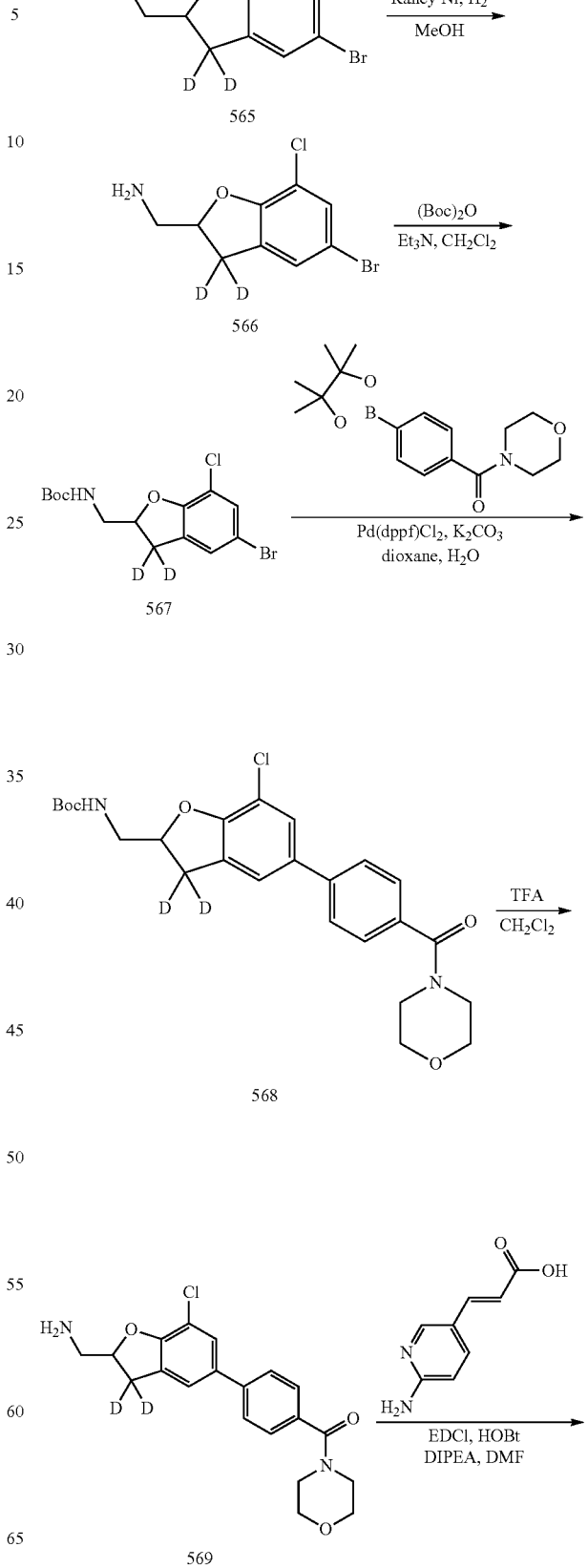

-continued

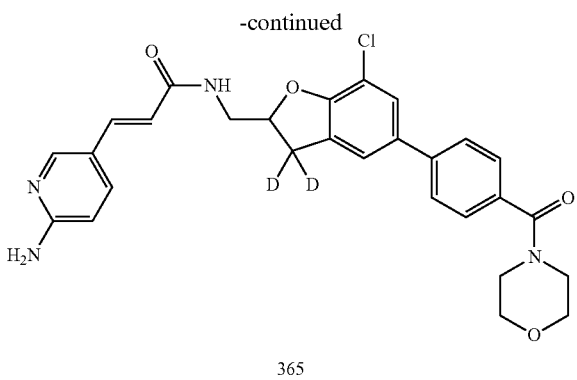

365

Synthesis of 4-bromo-2-chloro-1-(2,2-diethoxyethoxy)benzene (559): 4-Bromo-2-chlorophenol 9 (10.3 g, 50 mmol) was dissolved in DMF (200 mL). $K_2CO_3$ (10.4 g, 75 mmol) and 2-bromo-1,1-diethoxyethane (12.8 g, 65 mmol) were added at 25° C. and the reaction mixture was stirred at 80° C. overnight. The reaction mixture was transferred into iced water and extracted with ethyl acetate (50 mL×3). The combined organic layers were washed with brine, dried over anhydrous $Na_2SO_4$, and concentrated under reduced pressure. The crude product was purified by silica gel chromatography (10% ethyl acetate/petroleum ether) to provide 4-bromo-2-chloro-1-(2,2-diethoxyethoxy)benzene 559. Yield (15 g, 93%) as a colorless liquid. LCMS: m/z 344.9 $[M+Na]^+$, $t_R$=2.03 min.

Synthesis of 2-(4-bromo-2-chlorophenoxy)acetaldehyde (560): 4-Bromo-2-chloro-1-(2,2-diethoxyethoxy)benzene 559 (8 g, 24.8 mmol) was dissolved in $CHCl_3$ (40 mL). TFA (40 mL) and $H_2O$ (40 mL) were added to this mixture. The resulting mixture was stirred at room temperature for 4 h. The organic phase was separated and the aqueous phase was extracted with $CH_2Cl_2$ (20 mL×2). The combined organic phases were washed with aqueous solution of $NaHCO_3$, brine, dried over anhydrous $Na_2SO_4$, and concentrated under reduced pressure. The crude product was purified by silica gel chromatography (25% ethyl acetate/petroleum ether) to provide 2-(4-bromo-2-chlorophenoxy)acetaldehyde 560. Yield (4.5 g, 93%) as a colorless oil. $^1$H NMR (400 MHz, $CDCl_3$) δ 9.88 (t, J=1 Hz, 1H), 7.56 (d, J=2 Hz, 1H), 7.34 (dd, $J_1$=2 Hz, $J_2$=9 Hz, 1H), 6.70 (d, J=9 Hz, 1H), 4.62 (J=1 Hz, 2H).

Synthesis of 4-bromo-2-chloro-1-(3,3-dideuteroallyloxy)benzene (561): Lithium hexamethyldisilazide (19.8 mL, 19.8 mmol, 1N in THF) was added to a slurry of $Ph_3P^+$ $CD_3I^-$ (8.8 g, 21.6 mmol) in THF (100 mL) under nitrogen atmosphere at 0° C. After stirring for 30 min, 2-(4-bromo-2-chlorophenoxy)acetaldehyde 560 (4.5 g, 18 mmol) was added. The mixture was then allowed to warm to room temperature and stirred overnight. The reaction mixture was transferred into iced water and extracted with ethyl acetate (50 mL×3). The combined organic layers were washed with brine, dried over anhydrous $Na_2SO_4$ and concentrated under reduced pressure to give the crude product which was purified by silica gel chromatography (petroleum ether) providing 4-bromo-2-chloro-1-(3,3-dideuteroallyloxy)benzene 561 as colorless liquid. Yield (1,48 g, 33%). $^1$H NMR (400 MHz, $CDCl_3$) δ 7.50 (d, J=3 Hz, 1H), 7.31-7.26 (m, 1H), 6.79 (d, J=9 Hz, 1H), 6.05-6.01 (m, 1H), 4.59 (d, J=5 Hz, 2H).

Synthesis of 4-bromo-2-chloro-6-(1,1-dideuteroallyl)phenol (562): 4-Bromo-2-chloro-1-(3,3-dideuteroallyloxy)benzene 561 (1 g, 4 mmol) was dissolved in DMF (20 mL) and the reaction mixture was heated at 185° C. for 2 days. The reaction mixture was cooled to room temperature, transferred into iced water and extracted with ethyl acetate (20 mL×3). The combined organic layers were washed with brine, dried over anhydrous $Na_2SO_4$ and concentrated under reduced pressure. The crude product was purified by silica gel chromatography (0-1% ethyl acetate/petroleum ether) to obtain 4-bromo-2-chloro-6-(1,1-dideuteroallyl)phenol 562. Yield (480 mg, 48%). LCMS: $t_R$=1.98 min.

Synthesis of (5-bromo-7-chloro-3,3-dideutero-2,3-dihydrobenzofuran-2-yl)methanol (563): 4-Bromo-2-chloro-6-(1,1-dideuteroallyl)phenol 562 (480 mg, 1.9 mmol) was dissolved in dichloromethane (10 mL). mCPBA (677 mg, 3.9 mmol) was added at 0° C. and stirred at room temperature for 4 h. The reaction mixture was diluted with dichloromethane (25 mL) and washed with saturated sodium bicarbonate solution, saturated sodium thiosulphate solution, and brine. The organic layer was dried over anhydrous $Na_2SO_4$, and concentrated under reduced pressure to give 512 mg of the crude epoxy intermediate. The crude epoxy intermediate was then dissolved in DMSO (18 mL) and cooled to 0° C. where KOH (152 mg, 2.7 mmol) in water (1.5 mL) was added. The reaction mixture was allowed to warm to room temperature where it was stirred for 4 h. The reaction mixture was then transferred into iced water and extracted with ethyl acetate (15 mL×3). The combined organic layers were washed with brine, dried over anhydrous $Na_2SO_4$, and concentrated under reduced pressure to give the crude product which was purified by silica gel chromatography (0-30% ethyl acetate/petroleum ether) to give (5-bromo-7-chloro-3,3-dideutero-2,3-dihydrobenzofuran-2-yl)methanol 563. Yield (310 mg, 60%). $^1$H NMR (400 MHz, $CDCl_3$) δ 7.29-7.24 (m, 1H), 7.19-7.16 (m, 1H), 5.07-4.94 (m, 1H), 3.97-3.88 (m, 1H), 3.83-3.70 (m, 1H).

Synthesis of (5-bromo-7-chloro-3,3-dideutero-2,3-dihydrobenzofuran-2-yl)methyl methanesulfonate (564): (5-Bromo-7-chloro-3,3-dideutero-2,3-dihydrobenzofuran-2-yl)methanol 563 (310 mg, 1.2 mmol) was dissolved in dichloromethane (10 mL). Methane sulfonyl chloride (160 mg, 1.4 mmol) and triethylamine (178 mg, 1.8 mmol) were added at 0° C. and the reaction mixture was allowed to warm to room temperature where it was stirred for 4 h. The reaction mixture was transferred into iced water and extracted with dichloromethane (10 mL×3). The combined organic layers were washed with brine, dried over anhydrous $Na_2SO_4$, and concentrated under reduced pressure to give the crude product, which was purified by silica gel chromatography (20% ethyl acetate/petroleum ether) to give (5-bromo-7-chloro-3,3-dideutero-2,3-dihydrobenzofuran-2-yl)methyl methanesulfonate 564. Yield (340 mg, 85%). LCMS: m/z 368.9 $[M+Na]^+$; $t_R$=1.76 min.

Synthesis of 2-(azidomethyl)-5-bromo-7-chloro-3,3-dideutero-2,3-dihydrobenzofuran (565): (5-Bromo-7-chloro-3,3-dideutero-2,3-dihydrobenzofuran-2-yl)methyl methanesulfonate 564 (340 mg, 1 mmol) was dissolved in DMF (8 mL). Sodium azide (129 mg, 2 mmol) and $K_2CO_3$ (206 mg, 1.5 mmol) were added at room temperature. The reaction mixture was stirred at 80° C. for 6 h, cooled to room temperature, transferred into iced water, and extracted with ethyl acetate (15 mL×3). The combined organic layers were washed with brine, dried over anhydrous $Na_2SO_4$, and concentrated under reduced pressure to give the crude product, which was purified by silica gel chromatography (6% ethyl acetate/petroleum ether to obtain 2-(azidomethyl)-5-bromo-7-chloro-3,3-dideutero-2,3-dihydrobenzofuran 565. Yield (260 mg, 90% yield). LCMS: $t_R$=1.91 min.

Synthesis of (5-bromo-7-chloro-3,3-dideutero-2,3-dihydrobenzofuran-2-yl)methanamine (566): 2-(Azidomethyl)-5-bromo-7-chloro-3,3-dideutero-2,3-dihydrobenzofuran 565 (260 mg, 0.9 mmol) was dissolved in methanol (20 mL). Raney Ni (200 mg) was added and hydrogen gas was purged at room temperature for 0.5 h. The reaction mixture was filtered and the filtrate was concentrated under reduced pressure to give the crude (5-bromo-7-chloro-3,3-dideutero-2,3-dihydrobenzofuran-2-yl)methanamine 566, which was used without further purification in the next step. Yield (234 mg, 99%). LCMS: m/z 266.0 [M+H]$^+$; $t_R$=1.23 min.

Synthesis of tert-butyl (5-bromo-7-chloro-3,3-dideutero-2,3-dihydrobenzofuran-2-yl)methylcarbamate (567): (5-Bromo-7-chloro-3,3-dideutero-2,3-dihydrobenzofuran-2-yl)methanamine 566 (270 mg, 1.0 mmol) was dissolved in dichloromethane (10 mL) and di-tert-butyl dicarbonate (268 mg, 1.2 mmol) was added at 0° C. Triethylamine (208 mg, 2.1 mmol) was added and the reaction mixture was stirred at room temperature for 4 h. The reaction mixture was transferred into iced water and extracted with dichloromethane (15 mL×3). The combined organic layers were washed with brine, dried over anhydrous Na$_2$SO$_4$, and concentrated under reduced pressure to give the crude product, which was purified by silica gel chromatography (1-2% ethyl acetate/petroleum ether to obtain tert-butyl (5-bromo-7-chloro-3,3-dideutero-2,3-dihydrobenzofuran-2-yl)methylcarbamate 567. Yield (310 mg, 83%). LCMS: m/z 364.0 [M+H]$^+$; $t_R$=1.94 min.

Synthesis of tert-butyl (7-chloro-3,3-dideutero-5-(4-(morpholine-4-carbonyl)phenyl)-2,3-dihydrobenzofuran-2-yl)methylcarbamate (568): A mixture of tert-butyl (5-bromo-7-chloro-3,3-dideutero-2,3-dihydrobenzofuran-2-yl)methylcarbamate 567 (181 mg, 0.5 mmol), morpholino(4-(4,4,5,5-tetramethyl-1,3,2-dioxaborolan-2-yl)phenyl)methanone (190 mg, 0.6 mmol), Pd(dppf)Cl$_2$ (39 mg, 0.05 mmol) and potassium carbonate (138 mg, 1 mmol) in dioxane (6 mL) and H$_2$O (0.6 mL) was stirred at 85° C. under nitrogen atmosphere for 2 h. The mixture was extracted with EtOAc (10 mL×3). The combined organic layers were washed with brine, dried over anhydrous Na$_2$SO$_4$, and the solvents were removed under reduced pressure to give the crude product, which was purified by silica gel chromatography (50-66% EtOAc/petroleum ether) to give tert-butyl (7-chloro-3,3-dideutero-5-(4-(morpholine-4-carbonyl)phenyl)-2,3-dihydrobenzofuran-2-yl)methylcarbamate 568 as a white solid. Yield (112 mg, 47%). LCMS: m/z 475.1 [M+H]$^+$, $t_R$=1.75 min.

Synthesis of (4-(2-(aminomethyl)-7-chloro-3,3-dideutero-2,3-dihydrobenzofuran-5-yl)phenyl)(morpholino)methanone (569): tert-Butyl (7-chloro-3,3-dideutero--5-(4-(morpholine-4-carbonyl)phenyl)-2,3-dihydrobenzofuran-2-yl)methylcarbamate 568 (112 mg, 0.24 mmol) was dissolved in dichloromethane (4 mL) and TFA (1 mL) was added at 0° C. The reaction mixture was allowed to warm to room temperature and stirred for 1 h. The reaction mixture was concentrated under reduced pressure to give crude (4-(2-(aminomethyl)-7-chloro-3,3-dideutero-2,3-dihydrobenzofuran-5-yl)phenyl)(morpholino)methanone 569, which was used without further purification in the next step. Yield (113 mg, 100%). LCMS: m/z 375.1 [M+H]$^+$; $t_R$=1.19 min.

Synthesis of (E)-3-(6-aminopyridin-3-yl)-N-((7-chloro-3,3-dideutero-5-(4-(morpholine-4-carbonyl)phenyl)-2,3-dihydrobenzofuran-2-yl)methyl)acrylamide (365): The crude (4-(2-(aminomethyl)-7-chloro-3,3-dideutero-2,3-dihydrobenzofuran-5-yl)phenyl)(morpholino)methanone 569 (113 mg, 0.24 mmol) was dissolved in DMF (3 mL) and (E)-3-(6-aminopyridin-3-yl)acrylic acid (46 mg, 0.28 mmol) was added at 0° C. EDCI (54 mg, 0.28 mmol) and HOBt (38 mg, 0.28 mmol) were added to this reaction mixture at 0° C. followed by DIPEA (61 mg, 0.47 mmol) dropwise. The reaction mixture was allowed to warm to room temperature and stirred overnight. The crude mixture was purified by semi-preparative HPLC without workup to afford (E)-3-(6-aminopyridin-3-yl)-N-((7-chloro-3,3-dideutero-5-(4-(morpholine-4-carbonyl)phenyl)-2,3-dihydrobenzofuran-2-yl)methyl)acrylamide 365. Yield (35 mg, 29% yield). $^1$H NMR (400 MHz, DMSO-d$_6$) δ 8.27 (t, J=6 Hz, 1H), 8.06 (d, J=2 Hz, 1H), 7.70-7.29 (m, 8H), 6.47-6.41 (m, 4H), 5.07-5.04 (m, 1H), 3.60-3.26 (m, 10H). LCMS: m/z 521.2 [M+H]$^+$; $t_R$=1.53 min.

Synthesis of (E)-N-((6-aminopyridin-3-yl)methyl)-3-(7-chloro-5-(4-(3-fluoro-3-methylazetidine-1-carbonyl)phenyl)-2,3-dihydrobenzofuran-2-yl)acrylamide (366)

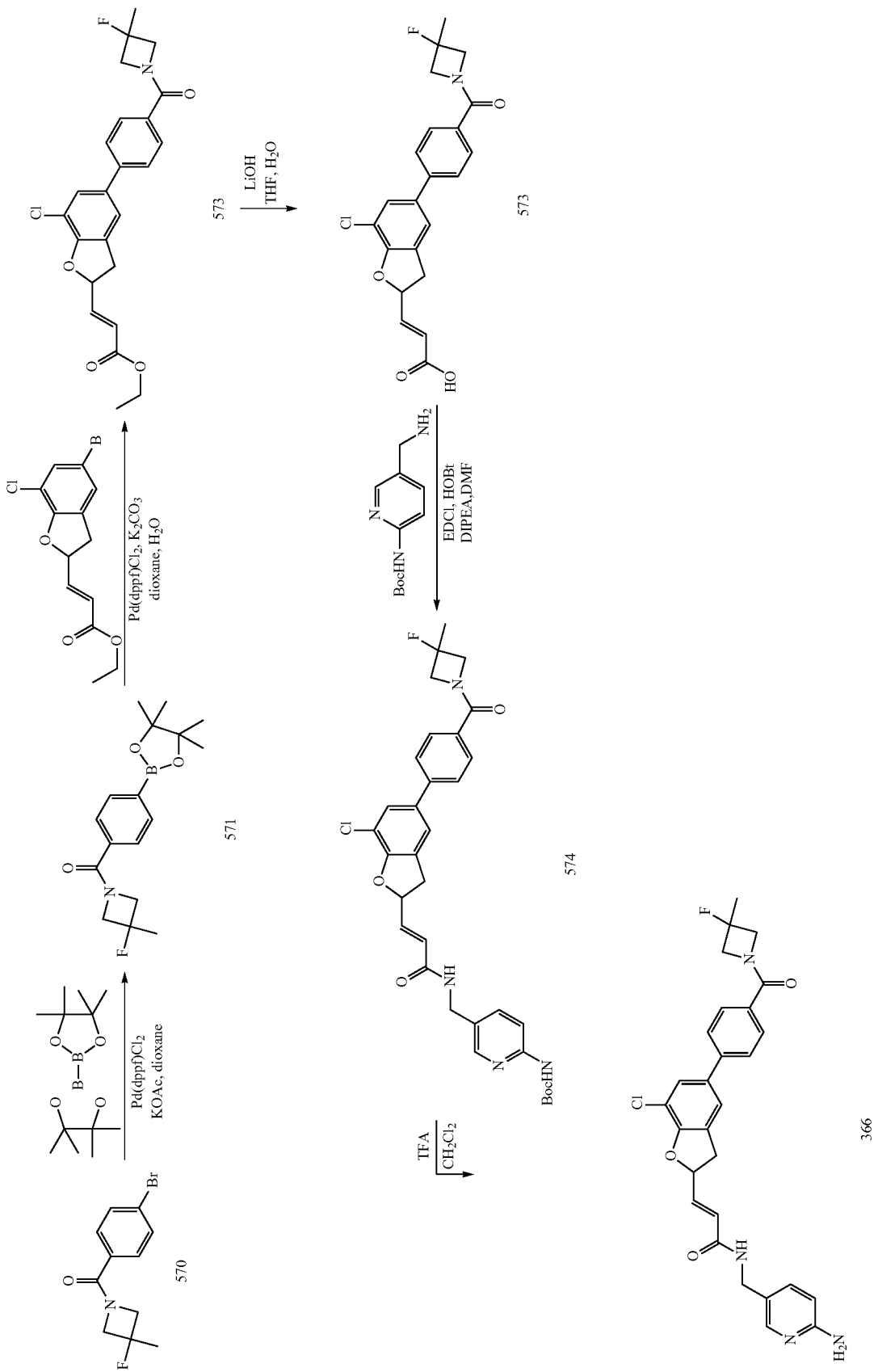

(3-Fluoro-3-methylazetidin-1-yl)(4-(4,4,5,5-tetramethyl-1,3,2-dioxaborolan-2-yl)phenyl)methanone 571 was synthesized using General Procedure 1. Yield (200 mg, 42%). LCMS: m/z 320.2 [M+H]$^+$; $t_R$=1.84 min.

(E)-Ethyl 3-(7-chloro-5-(4-(3-fluoro-3-methylazetidine-1-carbonyl)phenyl)-2,3-dihydrobenzofuran-2-yl)acrylate 572 was synthesized using General Procedure 1. Yield (80 mg, 36%). LCMS: m/z 444.1 [M+H]$^+$; $t_R$=2.03 min.

(E)-3-(7-Chloro-5-(4-(3-fluoro-3-methylazetidine-1-carbonyl)phenyl)-2,3-dihydrobenzofuran-2-yl)acrylic acid 573 was synthesized similar to (E)-3-(7-chloro-5-(3-(morpholinosulfonyl)phenyl)-2,3-dihydrobenzofuran-2-yl)acrylic acid 528 (conversion of 527 to 528). Yield (60 mg, 63%). LCMS: m/z 416.1 [M+H]$^+$; $t_R$=1.61 min.

(E)-tert-Butyl 5-((3-(7-chloro-5-(4-(3-fluoro-3-methylazetidine-1-carbonyl)phenyl)-2,3-dihydrobenzofuran-2-yl)acrylamido)methyl)pyridin-2-ylcarbamate 574 was synthesized using General Procedure 3. Yield (74 mg, 60%). LCMS: m/z 621.2 [M+H]$^+$; $t_R$=1.69 min.

(E)-N-((6-Aminopyridin-3-yl)methyl)-3-(7-chloro-5-(4-(3-fluoro-3-methylazetidine-1-carbonyl)phenyl)-2,3-dihydrobenzofuran-2-yl)acrylamide 366 was synthesized was synthesized using General Procedure 2. Yield(10 mg, 30%). $^1$H NMR (400 MHz, DMSO-d$_6$) δ 8.76-8.73 (m, 1H), 7.99 (s, 2H), 7.83-7.57 (m, 7H), 6.96-6.79 (m, 2H), 6.24-6.20 (m, 1H), 5.67-5.62 (m, 1H), 4.51-4.17 (m, 6H), 3.68-3.57 (m, 1H), 3.17 (s, 2H), 1.60 (d, J=22 Hz, 3H). LCMS: m/z 521.3 [M+H]$^+$; $t_R$=1.36 min.

Synthesis of (E)-N-((6-aminopyridin-3-yl)methyl)-3-(7-chloro-5-(4-(3,3-dimethylmorpholine-4-carbonyl)phenyl)-2,3-dihydrobenzofuran-2-yl)acrylamide (367)

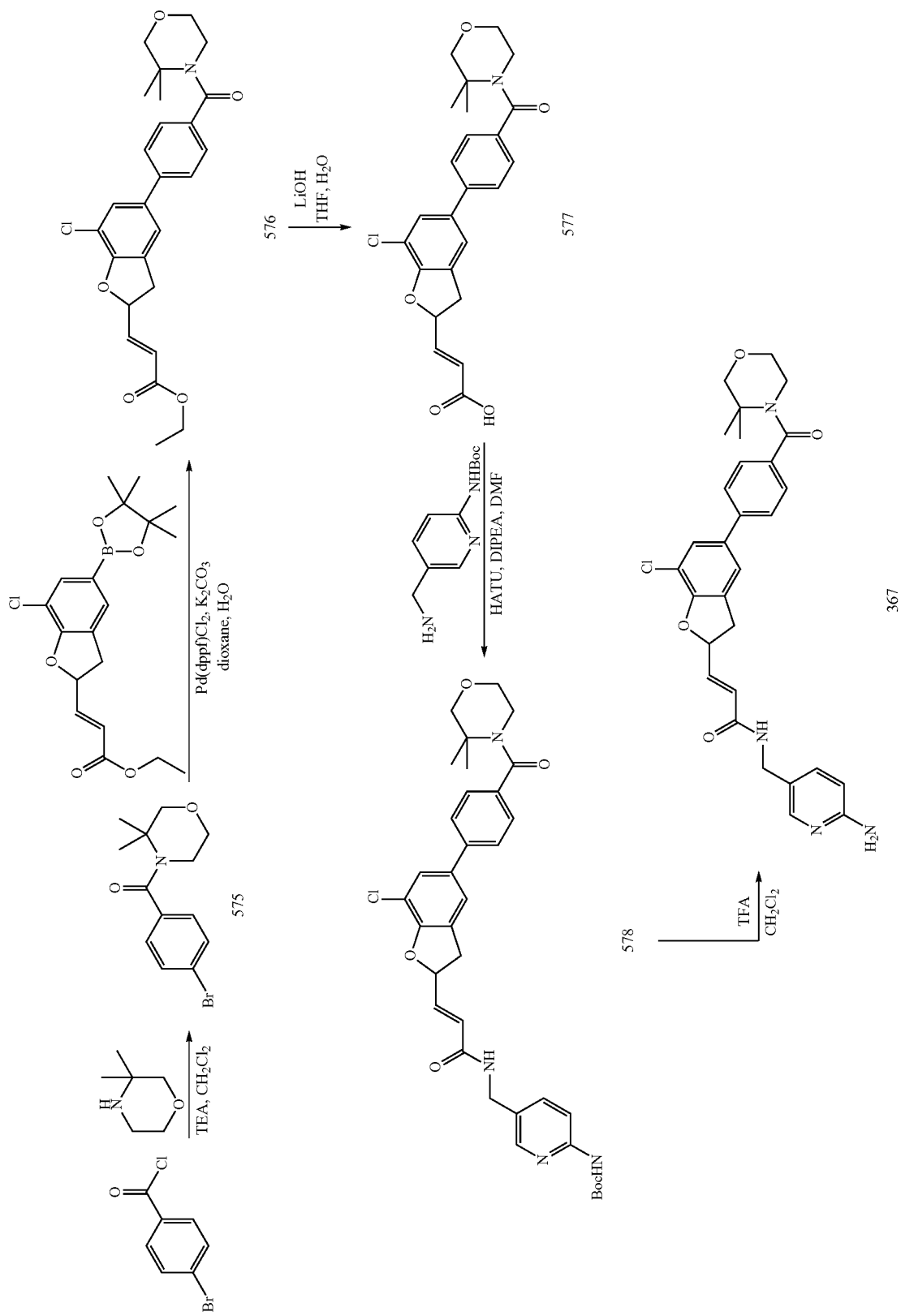

(4-Bromophenyl)(3,3-dimethylmorpholino)methanone (575): Triethylamine (202 mg, 2 mmol) and 4-bromobenzoyl chloride (219 mg, 1.0 mmol) was added to a solution of 3,3-dimethylmorpholine (115 mg, 1.0 mmol) in CH$_2$Cl$_2$ (10 mL) at 0° C. The reaction mixture was stirred at 25° C. for 16 h. The mixture was washed with water (20 mL), dried over anhydrous Na$_2$SO$_4$ and concentrated under reduced pressure to give (4-bromophenyl)(3,3-dimethylmorpholino)methanone 575 as a white solid. Yield (260 mg, 87%). LCMS: m/z 298 [M+H]$^+$; t$_R$=1.58 min.

(E)-Ethyl 3-(7-chloro-5-(4-(3,3-dimethylmorpholine-4-carbonyl)phenyl)-2,3-dihydrobenzofuran-2-yl)acrylate 576 was synthesized using General Procedure 1. Yield (110 mg, 75%). LCMS: m/z 470.1 [M+H]$^+$, t$_R$=1.96 min.

(E)-3-(7-Chloro-5-(4-(3,3-dimethylmorpholine-4-carbonyl)phenyl)-2,3-dihydrobenzofuran-2-yl)acrylic acid 577 was synthesized similar to (E)-3-(7-chloro-5-(3-(morpholinosulfonyl)phenyl)-2,3-dihydrobenzofuran-2-yl) acrylic acid 528 (conversion of 527 to 528). Yield (90 mg, 85%). LCMS: m/z 442.0 [M+H]$^+$, t$_R$=1.52 min.

(E)-tert-Butyl 5-((3-(7-chloro-5-(4-(3,3-dimethylmorpholine-4-carbonyl)phenyl)-2,3-dihydrobenzofuran-2-yl)acrylamido)methyl)pyridin-2-ylcarbamate 578 was synthesized using General Procedure 3. Yield (110 mg, 83%). LCMS: m/z 647.0 [M+H]$^+$, t$_R$=1.84 min.

(E)-N-((6-Aminopyridin-3-yl)methyl)-3-(7-chloro-5-(4-(3,3-dimethylmorpholine-4-carbonyl)phenyl)-2,3-dihydrobenzofuran-2-yl)acrylamide 367 was synthesized using General Procedure 2. Yield (32 mg, 30%). $^1$H NMR (400 MHz, DMSO-d$_6$) δ 9.95 (s, 1H), 8.65 (t, J=6 Hz, 1H), 8.00 (s, 1H), 7.92-7.68 (m, 6H), 7.48 (d, J=8 Hz, 2H), 7.30-7.23 (m, 2H), 6.98 (d, J=9 Hz, 1H), 6.26-6.13 (m, 1H), 4.25 (d, J=6 Hz, 2H), 3.71-3.50 (m, 6H), 3.33-3.27 (m, 2H), 1.42 (s, 6H). LCMS: m/z 547.1 [M+H]$^+$, t$_R$=1.37 min.

Synthesis of (E)-N-((6-aminopyridin-3-yl)methyl)-3-(7-chloro-5-(5-(3,3-dimethylmorpholine-4-carbonyl)pyridin-2-yl)-2,3-dihydrobenzofuran-2-yl)acrylamide (368)

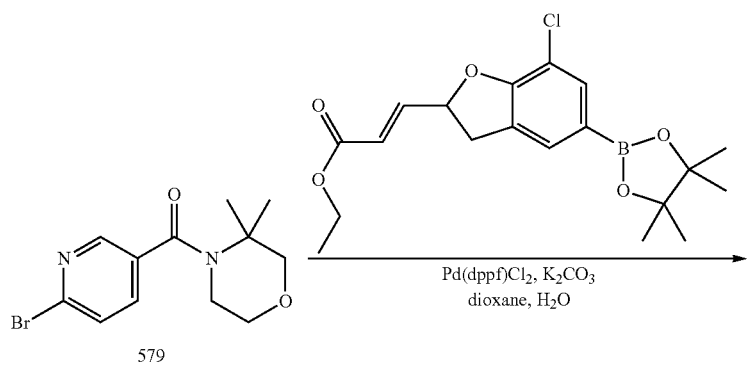

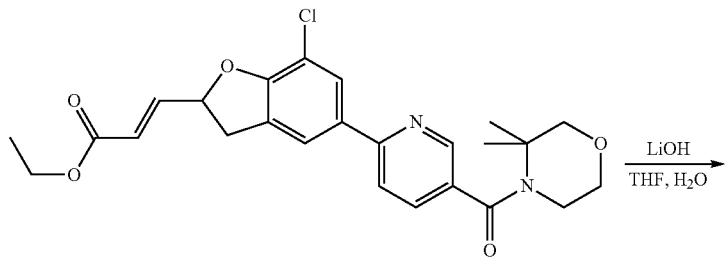

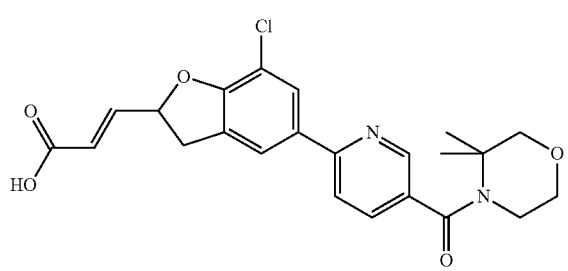

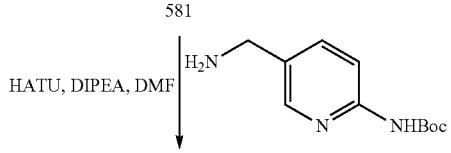

-continued

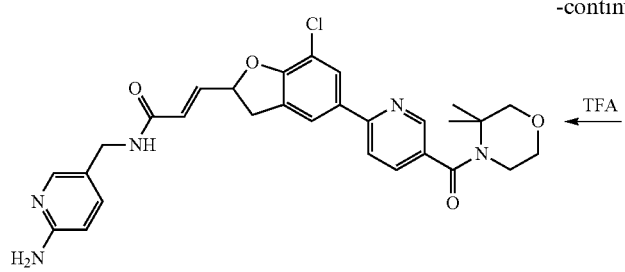

368

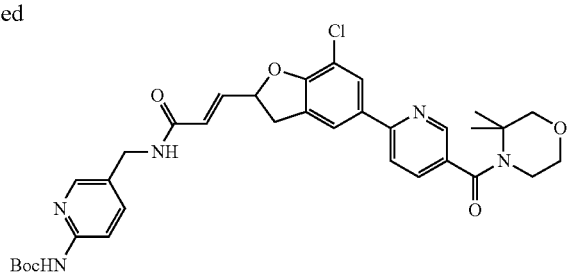

582

(E)-Ethyl 3-(7-chloro-5-(5-(3,3-dimethylmorpholine-4-carbonyl)pyridin-2-yl)-2,3-dihydrobenzofuran-2-yl)acrylate 580 was synthesized using General Procedure 1. Yield (110 mg, 43%). LCMS: m/z 471.0 [M+H]$^+$, $t_R$=1.78 min.

(E)-3-(7-Chloro-5-(5-(3,3-dimethylmorpholine-4-carbonyl)pyridin-2-yl)-2,3-dihydrobenzofuran-2-yl)acrylic acid 581 was synthesized similar to (E)-3-(7-chloro-5-(3-(morpholinosulfonyl)phenyl)-2,3-dihydrobenzofuran-2-yl) acrylic acid 528 (conversion of 527 to 528). Yield (75 mg, 82%). LCMS: m/z 443.0 [M+H]$^+$, $t_R$=1.33 min.

(E)-tert-Butyl 5-((3-(7-chloro-5-(5-(3,3-dimethylmorpholine-4-carbonyl)pyridin-2-yl)-2,3-dihydrobenzofuran-2-yl) acrylamido)methyl)pyridin-2-ylcarbamate 582 was synthesized using General Procedure 3. Yield (100 mg, 90%). LCMS: m/z 648.2 [M+H]$^+$, $t_R$=1.65 min.

(E)-N-((6-Aminopyridin-3-yl)methyl)-3-(7-chloro-5-(5-(3,3-dimethylmorpholine-4-carbonyl)pyridin-2-yl)-2,3-dihydrobenzofuran-2-yl)acrylamide 368 was synthesized using General Procedure 7. Yield (42 mg, 43%). $^1$H NMR (400 MHz, DMSO-d$_6$) δ 8.67 (s, 2H), 8.35-7.79 (m, 8H), 7.38-7.20 (m, 2H), 6.99 (d, J=9 Hz, 1H), 6.22 (d, J=14 Hz, 1H), 4.42-4.17 (m, 4H), 3.71 (s, 2H), 3.48-3.28 (m, 4H), 1.43 (s, 6H). LCMS: m/z 548.2 [M+H]$^+$, $t_R$=1.31 min.

Synthesis of N-((5-(5-acetylthiophen-2-yl)-7-chloro-2,3-dihydrobenzo furan-2-yl)methyl)-3-(pyridin-3-yl) propanamide (369)

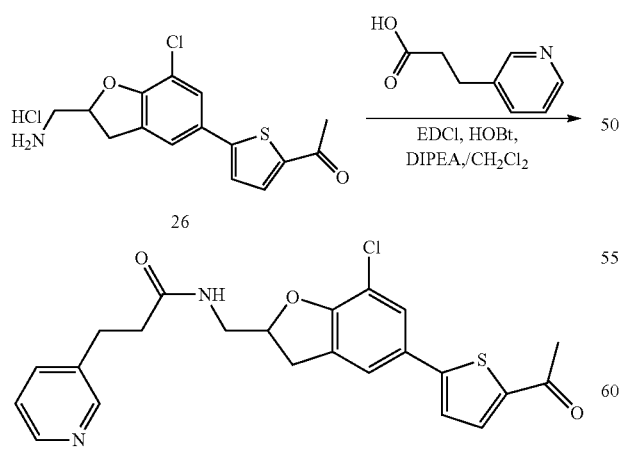

N-((5-(5-Acetylthiophen-2-yl)-7-chloro-2,3-dihydrobenzofuran-2-yl)methyl)-3-(pyridin-3-yl)propanamide 369 was synthesized using General Procedure 3. Yield (31%). $^1$H NMR (400 MHz, DMSO-d$_6$) δ 8.42 (s, 1H), 8.36-8.38 (m, 1H), 8.21-8.24 (t, 1H), 7.92-7.93 (d, J=4Hz, 1H), 7.64 (s, 1H), 7.56-7.62 (m, 3H), 7.25-7.28 (m, 2H), 4.95-4.99 (m, 1H), 3.43-3.49 (m, 1H), 3.37-3.40 (m, 1H), 3.28-3.32 (m, 1H), 2.94-3.00 (m, 1H), 2.53 (s, 3H), 2.43-2.47 (m, 2H). LCMS: m/z 441.21 [M+H]$^+$, $t_R$=1.84 min.

Synthesis of N-((5-(5-acetylthiophen-2-yl)-7-chloro-2,3-dihydrobenzofuran-2-yl)methyl)-3-(6-amino-5-bromopyridin-3-yl)propanamide (371)

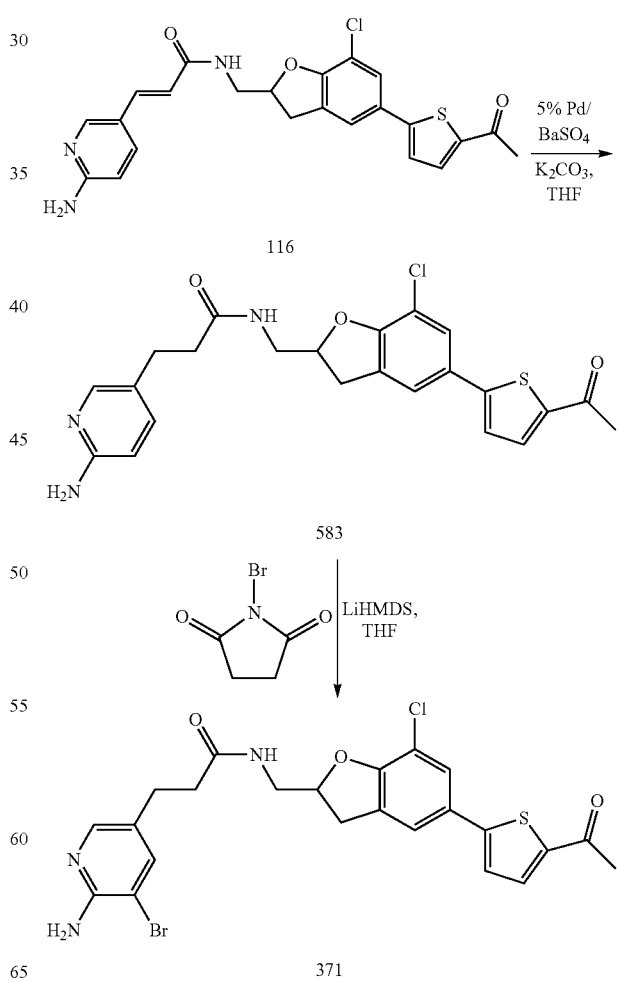

N-((5-(5-Acetylthiophen-2-yl)-7-chloro-2,3-dihydrobenzofuran-2-yl)methyl)-3-(6-aminopyridin-3-yl)propanamide (583): (E)-N-((5-(5-acetylthiophen-2-yl)-7-chloro-2,3-dihydrobenzofuran-2-yl)methyl)-3-(6-amino pyridin-3-yl) acrylamide 116 (0.2 g, 0.4 mmol) was dissolved in THF (5 mL) at room temperature. Lindlar's catalyst (5% Pd/BaSO$_4$) (0.11 g, 1.1 mmol), K$_2$CO$_3$ (0.09 g, 0.6 mmol) were added and hydrogen gas was purged for 12 h. The reaction mixture was filter through celite and the filtrate was concentrated under reduced pressure to give crude product which was purified by silica gel column chromatography (0-7% MeOH/CH$_2$Cl$_2$) to obtain N-((5-(5-acetylthiophen-2-yl)-7-chloro-2,3-dihydrobenzofuran-2-yl)methyl)-3-(6-aminopyridin-3-yl)propanamide 583. (Yield: 0.06 g, 35%). LCMS: m/z 456.17 [M+H]$^+$, t$_R$=1.9 min.

N-((5-(5-Acetylthiophen-2-yl)-7-chloro-2,3-dihydrobenzofuran-2-yl)methyl)-3-(6-amino-5-bromopyridin-3-yl)propanamide (371): N-((5-(5-acetylthiophen-2-yl)-7-chloro-2,3-dihydrobenzofuran-2-yl)methyl)-3-(6-aminopyridin-3-yl) propanamide 583 (0.05 g, 0.1 mmol) was dissolved in THF (3 mL) at room temperature. The reaction mixture was cooled to −70° C. and N-bromosuccinimide (0.023 g, 0.13 mmol) followed by LiHMDS (1 M in THF) (0.022 g, 0.13 mmol) were added. The reaction mixture was allowed to warm to room temperature and stirred for 4 h. The reaction mixture was transferred into iced water and extracted with ethyl acetate (3×50 mL). The combined organic layers were washed with brine, dried over anhydrous Na$_2$SO$_4$ and concentrated under reduced pressure to give the crude product which was purified by silica gel chromatography (0-3% MeOH/CH$_2$Cl$_2$) to obtain N-((5-(5-acetylthiophen-2-yl)-7-chloro-2,3-dihydrobenzofuran-2-yl)methyl)-3-(6-amino-5-bromopyridin-3-yl)propanamide 371. (Yield: 0.01 g, 35%). $^1$H NMR (400 MHz, DMSO-d$_6$) δ 8.18 (t, J=6 Hz, 1H), 7.92 (d, J=4 Hz, 1H), 7.77 (s, 1H), 7.64 (s, 1H), 7.58 (t, J=3 Hz, 3H), 6.01 (s, 2H), 5.01-4.96 (m, 1H), 3.49-3.38 (m, 1H), 3.37 (s, 1H), 3.35-3.28 (m, 1H), 3.01-2.95 (m, 1H), 2.63 (t, J=7.4 Hz, 2H), 2.51 (s, 3H), 2.35 (t, J=7.4 Hz, 2H). LCMS: m/z 536.2 [M+2], t$_R$=2.1 min.

Synthesis of (E)-N-((5-(5-acetylthiophen-2-yl)-7-chloro-2,3-dihydroBenzofuran-2-1)methyl)-3-(6-hydrazinylpyridin-3-yl)acrylamide (900)

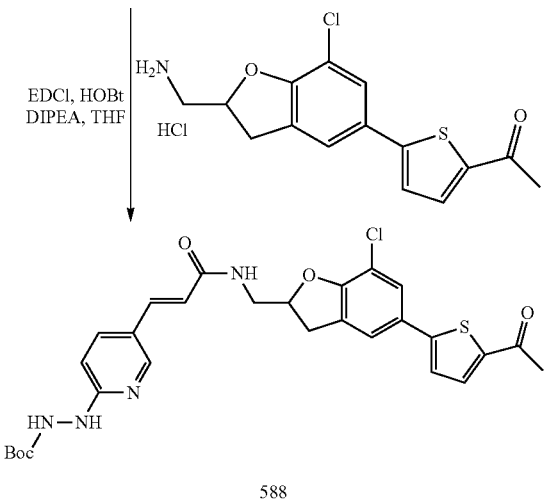
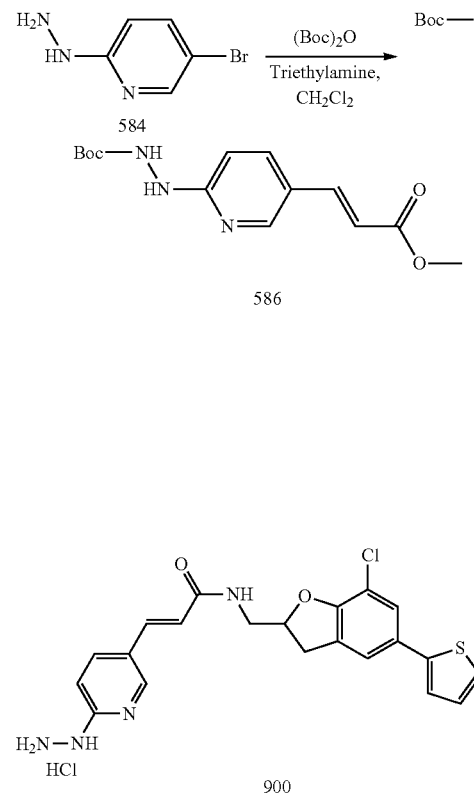

Synthesis of tert-butyl 2-(5-bromopyridin-2-yl) hydrazinecarboxylate (585): 5-Bromo-2-hydrazinopyridine 584 (1.0 g, 5.31mmol) was dissolved in dichloromethane (20 mL). Triethylamine (2.2 mL, 15.95 mmol), was added at room temperature and cooled to 0° C. Boc-anhydride (2.5 mL, 10.63 mmol) was added to reaction mixture at 0° C., stirred for 15 minutes. The reaction mixture was slowly warmed to room temperature and stirred for 3-4 h. The reaction mixture was transferred into water and extracted with dichloromethane (3×50 mL). The combined organic layers were washed with brine, dried over anhydrous Na$_2$SO$_4$, and concentrated under reduced pressure to give tert-butyl 2-(5-bromopyridin-2-yl) hydrazinecarboxylate 585. Yield (1.1 g, 72%). $^1$H NMR (400 MHz, DMSO-d$_6$) δ 8.88 (s, 1H), 8.44 (s, 1H), 8.11 (d, J=2 Hz, 1H), 7.71-7.68 (m, 1H), 6.50 (d, J=8.8 Hz, 1H), 1.41 (s, 9H).

Synthesis of (E)-tert-butyl 2-(5-(3-methoxy-3-oxoprop-1-enyl)pyridin-2-yl)hydrazine carboxylate (586): tert-Butyl 2-(5-bromopyridin-2-yl) hydrazinecarboxylate 585 (1.0 g, 3.47 mmol) was dissolved in dry DMF (5 mL) and degassed using N₂ for 5 min. Tris(2-methylphenyl)phosphine (0.5 g, 1.73 mmol), Pd(OAc)₂ (0.076 g, 0.347 mmol) and DIPEA (1.8 mL, 10.41mmol) were added to reaction mixture and degassed using N₂ for 5 min. Methyl acrylate (0.5 mL, 5.20 mmol) was added to the degassed reaction mixture and heated at 120° C. for 12 h. The reaction mixture was transferred into water and extracted with ethyl acetate (3×50 mL). The combined organic layers were washed with brine, dried over anhydrous Na₂SO₄, and concentrated under reduced pressure to give the crude product, which was purified by chromatography (0-50% ethyl acetate/n-hexane) to give (E)-tert-butyl 2-(5-(3-methoxy-3-oxoprop-1-enyl)pyridin-2-yl)Hydrazinecarboxylate 586. Yield: 0.25 g, 23%. ¹H NMR (400 MHz, CDCl₃) δ 8.25 (d, J=1.4 Hz, 1H), 7.82-7.79 (m, 1H), 7.63-7.59 (d, J=16 Hz, 1H), 6.85-6.83 (d, J=8.8 Hz, 1H), 6.63 (bs, 1H), 6.34 (d, J=16 Hz, 1H), 3.79 (s, 3H), 1.49 (s, 9H). LCMS: m/z 294.20 [M+H]⁺, t_R=1.92 min.

Synthesis of lithium (E)-3-(6-(2-(tert-butoxycarbonyl)hydrazinyl)pyridin-3-yl)acrylate (587): (E)-tert-Butyl 2-(5-(3-methoxy-3-oxoprop-1-enyl)pyridin-2-yl)hydrazinecarboxylate (586) (0.1 g, 0.34 mmol) was dissolved in THF: H₂O (1:1, 4 mL) at room temperature. LiOH.H₂O (0.03 g, 0.68 mmol) was added and stirred for 2 h. The reaction mixture was concentrated under reduced pressure to give crude of lithium (E)-3-(6-(2-(tert-butoxycarbonyl)hydrazinyl)pyridin-3-yl)acrylate 587, which was used for next step without further purification.

Synthesis of (E)-tert-butyl 2-(5-(3-((5-(5-acetylthiophen-2-yl)-7-chloro-2,3-dihydrobenzofuran-2-yl)methylamino)-3-oxoprop-1-enyl)pyridin-2-yl)hydrazinecarboxylate (900): Lithium (E)-3-(6-(2-(tert-butoxycarbonyl)hydrazinyl)pyridin-3-yl)acrylate 587 (0.09 g, 0.32 mmol) was dissolved in DMF (5 mL) at room temperature. 1-(5-(2-(aminomethyl)-7-chloro-2,3-dihydrobenzofuran-5-yl)thiophen-2-yl)ethanone hydrochloride 26 (0.1 g, 0.32 mmol), HOBt (0.09 g, 0.64 mmol), EDCI (0.12 g, 0.64 mmol) was added to the above reaction mixture at room temperature followed by drop wise addition of DIPEA (0.3 mL, 1.28 mmol) and stirred the reaction mixture at room temperature for 16 h. The reaction mixture was transferred into iced water and extracted with ethyl acetate (3×50 mL). The combined organic layers were washed with brine and dried over anhydrous Na₂SO₄, concentrated under reduced pressure to give the crude which was purified by Preparative HPLC to obtain (E)-tert-butyl 2-(5-(3-((5-(5-acetylthiophen-2-yl)-7-chloro-2,3-dihydrobenzofuran-2-yl)methylamino)-3-oxoprop-1-enyl)pyridin-2-yl)hydrazine carboxylate 588. (Yield: 0.008 g, 5%). ¹H NMR (400 MHz, DMSO-d₆) δ 8.92 (s, 1H), 8.61 (s, 1H), 8.36-8.33 (m, 1H), 8.22 (s, 1H), 7.91 (d, J=4 Hz, 1H), 7.75 (d, J=8.8 Hz, 1H), 7.65 (d, J=8.8 Hz, 1H), 7.61-7.58 (m, 2H), 7.37 (d, J=15.6 Hz, 1H), 6.56-6.50 (m, 2H), 5.10-5.04 (m, 1H), 3.59-3.53 (m, 3H), 3.13-3.09 (m, 1H), 2.42 (s, 3H), 1.42 (s, 9H).

Synthesis of (E)-N-((5-(5-acetylthiophen-2-yl)-7-chloro-2,3-dihydrobenzofuran-2-yl)methyl)-3-(6-hydrazinylpyridin-3-yl)acrylamide (900): (E)-tert-Butyl 2-(5-(3-((5-(5-acetylthiophen-2-yl)-7-chloro-2,3-dihydrobenzofuran-2-yl)methylamino)-3-oxoprop-1-enyl)pyridin-2-yl)hydrazinecarboxylate 588 (0.01 g, 0.01 mmol) was dissolved in THF (2 mL) at room temperature. The reaction mixture was cooled to 0° C. and added drop wise 3N HCl in dioxane (0.1 mL). The reaction mixture was slowly allowed to come at room temperature and stirred for 4 h. The reaction mixture was concentrated under reduced pressure and crude product was crystallized with diethyl ether to obtain (E)-N-((5-(5-acetylthiophen-2-yl)-7-chloro-2,3-dihydrobenzofuran-2-yl)methyl)-3-(6-hydrazinylpyridin-3-yl)acrylamide 900. (Yield: 0.002 g, 25%). ¹H NMR (400 MHz, DMSO-d₆) δ 8.53 (s, 1H), 8.33 (s, 2H), 8.10 (s, 2H), 7.56-7.46 (m, 5H), 6.66 (d, J=10 Hz, 1H), 5.09 (s, 1H), 3.57-3.48 (m, 3H), 3.43-3.40 (m, 1H), 3.17-3.09 (m, 1H), 2.50 (s, 3H).

Synthesis of (E)-3-(6-aminopyridin-3-yl)-N-((7-chloro-5-(2,3-difluoro-4-(morpholine-4-carbonyl)phenyl)-2,3-dihydrobenzofuran-2-yl)methyl)acrylamide (901)

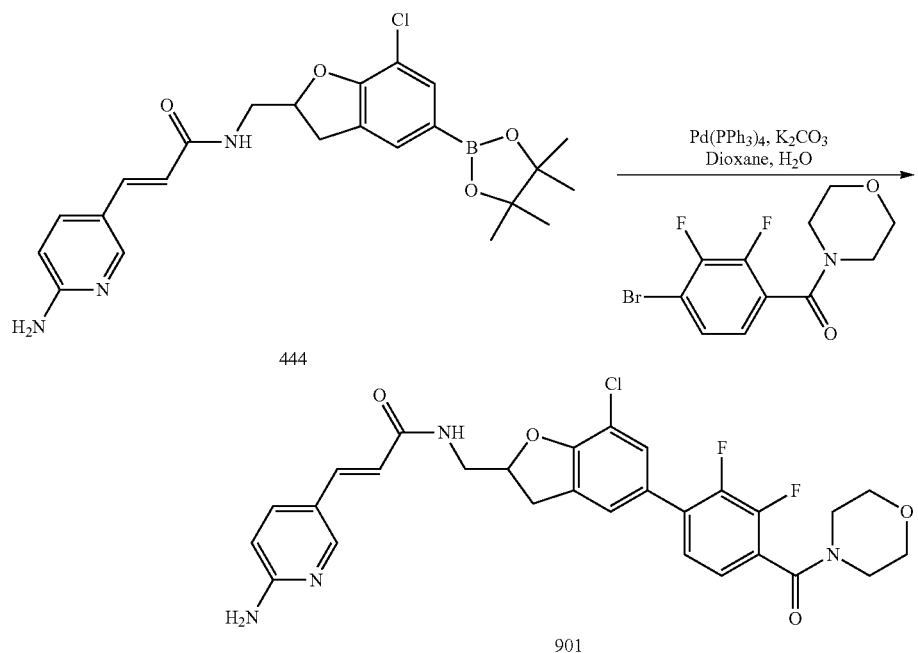

(E)-3-(6-Aminopyridin-3-yl)-N-((7-chloro-5-(2,3-difluoro-4-(morpholine-4-carbonyl)phenyl)-2,3-dihydrobenzofuran-2-yl)methyl)acrylamide 901 was synthesized using General Procedure 1. (Yield: 0.012 g, 9%). $^1$H NMR (400 MHz, DMSO-$d_6$) δ 8.28 (t, J=5.8 Hz, 1H), 8.07 (d, J=2 Hz 1H), 7.59 (dd, $J_1$=2 Hz, $J_2$=2 Hz, 1H), 7.43-7.39 (m, 3H), 7.33-7.26 (m, 2H), 6.47-6.40 (m, 4H), 5.09-5.07 (m, 1H), 3.66 (s, 4H), 3.63-3.55 (m, 4H), 3.43-3.37 (m, 2H), 3.34-3.31 (m, 1H), 3.18-3.09 (m, 1H). LCMS: m/z 555.89 [M+H]$^+$, $t_R$=1.84 min.

Synthesis of (E)-3-(6-aminopyridin-3-yl)-N-((7-chloro-5-(2,6-difluoro-4-(morpholine-4-carbonyl)phenyl)-2,3-dihydrobenzofuran-2-yl)methyl)acrylamide (902)

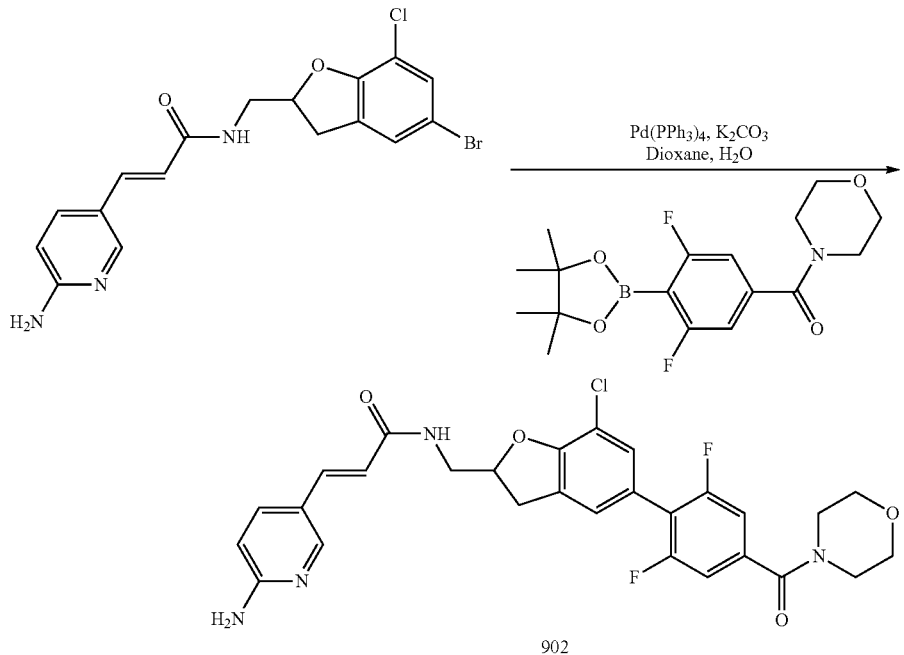

(E)-3-(6-Aminopyridin-3-yl)-N-((7-chloro-5-(2,6-difluoro-4-(morpholine-4-carbonyl)phenyl)-2,3-dihydrobenzofuran-2-yl)methyl)acrylamide 902 was synthesized using General Procedure 1. (Yield: 0.01 g, 9%). $^1$H NMR (400 MHz, DMSO-$d_6$) δ 8.29 (t, J=5.8 Hz, 1H), 8.07 (d, J=2.4 Hz, 1H), 7.59 (dd, $J_1$, $J_2$=2 Hz, 1H), 7.44-7.39 (m, 3H), 7.33-7.26 (m, 2H), 6.47-6.40 (m, 4H), 5.10-5.07 (m, 1H), 3.66 (s, 4H), 3.62-3.51 (m, 4H), 3.45-3.39 (m, 1H), 3.32-3.31 (m, 2H), 3.15-3.09 (m, 1H). LCMS: m/z 555.79 [M+H]$^+$, $t_R$=1.84 min.

Synthesis of (E)-3-(6-aminopyridin-3-yl)-N-((7-chloro-5-(3-fluoro-4-(morpholine-4-carbonyl)phenyl)-2,3-dihydrobenzofuran-2-yl)methyl)acrylamide (903)

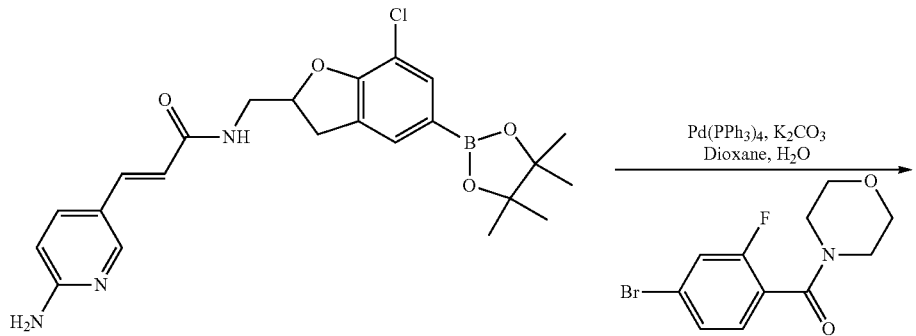

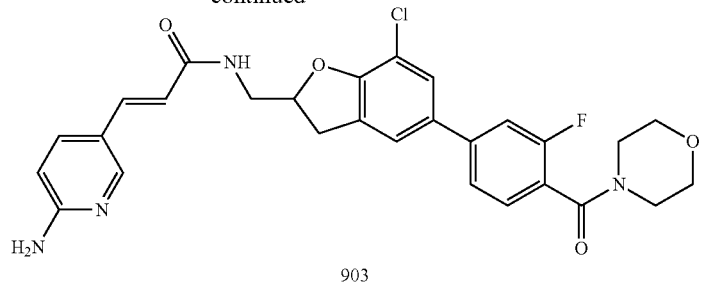
903

(E)-3-(6-Aminopyridin-3-yl)-N-((7-chloro-5-(3-fluoro-4-(morpholine-4-carbonyl)phenyl)-2,3-dihydrobenzofuran-2-yl)methyl)acrylamide 903 was synthesized using General Procedure 1. (Yield: 0.013 g, 11%). $^1$H NMR (400 MHz, DMSO-$d_6$) δ 8.27 (t, J=3.2 Hz, 1H), 8.07 (s, 1H), 7.62-7.56 (m, 5H), 7.45-7.44 (m, 1H), 7.31 (d, J=16 Hz, 1H), 6.47-6.40 (m, 4H), 5.09-5.06 (m, 1H), 3.66 (s, 4H), 3.54 (s, 4H), 3.44-3.37 (m, 2H), 3.29-3.27 (m, 1H), 3.14-3.12 (m, 1H). LCMS: m/z 537.89 [M+H]$^+$, $t_R$=1.82 min.

Synthesis of (E)-3-(6-aminopyridin-3-yl)-N-((7-chloro-5-(4-(2-(pyrazin-2-yl) hydrazine-1-carbonyl) phenyl)-2,3-dihydrobenzofuran-2-yl)methyl)acrylamide (904)

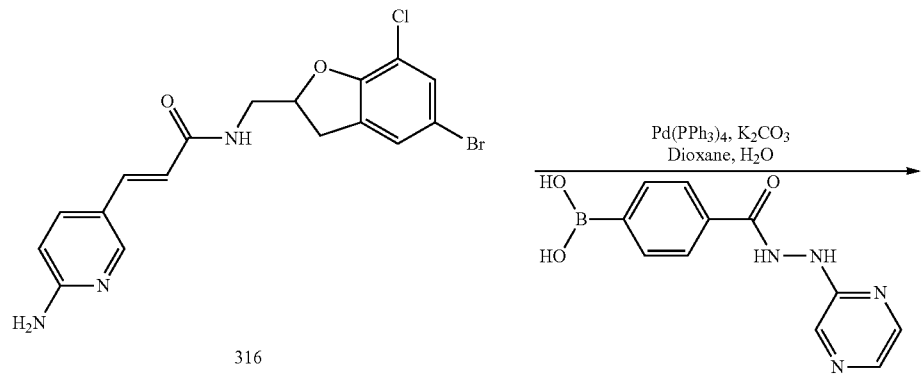

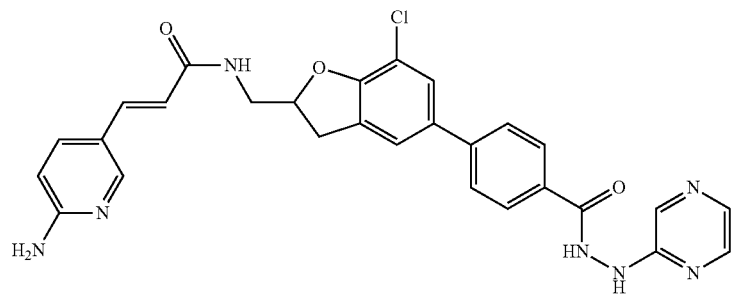
904

(E)-3-(6-Aminopyridin-3-yl)-N-((7-chloro-5-(4-(2-(pyrazin-2-yl) hydrazine-1-carbonyl) phenyl)-2,3-dihydrobenzofuran-2-yl)methyl)acrylamide 904 was synthesized using General Procedure 1. Yield (0.015 g, 3%). $^1$H NMR (400 MHz, DMSO-d$_6$) δ 9.06 (bs, 1H), 8.31-8.26 (m, 3H), 8.08-8.07 (m, 3H), 7.98 (d, J=8.4 Hz, 1H), 7.88 (d, J=2.4 Hz, 1H), 7.78 (d, J=8.4 Hz, 2H), 7.61-7.58 (m, 3H), 7.32 (d, J=15.6 Hz, 1H), 6.48-6.41 (m, 4H), 5.10-5.08 (m, 1H), 3.43-3.40 (m, 2H), 3.15-3.12 (m, 2H). LCMS: m/z 542.2 [M]$^+$, $t_R$=1.71 min.

(E)-3-(6-aminopyridin-3-yl)-N-((7-chloro-5-(4-(2-morpholinoacetyl)phenyl)-2,3-dihydro benzofuran-2-yl)methyl)acrylamide (906)

(E)-3-(6-Aminopyridin-3-yl)-N-((7-chloro-5-(4-(2-morpholinoacetyl)phenyl)-2,3-dihydrobenzofuran-2-yl)methyl) acrylamide 906 was synthesized using General Procedure 1. (Yield: 0.014 g, 6%). $^1$H NMR (400 MHz, DMSO-d$_6$) δ 8.28 (t, J=11.6 Hz, 1H), 8.07 (s, 1H), 8.02 (d, J=8.4 Hz, 1H), 7.73-7.86 (m, 4H), 7.58-7.62 (m, 2H), 7.31 (d, J=15.6 Hz, 1H), 6.40-6.48 (m, 3H), 5.08-5.10 (m, 1H), 3.86 (s, 2H), 3.51-3.62 (m, 8H), 3.39-3.46 (m, 3H), 3.09-3.37 (m, 1H). LCMS: m/z 534 [M+H]$^+$, $t_R$=1.63 min.

Synthesis of (E)-N-((6-aminopyridin-3-yl)methyl)-3-(7-chloro-5-(4-(morpholine-4-carbonyl) phenyl)-2,3-dihydrobenzofuran-2-yl)acrylamide hydrochloride (907)

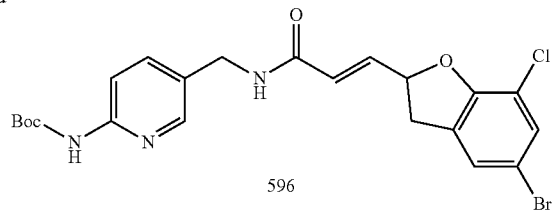

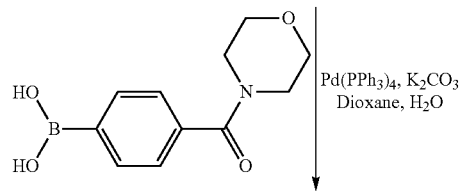

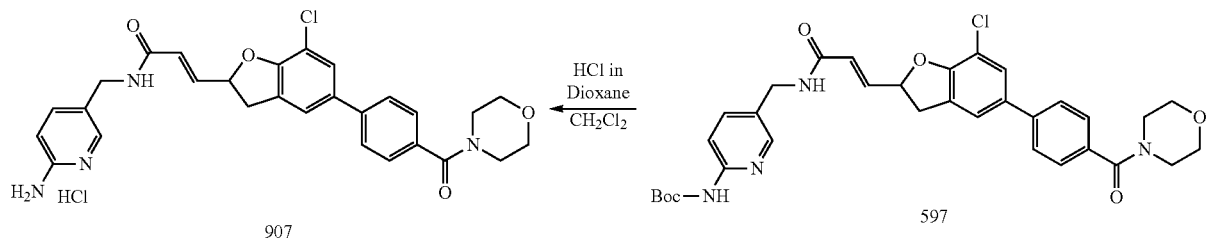

tert-Butyl (E)-(5-((3-(5-bromo-7-chloro-2,3-dihydrobenzofuran-2-yl) acrylamido)methyl)pyridin-2-yl)carbamate 596 was synthesized by General Procedure 3. (Yield: 0.11 g, 44%). $^1$H NMR (400 MHz, DMSO-$d_6$) δ 9.74 (s, 1H), 8.68 (t, J=12 Hz, 1H), 7.76-7.73 (m, 1H), 7.61 (dd, $J_1$=2.4 Hz, $J_2$=2 Hz, 1H), 7.46 (s, 1H), 7.39 (s, 1H), 6.76 (d, $J_1$, $J_2$=5.2 Hz, 1H), 6.18 (d, $J_1$=14.4 Hz, 1H), 5.58-5.62 (m, 1H), 4.27 (d, J=6 Hz, 2H), 3.61-3.36 (m, 2H), 1.46 (s, 9H). LCMS: m/z 510.18 [M+2], $t_R$=2.60 min.

tert-Butyl (E)-(5-((3-(7-chloro-5-(4-(morpholine-4-carbonyl)phenyl)-2,3-dihydrobenzofuran-2-yl)acrylamido)methyl)pyridin-2-yl)carbamate 597 was synthesized by General Procedure 1. (Yield: 0.06 g, 45%). $^1$H NMR (400 MHz, DMSO-$d_6$) δ 9.75 (s, 1H), 8.62 (t, J=5.6 Hz, 1H), 8.17 (s, 1H), 7.90 (s, 1H), 7.80-7.74 (m, 2H), 7.69 (d, J=2.4 Hz, 1H), 7.64 (dd, $J_1$, $J_2$=2.4 Hz, 1H), 7.49 (s, 1H), 7.47 (s, 1H), 7.29-7.24 (m, 2H), 6.21-6.19 (m, 1H), 4.32 (d, J=5.6 Hz, 2H), 3.62-3.46 (m, 10H), 3.14-3.08 (m, 1H), 1.46 (s, 9H). LCMS: m/z 619.50 [M+H]$^+$, $t_R$=2.17 min.

(E)-N-((6-Aminopyridin-3-yl)methyl)-3-(7-chloro-5-(4-(morpholine-4-carbonyl) phenyl)-2,3-dihydrobenzofuran-2-yl)acrylamide hydrochloride 907 was synthesized by General Procedure 2. (Yield: 0.03 g, 73%). $^1$H NMR (400 MHz, DMSO-$d_6$) δ 13.50 (s, 1H), 8.70 (t, J=11.2 Hz, 1H), 7.99 (bs, 2H), 7.89-7.85 (m, 3H), 7.81 (d, J=8 Hz, 2H), 7.70 (s, 1H), 7.48 (d, J=8.4 Hz, 2H), 7.38-7.21 (m, 3H), 6.98 (d, J=8.8 Hz, 1H), 6.21-6.18 (m, 1H), 4.25 (d, J=5.2 Hz, 2H), 3.62-3.36 (m, 10H). LCMS: m/z 520.1 [M+H]$^+$, $t_R$=1.76 min.

Synthesis of (E)-3-(6-aminopyridin-3-yl)-N-((7-chloro-4-(3,5-difluoro-4-(morpholine-4-carbonyl)phenyl)-2,3-dihydrobenzofuran-2-yl)methyl)acrylamide (908)

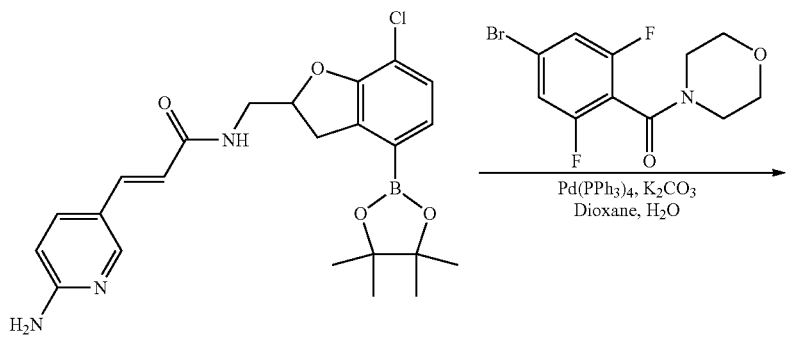

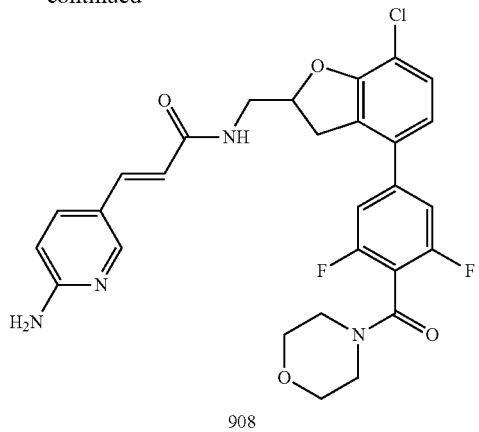

908

(E)-3-(6-Aminopyridin-3-yl)-N-((7-chloro-4-(3,5-difluoro-4-(morpholine-4-carbonyl)phenyl)-2,3-dihydrobenzofuran-2-yl)methyl)acrylamide 908 was synthesized using General Procedure 1. Yield: 0.015 g, 13%. $^1$H NMR (400 MHz, DMSO-$d_6$) δ 8.25 (t, J=6 Hz, 1H), 8.06 (d, J=2 Hz, 1H), 7.59 (dd, J,, J2 =2 Hz, 1H), 7.41 (d, J=9.6 Hz, 2H), 7.35-7.27 (m, 2H), 7.02 (d, J=8.4 Hz, 1H), 6.47-6.37 (m, 4H), 5.04-5.01 (m, 1H), 3.68-3.67 (m, 4H), 3.61-3.44 (m, 5H), 3.32-3.31 (m, 2H), 3.26-3.20 (m, 1H). LCMS: m/z 555.29 [M+H]$^+$, $t_R$=1.88 min.

Synthesis of (E)-3-(6-aminopyridin-3-yl)-N-((7-chloro-5-(4-(2-morpholino-2-oxoacetyl) phenyl)-2,3-dihydrobenzofuran-2-yl)methyl)acrylamide (909)

(E)-3-(6-Aminopyridin-3-yl)-N-((7-chloro-5-(4-(2-morpholino-2-oxoacetyl) phenyl)-2,3-dihydrobenzofuran-2-yl) methyl)acrylamide 909 was synthesized using General Procedure 1. (Yield: 0.014 g, 6%). $^1$H NMR (400 MHz, DMSO-$d_6$) δ 8.28 (t, J=5.8 Hz, 1H), 8.17 (s, 1H), 8.07 (s, 1H), 7.95-7.87 (m, 4H), 7.66-7.58 (m, 3H), 7.31 (d, J=15.6 Hz, 1H), 6.47-6.41 (m, 4H), 5.12-5.06 (m, 1H), 3.72-3.59 (m, 4H), 3.55-3.47 (m, 4H), 3.44-3.37 (m, 2H), 3.16-3.10 (m, 1H). LCMS: m/z 547.13 [M+H]$^+$, $t_R$=1.85 min.

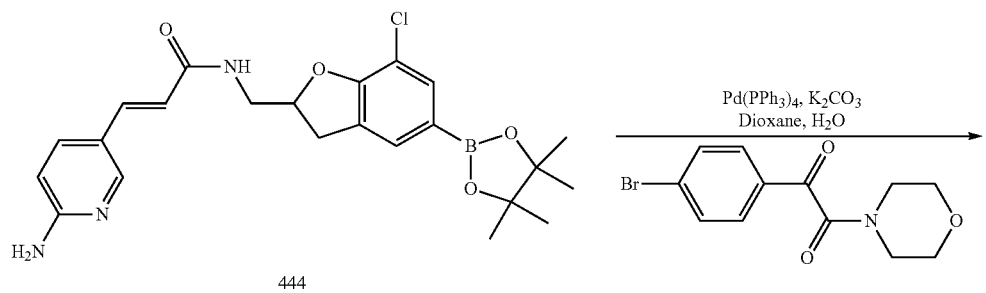

444

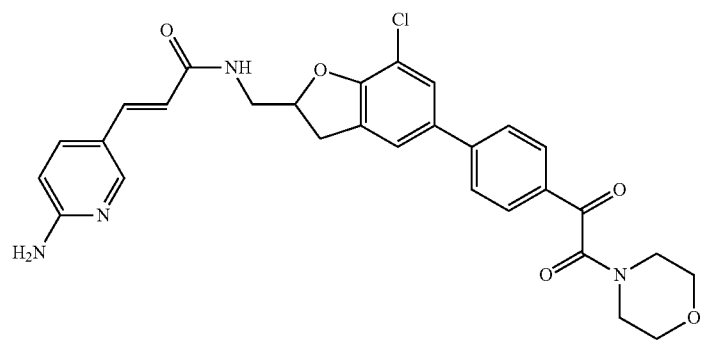

909

(E)-3-(6-aminopyridin-3-yl)-N-((7-chloro-4-(6-(morpholine-4-carbonyl)pyridin-3-yl)-2,3-dihydrobenzofuran-2-yl)methyl)acrylamide (910)

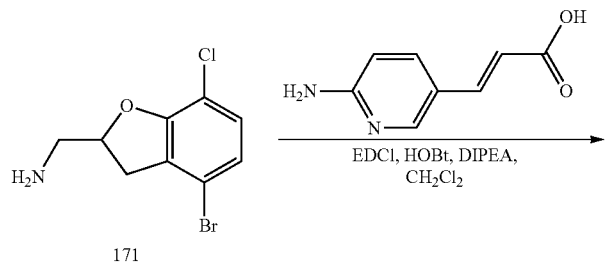

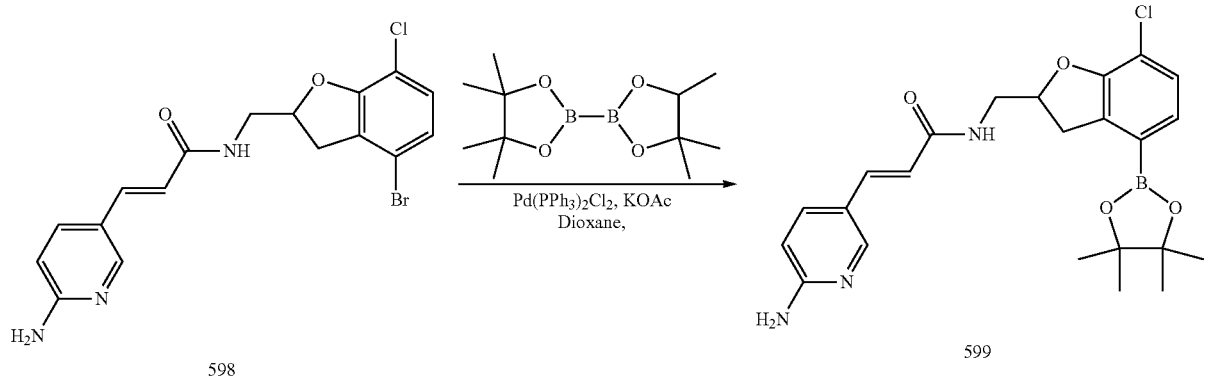

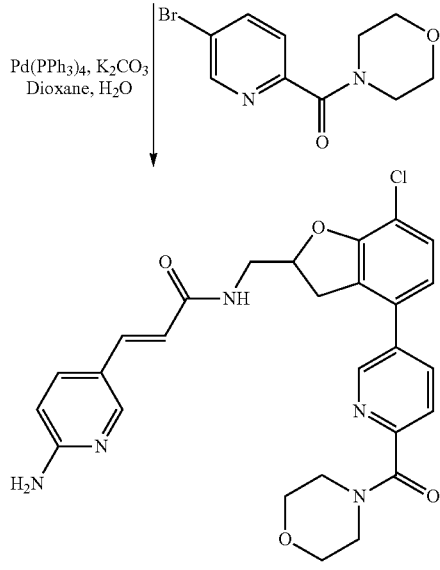

(E)-3-(6-Aminopyridin-3-yl)-N-((4-bromo-7-chloro-2,3-dihydrobenzofuran-2-yl)methyl)acrylamide 598 was synthesized by General Procedure 3. (Yield: 0.15 g, 25%). $^1$H NMR (400 MHz, DMSO-d$_6$) δ 8.26 (t, J=6 Hz, 1H), 8.07 (d, J=2 Hz, 1H), 7.59 (dd, J$_1$, J$_2$=2.4 Hz, 1H), 7.31 (d, J=16 Hz, 1H), 7.17 (d, J=8.8 Hz, 1H), 7.04 (d, J=8.4 Hz, 1H), 6.47-6.38 (m, 4H), 5.09-5.05 (m, 1H), 3.61-3.56 (m, 1H), 3.53-3.48 (m, 2H), 3.07-3.01 (m, 1H). LCMS: m/z 410.18 [M+2], t$_R$=1.90 min.

(E)-3-(6-Aminopyridin-3-yl)-N-((7-chloro-4-(4,4,5,5-tetramethyl-1,3,2-dioxaborolan-2-yl)-2,3-dihydrobenzofuran-2-yl)methyl)acrylamide 599 was synthesized by General Procedure 1. (Yield: 0.1 g, 30%). $^1$H NMR (400 MHz, DMSO-d$_6$) δ 8.24 (t, J=5.8 Hz, 1H), 8.06 (d, J=2 Hz, 1H), 7.58 (dd, J$_1$, J$_2$=2.4 Hz, 1H), 7.42 (d, J=1.2 Hz, 1H), 7.38 (s, 1H), 7.30 (dd, J$_1$=2.8 Hz, J$_2$=3.2 Hz, 1H), 6.47-6.38 (m, 4H), 5.05-5.03 (m, 1H), 3.57-3.49 (m, 2H), 3.35-3.31 (m, 1H), 3.06-3.00 (m, 1H), 1.26 (s, 12H).

(E)-3-(6-Aminopyridin-3-yl)-N-((7-chloro-4-(6-(morpholine-4-carbonyl)pyridin-3-yl)-2,3-dihydrobenzofuran-2-yl)methyl)acrylamide 910 was synthesized by General Procedure 1. (Yield: 0.015 g, 19%). $^1$H NMR (400 MHz, DMSO-d$_6$) δ 8.74 (s, 1H), 8.25 (t, J=5.6 Hz, 1H), 8.10-8.05 (m, 2H), 7.71 (d, J=8.8 Hz, 1H), 7.58 (dd, J$_1$, J$_2$=2.4 Hz, 1H), 7.36 (d, J=8.4 Hz, 1H), 7.29 (d, J=15.6 Hz, 1H), 7.04 (d, J=8.4 Hz, 1H), 6.47-6.37 (m, 4H), 5.04-5.00 (m, 1H), 3.68

(s, 4H), 3.60-3.44 (m, 7H), 3.25-3.19 (m, 1H). LCMS: m/z 520.28 [M+H]$^+$, $t_R$=1.74 min.

Synthesis of (E)-3-(6-aminopyridin-3-yl)-N-((7-chloro-4-(2-fluoro-4-(morpholine-4-carbonyl)phenyl)-2,3-dihydrobenzofuran-2-yl)methyl)acrylamide (911)

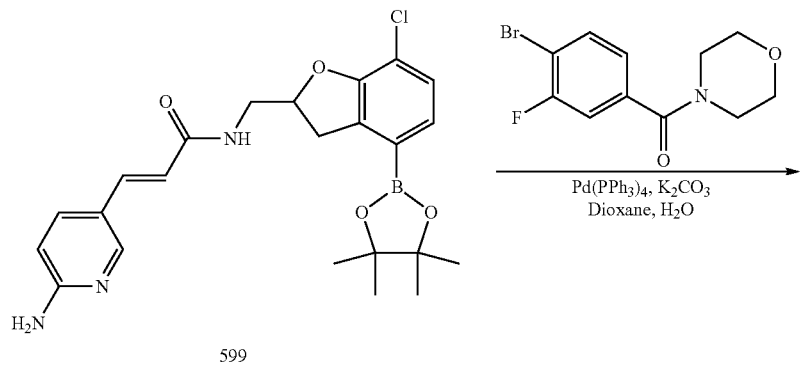

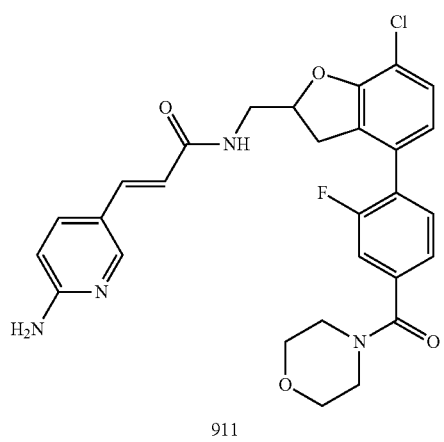

(E)-3-(6-Aminopyridin-3-yl)-N-((7-chloro-4-(2-fluoro-4-(morpholine-4-carbonyl)phenyl)-2,3-dihydrobenzofuran-2-yl)methyl)acrylamide 911 was synthesized using General Procedure 1. (Yield: 0.015 g, 13%). $^1$H NMR (400 MHz, DMSO-d$_6$) δ 8.25 (t, J=5.8 Hz, 1H), 8.06 (d, J=2.4 Hz, 1H), 7.60 (dd, J$_1$, J$_2$=2.4 Hz, 1H), 7.52 (t, J=7.8 Hz, 1H), 7.41 (dd, J$_1$, J$_2$=1.6 Hz, 1H), 7.34-7.27 (m, 3H), 6.89 (d, J=8 Hz, 1H), 6.48-6.38 (m, 4H), 5.04-5.00 (m, 1H), 3.63-3.57 (m, 6H), 3.50-3.36 (m, 4H), 3.31-3.25 (m, 1H), 3.03-2.97 (m, 1H). LCMS: m/z 537.28 [M+H]$^+$, $t_R$=1.85 min.

Synthesis of (E)-3-(6-aminopyridin-3-yl)-N-((7-chloro-4-(5-(morpholine-4-carbonyl) pyridin-2-yl)-2,3-dihydrobenzofuran-2-yl)methyl)acrylamide (912)

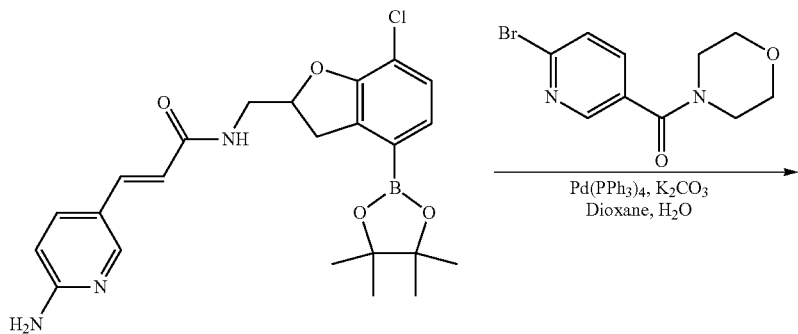

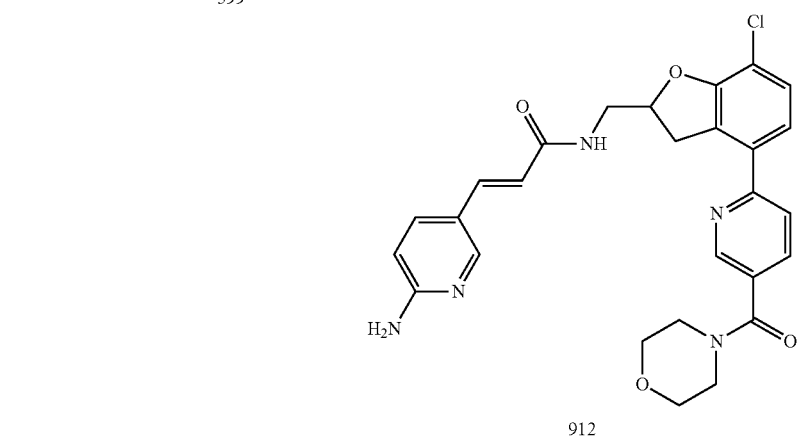

(E)-3-(6-Aminopyridin-3-yl)-N-((7-chloro-4-(5-(morpholine-4-carbonyl) pyridin-2-yl)-2,3-dihydrobenzofuran-2-yl)methyl)acrylamide 912 was synthesized using General Procedure 1. (Yield: 0.012 g, 15%). $^1$H NMR (400 MHz, DMSO-$d_6$) δ 8.72 (d, J=1.6 Hz, 1H), 8.27 (t, J=5.8 Hz, 1H), 8.06 (t, J=3.2 Hz, 1H), 7.95 (dd, J$_1$, J2 =2.4 Hz, 1H), 7.88 (d, J=8 Hz, 1H), 7.58 (dd, J$_1$, J$_2$=2.4 Hz, 1H), 7.41-7.27 (m 3H), 6.47-6.39 (m, 4H), 5.06-5.02 (m, 1H), 3.74-3.50 (m, 8H), 3.48-3.40 (m, 4H). LCMS: m/z 520.33 [M+H]$^+$, t$_R$=1.73 min.

Synthesis of (E)-3-(6-aminopyridin-3-yl)-N-((7-chloro-4-(5-(morpholine-4-carbonyl) pyridin-3-yl)-2,3-dihydrobenzofuran-2-yl)methyl)acrylamide (913)

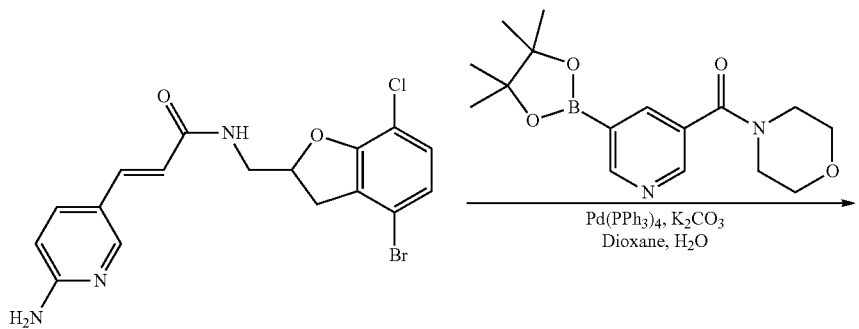

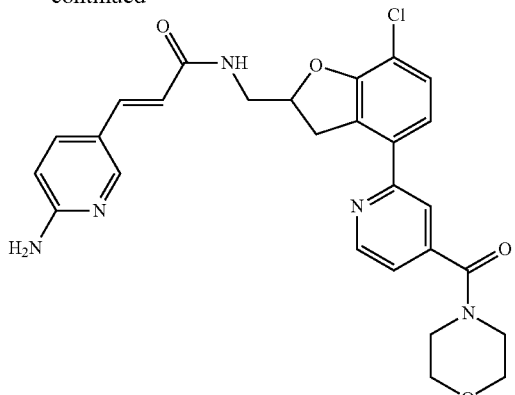

913

(E)-3-(6-Aminopyridin-3-yl)-N-((7-chloro-4-(5-(morpholine-4-carbonyl)pyridine-3-yl)-2,3-dihydrobenzofuran-2-yl)methyl)acrylamide 913 was synthesized using General Procedure 1. (Yield: 0.025 g, 10%). $^1$H NMR (400 MHz, DMSO-d$_6$) δ 8.80 (d, J=2.4 Hz, 1H), 8.64 (d, J=2 Hz, 1H), 8.26 (t, J=5.8 Hz, 1H), 8.05 (s, 1H), 7.97 (m, 1H), 7.58 (dd, J$_1$=2.0 Hz, J$_2$=2.4 Hz, 1H), 7.35 (d, J=8 Hz, 1H), 7.29 (d, J=15.6 Hz, 1H), 7.04 (d, J=8.4 Hz, 1H), 6.47-6.40 (m, 3H), 5.03-5.00 (m, 1H), 3.68 (s, 4H), 3.60-3.44 (m, 7H), 3.25-3.19 (m, 1H). LCMS: m/z 520.33 [M+H]$^+$, t$_R$=1.72 min.

Synthesis of (E)-3-(6-aminopyridin-3-yl)-N-((7-chloro-5-(4-(morpholinosulfonyl)phenyl)-2,3-dihydrobenzofuran-2-yl)methyl)acrylamide (914)

(E)-3-(6-Aminopyridin-3-yl)-N-((7-chloro-5-(4-(morpholinosulfonyl)phenyl)-2,3-dihydrobenzofuran-2-yl)methyl)acrylamide 914 was synthesized using General Procedure 1. (Yield: 0.05 g, 14%). $^1$H NMR (400 MHz, DMSO-d$_6$) δ 8.28 (t, J=11.6 Hz, 1H), 8.07 (d, J=2.4 Hz, 1H), 7.93 (s, 1H), 7.91 (s, 1H), 7.76 (s, 1H), 7.74 (s. 1H), 7.63-7.58 (m, 3H), 7.31 (d, J=16 Hz, 1H), 6.48-6.41 (m, 4H), 5.09-5.07 (m, 1H), 3.65-3.63 (m, 4H), 3.60-3.51 (m, 2H), 3.47-3.40 (m, 1H), 3.16-3.10 (m, 1H), 2.90-2.88 (m, 4H). LCMS: m/z 555.39 [M]$^+$, t$_R$=1.80 min.

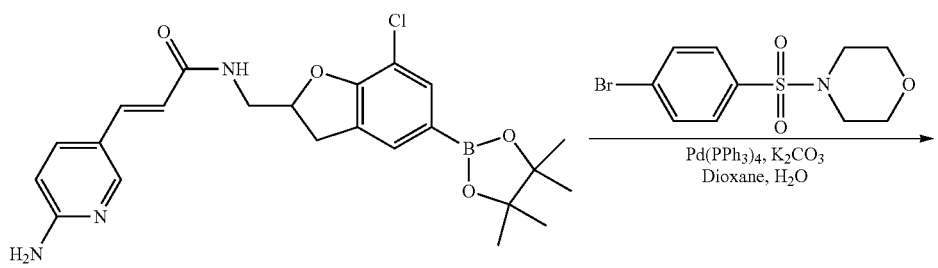

444

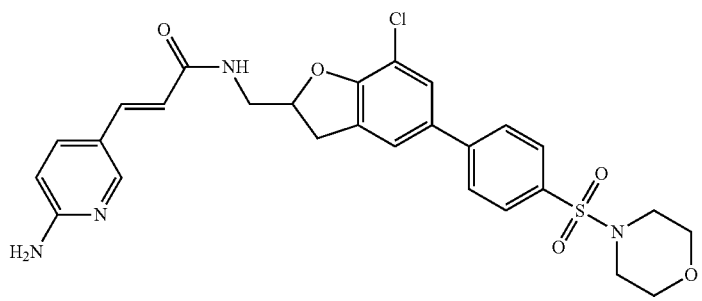

914

Synthesis of (E)-3-(6-aminopyridin-3-yl)-N-((7-chloro-4-(3-(morpholine-4-carbonyl)phenyl)-2,3-dihydrobenzofuran-2-yl)methyl)acrylamide (915)

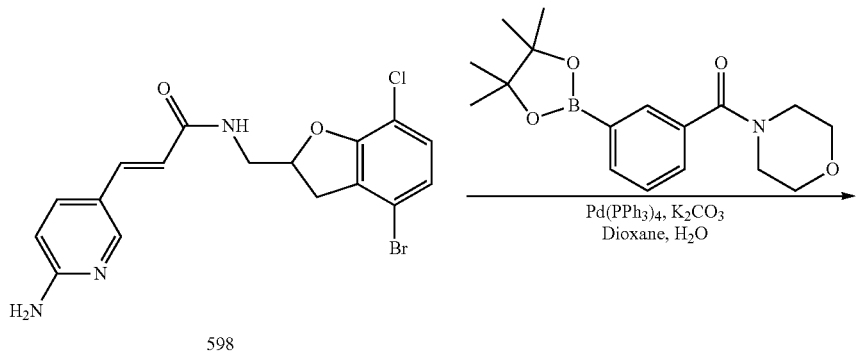

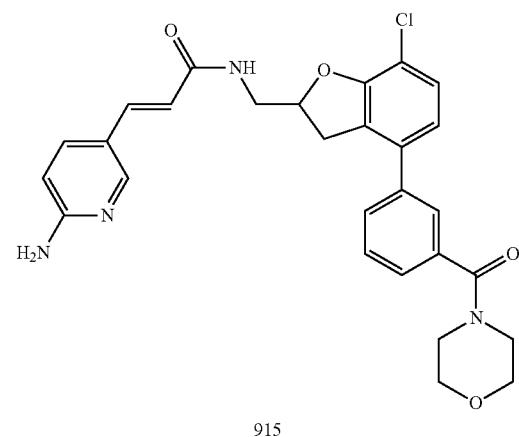

(E)-3-(6-Aminopyridin-3-yl)-N-((7-chloro-4-(3-(morpholine-4-carbonyl)phenyl)-2,3-dihydrobenzofuran-2-yl)methyl)acrylamide 915 was synthesized using General Procedure 1. (Yield: 0.018 g, 7%). $^1$H NMR (400 MHz, DMSO-$d_6$) δ 8.26 (t, J=5.8 Hz, 1H), 8.05 (d, J=2 Hz, 1H), 7.58-7.50 (m, 4H), 7.42 (d, J=7.6 Hz, 1H), 7.32-7.27 (m, 2H), 6.97 (d, J=8 Hz, 1H), 6.46-6.41 (m, 3H), 5.04-5.01 (m, 1H), 3.68 (s, 4H), 3.60-3.44 (m, 7H), 3.25-3.19 (m, 2H). LCMS: m/z 519.33 [M+H]$^+$, $t_R$=1.83 min.

Synthesis of 3-(6-aminopyridin-3-yl)-N-((7-chloro-5-(4-(piperazine-1-carbonyl)phenyl)-2,3-dihydrobenzofuran-2-yl)methyl)propanamide (920)

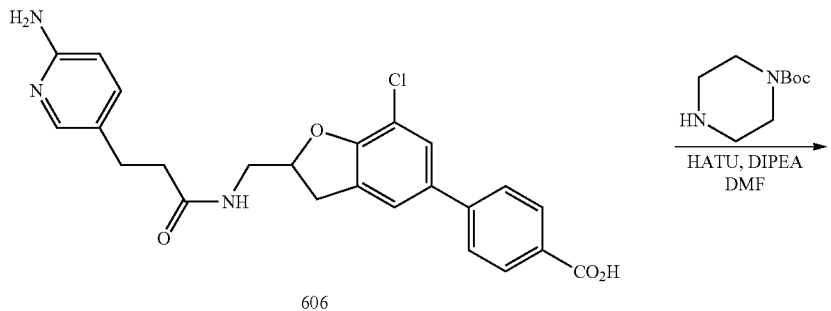

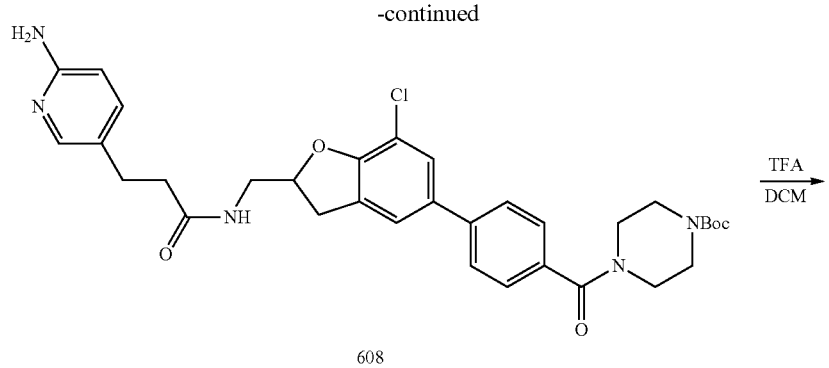

608

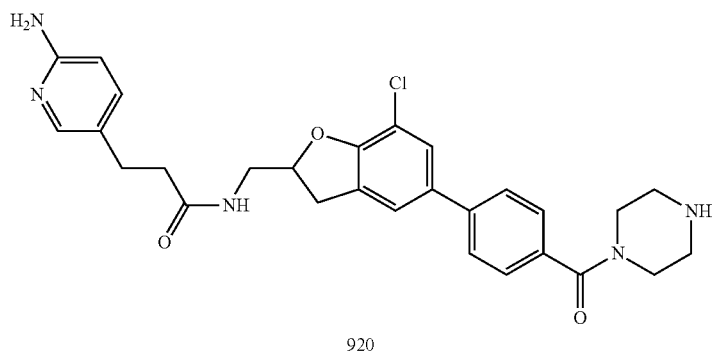

920 tert-Butyl 4-(4-(2-((3-(6-aminopyridin-3-yl)propanamido)methyl)-7-chloro-2,3-dihydrobenzofuran-5-yl)benzoyl)piperazine-1-carboxylate 608 was synthesized using General Procedure 3. Yield (0.13 g, 59%). LCMS: m/z 620.2 [M+H]+, $t_R$=1.42 min.

3-(6-Aminopyridin-3-yl)-N-((7-chloro-5-(4-(piperazine-1-carbonyl)phenyl)-2,3-dihydrobenzofuran-2-yl)methyl)propanamide 920 was synthesized using General Procedure 2. Yield (60 mg, 55%). $^1$H NMR (400 MHz, DMSO-d$_6$) δ 8.20-8.12 (m, 1H), 7.75-7.65 (m, 3H), 7.54-7.39 (m, 4H), 7.25-7.16 (m, 1H), 6.35 (d, J=8 Hz, 1H), 5.66 (s, 2H), 5.0-4.88 (m, 1H), 3.60-3.25 (m, 8H), 3.05-2.96 (m, 1H), 2.77-2.56 (m, 6H), 2.33 (t, J=8 Hz, 2H). LCMS: m/z 520.0 [M+H]+, $t_R$=1.54 min.

(E)-3-(6-aminopyridin-3-yl)-N-((7-chloro-5-(4-(2-morpholino-2-oxoethyl)phenyl)-2,3-dihydrobenzofuran-2-yl)methyl)acrylamide (921)

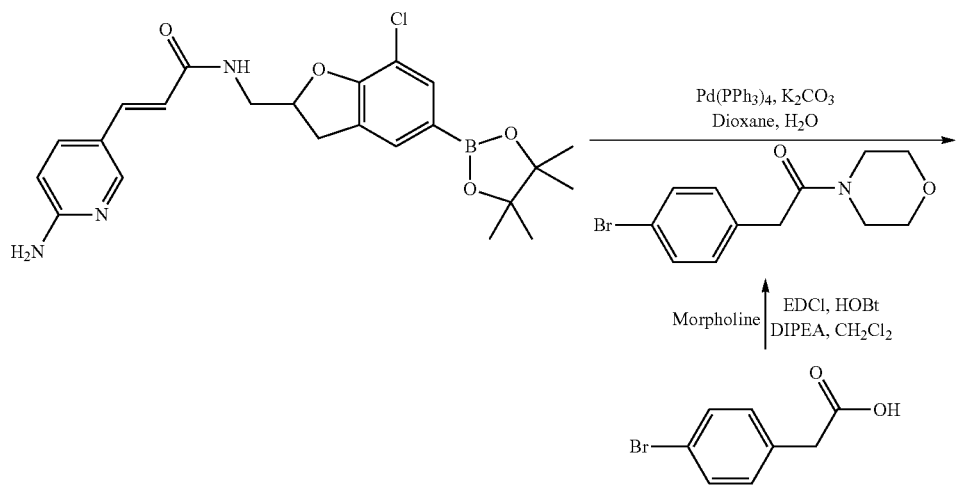

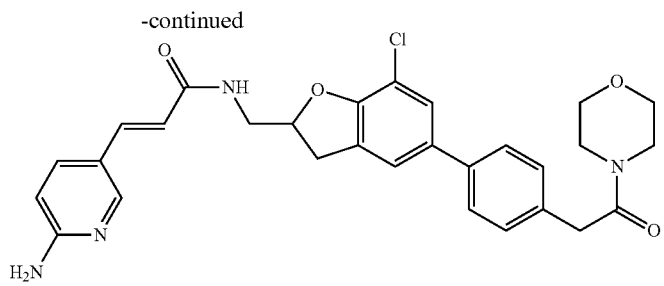

Synthesis of 2-(4-bromophenyl)-1-morpholinoethanone: 2-(4-bromophenyl)acetic acid (1 g, 4.65 mmol) was dissolved in dichloromethane (50 mL) at room temperature. The reaction mixture was cooled to 0° C. and morpholine (0.5 mL, 5.58 mmol) was added dropwise. EDCI (1.1 g, 5.55 mmol), HOBt (0.75 g, 5.55 mmol) followed by DIPEA (1.6 mL, 9.3 mmol) was then added. The reaction mixture was allowed to warm to room temperature and stirred for 13 h. The reaction mixture was transferred into iced water and extracted with ethyl acetate (3×50 mL). The combined organic layers were washed with brine and dried over anhydrous $Na_2SO_4$ and concentrated under reduced pressure to obtain 2-(4-bromophenyl)-1-morpholinoethanone, which was used for next step without further purification. LCMS: m/z 285.94 [M+H]$^+$, $t_R$=2.01 min.

(E)-3-(6-aminopyridin-3-yl)-N-((7-chloro-5-(4-(2-morpholino-2-oxoethyl)phenyl)-2,3-dihydrobenzofuran-2-yl)methyl)acrylamide (921) was synthesized using a procedure similar to that used to synthesize Compound 906 using the appropriate reagents. (Yield: 0.014 g, 6%). $^1$H NMR (400 MHz, DMSO-d$_6$) δ 8.28 (t, J=11.6 Hz, 1H), 8.14 (s, 1H), 8.07 (d, J=2.4 Hz, 1H), 7.60-7.54 (m, 3H), 7.46 (s, 1H), 7.33-7.20 (m, 4H), 6.47-6.41 (m, 3H), 5.04 (s, 1H), 3.74 (s, 2H), 3.58-3.50 (m, 8H), 3.45-3.39 (m, 4H), LCMS: m/z 533.38 [M+H]$^+$, $t_R$=1.80 min.

Example 2

MTT Cell Proliferation Assay

The MTT cell proliferation assay was used to study the cytotoxic properties of the compounds. The assay was performed according to the method described by Roche Molecular Biochemicals, with minor modifications. The assay is based on the cleavage of the tetrazolium salt, MTT, in the presence of an electron-coupling reagent. The water-insoluble formazan salt produced must be solubilized in an additional step. Cells grown in a 96-well tissue culture plate were incubated with the MTT solution for approximately 4 hours. After this incubation period, a water-insoluble formazan dye formed. After solubilization, the formazan dye was quantitated using a scanning multi-well spectrophotometer (ELISA reader). The absorbance revealed directly correlates to the cell number. The cells were seeded at 5,000-10,000 cells in each well of 96-well plate in 100 μL of fresh culture medium and were allowed to attach overnight. The stock solutions of the compounds were diluted in 100 μL cell culture medium to obtain eight concentrations of each test compound, ranging from 1 nM to 30 μM. After incubation for approximately 64-72 hours, 20 uL of CellTiter 96 Aqueous One Solution Reagent (Promega, G358B) was added to each well and the plate was returned to the incubator (37° C.; 5% $CO_2$) until an absolute OD of 1.5 was reached for the control cells. All optical densities were measured at 490 nm using a Vmax Kinetic Microplate Reader (Molecular Devices). In most cases, the assay was performed in duplicate and the results were presented as a mean percent inhibition to the negative control±SE. The following formula was used to calculate the percent of inhibition: Inhibition (%)=(1-(OD$_c$/OD)) ×100.

The compounds were tested against MS751, Z138 and 3T3 cells. The MS751 cell line is derived from a metastasis to lymph node of human cervix from a patient diagnosed with squameous cell carcinoma of the cervix. The Z138 cell line is a mature B-cell acute lymphoblastic leukemia cell line derived from a patient with chronic lumphocytic leukemia. 3T3 cells are standard fibroblast cells; they were originally isolated from Swiss mouse embryo tissue.

The results of the MTT assay are reported in Table 2.

TABLE 2

MTT Assay

| Compound Number | Compound Structure |
|---|---|
| 15 | 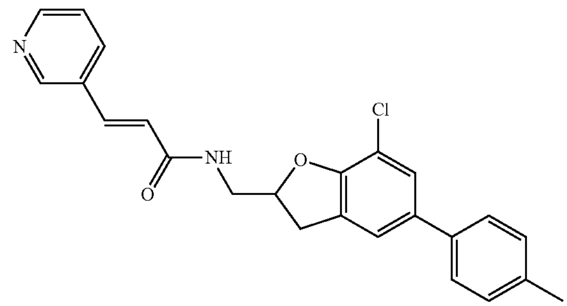 [SMILES: Cc1ccc(-c2cc(Cl)c3c(c2)CC(CNC(=O)/C=C/c2cccnc2)O3)cc1] |
| 18 | 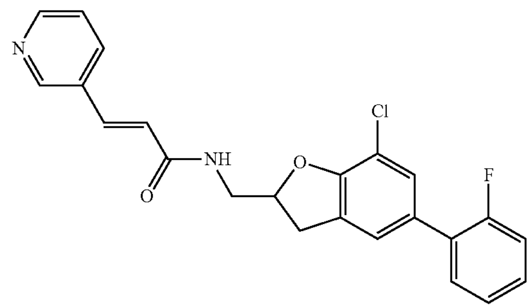 [SMILES: O=C(/C=C/c1cccnc1)NCC1Cc2cc(-c3ccccc3F)cc(Cl)c2O1] |
| 21 | 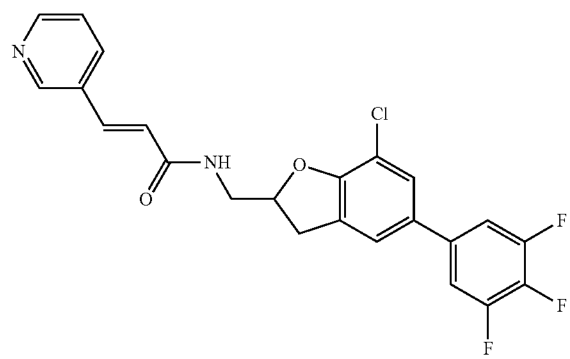 [SMILES: O=C(/C=C/c1cccnc1)NCC1Cc2cc(-c3cc(F)c(F)c(F)c3)cc(Cl)c2O1] |
| 24 | 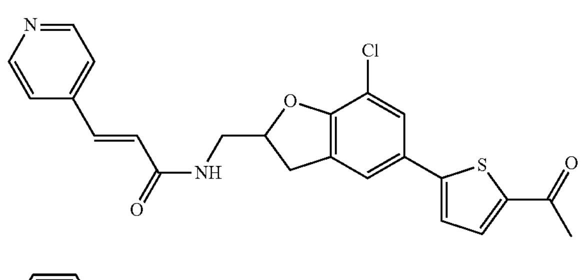 |
| 27 | 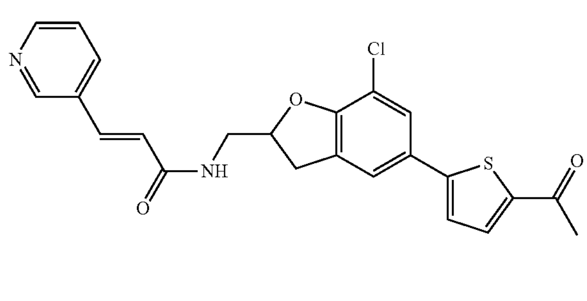 [SMILES: CC(=O)c1ccc(-c2cc(Cl)c3c(c2)CC(CNC(=O)/C=C/c2cccnc2)O3)s1] |

TABLE 2-continued
| 28 | 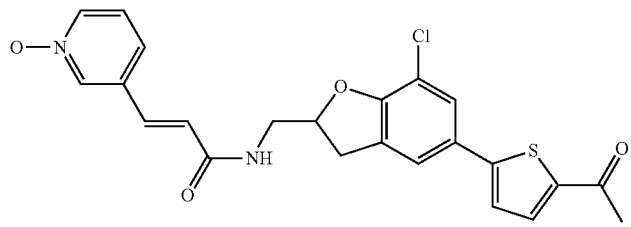 |
| --- | --- |
| 29 | 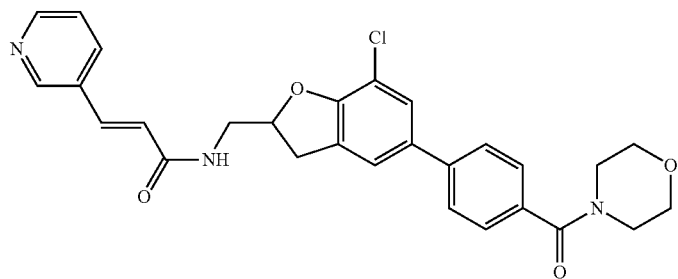 [SMILES: O=C(/C=C/c1cccnc1)NCC1Cc2cc(-c3ccc(C(=O)N4CCOCC4)cc3)cc(Cl)c2O1] |
| 32 | 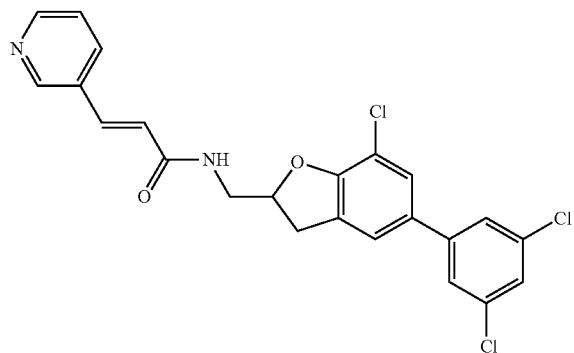 [SMILES: O=C(/C=C/c1cccnc1)NCC1Cc2cc(-c3cc(Cl)cc(Cl)c3)cc(Cl)c2O1] |
| 35 | 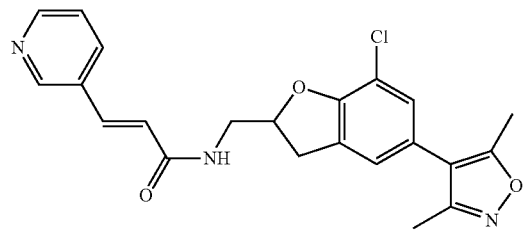 [SMILES: Cc1noc(C)c1-c1cc(Cl)c2c(c1)CC(CNC(=O)/C=C/c1cccnc1)O2] |
| 38 | 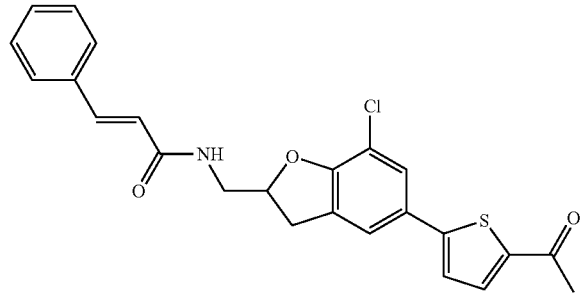 [SMILES: CC(=O)c1ccc(-c2cc(Cl)c3c(c2)CC(CNC(=O)/C=C/c2ccccc2)O3)s1] |

TABLE 2-continued
| | |
|---|---|
| 39 | 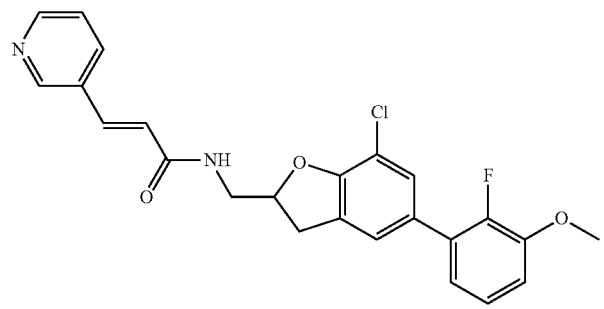 [SMILES: COc1cccc(-c2cc(Cl)c3c(c2)CC(CNC(=O)/C=C/c2cccnc2)O3)c1F] |
| 42 | 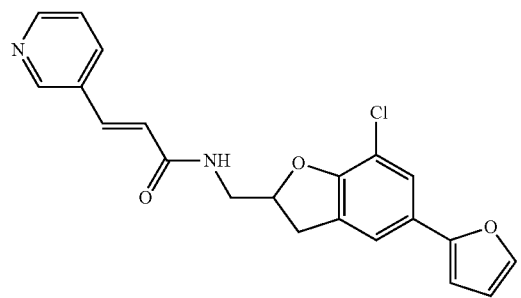 [SMILES: O=C(/C=C/c1cccnc1)NCC1Cc2cc(-c3ccco3)cc(Cl)c2O1] |
| 45 | 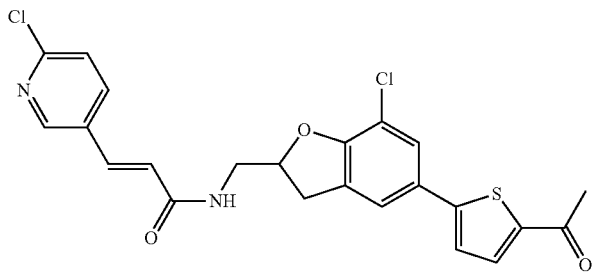 [SMILES: CC(=O)c1ccc(-c2cc(Cl)c3c(c2)CC(CNC(=O)/C=C/c2ccc(Cl)nc2)O3)s1] |
| 49 | 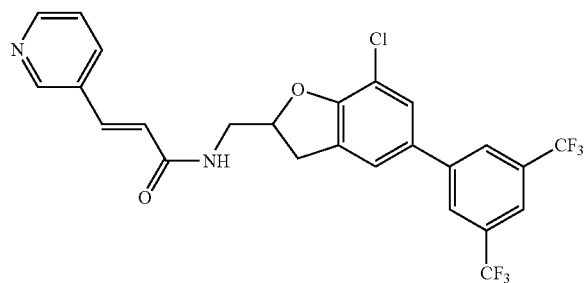 [SMILES: O=C(/C=C/c1cccnc1)NCC1Cc2cc(-c3cc(C(F)(F)F)cc(C(F)(F)F)c3)cc(Cl)c2O1] |
| 52 | 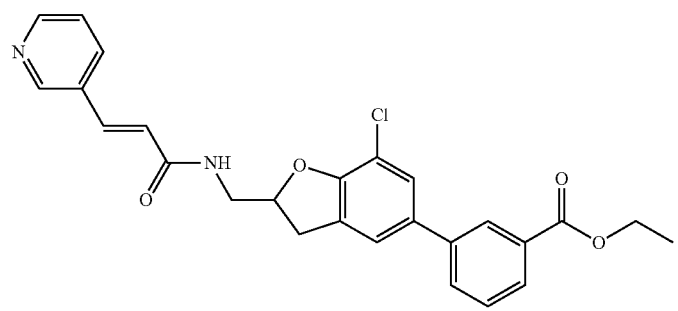 [SMILES: CCOC(=O)c1cccc(-c2cc(Cl)c3c(c2)CC(CNC(=O)/C=C/c2cccnc2)O3)c1] |

TABLE 2-continued
55 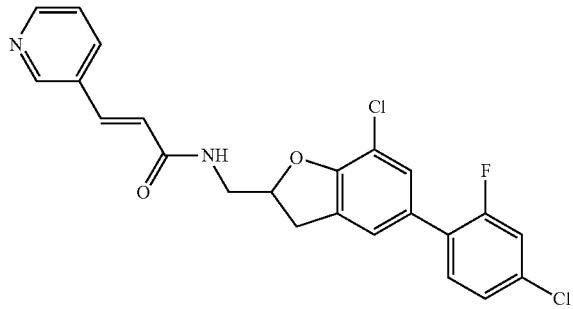 [SMILES: O=C(/C=C/c1cccnc1)NCC1Cc2cc(-c3ccc(Cl)cc3F)cc(Cl)c2O1]
58 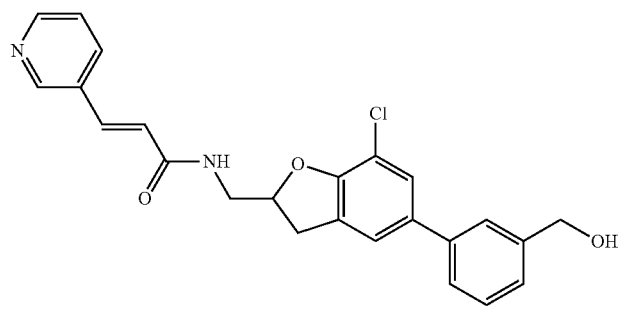 [SMILES: O=C(/C=C/c1cccnc1)NCC1Cc2cc(-c3cccc(CO)c3)cc(Cl)c2O1]
61 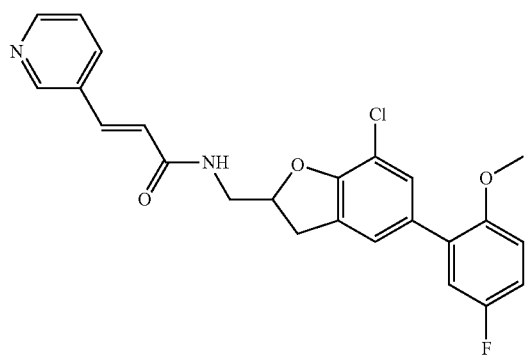 [SMILES: COc1ccc(F)cc1-c1cc(Cl)c2c(c1)CC(CNC(=O)/C=C/c1cccnc1)O2]
64 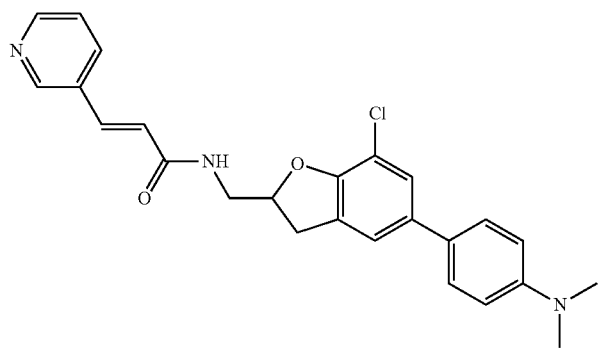 [SMILES: CN(C)c1ccc(-c2cc(Cl)c3c(c2)CC(CNC(=O)/C=C/c2cccnc2)O3)cc1]
67 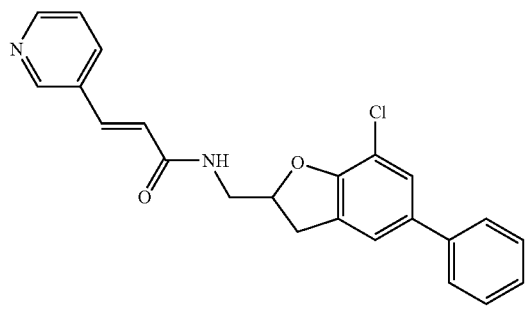 [SMILES: O=C(/C=C/c1cccnc1)NCC1Cc2cc(-c3ccccc3)cc(Cl)c2O1]

TABLE 2-continued
70 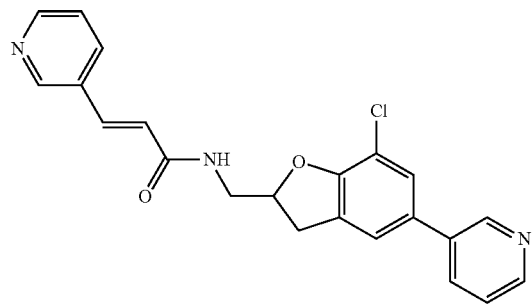 [SMILES: O=C(/C=C/c1cccnc1)NCC1Cc2cc(-c3cccnc3)cc(Cl)c2O1]
73 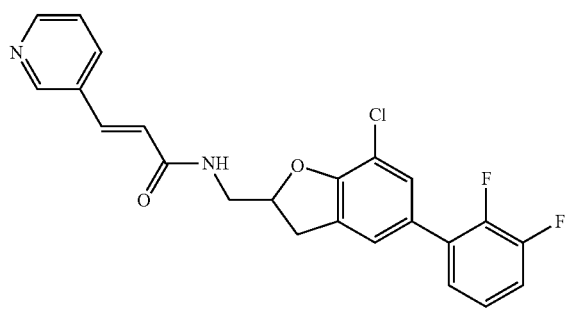 [SMILES: O=C(/C=C/c1cccnc1)NCC1Cc2cc(-c3cccc(F)c3F)cc(Cl)c2O1]
76 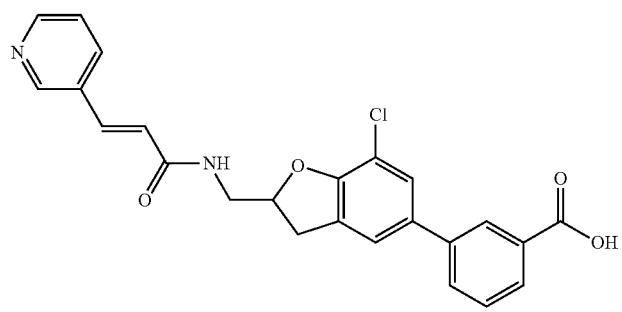 [SMILES: O=C(/C=C/c1cccnc1)NCC1Cc2cc(-c3cccc(C(=O)O)c3)cc(Cl)c2O1]
77 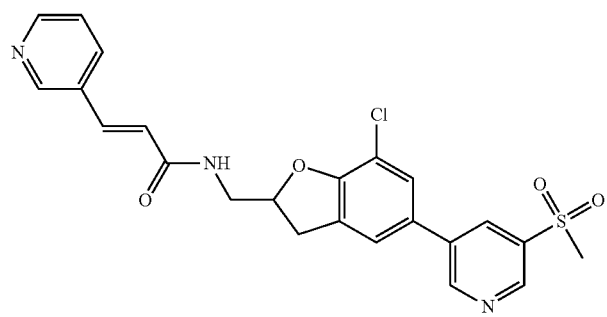 [SMILES: CS(=O)(=O)c1cncc(-c2cc(Cl)c3c(c2)CC(CNC(=O)/C=C/c2cccnc2)O3)c1]
80 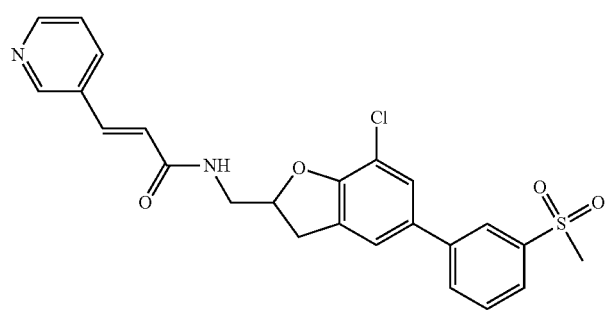 [SMILES: CS(=O)(=O)c1cccc(-c2cc(Cl)c3c(c2)CC(CNC(=O)/C=C/c2cccnc2)O3)c1]

TABLE 2-continued
| | |
|---|---|
| 83 | 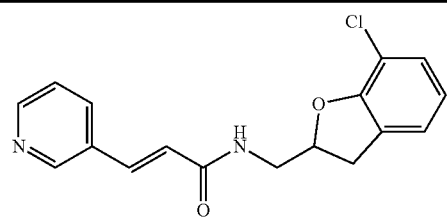 |
| 84 | 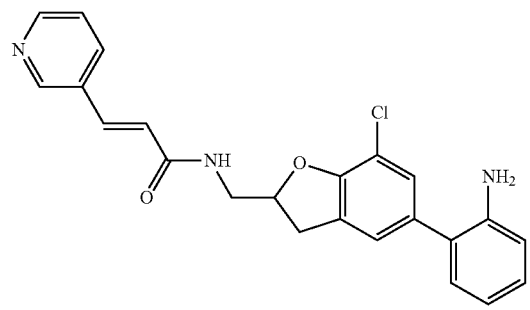 [SMILES: Nc1ccccc1-c1cc(Cl)c2c(c1)CC(CNC(=O)/C=C/c1cccnc1)O2] |
| 87 | 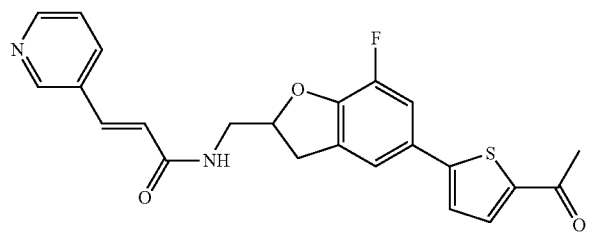 [SMILES: CC(=O)c1ccc(-c2cc(F)c3c(c2)CC(CNC(=O)/C=C/c2cccnc2)O3)s1] |
| 99 | 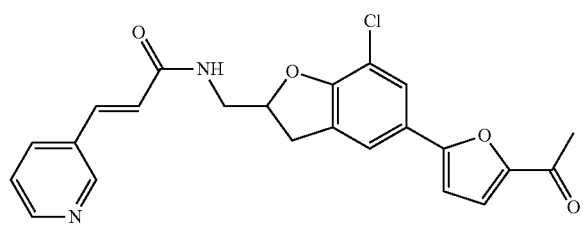 [SMILES: CC(=O)c1ccc(-c2cc(Cl)c3c(c2)CC(CNC(=O)/C=C/c2cccnc2)O3)o1] |
| 103 | 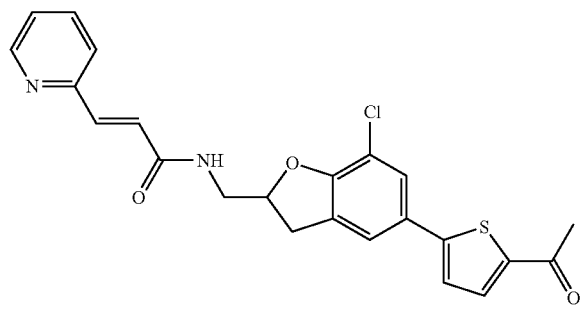 [SMILES: CC(=O)c1ccc(-c2cc(Cl)c3c(c2)CC(CNC(=O)/C=C/c2ccccn2)O3)s1] |
| 104 | 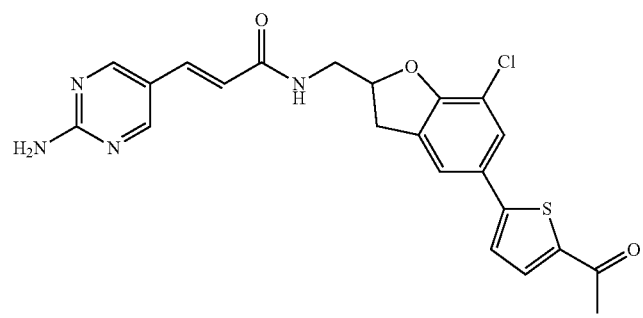 [SMILES: CC(=O)c1ccc(-c2cc(Cl)c3c(c2)CC(CNC(=O)/C=C/c2cnc(N)nc2)O3)s1] |

TABLE 2-continued
106
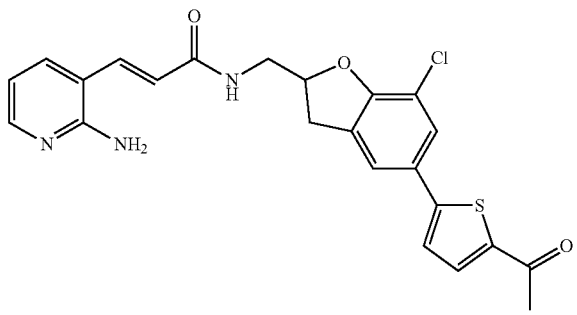 [SMILES: CC(=O)c1ccc(-c2cc(Cl)c3c(c2)CC(CNC(=O)/C=C/c2cccnc2N)O3)s1]
108
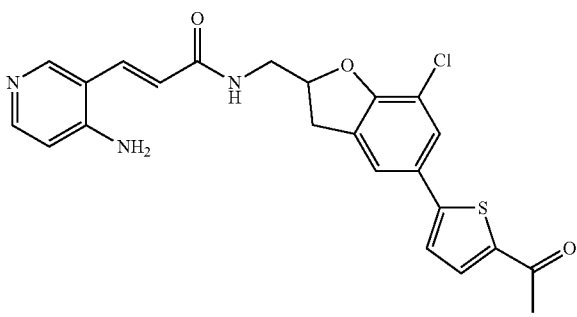 [SMILES: CC(=O)c1ccc(-c2cc(Cl)c3c(c2)CC(CNC(=O)/C=C/c2cnccc2N)O3)s1]
110
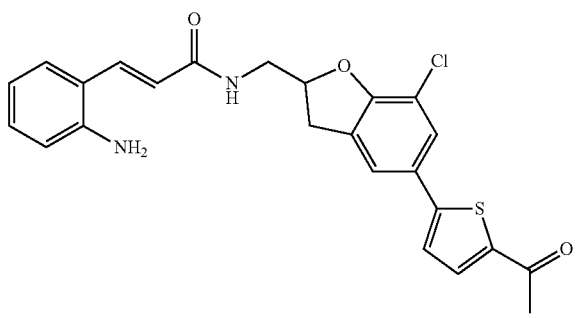 [SMILES: CC(=O)c1ccc(-c2cc(Cl)c3c(c2)CC(CNC(=O)/C=C/c2ccccc2N)O3)s1]
112
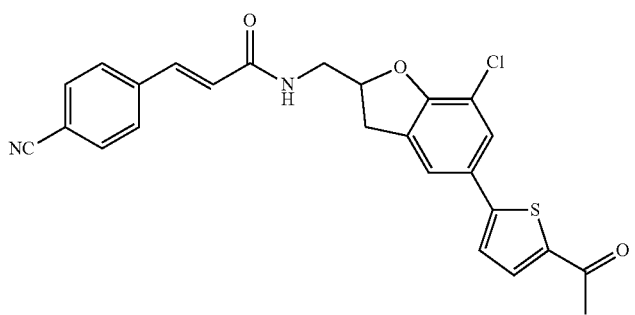 [SMILES: CC(=O)c1ccc(-c2cc(Cl)c3c(c2)CC(CNC(=O)/C=C/c2ccc(C#N)cc2)O3)s1]
114
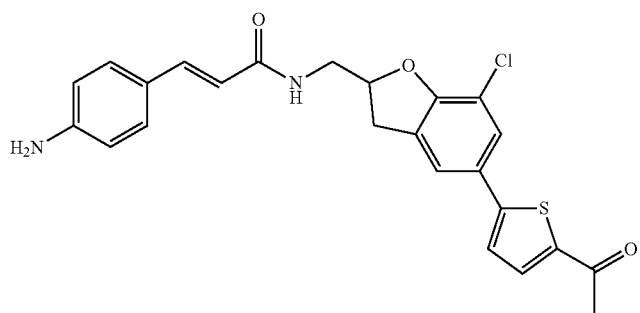 [SMILES: CC(=O)c1ccc(-c2cc(Cl)c3c(c2)CC(CNC(=O)/C=C/c2ccc(N)cc2)O3)s1]

TABLE 2-continued
| | |
|---|---|
| 116 | 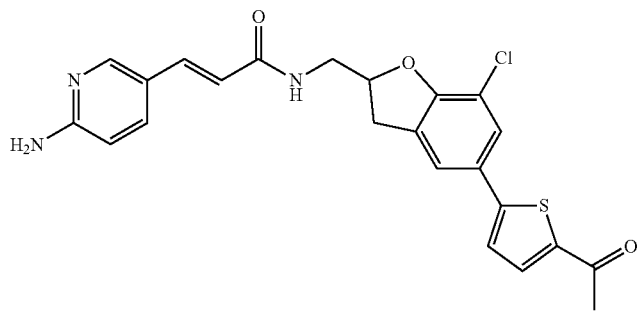 [SMILES: CC(=O)c1ccc(-c2cc(Cl)c3c(c2)CC(CNC(=O)/C=C/c2ccc(N)nc2)O3)s1] |
| 118 | 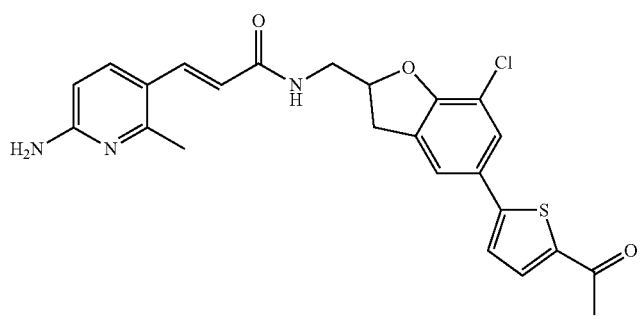 [SMILES: CC(=O)c1ccc(-c2cc(Cl)c3c(c2)CC(CNC(=O)/C=C/c2ccc(N)nc2C)O3)s1] |
| 120 | 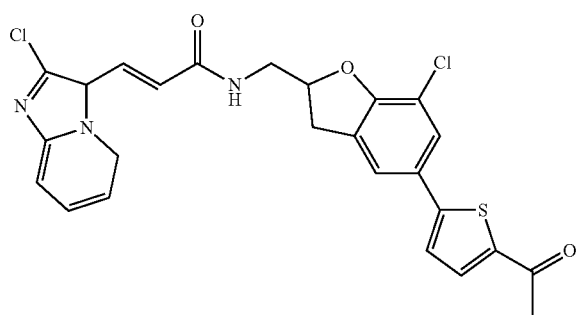 [SMILES: CC(=O)c1ccc(-c2cc(Cl)c3c(c2)CC(CNC(=O)/C=C/C2C(Cl)=NC4=CC=CCN42)O3)s1] |
| 122[2] | 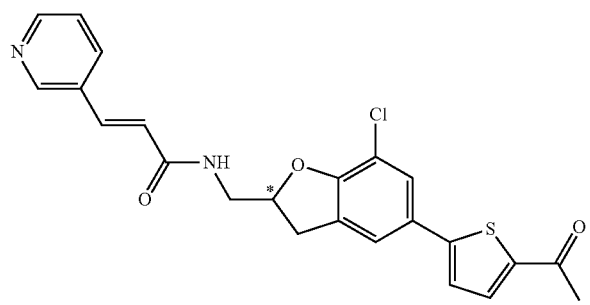<br>isomer 1<br>Rt = 5.1 min |

TABLE 2-continued
123[2] 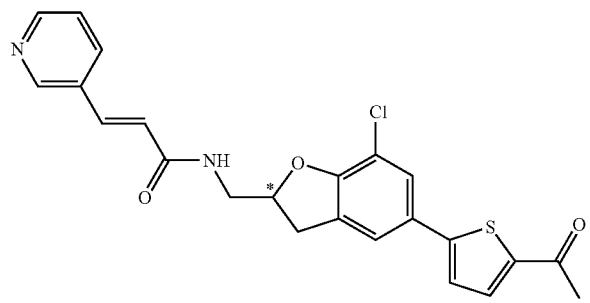
isomer 2
Rt = 5.6 min
124 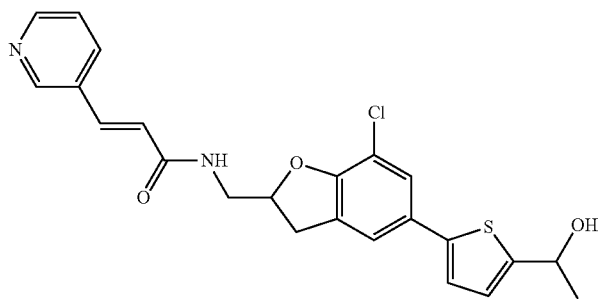 [SMILES: CC(O)c1ccc(-c2cc(Cl)c3c(c2)CC(CNC(=O)/C=C/c2cccnc2)O3)s1]
125 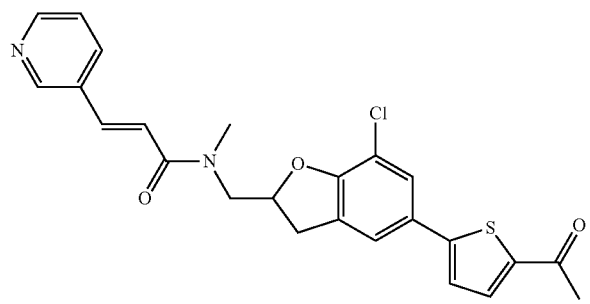 [SMILES: CC(=O)c1ccc(-c2cc(Cl)c3c(c2)CC(CN(C)C(=O)/C=C/c2cccnc2)O3)s1]
128 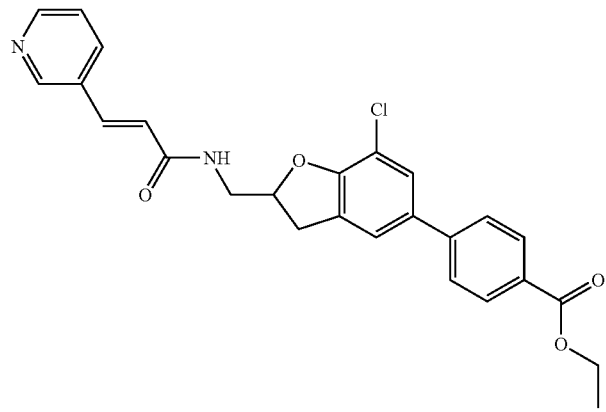 [SMILES: CCOC(=O)c1ccc(-c2cc(Cl)c3c(c2)CC(CNC(=O)/C=C/c2cccnc2)O3)cc1]

TABLE 2-continued
| 129 | 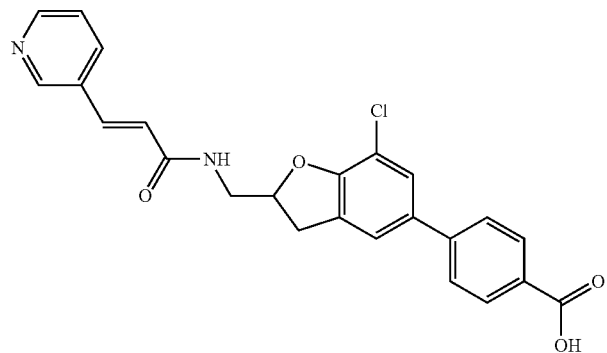 [SMILES: O=C(/C=C/c1cccnc1)NCC1Cc2cc(-c3ccc(C(=O)O)cc3)cc(Cl)c2O1] |
| --- | --- |
| 138 | 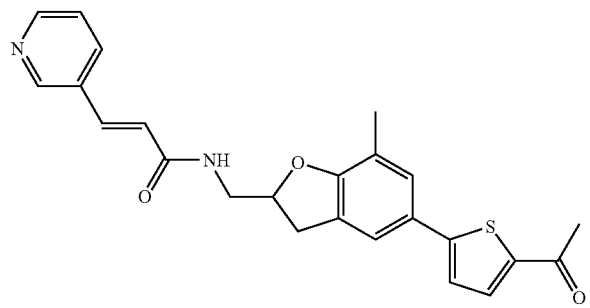 [SMILES: CC(=O)c1ccc(-c2cc(C)c3c(c2)CC(CNC(=O)/C=C/c2cccnc2)O3)s1] |
| 142 | 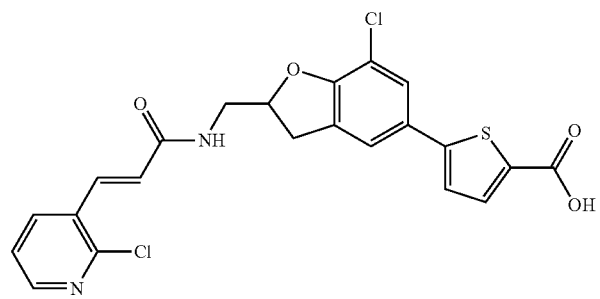 [SMILES: O=C(/C=C/c1cccnc1Cl)NCC1Cc2cc(-c3ccc(C(=O)O)s3)cc(Cl)c2O1] |
| 146 | 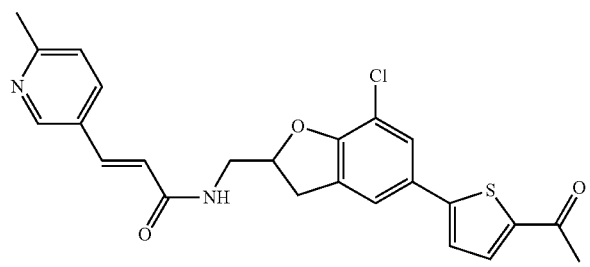 [SMILES: CC(=O)c1ccc(-c2cc(Cl)c3c(c2)CC(CNC(=O)/C=C/c2ccc(C)nc2)O3)s1] |
| 147 | 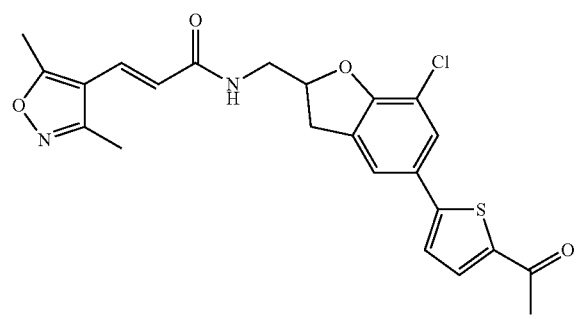 [SMILES: CC(=O)c1ccc(-c2cc(Cl)c3c(c2)CC(CNC(=O)/C=C/c2c(C)noc2C)O3)s1] |

TABLE 2-continued
| | |
|---|---|
| 148 | 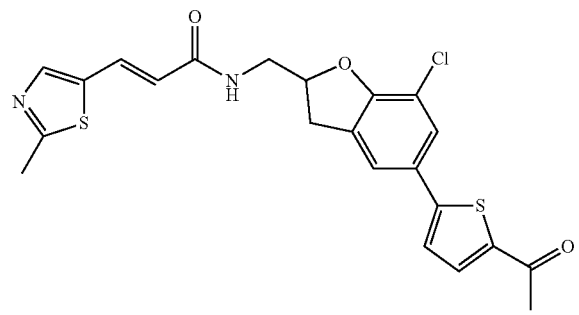 [SMILES: CC(=O)c1ccc(-c2cc(Cl)c3c(c2)CC(CNC(=O)/C=C/c2cnc(C)s2)O3)s1] |
| 149 | 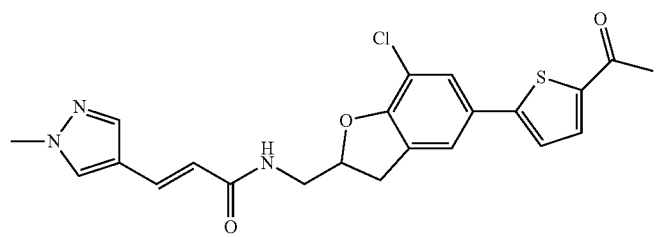 [SMILES: CC(=O)c1ccc(-c2cc(Cl)c3c(c2)CC(CNC(=O)/C=C/c2cnn(C)c2)O3)s1] |
| 150 | 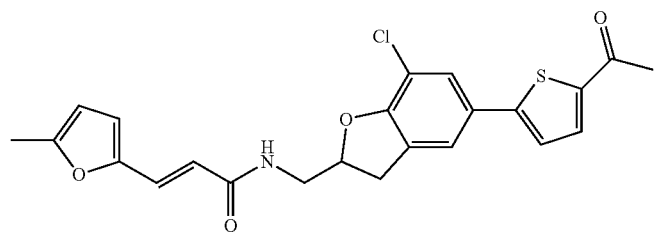 [SMILES: CC(=O)c1ccc(-c2cc(Cl)c3c(c2)CC(CNC(=O)/C=C/c2ccc(C)o2)O3)s1] |
| 151 | 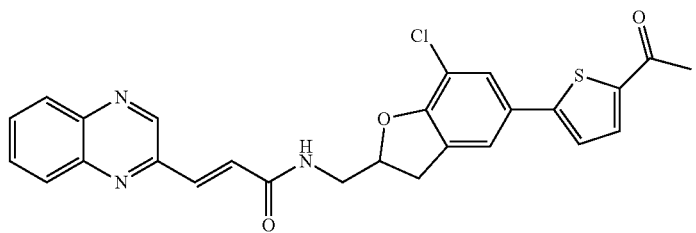 [SMILES: CC(=O)c1ccc(-c2cc(Cl)c3c(c2)CC(CNC(=O)/C=C/c2cnc4ccccc4n2)O3)s1] |
| 152 | 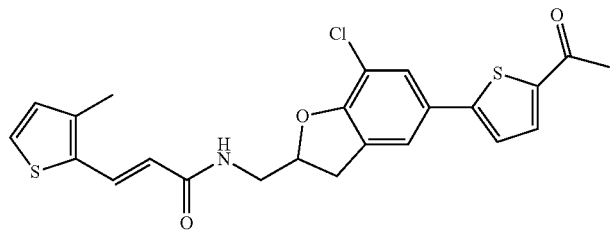 [SMILES: CC(=O)c1ccc(-c2cc(Cl)c3c(c2)CC(CNC(=O)/C=C/c2sccc2C)O3)s1] |
| 153 | 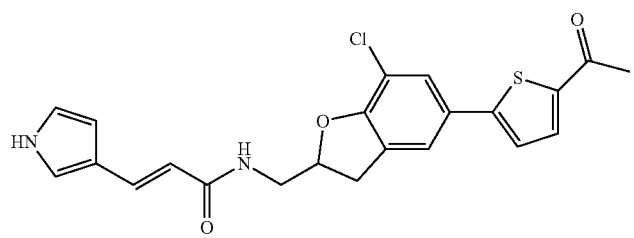 [SMILES: CC(=O)c1ccc(-c2cc(Cl)c3c(c2)CC(CNC(=O)/C=C/c2cc[nH]c2)O3)s1] |

TABLE 2-continued
154 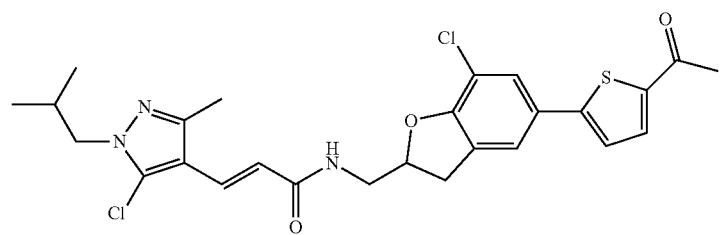 [SMILES: CC(=O)c1ccc(-c2cc(Cl)c3c(c2)CC(CNC(=O)/C=C/c2c(C)nn(CC(C)C)c2Cl)O3)s1]
155 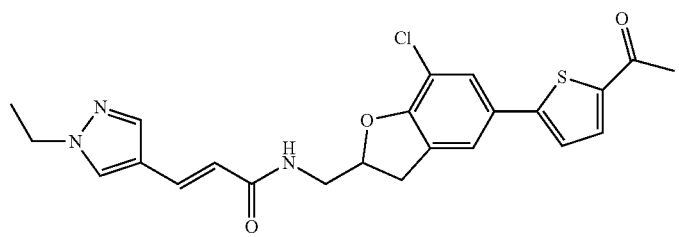 [SMILES: CCn1cc(/C=C/C(=O)NCC2Cc3cc(-c4ccc(C(C)=O)s4)cc(Cl)c3O2)cn1]
156 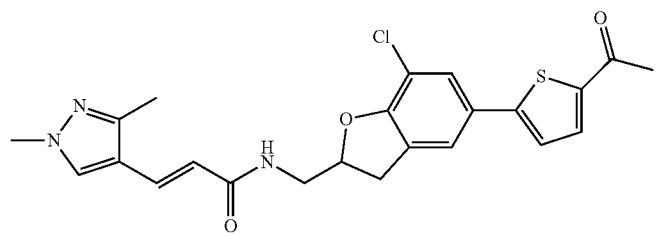 [SMILES: CC(=O)c1ccc(-c2cc(Cl)c3c(c2)CC(CNC(=O)/C=C/c2cn(C)nc2C)O3)s1]
157 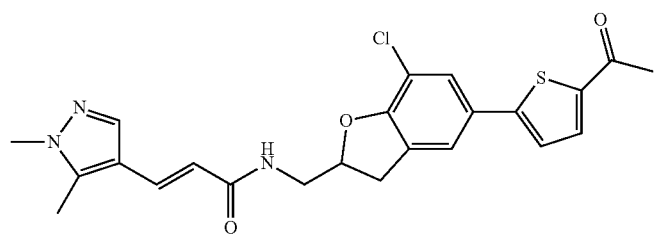 [SMILES: CC(=O)c1ccc(-c2cc(Cl)c3c(c2)CC(CNC(=O)/C=C/c2cnn(C)c2C)O3)s1]
159 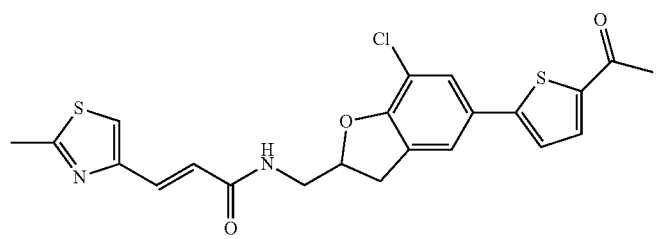
160 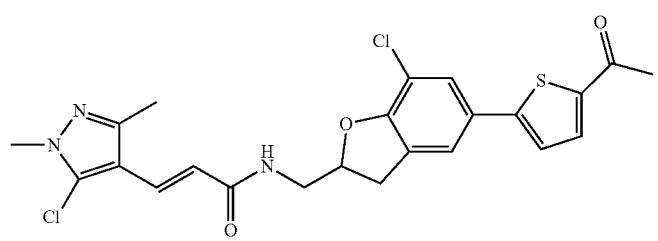 [SMILES: CC(=O)c1ccc(-c2cc(Cl)c3c(c2)CC(CNC(=O)/C=C/c2c(C)nn(C)c2Cl)O3)s1]

TABLE 2-continued
161
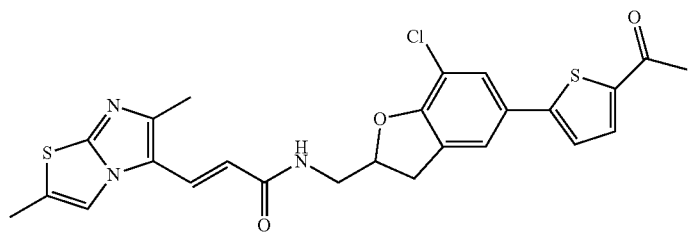 [SMILES: CC(=O)c1ccc(-c2cc(Cl)c3c(c2)CC(CNC(=O)/C=C/c2c(C)nc4sc(C)cn24)O3)s1]
162
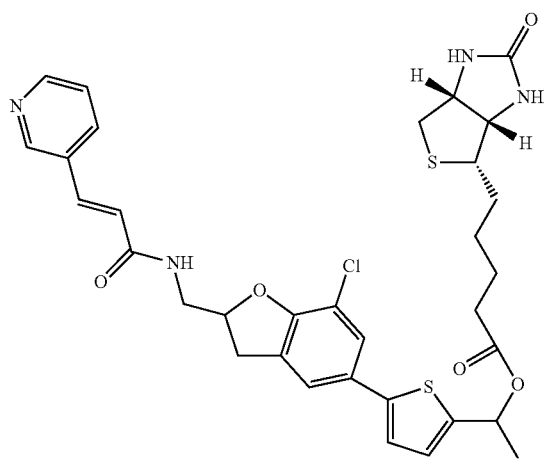 [SMILES: CC(OC(=O)CCCC[C@@H]1SC[C@@H]2NC(=O)N[C@@H]21)c1ccc(-c2cc(Cl)c3c(c2)CC(CNC(=O)/C=C/c2cccnc2)O3)s1]
163
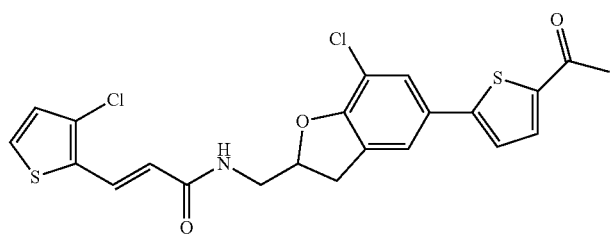
164
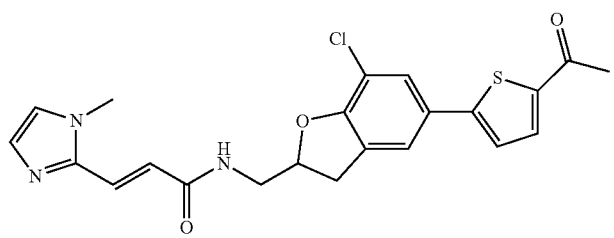 [SMILES: CC(=O)c1ccc(-c2cc(Cl)c3c(c2)CC(CNC(=O)/C=C/c2nccn2C)O3)s1]
173
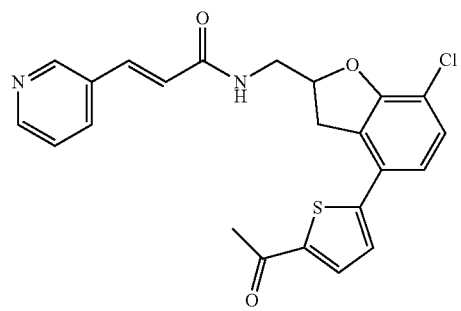 [SMILES: CC(=O)c1ccc(-c2ccc(Cl)c3c2CC(CNC(=O)/C=C/c2cccnc2)O3)s1]

TABLE 2-continued
| | |
|---|---|
| 26 | 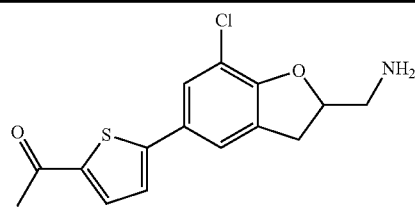 |
| 174 | 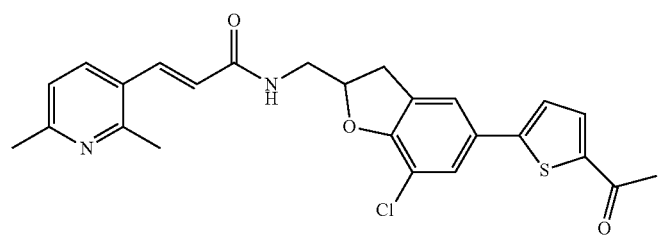 [SMILES: CC(=O)c1ccc(-c2cc(Cl)c3c(c2)CC(CNC(=O)/C=C/c2ccc(C)nc2C)O3)s1] |
| 251 | 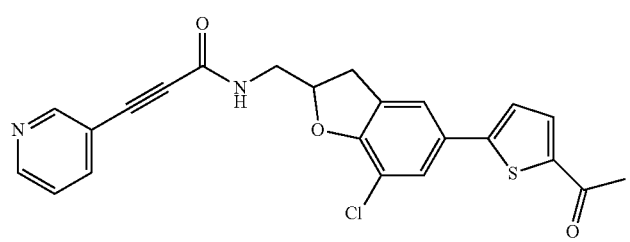 [SMILES: CC(=O)c1ccc(-c2cc(Cl)c3c(c2)CC(CNC(=O)C#Cc2cccnc2)O3)s1] |
| 254 | 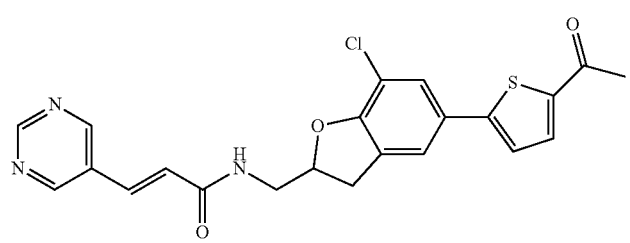 |
| 272 | 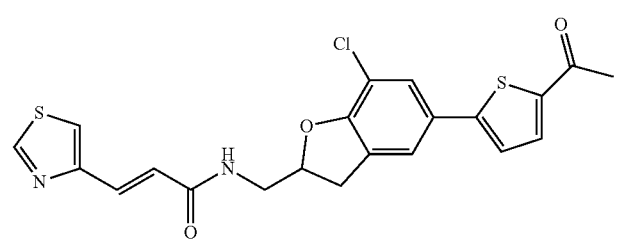 [SMILES: CC(=O)c1ccc(-c2cc(Cl)c3c(c2)CC(CNC(=O)/C=C/c2cscn2)O3)s1] |
| 177 | 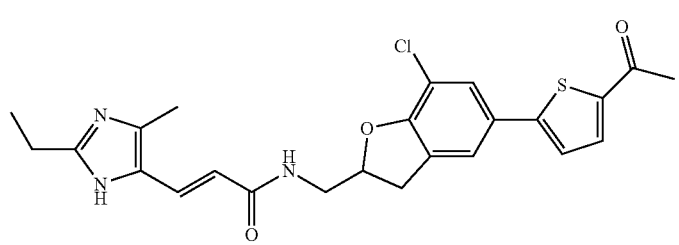 [SMILES: CCc1nc(C)c(/C=C/C(=O)NCC2Cc3cc(-c4ccc(C(C)=O)s4)cc(Cl)c3O2)[nH]1] |
| 273 | 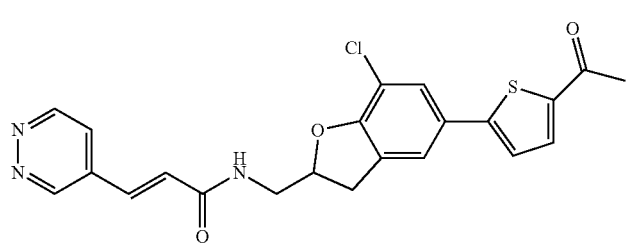 [SMILES: CC(=O)c1ccc(-c2cc(Cl)c3c(c2)CC(CNC(=O)/C=C/c2ccnnc2)O3)s1] |

TABLE 2-continued
181 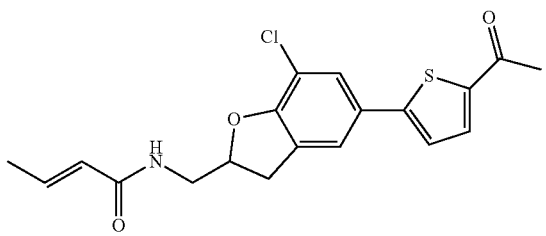 [SMILES: C/C=C/C(=O)NCC1Cc2cc(-c3ccc(C(C)=O)s3)cc(Cl)c2O1]
274 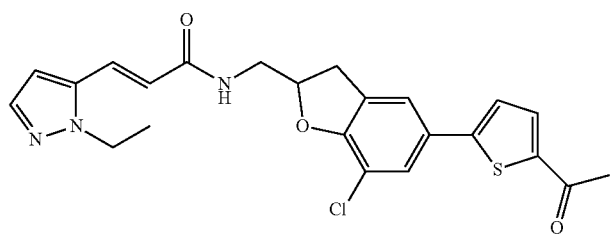 [SMILES: CCn1nccc1/C=C/C(=O)NCC1Cc2cc(-c3ccc(C(C)=O)s3)cc(Cl)c2O1]
258 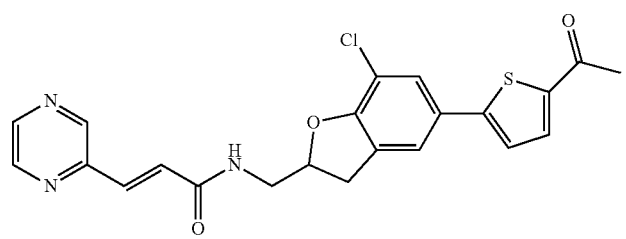 [SMILES: CC(=O)c1ccc(-c2cc(Cl)c3c(c2)CC(CNC(=O)/C=C/c2cnccn2)O3)s1]
275 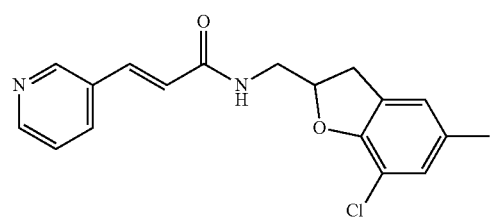 [SMILES: Cc1cc(Cl)c2c(c1)CC(CNC(=O)/C=C/c1cccnc1)O2]
262[1] 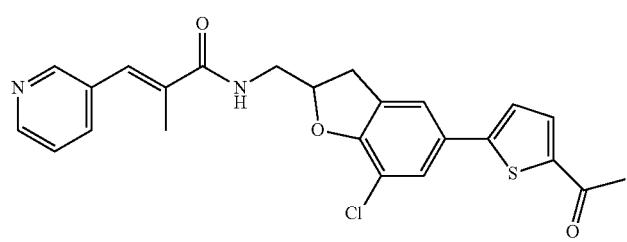 [SMILES: CC(=O)c1ccc(-c2cc(Cl)c3c(c2)CC(CNC(=O)/C(C)=C/c2cccnc2)O3)s1]
182 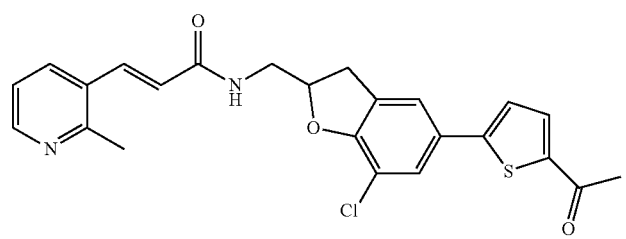 [SMILES: CC(=O)c1ccc(-c2cc(Cl)c3c(c2)CC(CNC(=O)/C=C/c2cccnc2C)O3)s1]

TABLE 2-continued
185
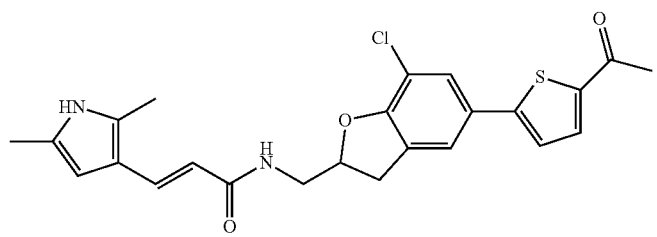 [SMILES: CC(=O)c1ccc(-c2cc(Cl)c3c(c2)CC(CNC(=O)/C=C/c2cc(C)[nH]c2C)O3)s1]
189
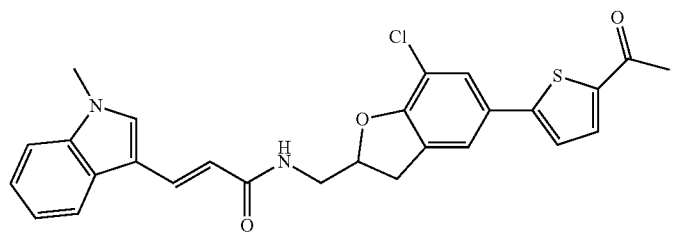 [SMILES: CC(=O)c1ccc(-c2cc(Cl)c3c(c2)CC(CNC(=O)/C=C/c2cn(C)c4ccccc24)O3)s1]
190
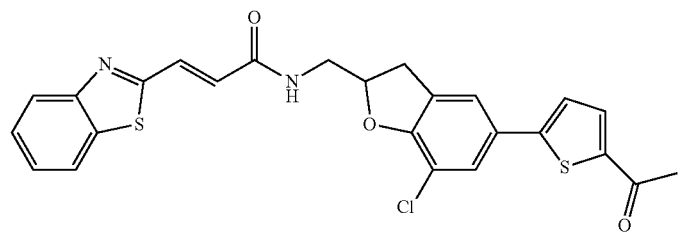
276
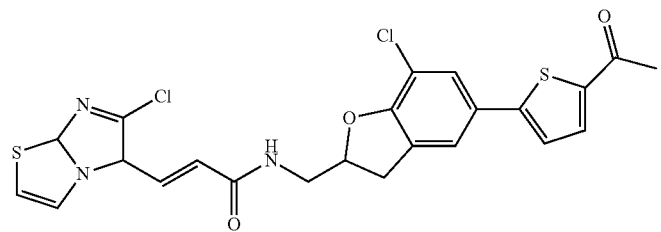 [SMILES: CC(=O)c1ccc(-c2cc(Cl)c3c(c2)CC(CNC(=O)/C=C/C2C(Cl)=NC4SC=CN42)O3)s1]
277
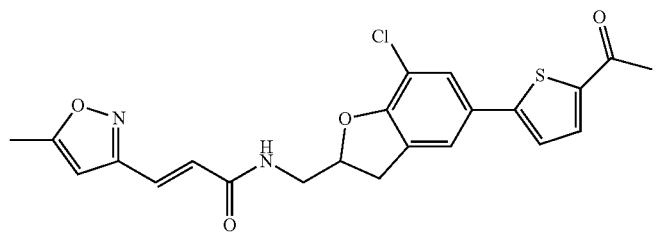
278
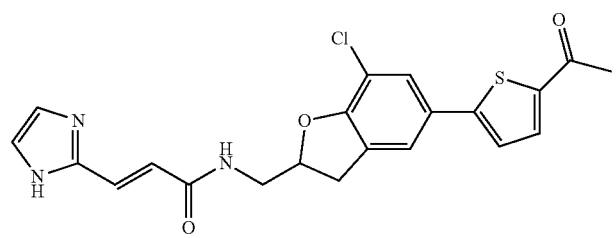 [SMILES: CC(=O)c1ccc(-c2cc(Cl)c3c(c2)CC(CNC(=O)/C=C/c2ncc[nH]2)O3)s1]

TABLE 2-continued
279
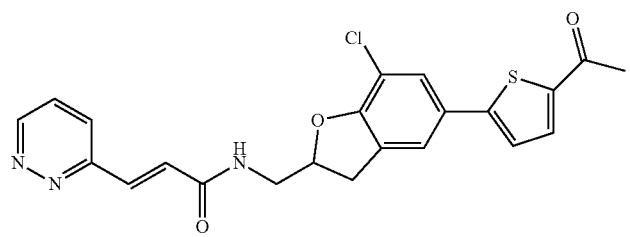 [SMILES: CC(=O)c1ccc(-c2cc(Cl)c3c(c2)CC(CNC(=O)/C=C/c2cccnn2)O3)s1]
280
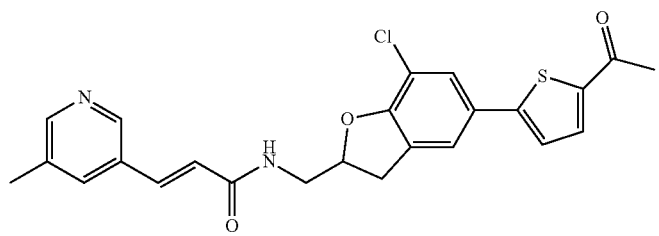 [SMILES: CC(=O)c1ccc(-c2cc(Cl)c3c(c2)CC(CNC(=O)/C=C/c2cncc(C)c2)O3)s1]
191
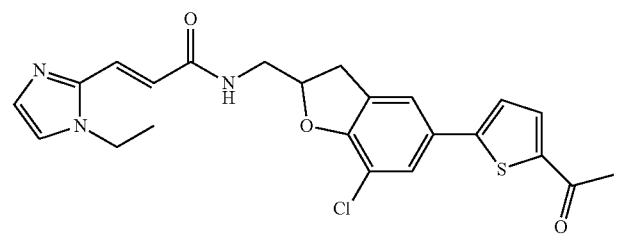 [SMILES: CCn1ccnc1/C=C/C(=O)NCC1Cc2cc(-c3ccc(C(C)=O)s3)cc(Cl)c2O1]
195[1]
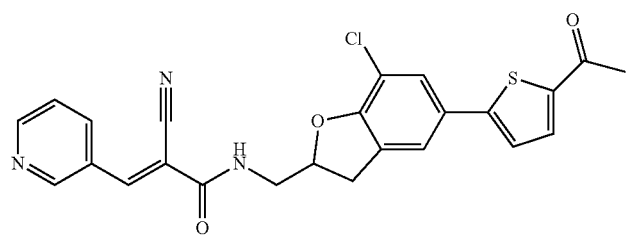 [SMILES: CC(=O)c1ccc(-c2cc(Cl)c3c(c2)CC(CNC(=O)/C(C#N)=C/c2cccnc2)O3)s1]
196
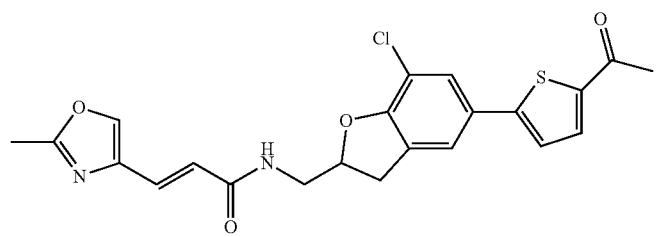 [SMILES: CC(=O)c1ccc(-c2cc(Cl)c3c(c2)CC(CNC(=O)/C=C/c2coc(C)n2)O3)s1]
281
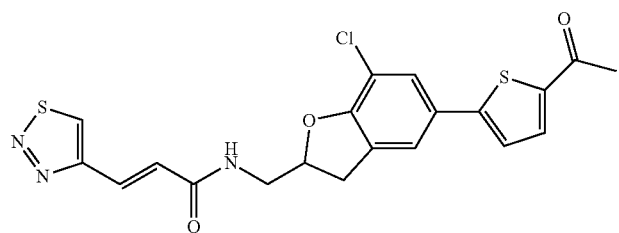 [SMILES: CC(=O)c1ccc(-c2cc(Cl)c3c(c2)CC(CNC(=O)/C=C/c2csnn2)O3)s1]

TABLE 2-continued
282 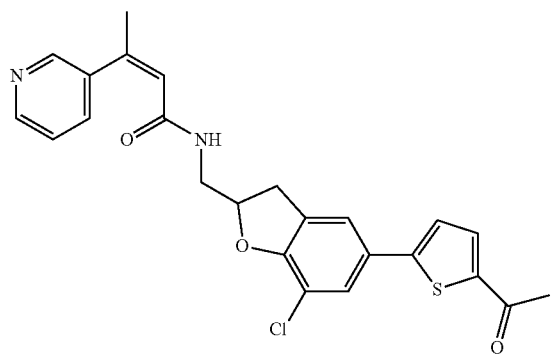 [SMILES: CC(=O)c1ccc(-c2cc(Cl)c3c(c2)CC(CNC(=O)/C=C(/C)c2cccnc2)O3)s1]
283[1] 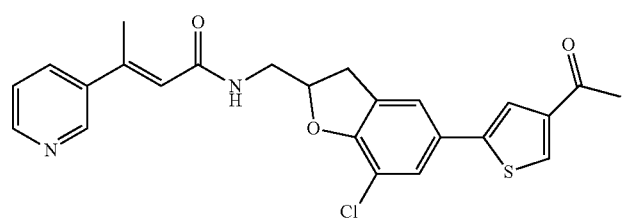 [SMILES: CC(=O)c1csc(-c2cc(Cl)c3c(c2)CC(CNC(=O)/C=C(\C)c2cccnc2)O3)c1]
284 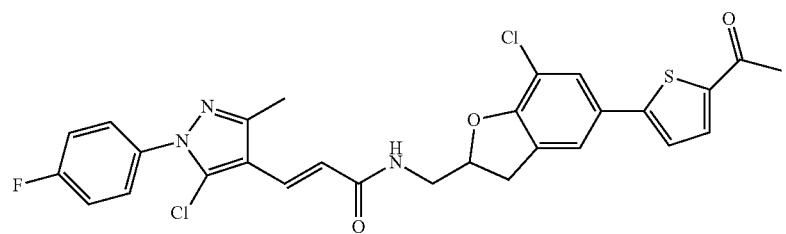
285 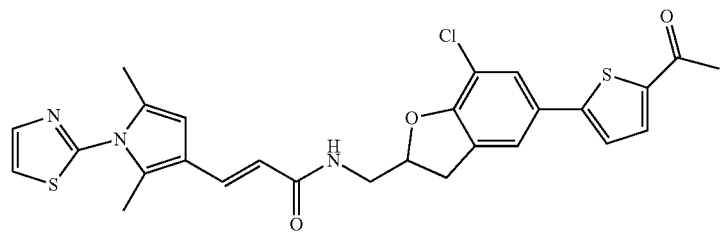 [SMILES: CC(=O)c1ccc(-c2cc(Cl)c3c(c2)CC(CNC(=O)/C=C/c2cc(C)n(-c4nccs4)c2C)O3)s1]
200 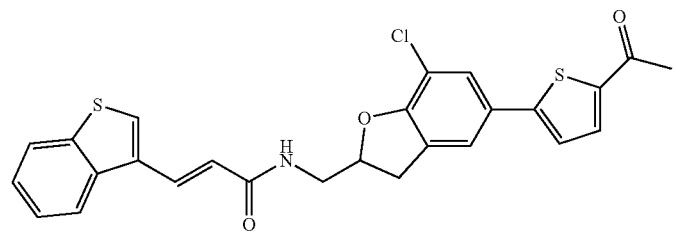 [SMILES: CC(=O)c1ccc(-c2cc(Cl)c3c(c2)CC(CNC(=O)/C=C/c2csc4ccccc24)O3)s1]
286[1] 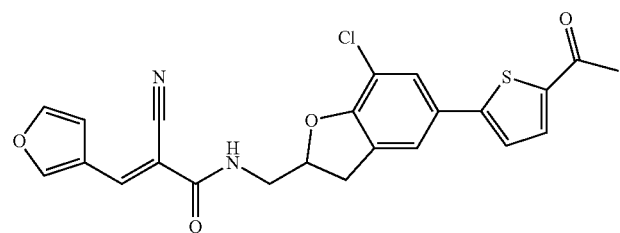 [SMILES: CC(=O)c1ccc(-c2cc(Cl)c3c(c2)CC(CNC(=O)/C(C#N)=C/c2ccoc2)O3)s1]

TABLE 2-continued
| | |
|---|---|
| 201 | 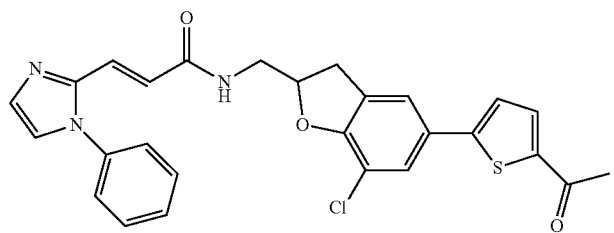 [SMILES: CC(=O)c1ccc(-c2cc(Cl)c3c(c2)CC(CNC(=O)/C=C/c2nccn2-c2ccccc2)O3)s1] |
| 287 | 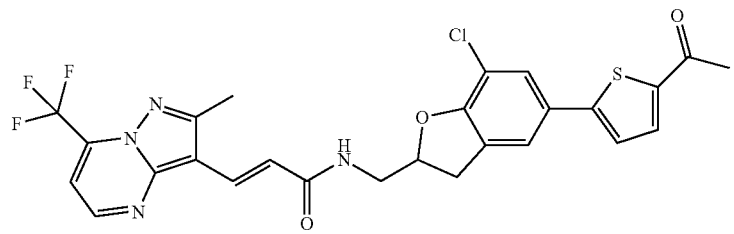 [SMILES: CC(=O)c1ccc(-c2cc(Cl)c3c(c2)CC(CNC(=O)/C=C/c2c(C)nn4c(C(F)(F)F)ccnc24)O3)s1] |
| 288 | 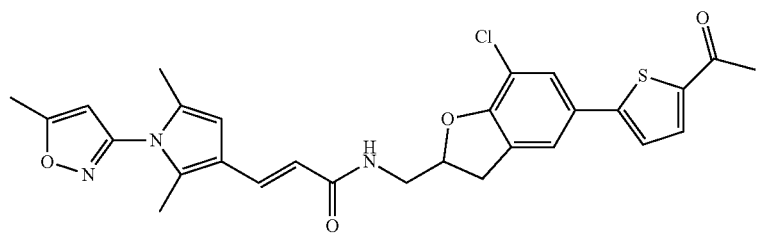 [SMILES: CC(=O)c1ccc(-c2cc(Cl)c3c(c2)CC(CNC(=O)/C=C/c2cc(C)n(-c4cc(C)on4)c2C)O3)s1] |
| 289 | 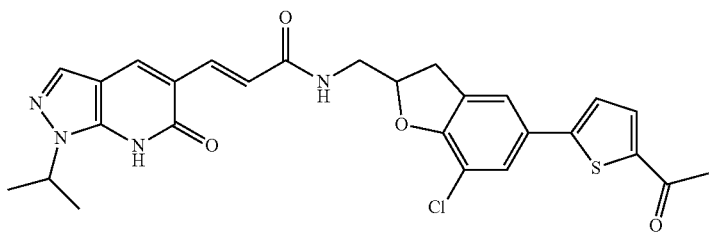 [SMILES: CC(=O)c1ccc(-c2cc(Cl)c3c(c2)CC(CNC(=O)/C=C/c2cc4cnn(C(C)C)c4[nH]c2=O)O3)s1] |
| 205 | 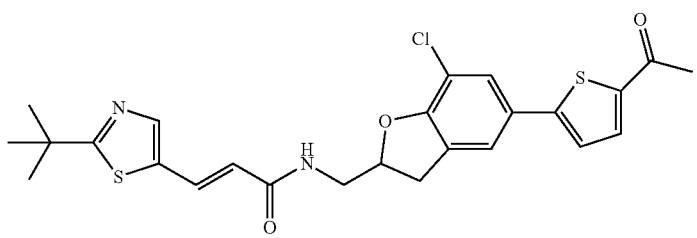 [SMILES: CC(=O)c1ccc(-c2cc(Cl)c3c(c2)CC(CNC(=O)/C=C/c2cnc(C(C)(C)C)s2)O3)s1] |
| 206 | 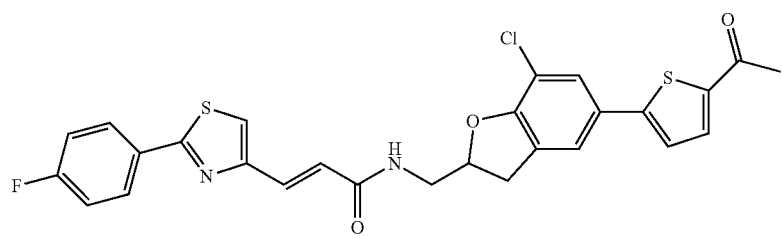 [SMILES: CC(=O)c1ccc(-c2cc(Cl)c3c(c2)CC(CNC(=O)/C=C/c2csc(-c4ccc(F)cc4)n2)O3)s1] |

TABLE 2-continued
207 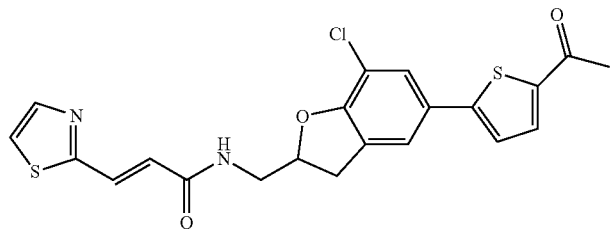 [SMILES: CC(=O)c1ccc(-c2cc(Cl)c3c(c2)CC(CNC(=O)/C=C/c2nccs2)O3)s1]
290 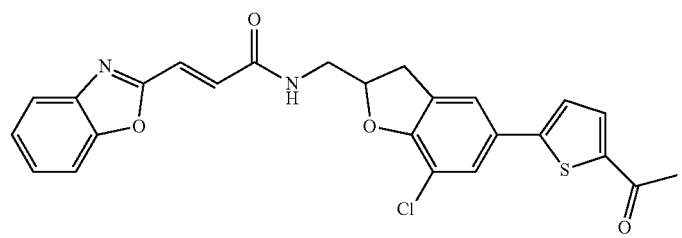 [SMILES: CC(=O)c1ccc(-c2cc(Cl)c3c(c2)CC(CNC(=O)/C=C/c2nc4ccccc4o2)O3)s1]
291 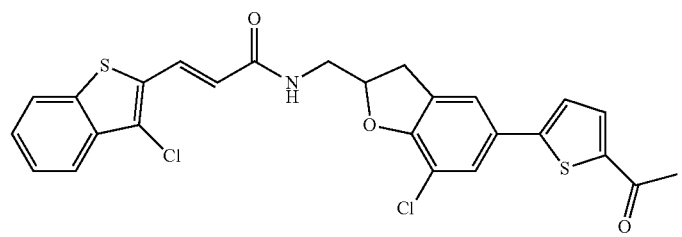 [SMILES: CC(=O)c1ccc(-c2cc(Cl)c3c(c2)CC(CNC(=O)/C=C/c2sc4ccccc4c2Cl)O3)s1]
208 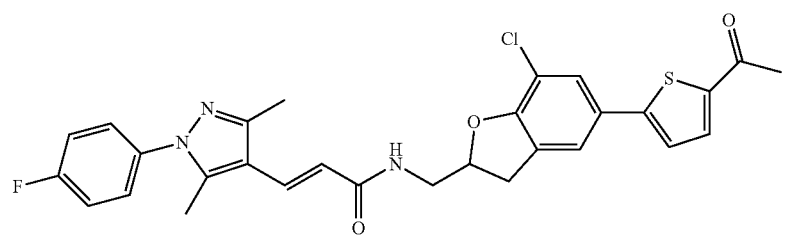 [SMILES: CC(=O)c1ccc(-c2cc(Cl)c3c(c2)CC(CNC(=O)/C=C/c2c(C)nn(-c4ccc(F)cc4)c2C)O3)s1]
292 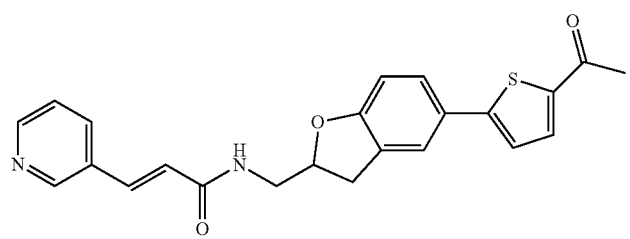 [SMILES: CC(=O)c1ccc(-c2ccc3c(c2)CC(CNC(=O)/C=C/c2cccnc2)O3)s1]
293 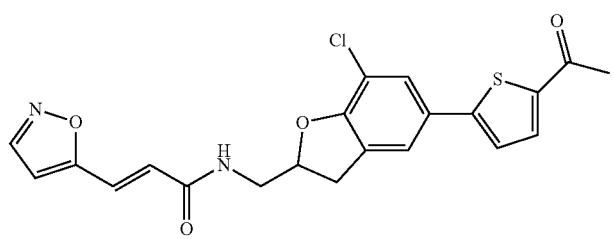 [SMILES: CC(=O)c1ccc(-c2cc(Cl)c3c(c2)CC(CNC(=O)/C=C/c2ccno2)O3)s1]

TABLE 2-continued
| 209 | 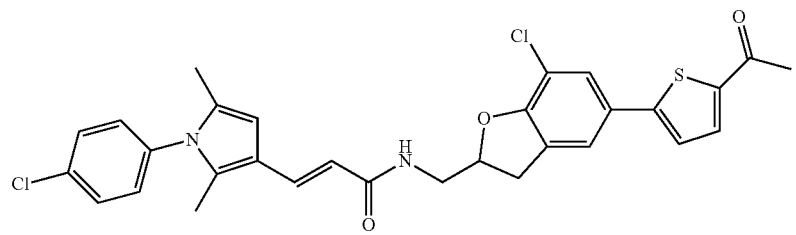 [SMILES: CC(=O)c1ccc(-c2cc(Cl)c3c(c2)CC(CNC(=O)/C=C/c2cc(C)n(-c4ccc(Cl)cc4)c2C)O3)s1] |
| --- | --- |
| 294 | 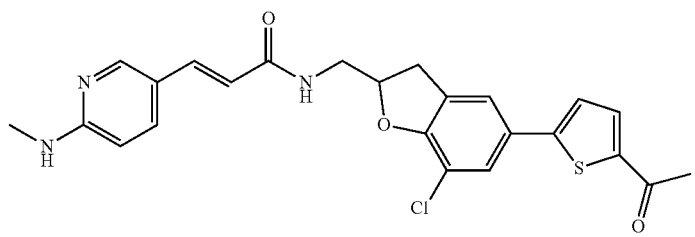 [SMILES: CNc1ccc(/C=C/C(=O)NCC2Cc3cc(-c4ccc(C(C)=O)s4)cc(Cl)c3O2)cn1] |
| 295 | 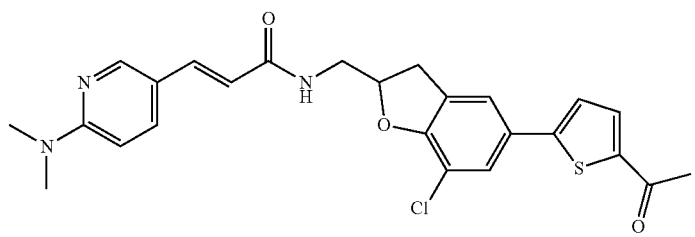 [SMILES: CC(=O)c1ccc(-c2cc(Cl)c3c(c2)CC(CNC(=O)/C=C/c2ccc(N(C)C)nc2)O3)s1] |
| 296 | 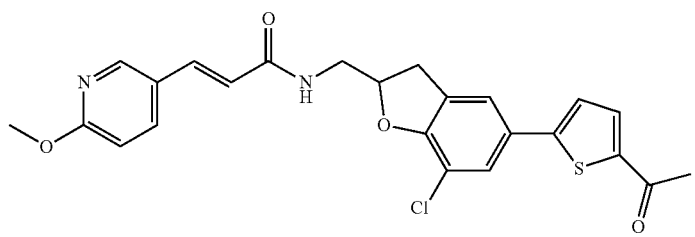 [SMILES: COc1ccc(/C=C/C(=O)NCC2Cc3cc(-c4ccc(C(C)=O)s4)cc(Cl)c3O2)cn1] |
| 210 | 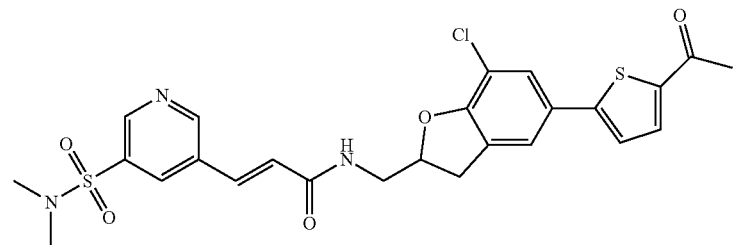 [SMILES: CC(=O)c1ccc(-c2cc(Cl)c3c(c2)CC(CNC(=O)/C=C/c2cncc(S(=O)(=O)N(C)C)c2)O3)s1] |
| 297 | 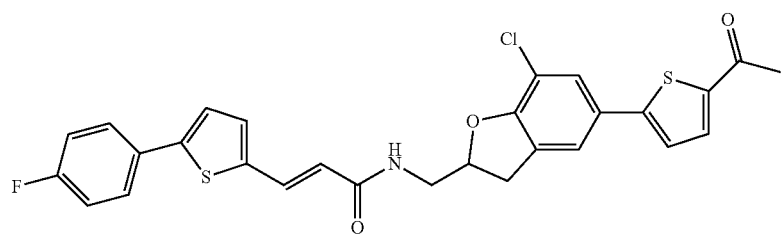 [SMILES: CC(=O)c1ccc(-c2cc(Cl)c3c(c2)CC(CNC(=O)/C=C/c2ccc(-c4ccc(F)cc4)s2)O3)s1] |

US 9,938,258 B2
TABLE 2-continued
298 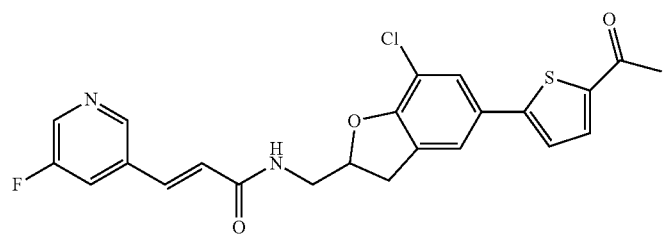 [SMILES: CC(=O)c1ccc(-c2cc(Cl)c3c(c2)CC(CNC(=O)/C=C/c2cncc(F)c2)O3)s1]
211 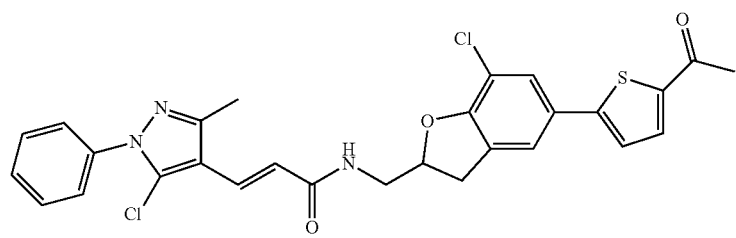 [SMILES: CC(=O)c1ccc(-c2cc(Cl)c3c(c2)CC(CNC(=O)/C=C/c2c(C)nn(-c4ccccc4)c2Cl)O3)s1]
299 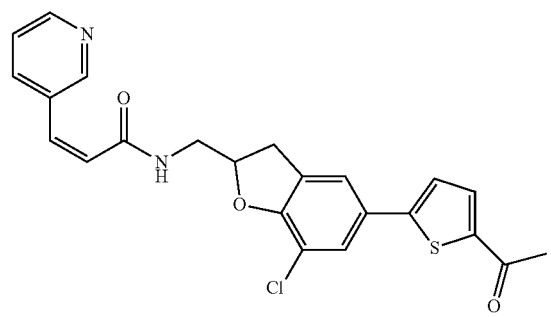 [SMILES: CC(=O)c1ccc(-c2cc(Cl)c3c(c2)CC(CNC(=O)/C=C\c2cccnc2)O3)s1]
212 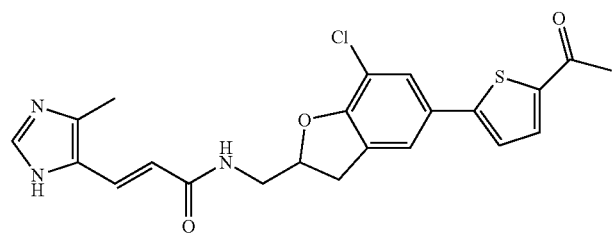 [SMILES: CC(=O)c1ccc(-c2cc(Cl)c3c(c2)CC(CNC(=O)/C=C/c2[nH]cnc2C)O3)s1]
369 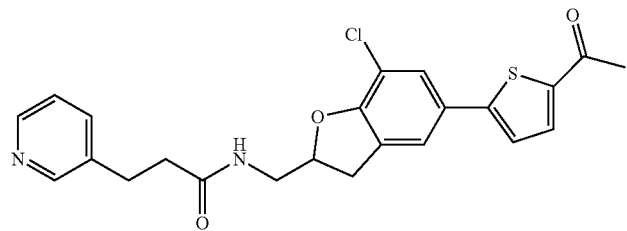 [SMILES: CC(=O)c1ccc(-c2cc(Cl)c3c(c2)CC(CNC(=O)CCc2cccnc2)O3)s1]
300 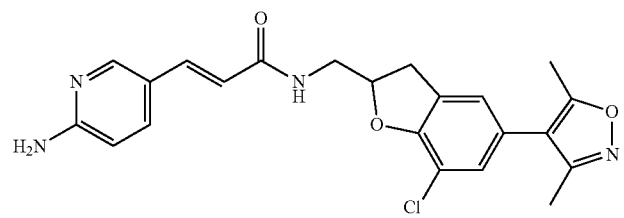 [SMILES: Cc1noc(C)c1-c1cc(Cl)c2c(c1)CC(CNC(=O)/C=C/c1ccc(N)nc1)O2]

TABLE 2-continued
| | |
|---|---|
| 213 | 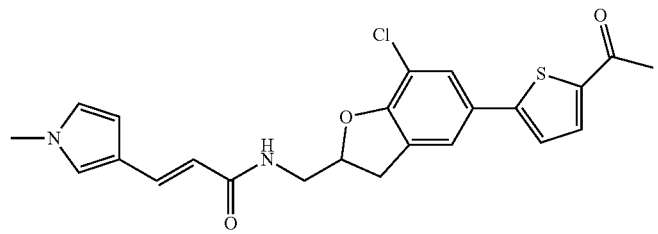 [SMILES: CC(=O)c1ccc(-c2cc(Cl)c3c(c2)CC(CNC(=O)/C=C/c2ccn(C)c2)O3)s1] |
| 218 | 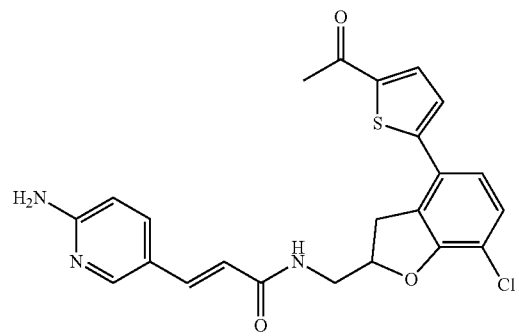 [SMILES: CC(=O)c1ccc(-c2ccc(Cl)c3c2CC(CNC(=O)/C=C/c2ccc(N)nc2)O3)s1] |
| 301 | 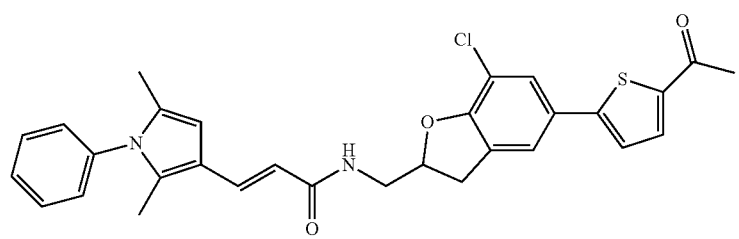 [SMILES: CC(=O)c1ccc(-c2cc(Cl)c3c(c2)CC(CNC(=O)/C=C/c2cc(C)n(-c4ccccc4)c2C)O3)s1] |
| 302 | 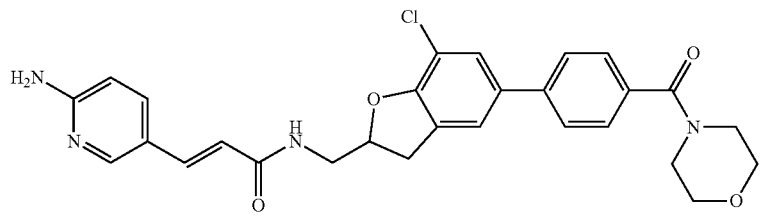 |
| 303 | 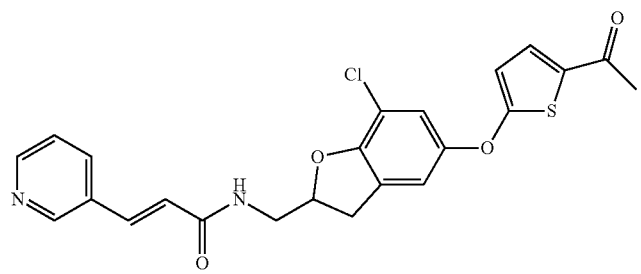 [SMILES: CC(=O)c1ccc(Oc2cc(Cl)c3c(c2)CC(CNC(=O)/C=C/c2cccnc2)O3)s1] |
| 222 | 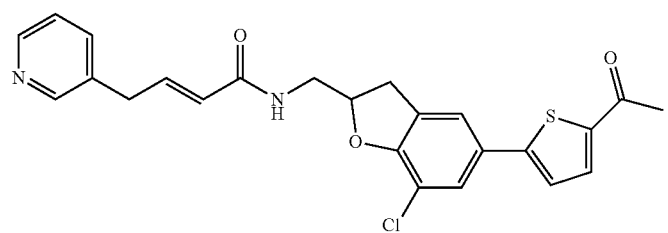 [SMILES: CC(=O)c1ccc(-c2cc(Cl)c3c(c2)CC(CNC(=O)/C=C/Cc2cccnc2)O3)s1] |

TABLE 2-continued
304
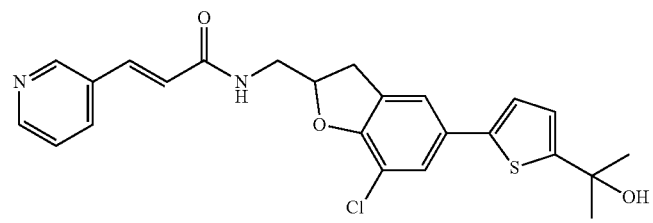 [SMILES: CC(C)(O)c1ccc(-c2cc(Cl)c3c(c2)CC(CNC(=O)/C=C/c2cccnc2)O3)s1]
305
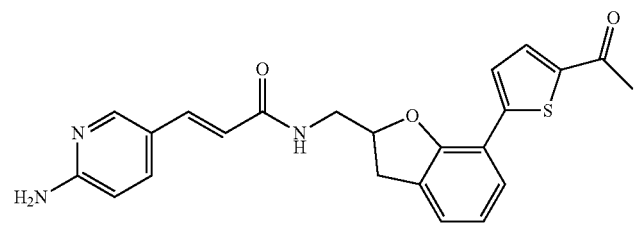 [SMILES: CC(=O)c1ccc(-c2cccc3c2OC(CNC(=O)/C=C/c2ccc(N)nc2)C3)s1]
226
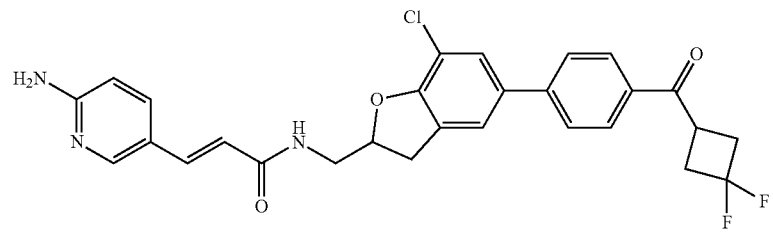 [SMILES: Nc1ccc(/C=C/C(=O)NCC2Cc3cc(-c4ccc(C(=O)C5CC(F)(F)C5)cc4)cc(Cl)c3O2)cn1]
229
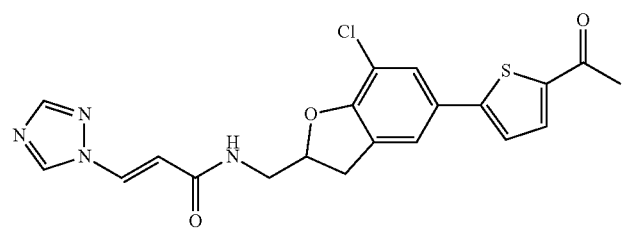 [SMILES: CC(=O)c1ccc(-c2cc(Cl)c3c(c2)CC(CNC(=O)/C=C/n2cncn2)O3)s1]
306
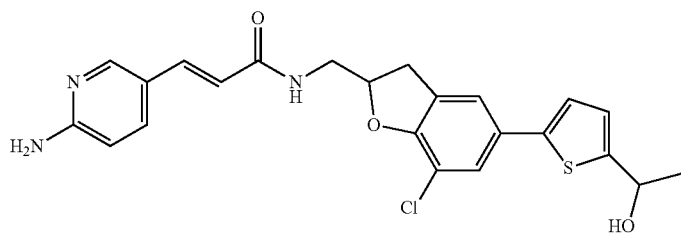 [SMILES: CC(O)c1ccc(-c2cc(Cl)c3c(c2)CC(CNC(=O)/C=C/c2ccc(N)nc2)O3)s1]
233
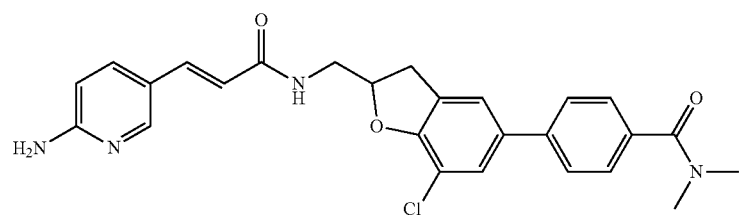 [SMILES: CN(C)C(=O)c1ccc(-c2cc(Cl)c3c(c2)CC(CNC(=O)/C=C/c2ccc(N)nc2)O3)cc1]
234
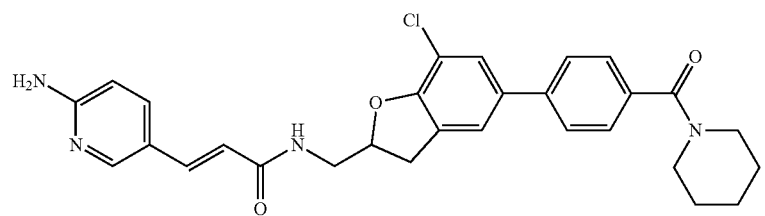

TABLE 2-continued
| | | |
|---|---|---|
| 235 | 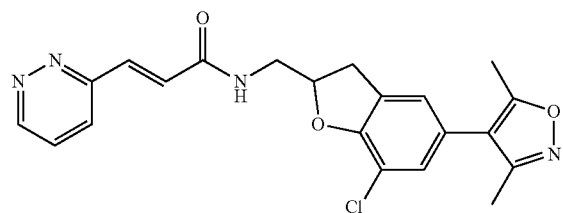 [SMILES: Cc1noc(C)c1-c1cc(Cl)c2c(c1)CC(CNC(=O)/C=C/c1cccnn1)O2] | |
| 236 | 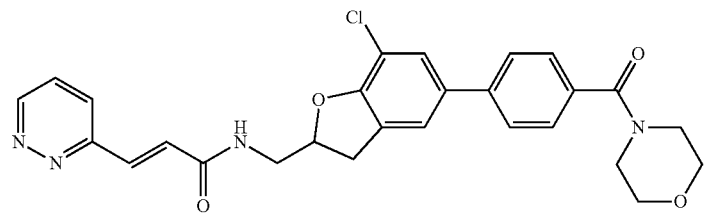 [SMILES: O=C(/C=C/c1cccnn1)NCC1Cc2cc(-c3ccc(C(=O)N4CCOCC4)cc3)cc(Cl)c2O1] | |
| 307 | 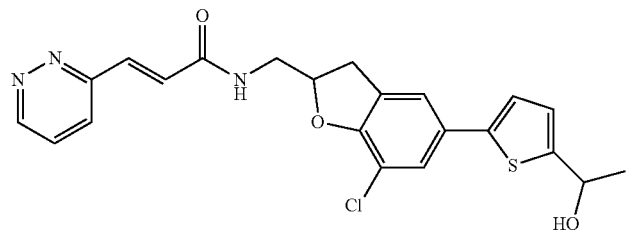 [SMILES: CC(O)c1ccc(-c2cc(Cl)c3c(c2)CC(CNC(=O)/C=C/c2cccnn2)O3)s1] | |
| 237 | 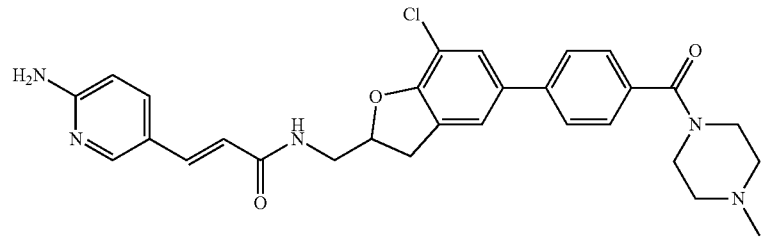 [SMILES: CN1CCN(C(=O)c2ccc(-c3cc(Cl)c4c(c3)CC(CNC(=O)/C=C/c3ccc(N)nc3)O4)cc2)CC1] | |
| 308[2] | 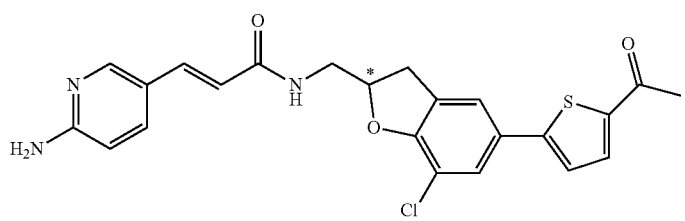 | |
| | isomer 1<br>Rt = 5.78 min | |
| 309[2] | 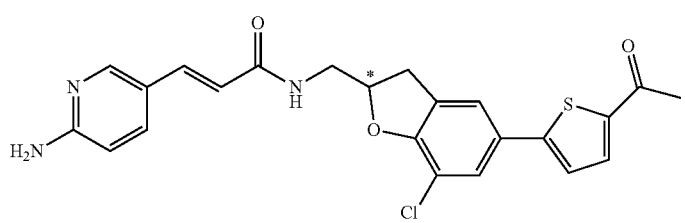 | |
| | isomer 2<br>Rt = 6.67 min | |

| | |
|---|---|
| 310 | 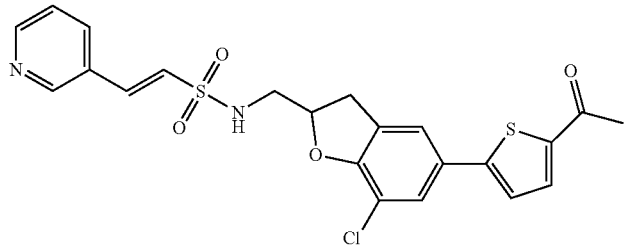 [SMILES: CC(=O)c1ccc(-c2cc(Cl)c3c(c2)CC(CNS(=O)(=O)/C=C/c2cccnc2)O3)s1] |
| 311 | 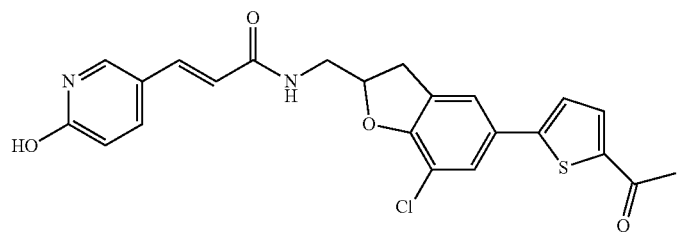 [SMILES: CC(=O)c1ccc(-c2cc(Cl)c3c(c2)CC(CNC(=O)/C=C/c2ccc(O)nc2)O3)s1] |
| 312[2] | 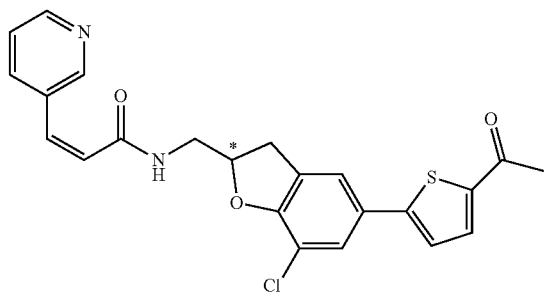<br>isomer 1<br>Rt = 9.55 min |
| 313[2] | 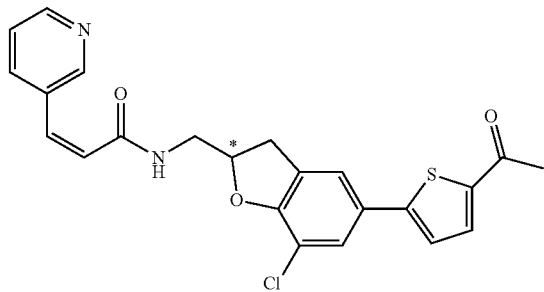<br>isomer 2<br>Rt = 8.84 min |
| 238 | 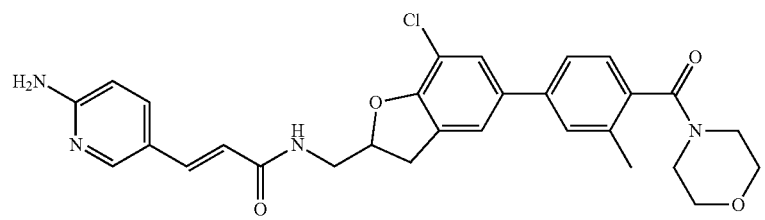 [SMILES: Cc1cc(-c2cc(Cl)c3c(c2)CC(CNC(=O)/C=C/c2ccc(N)nc2)O3)ccc1C(=O)N1CCOCC1] |

TABLE 2-continued
| 239 | 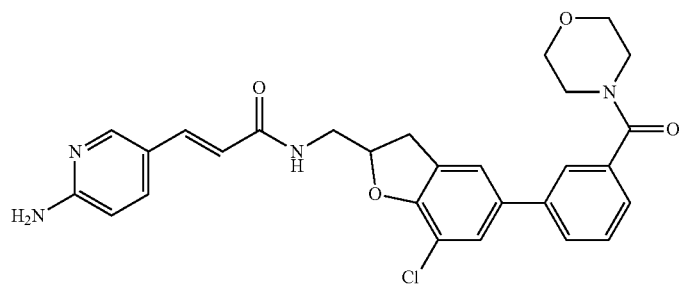 [SMILES: Nc1ccc(/C=C/C(=O)NCC2Cc3cc(-c4cccc(C(=O)N5CCOCC5)c4)cc(Cl)c3O2)cn1] |
| --- | --- |
| 314 | 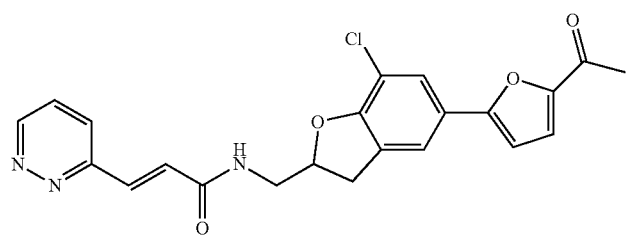 [SMILES: CC(=O)c1ccc(-c2cc(Cl)c3c(c2)CC(CNC(=O)/C=C/c2cccnn2)O3)o1] |
| 315 | 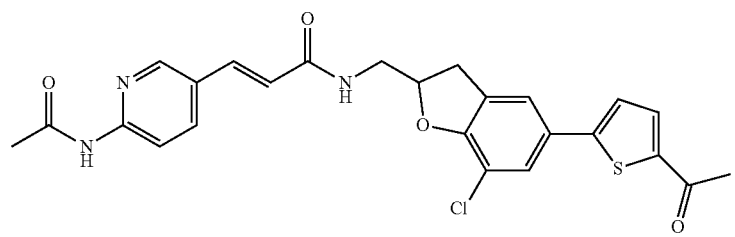 [SMILES: CC(=O)Nc1ccc(/C=C/C(=O)NCC2Cc3cc(-c4ccc(C(C)=O)s4)cc(Cl)c3O2)cn1] |
| 240 | 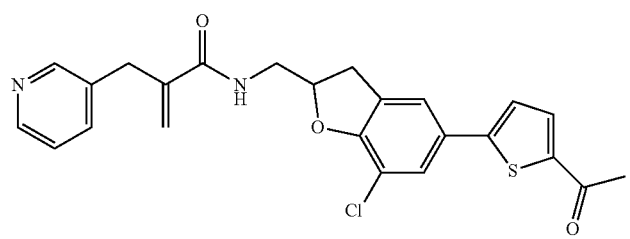 [SMILES: C=C(Cc1cccnc1)C(=O)NCC1Cc2cc(-c3ccc(C(C)=O)s3)cc(Cl)c2O1] |
| 316 | 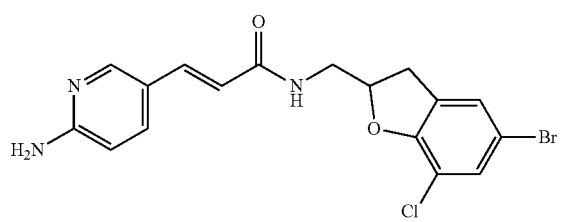 [SMILES: Nc1ccc(/C=C/C(=O)NCC2Cc3cc(Br)cc(Cl)c3O2)cn1] |
| 317[2] | 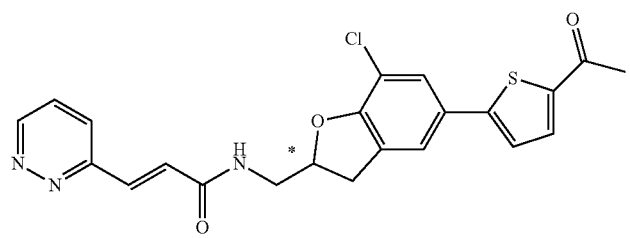<br>isomer 1<br>Rt = 16.53 min |

TABLE 2-continued
318[2]
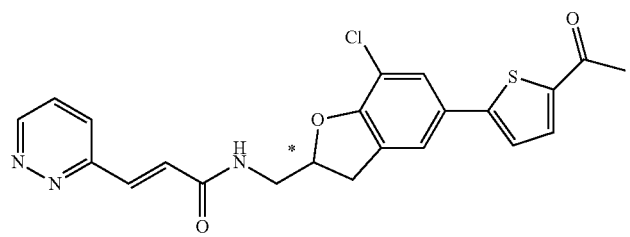
isomer 2
Rt = 30.13 min
246
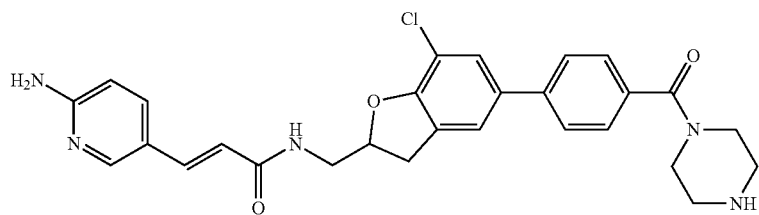
319
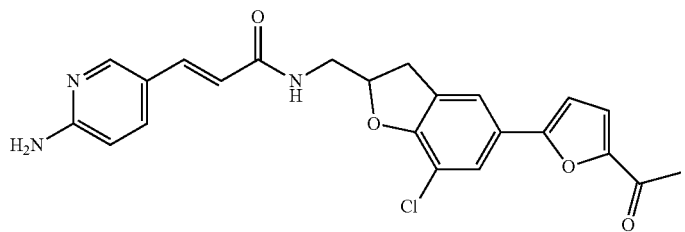 [SMILES: CC(=O)c1ccc(-c2cc(Cl)c3c(c2)CC(CNC(=O)/C=C/c2ccc(N)nc2)O3)o1]
248
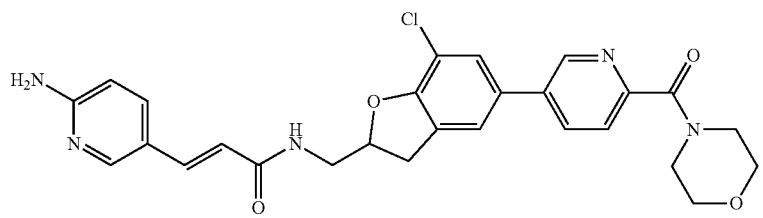 [SMILES: Nc1ccc(/C=C/C(=O)NCC2Cc3cc(-c4ccc(C(=O)N5CCOCC5)nc4)cc(Cl)c3O2)cn1]
320
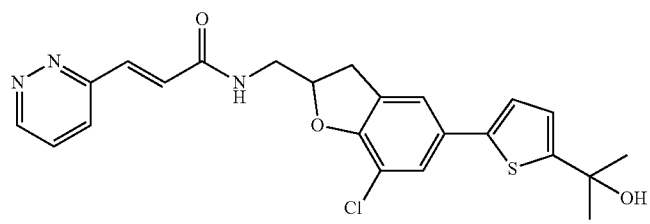 [SMILES: CC(C)(O)c1ccc(-c2cc(Cl)c3c(c2)CC(CNC(=O)/C=C/c2cccnn2)O3)s1]
321
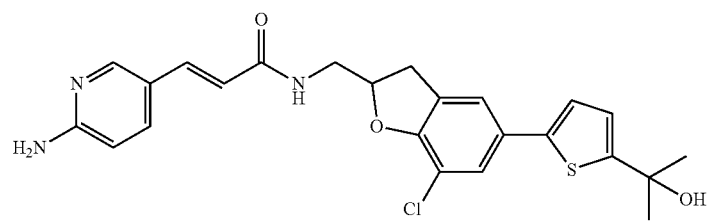 [SMILES: CC(C)(O)c1ccc(-c2cc(Cl)c3c(c2)CC(CNC(=O)/C=C/c2ccc(N)nc2)O3)s1]

TABLE 2-continued
| | |
|---|---|
| 322 | 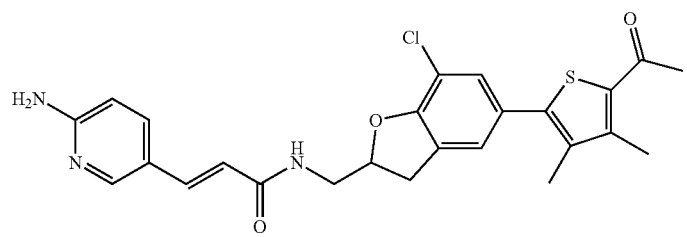 [SMILES: CC(=O)c1sc(-c2cc(Cl)c3c(c2)CC(CNC(=O)/C=C/c2ccc(N)nc2)O3)c(C)c1C] |
| 249 | 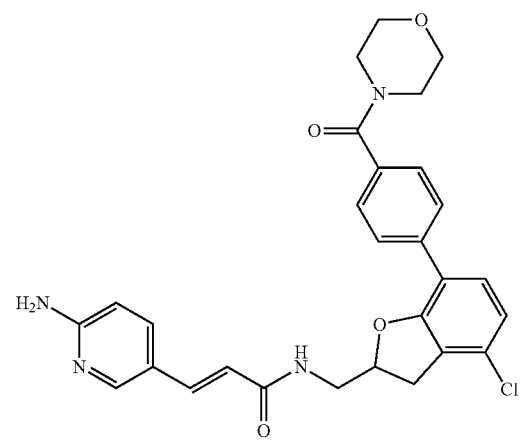 [SMILES: Nc1ccc(/C=C/C(=O)NCC2Cc3c(Cl)ccc(-c4ccc(C(=O)N5CCOCC5)cc4)c3O2)cn1] |
| 323 | 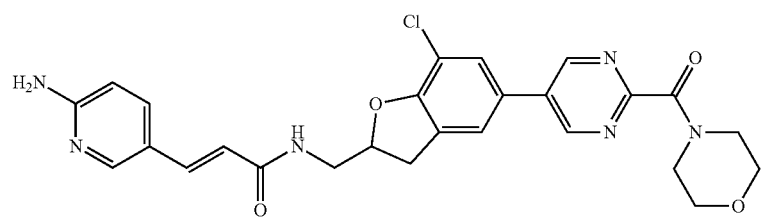 [SMILES: Nc1ccc(/C=C/C(=O)NCC2Cc3cc(-c4cnc(C(=O)N5CCOCC5)nc4)cc(Cl)c3O2)cn1] |
| 324 | 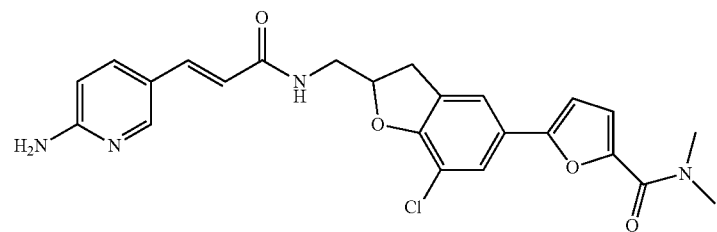 [SMILES: CN(C)C(=O)c1ccc(-c2cc(Cl)c3c(c2)CC(CNC(=O)/C=C/c2ccc(N)nc2)O3)o1] |
| 371 | 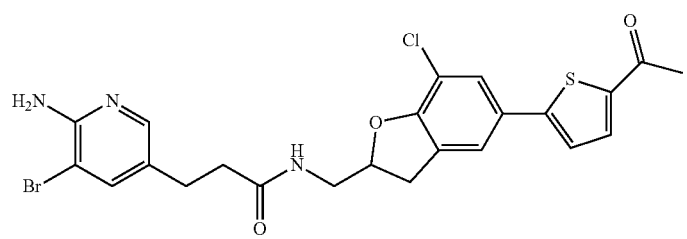 [SMILES: CC(=O)c1ccc(-c2cc(Cl)c3c(c2)CC(CNC(=O)CCc2cnc(N)c(Br)c2)O3)s1] |

TABLE 2-continued
325 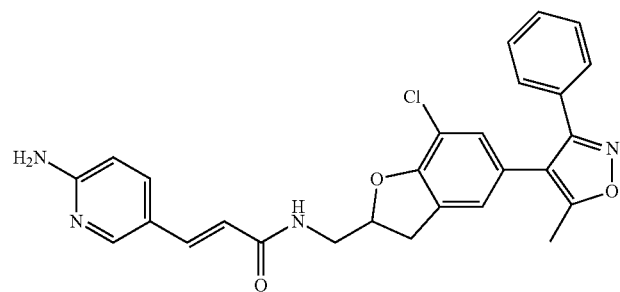 [SMILES: Cc1onc(-c2ccccc2)c1-c1cc(Cl)c2c(c1)CC(CNC(=O)/C=C/c1ccc(N)nc1)O2]
326 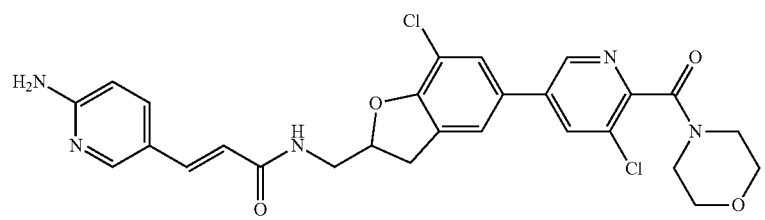 [SMILES: Nc1ccc(/C=C/C(=O)NCC2Cc3cc(-c4cnc(C(=O)N5CCOCC5)c(Cl)c4)cc(Cl)c3O2)cn1]
327 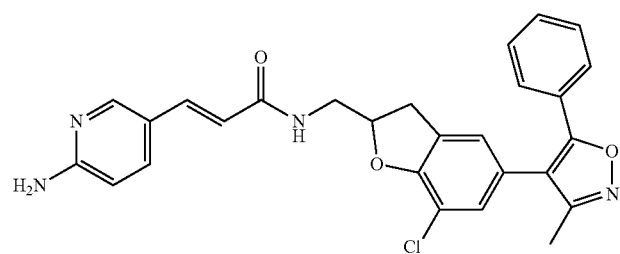 [SMILES: Cc1noc(-c2ccccc2)c1-c1cc(Cl)c2c(c1)CC(CNC(=O)/C=C/c1ccc(N)nc1)O2]
328 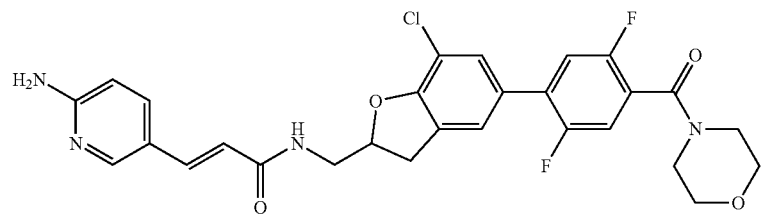
329 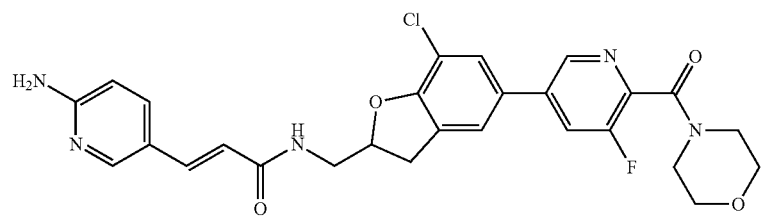 [SMILES: Nc1ccc(/C=C/C(=O)NCC2Cc3cc(-c4cnc(C(=O)N5CCOCC5)c(F)c4)cc(Cl)c3O2)cn1]
330 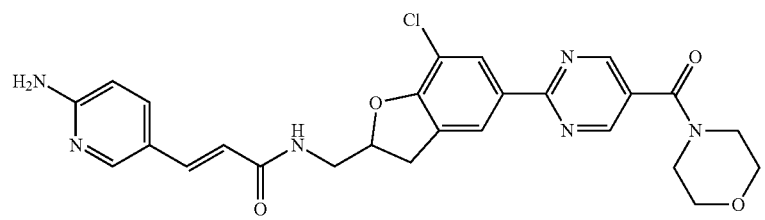

TABLE 2-continued
| | |
|---|---|
| 331 | 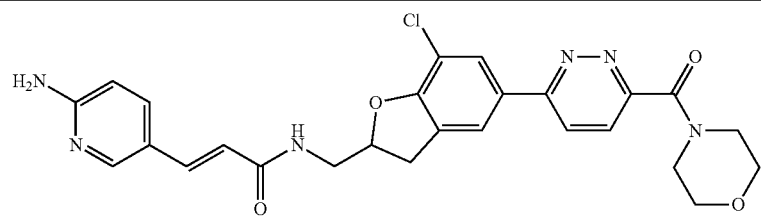 |
| 332 | 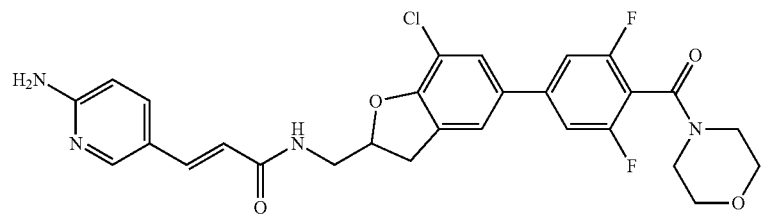 |
| 333 | 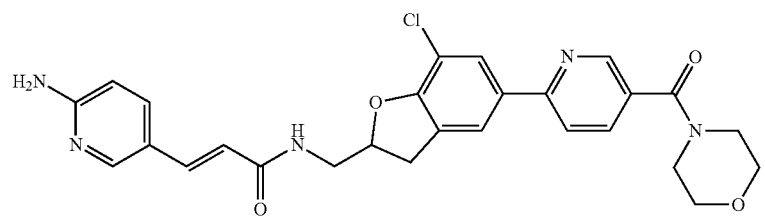 |
| 334 | 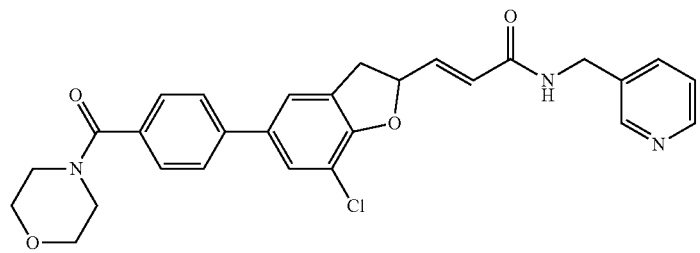 [SMILES: O=C(/C=C/C1Cc2cc(-c3ccc(C(=O)N4CCOCC4)cc3)cc(Cl)c2O1)NCc1cccnc1] |
| 335 | 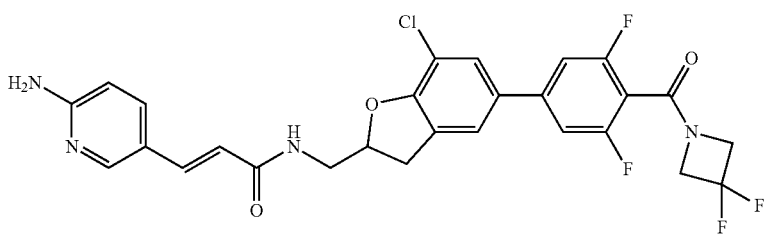 [SMILES: Nc1ccc(/C=C/C(=O)NCC2Cc3cc(-c4cc(F)c(C(=O)N5CC(F)(F)C5)c(F)c4)cc(Cl)c3O2)cn1] |
| 336 | 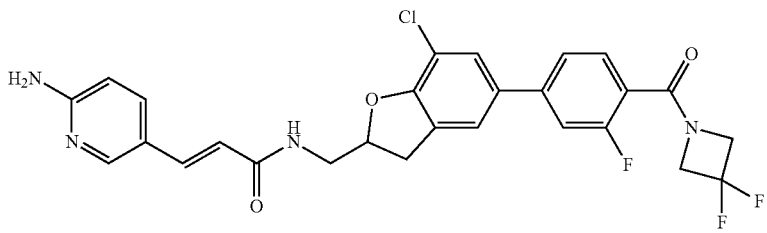 [SMILES: Nc1ccc(/C=C/C(=O)NCC2Cc3cc(-c4ccc(C(=O)N5CC(F)(F)C5)c(F)c4)cc(Cl)c3O2)cn1] |
| 337 | 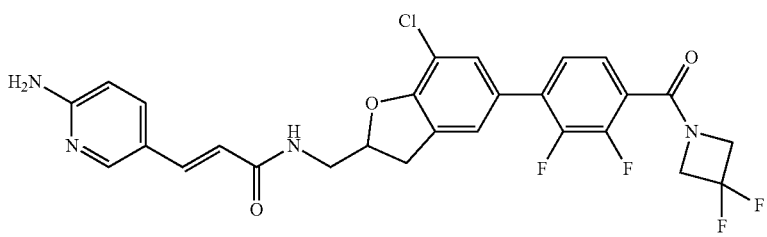 [SMILES: Nc1ccc(/C=C/C(=O)NCC2Cc3cc(-c4ccc(C(=O)N5CC(F)(F)C5)c(F)c4F)cc(Cl)c3O2)cn1] |

TABLE 2-continued
338 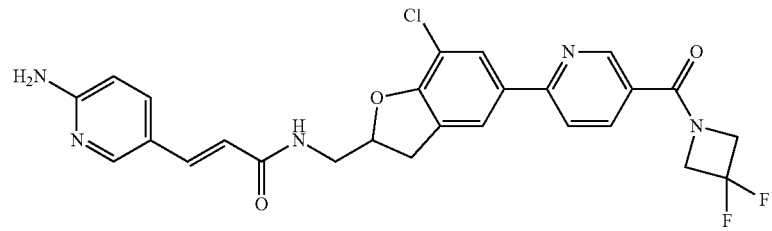 [SMILES: Nc1ccc(/C=C/C(=O)NCC2Cc3cc(-c4ccc(C(=O)N5CC(F)(F)C5)cn4)cc(Cl)c3O2)cn1]
339 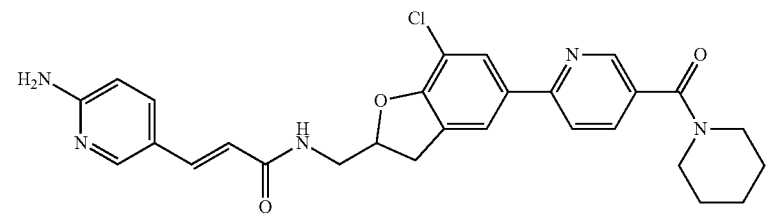
340 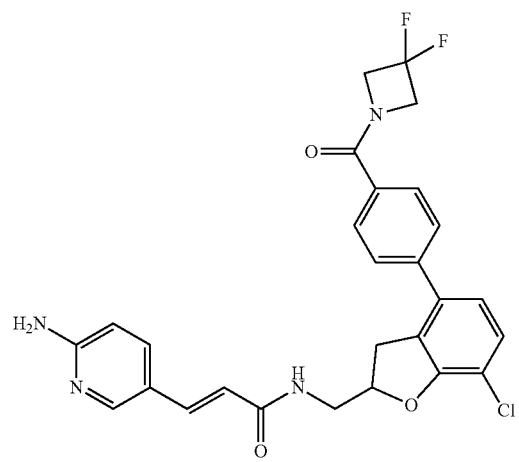 [SMILES: Nc1ccc(/C=C/C(=O)NCC2Cc3c(-c4ccc(C(=O)N5CC(F)(F)C5)cc4)ccc(Cl)c3O2)cn1]
341 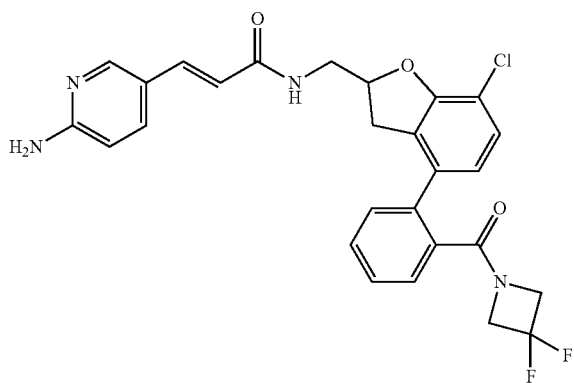 [SMILES: Nc1ccc(/C=C/C(=O)NCC2Cc3c(-c4ccccc4C(=O)N4CC(F)(F)C4)ccc(Cl)c3O2)cn1]
342 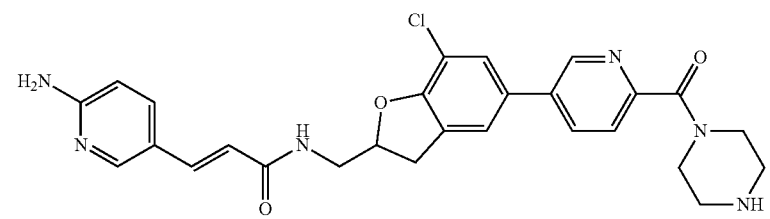 [SMILES: Nc1ccc(/C=C/C(=O)NCC2Cc3cc(-c4ccc(C(=O)N5CCNCC5)nc4)cc(Cl)c3O2)cn1]

TABLE 2-continued
343 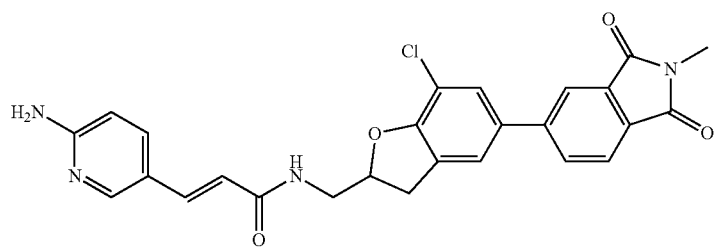 [SMILES: CN1C(=O)c2ccc(-c3cc(Cl)c4c(c3)CC(CNC(=O)/C=C/c3ccc(N)nc3)O4)cc2C1=O]
344 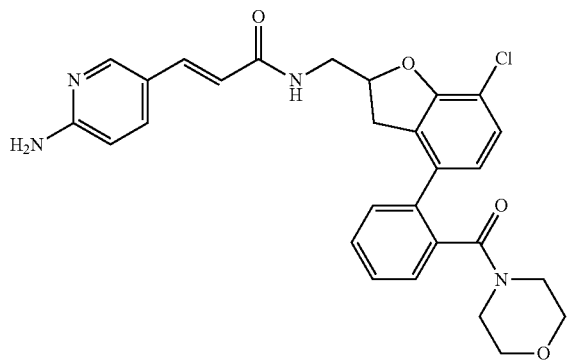 [SMILES: Nc1ccc(/C=C/C(=O)NCC2Cc3c(-c4ccccc4C(=O)N4CCOCC4)ccc(Cl)c3O2)cn1]
345 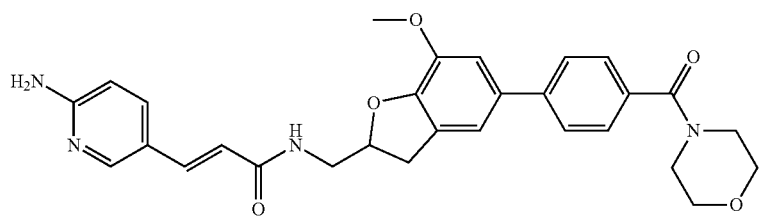
346 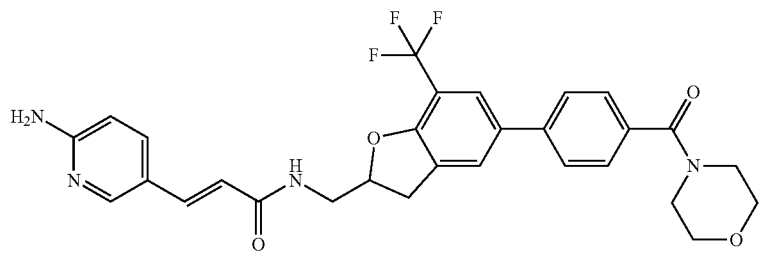 [SMILES: Nc1ccc(/C=C/C(=O)NCC2Cc3cc(-c4ccc(C(=O)N5CCOCC5)cc4)cc(C(F)(F)F)c3O2)cn1]
347 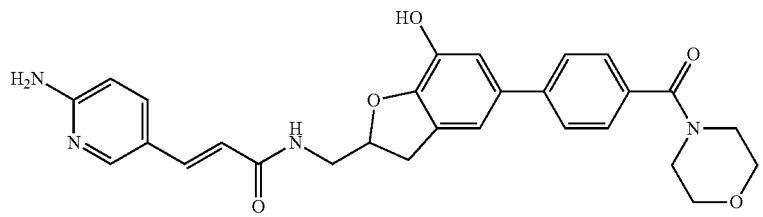 [SMILES: Nc1ccc(/C=C/C(=O)NCC2Cc3cc(-c4ccc(C(=O)N5CCOCC5)cc4)cc(O)c3O2)cn1]
348 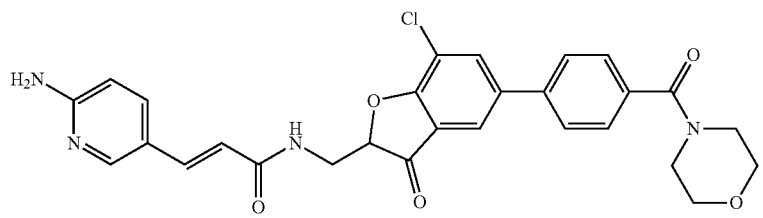 [SMILES: Nc1ccc(/C=C/C(=O)NCC2Oc3c(Cl)cc(-c4ccc(C(=O)N5CCOCC5)cc4)cc3C2=O)cn1]

TABLE 2-continued
349
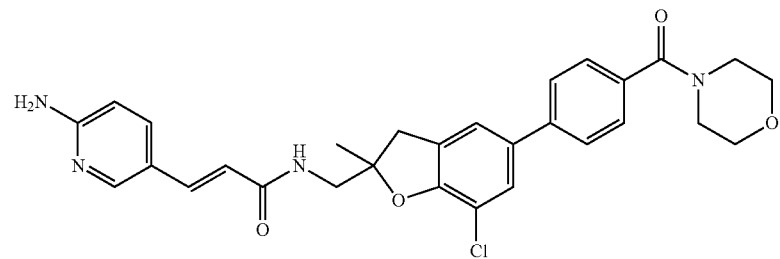 [SMILES: CC1(CNC(=O)/C=C/c2ccc(N)nc2)Cc2cc(-c3ccc(C(=O)N4CCOCC4)cc3)cc(Cl)c2O1]
350
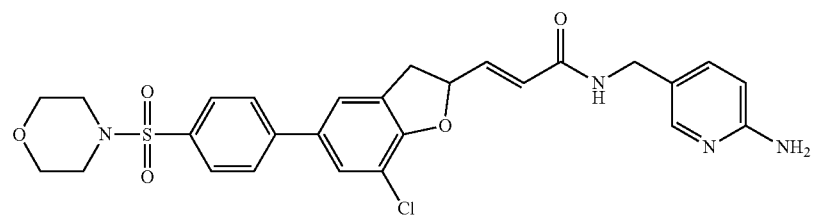 [SMILES: Nc1ccc(CNC(=O)/C=C/C2Cc3cc(-c4ccc(S(=O)(=O)N5CCOCC5)cc4)cc(Cl)c3O2)cn1]
351
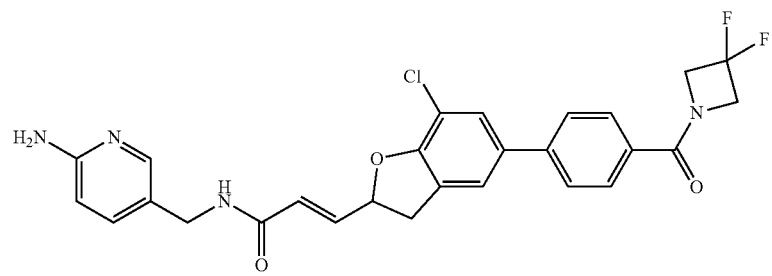 [SMILES: Nc1ccc(CNC(=O)/C=C/C2Cc3cc(-c4ccc(C(=O)N5CC(F)(F)C5)cc4)cc(Cl)c3O2)cn1]
352
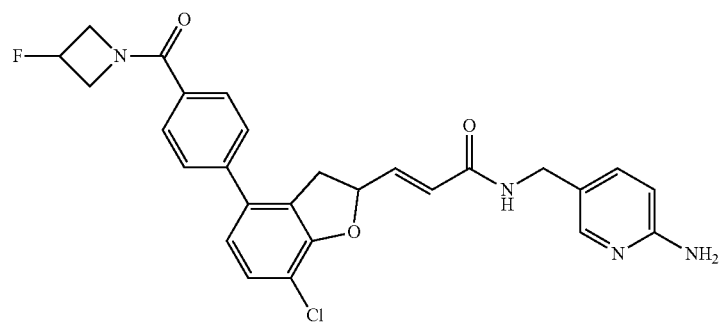 [SMILES: Nc1ccc(CNC(=O)/C=C/C2Cc3c(-c4ccc(C(=O)N5CC(F)C5)cc4)ccc(Cl)c3O2)cn1]
354
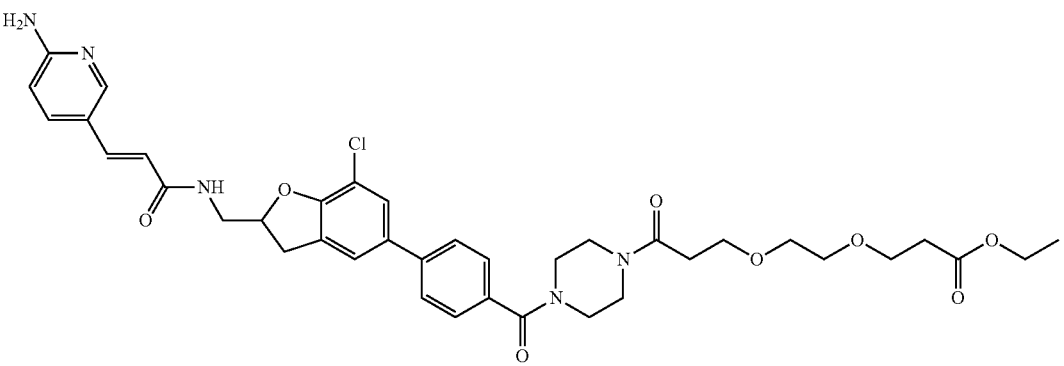 [SMILES: CCOC(=O)CCOCCOCCC(=O)N1CCN(C(=O)c2ccc(-c3cc(Cl)c4c(c3)CC(CNC(=O)/C=C/c3ccc(N)nc3)O4)cc2)CC1]

TABLE 2-continued
355 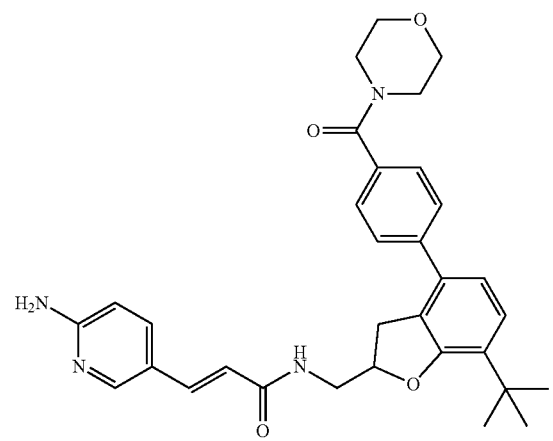 [SMILES: CC(C)(C)c1ccc(-c2ccc(C(=O)N3CCOCC3)cc2)c2c1OC(CNC(=O)/C=C/c1ccc(N)nc1)C2]
357 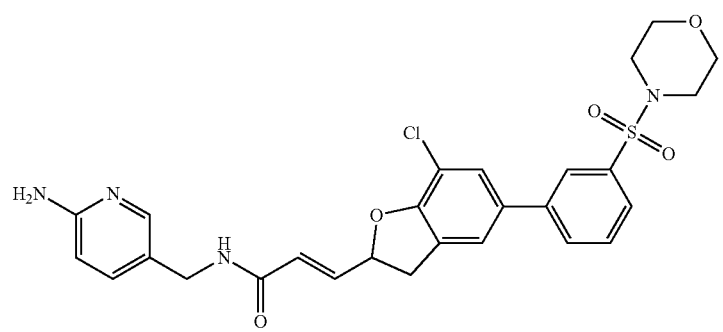 [SMILES: Nc1ccc(CNC(=O)/C=C/C2Cc3cc(-c4cccc(S(=O)(=O)N5CCOCC5)c4)cc(Cl)c3O2)cn1]
358 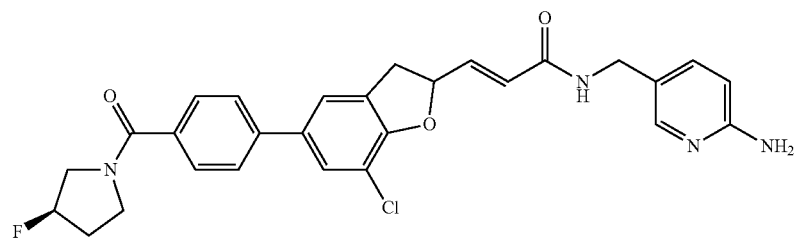 [SMILES: Nc1ccc(CNC(=O)/C=C/C2Cc3cc(-c4ccc(C(=O)N5CC[C@@H](F)C5)cc4)cc(Cl)c3O2)cn1]
359 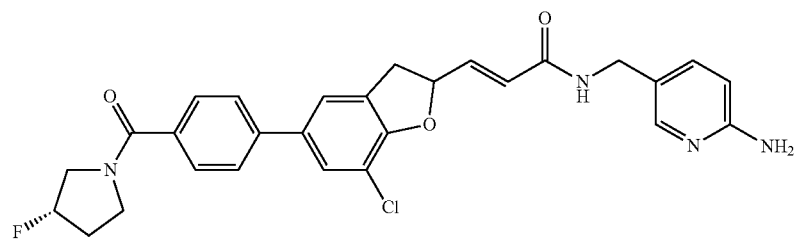 [SMILES: Nc1ccc(CNC(=O)/C=C/C2Cc3cc(-c4ccc(C(=O)N5CC[C@H](F)C5)cc4)cc(Cl)c3O2)cn1]
360 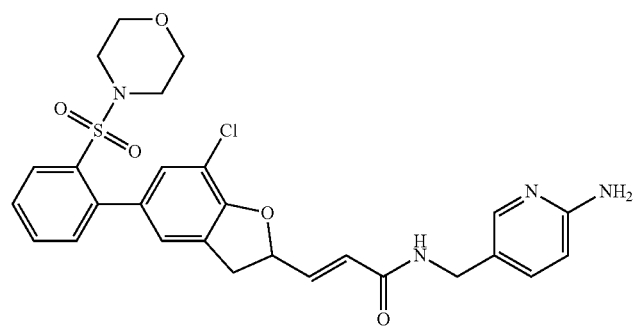 [SMILES: Nc1ccc(CNC(=O)/C=C/C2Cc3cc(-c4ccccc4S(=O)(=O)N4CCOCC4)cc(Cl)c3O2)cn1]

US 9,938,258 B2
473
474
TABLE 2-continued
361 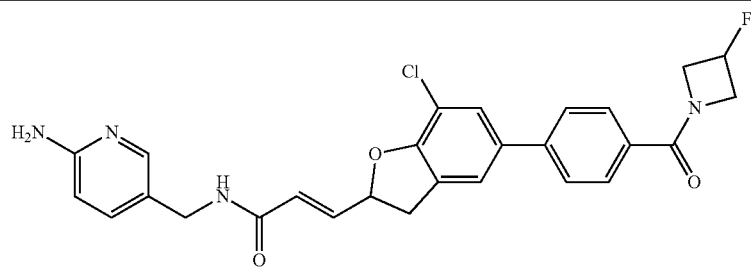
362 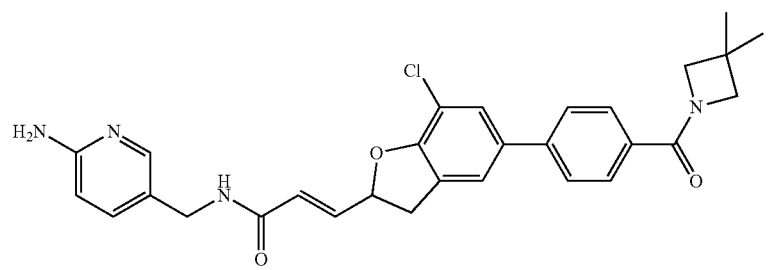 [SMILES: CC1(C)CN(C(=O)c2ccc(-c3cc(Cl)c4c(c3)CC(/C=C/C(=O)NCc3ccc(N)nc3)O4)cc2)C1]
363 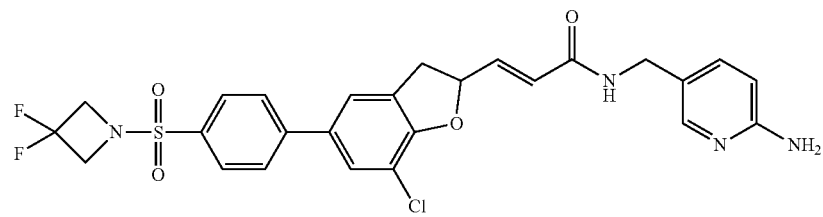 [SMILES: Nc1ccc(CNC(=O)/C=C/C2Cc3cc(-c4ccc(S(=O)(=O)N5CC(F)(F)C5)cc4)cc(Cl)c3O2)cn1]
364 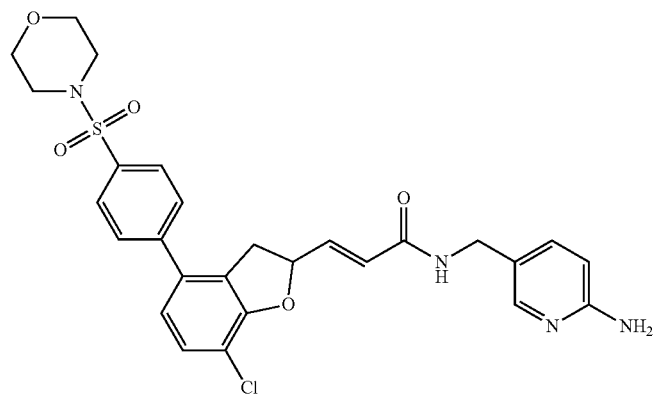 [SMILES: Nc1ccc(CNC(=O)/C=C/C2Cc3c(-c4ccc(S(=O)(=O)N5CCOCC5)cc4)ccc(Cl)c3O2)cn1]
365 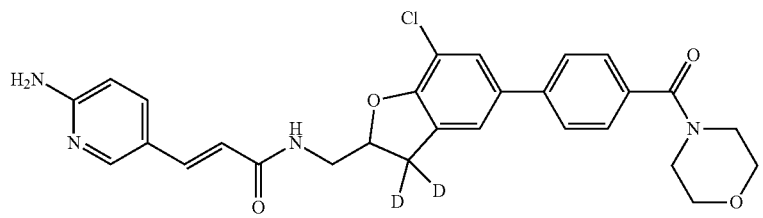 [SMILES: [2H]C1([2H])c2cc(-c3ccc(C(=O)N4CCOCC4)cc3)cc(Cl)c2OC1CNC(=O)/C=C/c1ccc(N)nc1]
366 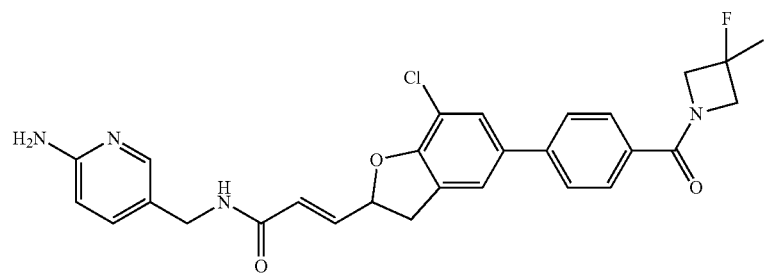 [SMILES: CC1(F)CN(C(=O)c2ccc(-c3cc(Cl)c4c(c3)CC(/C=C/C(=O)NCc3ccc(N)nc3)O4)cc2)C1]

TABLE 2-continued
367
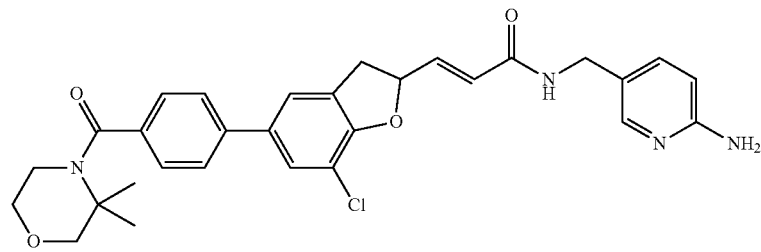 [SMILES: CC1(C)COCCN1C(=O)c1ccc(-c2cc(Cl)c3c(c2)CC(/C=C/C(=O)NCc2ccc(N)nc2)O3)cc1]
368
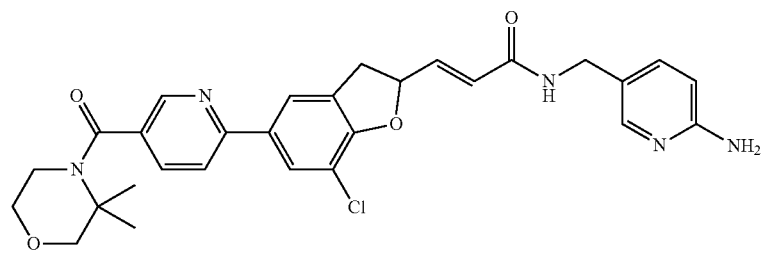 [SMILES: CC1(C)COCCN1C(=O)c1ccc(-c2cc(Cl)c3c(c2)CC(/C=C/C(=O)NCc2ccc(N)nc2)O3)nc1]
901
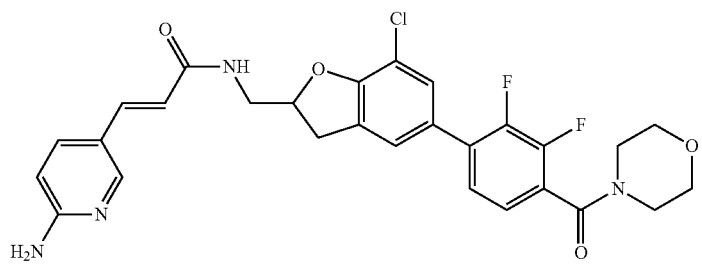 [SMILES: Nc1ccc(/C=C/C(=O)NCC2Cc3cc(-c4ccc(C(=O)N5CCOCC5)c(F)c4F)cc(Cl)c3O2)cn1]
902
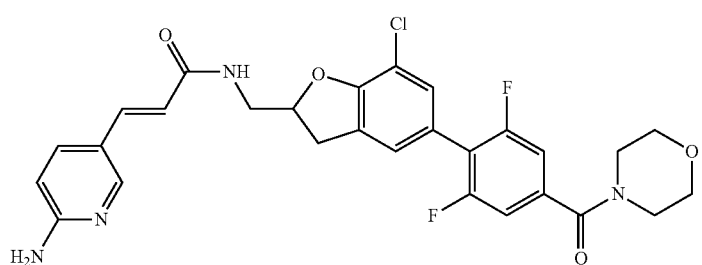 [SMILES: Nc1ccc(/C=C/C(=O)NCC2Cc3cc(-c4c(F)cc(C(=O)N5CCOCC5)cc4F)cc(Cl)c3O2)cn1]
903
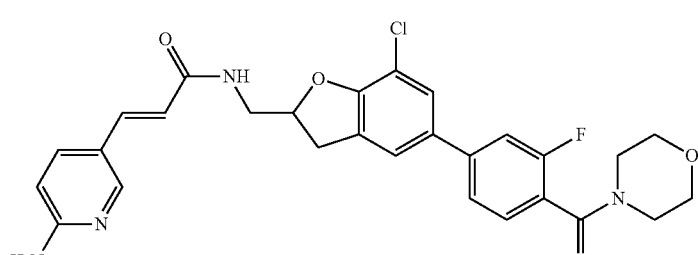
904
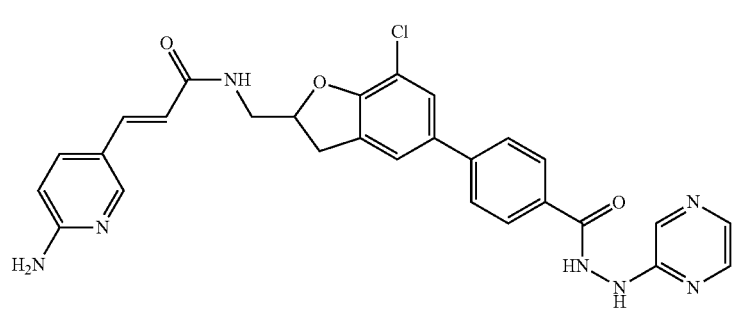 [SMILES: Nc1ccc(/C=C/C(=O)NCC2Cc3cc(-c4ccc(C(=O)NNc5cnccn5)cc4)cc(Cl)c3O2)cn1]

TABLE 2-continued
906 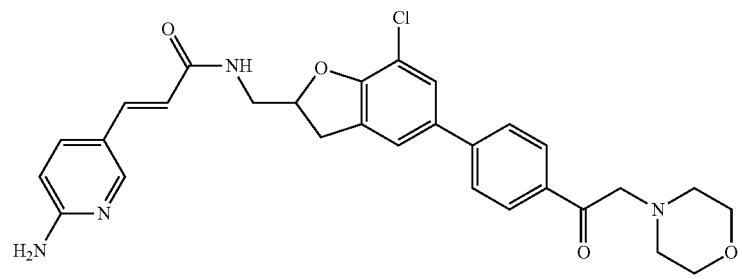 [SMILES: Nc1ccc(/C=C/C(=O)NCC2Cc3cc(-c4ccc(C(=O)CN5CCOCC5)cc4)cc(Cl)c3O2)cn1]
907 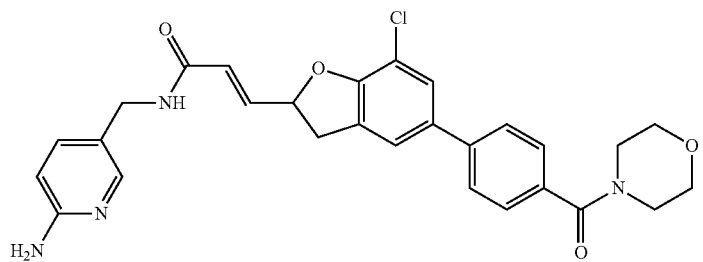 [SMILES: Nc1ccc(CNC(=O)/C=C/C2Cc3cc(-c4ccc(C(=O)N5CCOCC5)cc4)cc(Cl)c3O2)cn1]
908 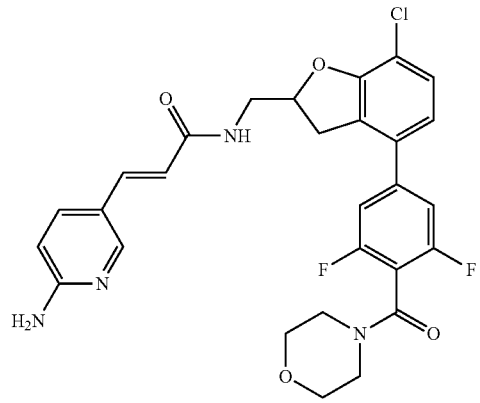 [SMILES: Nc1ccc(/C=C/C(=O)NCC2Cc3c(-c4cc(F)c(C(=O)N5CCOCC5)c(F)c4)ccc(Cl)c3O2)cn1]
909 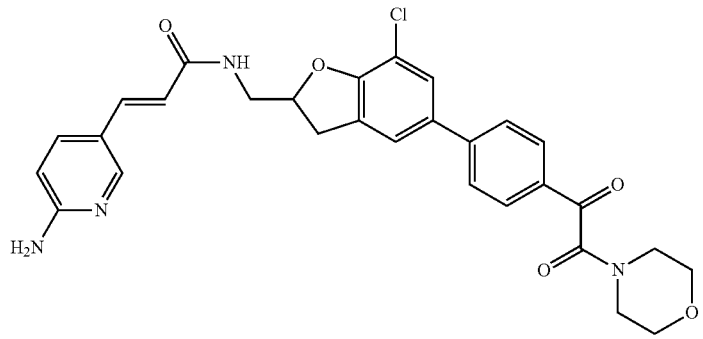 [SMILES: Nc1ccc(/C=C/C(=O)NCC2Cc3cc(-c4ccc(C(=O)C(=O)N5CCOCC5)cc4)cc(Cl)c3O2)cn1]

TABLE 2-continued
910 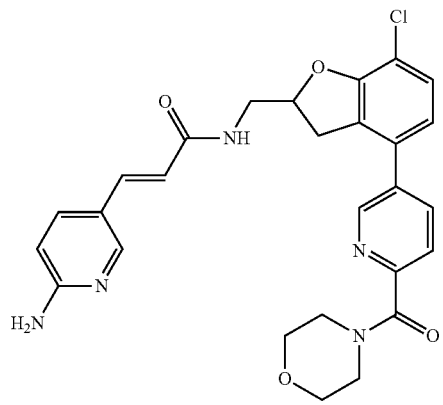 [SMILES: Nc1ccc(/C=C/C(=O)NCC2Cc3c(-c4ccc(C(=O)N5CCOCC5)nc4)ccc(Cl)c3O2)cn1]
911 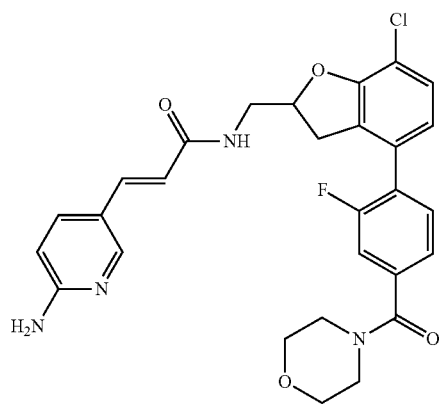 [SMILES: Nc1ccc(/C=C/C(=O)NCC2Cc3c(-c4ccc(C(=O)N5CCOCC5)cc4F)ccc(Cl)c3O2)cn1]
912 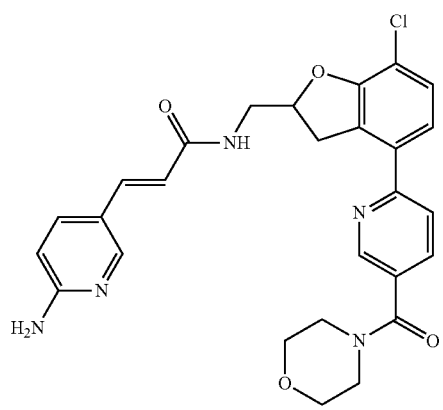 [SMILES: Nc1ccc(/C=C/C(=O)NCC2Cc3c(-c4ccc(C(=O)N5CCOCC5)cn4)ccc(Cl)c3O2)cn1]
913 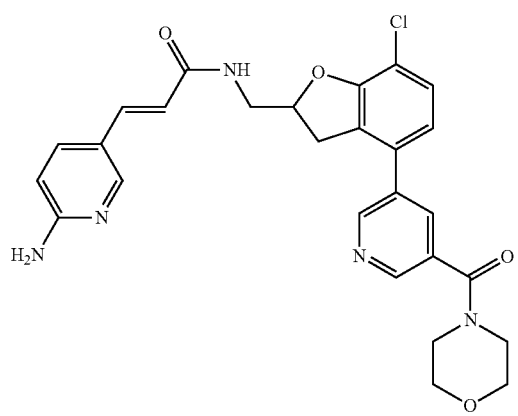 [SMILES: Nc1ccc(/C=C/C(=O)NCC2Cc3c(-c4cncc(C(=O)N5CCOCC5)c4)ccc(Cl)c3O2)cn1]

TABLE 2-continued

914
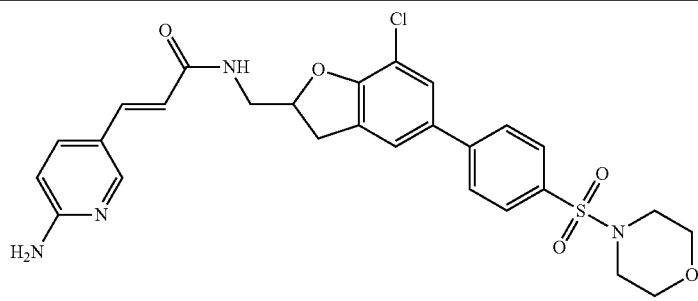

915
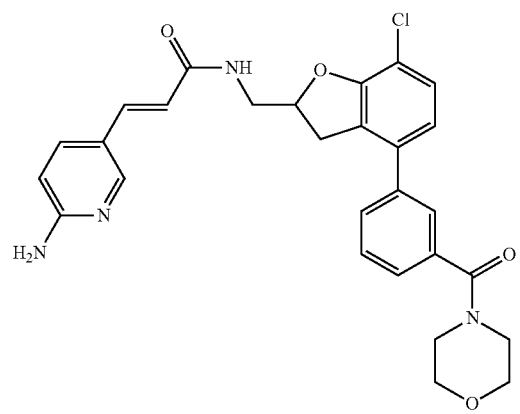 [SMILES: Nc1ccc(/C=C/C(=O)NCC2Cc3c(-c4cccc(C(=O)N5CCOCC5)c4)ccc(Cl)c3O2)cn1]

920
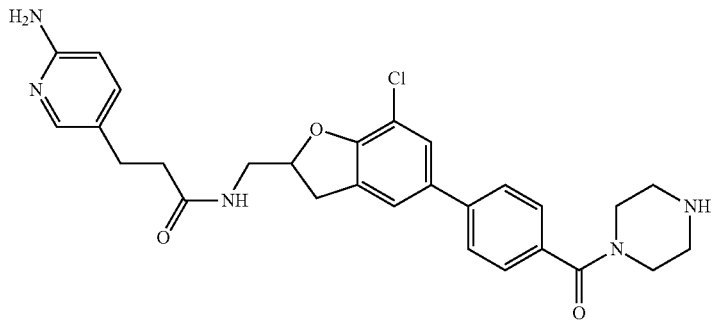 [SMILES: Nc1ccc(CCC(=O)NCC2Cc3cc(-c4ccc(C(=O)N5CCNCC5)cc4)cc(Cl)c3O2)cn1]

921
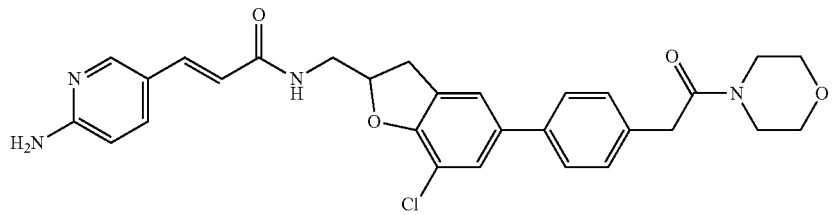 [SMILES: Nc1ccc(/C=C/C(=O)NCC2Cc3cc(-c4ccc(CC(=O)N5CCOCC5)cc4)cc(Cl)c3O2)cn1]

| Compound Number | MS751 | Z138 | 3T3 | Compound Name |
|---|---|---|---|---|
| 15 | B | B | C | (E)-N-((7-chloro-5-(p-tolyl)-2,3-dihydrobenzofuran-2-yl)methyl)-3-(pyridin-3-yl)acrylamide |
| 18 | B | B | C | (E)-N-((7-chloro-5-(2-fluorophenyl)-2,3-dihydrobenzofuran-2-yl)methyl)-3-(pyridin-3-yl)acrylamide |
| 21 | B | B | D | (E)-N-((7-chloro-5-(3,4,5-trifluorophenyl)-2,3-dihydrobenzofuran-2-yl)methyl)-3-(pyridin-3-yl)acrylamide |
| 24 | D | D | D | (E)-N-((5-(5-acetylthiophen-2-yl)-7-chloro-2,3-dihydrobenzofuran-2-yl)methyl)-3-(pyridin-4-yl)acrylamide |

TABLE 2-continued

| | | | | |
|---|---|---|---|---|
| 27 | A | A | B | (E)-N-((5-(5-acetylthiophen-2-yl)-7-chloro-2,3-dihydrobenzofuran-2-yl)methyl)-3-(pyridin-3-yl)acrylamide |
| 28 | D | D | D | (E)-3-(3-(((5-(5-acetylthiophen-2-yl)-7-chloro-2,3-dihydrobenzofuran-2-yl)methyl)amino)-3-oxoprop-1-en-1-yl)pyridine 1-oxide |
| 29 | A | A | B | (E)-N-((7-chloro-5-(4-(morpholine-4-carbonyl)phenyl)-2,3-dihydrobenzofuran-2-yl)methyl)-3-(pyridin-3-yl)acrylamide |
| 32 | B | B | D | (E)-N-((7-chloro-5-(3,5-dichlorophenyl)-2,3-dihydrobenzofuran-2-yl)methyl)-3-(pyridin-3-yl)acrylamide |
| 35 | B | A | B | (E)-N-((7-chloro-5-(3,5-dimethylisoxazol-4-yl)-2,3-dihydrobenzofuran-2-yl)methyl)-3-(pyridin-3-yl)acrylamide |
| 38 | D | D | D | N-((5-(5-acetylthiophen-2-yl)-7-chloro-2,3-dihydrobenzofuran-2-yl)methyl)cinnamamide |
| 39 | B | B | B | (E)-N-((7-chloro-5-(2-fluoro-3-methoxyphenyl)-2,3-dihydrobenzofuran-2-yl)methyl)-3-(pyridin-3-yl)acrylamide |
| 42 | B | B | C | (E)-N-((7-chloro-5-(furan-2-yl)-2,3-dihydrobenzofuran-2-yl)methyl)-3-(pyridin-3-yl)acrylamide |
| 45 | D | D | D | (E)-N-((5-(5-acetylthiophen-2-yl)-7-chloro-2,3-dihydrobenzofuran-2-yl)methyl)-3-(6-chloropyridin-3-yl)acrylamide |
| 49 | B | B | B | (E)-N-((5-(3,5-bis(trifluoromethyl)phenyl)-7-chloro-2,3-dihydrobenzofuran-2-yl)methyl)-3-(pyridin-3-yl)acrylamide |
| 52 | B | B | B | (E)-ethyl 3-(7-chloro-2-((3-(pyridin-3-yl)acrylamido)methyl)-2,3-dihydrobenzofuran-5-yl)benzoate |
| 55 | B | B | D | (E)-N-((7-chloro-5-(4-chloro-2-fluorophenyl)-2,3-dihydrobenzofuran-2-yl)methyl)-3-(pyridin-3-yl)acrylamide |
| 58 | B | B | B | (E)-N-((7-chloro-5-(3-(hydroxymethyl)phenyl)-2,3-dihydrobenzofuran-2-yl)methyl)-3-(pyridin-3-yl)acrylamide |
| 61 | B | B | B | (E)-N-((7-chloro-5-(5-fluoro-2-methoxyphenyl)-2,3-dihydrobenzofuran-2-yl)methyl)-3-(pyridin-3-yl)acrylamide |
| 64 | B | A | B | (E)-N-((7-chloro-5-(4-(dimethylamino)phenyl)-2,3-dihydrobenzofuran-2-yl)methyl)-3-(pyridin-3-yl)acrylamide |
| 67 | B | B | C | (E)-N-((7-chloro-5-phenyl-2,3-dihydrobenzofuran-2-yl)methyl)-3-(pyridin-3-yl)acrylamide |
| 70 | B | B | C | (E)-N-((7-chloro-5-(pyridin-3-yl)-2,3-dihydrobenzofuran-2-yl)methyl)-3-(pyridin-3-yl)acrylamide |
| 73 | B | B | C | (E)-N-((7-chloro-5-(2,3-difluorophenyl)-2,3-dihydrobenzofuran-2-yl)methyl)-3-(pyridin-3-yl)acrylamide |
| 76 | C | C | C | (E)-3-(7-chloro-2-((3-(pyridin-3-yl)acrylamido)methyl)-2,3-dihydrobenzofuran-5-yl)benzoic acid |
| 77 | B | B | B | (E)-N-((7-chloro-5-(5-(methylsulfonyl)pyridin-3-yl)- |

TABLE 2-continued

| | | | | |
|---|---|---|---|---|
| 80 | B | B | B | (E)-N-((7-chloro-5-(3-(methylsulfonyl)phenyl)-2,3-dihydrobenzofuran-2-yl)methyl)-3-(pyridin-3-yl)acrylamide |
| 83 | C | C | D | (E)-N-((7-chloro-2,3-dihydrobenzofuran-2-yl)methyl)-3-(pyridin-3-yl)acrylamide |
| 84 | B | B | C | (E)-N-((5-(2-aminophenyl)-7-chloro-2,3-dihydrobenzofuran-2-yl)methyl)-3-(pyridin-3-yl)acrylamide |
| 87 | B | B | B | (E)-N-((5-(5-acetylthiophen-2-yl)-7-fluoro-2,3-dihydrobenzofuran-2-yl)methyl)-3-(pyridin-3-yl)acrylamide |
| 99 | A | A | B | (E)-N-((5-(5-acetylfuran-2-yl)-7-chloro-2,3-dihydrobenzofuran-2-yl)methyl)-3-(pyridin-3-yl)acrylamide |
| 103 | D | D | D | (E)-N-((5-(5-acetylthiophen-2-yl)-7-chloro-2,3-dihydrobenzofuran-2-yl)methyl)-3-(pyridin-2-yl)acrylamide |
| 104 | D | D | D | (E)-N-((5-(5-acetylthiophen-2-yl)-7-chloro-2,3-dihydrobenzofuran-2-yl)methyl)-3-(2-aminopyrimidin-5-yl)acrylamide |
| 106 | C | C | C | (E)-N-((5-(5-acetylthiophen-2-yl)-7-chloro-2,3-dihydrobenzofuran-2-yl)methyl)-3-(2-aminopyridin-3-yl)acrylamide |
| 108 | B | B | C | (E)-N-((5-(5-acetylthiophen-2-yl)-7-chloro-2,3-dihydrobenzofuran-2-yl)methyl)-3-(4-aminopyridin-3-yl)acrylamide |
| 110 | D | D | D | (E)-N-((5-(5-acetylthiophen-2-yl)-7-chloro-2,3-dihydrobenzofuran-2-yl)methyl)-3-(2-aminophenyl)acrylamide |
| 112 | D | D | D | (E)-N-((5-(5-acetylthiophen-2-yl)-7-chloro-2,3-dihydrobenzofuran-2-yl)methyl)-3-(4-cyanophenyl)acrylamide |
| 114 | D | D | D | (E)-N-((5-(5-acetylthiophen-2-yl)-7-chloro-2,3-dihydrobenzofuran-2-yl)methyl)-3-(4-aminophenyl)acrylamide |
| 116 | B | B | C | (E)-N-((5-(5-acetylthiophen-2-yl)-7-chloro-2,3-dihydrobenzofuran-2-yl)methyl)-3-(6-aminopyridin-3-yl)acrylamide |
| 118 | C | B | C | (E)-N-((5-(5-acetylthiophen-2-yl)-7-chloro-2,3-dihydrobenzofuran-2-yl)methyl)-3-(6-amino-2-methylpyridin-3-yl)acrylamide |
| 120 | C | C | C | (E)-N-((5-(5-acetylthiophen-2-yl)-7-chloro-2,3-dihydrobenzofuran-2-yl)methyl)-3-(2-chloro-3,5-dihydroimidazo[1,2-a]pyridin-3-yl)acrylamide |
| 122[2] | B | B | B | (E)-N-((5-(5-acetylthiophen-2-yl)-7-chloro-2,3-dihydrobenzofuran-2-yl)methyl)-3-(pyridin-3-yl)acrylamide |
| 123[2] | A | A | B | (E)-N-((5-(5-acetylthiophen-2-yl)-7-chloro-2,3-dihydrobenzofuran-2-yl)methyl)-3-(pyridin-3-yl)acrylamide |
| 124 | A | A | B | (E)-N-((7-chloro-5-(5-(1-hydroxyethyl)thiophen-2-yl)-2,3-dihydrobenzofuran-2-yl)methyl)-3-(pyridin-3-yl)acrylamide |
| 125 | C | C | C | (E)-N-((5-(5-acetylthiophen-2-yl)-7-chloro-2,3-dihydrobenzofuran-2-yl)methyl)-N-methyl-3-(pyridin-3-yl)acrylamide |

TABLE 2-continued

| | | | | |
|---|---|---|---|---|
| 128 | B | A | B | (E)-ethyl 4-(7-chloro-2-((3-(pyridin-3-yl)acrylamido)methyl)-2,3-dihydrobenzofuran-5-yl)benzoate |
| 129 | C | C | C | (E)-4-(7-chloro-2-((3-(pyridin-3-yl)acrylamido)methyl)-2,3-dihydrobenzofuran-5-yl)benzoic acid |
| 138 | A | A | B | (E)-N-((5-(5-acetylthiophen-2-yl)-7-methyl-2,3-dihydrobenzofuran-2-yl)methyl)-3-(pyridin-3-yl)acrylamide |
| 142 | C | B | D | (E)-N-((5-(5-acetylthiophen-2-yl)-7-chloro-2,3-dihydrobenzofuran-2-yl)methyl)-3-(2-chloropyridin-3-yl)acrylamide |
| 146 | C | D | D | (E)-N-((5-(5-acetylthiophen-2-yl)-7-chloro-2,3-dihydrobenzofuran-2-yl)methyl)-3-(6-methylpyridin-3-yl)acrylamide |
| 147 | B | B | D | (E)-N-((5-(5-acetylthiophen-2-yl)-7-chloro-2,3-dihydrobenzofuran-2-yl)methyl)-3-(3,5-dimethylisoxazol-4-yl)acrylamide |
| 148 | C | D | D | (E)-N-((5-(5-acetylthiophen-2-yl)-7-chloro-2,3-dihydrobenzofuran-2-yl)methyl)-3-(2-methylthiazol-5-yl)acrylamide |
| 149 | D | D | D | (E)-N-((5-(5-acetylthiophen-2-yl)-7-chloro-2,3-dihydrobenzofuran-2-yl)methyl)-3-(1-methyl-1H-pyrazol-4-yl)acrylamide |
| 150 | D | D | D | (E)-N-((5-(5-acetylthiophen-2-yl)-7-chloro-2,3-dihydrobenzofuran-2-yl)methyl)-3-(5-methylfuran-2-yl)acrylamide |
| 151 | D | D | D | (E)-N-((5-(5-acetylthiophen-2-yl)-7-chloro-2,3-dihydrobenzofuran-2-yl)methyl)-3-(quinoxalin-2-yl)acrylamide |
| 152 | D | D | D | (E)-N-((5-(5-acetylthiophen-2-yl)-7-chloro-2,3-dihydrobenzofuran-2-yl)methyl)-3-(3-methylthiophen-2-yl)acrylamide |
| 153 | D | D | D | (E)-N-((5-(5-acetylthiophen-2-yl)-7-chloro-2,3-dihydrobenzofuran-2-yl)methyl)-3-(1H-pyrrol-3-yl)acrylamide |
| 154 | D | D | D | (E)-N-((5-(5-acetylthiophen-2-yl)-7-chloro-2,3-dihydrobenzofuran-2-yl)methyl)-3-(5-chloro-1-isobutyl-3-methyl-1H-pyrazol-4-yl)acrylamide |
| 155 | D | D | D | (E)-N-((5-(5-acetylthiophen-2-yl)-7-chloro-2,3-dihydrobenzofuran-2-yl)methyl)-3-(1-ethyl-1H-pyrazol-4-yl)acrylamide |
| 156 | D | D | D | (E)-N-((5-(5-acetylthiophen-2-yl)-7-chloro-2,3-dihydrobenzofuran-2-yl)methyl)-3-(1,3-dimethyl-1H-pyrazol-4-yl)acrylamide |
| 157 | D | D | D | (E)-N-((5-(5-acetylthiophen-2-yl)-7-chloro-2,3-dihydrobenzofuran-2-yl)methyl)-3-(1,5-dimethyl-1H-pyrazol-4-yl)acrylamide |
| 159 | D | D | D | (E)-N-((5-(5-acetylthiophen-2-yl)-7-chloro-2,3-dihydrobenzofuran-2-yl)methyl)-3-(2-methylthiazol-4-yl)acrylamide |
| 160 | D | D | D | (E)-N-((5-(5-acetylthiophen-2-yl)-7-chloro-2,3-dihydrobenzofuran-2-yl)methyl)-3-(5-chloro-1,3-dimethyl-1H-pyrazol-4-yl)acrylamide |
| 161 | D | D | D | (E)-N-((5-(5-acetylthiophen-2-yl)-7-chloro-2,3-dihydrobenzofuran-2-yl)methyl)-3-(2,6-dimethylimidazo[2,1-b]thiazol-5-yl)acrylamide |

TABLE 2-continued

| | | | | |
|---|---|---|---|---|
| 162 | A | A | B | 1-(5-(7-chloro-2-(((E)-3-(pyridin-3-yl)acrylamido)methyl)-2,3-dihydrobenzofuran-5-yl)thiophen-2-yl)ethyl 5-((3aS,4S,6aR)-2-oxohexahydro-1H-thieno[3,4-d]imidazol-4-yl)pentanoate |
| 163 | D | D | D | (E)-N-((5-(5-acetylthiophen-2-yl)-7-chloro-2,3-dihydrobenzofuran-2-yl)methyl)-3-(3-chlorothiophen-2-yl)acrylamide |
| 164 | D | D | D | (E)-N-((5-(5-acetylthiophen-2-yl)-7-chloro-2,3-dihydrobenzofuran-2-yl)methyl)-3-(1-methyl-1H-imidazol-2-yl)acrylamide |
| 173 | B | B | B | (E)-N-((4-(5-acetylthiophen-2-yl)-7-chloro-2,3-dihydrobenzofuran-2-yl)methyl)-3-(pyridin-3-yl)acrylamide |
| 26 | C | C | C | 1-(5-(2-(aminomethyl)-7-chloro-2,3-dihydrobenzofuran-5-yl)thiophen-2-yl)ethan-1-one |
| 174 | D | D | D | (E)-N-((5-(5-acetylthiophen-2-yl)-7-chloro-2,3-dihydrobenzofuran-2-yl)methyl)-3-(2,6-dimethylpyridin-3-yl)acrylamide |
| 251 | B | B | C | N-((5-(5-acetylthiophen-2-yl)-7-chloro-2,3-dihydrobenzofuran-2-yl)methyl)-3-(pyridin-3-yl)propiolamide |
| 254 | D | D | D | (E)-N-((5-(5-acetylthiophen-2-yl)-7-chloro-2,3-dihydrobenzofuran-2-yl)methyl)-3-(pyrimidin-5-yl)acrylamide |
| 272 | D | D | C | (E)-N-((5-(5-acetylthiophen-2-yl)-7-chloro-2,3-dihydrobenzofuran-2-yl)methyl)-3-(thiazol-4-yl)acrylamide |
| 177 | B | B | D | (E)-N-((5-(5-acetylthiophen-2-yl)-7-chloro-2,3-dihydrobenzofuran-2-yl)methyl)-3-(2-ethyl-4-methyl-1H-imidazol-5-yl)acrylamide |
| 273 | D | C | D | (E)-N-((5-(5-acetylthiophen-2-yl)-7-chloro-2,3-dihydrobenzofuran-2-yl)methyl)-3-(pyridazin-4-yl)acrylamide |
| 181 | D | D | D | (E)-N-((5-(5-acetylthiophen-2-yl)-7-chloro-2,3-dihydrobenzofuran-2-yl)methyl)but-2-enamide |
| 274 | C | C | D | (E)-N-((5-(5-acetylthiophen-2-yl)-7-chloro-2,3-dihydrobenzofuran-2-yl)methyl)-3-(1-ethyl-1H-pyrazol-5-yl)acrylamide |
| 258 | D | D | D | (E)-N-((5-(5-acetylthiophen-2-yl)-7-chloro-2,3-dihydrobenzofuran-2-yl)methyl)-3-(pyrazin-2-yl)acrylamide |
| 275 | C | C | D | (E)-N-((7-chloro-5-methyl-2,3-dihydrobenzofuran-2-yl)methyl)-3-(pyridin-3-yl)acrylamide |
| 262[1] | C | C | D | (E)-N-((5-(5-acetylthiophen-2-yl)-7-chloro-2,3-dihydrobenzofuran-2-yl)methyl)-2-methyl-3-(pyridin-3-yl)acrylamide |
| 182 | C | D | D | (E)-N-((5-(5-acetylthiophen-2-yl)-7-chloro-2,3-dihydrobenzofuran-2-yl)methyl)-3-(2-methylpyridin-3-yl)acrylamide |
| 185 | D | D | D | (E)-N-((5-(5-acetylthiophen-2-yl)-7-chloro-2,3-dihydrobenzofuran-2-yl)methyl)-3-(2,5-dimethyl-1H-pyrrol-3-yl)acrylamide |
| 189 | D | D | D | (E)-N-((5-(5-acetylthiophen-2-yl)-7-chloro-2,3-dihydrobenzofuran-2-yl)methyl)-3-(1-methyl-1H-indol-3-yl)acrylamide |

TABLE 2-continued

| | | | | |
|---|---|---|---|---|
| 190 | D | D | D | (E)-N-((5-(5-acetylthiophen-2-yl)-7-chloro-2,3-dihydrobenzofuran-2-yl)methyl)-3-(benzo[d]thiazol-2-yl)acrylamide |
| 276 | D | D | D | (E)-N-((5-(5-acetylthiophen-2-yl)-7-chloro-2,3-dihydrobenzofuran-2-yl)methyl)-3-(6-chloro-5,7a-dihydroimidazo[2,1-b]thiazol-5-yl)acrylamide |
| 277 | B | D | D | (E)-N-((5-(5-acetylthiophen-2-yl)-7-chloro-2,3-dihydrobenzofuran-2-yl)methyl)-3-(5-methylisoxazol-3-yl)acrylamide |
| 278 | D | D | D | (E)-N-((5-(5-acetylthiophen-2-yl)-7-chloro-2,3-dihydrobenzofuran-2-yl)methyl)-3-(1H-imidazol-2-yl)acrylamide |
| 279 | B | B | B | (E)-N-((5-(5-acetylthiophen-2-yl)-7-chloro-2,3-dihydrobenzofuran-2-yl)methyl)-3-(pyridazin-3-yl)acrylamide |
| 280 | B | B | D | (E)-N-((5-(5-acetylthiophen-2-yl)-7-chloro-2,3-dihydrobenzofuran-2-yl)methyl)-3-(5-methylpyridin-3-yl)acrylamide |
| 191 | C | C | D | (E)-N-((5-(5-acetylthiophen-2-yl)-7-chloro-2,3-dihydrobenzofuran-2-yl)methyl)-3-(1-ethyl-1H-imidazol-2-yl)acrylamide |
| 195[1] | C | C | D | (E)-N-((5-(5-acetylthiophen-2-yl)-7-chloro-2,3-dihydrobenzofuran-2-yl)methyl)-2-cyano-3-(pyridin-3-yl)acrylamide |
| 196 | D | D | D | (E)-N-((5-(5-acetylthiophen-2-yl)-7-chloro-2,3-dihydrobenzofuran-2-yl)methyl)-3-(2-methyloxazol-4-yl)acrylamide |
| 281 | D | D | D | (E)-N-((5-(5-acetylthiophen-2-yl)-7-chloro-2,3-dihydrobenzofuran-2-yl)methyl)-3-(1,2,3-thiadiazol-4-yl)acrylamide |
| 282 | B | B | D | (Z)-N-((5-(5-acetylthiophen-2-yl)-7-chloro-2,3-dihydrobenzofuran-2-yl)methyl)-3-(pyridin-3-yl)but-2-enamide |
| 283[1] | C | C | D | (E)-N-((5-(5-acetylthiophen-2-yl)-7-chloro-2,3-dihydrobenzofuran-2-yl)methyl)-3-(pyridin-3-yl)but-2-enamide |
| 284 | D | D | D | (E)-N-((5-(5-acetylthiophen-2-yl)-7-chloro-2,3-dihydrobenzofuran-2-yl)methyl)-3-(5-chloro-1-(4-fluorophenyl)-3-methyl-1H-pyrazol-4-yl)acrylamide |
| 285 | D | D | D | (E)-N-((5-(5-acetylthiophen-2-yl)-7-chloro-2,3-dihydrobenzofuran-2-yl)methyl)-3-(2,5-dimethyl-1-(thiazol-2-yl)-1H-pyrrol-3-yl)acrylamide |
| 200 | D | D | D | (E)-N-((5-(5-acetylthiophen-2-yl)-7-chloro-2,3-dihydrobenzofuran-2-yl)methyl)-3-(benzo[b]thiophen-3-yl)acrylamide |
| 286[1] | C | C | D | (E)-N-((5-(5-acetylthiophen-2-yl)-7-chloro-2,3-dihydrobenzofuran-2-yl)methyl)-2-cyano-3-(furan-3-yl)acrylamide |
| 201 | C | C | C | (E)-N-((5-(5-acetylthiophen-2-yl)-7-chloro-2,3-dihydrobenzofuran-2-yl)methyl)-3-(1-phenyl-1H-imidazol-2-yl)acrylamide |
| 287 | D | D | D | (E)-N-((5-(5-acetylthiophen-2-yl)-7-chloro-2,3-dihydrobenzofuran-2-yl)methyl)-3-(2-methyl-7-(trifluoromethyl)pyrazolo[1,5-a]pyrimidin-3-yl)acrylamide |
| 288 | D | D | D | (E)-N-((5-(5-acetylthiophen-2-yl)-7-chloro-2,3-dihydrobenzofuran-2-yl)methyl)-3-(2,5-dimethyl-1- |

TABLE 2-continued

| | | | | |
|---|---|---|---|---|
| 289 | C | B | D | (E)-N-((5-(5-acetylthiophen-2-yl)-7-chloro-2,3-dihydrobenzofuran-2-yl)methyl)-3-(1-isopropyl-6-oxo-6,7-dihydro-1H-pyrazolo[3,4-b]pyridin-5-yl)acrylamide |
| | | | | (5-methylisoxazol-3-yl)-1H-pyrrol-3-yl)acrylamide |
| 205 | C | B | D | (E)-N-((5-(5-acetylthiophen-2-yl)-7-chloro-2,3-dihydrobenzofuran-2-yl)methyl)-3-(2-(tert-butyl)thiazol-5-yl)acrylamide |
| 206 | D | D | D | (E)-N-((5-(5-acetylthiophen-2-yl)-7-chloro-2,3-dihydrobenzofuran-2-yl)methyl)-3-(2-(4-fluorophenyl)thiazol-4-yl)acrylamide |
| 207 | D | D | D | (E)-N-((5-(5-acetylthiophen-2-yl)-7-chloro-2,3-dihydrobenzofuran-2-yl)methyl)-3-(thiazol-2-yl)acrylamide |
| 290 | D | D | D | (E)-N-((5-(5-acetylthiophen-2-yl)-7-chloro-2,3-dihydrobenzofuran-2-yl)methyl)-3-(benzo[d]oxazol-2-yl)acrylamide |
| 291 | D | D | D | (E)-N-((5-(5-acetylthiophen-2-yl)-7-chloro-2,3-dihydrobenzofuran-2-yl)methyl)-3-(3-chlorobenzo[b]thiophen-2-yl)acrylamide |
| 208 | C | C | D | (E)-N-((5-(5-acetylthiophen-2-yl)-7-chloro-2,3-dihydrobenzofuran-2-yl)methyl)-3-(1-(4-fluorophenyl)-3,5-dimethyl-1H-pyrazol-4-yl)acrylamide |
| 292 | B | B | B | (E)-N-((5-(5-acetylthiophen-2-yl)-2,3-dihydrobenzofuran-2-yl)methyl)-3-(pyridin-3-yl)acrylamide |
| 293 | D | D | D | (E)-N-((5-(5-acetylthiophen-2-yl)-7-chloro-2,3-dihydrobenzofuran-2-yl)methyl)-3-(isoxazol-5-yl)acrylamide |
| 209 | D | D | D | (E)-N-((5-(5-acetylthiophen-2-yl)-7-chloro-2,3-dihydrobenzofuran-2-yl)methyl)-3-(1-(4-chlorophenyl)-2,5-dimethyl-1H-pyrrol-3-yl)acrylamide |
| 294 | B | B | C | (E)-N-((5-(5-acetylthiophen-2-yl)-7-chloro-2,3-dihydrobenzofuran-2-yl)methyl)-3-(6-(methylamino)pyridin-3-yl)acrylamide |
| 295 | D | D | D | (E)-N-((5-(5-acetylthiophen-2-yl)-7-chloro-2,3-dihydrobenzofuran-2-yl)methyl)-3-(6-(dimethylamino)pyridin-3-yl)acrylamide |
| 296 | C | C | D | (E)-N-((5-(5-acetylthiophen-2-yl)-7-chloro-2,3-dihydrobenzofuran-2-yl)methyl)-3-(6-methoxypyridin-3-yl)acrylamide |
| 210 | C | D | D | (E)-N-((5-(5-acetylthiophen-2-yl)-7-chloro-2,3-dihydrobenzofuran-2-yl)methyl)-3-(5-(N,N-dimethylsulfamoyl)pyridin-3-yl)acrylamide |
| 297 | D | D | D | (E)-N-((5-(5-acetylthiophen-2-yl)-7-chloro-2,3-dihydrobenzofuran-2-yl)methyl)-3-(5-(4-fluorophenyl)thiophen-2-yl)acrylamide |
| 298 | D | B | D | (E)-N-((5-(5-acetylthiophen-2-yl)-7-chloro-2,3-dihydrobenzofuran-2-yl)methyl)-3-(5-fluoropyridin-3-yl)acrylamide |

TABLE 2-continued

| | | | | |
|---|---|---|---|---|
| 211 | D | D | D | (E)-N-((5-(5-acetylthiophen-2-yl)-7-chloro-2,3-dihydrobenzofuran-2-yl)methyl)-3-(5-chloro-3-methyl-1-phenyl-1H-pyrazol-4-yl)acrylamide |
| 299 | B | B | D | (Z)-N-((5-(5-acetylthiophen-2-yl)-7-chloro-2,3-dihydrobenzofuran-2-yl)methyl)-3-(pyridin-3-yl)acrylamide |
| 212 | C | C | D | (E)-N-((5-(5-acetylthiophen-2-yl)-7-chloro-2,3-dihydrobenzofuran-2-yl)methyl)-3-(4-methyl-1H-imidazol-5-yl)acrylamide |
| 369 | B | B | C | N-((5-(5-acetylthiophen-2-yl)-7-chloro-2,3-dihydrobenzofuran-2-yl)methyl)-3-(pyridin-3-yl)propanamide |
| 300 | B | A | D | (E)-3-(6-aminopyridin-3-yl)-N-((7-chloro-5-(3,5-dimethylisoxazol-4-yl)-2,3-dihydrobenzofuran-2-yl)methyl)acrylamide |
| 213 | D | D | D | (E)-N-((5-(5-acetylthiophen-2-yl)-7-chloro-2,3-dihydrobenzofuran-2-yl)methyl)-3-(1-methyl-1H-pyrrol-3-yl)acrylamide |
| 218 | A | A | C | (E)-N-((4-(5-acetylthiophen-2-yl)-7-chloro-2,3-dihydrobenzofuran-2-yl)methyl)-3-(6-aminopyridin-3-yl)acrylamide |
| 301 | D | D | D | (E)-N-((5-(5-acetylthiophen-2-yl)-7-chloro-2,3-dihydrobenzofuran-2-yl)methyl)-3-(2,5-dimethyl-1-phenyl-1H-pyrrol-3-yl)acrylamide |
| 302 | A | A | B | (E)-3-(6-aminopyridin-3-yl)-N-((7-chloro-5-(4-(morpholine-4-carbonyl)phenyl)-2,3-dihydrobenzofuran-2-yl)methyl)acrylamide |
| 303 | B | B | B | (E)-N-((5-((5-acetylthiophen-2-yl)oxy)-7-chloro-2,3-dihydrobenzofuran-2-yl)methyl)-3-(pyridin-3-yl)acrylamide |
| 222 | B | B | C | (E)-N-((5-(5-acetylthiophen-2-yl)-7-chloro-2,3-dihydrobenzofuran-2-yl)methyl)-4-(pyridin-3-yl)but-2-enamide |
| 304 | A | A | B | (E)-N-((7-chloro-5-(5-(2-hydroxypropan-2-yl)thiophen-2-yl)-2,3-dihydrobenzofuran-2-yl)methyl)-3-(pyridin-3-yl)acrylamide |
| 305 | B | B | C | (E)-N-((7-(5-acetylthiophen-2-yl)-2,3-dihydrobenzofuran-2-yl)methyl)-3-(6-aminopyridin-3-yl)acrylamide |
| 226 | A | A | C | (E)-3-(6-aminopyridin-3-yl)-N-((7-chloro-5-(4-(3,3-difluorocyclobutanecarbonyl)phenyl)-2,3-dihydrobenzofuran-2-yl)methyl)acrylamide |
| 229 | D | D | D | (E)-N-((5-(5-acetylthiophen-2-yl)-7-chloro-2,3-dihydrobenzofuran-2-yl)methyl)-3-(1H-1,2,4-triazol-1-yl)acrylamide |
| 306 | B | B | D | (E)-3-(6-aminopyridin-3-yl)-N-((7-chloro-5-(5-(1-hydroxyethyl)thiophen-2-yl)-2,3-dihydrobenzofuran-2-yl)methyl)acrylamide |
| 233 | B | A | C | (E)-4-(2-((3-(6-aminopyridin-3-yl)acrylamido)methyl)-7-chloro-2,3-dihydrobenzofuran-5-yl)-N,N-dimethylbenzamide |
| 234 | A | A | C | (E)-3-(6-aminopyridin-3-yl)-N-((7-chloro-5-(4-(piperidine-1-carbonyl)phenyl)-2,3-dihydrobenzofuran-2-yl)methyl)acrylamide |

TABLE 2-continued

| | | | | |
|---|---|---|---|---|
| 235 | B | B | C | (E)-N-((7-chloro-5-(3,5-dimethylisoxazol-4-yl)-2,3-dihydrobenzofuran-2-yl)methyl)-3-(pyridazin-3-yl)acrylamide |
| 236 | B | B | B | (E)-N-((7-chloro-5-(4-(morpholine-4-carbonyl)phenyl)-2,3-dihydrobenzofuran-2-yl)methyl)-3-(pyridazin-3-yl)acrylamide |
| 307 | B | B | B | (E)-N-((7-chloro-5-(5-(1-hydroxyethyl)thiophen-2-yl)-2,3-dihydrobenzofuran-2-yl)methyl)-3-(pyridazin-3-yl)acrylamide |
| 237 | A | A | B | (E)-3-(6-aminopyridin-3-yl)-N-((7-chloro-5-(4-(4-methylpiperazine-1-carbonyl)phenyl)-2,3-dihydrobenzofuran-2-yl)methyl)acrylamide |
| 308[2] | B | B | C | (E)-N-((5-(5-acetylthiophen-2-yl)-7-chloro-2,3-dihydrobenzofuran-2-yl)methyl)-3-(6-aminopyridin-3-yl)acrylamide |
| 309[2] | B | A | C | (E)-N-((5-(5-acetylthiophen-2-yl)-7-chloro-2,3-dihydrobenzofuran-2-yl)methyl)-3-(6-aminopyridin-3-yl)acrylamide |
| 310 | D | C | D | (E)-N-((5-(5-acetylthiophen-2-yl)-7-chloro-2,3-dihydrobenzofuran-2-yl)methyl)-2-(pyridin-3-yl)ethene-1-sulfonamide |
| 311 | D | D | D | (E)-N-((5-(5-acetylthiophen-2-yl)-7-chloro-2,3-dihydrobenzofuran-2-yl)methyl)-3-(6-hydroxypyridin-3-yl)acrylamide |
| 312[2] | C | B | C | (Z)-N-((5-(5-acetylthiophen-2-yl)-7-chloro-2,3-dihydrobenzofuran-2-yl)methyl)-3-(pyridin-3-yl)acrylamide |
| 313[2] | B | B | D | (Z)-N-((5-(5-acetylthiophen-2-yl)-7-chloro-2,3-dihydrobenzofuran-2-yl)methyl)-3-(pyridin-3-yl)acrylamide |
| 238 | A | A | B | (E)-3-(6-aminopyridin-3-yl)-N-((7-chloro-5-(3-methyl-4-(morpholine-4-carbonyl)phenyl)-2,3-dihydrobenzofuran-2-yl)methyl)acrylamide |
| 239 | A | A | B | (E)-3-(6-aminopyridin-3-yl)-N-((7-chloro-5-(3-(morpholine-4-carbonyl)phenyl)-2,3-dihydrobenzofuran-2-yl)methyl)acrylamide |
| 314 | B | B | B | (E)-N-((5-(5-acetylfuran-2-yl)-7-chloro-2,3-dihydrobenzofuran-2-yl)methyl)-3-(pyridazin-3-yl)acrylamide |
| 315 | D | D | D | (E)-3-(6-acetamidopyridin-3-yl)-N-((5-(5-acetylthiophen-2-yl)-7-chloro-2,3-dihydrobenzofuran-2-yl)methyl)acrylamide |
| 240 | C | C | D | N-((5-(5-acetylthiophen-2-yl)-7-chloro-2,3-dihydrobenzofuran-2-yl)methyl)-2-(pyridin-3-ylmethyl)acrylamide |
| 316 | NT | NT | NT | (E)-3-(6-aminopyridin-3-yl)-N-((5-bromo-7-chloro-2,3-dihydrobenzofuran-2-yl)methyl)acrylamide |
| 317[2] | B | B | D | (E)-N-((5-(5-acetylthiophen-2-yl)-7-chloro-2,3-dihydrobenzofuran-2-yl)methyl)-3-(pyridazin-3-yl)acrylamide |
| 318[2] | B | B | D | (E)-N-((5-(5-acetylthiophen-2-yl)-7-chloro-2,3-dihydrobenzofuran-2-yl)methyl)-3-(pyridazin-3-yl)acrylamide |
| 246 | A | A | B | (E)-3-(6-aminopyridin-3-yl)-N-((7-chloro-5-(4-(piperazine-1-carbonyl)phenyl)-2,3- |

| | | | | |
|---|---|---|---|---|
| | | | | dihydrobenzofuran-2-yl)methyl)acrylamide |
| 319 | B | A | C | (E)-N-((5-(5-acetylfuran-2-yl)-7-chloro-2,3-dihydrobenzofuran-2-yl)methyl)-3-(6-aminopyridin-3-yl)acrylamide |
| 248 | B | A | D | (E)-3-(6-aminopyridin-3-yl)-N-((7-chloro-5-(6-(morpholine-4-carbonyl)pyridin-3-yl)-2,3-dihydrobenzofuran-2-yl)methyl)acrylamide |
| 320 | B | B | B | (E)-N-((7-chloro-5-(5-(2-hydroxypropan-2-yl)thiophen-2-yl)-2,3-dihydrobenzofuran-2-yl)methyl)-3-(pyridazin-3-yl)acrylamide |
| 321 | B | A | C | (E)-3-(6-aminopyridin-3-yl)-N-((7-chloro-5-(5-(2-hydroxypropan-2-yl)thiophen-2-yl)-2,3-dihydrobenzofuran-2-yl)methyl)acrylamide |
| 322 | A | A | C | (E)-N-((5-(5-acetyl-3,4-dimethylthiophen-2-yl)-7-chloro-2,3-dihydrobenzofuran-2-yl)methyl)-3-(6-aminopyridin-3-yl)acrylamide |
| 249 | A | A | B | (E)-3-(6-aminopyridin-3-yl)-N-((7-chloro-4-(4-(morpholine-4-carbonyl)phenyl)-2,3-dihydrobenzofuran-2-yl)methyl)acrylamide |
| 323 | B | B | C | (E)-3-(6-aminopyridin-3-yl)-N-((7-chloro-5-(2-(morpholine-4-carbonyl)pyrimidin-5-yl)-2,3-dihydrobenzofuran-2-yl)methyl)acrylamide |
| 324 | A | A | C | (E)-5-(2-((3-(6-aminopyridin-3-yl)acrylamido)methyl)-7-chloro-2,3-dihydrobenzofuran-5-yl)-N,N-dimethylfuran-2-carboxamide |
| 371 | C | C | D | N-((5-(5-acetylthiophen-2-yl)-7-chloro-2,3-dihydrobenzofuran-2-yl)methyl)-3-(6-amino-5-bromopyridin-3-yl)propanamide |
| 325 | B | A | B | (E)-3-(6-aminopyridin-3-yl)-N-((7-chloro-5-(5-methyl-3-phenylisoxazol-4-yl)-2,3-dihydrobenzofuran-2-yl)methyl)acrylamide |
| 326 | B | A | C | (E)-3-(6-aminopyridin-3-yl)-N-((7-chloro-5-(5-chloro-6-(morpholine-4-carbonyl)pyridin-3-yl)-2,3-dihydrobenzofuran-2-yl)methyl)acrylamide |
| 327 | B | A | B | (E)-3-(6-aminopyridin-3-yl)-N-((7-chloro-5-(3-methyl-5-phenylisoxazol-4-yl)-2,3-dihydrobenzofuran-2-yl)methyl)acrylamide |
| 328 | A | A | B | (E)-3-(6-aminopyridin-3-yl)-N-((7-chloro-5-(2,5-difluoro-4-(morpholine-4-carbonyl)phenyl)-2,3-dihydrobenzofuran-2-yl)methyl)acrylamide |
| 329 | B | A | C | (E)-3-(6-aminopyridin-3-yl)-N-((7-chloro-5-(5-fluoro-6-(morpholine-4-carbonyl)pyridin-3-yl)-2,3-dihydrobenzofuran-2-yl)methyl)acrylamide |
| 330 | A | A | C | (E)-3-(6-aminopyridin-3-yl)-N-((7-chloro-5-(5-(morpholine-4-carbonyl)pyrimidin-2-yl)-2,3-dihydrobenzofuran-2-yl)methyl)acrylamide |
| 331 | B | A | C | (E)-3-(6-aminopyridin-3-yl)-N-((7-chloro-5-(6-(morpholine-4-carbonyl)pyridazin-3-yl)-2,3-dihydrobenzofuran-2-yl)methyl)acrylamide |

TABLE 2-continued

| | | | | |
|---|---|---|---|---|
| 332 | A | A | B | (E)-3-(6-aminopyridin-3-yl)-N-((7-chloro-5-(3,5-difluoro-4-(morpholine-4-carbonyl)phenyl)-2,3-dihydrobenzofuran-2-yl)methyl)acrylamide |
| 333 | A | A | C | (E)-3-(6-aminopyridin-3-yl)-N-((7-chloro-5-(5-(morpholine-4-carbonyl)pyridin-2-yl)-2,3-dihydrobenzofuran-2-yl)methyl)acrylamide |
| 334 | B | B | C | (E)-3-(7-chloro-5-(4-(morpholine-4-carbonyl)phenyl)-2,3-dihydrobenzofuran-2-yl)-N-(pyridin-3-ylmethyl)acrylamide |
| 335 | A | A | B | (E)-3-(6-aminopyridin-3-yl)-N-((7-chloro-5-(4-(3,3-difluoroazetidine-1-carbonyl)-3,5-difluorophenyl)-2,3-dihydrobenzofuran-2-yl)methyl)acrylamide |
| 336 | A | A | B | (E)-3-(6-aminopyridin-3-yl)-N-((7-chloro-5-(4-(3,3-difluoroazetidine-1-carbonyl)-3-fluorophenyl)-2,3-dihydrobenzofuran-2-yl)methyl)acrylamide |
| 337 | A | A | B | (E)-3-(6-aminopyridin-3-yl)-N-((7-chloro-5-(4-(3,3-difluoroazetidine-1-carbonyl)-2,3-difluorophenyl)-2,3-dihydrobenzofuran-2-yl)methyl)acrylamide |
| 338 | A | A | B | (E)-3-(6-aminopyridin-3-yl)-N-((7-chloro-5-(5-(3,3-difluoroazetidine-1-carbonyl)pyridin-2-yl)-2,3-dihydrobenzofuran-2-yl)methyl)acrylamide |
| 339 | B | A | C | (E)-3-(6-aminopyridin-3-yl)-N-((7-chloro-5-(5-(piperidine-1-carbonyl)pyridin-2-yl)-2,3-dihydrobenzofuran-2-yl)methyl)acrylamide |
| 340 | A | B | A | (E)-3-(6-aminopyridin-3-yl)-N-((7-chloro-4-(3,3-difluoroazetidine-1-carbonyl)phenyl)-2,3-dihydrobenzofuran-2-yl)methyl)acrylamide |
| 341 | A | B | A | (E)-3-(6-aminopyridin-3-yl)-N-((7-chloro-4-(2-(3,3-difluoroazetidine-1-carbonyl)phenyl)-2,3-dihydrobenzofuran-2-yl)methyl)acrylamide |
| 342 | B | D | B | (E)-3-(6-aminopyridin-3-yl)-N-((7-chloro-5-(6-(piperazine-1-carbonyl)pyridin-3-yl)-2,3-dihydrobenzofuran-2-yl)methyl)acrylamide |
| 343 | B | D | A | (E)-3-(6-aminopyridin-3-yl)-N-((7-chloro-5-(2-methyl-1,3-dioxoisoindolin-5-yl)-2,3-dihydrobenzofuran-2-yl)methyl)acrylamide |
| 344 | A | B | A | (E)-3-(6-aminopyridin-3-yl)-N-((7-chloro-4-(2-(morpholine-4-carbonyl)phenyl)-2,3-dihydrobenzofuran-2-yl)methyl)acrylamide |
| 345 | A | B | A | (E)-3-(6-aminopyridin-3-yl)-N-((7-methoxy-5-(4-(morpholine-4-carbonyl)phenyl)-2,3-dihydrobenzofuran-2-yl)methyl)acrylamide |

TABLE 2-continued

| | | | | |
|---|---|---|---|---|
| 346 | A | B | A | (E)-3-(6-aminopyridin-3-yl)-N-((5-(4-(morpholine-4-carbonyl)phenyl)-7-(trifluoromethyl)-2,3-dihydrobenzofuran-2-yl)methyl)acrylamide |
| 347 | B | D | B | (E)-3-(6-aminopyridin-3-yl)-N-((7-hydroxy-5-(4-(morpholine-4-carbonyl)phenyl)-2,3-dihydrobenzofuran-2-yl)methyl)acrylamide |
| 348 | B | C | B | (E)-3-(6-aminopyridin-3-yl)-N-((7-chloro-5-(4-(morpholine-4-carbonyl)phenyl)-3-oxo-2,3-dihydrobenzofuran-2-yl)methyl)acrylamide |
| 349 | B | B | A | (E)-3-(6-aminopyridin-3-yl)-N-((7-chloro-2-methyl-5-(4-(morpholine-4-carbonyl)phenyl)-2,3-dihydrobenzofuran-2-yl)methyl)acrylamide |
| 350 | B | D | B | (E)-N-((6-aminopyridin-3-yl)methyl)-3-(7-chloro-5-(4-(morpholinosulfonyl)phenyl)-2,3-dihydrobenzofuran-2-yl)acrylamide |
| 351 | B | B | B | (E)-N-((6-aminopyridin-3-yl)methyl)-3-(7-chloro-5-(4-(3,3-difluoroazetidine-1-carbonyl)phenyl)-2,3-dihydrobenzofuran-2-yl)acrylamide |
| 352 | B | D | C | (E)-N-((6-aminopyridin-3-yl)methyl)-3-(7-chloro-4-(4-(3-fluoroazetidine-1-carbonyl)phenyl)-2,3-dihydrobenzofuran-2-yl)acrylamide |
| 354 | A | C | A | ethyl (E)-3-(2-(3-(4-(4-(2-((3-(6-aminopyridin-3-yl)acrylamido)methyl)-7-chloro-2,3-dihydrobenzofuran-5-yl)benzoyl)piperazin-1-yl)-3-oxopropoxy)ethoxy)propanoate |
| 355 | D | D | B | (E)-3-(6-aminopyridin-3-yl)-N-((7-(tert-butyl)-4-(4-(morpholine-4-carbonyl)phenyl)-2,3-dihydrobenzofuran-2-yl)methyl)acrylamide |
| 357 | A | B | A | (E)-N-((6-aminopyridin-3-yl)methyl)-3-(7-chloro-5-(3-(morpholinosulfonyl)phenyl)-2,3-dihydrobenzofuran-2-yl)acrylamide |
| 358 | B | D | B | (E)-N-((6-aminopyridin-3-yl)methyl)-3-(7-chloro-5-(4-((R)-3-fluoropyrrolidine-1-carbonyl)phenyl)-2,3-dihydrobenzofuran-2-yl)acrylamide |
| 359 | B | D | C | (E)-N-((6-aminopyridin-3-yl)methyl)-3-(7-chloro-5-(4-((S)-3-fluoropyrrolidine-1-carbonyl)phenyl)-2,3-dihydrobenzofuran-2-yl)acrylamide |
| 360 | A | B | A | (E)-N-((6-aminopyridin-3-yl)methyl)-3-(7-chloro-5-(2-(morpholinosulfonyl)phenyl)-2,3-dihydrobenzofuran-2-yl)acrylamide |
| 361 | B | B | B | (E)-N-((6-aminopyridin-3-yl)methyl)-3-(7-chloro-5-(4-(3-fluoroazetidine-1-carbonyl)phenyl)-2,3-dihydrobenzofuran-2-yl)acrylamide |
| 362 | A | D | A | (E)-N-((6-aminopyridin-3-yl)methyl)-3-(7-chloro-5-(4-(3,3-dimethylazetidine-1- |

TABLE 2-continued

| | | | | |
|---|---|---|---|---|
| 363 | D | D | C | (E)-N-((6-aminopyridin-3-yl)methyl)-3-(7-chloro-5-(4-((3,3-difluoroazetidin-1-yl)sulfonyl)phenyl)-2,3-dihydrobenzofuran-2-yl)acrylamide ...carbonyl)phenyl)-2,3-dihydrobenzofuran-2-yl)acrylamide |
| 364 | B | D | C | (E)-N-((6-aminopyridin-3-yl)methyl)-3-(7-chloro-4-(4-(morpholinosulfonyl)phenyl)-2,3-dihydrobenzofuran-2-yl)acrylamide |
| 365 | A | B | A | (E)-3-(6-aminopyridin-3-yl)-N-((7-chloro-5-(4-(morpholine-4-carbonyl)phenyl)-2,3-dihydrobenzofuran-2-yl-3,3-d2)methyl)acrylamide |
| 366 | D | D | B | (E)-N-((6-aminopyridin-3-yl)methyl)-3-(7-chloro-5-(4-(3-fluoro-3-methylazetidine-1-carbonyl)phenyl)-2,3-dihydrobenzofuran-2-yl)acrylamide |
| 367 | A | A | B | (E)-N-((6-aminopyridin-3-yl)methyl)-3-(7-chloro-5-(4-(3,3-dimethylmorpholine-4-carbonyl)phenyl)-2,3-dihydrobenzofuran-2-yl)acrylamide |
| 368 | A | A | B | (E)-N-((6-aminopyridin-3-yl)methyl)-3-(7-chloro-5-(5-(3,3-dimethylmorpholine-4-carbonyl)pyridin-2-yl)-2,3-dihydrobenzofuran-2-yl)acrylamide |
| 901 | A | A | B | (E)-3-(6-aminopyridin-3-yl)-N-((7-chloro-5-(2,3-difluoro-4-(morpholine-4-carbonyl)phenyl)-2,3-dihydrobenzofuran-2-yl)methyl)acrylamide |
| 902 | A | A | B | E)-3-(6-aminopyridin-3-yl)-N-((7-chloro-5-(2,6-difluoro-4-(morpholine-4-carbonyl)phenyl)-2,3-dihydrobenzofuran-2-yl)methyl)acrylamide |
| 903 | A | A | B | (E)-3-(6-aminopyridin-3-yl)-N-((7-chloro-5-(3-fluoro-4-(morpholine-4-carbonyl)phenyl)-2,3-dihydrobenzofuran-2-yl)methyl)acrylamide |
| 904 | A | A | B | (E)-3-(6-aminopyridin-3-yl)-N-((7-chloro-5-(4-(2-(pyrazin-2-yl)hydrazine-1-carbonyl)phenyl)-2,3-dihydrobenzofuran-2-yl)methyl)acrylamide |
| 906 | A | A | B | (E)-3-(6-aminopyridin-3-yl)-N-((7-chloro-5-(4-(2-morpholinoacetyl)phenyl)-2,3-dihydrobenzofuran-2-yl)methyl)acrylamide |
| 907 | A | A | C | (E)-N-((6-aminopyridin-3-yl)methyl)-3-(7-chloro-5-(4-(morpholine-4-carbonyl)phenyl)-2,3-dihydrobenzofuran-2-yl)acrylamide |
| 908 | A | A | B | (E)-3-(6-aminopyridin-3-yl)-N-((7-chloro-4-(3,5-difluoro-4-(morpholine-4-carbonyl)phenyl)-2,3-dihydrobenzofuran-2-yl)methyl)acrylamide |
| 909 | A | A | B | (E)-3-(6-aminopyridin-3-yl)-N-((7-chloro-5-(4-(2-morpholino-2-oxoacetyl)phenyl)-2,3-dihydrobenzofuran-2-yl)methyl)acrylamide |
| 910 | B | A | C | (E)-3-(6-aminopyridin-3-yl)-N-((7-chloro-4-(6-(morpholine-4-carbonyl)pyridin-3-yl)-2,3- |

TABLE 2-continued

| | | | | |
|---|---|---|---|---|
| 911 | A | A | B | (E)-3-(6-aminopyridin-3-yl)-N-((7-chloro-4-(2-fluoro-4-(morpholine-4-carbonyl)phenyl)-2,3-dihydrobenzofuran-2-yl)methyl)acrylamide |
| 912 | B | A | B | (E)-3-(6-aminopyridin-3-yl)-N-((7-chloro-4-(5-(morpholine-4-carbonyl)pyridin-2-yl)-2,3-dihydrobenzofuran-2-yl)methyl)acrylamide |
| 913 | B | B | C | (E)-3-(6-aminopyridin-3-yl)-N-((7-chloro-4-(5-(morpholine-4-carbonyl)pyridin-3-yl)-2,3-dihydrobenzofuran-2-yl)methyl)acrylamide |
| 914 | A | A | B | (E)-3-(6-aminopyridin-3-yl)-N-((7-chloro-5-(4-(morpholinosulfonyl)phenyl)-2,3-dihydrobenzofuran-2-yl)methyl)acrylamide |
| 915 | A | A | B | (E)-3-(6-aminopyridin-3-yl)-N-((7-chloro-4-(3-(morpholine-4-carbonyl)phenyl)-2,3-dihydrobenzofuran-2-yl)methyl)acrylamide |
| 920 | D | D | D | 3-(6-aminopyridin-3-yl)-N-((7-chloro-5-(4-(piperazine-1-carbonyl)phenyl)-2,3-dihydrobenzofuran-2-yl)methyl)propanamide |
| 921 | A | A | B | (E)-3-(6-aminopyridin-3-yl)-N-((7-chloro-5-(4-(2-morpholino-2-oxoethyl)phenyl)-2,3-dihydrobenzofuran-2-yl)methyl)acrylamide |

($IC_{50}$: A = <100 nM;
B = 100 nM to <5 μM;
C = 5 μM to <30 μM;
D = 30 μM and above;
NT = Not tested)
[1]Compounds 195, 262, 283 and 286 were isolated as single geometric (E/Z) isomers.
Compounds 195, 262, 283 and 286 are shown and named as E isomers; the assignments are tentative.
[2]Compounds 122, 123, 308, 309, 312, 313, 317 and 318 were isolated as single enantiomers.
The chiral carbon for each compound is indicated by an asterisk.
The absolute configuration of each chiral carbon has not been determined.
Identification of the enantiomers is based on the retention time determined by the separation method used to obtain the single enantiomer.

Selected compounds were further tested in the MTT cell proliferation assay against the cell lines listed in Table 3. The M24 cell line is derived from human melanoma cells. The U2OS cell line is a human osteosarcoma cell line expressing wild type p53 and Rb, but lacking p16. The MM1S cell line is a multiple myeloma cell line; the parent cell line, MM.1, was established from peripheral blood of a multiple myeloma patient who had become resistant to steroid-based therapy. The RPMI8226 cell line is derived from human B lymphocyte cells. NHDF cells are normal human dermal fibroblast cells. The MRC-5 cell line is derived from normal lung tissue of a male fetus. The LN18 cell line is a human malignant glioma cell line. The DU-145 cell line is a human prostate cancer cell line. A549 cells are human adenocarcinomic human alveolar basal epithelial cells. The MOLT4 cell line is a human acute lymphoblastic leukemia cell line. The THP1 cell line is a human leukemic monocytic cell line derived from peripheral blood. The OCIAML5 cell line is a human acute myeloid leukemia cell line. The MDA-MB-231 cell line is a human breast adenocarcinoma cell line. The MDA-MB-468 cell line is a human breast carcinoma cell line. HL-60 cells are human promyelocytic leukemia cells. Hep G2 cells are human hepatocellular carcinoma cells. HEP 3B cells are human hepatocellular carcinoma cells. The DLD-1 cell line is a colorectal adenocarcinoma cell line. The HCT-15 cell line is a human colon carcinoma cell line. The Colo-205 cell line is derived from a human adenocarcinoma of the colon. The LoVo cell line is a human colon adenocarcinoma cell line. The UCH-2 cell line is a chordoma cell line. The SNU-182 cell line is a human hepatoma cell line. The Daudi cell line is a human Burkitt's lymphoma cell line. The L3.6pl cell line is a pancreatic cancer cell line.

Further results of the MTT assay are reported in Table 3.

TABLE 3

| | MTT Assay | | | |
|---|---|---|---|---|
| | Compound Number | | | |
| Cell Line | 124 | 302 | 226 | 246 |
| M24 | B | NT | NT | B |
| U2OS | A | NT | NT | A |
| MM1S | A | A | NT | A |
| RPMI8226 | B | NT | NT | B |
| NHDF | B | NT | NT | B |
| MRC-5 | A | NT | NT | NT |
| LN18 | NT | B | NT | NT |
| DU-145 | B | NT | NT | NT |

TABLE 3-continued

MTT Assay

| Cell Line | Compound Number | | | |
|---|---|---|---|---|
| | 124 | 302 | 226 | 246 |
| A549 | NT | B | NT | NT |
| MOLT4 | NT | A | NT | NT |
| THP1 | NT | B | NT | NT |
| OCIAML5 | NT | A | NT | NT |
| MDA-MB-231 | B | B | NT | NT |
| MDA-MB-468 | B | NT | NT | NT |
| HL-60 | NT | B | NT | B |
| Hep G2 | B | A | A | B |
| HEP 3B | B | NT | A | A |
| DLD-1 | B | NT | NT | NT |
| HCT-15 | B | A | NT | NT |
| Colo-205 | B | NT | NT | NT |
| LoVo | B | NT | NT | NT |
| UCH-2 | NT | NT | D | NT |
| SNU-182 | NT | NT | A | NT |
| Daudi | NT | A | NT | NT |
| L3.6pl | NT | B | NT | NT |

($IC_{50}$: A = <100 nM;
B = 100 nM to <5 µM;
C = 5 µM to 30 µM;
D = >30 µM;
NT = Not tested)

Example 3

Z-138 Mouse Xenograft Model

The oncological impact of selected substituted 2,3-dihydrobenzofuranyl compounds was tested using a Z-138 mantle cell lymphoma cancer xenograft model in SCID mice. SCID Mice were inoculated s.c. in both flanks with $5 \times 10^6$ Z-138 cells. When the tumors reached a mean size of between 100 and 200 mm$^3$, mice were randomly and prospectively divided. Tumor-bearing mice were treated with vehicle, cyclophosphamide (positive control) or Compound 123 on M-F (QDx5/week) for 4 weeks. Compound 123 was administered orally (PO) at initial doses of 30 and 100 mg/kg five times a week. Cyclophosphamide was given as a positive control at 80 mg/kg on Days 1-3. Animals' weights and conditions were recorded daily, and tumors were measured on Mondays-Wednesdays-Fridays.

Figure 2A:
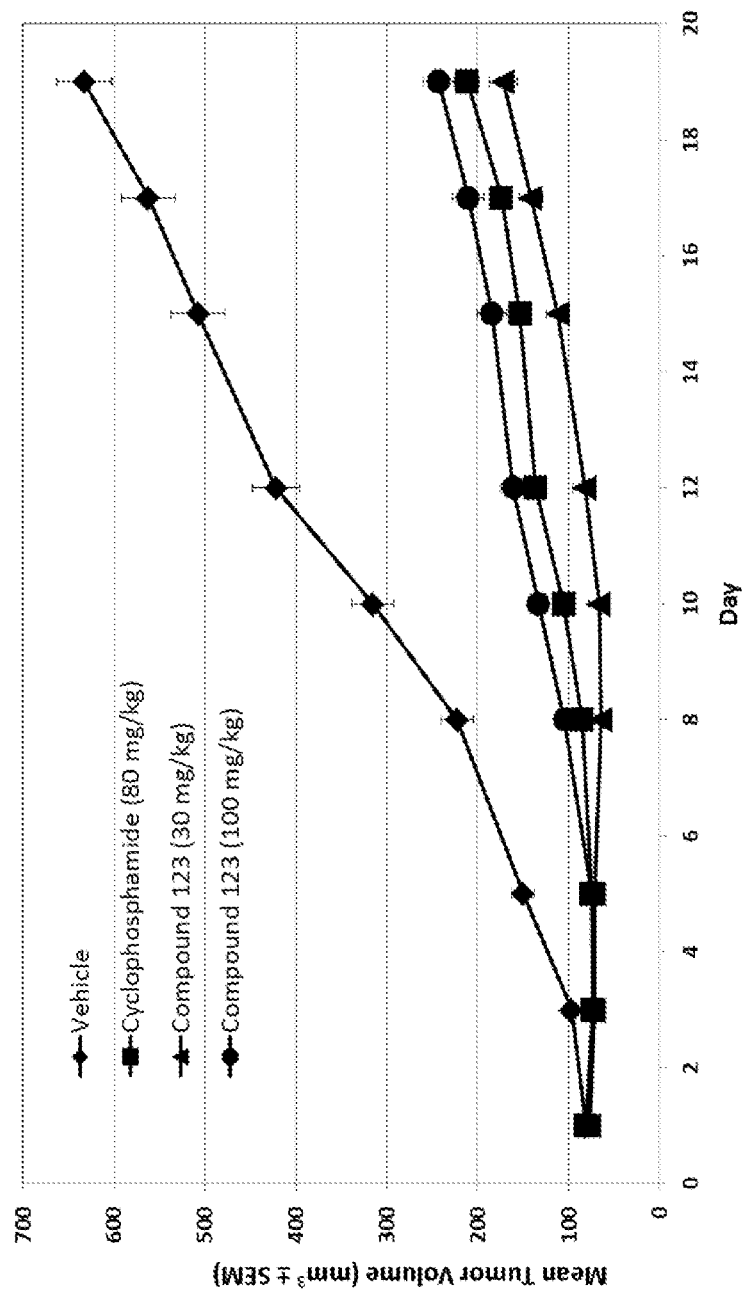
FIG. 2A is a graph of mean tumor volume versus time, and shows the mean tumor volume of Z-138 tumors on tumor-bearing mice treated with vehicle, cyclophosphamide (80 mg/kg) or Compound 123 (30 mg/kg or 100 mg/kg).
Figure 2B:
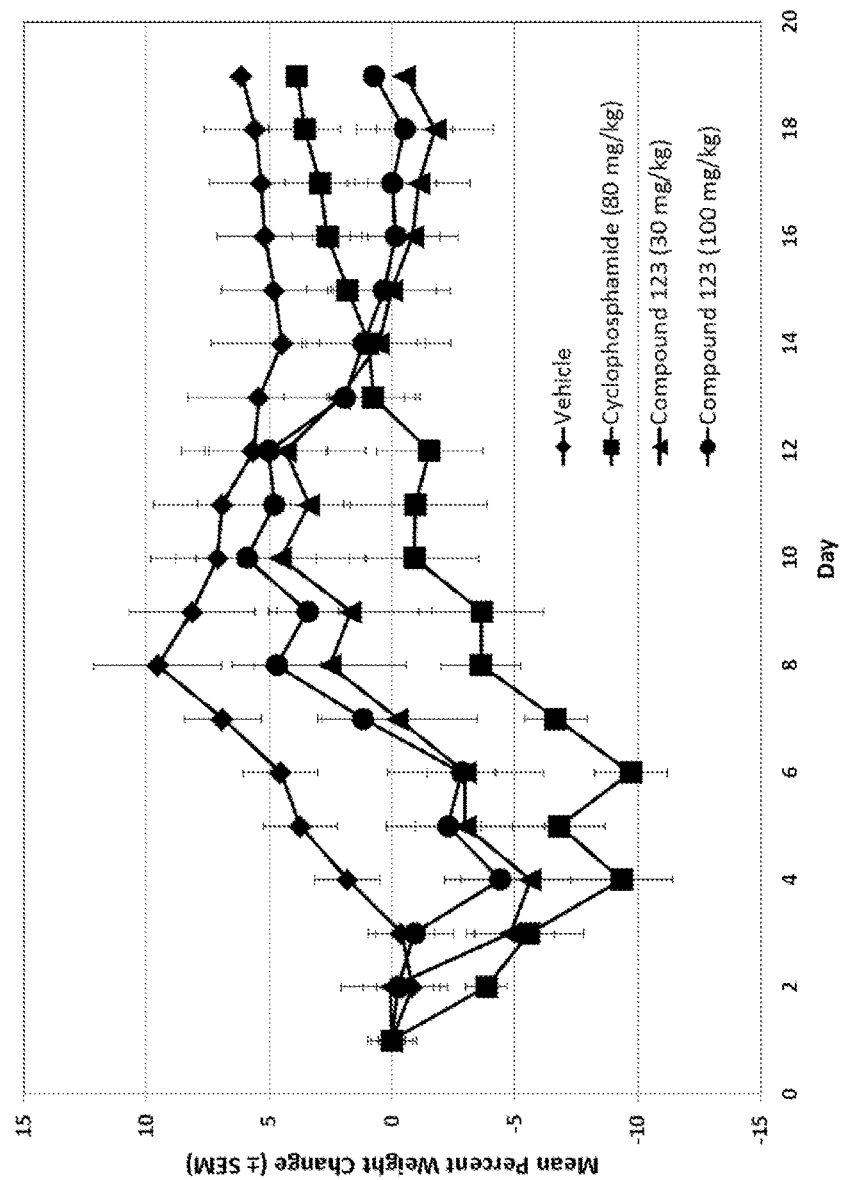
FIG. 2B is a graph of mean percent weight change versus time, and shows the mean percent weight change of mice bearing Z-138 tumors and treated with vehicle, cyclophosphamide (80 mg/kg) or Compound 123 (30 mg/kg or 100 mg/kg).

The results of the Z-138 mouse xenograft model are shown in FIGS. 2A and 2B. FIG. 2A shows that 100 mg/kg of Compound 123 inhibited tumor growth with an efficacy similar to cyclophosphamide, while 30 mg/kg of Compound 123 inhibited tumor growth with an efficacy better than that of cyclophosphamide. FIG. 2B shows that Compound 123 was tolerated at both doses.

Example 4

Cell Cycle Arrest

Z-138 cells (mantle cell lymphoma) were plated at a density of $1 \times 10^6$ cells/well and treated with no drug (DMSO control) or with 1 µM Compound 123 for 1, 2, and 3 days in culture. For each time point, cells were treated with 10 µM BrdU for 2 hours, then collected by centrifugation. Cells were subsequently washed, fixed, and then stained for BrdU and total DNA (7-AAD). BrdU incorporation and cell cycle analysis were analyzed by flow cytometry at the Dana Farber Cancer Institute on a BD Fortessa Analyzer. Data was then analyzed using FCS Express 4 software.

Figure 1D:
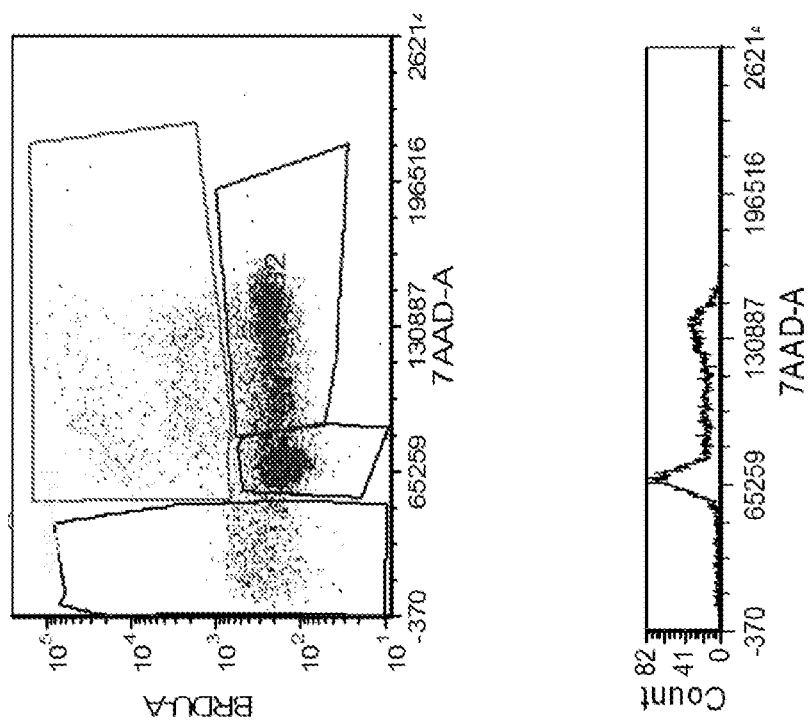
FIG. 1D is a single-cell scatter plot and shows BrdU versus 7-AAD for Z138 cells treated with 1 μM Compound 123 for 3 days. A graph showing cell count versus 7-AAD intensity is depicted below its corresponding scatter plot.
Figure 1E:
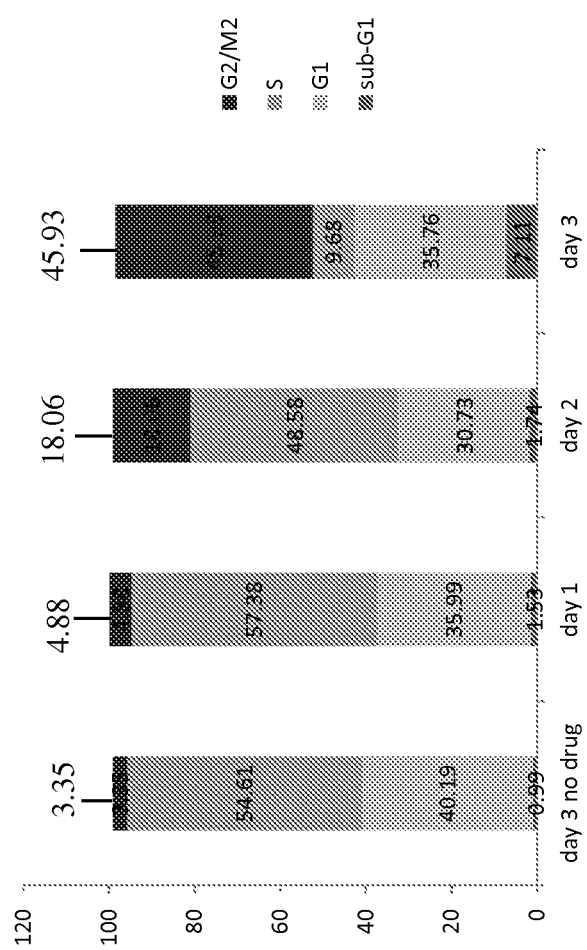
FIG. 1E is a graphical representation of the gated data from the single-cell scatter plots shown in FIGS. 1A, 1B, 1C and 1D.

FIGS. 1A, 1B, 1C and 1D are single-cell scatter plots and show BrdU versus 7-AAD for Z138 cells treated with no drug (FIG. 1A) or treated with 1 µM Compound 123 for 1 day (FIG. 1B), 2 days (FIG. 1C), or 3 days (FIG. 1D). Graphs showing cell count versus 7-AAD intensities are depicted below their corresponding scatter plots. FIG. 1E is a graphical representation of the gated data from the single-cell scatter plots shown in FIGS. 1A, 1B, 1C and 1D.

Compound 123-treated cells showed a small increase in sub-G1 fraction, no change in G1, significant decrease in S phase, and increased G2/M. These data suggest Compound 123 induces G2/M arrest.

Example 5

Target Identification

Without being bound by a particular theory, it is believed that the compounds described herein can modulate (e.g., inhibit) one or more p21-activated kinases (PAK), for example, one or more of PAKs 1-6. More specifically, and without being bound by a particular theory, it is believed that the compounds described herein can bind to one or more PAKs and function as allosteric modulators of one or more PAKs. For example, the compounds described herein may exert their modulatory effect(s) on one or more PAKs by binding to and destabilizing one or more PAKs or contributing to the degradation of one or more PAKs, thereby modulating (e.g., inhibiting) the effect of one or more PAKs on one or more proteins downstream of the one or more PAKs, for example, growth signaling proteins such as Akt, ERK1/2, p90RSK, β-catenin, cofilin, p21 and cyclin D1.

In a particular embodiment, one or more of the Group I PAKs (e.g., PAK1, PAK2, PAK3) is modulated. For example, PAK1 is modulated, PAK2 is modulated, PAK3 is modulated or a combination of PAK1, PAK2 and PAK3, such as PAK1 and PAK2, PAK1 and PAK3, PAK2 and PAK3, or PAK1, PAK2 and PAK3 is modulated. In a particular embodiment, one or more of the group II PAKs (e.g., PAK4, PAK5, PAK6) is modulated. For example, PAK4 is modulated, PAK5 is modulated, PAK6 is modulated or a combination of PAK4, PAK5 and PAK6, such as PAK4 and PAK5, PAK4 and PAK6, PAK5 and PAK6 or PAK4, PAK5 and PAK6 is modulated. Therefore, the compounds described herein can be useful for treating PAK-mediated disorders.

In another particular embodiment, one or more of the Group I PAKs (e.g., PAK1, PAK2, PAK3) is inhibited. For example, PAK1 is inhibited, PAK2 is inhibited, PAK3 is inhibited or a combination of PAK1, PAK2 and PAK3, such as PAK1 and PAK2, PAK1 and PAK3, PAK2 and PAK3, or PAK1, PAK2 and PAK3 is inhibited. In a particular embodiment, one or more of the group II PAKs (e.g., PAK4, PAK5, PAK6) is inhibited. For example, PAK4 is inhibited, PAK5 is inhibited, PAK6 is inhibited or a combination of PAK4, PAK5 and PAK6, such as PAK4 and PAK5, PAK4 and PAK6, PAK5 and PAK6 or PAK4, PAK5 and PAK6 is inhibited. Therefore, the compounds described herein can be useful for treating PAK-mediated disorders.

PAKs are a family of serine/threonine kinases that are involved in multiple intracellular signaling pathways. Six human PAKs have been identified to date (PAKs 1-6). The PAKs can be classified into two subfamilies based on domain structure, sequence homology, and regulation: Group 1, which includes PAKs 1-3, and Group 2, which includes PAKs 4-6 (1).

Group I PAKs are characterized by an N-terminal region that includes a conserved p21 binding domain (PBD) that overlaps with an autoinhibitory domain (AID), and a C-terminal kinase domain. Group I PAKs are known to be involved in regulating normal cellular activities and can play a role in disease progression. For example, PAK1 plays an important role in cytoskeleton dynamics, cell adhesion, migration, proliferation, apoptosis, mitosis and vesicle-mediated transport processes, and has been shown to be up-regulated in breast, ovary and thyroid cancer. PAK1 activity has also been shown to be suppressed in brain lysates from Alzheimer's disease patients. PAK2 plays a role in a variety of different signaling pathways including cytoskeleton regulation, cell motility, cell cycle progression, apoptosis and proliferation. PAK3 plays a role in cytoskeleton regulation, cell migration, and cell cycle regulation.

Group II PAKs are characterized by an N-terminal PBD and a C-terminal kinase domain, but lack other motifs found in the group I PAKs. PAK4 is a pluripotent kinase known to mediate cell motility and morphology, proliferation, embryonic development, cell survival, immune defense, and oncogenic transformation (2), and is a key effector for Cdc42, a subset of the Rho GTPase family, which has been shown to be required for Ras driven tumorigenesis (3). PAK5 is unique amongst the PAK family, as it is constitutively localized to the mitochondria, and its localization is independent of kinase activity and Cdc42 binding. The mitochondrial localization of PAK5 is required for it to exert its anti-apoptotic effects and to promote cell survival. One report suggests that PAK5 is overexpressed in colorectal cancer and promotes cancer cell invasion. Both PAK4 and PAK5 have been linked to the regulation of neurite outgrowth; whereas PAK5 induces neurite outgrowth, PAK4 inhibits neurite outgrowth. The link of PAK4 and PAK5 to neuronal development suggests that PAK4 and PAK5 may be involved in the progression of neurological disorders, such as Parkinson's disease, dementia and brain atrophy. PAK6 has been found to specifically bind to androgen receptor (AR) and estrogen receptor α (ERα), and co-translocates into the nucleus with AR in response to androgen. PAK6 expression in adult tissue is mainly restricted to the prostrate and testis. However, PAK6 has been found to be overexpressed in many cancer cell lines, particularly breast and prostate cancers.

Since the PAKs and, in particular, PAK4, are critical hubs of signaling cascades, inhibiting their function can be beneficial for the treatment of cancers, neurodegenerative diseases, and immune system diseases as described herein.

Target Identification Using SILAC (Stable Isotope Labeling of Amino Acids in Cells)

Figure 3A:
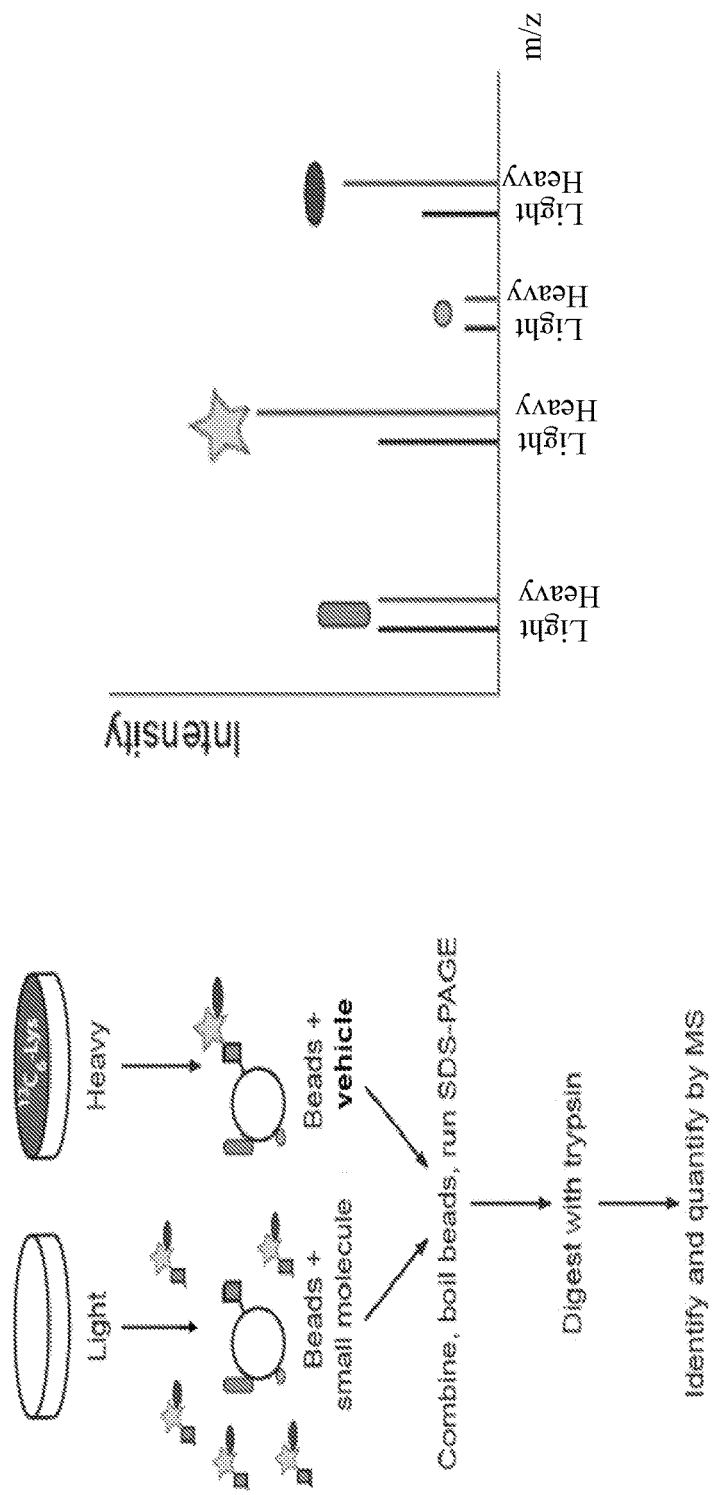
FIG. 3A is a schematic representation of a SILAC experiment and shows the experimental design.

MS751 cellular proteins were labeled with non-radioactive heavy lysine (L-Lysine-2HCl, $^{13}C_6$, $^{15}N_2$) and arginine (L-Arginine-HCl, $^{13}C_6$, $^{15}N_4$) for 7 to 8 doublings. The heavy isotopes were incorporated efficiently with greater than 95% heavy proteins identified by LC-MS. Separate plates of cells were maintained in light amino acids. FIG. 3A is a schematic representation of the SILAC experiment, and shows the experimental design.

After successful isotope labeling, heavy and light plates of MS751 cells were collected and lysed in ModRIPA buffer (50 mM Tris-HCl, pH 7.8, 150 mM NaCl, 1% NP-40, 0.1% sodium deoxycholate, 1 mM EDTA), and the protein quantified using Pierce 660 reagent. Two milligrams of light total protein were mixed with a 50-fold excess of soluble competitor (PEGylated Compound 246) while two milligrams of heavy protein lysate were mixed with an equal amount of vehicle (DMSO). In the second replicate, the heavy and light proteins were flipped. The mixture was incubated at 4° C. for 1 h with constant rotation. 30 µL of slurry (15 µL of 12.5% Resin-immobilized PEGylated Compound 246 in 15 µL of PBS) was added to separate tubes with the protein mixtures of DMSO or soluble competitor (PEGylated Compound 246) and incubated for 16 to 24 h with constant rotation. PEGylated Compound 246 is also referred to herein as Compound 354.

The following day, the beads were collected by quick centrifugation and the supernatant removed. The resin was washed separately twice in ModRIPA buffer with spins after washes. The light (PEGylated Compound 246) and heavy (DMSO) resins were mixed together then washed twice with ModRIPA, with spins after washes, and prepared for SDS-PAGE.

The lysates were run on a gradient SDS-PAGE gel and stained with Coomassie blue. Six bands from each replicate were cut from the gel, digested with trypsin, desalted, and prepared for LC-MS proteomics.

Figure 3B:
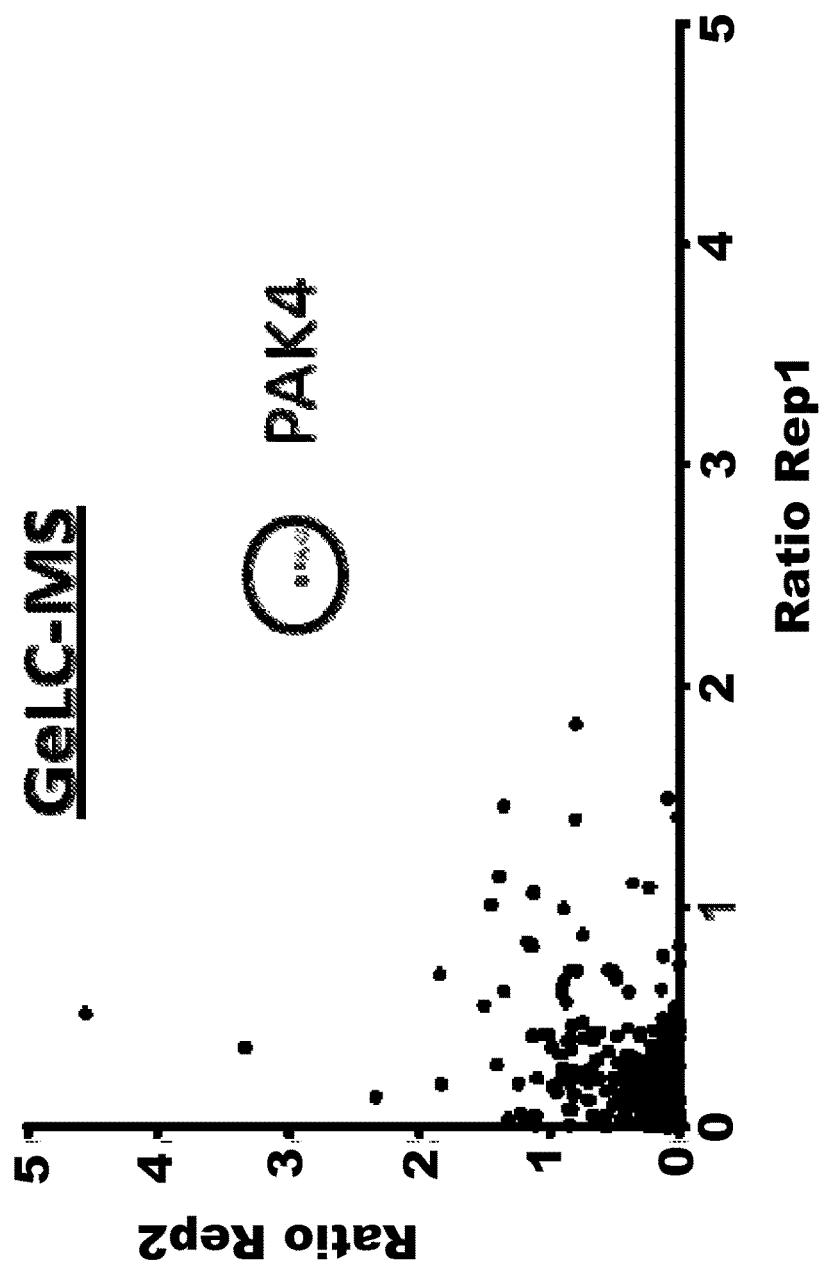
FIG. 3B is a graph of the statistical analysis data from a SILAC experiment used to identify PAK4.

Samples were run on a Q-Exactive, and the heavy and light peptides were identified using MaxQuan and R Moderated T Test for statistical analysis. FIG. 3B is a graph of the statistical analysis data used to identify PAK4 and shows the enrichment of PAK4 in DMSO samples compared to the soluble competitor samples.

Pull-Down of Proteins Using Immobilized Inhibitor

MS751, U2OS, or HeLa cells were collected and lysed in ModRIPA buffer, and the protein content quantified using Pierce 660 reagent. Two milligrams of total protein was mixed with a 50-fold excess of soluble competitor (PEGylated Compound 246 or Compound 246) or an equal amount of DMSO in three separate tubes. The mixture was incubated at 4° C. for 1 h with constant rotation. 30 µL of slurry (15 µL of 12.5% Resin-immobilized PEGylated Compound 246 in 15 µL of PBS) was added to separate tubes with the protein mixtures of DMSO, PEGylated Compound 246 or Compound 246 and incubated for 16 to 24 h with constant rotation.

The following day, the beads were collected by quick centrifugation and the supernatant removed. The resin was washed separately three times in ModRIPA buffer with spins after each wash. Each sample along with input lysate was prepared for SDS-PAGE.

Figure 3C:
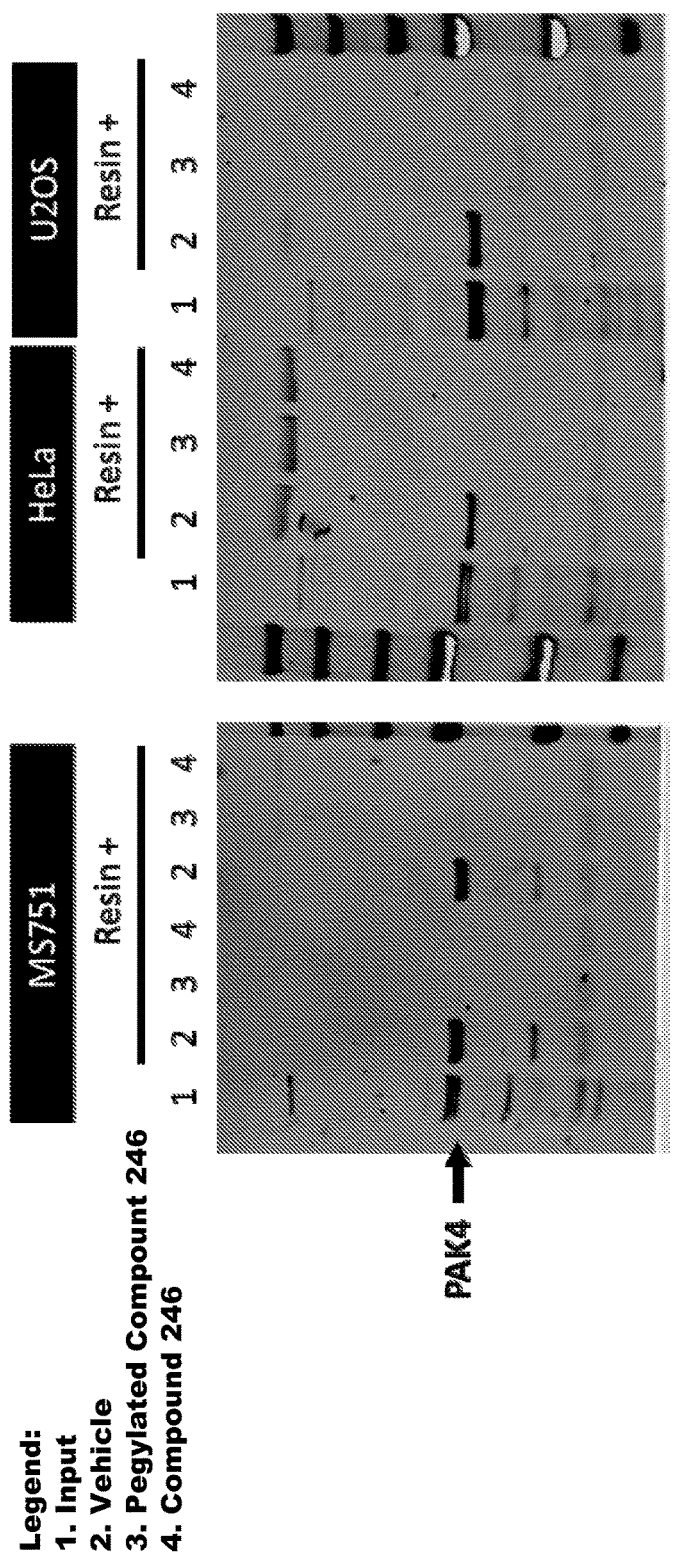
FIG. 3C is an image of a Western blot and shows the enrichment of PAK4 from MS751, HeLa and U2O2 cell lysates treated with PEGylated Compound 246-functionalized resin in the absence of soluble competitor.

Samples were boiled, run on a 4-20% SDS-PAGE gel and transferred to nitrocellulose membranes for Western blotting. Anti-PAK4 primary antibody was incubated on the membrane overnight and detected with fluorescent secondary antibody. The results of the Western blot experiment are shown in FIG. 3C. PAK4 bound to the resin pre-treated with DMSO but not the resin corresponding to samples pre-treated with PEGylated Compound 246 or Compound 246.

Example 6

Effects of Exemplary Compounds on PAK4 Interactors and Downstream Proteins

Immunoblots were used to measure the effects of exemplary compounds on protein steady-state levels and phophorylation of PAK4 interactor and downstream proteins. Specifically, U2OS (osteosarcoma) cells were split and plated on day 1. After overnight attachment to the tissue culture plate, cells were treated with either DMSO (0), 37 nM, 111 nM, 333 nM, 1 µM, or 3 µM Compound 246 for 72 hours. Cells were collected, washed and lysed in RIPA buffer. After obtaining the protein concentration by BCA assay, lysates were boiled in loading buffer and run on SDS-PAGE. The gels were transferred to nitrocellulose membranes and blotted with antibodies raised against phosphor-PAK4, PAK4, phophos-beta-catenin, beta-catenin, GEF-H1, phospho-Akt, Akt, phospho-ERK1/2, ERK1/2, phospho-cofilin, cofilin, phospho-histone H3, histone H3, cyclin D1, Mcl-1, Bcl-2, p21, survivin, caspase 8, caspase 3, PARP, and beta-actin (loading control).

Figure 4A:
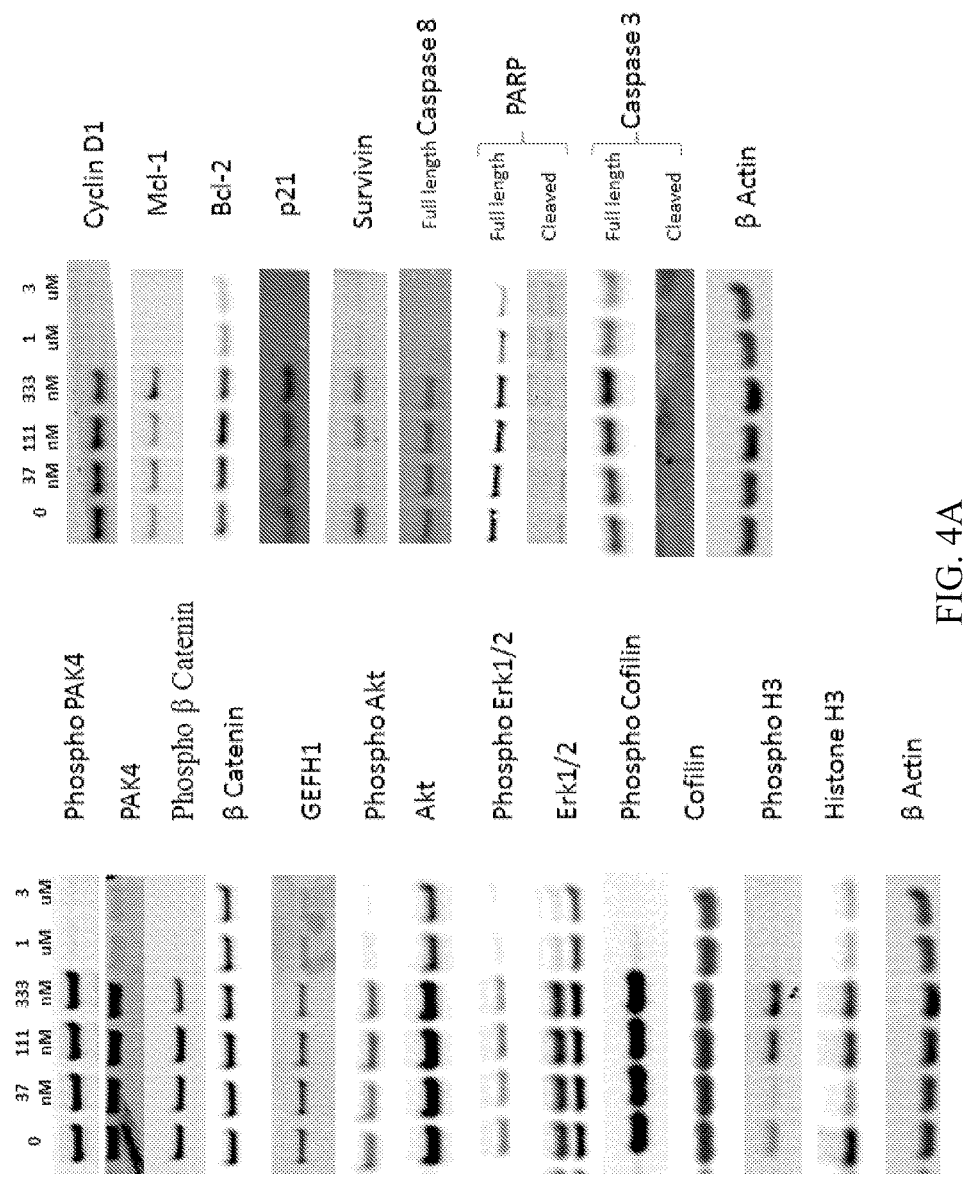
FIG. 4A is images of Western blots, and shows the effects of treatment for 72 hours with increasing concentrations of Compound 246 on PAK4 interactors and downsteam proteins in U20S cells.

FIG. 4A shows that Compound 246 led to a decrease in PAK4 total protein as well as a decrease in phosphorylation or the total level of PAK4 signaling proteins such as Akt, ERK1/2, beta-catenin, cofilin, p21 and cyclin D1. There were also increases in cleavage of apoptosis markers caspase 3, caspase 8 and PARP.

In another experiment, U2OS (osteosarcoma) cells were split and plated on day 1. After overnight attachment to the tissue culture plate, cells were treated with DMSO (Ct), 0.5 µM, or 5 µM of Compound 124, 369, 226, 246, or 907 for 72 hours. Cells were collected, washed and lysed in RIPA buffer. After obtaining the protein concentration by BCA assay, lysates were boiled in loading buffer and run on SDS-PAGE. The gels were transferred to nitrocellulose membranes and blotted with antibodies raised against phophos-beta-catenin, cyclin D1, PAK4, phospho-cofilin, and beta-actin (loading control).

Figure 4B:
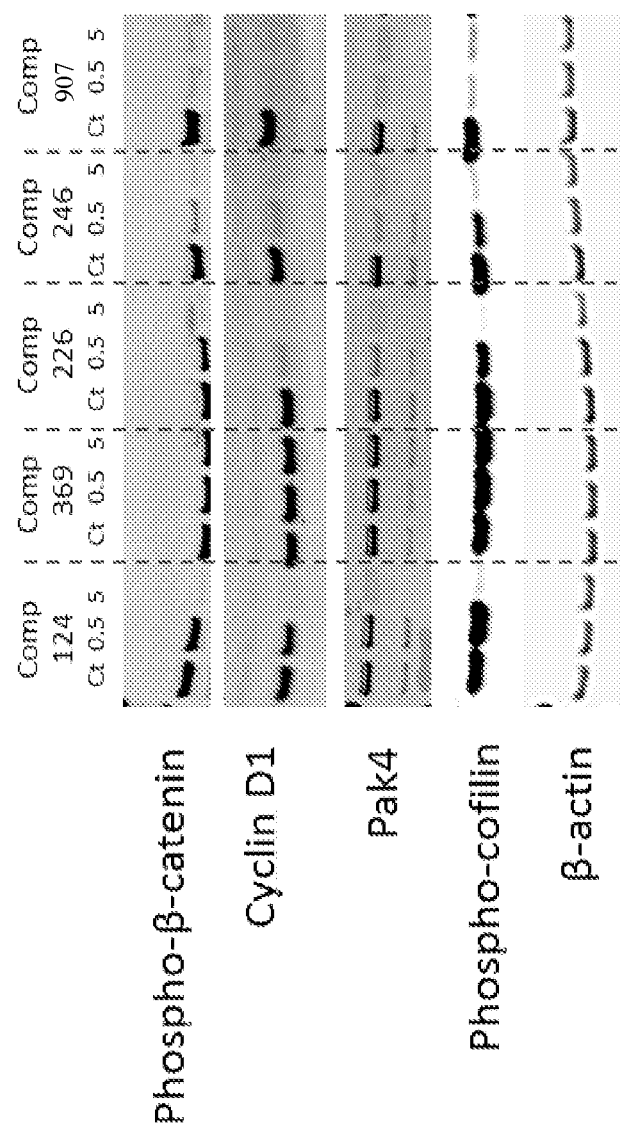
FIG. 4B is images of Western blots, and shows the effects of treatment for 72 hours with increasing concentrations of Compounds 124, 369, 226, 246 and 907 on PAK4 interactors and downsteam proteins in U20S cells.

FIG. 4B shows that treatment with Compounds 124, 369, 226, 246 and 907 led to a decrease in PAK4 total protein as well as decreases in phosphorylation of PAK4 signaling proteins beta-catenin and cofilin.

Example 7

MDA-MB-468 Mouse Xenograft Model

The oncological impact of Compound 116 was tested using a MDA-MB-468 (triple negative breast) cancer xenograft model in CB-17 SCID mice. MDA-MB-468 (ATCC # HTB-102) breast adenocarcinoma cells were obtained from ATCC. These cells were grown in high glucose DMEM medium supplemented with 10% fetal bovine serum, 1% penicillin and streptomycin, and 2 mM L-glutamine. Cells were sub-cultured by dilution at a ratio of 1:4. MDA-MB-468 cells were harvested by trypsinization and counted using a hemocytometer. Cells were resuspended in PBS at a concentration of $4 \times 10^8$ cells per mL. Cells were placed on ice and mixed with an equal volume of Matrigel (BD Biosciences CB-40234). This mixture was kept on ice and injected into the left flank of mice in a volume of 0.2 mL, equivalent to $4 \times 10^7$ cells per mouse. When the tumors reached a mean size of between 100 and 200 mm³, mice were randomly and prospectively divided. Tumor bearing mice were treated with vehicle or Compound 116 on M-F (QDx5/week) for 9 weeks. Compound 116 was administered orally (PO) at initial doses of 15 and 30 mg/kg five times a week. Animals' weights and condition were recorded daily, tumors were measured once every two days with microcalipers, and tumor volume was calculated as (length× width×width)/2.

Figure 5:
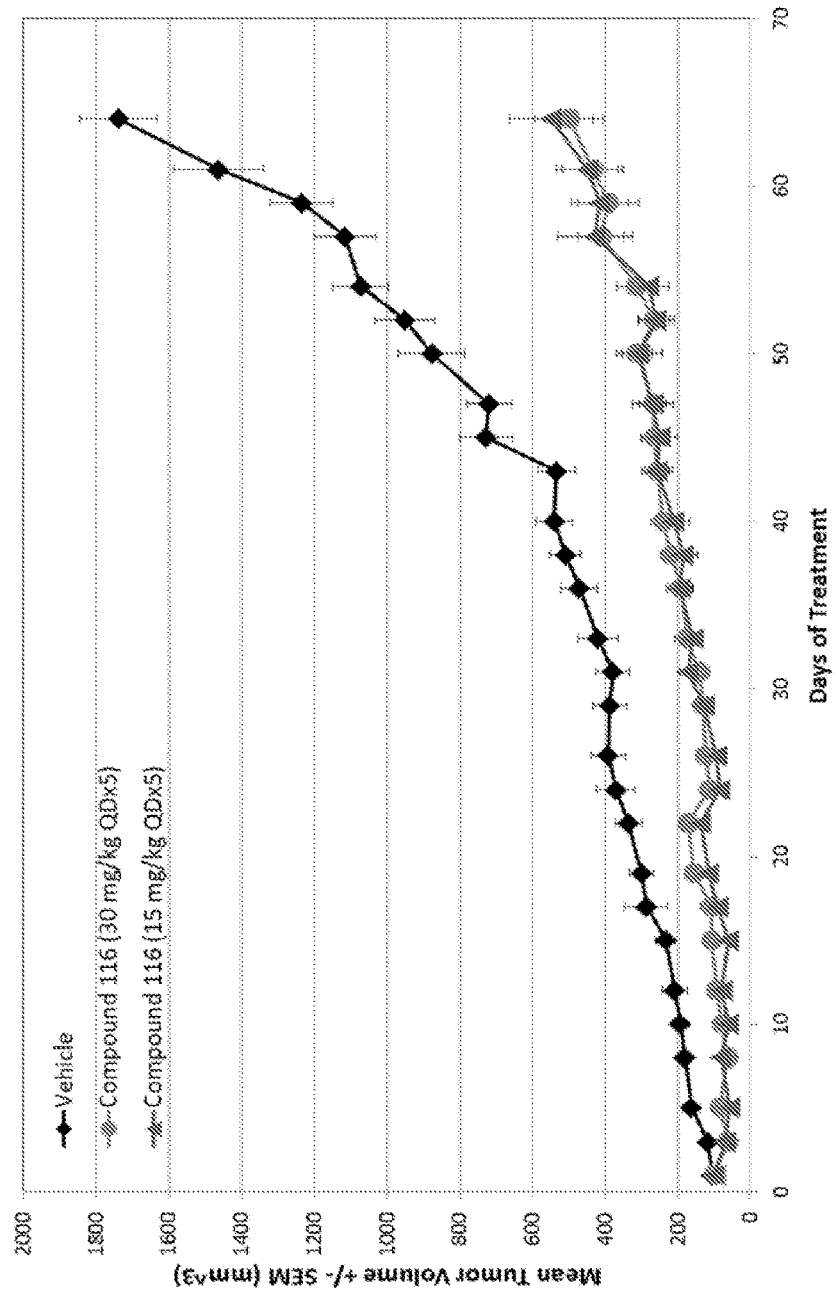
FIG. 5 is a graph of mean tumor volume versus time, and shows the mean tumor volume of MDA-MB-468 tumors on tumor-bearing SCID mice treated with vehicle, or Compound 116 (30 mg/kg QDx5 or 15 mg/kg QDx5).

FIG. 5 is a graph of mean tumor volume versus time, and shows that the mean tumor volume of MDA-MB-468 tumors on tumor-bearing SCID mice treated with Compound 116 (30 mg/kg QDx5 or 15 mg/kg QDx5) was reduced compared to the mean tumor volume of MDA-MB-468 tumors on tumor-bearing SCID mice treated with vehicle.

REFERENCES

1. Arias-Romano, L. E.; Chernoff, J. *Biol. Cell,* 2008, 100, 97-108.
2. a) Dart, A. E.; Wells, C. M. *European Journal of Cell Biology,* 2013, 92, 129-138. b) Clairvoyant, F.; Zhu. S. et al. *J Biol Chem,* 2002, 277, 550-8. c) Cammarano, M. S. et al. *Mol Cell Biol.,* 2005, 21, 9532-42. d) Wells, C. M. et al, *J Cell Sci.,* 2010, 123, 1663-73. d) Siu, M. K. et al. *Proc. Natl. Acad. Sci. USA,* 2010, 107(43), 18622-7.
3. a) Guo, C. et al.; *J. Med. Chem.,* 2012, 55, 4728-4739 b) Deacon, S. W. et al. *Chemistry & Biology,* 2008, 15, 322-331 c) Wells, C. M.; Jones, G. E. *Biochem. J.,* 2010, 425, 465-473.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by Structural Formula IXa or Xa:

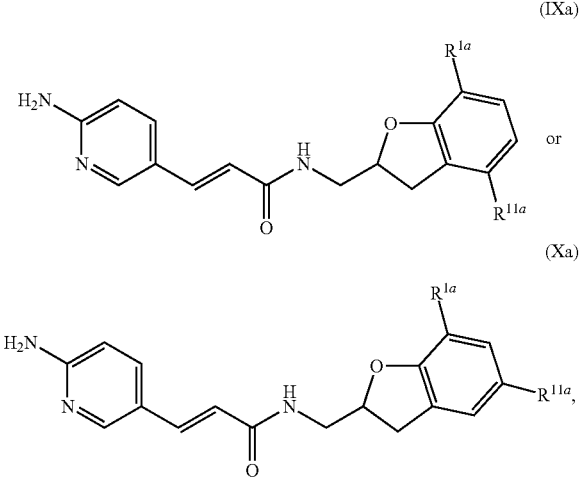

or a pharmaceutically acceptable salt thereof, wherein:
  $R^{1a}$ is selected from halo, hydroxyl, halo($C_1$-$C_4$)alkyl, ($C_1$-$C_4$)alkyl and ($C_1$-$C_4$)alkoxy; and
  $R^{11a}$ is phenyl or a 5-6-membered heteroaryl having 1, 2 or 3 heteroatoms selected from nitrogen, oxygen and sulfur optionally and is independently substituted with 1, 2 or 3 optional substituents.

2. The compound of claim 1, wherein $R^{1a}$ is selected from halogen and halo($C_1$-$C_4$)alkyl.

3. The compound of claim 1, wherein $R^{1a}$ is selected from fluoro, chloro, —$CF_3$ and —$CHF_2$.

4. The compound of claim 1, wherein $R^{11a}$ is substituted with one substituent selected from halogen; ($C_1$-$C_4$)alkyl optionally substituted with hydroxyl; ($C_2$-$C_4$)alkenyl; ($C_1$-$C_4$)haloalkyl; —C(O)($C_1$-$C_4$)alkyl; —C(O)O($C_1$-$C_4$)alkyl; —C(O)($CH_2$)$_{0-1}$($C_3$-$C_7$)carbocyclyl; phenyl; —C(O)($CH_2$)$_{0-1}$$NR^{12}R^{13}$, wherein $R^{12}$ and $R^{13}$ are each methyl, or $R^{12}$ and $R^{13}$ are taken together with the nitrogen atom to which they are commonly attached to form an optionally substituted saturated ($C_3$-$C_7$)heterocyclyl; and —S(O)$_2$$NR^{12}R^{13}$, wherein $R^{12}$ and $R^{13}$ are taken together with the nitrogen atom to which they are commonly attached to form an optionally substituted saturated ($C_3$-$C_7$)heterocyclyl.

5. The compound of claim 1, wherein $R^{11a}$ is substituted with a first substituent selected from halogen; $(C_1-C_4)$alkyl optionally substituted with hydroxyl; $(C_2-C_4)$alkenyl; $(C_1-C_4)$haloalkyl; —C(O)$(C_1-C_4)$alkyl; —C(O)O$(C_1-C_4)$alkyl; —C(O)$(CH_2)_{0-1}(C_3-C_7)$carbocyclyl; phenyl; —C(O)$(CH_2)_{0-1}NR^{12}R^{13}$, wherein $R^{12}$ and $R^{13}$ are each methyl, or $R^{12}$ and $R^{13}$ are taken together with the nitrogen atom to which they are commonly attached to form an optionally substituted saturated $(C_3-C_7)$heterocyclyl; and —S(O)$_2$NR$^{12}$R$^{13}$, wherein $R^{12}$ and $R^{13}$ are taken together with the nitrogen atom to which they are commonly attached to form an optionally substituted saturated $(C_3-C_7)$heterocyclyl, and a second substituent selected from halogen, $(C_1-C_4)$alkyl and $(C_1-C_4)$haloalkyl.

6. The compound of claim 1, wherein $R^{11a}$ is selected from phenyl, thiophenyl, pyridinyl, pyrimidinyl, isoxazolyl, furanyl, pyridazinyl and oxadiazolyl, and is substituted with 1, 2 or 3 independently selected substituents.

7. The compound of claim 1, wherein the saturated heterocyclyl formed by $R^{12}$ and $R^{13}$ together with the nitrogen atom to which they are attached is optionally substituted with 1 or 2 substituents independently selected from halogen, $(C_1-C_4)$alkyl and $(C_1-C_4)$haloalkyl.

8. A compound selected from:

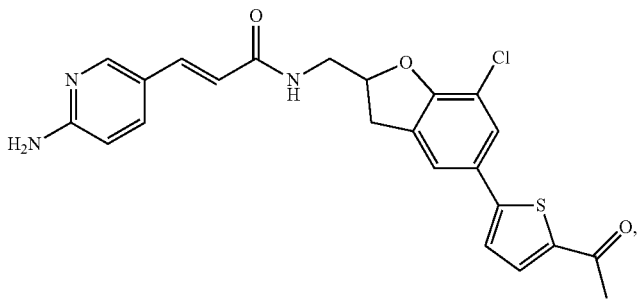

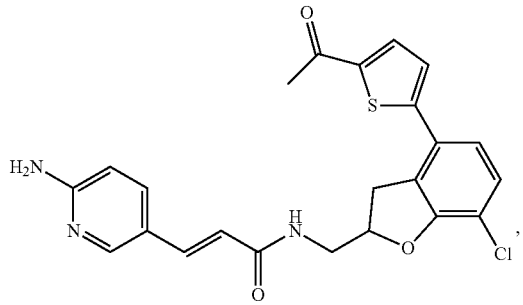

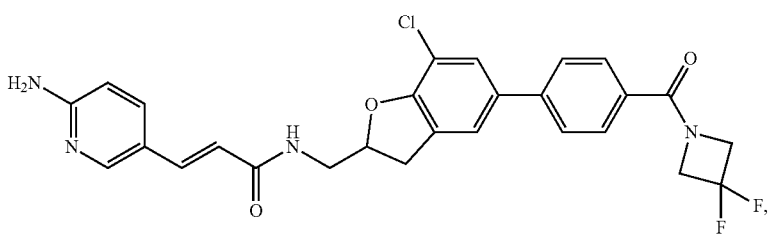

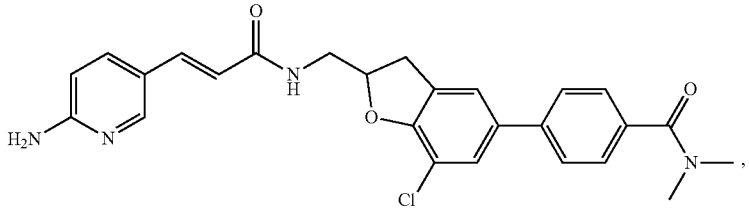

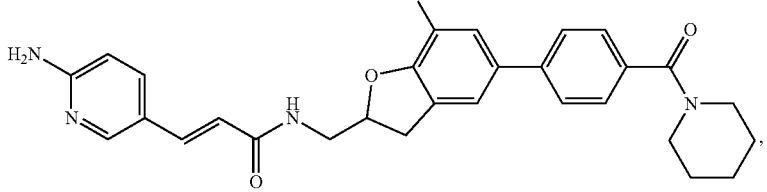

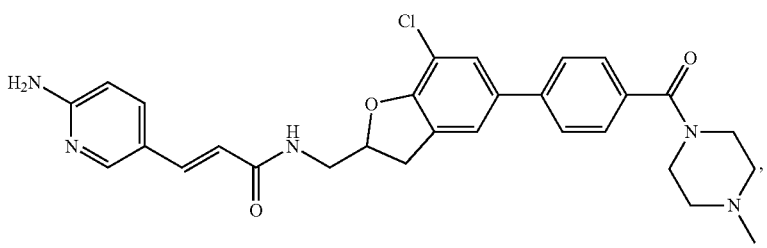

-continued
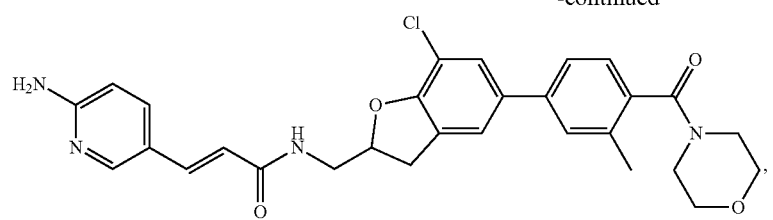
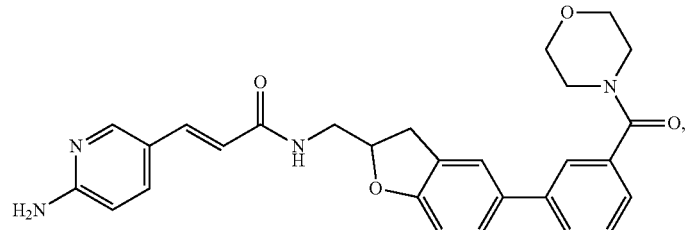
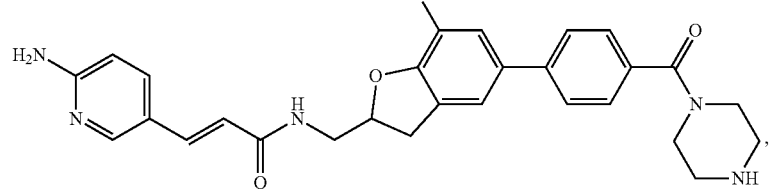
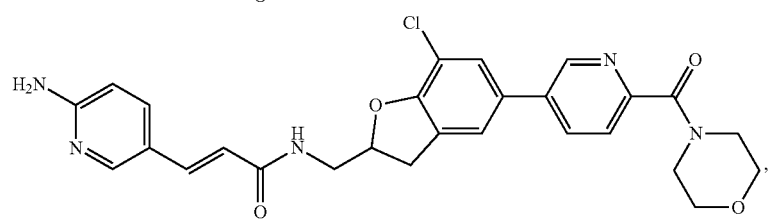
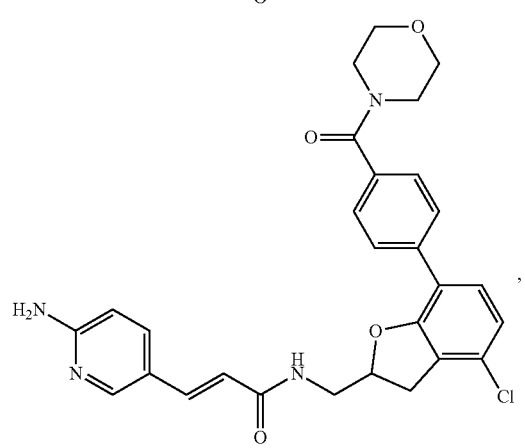
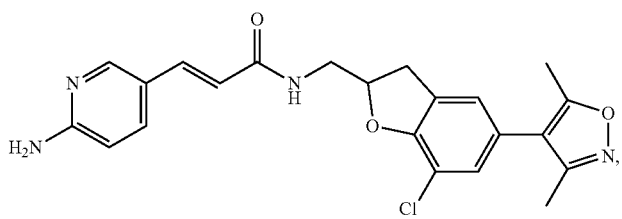
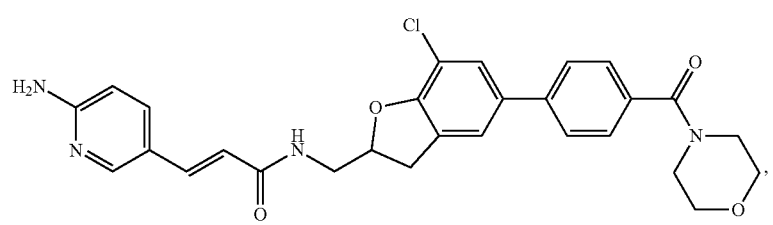

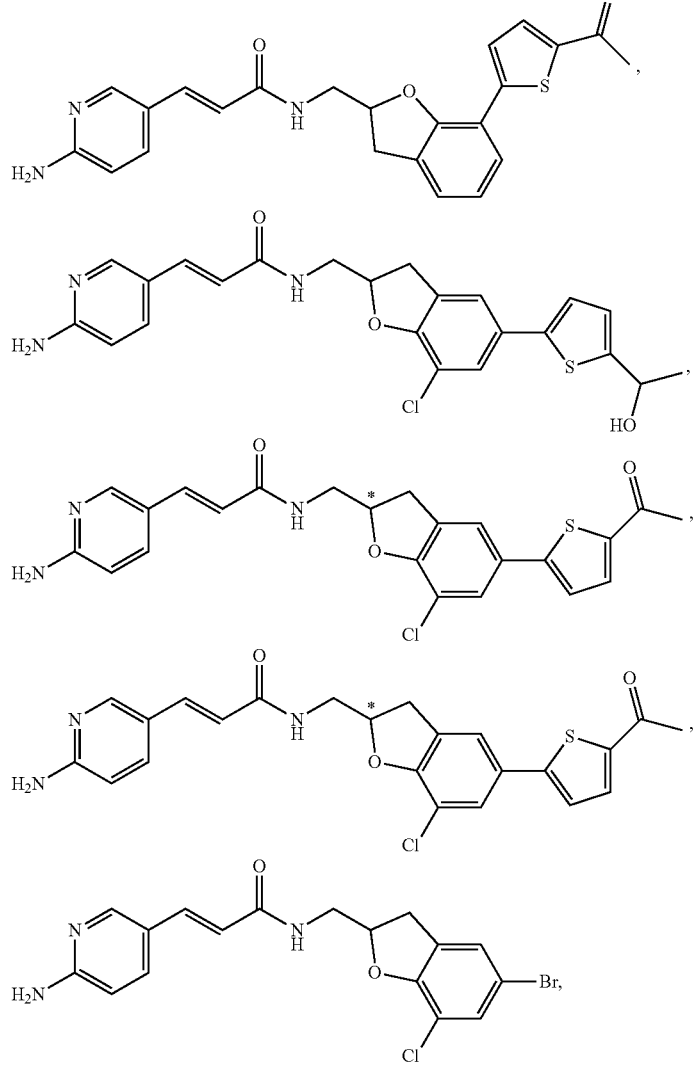
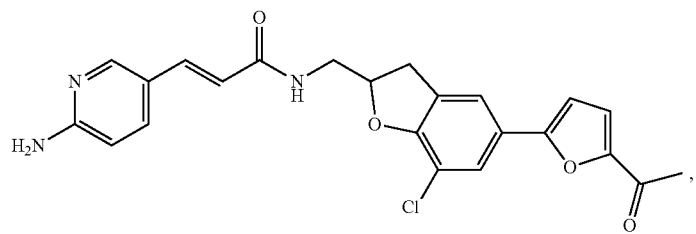
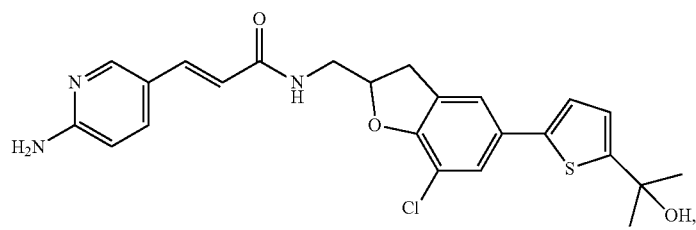

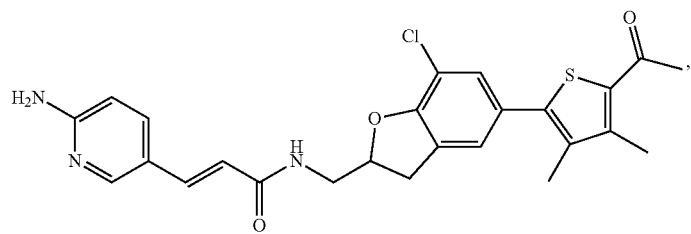
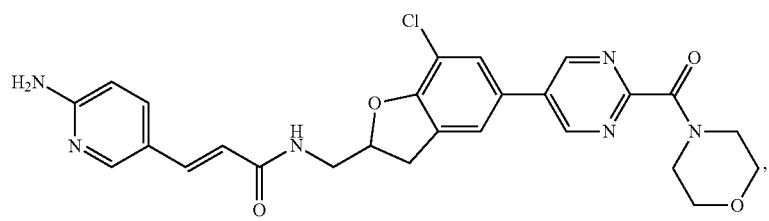
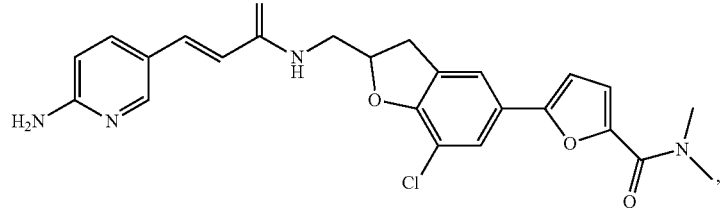
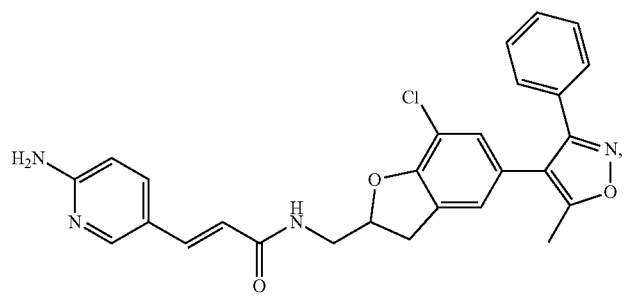
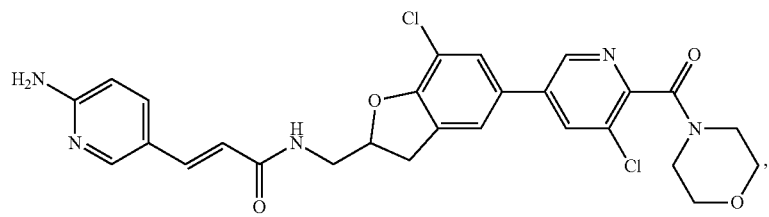
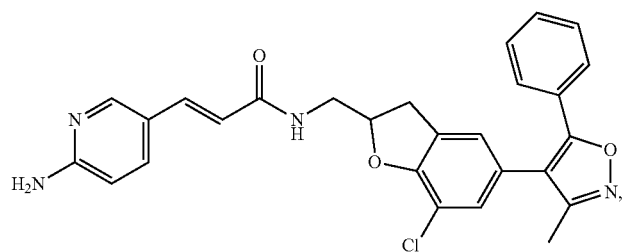
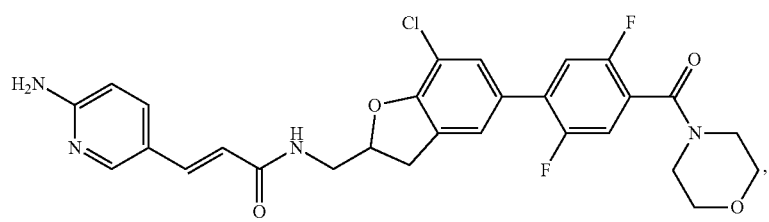

-continued
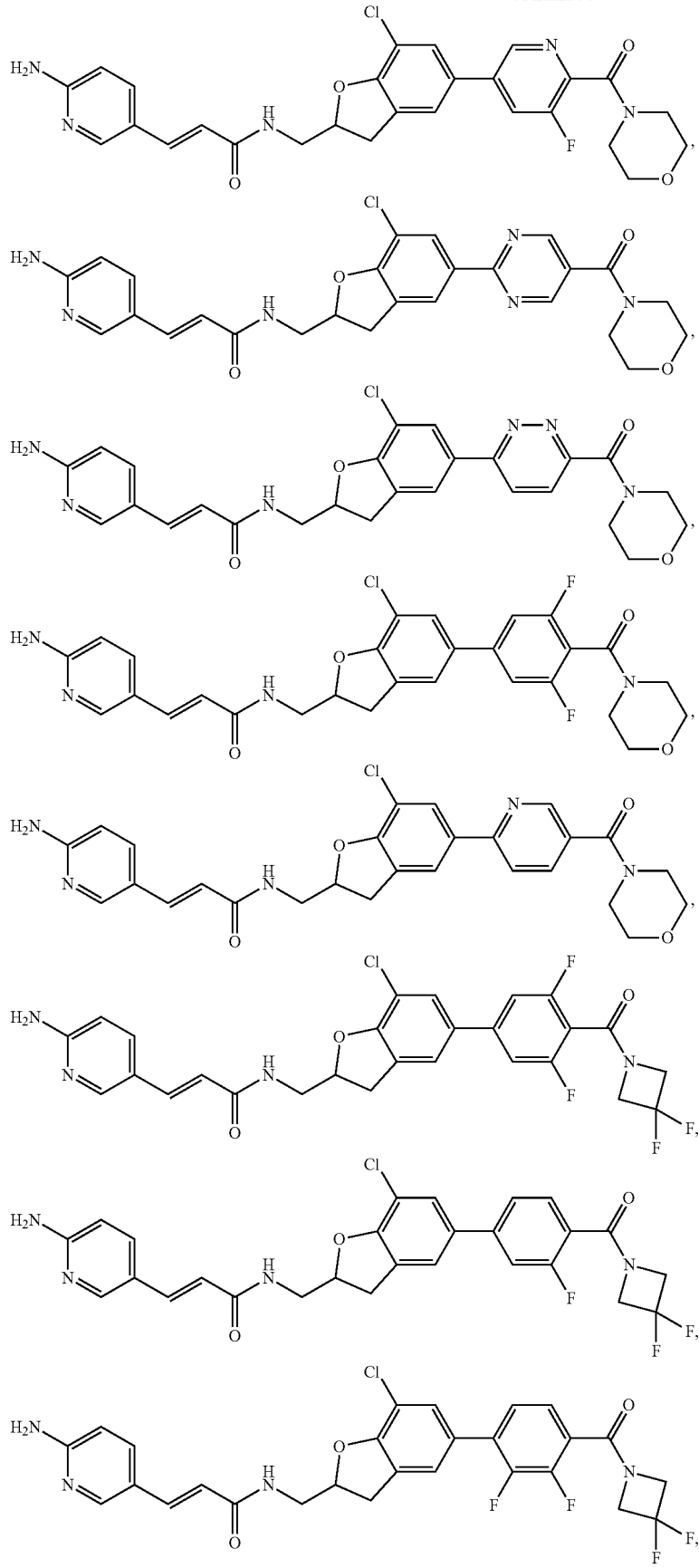

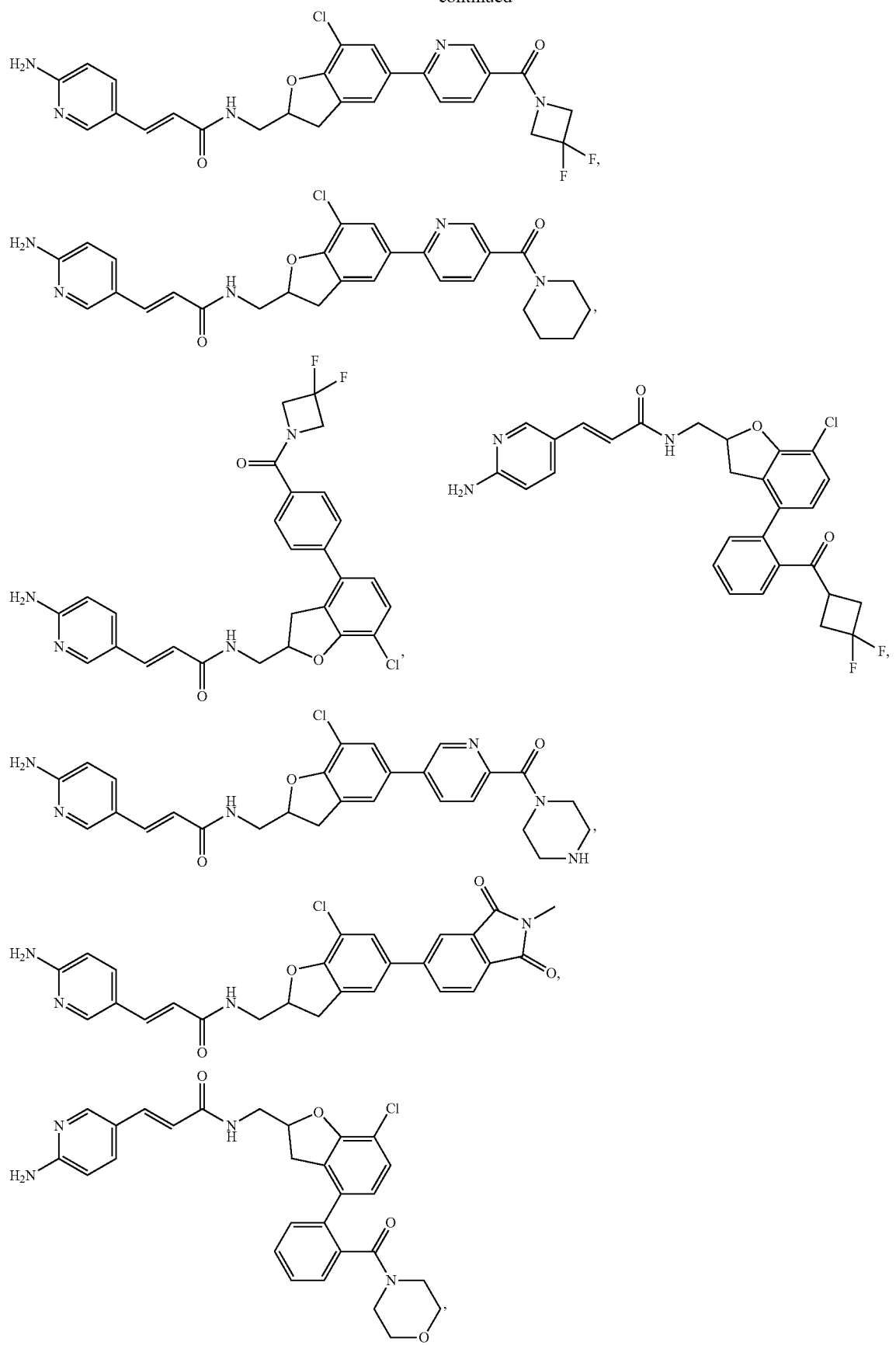

-continued
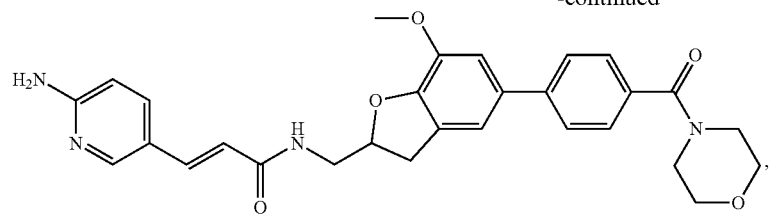
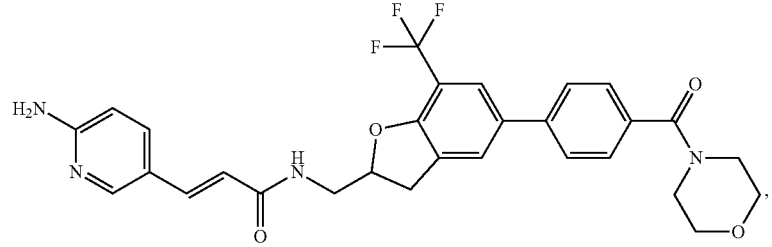
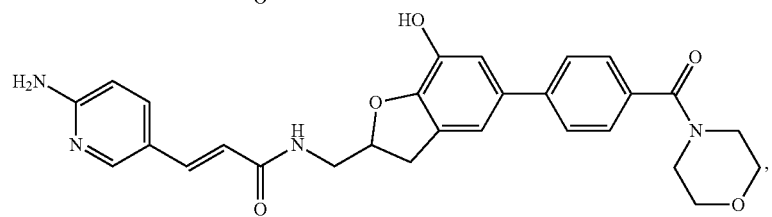
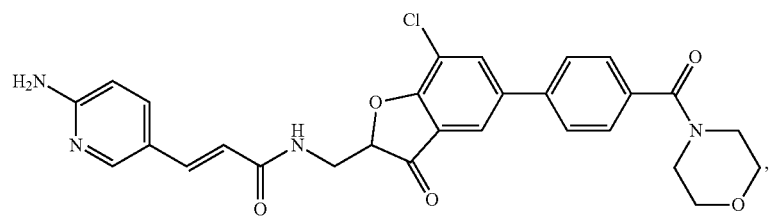
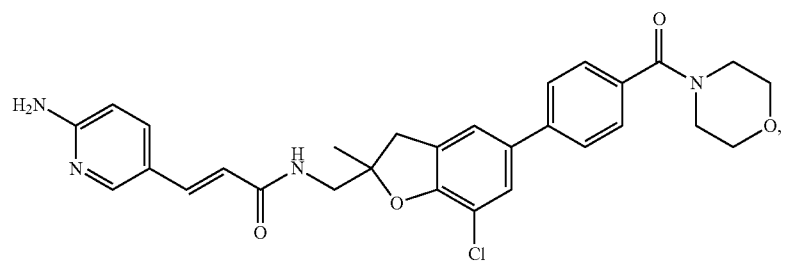
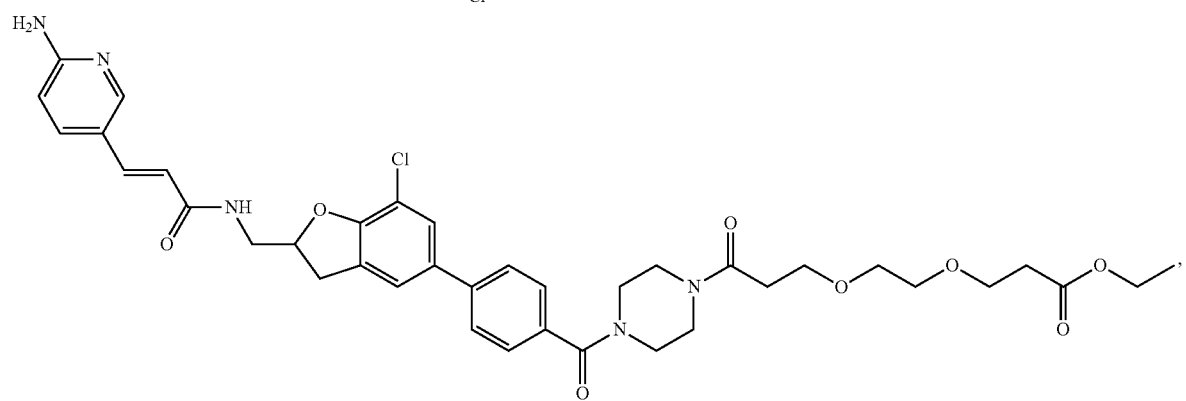

-continued
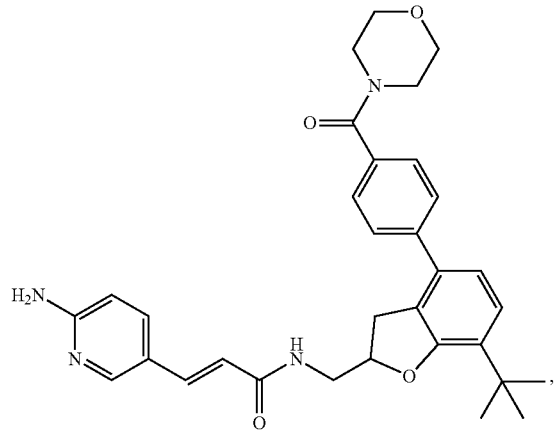
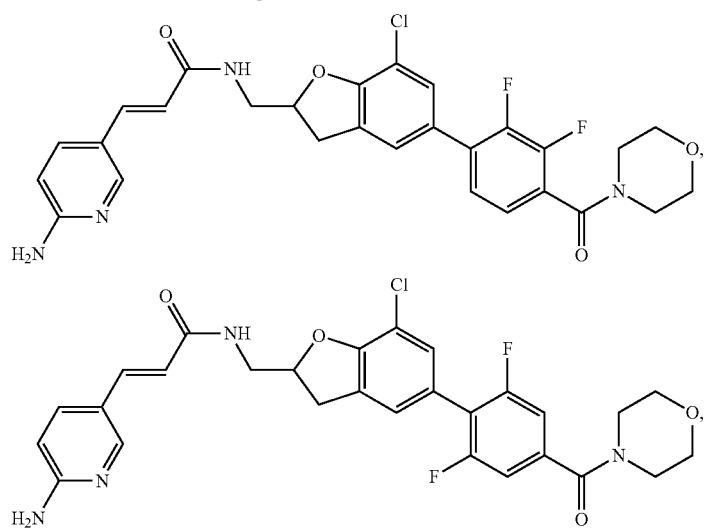
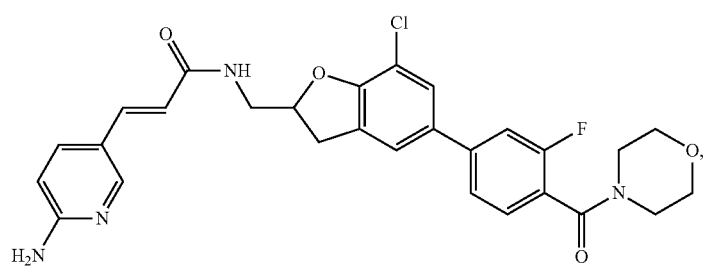
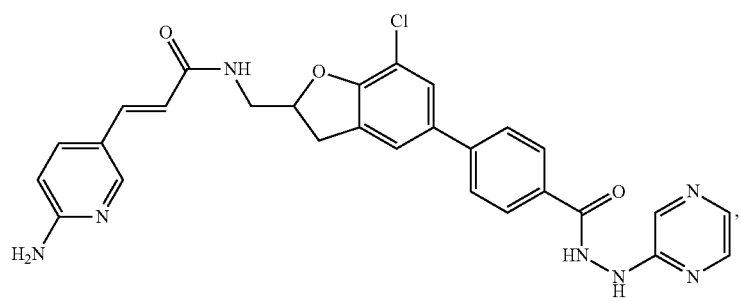

531
-continued
532
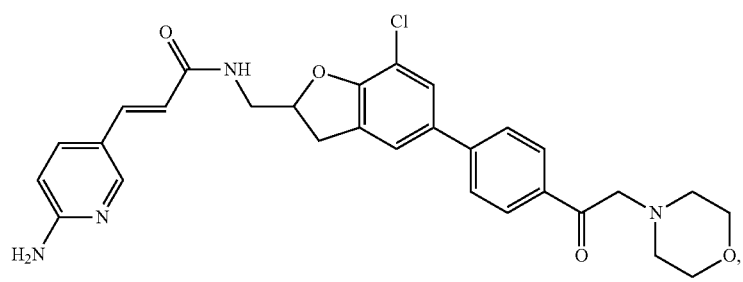
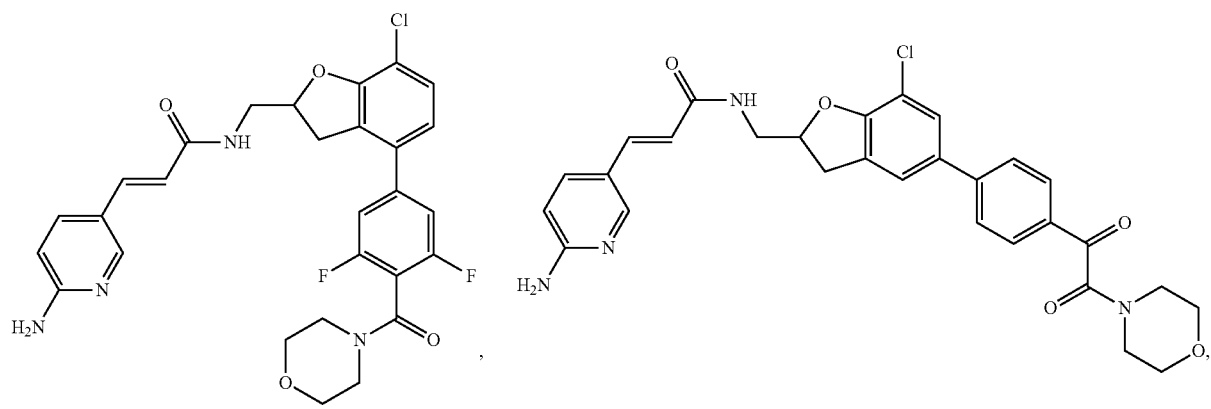
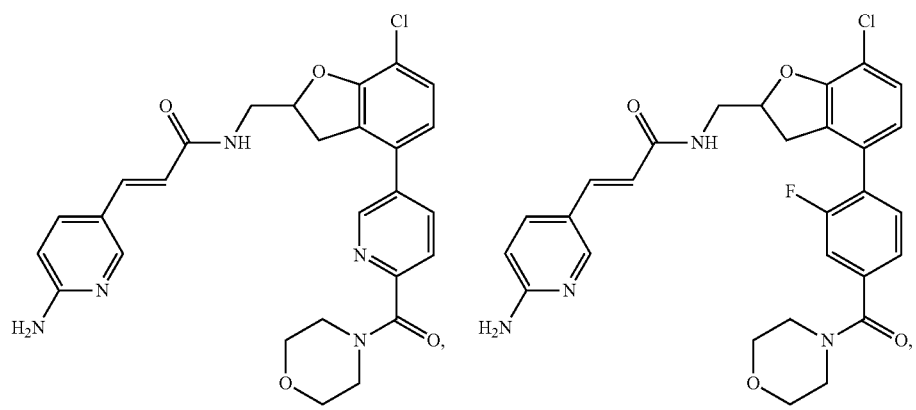
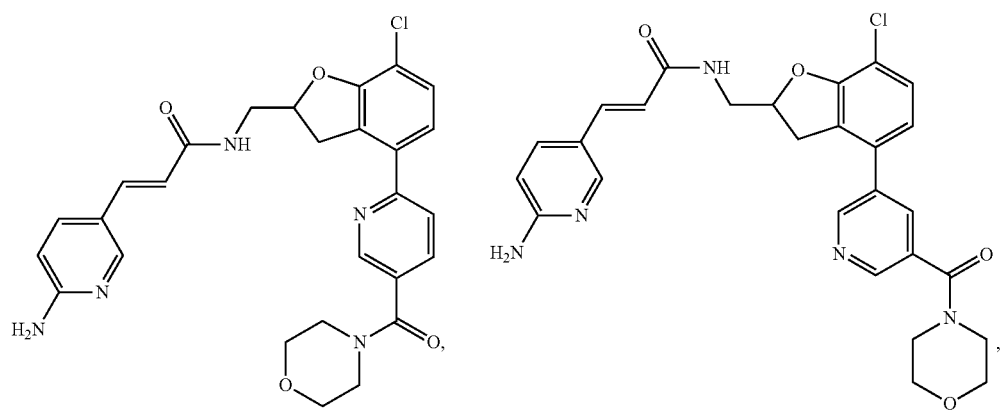

533

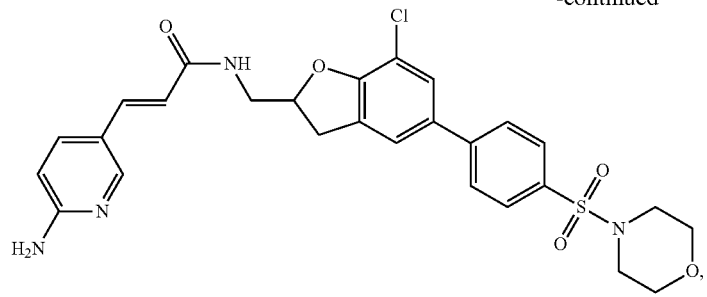

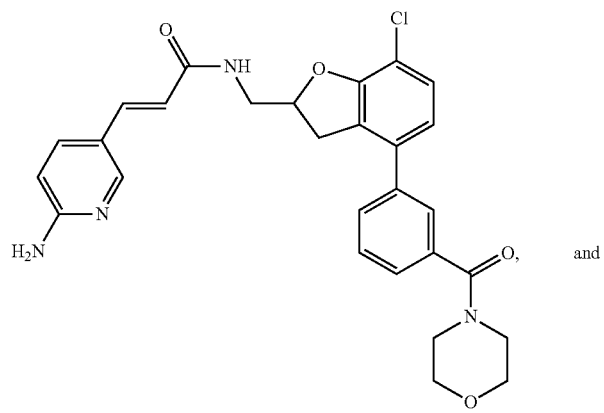

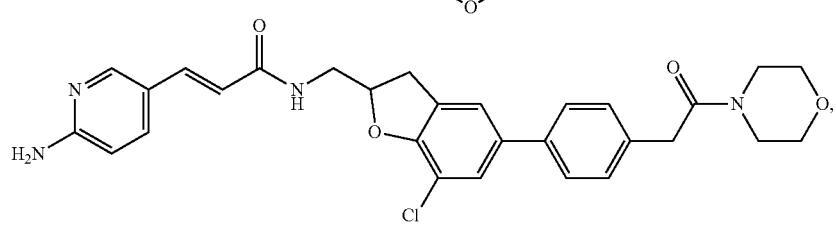

or a pharmaceutically acceptable salt thereof.

9. A compound selected from one of the following:

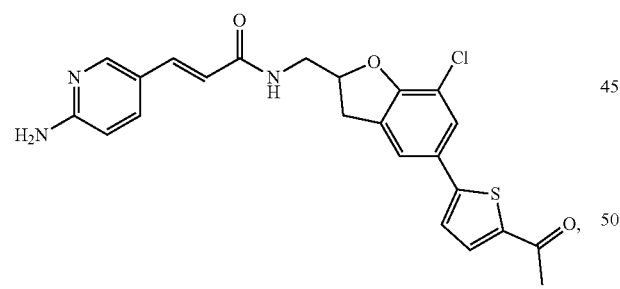

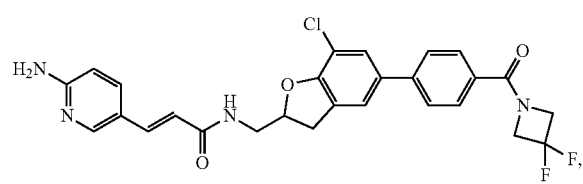

534

-continued

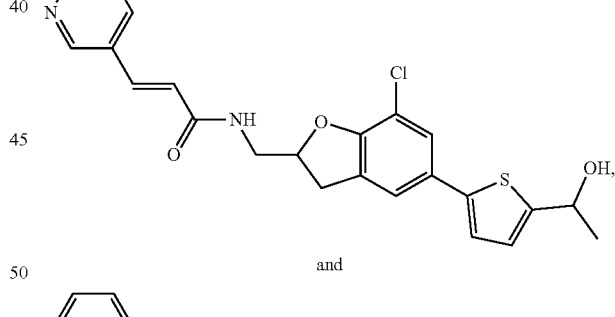

and

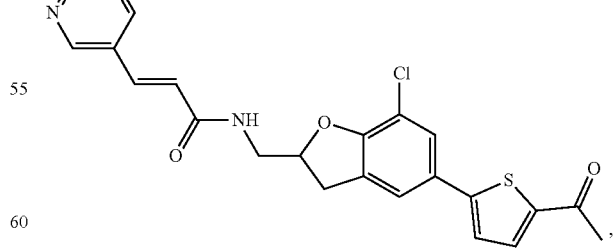

or a pharmaceutically acceptable salt thereof.

10. A pharmaceutical composition comprising a compound of claim 1, and a pharmaceutically acceptable carrier.

11. A method of treating lymphoma in a subject in need thereof, comprising administering to the subject a therapeutically effective amount of a compound of claim 1, or a pharmaceutically acceptable salt thereof.

12. The method of claim 11, wherein the lymphoma is mantle cell lymphoma.

* * * * *